United States Patent
Harrison et al.

(10) Patent No.: US 12,012,397 B2
(45) Date of Patent: *Jun. 18, 2024

(54) SULPHONYL UREA DERIVATIVES AS NLRP3 INFLAMMASOME MODULATORS

(71) Applicant: NodThera Limited, Essex (GB)

(72) Inventors: David Harrison, Essex (GB); Alan Paul Watt, Edinburgh (GB); Mark G. Bock, Lexington, MA (US)

(73) Assignee: NodThera Limited, Little Chesterford (GB)

( * ) Notice: Subject to any disclaimer, the term of this patent is extended or adjusted under 35 U.S.C. 154(b) by 0 days.

This patent is subject to a terminal disclaimer.

(21) Appl. No.: 17/967,599

(22) Filed: Oct. 17, 2022

(65) Prior Publication Data

US 2023/0145050 A1 May 11, 2023

Related U.S. Application Data

(63) Continuation of application No. 16/955,284, filed as application No. PCT/EP2018/085511 on Dec. 18, 2018, now Pat. No. 11,518,757.

(30) Foreign Application Priority Data

Dec. 18, 2017 (GB) .................................... 1721185

(51) Int. Cl.
| | | |
|---|---|---|
| C07D 403/12 | (2006.01) | |
| C07D 231/38 | (2006.01) | |
| C07D 237/20 | (2006.01) | |
| C07D 239/42 | (2006.01) | |
| C07D 249/04 | (2006.01) | |
| C07D 249/14 | (2006.01) | |
| C07D 261/14 | (2006.01) | |
| C07D 277/52 | (2006.01) | |
| C07D 285/135 | (2006.01) | |
| C07D 307/66 | (2006.01) | |
| C07D 401/12 | (2006.01) | |
| C07D 405/12 | (2006.01) | |
| C07D 471/08 | (2006.01) | |

(52) U.S. Cl.
CPC ......... *C07D 403/12* (2013.01); *C07D 231/38* (2013.01); *C07D 237/20* (2013.01); *C07D 239/42* (2013.01); *C07D 249/04* (2013.01); *C07D 249/14* (2013.01); *C07D 261/14* (2013.01); *C07D 277/52* (2013.01); *C07D 285/135* (2013.01); *C07D 307/66* (2013.01); *C07D 401/12* (2013.01); *C07D 405/12* (2013.01); *C07D 471/08* (2013.01); *C07B 2200/05* (2013.01)

(58) Field of Classification Search
CPC .................................................. C07D 403/12
See application file for complete search history.

(56) References Cited

U.S. PATENT DOCUMENTS

| | | |
|---|---|---|
| 4,515,620 A | 5/1985 | Bohner |
| 5,288,757 A | 2/1994 | Picard et al. |
| 5,424,450 A | 6/1995 | Boswell et al. |
| 5,512,681 A | 4/1996 | Boswell et al. |
| 5,604,178 A | 2/1997 | Kanda et al. |
| 5,610,121 A | 3/1997 | Riebel et al. |
| 5,612,287 A | 3/1997 | Kanda et al. |
| 5,683,964 A | 11/1997 | Kanda et al. |
| 6,028,201 A | 2/2000 | Dinsmore et al. |
| 6,303,541 B1 | 10/2001 | Gesing et al. |
| 6,329,323 B1 | 12/2001 | Bettarini et al. |
| 6,593,356 B2 | 7/2003 | Nugiel et al. |
| 6,887,831 B1 | 5/2005 | Gesing et al. |
| 7,144,911 B2 | 12/2006 | Flynn et al. |
| 7,202,257 B2 | 4/2007 | Flynn et al. |

(Continued)

FOREIGN PATENT DOCUMENTS

| | | |
|---|---|---|
| CN | 103288750 A | 9/2013 |
| CN | 107428696 A | 12/2017 |

(Continued)

OTHER PUBLICATIONS

Aggarwal, B.B. et al. (2009) "Targeting inflammatory pathways for prevention and therapy of cancer: short-term friend, long-term foe" Clinical Cancer Research, 15(2):425-430.
Ahmad, I. et al. (Jul. 2013) "Thymoquinone suppresses metastasis of melanoma cells by inhibition of NLRPB inflammasome" Toxicology and Applied Pharmacology, 270(1):70-76.
Amieva, M. and R.M. Peek (Jan. 2016) "Pathobiology of Helicobacter pylori-Induced Gastric Cancer" Gastroenterology, 150(1):64-78.
Apte, R.N. et al. (Sep. 2006) "The involvement of IL-1 in tumorigenesis, tumor invasiveness, metastasis and tumor-host interactions" Cancer and Metastasis Reviews, 25(3):387-408.
Basso, D. et al. (1996) "Helicobacter pylori infection enhances mucosal interleukin-1beta, interleukin-6, and the soluble receptor of interleukin-2" Int J Clin Lab Res, 26:207-210.

(Continued)

*Primary Examiner* — Matthew P Coughlin
(74) *Attorney, Agent, or Firm* — COOLEY LLP; Heidi A. Erlacher; Christine E. Dunne

(57) ABSTRACT

The present disclosure relates to compounds of Formula (I):

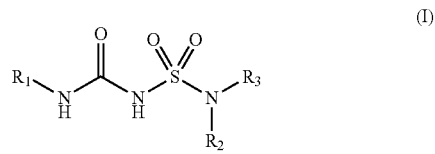

and to their pharmaceutically acceptable salts, pharmaceutical compositions, methods of use, and methods for their preparation. The compounds disclosed herein are useful for inhibiting the maturation of cytokines of the IL-1 family by inhibiting inflammasomes and may be used in the treatment of disorders in which inflammasome activity is implicated, such as inflammatory, autoinflammatory and autoimmune diseases and cancers.

20 Claims, No Drawings

(56) References Cited

U.S. PATENT DOCUMENTS

| | | | |
|---|---|---|---|
| 7,279,576 B2 | 10/2007 | Flynn et al. | |
| 7,342,037 B2 | 3/2008 | Flynn et al. | |
| 7,531,566 B2 | 5/2009 | Flynn et al. | |
| 7,666,895 B2 | 2/2010 | Flynn et al. | |
| 7,737,283 B2 | 6/2010 | Flynn et al. | |
| 8,642,660 B2 | 2/2014 | Goldfarb | |
| 9,271,969 B2 | 3/2016 | Kim et al. | |
| 9,410,217 B2 | 8/2016 | Lipiecki et al. | |
| 11,518,757 B2 * | 12/2022 | Harrison | C07D 453/02 |
| 2003/0134898 A1 | 7/2003 | Homan | |
| 2007/0191336 A1 | 8/2007 | Flynn et al. | |
| 2008/0187978 A1 | 8/2008 | Flynn et al. | |
| 2009/0069310 A1 | 3/2009 | Flynn et al. | |
| 2009/0105230 A1 | 4/2009 | Flynn et al. | |
| 2009/0137021 A1 | 5/2009 | Flynn et al. | |
| 2009/0312349 A1 | 12/2009 | Flynn et al. | |
| 2017/0304270 A1 | 10/2017 | Or et al. | |
| 2017/0304271 A1 | 10/2017 | Or et al. | |
| 2017/0304272 A1 | 10/2017 | Or et al. | |
| 2017/0333399 A1 | 11/2017 | Or et al. | |
| 2017/0334893 A1 | 11/2017 | Or et al. | |
| 2017/0334894 A1 | 11/2017 | Or et al. | |
| 2020/0299284 A1 | 9/2020 | O'Neill et al. | |
| 2022/0227715 A1 | 7/2022 | Bock et al. | |
| 2022/0267300 A1 | 8/2022 | Bock et al. | |
| 2023/0083495 A1 | 3/2023 | Bock et al. | |

FOREIGN PATENT DOCUMENTS

| | | |
|---|---|---|
| EP | 0569193 B1 | 2/1997 |
| EP | 3272739 A1 | 1/2018 |
| EP | 3259253 B1 | 1/2020 |
| GB | 2110689 A | 6/1983 |
| JP | S60214785 A | 10/1985 |
| JP | H09132574 A | 5/1997 |
| JP | H1029990 A | 2/1998 |
| JP | 2001026574 A | 1/2001 |
| JP | 4112127 B2 | 7/2008 |
| WO | WO-9208694 A1 | 5/1992 |
| WO | WO-9304045 A1 | 3/1993 |
| WO | WO-9304046 A1 | 3/1993 |
| WO | WO-9324482 A1 | 12/1993 |
| WO | WO-9418176 A1 | 8/1994 |
| WO | WO-9418177 A1 | 8/1994 |
| WO | WO-9800408 A1 | 1/1998 |
| WO | WO-9832733 A1 | 7/1998 |
| WO | WO-0123349 A1 | 4/2001 |
| WO | WO-03029226 A1 | 4/2003 |
| WO | WO-2016131098 A1 | 8/2016 |
| WO | WO-2017140778 A1 | 8/2017 |
| WO | WO-2018015445 A1 | 1/2018 |
| WO | WO-2019023147 A1 | 1/2019 |
| WO | WO-2019034686 A1 | 2/2019 |
| WO | WO-2019034688 A1 | 2/2019 |
| WO | WO-2019034690 A1 | 2/2019 |
| WO | WO-2019034692 A1 | 2/2019 |
| WO | WO-2019034693 A1 | 2/2019 |
| WO | WO-2019034696 A1 | 2/2019 |
| WO | WO-2019034697 A1 | 2/2019 |
| WO | WO-2019121691 A1 | 6/2019 |
| WO | WO-2020035464 A1 | 2/2020 |
| WO | WO-2020035466 A1 | 2/2020 |
| WO | WO-2020249664 A1 | 12/2020 |
| WO | WO-2020249667 A1 | 12/2020 |
| WO | WO-2020249669 A1 | 12/2020 |
| WO | WO-2022051582 A1 | 3/2022 |

OTHER PUBLICATIONS

Bernstein, C.N. et al. (Feb. 2001) "Cancer risk in patients with inflammatory bowel disease: a population-based study" Cancer, 91(4):854-862.

Bruchard, M. et al. (Jan. 2013) "Chemotherapy-triggered cathepsin B release in myeloid-derived suppressor cells activates the Nlrp3 inflammasome and promotes tumor growth" Nature Medicine, 19(1):57-64; including "Online Methods", 2 pages.

Carrascal, M.T. et al. (2003) "Interleukin-18 binding protein reduces B16 melanoma hepatic metastasis by neutralizing adhesiveness and growth factors of sinusoidal endothelium" Cancer Research, 63(2):491-497.

Chae, J.J. et al. (May 2, 20117) "Gain-of-Function Pyrin Mutations Induce NLRP3 Protein-Independent Interleukin-1 beta Activation and Severe Autoinflammation in Mice" Immunity, 34:755-768.

Coll et al. A small-molecule inhibitor of the NLRP3 inflammasome for the treatment of inflammatory diseases. Nat Med. Mar. 2015;21(3):248-55. doi: 10.1038/nm.3806. Epub Feb. 16, 2015.

Dinarello, C.A. (Mar. 2004) "Unraveling the NALP-3/IL-1beta inflammasome: a big lesson from a small mutation" Immunity, 20(3): 243-244.

Dinarello, C.A. et al. (Aug. 2010) "Role of IL-1beta in type 2 diabetes" Curr Opin Endocrinol Diabetes Obes, 17(4):314-321.

Elaraj, D.M. et al. (Feb. 2006) "The role of interleukin 1 in growth and metastasis of human cancer xenografts" Clinical Cancer Research, 12(4):1088-1096.

Gabay, C. and I.B. McInnes (2009) "The biological and clinical importance of the 'new generation' cytokines in rheumatic diseases" Arthritis Research & Therapy, 11(3):230, 14 pages.

Gasse, P. et al. (May 2009) "Uric acid is a danger signal activating NALP3 inflammasome in lung injury inflammation and fibrosis" Am J Respir Crit Care Med, 179(10):903-913.

Graf, R., "Umsetzungen mit N-Carbonyl-sulfamidsäure-chlorid1, II2), Alkohole und Phenole," Chemische Berichte, vol. 96, Issue 1, pp. 56-67, https://doi.org/10.1002/cber.19630960106 (Jan. 1963).

Grivennikov, S.I. et al. (Mar. 2010) "Immunity, inflammation, and cancer" Cell, 140(6):883-899.

Halle, A. et al. (Aug. 2008) "The NALP3 inflammasome is involved in the innate immune response to amyloid-beta" Nat Immunol, 9(8):857-865.

Heneka, M.T. et al. (Jan. 31, 2013) "NLRP3 is activated in Alzheimer's disease and contributes to pathology in APP/PS1 mice" Nature, 493:674-678, including Methods, 3 pages.

Hoffman, H.M. et al. (Nov. 2001) "Mutation of a new gene encoding a putative pyrin-like protein causes familial cold autoinflammatory syndrome and Muckle-Wells syndrome" Nat Genet, 29(3):301-305.

Hoffman, H.M. et al., "Periodic Fever Disorders" Reumatología, 21(3):96-100 (2005).

Holen, I. et al. (Nov. 2016) "IL-1 drives breast cancer growth and bone metastasis in vivo" Oncotarget, 7(46):75571-75584.

Jee, C.D. et al. (2005) "Loss of caspase-1 gene expression in human gastric carcinomas and cell lines" Int J Oncol, 26:1265-1271.

Kagan, J. and Horng, T. (Aug. 2013) "NLRP3 inflammasome activation: CD36 serves double duty" Nature Immunology, 14(8):772-774.

Kim, J.M. (Dec. 2011) "Inflammatory Bowel Diseases and Inflammasome" Korean J Gastroenterol, vol. 58 No. 6, pp. 300-310 (Korean, English Abstract on p. 300).

Latz, E. et al. (Jun. 2013) "Activation and regulation of the inflammasomes" Nat Rev Immunol, 13(6):397-411.

Lazar-Molnar, E. et al. (2000) "Autocrine and paracrine regulation by cytokines and growth factors in melanoma" Cytokine, 12(6):547-554.

Lewis, A.M. et al. (Nov. 2006) "Interleukin-1 and cancer progression: the emerging role of interleukin-1 receptor antagonist as a novel therapeutic agent in cancer treatment" Journal of Translational Medicine, 4:48; 12 pages.

Li, L. and Liu, Y. (Dec. 2014) "Aging-related gene signature regulated by NlrpB predicts glioma progression" American Journal of Cancer Research, 5(1):442-449.

Luo, J. et al., "Principles of Cancer Therapy: Oncogene and Non-oncogene Addiction" Cell, 136, pp. 823-837 (Mar. 2009).

Martinon, F. et al. (2009) "The inflammasomes: guardians of the body" Annu Rev Immunol, 27:229-265 (39 total pages).

Masters, S.L. et al. (2009) "Horror Autoinflammaticus: The Molecular Pathophysiology of Autoinflammatory Disease" Annu Rev Immunol, 27:621-668 (54 total pages).

Mortaz, E. et al. (2011) "Identification of Novel Therapeutic Targets in COPD" Tanaffos, 10(2):9-14.

(56) References Cited

OTHER PUBLICATIONS

Mucke, L., "Alzheimer's disease," Nature, vol. 461, pp. 895-897 (Oct. 2009).
Nath, A. et al. (Oct. 2015) "Elevated free fatty acid uptake via CD36 promotes epithelial-mesenchymal transition in hepatocellular carcinoma" Scientific Reports, 5:14752; 19 pages.
NIH National Institute on Aging, "Preventing Alzheimer's Disease: What Do We Know?" Obtained from https://www.nia.nih.gov/health/preventing-alzheimers-disease-what-do-we-know on Dec. 30, 2020 (Sep. 2018) (8 total pages).
Ozaki, E., et al., Targeting the NLRP3 inflammasome in chronic inflammatory diseases: current perspectives. Journal Inflammation Research, Jan. 16, 2015, vol. 8, pp. 15-27.
Pascual, G. et al. (Jan. 2017) "Targeting metastasis-initiating cells through the fatty acid receptor CD36" Nature, 541(7635):41-45; including Supplementary Information, 25 pages.
Perregaux, D.G. et al. (Oct. 2001) "Identification and characterization of a novel class of interleukin-1 post-translational processing inhibitors" J Pharmacol Exp Ther, 299(1):187-197.
Saresella, M. et al. (Mar. 2016) "The NLRP3 and NLRP1 inflammasomes are activated in Alzheimer's disease" Mol Neurodegener, 11:23; 14 pages.
Schett, G. et al. (Jan. 2016) "Interleukin-1 function and role in rheumatic disease" Nat Rev Rheumatol, 12(1):14-24.
Sims, J. and Smith, D.E. (Feb. 2010) "The IL-1 family: regulators of immunity" Nature Reviews Immunology, 10:89-102.
Voronov, E. et al. (Mar. 2003) "IL-1 is required for tumor invasiveness and angiogenesis" Proceedings of the National Academy of Sciences USA, 100(5):2645-2650.
Wang, P. et al. (2006) "Association of interleukin-1 gene polymorphisms with gastric cancer: a meta-analysis" Int J Cancer, 120:552-562.
WebMD, Crohn's Disease Health Center, Crohn's Disease—Prevention, obtained from www.webmd.com/ibd-crohns-disease/crohns-disease/tc/crohns-disease- prevention, on Apr. 5, 2015 (May 2013) (2 total pages).
WebMD "Diabetes Health Center, Prevention", obtained from www.webmd.com/diabetes/guide/type-1-diabetes-prevention, on Apr. 5, 2015 (Jan. 2014) (3 total pages).
Xu, Y. et al. (Nov. 2013) "Mycoplasma hyorhinis Activates the NLRP3 Inflammasome and Promotes Migration and Invasion of Gastric Cancer Cells" PLoS One, 8(11):e77955, 14 pages.
Zahid, A. et al., "Pharmacological Inhibitors of the NLRP3 Inflammasome" Frontiers in Immunology, 10:2538, 10 pages (Oct. 2019).
Zhang, B. et al. (2004) "IL-18 increases invasiveness of HL-60 myeloid leukemia cells: up-regulation of matrix metalloproteinases-9 (MMP-9) expression" Leukemia Research, 28(1):91-95.
Chen et al. "Blockage of the NLRP3 inflammasome by MCC950 improves anti-tumor immune responses in head and neck squamous cell carcinoma", Cellular and Molecular Life Sciences, (2018); 75:2045-2058.
Cuisset et al. "Genetic linkage of the Muckle-Wells syndrome to chromosome 1q44", The American Journal of Human Genetics, (1999); 65(4):1054-1059.
Feldman et al. "Chronic infantile neurological cutaneous and articular syndrome is caused by mutations in CIAS1, a gene highly expressed in polymorphonuclear cells and chondrocytes", The American Journal of Human Genetics, (2002); 71(1):198-203.
Fusco, R., et al.; "Focus on the Role of NLRP3 Inflammasome in Diseases," Int J Mol Sci., (2020); 21(12):4223, 26 pages.
Hoffman, H.M. et al. "Familial cold autoinflammatory syndrome: phenotype and genotype of an autosomal dominant periodic fever", Journal of Allergy and Clinical Immunology, (2001); 108(4):615-620.
Ising et al. "NLRP3 inflammasome activation drives tau pathology", Nature, (2019); 575:669-673 (24 pages).
Mangan, M.S.J., et al.; "Targeting the NLRP3 inflammasome in inflammatory diseases," Nat Rev Drug Discov., (2018); 17(8):588-606.
Matthews, C. P. et al., "Dominant-Negative Activator Protein 1 (TAM67) Targets Cyclooxygenase-2 and Osteopontin under Conditions in Which it Specifically Inhibits Tumorigenesis," Cancer Res., 2007, vol. 67. No. 6, pp. 2430-2438.
Moossavi, M., et al.; "Role of the NLRP3 inflammasome in cancer," Mol. Cancer (2018); 17(1):158, 13 pages.
Rheinheimer, J., et al.; "Current role of the NLRP3 inflammasome on obesity and insulin resistance: A systematic review," Metabolism (2017); 74, pp. 1-9.
Shahbaz, S.K., et al.; "Inflammasomes and Colorectal Cancer," Cells (2021); 10(9):2172, 22 pages.
Shen et al. "NLRP3: A promising therapeutic target for autoimmune diseases", Autoimmunity Reviews, (2018); 17(7):694-702.
Stancu et al. "Aggregated Tau activates NLRP3-ASC inflammasome exacerbating exogenously seeded and non-exogenously seeded Tau pathology in vivo", Acta Neuropathologica, (2019); 137:599-617.
Thi et al. "Inflammasome as a therapeutic target for cancer prevention and treatment", Journal of Cancer Prevention, (2017); 22(2):62-73.
Wang, H., et al.; "NLRP3 promotes tumor growth and metastasis in human oral squamous cell carcinoma," BMC Cancer (2018); 18(1):500, 10 pages.
Yu, L., et al.; "The NLRP3 Inflammasome in Non-Alcoholic Fatty Liver Disease and Steatohepatitis: Therapeutic Targets and Treatment," Front Pharmacol., (2022); 13:780496, 19 pages.
Zhang, W-J., et al.; "Inflammasomes and Fibrosis," Front Immunol., (2021); 12:643149, 13 pages.
Zhen, Y., et al., "NLRP3 Inflammasome and Inflammatory Bowel Disease, " Front Immunol., (2019); 10:276, 10 pages.

* cited by examiner

SULPHONYL UREA DERIVATIVES AS NLRP3 INFLAMMASOME MODULATORS

RELATED APPLICATION

This application is a continuation of U.S. patent application Ser. No. 16/955,284, filed Jun. 18, 2020, now U.S. Pat. No. 11,518,757, which is a U.S. National Phase application, filed under 35 U.S.C. § 371, of International Application No. PCT/EP2018/085511, filed Dec. 18, 2018, which claims priority to United Kingdom Patent Application No. 1721185.5, filed Dec. 18, 2017, the entire contents of each of which are incorporated herein by reference in their entireties.

FIELD OF THE DISCLOSURE

The present disclosure concerns sulphonyl urea derivatives, prodrugs, and pharmaceutically acceptable salts thereof, which may possess inflammasome inhibitory activity and are accordingly useful in methods of treatment of the human or animal body. The present disclosure also relates to processes for the preparation of these compounds, to pharmaceutical compositions comprising them and to their use in the treatment of disorders in which inflammasome activity is implicated, such as inflammatory, autoinflammatory and autoimmune and oncological diseases.

BACKGROUND

Autoimmune diseases are associated with the overproduction of pro-inflammatory factors. One of them is interleukin-1 (IL-1), produced by activated macrophages, monocytes, fibroblasts, and other components of the innate immune system like dendritic cells. IL-1 is involved in a variety of cellular activities, including cell proliferation, differentiation and apoptosis (Seth L. al. Rev. Immunol. 2009. 27:621-68).

In humans, 22 NLR proteins are divided into four NLR subfamilies according to their N-terminal domains. NLRA contains a CARD-AT domain, NLRB (NAIP) contains a BIR domain, NLRC (including NOD1 and NOD2) contains a CARD domain, and NLRP contains a pyrin domain. Multiple NLR family members are associated with inflammasome formation.

Although inflammasome activation appears to have evolved as an important component of host immunity to pathogens, the NLRP3 inflammasome is unique in its ability activate in response to endogenous sterile danger signals. Many such sterile signals have been elucidated, and their formation is associated with specific disease states. For example, uric acid crystals found in gout patients are effective triggers of NLRP3 activation. Similarly, cholesterol crystals found in atherosclerotic patients can also promote NLRP3 activation. Recognition of the role of sterile danger signals as NLRP3 activators led to IL-1 and IL-18 being implicated in a diverse range of pathophysiological indications including metabolic, physiologic, inflammatory, hematologic and immunologic disorders.

The disclosure arises from a need to provide further compounds for the specific modulation of NLRP3-dependent cellular processes. In particular, compounds with improved physicochemical, pharmacological and pharmaceutical properties to existing compounds are desirable.

SUMMARY

In some aspects, the present disclosure provides, inter alia, a compound of Formula (I):

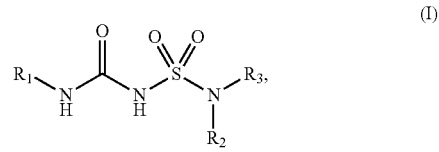

or a prodrug, solvate, or pharmaceutically acceptable salt thereof, wherein:
$R_1$ is $C_3$-$C_{16}$ cycloalkyl, or $C_5$-$C_{10}$ aryl, wherein the $C_3$-$C_8$ monocyclic cycloalkyl, polycyclic cycloalkyl, or $C_5$-$C_6$ aryl is optionally substituted by one or more $R_{1S}$; wherein each $R_{1S}$ is independently $C_1$-$C_6$ alkyl, $C_1$-$C_6$ haloalkyl, $C_1$-$C_6$ alkoxy, $C_1$-$C_6$ haloalkoxy, or halo;
$R_2$ is —$(CX_2X_2)_n$—$R_{2S}$, wherein n is 0, 1, or 2, and each $X_2$ is independently H, $C_1$-$C_6$ alkyl, $C_2$-$C_6$ alkenyl, or $C_2$-$C_6$ alkynyl, wherein the $C_1$-$C_6$ alkyl, $C_2$-$C_6$ alkenyl, or $C_2$-$C_6$ alkynyl is optionally substituted with one or more halo, —CN, —OH, —O($C_1$-$C_6$ alkyl), —NH$_2$, —NH($C_1$-$C_6$ alkyl), —N($C_1$-$C_6$ alkyl)$_2$, or oxo;
$R_{2S}$ is 4- to 8-membered heterocycloalkyl optionally substituted with one or more $C_1$-$C_6$ alkyl, $C_2$-$C_6$ alkenyl, $C_2$-$C_6$ alkynyl, $C_1$-$C_6$ haloalkyl, halo, —CN, —OH, —O($C_1$-$C_6$ alkyl), —NH$_2$, —NH($C_1$-$C_6$ alkyl), —N($C_1$-$C_6$ alkyl)$_2$, or oxo; and
$R_3$ is 7- to 12-membered heterocycloalkyl or 5- or 6-membered heteroaryl optionally substituted with one or more $R_{3S}$, wherein each $R_{3S}$ is independently $C_1$-$C_6$ alkyl, $C_1$-$C_6$ haloalkyl, $C_3$-$C_8$ cycloalkyl, halo, or $C_3$-$C_8$ heterocycloalkyl wherein the $C_1$-$C_6$ alkyl, $C_1$-$C_6$ haloalkyl, $C_3$-$C_8$ cycloalkyl, or $C_3$-$C_8$ heterocycloalkyl is optionally substituted with —O($C_1$-$C_6$ alkyl), —N($C_1$-$C_6$ alkyl)$_2$, halo, or —CN.

In some aspects, the present disclosure provides a compound obtainable by, or obtained by, a method for preparing a compound as described herein (e.g., a method comprising one or more steps described in Schemes 1-2).

In some aspects, the present disclosure provides a pharmaceutical composition comprising a compound of the present disclosure, or a pharmaceutically acceptable salt thereof, and a pharmaceutically acceptable diluent or carrier.

In some aspects, the present disclosure provides an intermediate as described herein, being suitable for use in a method for preparing a compound as described herein (e.g., the intermediate is selected from the intermediates described in Examples 1-166).

In some aspects, the present disclosure provides a method of inhibiting inflammasome (e.g., the NLRP3 inflammasome) activity (e.g., in vitro or in vivo), comprising contacting a cell with an effective amount of a compound of the present disclosure or a pharmaceutically acceptable salt thereof.

In some aspects, the present disclosure provides a method of treating or preventing a disease or disorder disclosed herein in a subject in need thereof, comprising administering to the subject a therapeutically effective amount of a compound of the present disclosure or a pharmaceutically acceptable salt thereof, or a pharmaceutical composition of the present disclosure.

In some aspects, the present disclosure provides a compound of the present disclosure or a pharmaceutically acceptable salt thereof for use in inhibiting inflammasome (e.g., the NLRP3 inflammasome) activity (e.g., in vitro or in vivo).

In some aspects, the present disclosure provides a compound of the present disclosure or a pharmaceutically acceptable salt thereof for use in treating or preventing a disease or disorder disclosed herein.

In some aspects, the present disclosure provides use of a compound of the present disclosure or a pharmaceutically acceptable salt thereof in the manufacture of a medicament for inhibiting inflammasome (e.g., the NLRP3 inflammasome) activity (e.g., in vitro or in vivo).

In some aspects, the present disclosure provides use of a compound of the present disclosure or a pharmaceutically acceptable salt thereof in the manufacture of a medicament for treating or preventing a disease or disorder disclosed herein.

In some aspects, the present disclosure provides a method of preparing a compound of the present disclosure.

In some aspects, the present disclosure provides a method of a compound, comprising one or more steps described herein.

Unless otherwise defined, all technical and scientific terms used herein have the same meaning as commonly understood by one of ordinary skill in the art to which this disclosure belongs. In the specification, the singular forms also include the plural unless the context clearly dictates otherwise. Although methods and materials similar or equivalent to those described herein can be used in the practice or testing of the present disclosure, suitable methods and materials are described below. All publications, patent applications, patents and other references mentioned herein are incorporated by reference. The references cited herein are not admitted to be prior art to the claimed invention. In the case of conflict, the present specification, including definitions, will control. In addition, the materials, methods and examples are illustrative only and are not intended to be limiting. In the case of conflict between the chemical structures and names of the compounds disclosed herein, the chemical structures will control.

Other features and advantages of the disclosure will be apparent from the following detailed description and claims.

DETAILED DESCRIPTION

Autoimmune diseases are associated with the overproduction of proinflammatory factors. One of them is interleukin-1 (IL-1), produced by activated macrophages, monocytes, fibroblasts, and other components of the innate immune system like dendritic cells, involved in a variety of cellular activities, including cell proliferation, differentiation and apoptosis (Seth L. al. Rev. Immunol. 2009. 27:621-68).

Autoimmune diseases are associated with the overproduction of proinflammatory factors. One of them is interleukin-1 (IL-1), produced by activated macrophages, monocytes, fibroblasts, and other components of the innate immune system like dendritic cells, involved in a variety of cellular activities, including cell proliferation, differentiation and apoptosis (Seth L. al. Rev. Immunol. 2009. 27:621-68).

Cytokines from the IL-1 family are highly active and, as important mediators of inflammation, primarily associated with acute and chronic inflammation (Sims J. et al. Nature Reviews Immunology 10, 89-102 (February 2010)). The overproduction of IL-1 is considered to be a mediator of some autoimmune and autoinflammatory diseases. Autoinflammatory diseases are characterised by recurrent and unprovoked inflammation in the absence of autoantibodies, infection, or antigen-specific T lymphocytes.

Proinflammatory cytokines of the IL-1 superfamily include IL-1a, IL-1β, IL-18, and IL-36α, β, λ and are produced in response to pathogens and other cellular stressors as part of a host innate immune response. Unlike many other secreted cytokines, which are processed and released via the standard cellular secretory apparatus consisting of the endoplasmic reticulum and Golgi apparatus, IL-1 family members lack leader sequences required for endoplasmic reticulum entry and thus are retained intracellularly following translation. In addition, IL-1β, IL-18, and IL-36α, β, λ are synthesised as procytokines that require proteolytic activation to become optimal ligands for binding to their cognate receptors on target cells.

In the case of IL-1α, IL-1β and IL-18, it is now appreciated that a multimeric protein complex known as an inflammasome is responsible for activating the proforms of IL-1β and IL-18 and for release of these cytokines extracellularly. An inflammasome complex typically consists of a sensor molecule, such as an NLR (Nucleotide-Oligerimisation Domain (NOD)-like receptor), an adaptor molecule ASC (Apoptosis-associated speck-like protein containing a CARD (Caspase Recruitment Domain)) and procaspase-1. In response to a variety of "danger signals", including pathogen-associated molecule patterns (PAMPs) and danger associated molecular patterns (DAMPs), subunits of an inflammasome oligomerise to form a supramolecular structure within the cell. PAMPs include molecules such as peptidoglycan, viral DNA or RNA and bacterial DNA or RNA. DAMPs, on the other hand, consist of a wide range of endogenous or exogenous sterile triggers including monosodium urate crystals, silica, alum, asbestos, fatty acids, ceramides, cholesterol crystals and aggregates of beta-amyloid peptide. Assembly of an inflammasome platform facilitates autocatalysis of procaspase-1 yielding a highly active cysteine protease responsible for activation and release of pro-IL-1β and pro-IL-18. Thus, release of these highly inflammatory cytokines is achieved only in response to inflammasome sensors detecting and responding to specific molecular danger signals.

In humans, 22 NLR proteins are divided into four NLR subfamilies according to their N-terminal domains. NLRA contains a CARD-AT domain, NLRB (NAIP) contains a BIR domain, NLRC (including NOD1 and NOD2) contains a CARD domain, and NLRP contains a pyrin domain. Multiple NLR family members are associated with inflammasome formation including NLRP1, NLRP3, NLRP6, NLRP7, NLRP12 and NLRC4 (IPAF).

Two other structurally distinct inflammasome structures containing a PYHIN domain (pyrin and HIN domain containing protein) namely Absent in Melanoma 2 (AIM2) and IFNλ-inducible protein 16 (IFI16) (Latz et al., Nat Rev Immunol 2013 13 (6) 397-311) serve as intracellular DNA sensors. Pyrin (encoded by the MEFV gene) represents another type of inflammasome platform associated with proIL-1β activation (Chae et al., Immunity 34, 755-768, 2011).

Requiring assembly of an inflammasome platform to achieve activation and release of IL-1β and IL-18 from monocytes and macrophages ensures their production is carefully orchestrated via a 2-step process. First, the cell must encounter a priming ligand (such as the TLR4 receptor ligand LPS, or an inflammatory cytokine such as TNFα) which leads to NFkB dependent transcription of NLRP3, pro-IL-1β and pro-IL-18. The newly translated procytokines remain intracellular and inactive unless producing cells encounter a second signal leading to activation of an inflammasome scaffold and maturation of procaspase-1.

In addition to proteolytic activation of pro-IL-1β and pro-IL-18, active caspase-1 also triggers a form of inflammatory cell death known as pyroptosis through cleavage of gasdermin-D. Pyroptosis allows the mature forms of IL-1β and IL-18 to be externalised along with release of alarmin molecules (compounds that promote inflammation and activate innate and adaptive immunity) such as high mobility group box 1 protein (HMGB1), IL-33, and IL-1α.

Although inflammasome activation appears to have evolved as an important component of host immunity to pathogens, the NLRP3 inflammasome is unique in its ability activate in response to endogenous and exogenous sterile danger signals. Many such sterile signals have been elucidated, and their formation is associated with specific disease states. For example, uric acid crystals found in gout patients are effective triggers of NLRP3 activation. Similarly, cholesterol crystals found in atherosclerotic patients can also promote NLRP3 activation. Recognition of the role of sterile danger signals as NLRP3 activators led to IL-1β and IL-18 being implicated in a diverse range of pathophysiological indications including metabolic, physiologic, inflammatory, hematologic and immunologic disorders.

A link to human disease is best exemplified by discovery that mutations in the NLRP3 gene which lead to gain-of-function confer a range of autoinflammatory conditions collectively known as cryopyrin-associated periodic syndromes (CAPS) including familial cold autoinflammatory syndrome (FCAS), Muckle-Wells syndrome (MWS) and Neonatal onset multisystem inflammatory disease (NOMID) (Hoffman et al., Nat Genet. 29 (3) (2001) 301-305). Likewise, sterile mediator-induced activation of NLRP3 has been implicated in a wide range of disorders including joint degeneration (gout, rheumatoid arthritis, osteoarthritis), cardiometabolic (type 2 diabetes, atherosclerosis, hypertension), Central Nervous System (Alzheimer's Disease, Parkinson's disease, multiple sclerosis), gastrointestinal (Crohn's disease, ulcerative colitis), lung (chronic obstructive pulmonary disease (COPD), asthma, idiopathic pulmonary fibrosis) and liver (fibrosis, non-alcoholic fatty liver disease, non-alcoholic steatohepatitis (NASH)). It is further believed that NLRP3 activation promotes kidney inflammation and thus contributes to chronic kidney disease (CKD).

Current treatment options for diseases where IL-1 is implicated as a contributor to pathogenesis include the IL-1 receptor antagonist anakinra, an Fc-containing fusion construct of the extracellular domains of the IL-1 receptor and IL-1 receptor accessory protein (rilonacept) and the anti-IL-1β monoclonal antibody canakinumab. For example, canakinumab is licensed for CAPS, Tumor Necrosis Factor Receptor Associated Periodic Syndrome (TRAPS), Hyper-immunoglobulin D Syndrome (HIDS)/Mevalonate Kinase Deficiency (MKD), Familial Mediterranean Fever (FMF) and gout.

Some small molecules have been reported to inhibit function of the NLRP3 inflammasome. Glyburide, for example, is a specific inhibitor of NLRP3 activation, albeit at micromolar concentrations which are unlikely attainable in vivo. Non-specific agents such as parthenolide, Bay 11-7082, and 3,4-methylenedioxy-β-nitrostyrene are reported to impair NLRP3 activation but are expected to possess limited therapeutic utility due to their sharing of a common structural feature consisting of an olefin activated by substitution with an electron withdrawing group; this can lead to undesirable formation of covalent adducts with protein-bearing thiol groups. A number of natural products, for example p-hydroxybutyrate, sulforaphane, quercetin, and salvianolic acid, also are reported to suppress NLRP3 activation. Likewise, numerous effectors/modulators of other molecular targets have been reported to impair NLRP3 activation including agonists of the G-protein coupled receptor TGR5, an inhibitor of sodium-glucose co-transport epigliflozin, the dopamine receptor antagonist A-68930, the serotonin reuptake inhibitor fluoxetine, fenamate non-steroidal anti-inflammatory drugs, and the β-adrenergic receptor blocker nebivolol. Utility of these molecules as therapeutics for the chronic treatment of NLRP3-dependent inflammatory disorders remains to be established. A series of sulphonylurea-containing molecules was previously identified as potent and selective inhibitors of post-translational processing of pro-IL-1β (Perregaux et al., J Pharmacol. Exp. Ther. 299, 187-197, 2001). The exemplar molecule CP-456, 773 from this work was recently characterised as a specific inhibitor of NLRP3 activation (Coll et al., Nat Med 21.3 (2015): 248-255.).

The disclosure relates to compounds useful for the specific modulation of NLRP3-dependent cellular processes. In particular, compounds with improved physicochemical, pharmacological and pharmaceutical properties to existing NLRP3-modulating compounds are desired.

Definitions

Unless otherwise stated, the following terms used in the specification and claims have the following meanings set out below.

It is to be appreciated that references to "treating" or "treatment" include the alleviation of established symptoms of a condition. "Treating" or "treatment" of a state, disorder or condition therefore includes: (1) preventing or delaying the appearance of clinical symptoms of the state, disorder or condition developing in a human that may be afflicted with or predisposed to the state, disorder or condition but does not yet experience or display clinical or subclinical symptoms of the state, disorder or condition, (2) inhibiting the state, disorder or condition, i.e., arresting, reducing or delaying the development of the disease or a relapse thereof (in case of maintenance treatment) or at least one clinical or subclinical symptom thereof, or (3) relieving or attenuating the disease, i.e., causing regression of the state, disorder or condition or at least one of its clinical or subclinical symptoms.

A "therapeutically effective amount" means the amount of a compound that, when administered to a mammal for treating a disease, is sufficient to effect such treatment for the disease. The "therapeutically effective amount" will vary depending on the compound, the disease and its severity and the age, weight, etc., of the mammal to be treated.

As used herein, "alkyl", "$C_1$, $C_2$, $C_3$, $C_4$, $C_5$ or $C_6$ alkyl" or "$C_1$-$C_6$ alkyl" is intended to include $C_1$, $C_2$, $C_3$, $C_4$, $C_5$ or $C_6$ straight chain (linear) saturated aliphatic hydrocarbon groups and $C_3$, $C_4$, $C_5$ or $C_6$ branched saturated aliphatic hydrocarbon groups. For example, $C_1$-$C_6$ alkyl is intends to include $C_1$, $C_2$, $C_3$, $C_4$, $C_5$ and $C_6$ alkyl groups. Examples of alkyl include, moieties having from one to six carbon atoms, such as, but not limited to, methyl, ethyl, n-propyl, i-propyl, n-butyl, s-butyl, t-butyl, n-pentyl, i-pentyl or n-hexyl. In some embodiments, a straight chain or branched alkyl has six or fewer carbon atoms (e.g., $C_1$-$C_6$ for straight chain, $C_3$-$C_6$ for branched chain), and in another embodiment, a straight chain or branched alkyl has four or fewer carbon atoms.

As used herein, the term "optionally substituted alkyl" refers to unsubstituted alkyl or alkyl having designated substituents replacing one or more hydrogen atoms on one or more carbons of the hydrocarbon backbone. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulphhydryl, alkylthio, arylthio, thiocarboxylate, sulphates, alkylsulphinyl, sulphonato, sulphamoyl, sulphonamido, nitro, trifluoromethyl, cyano, azido, heterocyclyl, alkylaryl, or an aromatic or heteroaromatic moiety.

As used herein, the term "alkenyl" includes unsaturated aliphatic groups analogous in length and possible substitution to the alkyls described above, but that contain at least one double bond. For example, the term "alkenyl" includes straight chain alkenyl groups (e.g., ethenyl, propenyl, butenyl, pentenyl, hexenyl, heptenyl, octenyl, nonenyl, decenyl), and branched alkenyl groups. In certain embodiments, a straight chain or branched alkenyl group has six or fewer carbon atoms in its backbone (e.g., $C_2$-$C_6$ for straight chain, $C_3$-$C_6$ for branched chain). The term "$C_2$-$C_6$" includes alkenyl groups containing two to six carbon atoms. The term "$C_3$-$C_6$" includes alkenyl groups containing three to six carbon atoms.

As used herein, the term "optionally substituted alkenyl" refers to unsubstituted alkenyl or alkenyl having designated substituents replacing one or more hydrogen atoms on one or more hydrocarbon backbone carbon atoms. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulphhydryl, alkylthio, arylthio, thiocarboxylate, sulphates, alkylsulphinyl, sulphonato, sulphamoyl, sulphonamido, nitro, trifluoromethyl, cyano, heterocyclyl, alkylaryl, or an aromatic or heteroaromatic moiety.

As used herein, the term "alkynyl" includes unsaturated aliphatic groups analogous in length and possible substitution to the alkyls described above, but which contain at least one triple bond. For example, "alkynyl" includes straight chain alkynyl groups (e.g., ethynyl, propynyl, butynyl, pentynyl, hexynyl, heptynyl, octynyl, nonynyl, decynyl), and branched alkynyl groups. In certain embodiments, a straight chain or branched alkynyl group has six or fewer carbon atoms in its backbone (e.g., $C_2$-$C_6$ for straight chain, $C_3$-$C_6$ for branched chain). The term "$C_2$-$C_6$" includes alkynyl groups containing two to six carbon atoms. The term "$C_3$-$C_6$" includes alkynyl groups containing three to six carbon atoms. As used herein, "$C_2$-$C_6$ alkenylene linker" or "$C_2$-$C_6$ alkynylene linker" is intended to include $C_2$, $C_3$, $C_4$, $C_5$ or $C_6$ chain (linear or branched) divalent unsaturated aliphatic hydrocarbon groups. For example, $C_2$-$C_6$ alkenylene linker is intended to include $C_2$, $C_3$, $C_4$, $C_5$ and $C_6$ alkenylene linker groups.

As used herein, the term "optionally substituted alkynyl" refers to unsubstituted alkynyl or alkynyl having designated substituents replacing one or more hydrogen atoms on one or more hydrocarbon backbone carbon atoms. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulphhydryl, alkylthio, arylthio, thiocarboxylate, sulphates, alkylsulphinyl, sulphonato, sulphamoyl, sulphonamido, nitro, trifluoromethyl, cyano, azido, heterocyclyl, alkylaryl, or an aromatic or heteroaromatic moiety.

Other optionally substituted moieties (such as optionally substituted cycloalkyl, heterocycloalkyl, aryl, or heteroaryl) include both the unsubstituted moieties and the moieties having one or more of the designated substituents. For example, substituted heterocycloalkyl includes those substituted with one or more alkyl groups, such as 2,2,6,6-tetramethyl-piperidinyl and 2,2,6,6-tetramethyl-1,2,3,6-tetrahydropyridinyl.

As used herein, the term "cycloalkyl" refers to a saturated or partially unsaturated hydrocarbon monocyclic or polycyclic (e.g., fused, bridged, or spiro rings) system having 3 to 30 carbon atoms (e.g., $C_3$-$C_{12}$, $C_3$-$C_{10}$, or $C_3$-$C_8$). Examples of cycloalkyl include, but are not limited to, cyclopropyl, cyclobutyl, cyclopentyl, cyclohexyl, cycloheptyl, cyclooctyl, cyclopentenyl, cyclohexenyl, cycloheptenyl, 1,2,3,4-tetrahydronaphthalenyl, and adamantyl. In the case of polycyclic cycloalkyl, only one of the rings in the cycloalkyl needs to be non-aromatic. In some embodiments, the cycloalkyl is hexahydroindacenyl. In some embodiments, the cycloalkyl is

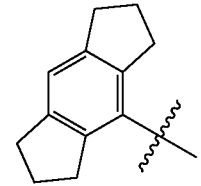

As used herein, the term "heterocycloalkyl" refers to a saturated or partially unsaturated 3-8 membered monocyclic, 7-12 membered bicyclic (fused, bridged, or spiro rings), or 11-14 membered tricyclic ring system (fused, bridged, or spiro rings) having one or more heteroatoms (such as O, N, S, P, or Se), e.g., 1 or 1-2 or 1-3 or 1-4 or 1-5 or 1-6 heteroatoms, or e.g., 1, 2, 3, 4, 5, or 6 heteroatoms, independently selected from the group consisting of nitrogen, oxygen and sulphur, unless specified otherwise. Examples of heterocycloalkyl groups include, but are not limited to, piperidinyl, piperazinyl, pyrrolidinyl, dioxanyl, tetrahydrofuranyl, isoindolinyl, indolinyl, imidazolidinyl, pyrazolidinyl, oxazolidinyl, isoxazolidinyl, triazolidinyl, oxiranyl, azetidinyl, oxetanyl, thietanyl, 1,2,3,6-tetrahydropyridinyl, tetrahydropyranyl, dihydropyranyl, pyranyl, morpholinyl, tetrahydrothiopyranyl, 1,4-diazepanyl, 1,4-oxazepanyl, 2-oxa-5-azabicyclo[2.2.1]heptanyl, 2,5-diazabicyclo[2.2.1]heptanyl, 2-oxa-6-azaspiro[3.3]heptanyl, 2,6-diazaspiro[3.3]heptanyl, 1,4-dioxa-8-azaspiro[4.5]decanyl, 1,4-dioxaspiro[4.5]decanyl, 1-oxaspiro[4.5]decanyl, 1-azaspiro[4.5]decanyl, 3'H-spiro[cyclohexane-1,1'-isobenzofuran]-yl, 7'H-spiro[cyclohexane-1,5'-furo[3,4-b]pyridin]-yl, 3'H-spiro[cyclohexane-1,1'-furo[3,4-c]pyridin]-yl, 3-azabicyclo[3.1.0]hexanyl, 3-azabicyclo[3.1.0]hexan-3-yl, 1,4,5,6-tetrahydropyrrolo[3,4-c]pyrazolyl, 3,4,5,6,7,8-hexahydropyrido[4,3-d]pyrimidinyl, 4,5,6,7-tetrahydro-1H-pyrazolo[3,4-c]pyridinyl, 5,6,7,8-tetrahydropyrido[4,3-d]

pyrimidinyl, 2-azaspiro[3.3]heptanyl, 2-methyl-2-azaspiro [3.3]heptanyl, 2-azaspiro[3.5]nonanyl, 2-methyl-2-azaspiro [3.5]nonanyl, 2-azaspiro[4.5]decanyl, 2-methyl-2-azaspiro [4.5]decanyl, 2-oxa-azaspiro[3.4]octanyl, 2-oxa-azaspiro [3.4]octan-6-yl, and the like. In the case of multicyclic heterocycloalkyl, only one of the rings in the heterocycloalkyl needs to be non-aromatic (e.g., 4,5,6,7-tetrahydrobenzo [c]isoxazolyl).

As used herein, the term "aryl" includes groups with aromaticity, including "conjugated," or multicyclic systems with one or more aromatic rings and do not contain any heteroatom in the ring structure. The term aryl includes both monovalent species and divalent species. Examples of aryl groups include, but are not limited to, phenyl, biphenyl, naphthyl and the like. Conveniently, an aryl is phenyl.

As used herein, the term "heteroaryl" is intended to include a stable 5-, 6-, or 7-membered monocyclic or 7-, 8-, 9-, 10-, 11- or 12-membered bicyclic aromatic heterocyclic ring which consists of carbon atoms and one or more heteroatoms, e.g., 1 or 1-2 or 1-3 or 1-4 or 1-5 or 1-6 heteroatoms, or e.g., 1, 2, 3, 4, 5, or 6 heteroatoms, independently selected from the group consisting of nitrogen, oxygen and sulphur. The nitrogen atom may be substituted or unsubstituted (i.e., N or NR wherein R is H or other substituents, as defined). The nitrogen and sulphur heteroatoms may optionally be oxidised (i.e., N→O and $S(O)_p$, where p=1 or 2). It is to be noted that total number of S and O atoms in the aromatic heterocycle is not more than 1. Examples of heteroaryl groups include pyrrole, furan, thiophene, thiazole, isothiazole, imidazole, triazole, tetrazole, pyrazole, oxazole, isoxazole, pyridine, pyrazine, pyridazine, pyrimidine, and the like. Heteroaryl groups can also be fused or bridged with alicyclic or heterocyclic rings, which are not aromatic so as to form a multicyclic system (e.g., 4,5,6,7-tetrahydrobenzo[c]isoxazolyl).

Furthermore, the terms "aryl" and "heteroaryl" include multicyclic aryl and heteroaryl groups, e.g., tricyclic, bicyclic, e.g., naphthalene, benzoxazole, benzodioxazole, benzothiazole, benzoimidazole, benzothiophene, quinoline, isoquinoline, naphthrydine, indole, benzofuran, purine, benzofuran, deazapurine, indolizine.

The cycloalkyl, heterocycloalkyl, aryl, or heteroaryl ring can be substituted at one or more ring positions (e.g., the ring-forming carbon or heteroatom such as N) with such substituents as described above, for example, alkyl, alkenyl, alkynyl, halogen, hydroxyl, alkoxy, alkylcarbonyloxy, arylcarbonyloxy, alkoxycarbonyloxy, aryloxycarbonyloxy, carboxylate, alkylcarbonyl, alkylaminocarbonyl, aralkylaminocarbonyl, alkenylaminocarbonyl, alkylcarbonyl, arylcarbonyl, aralkylcarbonyl, alkenylcarbonyl, alkoxycarbonyl, aminocarbonyl, alkylthiocarbonyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulphhydryl, alkylthio, arylthio, thiocarboxylate, sulphates, alkylsulphinyl, sulphonato, sulphamoyl, sulphonamido, nitro, trifluoromethyl, cyano, azido, heterocyclyl, alkylaryl, or an aromatic or heteroaromatic moiety. Aryl and heteroaryl groups can also be fused or bridged with alicyclic or heterocyclic rings, which are not aromatic so as to form a multicyclic system (e.g., tetralin, methylenedioxyphenyl such as benzo[d][1,3]dioxole-5-yl).

As used herein, the term "substituted," means that any one or more hydrogen atoms on the designated atom is replaced with a selection from the indicated groups, provided that the designated atom's normal valency is not exceeded, and that the substitution results in a stable compound. When a substituent is oxo or keto (i.e., =O), then 2 hydrogen atoms on the atom are replaced. Keto substituents are not present on aromatic moieties. Ring double bonds, as used herein, are double bonds that are formed between two adjacent ring atoms (e.g., C=C, C=N or N=N). "Stable compound" and "stable structure" are meant to indicate a compound that is sufficiently robust to survive isolation to a useful degree of purity from a reaction mixture, and formulation into an efficacious therapeutic agent.

When a bond to a substituent is shown to cross a bond connecting two atoms in a ring, then such substituent may be bonded to any atom in the ring. When a substituent is listed without indicating the atom via which such substituent is bonded to the rest of the compound of a given formula, then such substituent may be bonded via any atom in such formula. Combinations of substituents and/or variables are permissible, but only if such combinations result in stable compounds.

When any variable (e.g., R) occurs more than one time in any constituent or formula for a compound, its definition at each occurrence is independent of its definition at every other occurrence. Thus, for example, if a group is shown to be substituted with 0-2 R moieties, then the group may optionally be substituted with up to two R moieties and R at each occurrence is selected independently from the definition of R. Also, combinations of substituents and/or variables are permissible, but only if such combinations result in stable compounds.

As used herein, the term "hydroxy" or "hydroxyl" includes groups with an —OH or —O⁻.

As used herein, the term "halo" or "halogen" refers to fluoro, chloro, bromo and iodo.

The term "haloalkyl" or "haloalkoxyl" refers to an alkyl or alkoxyl substituted with one or more halogen atoms.

As used herein, the term "optionally substituted haloalkyl" refers to unsubstituted haloalkyl having designated substituents replacing one or more hydrogen atoms on one or more hydrocarbon backbone carbon atoms. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulphhydryl, alkylthio, arylthio, thiocarboxylate, sulphates, alkylsulphinyl, sulphonato, sulphamoyl, sulphonamido, nitro, trifluoromethyl, cyano, azido, heterocyclyl, alkylaryl, or an aromatic or heteroaromatic moiety.

As used herein, the term "alkoxy" or "alkoxyl" includes substituted and unsubstituted alkyl, alkenyl and alkynyl groups covalently linked to an oxygen atom. Examples of alkoxy groups or alkoxyl radicals include, but are not limited to, methoxy, ethoxy, isopropyloxy, propoxy, butoxy and pentoxy groups. Examples of substituted alkoxy groups include halogenated alkoxy groups. The alkoxy groups can be substituted with groups such as alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino, and alkylarylamino), acylamino (including alkylcarbonylamino, arylcarbonylamino, carbamoyl and ureido), amidino, imino, sulphhydryl, alkylthio, arylthio, thiocarboxylate, sulphates, alkylsulphinyl, sulphonato, sulphamoyl, sulphonamido, nitro, trifluoromethyl, cyano, azido, heterocyclyl, alkylaryl, or an aromatic or heteroaromatic moieties. Examples of halogen substituted alkoxy groups include, but are not limited to, fluoromethoxy, difluoromethoxy, trifluoromethoxy, chloromethoxy, dichloromethoxy and trichloromethoxy.

As used herein, the expressions "one or more of A, B, or C," "one or more A, B, or C," "one or more of A, B, and C," "one or more A, B, and C," "selected from the group consisting of A, B, and C", "selected from A, B, and C", and the like are used interchangeably and all refer to a selection from a group consisting of A, B, and/or C, i.e., one or more As, one or more Bs, one or more Cs, or any combination thereof, unless indicated otherwise.

It is to be understood that the present disclosure provides methods for the synthesis of the compounds of any of the Formulae described herein. The present disclosure also provides detailed methods for the synthesis of various disclosed compounds of the present disclosure according to the following schemes as well as those shown in the Examples.

It is to be understood that, throughout the description, where compositions are described as having, including, or comprising specific components, it is contemplated that compositions also consist essentially of, or consist of, the recited components. Similarly, where methods or processes are described as having, including, or comprising specific process steps, the processes also consist essentially of, or consist of, the recited processing steps. Further, it should be understood that the order of steps or order for performing certain actions is immaterial so long as the invention remains operable. Moreover, two or more steps or actions can be conducted simultaneously.

It is to be understood that the synthetic processes of the disclosure can tolerate a wide variety of functional groups, therefore various substituted starting materials can be used. The processes generally provide the desired final compound at or near the end of the overall process, although it may be desirable in certain instances to further convert the compound to a pharmaceutically acceptable salt thereof.

It is to be understood that compounds of the present disclosure can be prepared in a variety of ways using commercially available starting materials, compounds known in the literature, or from readily prepared intermediates, by employing standard synthetic methods and procedures either known to those skilled in the art, or which will be apparent to the skilled artisan in light of the teachings herein. Standard synthetic methods and procedures for the preparation of organic molecules and functional group transformations and manipulations can be obtained from the relevant scientific literature or from standard textbooks in the field. Although not limited to any one or several sources, classic texts such as Smith, M. B., March, J., *March's Advanced Organic Chemistry*: Reactions, Mechanisms, and Structure, 5$^{th}$ edition, John Wiley & Sons: New York, 2001; Greene, T. W., Wuts, P. G. M., *Protective Groups in Organic Synthesis*, 3$^{rd}$ edition, John Wiley & Sons: New York, 1999; R. Larock, Comprehensive Organic Transformations, VCH Publishers (1989); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), incorporated by reference herein, are useful and recognised reference textbooks of organic synthesis known to those in the art One of ordinary skill in the art will note that, during the reaction sequences and synthetic schemes described herein, the order of certain steps may be changed, such as the introduction and removal of protecting groups. One of ordinary skill in the art will recognise that certain groups may require protection from the reaction conditions via the use of protecting groups. Protecting groups may also be used to differentiate similar functional groups in molecules. A list of protecting groups and how to introduce and remove these groups can be found in Greene, T. W., Wuts, P. G. M., *Protective Groups in Organic Synthesis*, 3$^{rd}$ edition, John Wiley & Sons: New York, 1999.

It is to be understood that, unless otherwise stated, any description of a method of treatment includes use of the compounds to provide such treatment or prophylaxis as is described herein, as well as use of the compounds to prepare a medicament to treat or prevent such condition. The treatment includes treatment of human or non-human animals including rodents and other disease models.

As used herein, the term "subject" is interchangeable with the term "subject in need thereof", both of which refer to a subject having a disease or having an increased risk of developing the disease. A "subject" includes a mammal. The mammal can be e.g., a human or appropriate non-human mammal, such as primate, mouse, rat, dog, cat, cow, horse, goat, camel, sheep or a pig. The subject can also be a bird or fowl. In one embodiment, the mammal is a human. A subject in need thereof can be one who has been previously diagnosed or identified as having a disease or disorder disclosed herein. A subject in need thereof can also be one who has (e.g., is suffering from a disease or disorder disclosed herein. Alternatively, a subject in need thereof can be one who has an increased risk of developing such disease or disorder relative to the population at large (i.e., a subject who is predisposed to developing such disorder relative to the population at large). A subject in need thereof can have a refractory or resistant a disease or disorder disclosed herein (i.e., a disease or disorder disclosed herein that doesn't respond or hasn't yet responded to treatment). The subject may be resistant at start of treatment or may become resistant during treatment. In some embodiments, the subject in need thereof received and failed all known effective therapies for a disease or disorder disclosed herein. In some embodiments, the subject in need thereof received at least one prior therapy.

As used herein, the term "treating" or "treat" describes the management and care of a patient for the purpose of combating a disease, condition, or disorder and includes the administration of a compound of the present disclosure, or a pharmaceutically acceptable salt, polymorph or solvate thereof, to alleviate the symptoms or complications of a disease, condition or disorder, or to eliminate the disease, condition or disorder. The term "treat" can also include treatment of a cell in vitro or an animal model.

It is to be understood that a compound of the present disclosure, or a pharmaceutically acceptable salt, polymorph or solvate thereof, can or may also be used to prevent a relevant disease, condition or disorder, or used to identify suitable candidates for such purposes.

As used herein, the term "preventing," "prevent," or "protecting against" describes reducing or eliminating the onset of the symptoms or complications of such disease, condition or disorder.

It is to be understood that one skilled in the art may refer to general reference texts for detailed descriptions of known techniques discussed herein or equivalent techniques. These texts include Ausubel et al., *Current Protocols in Molecular Biology*, John Wiley and Sons, Inc. (2005); Sambrook et al., *Molecular Cloning, A Laboratory Manual* (3$^{rd}$ edition), Cold Spring Harbor Press, Cold Spring Harbor, N.Y. (2000); Coligan et al., *Current Protocols in Immunology*, John Wiley & Sons, N.Y.; Enna et al., *Current Protocols in Pharmacology*, John Wiley & Sons, N.Y.; Fingl et al., *The Pharmacological Basis of Therapeutics* (1975), *Remington's Pharmaceutical Sciences*, Mack Publishing Co., Easton, PA, 18$^{th}$ edition (1990). These texts can, of course, also be referred to in making or using an aspect of the disclosure.

It is to be understood that the present disclosure also provides pharmaceutical compositions comprising any compound described herein in combination with at least one pharmaceutically acceptable excipient or carrier.

As used herein, the term "pharmaceutical composition" is a formulation containing the compounds of the present disclosure in a form suitable for administration to a subject. In one embodiment, the pharmaceutical composition is in bulk or in unit dosage form. The unit dosage form is any of a variety of forms, including, for example, a capsule, an IV bag, a tablet, a single pump on an aerosol inhaler or a vial. The quantity of active ingredient (e.g., a formulation of the disclosed compound or salt, hydrate, solvate or isomer thereof) in a unit dose of composition is an effective amount and is varied according to the particular treatment involved. One skilled in the art will appreciate that it is sometimes necessary to make routine variations to the dosage depending on the age and condition of the patient. The dosage will also depend on the route of administration. A variety of routes are contemplated, including oral, pulmonary, rectal, parenteral, transdermal, subcutaneous, intravenous, intramuscular, intraperitoneal, inhalational, buccal, sublingual, intrapleural, intrathecal, intranasal, and the like. Dosage forms for the topical or transdermal administration of a compound of this disclosure include powders, sprays, ointments, pastes, creams, lotions, gels, solutions, patches and inhalants. In one embodiment, the active compound is mixed under sterile conditions with a pharmaceutically acceptable carrier, and with any preservatives, buffers, or propellants that are required.

As used herein, the term "pharmaceutically acceptable" refers to those compounds, anions, cations, materials, compositions, carriers, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, the term "pharmaceutically acceptable excipient" means an excipient that is useful in preparing a pharmaceutical composition that is generally safe, non-toxic and neither biologically nor otherwise undesirable, and includes excipient that is acceptable for veterinary use as well as human pharmaceutical use. A "pharmaceutically acceptable excipient" as used in the specification and claims includes both one and more than one such excipient.

It is to be understood that a pharmaceutical composition of the disclosure is formulated to be compatible with its intended route of administration. Examples of routes of administration include parenteral, e.g., intravenous, intradermal, subcutaneous, oral (e.g., ingestion), inhalation, transdermal (topical), and transmucosal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulphite; chelating agents such as ethylenediaminetetraacetic acid; buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

It is to be understood that a compound or pharmaceutical composition of the disclosure can be administered to a subject in many of the well-known methods currently used for chemotherapeutic treatment. For example, a compound of the disclosure may be injected into the blood stream or body cavities or taken orally or applied through the skin with patches. The dose chosen should be sufficient to constitute effective treatment but not so high as to cause unacceptable side effects. The state of the disease condition (e.g., a disease or disorder disclosed herein) and the health of the patient should preferably be closely monitored during and for a reasonable period after treatment.

As used herein, the term "therapeutically effective amount", refers to an amount of a pharmaceutical agent to treat, ameliorate, or prevent an identified disease or condition, or to exhibit a detectable therapeutic or inhibitory effect. The effect can be detected by any assay method known in the art. The precise effective amount for a subject will depend upon the subject's body weight, size, and health; the nature and extent of the condition; and the therapeutic or combination of therapeutics selected for administration. Therapeutically effective amounts for a given situation can be determined by routine experimentation that is within the skill and judgment of the clinician.

It is to be understood that, for any compound, the therapeutically effective amount can be estimated initially either in cell culture assays, e.g., of neoplastic cells, or in animal models, usually rats, mice, rabbits, dogs, or pigs. The animal model may also be used to determine the appropriate concentration range and route of administration. Such information can then be used to determine useful doses and routes for administration in humans. Therapeutic/prophylactic efficacy and toxicity may be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between toxic and therapeutic effects is the therapeutic index, and it can be expressed as the ratio, $LD_{50}/ED_{50}$. Pharmaceutical compositions that exhibit large therapeutic indices are preferred. The dosage may vary within this range depending upon the dosage form employed, sensitivity of the patient, and the route of administration.

Dosage and administration are adjusted to provide sufficient levels of the active agent(s) or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

The pharmaceutical compositions containing active compounds of the present disclosure may be manufactured in a manner that is generally known, e.g., by means of conventional mixing, dissolving, granulating, dragee-making, levigating, emulsifying, encapsulating, entrapping, or lyophilising processes. Pharmaceutical compositions may be formulated in a conventional manner using one or more pharmaceutically acceptable carriers comprising excipients and/or auxiliaries that facilitate processing of the active compounds into preparations that can be used pharmaceutically. Of course, the appropriate formulation is dependent upon the route of administration chosen.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol and sorbitol, and sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilisation. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible pharmaceutically acceptable carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser, which contains a suitable propellant, e.g., a gas such as carbon dioxide, or a nebuliser.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The active compounds can be prepared with pharmaceutically acceptable carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the disclosure are dictated by and directly dependent on the unique characteristics of the active compound and the particular therapeutic effect to be achieved.

In therapeutic applications, the dosages of the pharmaceutical compositions used in accordance with the disclosure vary depending on the agent, the age, weight, and clinical condition of the recipient patient, and the experience and judgment of the clinician or practitioner administering the therapy, among other factors affecting the selected dosage. Generally, the dose should be sufficient to result in slowing, and preferably regressing, the symptoms of the disease or disorder disclosed herein and also preferably causing complete regression of the disease or disorder. Dosages can range from about 0.01 mg/kg per day to about 5000 mg/kg per day. In preferred aspects, dosages can range from about 1 mg/kg per day to about 1000 mg/kg per day. In an aspect, the dose will be in the range of about 0.1 mg/day to about 50 g/day; about 0.1 mg/day to about 25 g/day; about 0.1 mg/day to about 10 g/day; about 0.1 mg to about 3 g/day; or about 0.1 mg to about 1 g/day, in single, divided, or continuous doses (which dose may be adjusted for the patient's weight in kg, body surface area in m², and age in years). An effective amount of a pharmaceutical agent is that which provides an objectively identifiable improvement as noted by the clinician or other qualified observer. Improvement in survival and growth indicates regression. As used herein, the term "dosage effective manner" refers to amount of an active compound to produce the desired biological effect in a subject or cell.

It is to be understood that the pharmaceutical compositions can be included in a container, pack, or dispenser together with instructions for administration.

It is to be understood that, for the compounds of the present disclosure being capable of further forming salts, all of these forms are also contemplated within the scope of the claimed disclosure.

As used herein, the term "pharmaceutically acceptable salts" refer to derivatives of the compounds of the present disclosure wherein the parent compound is modified by making acid or base salts thereof. Examples of pharmaceutically acceptable salts include, but are not limited to, mineral or organic acid salts of basic residues such as amines, alkali or organic salts of acidic residues such as carboxylic acids, and the like. The pharmaceutically acceptable salts include the conventional non-toxic salts or the quaternary ammonium salts of the parent compound formed, for example, from non-toxic inorganic or organic acids. For example, such conventional non-toxic salts include, but are not limited to, those derived from inorganic and organic acids selected from 2-acetoxybenzoic, 2-hydroxyethane sulphonic, acetic, ascorbic, benzene sulphonic, benzoic, bicarbonic, carbonic, citric, edetic, ethane disulphonic, 1,2-ethane sulphonic, fumaric, glucoheptonic, gluconic, glutamic, glycolic, glycollyarsanilic, hexylresorcinic, hydrabamic, hydrobromic, hydrochloric, hydroiodic, hydroxymaleic, hydroxynaphthoic, isethionic, lactic, lactobionic, lauryl sulphonic, maleic, malic, mandelic, methane sulphonic, napsylic, nitric, oxalic, pamoic, pantothenic, phenylacetic, phosphoric, polygalacturonic, propionic, salicylic, stearic, subacetic, succinic, sulphamic, sulphanilic, sulphuric, tannic, tartaric, toluene sulphonic, and the commonly occurring amine acids, e.g., glycine, alanine, phenylalanine, arginine, etc.

In some embodiments, the pharmaceutically acceptable salt is a sodium salt, a potassium salt, a calcium salt, a magnesium salt, a diethylamine salt, a choline salt, a meglumine salt, a benzathine salt, a tromethamine salt, an ammonia salt, an arginine salt, or a lysine salt.

Other examples of pharmaceutically acceptable salts include hexanoic acid, cyclopentane propionic acid, pyruvic acid, malonic acid, 3-(4-hydroxybenzoyl)benzoic acid, cinnamic acid, 4-chlorobenzenesulphonic acid, 2-naphthalenesulphonic acid, 4-toluenesulphonic acid, camphorsulphonic acid, 4-methylbicyclo-[2.2.2]-oct-2-ene-1-carboxylic acid, 3-phenylpropionic acid, trimethylacetic acid, tertiary butylacetic acid, muconic acid, and the like. The present disclosure also encompasses salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like. In the salt form, it is understood that the ratio of the compound to the cation or anion of the salt can be 1:1, or any ratio other than 1:1, e.g., 3:1, 2:1, 1:2, or 1:3.

It is to be understood that all references to pharmaceutically acceptable salts include solvent addition forms (solvates) or crystal forms (polymorphs) as defined herein, of the same salt.

The compounds, or pharmaceutically acceptable salts thereof, are administered orally, nasally, transdermally, pulmonary, inhalationally, buccally, sublingually, intraperitoneally, subcutaneously, intramuscularly, intravenously, rectally, intrapleurally, intrathecally and parenterally. In one embodiment, the compound is administered orally. One skilled in the art will recognise the advantages of certain routes of administration.

The dosage regimen utilising the compounds is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter, or arrest the progress of the condition.

Techniques for formulation and administration of the disclosed compounds of the disclosure can be found in *Remington: the Science* and Practice ofPharmacy, $19^h$ edition, Mack Publishing Co., Easton, PA (1995). In an embodiment, the compounds described herein, and the pharmaceutically acceptable salts thereof, are used in pharmaceutical preparations in combination with a pharmaceutically acceptable carrier or diluent. Suitable pharmaceutically acceptable carriers include inert solid fillers or diluents and sterile aqueous or organic solutions. The compounds will be present in such pharmaceutical compositions in amounts sufficient to provide the desired dosage amount in the range described herein.

All percentages and ratios used herein, unless otherwise indicated, are by weight. Other features and advantages of the present disclosure are apparent from the different examples. The provided examples illustrate different components and methodology useful in practicing the present disclosure. The examples do not limit the claimed disclosure. Based on the present disclosure the skilled artisan can identify and employ other components and methodology useful for practicing the present disclosure.

In the synthetic schemes described herein, compounds may be drawn with one particular configuration for simplicity. Such particular configurations are not to be construed as limiting the disclosure to one or another isomer, tautomer, regioisomer or stereoisomer, nor does it exclude mixtures of isomers, tautomers, regioisomers or stereoisomers; however, it will be understood that a given isomer, tautomer, regioisomer or stereoisomer may have a higher level of activity than another isomer, tautomer, regioisomer or stereoisomer.

All publications and patent documents cited herein are incorporated herein by reference as if each such publication or document was specifically and individually indicated to be incorporated herein by reference. Citation of publications and patent documents is not intended as an admission that any is pertinent prior art, nor does it constitute any admission as to the contents or date of the same. The invention having now been described by way of written description, those of skill in the art will recognize that the invention can be practiced in a variety of embodiments and that the foregoing description and examples below are for purposes of illustration and not limitation of the claims that follow.

As use herein, the phrase "compound of the disclosure" refers to those compounds which are disclosed herein, both generically and specifically.

Compounds of the Present Disclosure

In some aspects, the present disclosure relates to a compound of Formula (I):

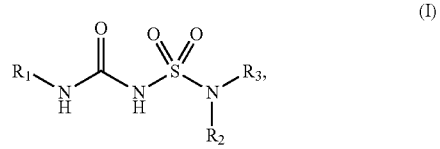

or a prodrug, solvate, or pharmaceutically acceptable salt thereof, wherein:

- $R_1$ is $C_3$-$C_{16}$ cycloalkyl, or $C_5$-$C_{10}$ aryl, wherein the $C_3$-$C_8$ monocyclic cycloalkyl, polycyclic cycloalkyl, or $C_5$-$C_6$ aryl is optionally substituted by one or more $R_{1S}$; wherein each $R_{1S}$ is independently $C_1$-$C_6$ alkyl, $C_1$-$C_6$ haloalkyl, $C_1$-$C_6$ alkoxy, $C_1$-$C_6$ haloalkoxy, or halo;
- $R_2$ is —$(CX_2X_2)_n$—$R_{2S}$, wherein n is 0, 1, or 2, and each $X_2$ is independently H, $C_1$-$C_6$ alkyl, $C_2$-$C_6$ alkenyl, or $C_2$-$C_6$ alkynyl, wherein the $C_1$-$C_6$ alkyl, $C_2$-$C_6$ alkenyl, or $C_2$-$C_6$ alkynyl is optionally substituted with one or more halo, —CN, —OH, —O($C_1$-$C_6$ alkyl), —NH$_2$, —NH($C_1$-$C_6$ alkyl), —N($C_1$-$C_6$ alkyl)$_2$, or oxo;
- $R_{2S}$ is 4- to 8-membered heterocycloalkyl optionally substituted with one or more $C_1$-$C_6$ alkyl, $C_2$-$C_6$ alkenyl, $C_2$-$C_6$ alkynyl, $C_1$-$C_6$ haloalkyl, halo, —CN, —OH, —O($C_1$-$C_6$ alkyl), —NH$_2$, —NH($C_1$-$C_6$ alkyl), —N($C_1$-$C_6$ alkyl)$_2$, or oxo; and
- $R_3$ is 7- to 12-membered heterocycloalkyl or 5- or 6-membered heteroaryl optionally substituted with one or more $R_{3S}$, wherein each $R_{3S}$ is independently $C_1$-$C_6$ alkyl, $C_1$-$C_6$ haloalkyl, $C_3$-$C_8$ cycloalkyl, halo, or $C_3$-$C_8$ heterocycloalkyl wherein the $C_1$-$C_6$ alkyl, $C_1$-$C_6$ haloalkyl, $C_3$-$C_8$ cycloalkyl, or $C_3$-$C_8$ heterocycloalkyl is optionally substituted with —O($C_1$-$C_6$ alkyl), —N($C_1$-$C_6$ alkyl)$_2$, halo, or —CN.

It is understood that, for a compound of Formula (I), $R_1$, $R_{1S}$, $R_2$, $R_{2S}$, $R_3$, and $R_{3S}$ can each be, where applicable, selected from the groups described herein, and any group described herein for any of $R_1$, $R_{1S}$, $R_2$, $R_{2S}$, $R_3$, and $R_{3S}$ can be combined, where applicable, with any group described herein for one or more of the remainder of $R_1$, $R_{1S}$, $R_2$, $R_{2S}$, $R_3$, and $R_{3S}$.

In some embodiments, $R_1$ is $C_3$-$C_{16}$ cycloalkyl, or $C_5$-$C_{10}$ aryl, wherein the $C_3$-$C_8$ monocyclic cycloalkyl, or $C_5$-$C_{16}$ polycyclic cycloalkyl, is optionally substituted by one or more $R_{1S}$ In some embodiments, $R_1$ is $C_3$-$C_7$ monocyclic cycloalkyl, $C_5$-$C_{16}$ polycyclic cycloalkyl, or $C_5$-$C_{10}$ aryl, wherein the $C_3$-$C_8$ monocyclic cycloalkyl, or $C_5$-$C_{16}$ polycyclic cycloalkyl, is optionally substituted by one or more $R_{1S}$.

In some embodiments, $R_1$ is $C_3$-$C_7$ monocyclic cycloalkyl, $C_9$-$C_{10}$ bicyclic cycloalkyl, $C_{12}$-$C_{16}$ tricyclic cycloalkyl, or $C_5$-$C_{10}$ aryl, wherein the $C_3$-$C_7$ monocyclic cycloalkyl, $C_9$-$C_{10}$ bicyclic cycloalkyl, or $C_{12}$-$C_{16}$ tricyclic cycloalkyl, is optionally substituted by one or more $R_{1S}$.

In some embodiments, $R_1$ is $C_3$-$C_7$ monocyclic cycloalkyl, polycyclic cycloalkyl, or $C_5$-$C_{10}$ aryl, wherein the $C_3$-$C_7$ monocyclic cycloalkyl, polycyclic cycloalkyl, or $C_5$-$C_6$ aryl is optionally substituted by one or more $R_{1S}$.

In some embodiments, $R_1$ is $C_3$-$C_7$ monocyclic cycloalkyl, $C_5$-$C_{16}$ polycyclic cycloalkyl, or $C_5$-$C_{10}$ aryl, wherein the $C_3$-$C_7$ monocyclic cycloalkyl, $C_5$-$C_{16}$ polycyclic cycloalkyl, or $C_5$-$C_6$ aryl is optionally substituted by one or more $R_{1S}$.

In some embodiments, $R_1$ is $C_3$-$C_7$ monocyclic cycloalkyl, $C_9$-$C_{10}$ bicyclic cycloalkyl, $C_{12}$-$C_{16}$ tricyclic cycloalkyl, or $C_5$-$C_{10}$ aryl, wherein the $C_3$-$C_7$ monocyclic cycloalkyl, $C_9$-$C_{10}$ bicyclic cycloalkyl, $C_{12}$-$C_{16}$ tricyclic cycloalkyl, or $C_5$-$C_{10}$ aryl, is optionally substituted by one or more $R_{1S}$.

In some embodiments, $R_1$ is $C_3$-$C_7$ monocyclic cycloalkyl optionally substituted by one or more $R_{1S}$.

In some embodiments, $R_1$ is $C_3$-$C_7$ monocyclic saturated cycloalkyl optionally substituted by one or more $R_{1S}$.

In some embodiments, $R_1$ is $C_3$-$C_7$ monocyclic partially saturated cycloalkyl optionally substituted by one or more $R_{1S}$.

In some embodiments, $R_1$ is $C_9$-$C_{10}$ bicyclic cycloalkyl optionally substituted by one or more $R_{1S}$.

In some embodiments, $R_1$ is $C_9$-$C_{10}$ bicyclic saturated cycloalkyl optionally substituted by one or more $R_{1S}$.

In some embodiments, $R_1$ is $C_9$-$C_{10}$ bicyclic partially saturated cycloalkyl optionally substituted by one or more $R_{1S}$.

In some embodiments, $R_1$ is $C_{12}$-$C_{16}$ tricyclic cycloalkyl optionally substituted by one or more $R_{1S}$.

In some embodiments, $R_1$ is $C_{12}$-$C_{16}$ tricyclic saturated cycloalkyl optionally substituted by one or more $R_{1S}$.

In some embodiments, $R_1$ is $C_{12}$-$C_{16}$ tricyclic partially unsaturated cycloalkyl optionally substituted by one or more $R_{1S}$.

In some embodiments, $R_1$ is $C_5$-$C_{16}$ polycyclic cycloalkyl substituted by one or more $R_{1S}$.

In some embodiments, $R_1$ is 2,3-dihydro-1H-indenyl optionally substituted by one or more $R_{1S}$.

In some embodiments, $R_1$ is 2,3-dihydro-1H-indenyl.

In some embodiments, $R_1$ is

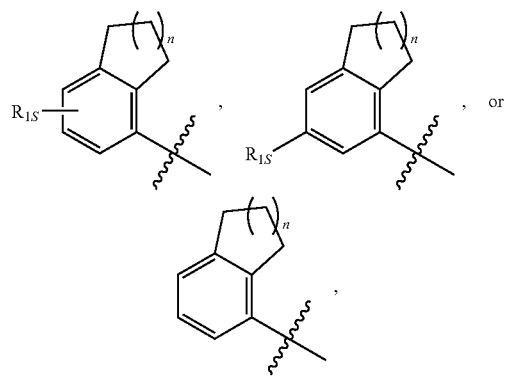

wherein n is 0, 1, or 2.

In some embodiments, $R_1$ is

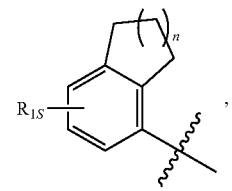

wherein n is 0, 1, or 2.

In some embodiments, $R_1$ is

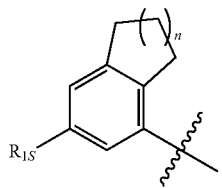

wherein n is 0, 1, or 2.

In some embodiments, $R_1$ is

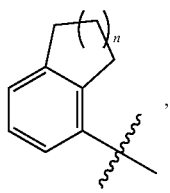

wherein n is 0, 1, or 2.

In some embodiments, $R_1$ is

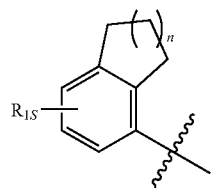

wherein n is 0, 1, or 2, and wherein $R_{1S}$ is $C_1$-$C_6$ alkyl, $C_1$-$C_6$ haloalkyl, $C_1$-$C_6$ alkoxy, $C_1$-$C_6$ haloalkoxy, or halo.

In some embodiments, $R_1$ is

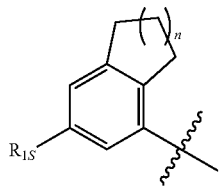

wherein n is 0, 1, or 2, and wherein $R_{1S}$ is $C_1$-$C_6$ alkyl, $C_1$-$C_6$ haloalkyl, $C_1$-$C_6$ alkoxy, $C_1$-$C_6$ haloalkoxy, or halo.

In some embodiments, $R_1$ is

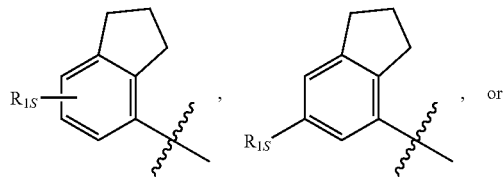

-continued

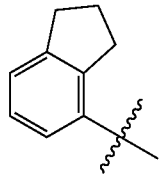

In some embodiments, $R_1$ is

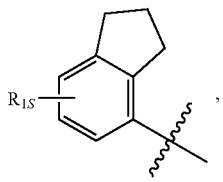

wherein $R_{1S}$ is $C_1$-$C_6$ alkyl, $C_1$-$C_6$ haloalkyl, $C_1$-$C_6$ alkoxy, $C_1$-$C_6$ haloalkoxy, or halo.

In some embodiments, $R_1$ is

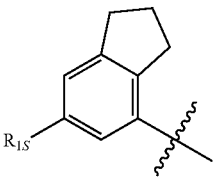

wherein $R_{1S}$ is $C_1$-$C_6$ alkyl, $C_1$-$C_6$ haloalkyl, $C_1$-$C_6$ alkoxy, $C_1$-$C_6$ haloalkoxy, or halo.

In some embodiments, $R_1$ is 2,3-dihydro-1H-indenyl optionally substituted by one, two, or three substituents independently selected from $C_1$-$C_6$ alkyl, $C_1$-$C_6$ haloalkyl, $C_1$-$C_6$ alkoxy, $C_1$-$C_6$ haloalkoxy, or halo.

In some embodiments, $R_1$ is unsubstituted 2,3-dihydro-1H-indenyl.

In some embodiments, $R_1$ is

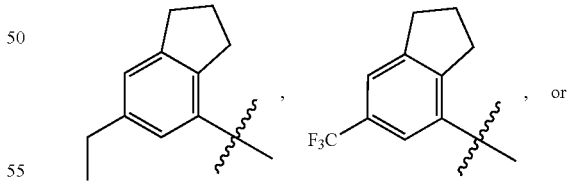

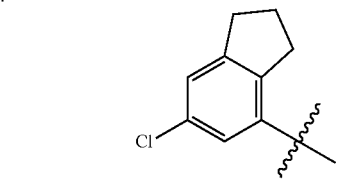

In some embodiments, $R_1$ is hexahydroindacenyl optionally substituted by one or more $R_{1S}$.

In some embodiments, $R_1$ is hexahydroindacenyl.

In some embodiments, $R_1$ is

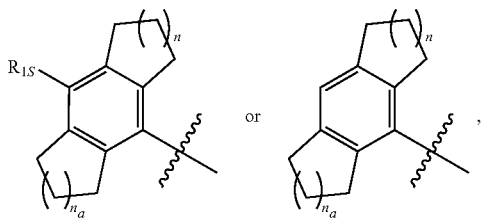

wherein n and $n_a$ each independently are 0, 1, 2, or 3.

In some embodiments, $R_1$ is

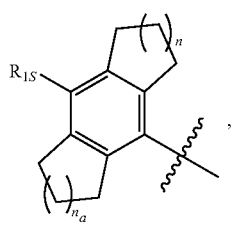

wherein n and $n_a$ each independently are 0, 1, 2, or 3.

In some embodiments, $R_1$ is

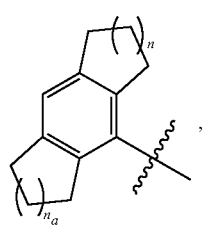

wherein n and $n_a$ each independently are 0, 1, 2, or 3.

In some embodiments, $R_1$ is

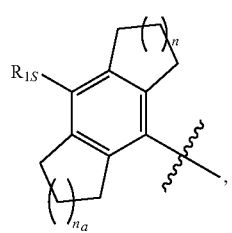

wherein n and $n_a$ each independently are 0, 1, 2, or 3, and wherein $R_{1S}$ is $C_1$-$C_6$ alkyl, $C_1$-$C_6$ haloalkyl, $C_1$-$C_6$ alkoxy, $C_1$-$C_6$ haloalkoxy, or halo.

In some embodiments, $R_1$ is

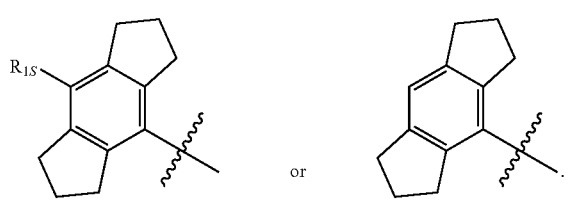

In some embodiments, $R_1$ is

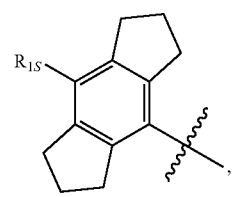

wherein $R_{1S}$ is $C_1$-$C_6$ alkyl, $C_1$-$C_6$ haloalkyl, $C_1$-$C_6$ alkoxy, $C_1$-$C_6$ haloalkoxy, or halo.

In some embodiments, $R_1$ is hexahydroindacenyl optionally substituted by one, two, three, or four substituents independently selected from $C_1$-$C_6$ alkyl, $C_1$-$C_6$ haloalkyl, $C_1$-$C_6$ alkoxy, $C_1$-$C_6$ haloalkoxy, or halo.

In some embodiments, $R_1$ is unsubstituted hexahydroindacenyl.

In some embodiments, $R_1$ is

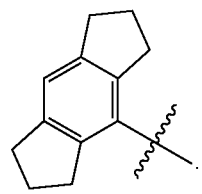 [SMILES: *c1c2c(cc3c1CCC3)CCC2]

In some embodiments, $R_1$ is $C_5$-$C_{10}$ aryl optionally substituted by one or more $R_{1S}$.

In some embodiments, $R_1$ is $C_5$-$C_{10}$ aryl substituted by one or more $R_{1S}$.

In some embodiments, $R_1$ is $C_5$-$C_6$ monocyclic aryl optionally substituted by one or more $R_{1S}$.

In some embodiments, $R_1$ is $C_5$-$C_6$ monocyclic aryl substituted by one or more $R_{1S}$.

In some embodiments, $R_1$ is phenyl optionally substituted by one or more $R_{1S}$.

In some embodiments, $R_1$ is phenyl substituted by one or more $R_{1S}$.

In some embodiments, $R_1$ is phenyl substituted by one $R_{1S}$.

In some embodiments, $R_1$ is

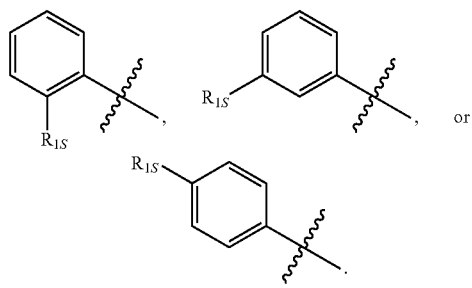

In some embodiments, $R_1$ is phenyl substituted by two $R_{1S}$.

In some embodiments, $R_1$ is

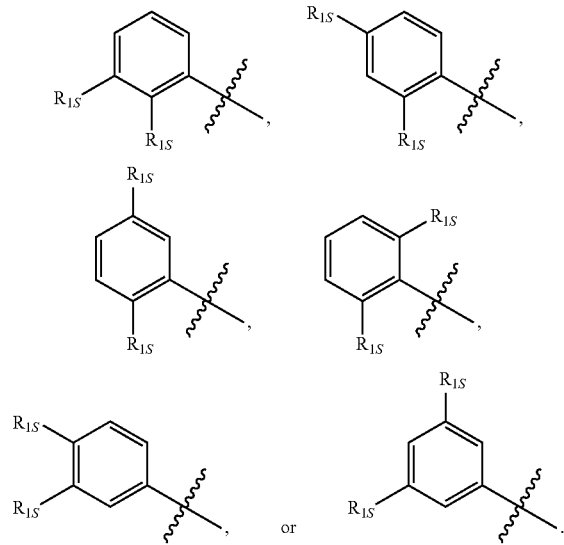

In some embodiments, $R_1$ is phenyl substituted by three $R_{1S}$.

In some embodiments, $R_1$ is

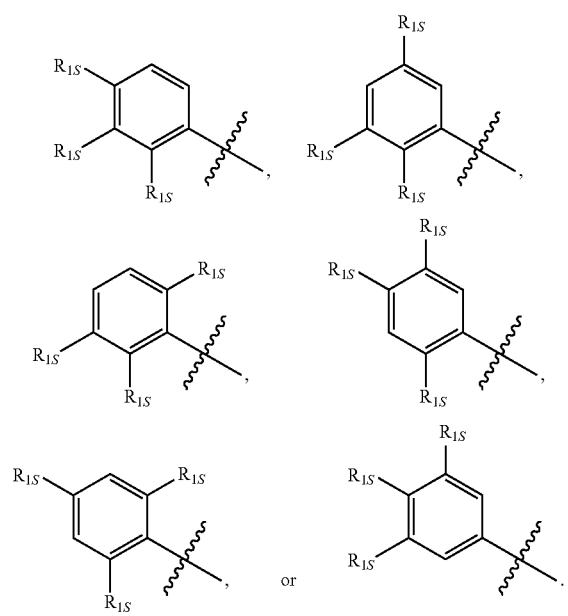

In some embodiments, $R_1$ is

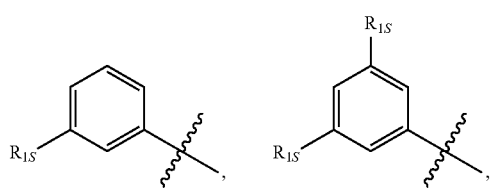

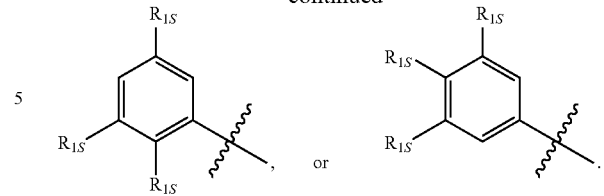

In some embodiments, $R_1$ is

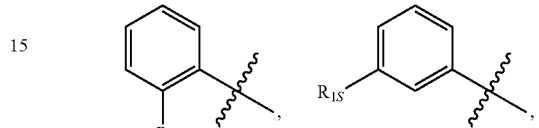

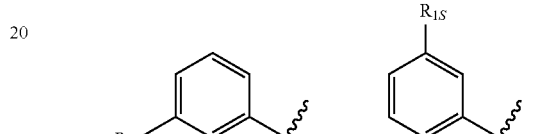

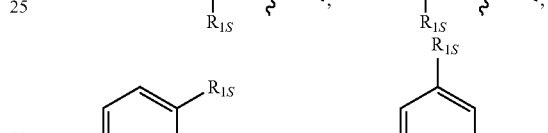

In some embodiments, $R_1$ is phenyl substituted by one or more substituents independently selected from $C_1$-$C_4$ alkyl, $C_1$-$C_2$ alkoxy, $C_1$-$C_2$ haloalkoxy, halo, and —$CF_3$.

In some embodiments, $R_1$ is phenyl optionally substituted by one, two, or three substituents independently selected $C_1$-$C_4$ alkyl (e.g. linear or branched).

In some embodiments, $R_1$ is phenyl optionally substituted by one, two, or three substituents independently selected from $C_1$ and F.

In some embodiments, $R_1$ is phenyl optionally substituted by one, two, or three substituents independently selected $C_1$-$C_2$ alkoxy.

In some embodiments, $R_1$ is phenyl optionally substituted by one, two, or three substituents independently selected $C_1$-$C_2$ haloalkoxy.

In some embodiments, $R_1$ is,

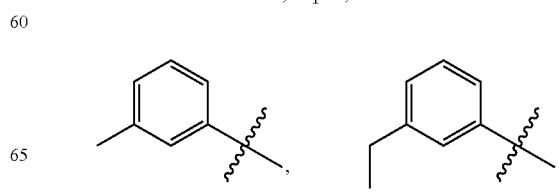

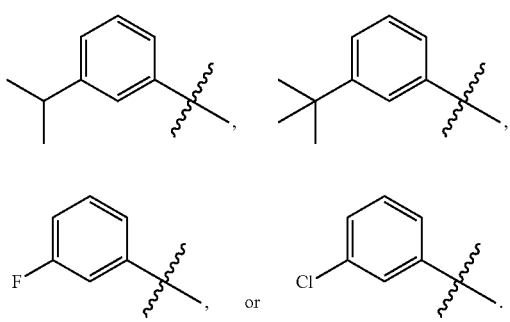
In some embodiments, $R_1$ is
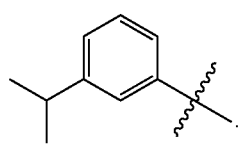 [SMILES: *c1cccc(C(C)C)c1]
In some embodiments, $R_1$ is
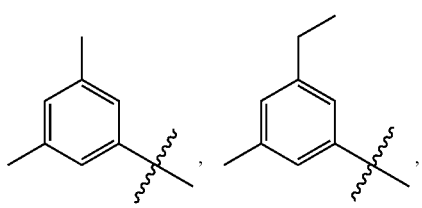
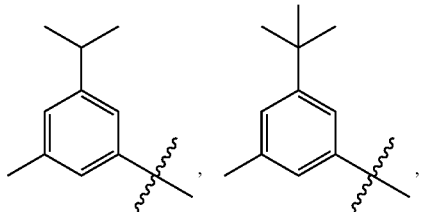
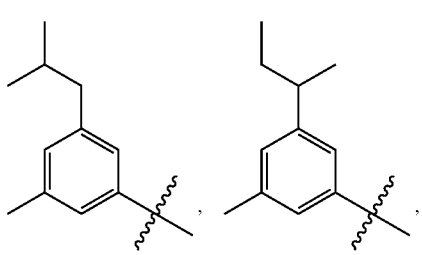
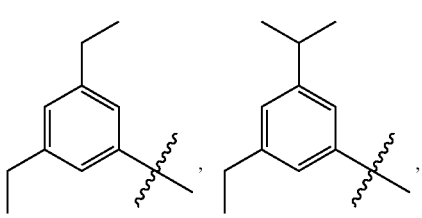
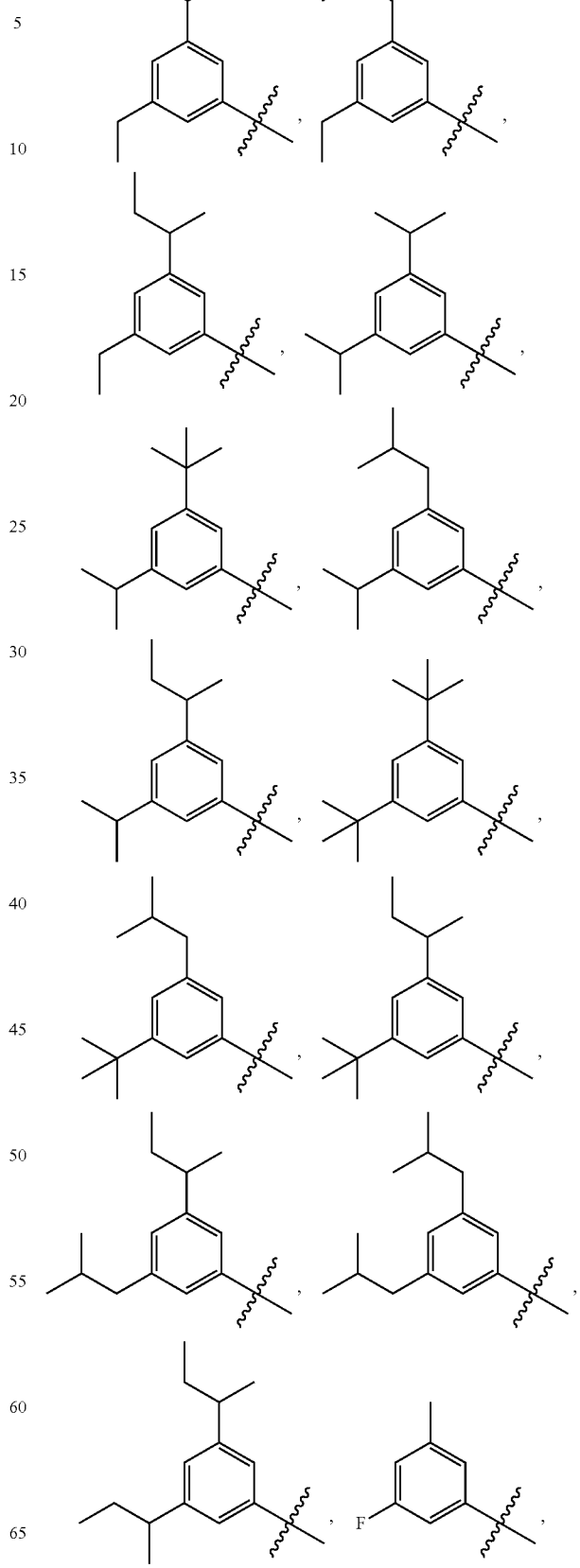

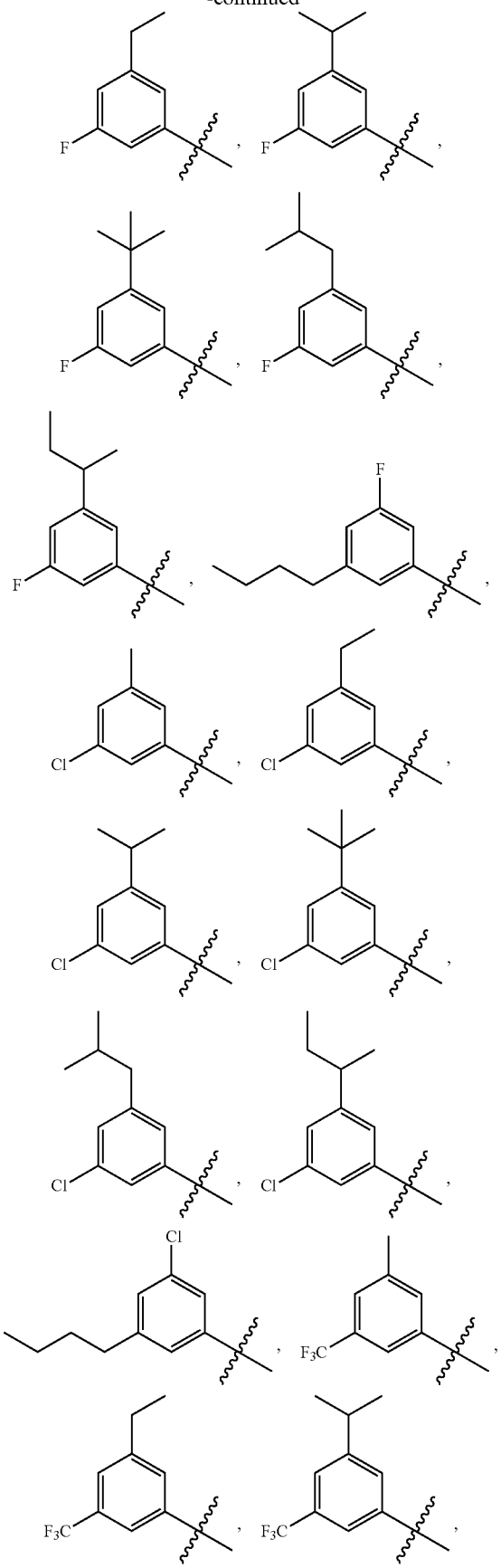
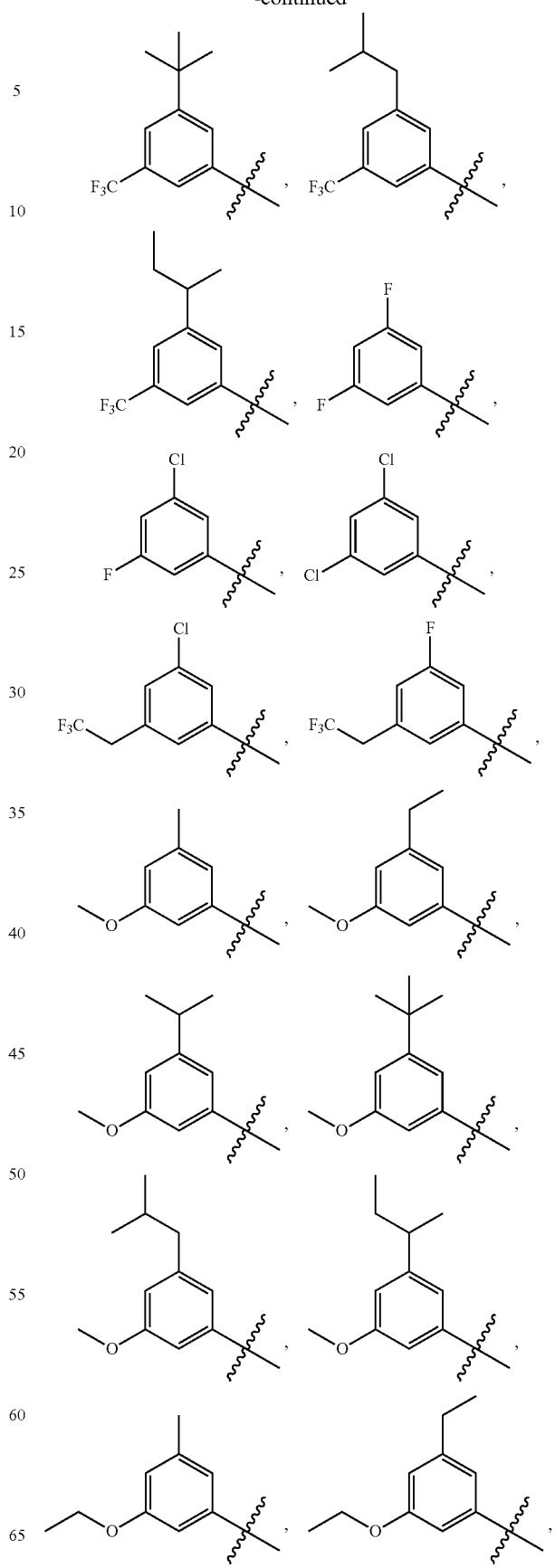

-continued
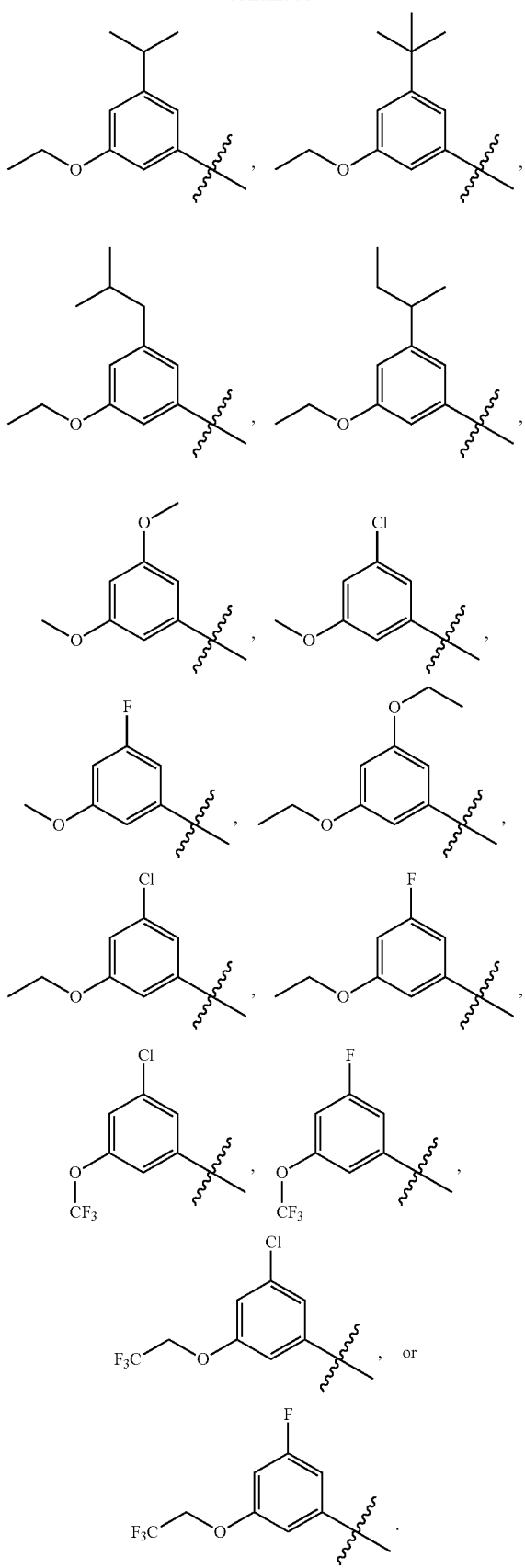
In some embodiments, $R_1$ is
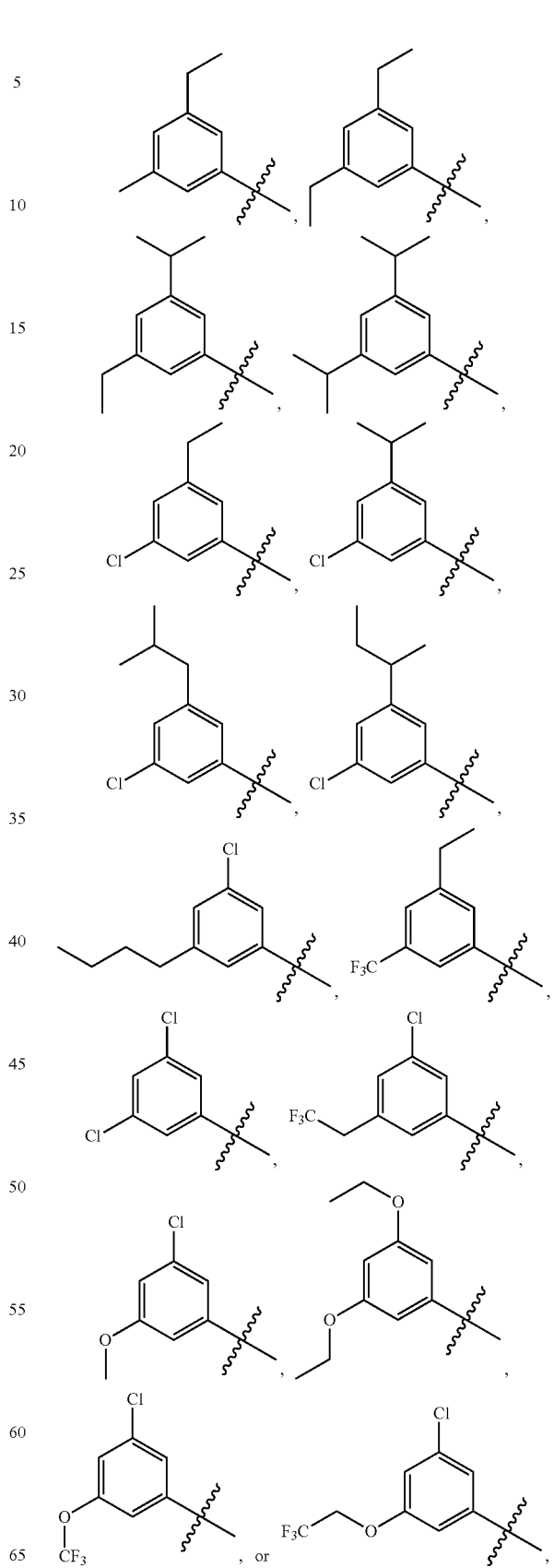

In some embodiments, $R_1$ is
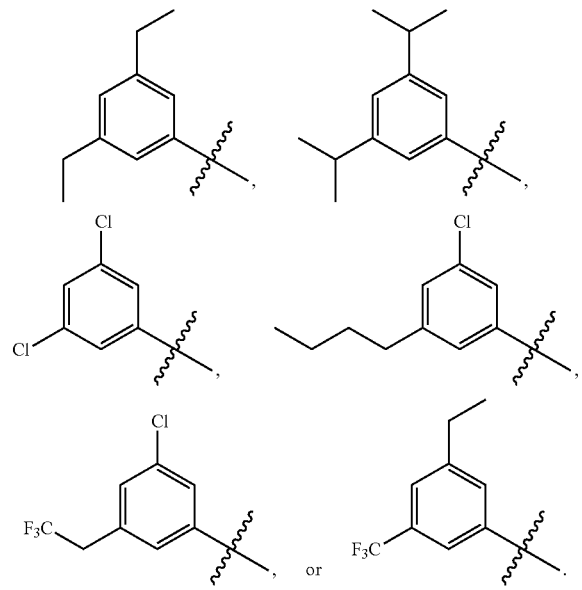
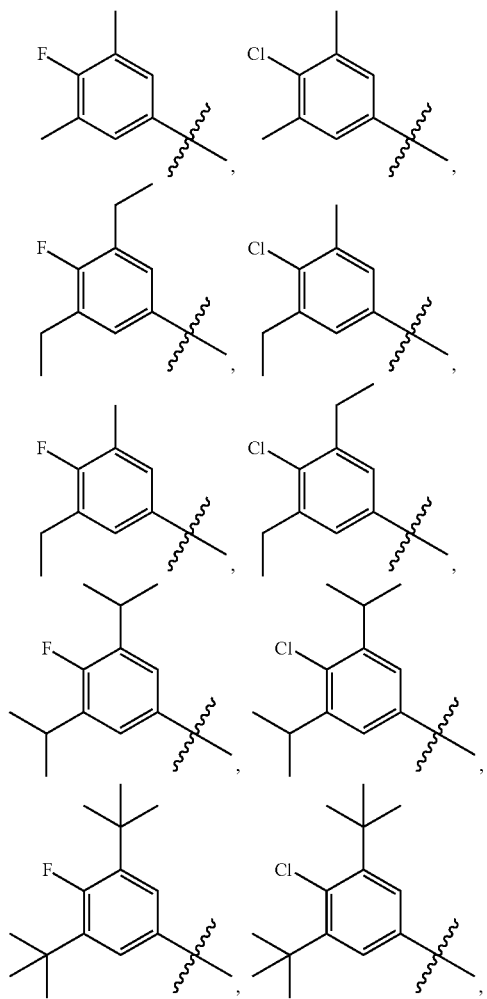
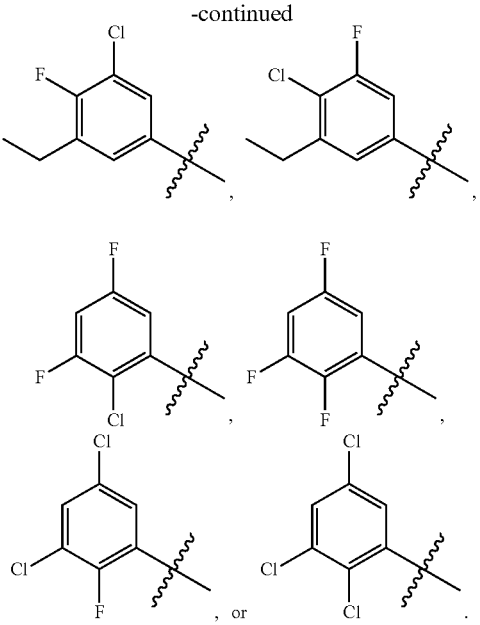
In some embodiments, $R_1$ is
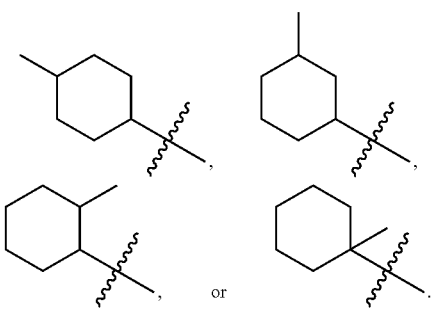
In some embodiments, $R_1$ is cyclopentyl, cyclohexyl, or cycloheptyl, wherein the cyclopentyl, cyclohexyl, or cycloheptyl is optionally substituted by one or more $R_{1S}$.
In some embodiments, $R_1$ is cyclopentyl, cyclohexyl, or cycloheptyl.
In some embodiments, $R_1$ is In some embodiments, $R_1$ is

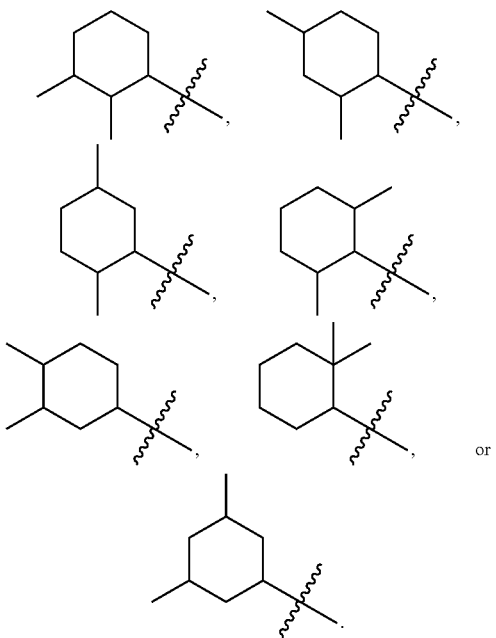

In some embodiments, $R_1$ is

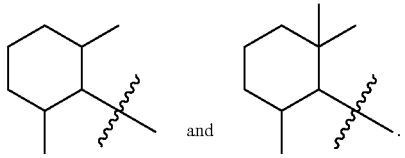

In some embodiments, $R_1$ is

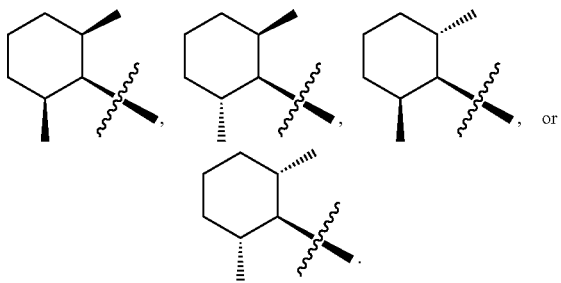

In some embodiments, at least one $R_{1S}$ is $C_1$-$C_6$ alkyl, $C_1$-$C_6$ haloalkyl, $C_1$-$C_6$ alkoxy, $C_1$-$C_6$ haloalkoxy, or halo.

In some embodiments, at least one $R_{1S}$ is $C_1$-$C_6$ alkyl, $C_1$-$C_6$ haloalkyl, $C_1$-$C_6$ alkoxy, or halo.

In some embodiments, at least one $R_{1S}$ is $C_1$-$C_6$ alkyl, $C_1$-$C_6$ haloalkyl, or halo.

In some embodiments, at least one $R_{1S}$ is $C_1$-$C_6$ alkyl or halo.

In some embodiments, at least one $R_{1S}$ is $C_1$-$C_6$ alkyl or $C_1$-$C_6$ haloalkyl.

In some embodiments, at least one $R_{1S}$ is $C_1$-$C_6$ alkyl (e.g. linear or branched).

In some embodiments, at least one $R_{1S}$ is methyl. In some embodiments, at least one $R_{1S}$ is ethyl. In some embodiments, at least one $R_{1S}$ is propyl. In some embodiments, at least one $R_{1S}$ is butyl. In some embodiments, at least one $R_{1S}$ is pentyl. In some embodiments, at least one $R_{1S}$ is hexyl. In some embodiments, at least one $R_{1S}$ is isopropyl. In some embodiments, at least one $R_{1S}$ is isobutyl. In some embodiments, at least one $R_{1S}$ is isopentyl. In some embodiments, at least one $R_{1S}$ is isohexyl. In some embodiments, at least one $R_{1S}$ is secbutyl. In some embodiments, at least one $R_{1S}$ is secpentyl. In some embodiments, at least one $R_{1S}$ is sechexyl.

In some embodiments, at least one $R_{1S}$ is $C_1$-$C_6$ haloalkyl (e.g. methyl, ethyl, propyl, butyl, pentyl, or hexyl substituted with one or more halogen).

In some embodiments, at least one $R_{1S}$ is —$CH_2F$, —$CHF_2$, —$CF_3$.

In some embodiments, at least one $R_{1S}$ is —$CH_2F$. In some embodiments, at least one $R_{1S}$ is —$CHF_2$. In some embodiments, at least one $R_{1S}$ is —$CF_3$.

In some embodiments, at least one $R_{1S}$ is $C_1$-$C_6$ alkoxy or $C_1$-$C_6$ haloalkoxy.

In some embodiments, at least one $R_{1S}$ is $C_1$-$C_6$ alkoxy.

In some embodiments, at least one $R_{1S}$ is methoxy. In some embodiments, at least one $R_{1S}$ is ethoxy. In some embodiments, at least one $R_{1S}$ is propoxy. In some embodiments, at least one $R_{1S}$ is butoxy. In some embodiments, at least one $R_{1S}$ is pentoxy. In some embodiments, at least one $R_{1S}$ is hexoxy.

In some embodiments, at least one $R_{1S}$ is $C_1$-$C_6$ haloalkoxy (e.g. methoxy, ethoxy, propoxy, butoxy, pentoxy, or hexoxy substituted with one or more halogen).

In some embodiments, at least one $R_{1S}$ is halomethoxy. In some embodiments, at least one $R_{1S}$ is haloethoxy. In some embodiments, at least one $R_{1S}$ is halopropoxy. In some embodiments, at least one $R_{1S}$ is halobutoxy. In some embodiments, at least one $R_{1S}$ is halopentoxy. In some embodiments, at least one $R_{1S}$ is halohexoxy.

In some embodiments, at least one $R_{1S}$ is —$OCF_3$.
In some embodiments, at least one $R_{1S}$ is —$OCH_2CF_3$.
In some embodiments, at least one $R_{1S}$ is halo.
In some embodiments, at least one $R_{1S}$ is F, Cl, Br, or I.
In some embodiments, at least one $R_{1S}$ is F or Cl.
In some embodiments, at least one $R_{1S}$ is F.
In some embodiments, at least one $R_{1S}$ is Cl.
In some embodiments, at least one $R_{1S}$ is methyl, ethyl, isopropyl, isobutyl, secbutyl, methoxy, ethoxy, —$CF_3$, —$OCF_3$, —$OCH_2CF_3$, F, or Cl.

In some embodiments, $R_2$ is $R_{2S}$.
In some embodiments, $R_2$ is —$(CX_2X_2)_n$—$R_{2S}$, wherein n is 1 or 2.
In some embodiments, $R_2$ is —$(CX_2X_2)$—$R_{2S}$.
In some embodiments, $R_2$ is —$(CX_2X_2)_2$—$R_{2S}$.
In some embodiments, $R_2$ is —$(CH_2)_n$—$R_{2S}$, wherein n is 1. In some embodiments, $R_2$ is —$(CH_2)_n$—$R_{2S}$, wherein n is 2.

In some embodiments, at least one $X_2$ is H.
In some embodiments, each $X_2$ is H.
In some embodiments, at least one $X_2$ is $C_1$-$C_6$ alkyl, $C_2$-$C_6$ alkenyl, or $C_2$-$C_6$ alkynyl, wherein the $C_1$-$C_6$ alkyl, $C_2$-$C_6$ alkenyl, or $C_2$-$C_6$ alkynyl is optionally substituted with one or more halo, —CN, —OH, —O($C_1$-$C_6$ alkyl), —$NH_2$, —NH($C_1$-$C_6$ alkyl), —N($C_1$-$C_6$ alkyl)$_2$, or oxo.

In some embodiments, at least one $X_2$ is $C_1$-$C_6$ alkyl (e.g., methyl, ethyl, propyl, butyl, pentyl, or hexyl) optionally substituted with one or more halo, —CN, —OH, —O($C_1$-$C_6$ alkyl), —$NH_2$, —NH($C_1$-$C_6$ alkyl), —N($C_1$-$C_6$ alkyl)$_2$, or oxo.

In some embodiments, at least one $X_2$ is $C_1$-$C_6$ alkyl (e.g., methyl, ethyl, propyl, butyl, pentyl, or hexyl).

In some embodiments, at least one $X_2$ is $C_2$-$C_6$ alkenyl (e.g., ethenyl, propenyl, butenyl, pentenyl, or hexenyl) optionally substituted with one or more halo, —CN, —OH, —O($C_1$-$C_6$ alkyl), —NH$_2$, —NH($C_1$-$C_6$ alkyl), —N($C_1$-$C_6$ alkyl)$_2$, or oxo.

In some embodiments, at least one $X_2$ is $C_2$-$C_6$ alkenyl (e.g., ethenyl, propenyl, butenyl, pentenyl, or hexenyl).

In some embodiments, at least one $X_2$ is $C_2$-$C_6$ alkynyl (e.g., ethynyl, propynyl, butynyl, pentynyl, or hexynyl) optionally substituted with one or more halo, —CN, —OH, —O($C_1$-$C_6$ alkyl), —NH$_2$, —NH($C_1$-$C_6$ alkyl), —N($C_1$-$C_6$ alkyl)$_2$, or oxo.

In some embodiments, at least one $X_2$ is $C_2$-$C_6$ alkynyl (e.g., ethynyl, propynyl, butynyl, pentynyl, or hexynyl).

In some embodiments, $R_{2S}$ is 4- to 8-membered heterocycloalkyl optionally substituted with one or more $C_1$-$C_6$ alkyl, $C_2$-$C_6$ alkenyl, $C_2$-$C_6$ alkynyl, $C_1$-$C_6$ haloalkyl, halo, —CN, —OH, —O($C_1$-$C_6$ alkyl), —NH$_2$, —NH($C_1$-$C_6$ alkyl), —N($C_1$-$C_6$ alkyl)$_2$, or oxo.

In some embodiments, $R_{2S}$ is 4- to 8-membered heterocycloalkyl optionally substituted with one or more $C_1$-$C_6$ alkyl, $C_2$-$C_6$ alkenyl, $C_2$-$C_6$ alkynyl, $C_1$-$C_6$ haloalkyl, halo, —CN, —OH, —NH$_2$, or oxo.

In some embodiments, $R_{2S}$ is 4- to 8-membered heterocycloalkyl optionally substituted with one or more $C_1$-$C_6$ alkyl, $C_2$-$C_6$ alkenyl, $C_2$-$C_6$ alkynyl, $C_1$-$C_6$ haloalkyl, halo, or oxo.

In some embodiments, $R_{2S}$ is 4- to 8-membered heterocycloalkyl optionally substituted with one or more $C_1$-$C_6$ alkyl, $C_1$-$C_6$ haloalkyl, or oxo.

In some embodiments, $R_{2S}$ is 4- to 8-membered heterocycloalkyl.

In some embodiments, $R_{2S}$ is 5- to 8-membered heterocycloalkyl.

In some embodiments, $R_{2S}$ is 5- to 7-membered heterocycloalkyl.

In some embodiments, $R_{2S}$ is 5- to 6-membered heterocycloalkyl.

In some embodiments, $R_{2S}$ is 5- or 6-membered heterocycloalkyl havine one or more heteroatoms selected from N and O.

In some embodiments, $R_{2S}$ is 5- or 6-membered heterocycloalkyl having one heteroatom selected from N and O.

In some embodiments, $R_{2S}$ is 5- or 6-membered heterocycloalkyl havine two heteroatoms selected from N or O.

In some embodiments, $R_{2S}$ is 6-membered heterocycloalkyl.

In some embodiments, $R_{2S}$ is 6-membered heterocycloalkyl optionally substituted with one or more $C_1$-$C_6$ alkyl, $C_2$-$C_6$ alkenyl, $C_2$-$C_6$ alkynyl, $C_1$-$C_6$ haloalkyl, halo, —CN, —OH, —O($C_1$-$C_6$ alkyl), —NH$_2$, —NH($C_1$-$C_6$ alkyl), —N($C_1$-$C_6$ alkyl)$_2$, or oxo.

In some embodiments, $R_{2S}$ is 6-membered heterocycloalkyl optionally substituted with one or more $C_1$-$C_6$ alkyl, $C_1$-$C_6$ haloalkyl, or oxo.

In some embodiments, $R_{2S}$ is 6-membered heterocycloalkyl optionally substituted with one or more $C_1$-$C_6$ alkyl or oxo.

In some embodiments, $R_{2S}$ is 6-membered heterocycloalkyl optionally substituted with one or more $C_1$-$C_6$ alkyl or $C_1$-$C_6$ haloalkyl.

In some embodiments, $R_{2S}$ is 6-membered heterocycloalkyl optionally substituted with one or more $C_1$-$C_6$ alkyl.

In some embodiments, $R_{2S}$ is tetrahydropyranyl optionally substituted with one or more $C_1$-$C_6$ alkyl, $C_1$-$C_6$ haloalkyl, or oxo.

In some embodiments, $R_{2S}$ is tetrahydropyranyl optionally substituted with one or more $C_1$-$C_6$ alkyl or oxo.

In some embodiments, $R_{2S}$ is tetrahydropyranyl optionally substituted with one or more $C_1$-$C_6$ alkyl or $C_1$-$C_6$ haloalkyl.

In some embodiments, $R_{2S}$ is tetrahydropyranyl optionally substituted with one or more $C_1$-$C_6$ alkyl.

In some embodiments, $R_{2S}$ is tetrahydropyranyl optionally substituted with one or more methyl. In some embodiments, $R_{2S}$ is tetrahydropyranyl optionally substituted with one or more ethyl. In some embodiments, $R_{2S}$ is tetrahydropyranyl optionally substituted with one or more propyl. In some embodiments, $R_{2S}$ is tetrahydropyranyl optionally substituted with one or more butyl. In some embodiments, $R_{2S}$ is tetrahydropyranyl optionally substituted with one or more pentyl. In some embodiments, $R_{2S}$ is tetrahydropyranyl optionally substituted with one or more hexyl.

In some embodiments, $R_{2S}$ is tetrahydropyranyl optionally substituted with one or more oxo.

In some embodiments, $R_{2S}$ is tetrahydropyranyl optionally substituted with one or more $C_1$-$C_6$ haloalkyl (e.g. methyl, ethyl, propyl, butyl, pentyl, or hexyl optionally substituted with one or more halo).

In some embodiments, $R_{2S}$ is

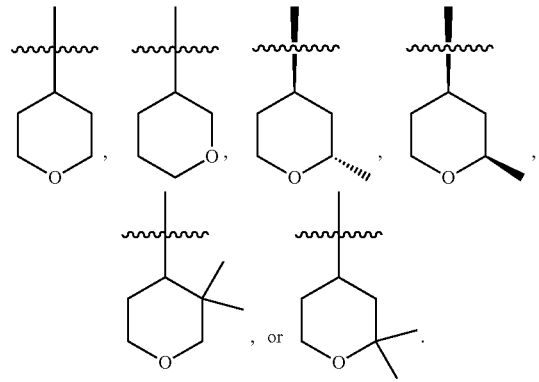

In some embodiments, $R_{2S}$ is

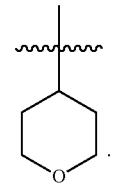 [SMILES: *C1CCOCC1]

In some embodiments, $R_{2S}$ is piperidinyl optionally substituted with one or more $C_1$-$C_6$ alkyl, $C_1$-$C_6$ haloalkyl, or oxo.

In some embodiments, $R_{2S}$ piperidinyl optionally substituted with one or more $C_1$-$C_6$ alkyl or oxo.

In some embodiments, $R_{2S}$ is piperidinyl optionally substituted with one or more $C_1$-$C_6$ alkyl or $C_1$-$C_6$ haloalkyl.

In some embodiments, $R_{2S}$ is piperidinyl optionally substituted with one or more $C_1$-$C_6$ alkyl.

In some embodiments, $R_{2S}$ is piperidinyl optionally substituted with one or more methyl. In some embodiments, $R_{2S}$ is piperidinyl optionally substituted with one or more ethyl. In some embodiments, $R_{2S}$ is piperidinyl optionally substituted with one or more propyl. In some embodiments, $R_{2S}$ is piperidinyl optionally substituted with one or more butyl. In some embodiments, R$_{2S}$ is piperidinyl optionally substituted with one or more pentyl. In some embodiments, R$_{2S}$ is piperidinyl optionally substituted with one or more hexyl.

In some embodiments, R$_{2S}$ is piperidinyl optionally substituted with one or more oxo.

In some embodiments, R$_{2S}$ is piperidinyl optionally substituted with one or more C$_1$-C$_6$ haloalkyl (e.g. methyl, ethyl, propyl, butyl, pentyl, or hexyl optionally substituted with one or more halo).

In some embodiments, R$_{2S}$ is piperidinyl optionally substituted with one or more —CH$_2$F, —CHF$_2$, —CF$_3$, —(CH)$_2$CH$_2$F, —(CH)$_2$CHF$_2$, or —(CH)$_2$CF$_3$.

In some embodiments, R$_{2S}$ is

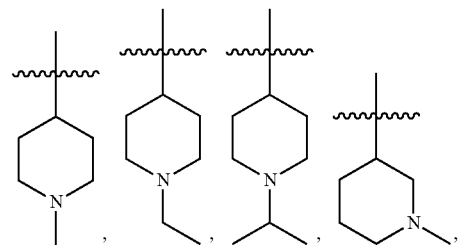

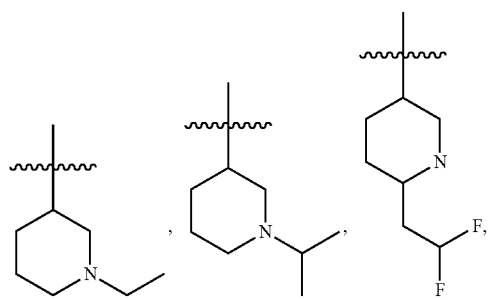

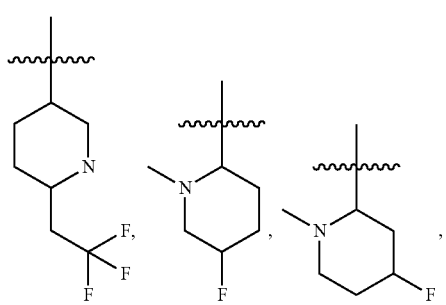

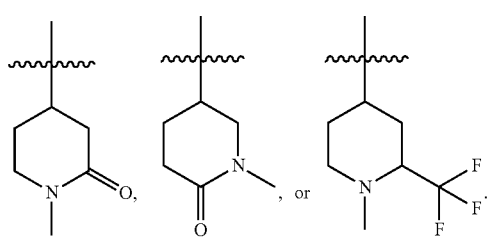

In some embodiments, R$_{2S}$ is

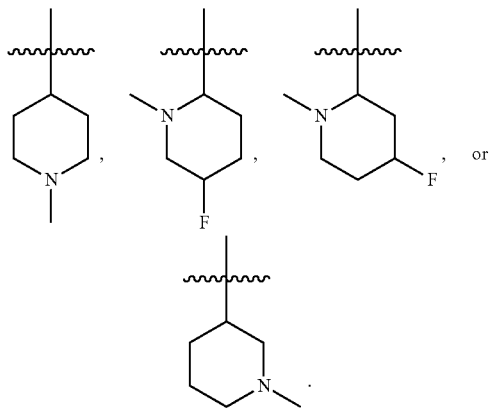

In some embodiments, R$_{2S}$ is morpholinyl.

In some embodiments, R$_{2S}$ is morpholinyl optionally substituted with one or more C$_1$-C$_6$ alkyl, C$_1$-C$_6$ haloalkyl, or oxo.

In some embodiments, R$_{2S}$ morpholinyl optionally substituted with one or more C$_1$-C$_6$ alkyl or oxo.

In some embodiments, R$_{2S}$ is morpholinyl optionally substituted with one or more C$_1$-C$_6$ alkyl or C$_1$-C$_6$ haloalkyl.

In some embodiments, R$_{2S}$ is morpholinyl optionally substituted with one or more C$_1$-C$_6$ alkyl.

In some embodiments, R$_{2S}$ is morpholinyl optionally substituted with one or more methyl. In some embodiments, R$_{2S}$ is morpholinyl optionally substituted with one or more ethyl.

In some embodiments, R$_{2S}$ is morpholinyl optionally substituted with one or more propyl. In some embodiments, R$_{2S}$ is morpholinyl optionally substituted with one or more butyl. In some embodiments, R$_{2S}$ is morpholinyl optionally substituted with one or more pentyl. In some embodiments, R$_{2S}$ is morpholinyl optionally substituted with one or more hexyl.

In some embodiments, R$_{2S}$ is morpholinyl optionally substituted with one or more oxo.

In some embodiments, R$_{2S}$ is morpholinyl optionally substituted with one or more C$_1$-C$_6$ haloalkyl (e.g. methyl, ethyl, propyl, butyl, pentyl, or hexyl optionally substituted with one or more halo).

In some embodiments, R$_{2S}$ is

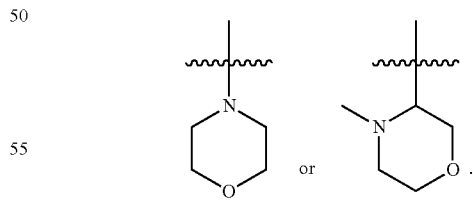

In some embodiments, R$_2$ is —(CH$_2$)$_n$—R$_{2S}$, wherein n is 0 and R$_{2S}$ is 6-membered heterocycloalkyl.

In some embodiments, R$_2$ is —(CH$_2$)$_n$—R$_{2S}$, wherein n is 0 and R$_{2S}$ is 6-membered heterocycloalkyl optionally substituted with one or more C$_1$-C$_6$ alkyl, C$_1$-C$_6$ haloalkyl, or oxo.

In some embodiments, R$_2$ is —(CH$_2$)$_n$—R$_{2S}$, wherein n is 0 and R$_{2S}$ is tetrahydropyranyl optionally substituted with one or more C$_1$-C$_6$ alkyl, C$_1$-C$_6$ haloalkyl, or oxo.

In some embodiments, $R_2$ is —$(CH_2)_n$—$R_{2S}$, wherein n is 0 and $R_{2S}$ is piperidinyl optionally substituted with one or more $C_1$-$C_6$ alkyl, $C_1$-$C_6$ haloalkyl, or oxo.

In some embodiments, $R_2$ is —$(CH_2)_n$—$R_{2S}$, wherein n is 0 and $R_{2S}$ is morpholinyl optionally substituted with one or more $C_1$-$C_6$ alkyl, $C_1$-$C_6$ haloalkyl, or oxo.

In some embodiments, $R_2$ is —$(CH_2)_n$—$R_{2S}$, wherein n is 1 and $R_{2S}$ is 6-membered heterocycloalkyl.

In some embodiments, $R_2$ is —$(CH_2)_n$—$R_{2S}$, wherein n is 1 and $R_{2S}$ is 6-membered heterocycloalkyl optionally substituted with one or more $C_1$-$C_6$ alkyl, $C_1$-$C_6$ haloalkyl, or oxo.

In some embodiments, $R_2$ is —$(CH_2)_n$—$R_{2S}$, wherein n is 1 and $R_{2S}$ is tetrahydropyranyl optionally substituted with one or more $C_1$-$C_6$ alkyl, $C_1$-$C_6$ haloalkyl, or oxo.

In some embodiments, $R_2$ is —$(CH_2)_n$—$R_{2S}$, wherein n is 1 and $R_{2S}$ is piperidinyl optionally substituted with one or more $C_1$-$C_6$ alkyl, $C_1$-$C_6$ haloalkyl, or oxo.

In some embodiments, $R_2$ is —$(CH_2)_n$—$R_{2S}$, wherein n is 1 and $R_{2S}$ is morpholinyl optionally substituted with one or more $C_1$-$C_6$ alkyl, $C_1$-$C_6$ haloalkyl, or oxo.

In some embodiments, $R_2$ is —$(CH_2)_n$—$R_{2S}$, wherein n is 2 and $R_{2S}$ is 6-membered heterocycloalkyl.

In some embodiments, $R_2$ is —$(CH_2)_n$—$R_{2S}$, wherein n is 2 and $R_{2S}$ is 6-membered heterocycloalkyl optionally substituted with one or more $C_1$-$C_6$ alkyl, $C_1$-$C_6$ haloalkyl, or oxo.

In some embodiments, $R_2$ is —$(CH_2)_n$—$R_{2S}$, wherein n is 2 and $R_{2S}$ is tetrahydropyranyl optionally substituted with one or more $C_1$-$C_6$ alkyl, $C_1$-$C_6$ haloalkyl, or oxo.

In some embodiments, $R_2$ is —$(CH_2)_n$—$R_{2S}$, wherein n is 2 and $R_{2S}$ is piperidinyl optionally substituted with one or more $C_1$-$C_6$ alkyl, $C_1$-$C_6$ haloalkyl, or oxo.

In some embodiments, $R_2$ is —$(CH_2)_n$—$R_{2S}$, wherein n is 2 and $R_{2S}$ is morpholinyl optionally substituted with one or more $C_1$-$C_6$ alkyl, $C_1$-$C_6$ haloalkyl, or oxo.

In some embodiments, $R_{2S}$ is 5-membered heterocycloalkyl.

In some embodiments, $R_{2S}$ is 5-membered heterocycloalkyl optionally substituted with one or more $C_1$-$C_6$ alkyl, $C_2$-$C_6$ alkenyl, $C_2$-$C_6$ alkynyl, $C_1$-$C_6$ haloalkyl, halo, —CN, —OH, —O($C_1$-$C_6$ alkyl), —$NH_2$, —NH($C_1$-$C_6$ alkyl), —N($C_1$-$C_6$ alkyl)$_2$, or oxo.

In some embodiments, $R_{2S}$ is 5-membered heterocycloalkyl optionally substituted with one or more $C_1$-$C_6$ alkyl, $C_1$-$C_6$ haloalkyl, or oxo.

In some embodiments, $R_{2S}$ is 5-membered heterocycloalkyl optionally substituted with one or more $C_1$-$C_6$ alkyl or oxo.

In some embodiments, $R_{2S}$ is 5-membered heterocycloalkyl optionally substituted with one or more $C_1$-$C_6$ alkyl or $C_1$-$C_6$ haloalkyl.

In some embodiments, $R_{2S}$ is 5-membered heterocycloalkyl optionally substituted with one or more $C_1$-$C_6$ alkyl.

In some embodiments, $R_{2S}$ is tetrahydrofuranyl optionally substituted with one or more $C_1$-$C_6$ alkyl, $C_1$-$C_6$ haloalkyl, or oxo.

In some embodiments, $R_{2S}$ is tetrahydrofuranyl optionally substituted with one or more $C_1$-$C_6$ alkyl or oxo.

In some embodiments, $R_{2S}$ is tetrahydrofuranyl optionally substituted with one or more $C_1$-$C_6$ alkyl or $C_1$-$C_6$ haloalkyl.

In some embodiments, $R_{2S}$ is tetrahydrofuranyl optionally substituted with one or more $C_1$-$C_6$ alkyl.

In some embodiments, $R_{2S}$ is tetrahydrofuranyl optionally substituted with one or more methyl. In some embodiments, $R_{2S}$ is tetrahydrofuranyl optionally substituted with one or more ethyl. In some embodiments, $R_{2S}$ is tetrahydrofuranyl optionally substituted with one or more propyl. In some embodiments, $R_{2S}$ is tetrahydrofuranyl optionally substituted with one or more butyl. In some embodiments, $R_{2S}$ is tetrahydrofuranyl optionally substituted with one or more pentyl. In some embodiments, $R_{2S}$ is tetrahydrofuranyl optionally substituted with one or more hexyl.

In some embodiments, $R_{2S}$ is tetrahydrofuranyl optionally substituted with one or more oxo.

In some embodiments, $R_{2S}$ is tetrahydrofuranyl optionally substituted with one or more $C_1$-$C_6$ haloalkyl (e.g. methyl, ethyl, propyl, butyl, pentyl, or hexyl optionally substituted with one or more halo).

In some embodiments, $R_{2S}$ is

In some embodiments, $R_{2S}$ is pyrrolidinyl optionally substituted with one or more $C_1$-$C_6$ alkyl, $C_1$-$C_6$ haloalkyl, or oxo.

In some embodiments, $R_{2S}$ is pyrrolidinyl optionally substituted with one or more $C_1$-$C_6$ alkyl or oxo.

In some embodiments, $R_{2S}$ is pyrrolidinyl optionally substituted with one or more $C_1$-$C_6$ alkyl or $C_1$-$C_6$ haloalkyl.

In some embodiments, $R_{2S}$ is pyrrolidinyl optionally substituted with one or more $C_1$-$C_6$ alkyl.

In some embodiments, $R_{2S}$ is pyrrolidinyl optionally substituted with one or more methyl. In some embodiments, $R_{2S}$ is pyrrolidinyl optionally substituted with one or more ethyl. In some embodiments, $R_{2S}$ is pyrrolidinyl optionally substituted with one or more propyl. In some embodiments, $R_{2S}$ is pyrrolidinyl optionally substituted with one or more butyl. In some embodiments, $R_{2S}$ is pyrrolidinyl optionally substituted with one or more pentyl. In some embodiments, $R_{2S}$ is pyrrolidinyl optionally substituted with one or more hexyl.

In some embodiments, $R_{2S}$ is pyrrolidinyl optionally substituted with one or more oxo.

In some embodiments, $R_{2S}$ is pyrrolidinyl optionally substituted with one or more $C_1$-$C_6$ haloalkyl (e.g. methyl, ethyl, propyl, butyl, pentyl, or hexyl optionally substituted with one or more halo).

In some embodiments, $R_{2S}$ is

In some embodiments, $R_2$ is —$(CH_2)_n$—$R_{2S}$, wherein n is 0 and $R_{2S}$ is 5-membered heterocycloalkyl.

In some embodiments, $R_2$ is —$(CH_2)_n$—$R_{2S}$, wherein n is 0 and $R_{2S}$ is 5-membered heterocycloalkyl optionally substituted with one or more $C_1$-$C_6$ alkyl, $C_1$-$C_6$ haloalkyl, or oxo.

In some embodiments, $R_2$ is —$(CH_2)_n$—$R_{2S}$, wherein n is 0 and $R_{2S}$ is tetrahydrofuranyl optionally substituted with one or more $C_1$-$C_6$ alkyl, $C_1$-$C_6$ haloalkyl, or oxo.

In some embodiments, $R_2$ is —$(CH_2)_n$—$R_{2S}$, wherein n is 0 and $R_{2S}$ is pyrrolidinyl optionally substituted with one or more $C_1$-$C_6$ alkyl, $C_1$-$C_6$ haloalkyl, or oxo.

In some embodiments, $R_2$ is —$(CH_2)_n$—$R_{2S}$, wherein n is 1 and $R_{2S}$ is 5-membered heterocycloalkyl.

In some embodiments, $R_2$ is —$(CH_2)_n$—$R_{2S}$, wherein n is 1 and $R_{2S}$ is 5-membered heterocycloalkyl optionally substituted with one or more $C_1$-$C_6$ alkyl, $C_1$-$C_6$ haloalkyl, or oxo.

In some embodiments, $R_2$ is —$(CH_2)_n$—$R_{2S}$, wherein n is 1 and $R_{2S}$ is tetrahydrofuranyl optionally substituted with one or more $C_1$-$C_6$ alkyl, $C_1$-$C_6$ haloalkyl, or oxo.

In some embodiments, $R_2$ is —$(CH_2)_n$—$R_{2S}$, wherein n is 1 and $R_{2S}$ is pyrrolidinyl optionally substituted with one or more $C_1$-$C_6$ alkyl, $C_1$-$C_6$ haloalkyl, or oxo.

In some embodiments, $R_2$ is —$(CH_2)_n$—$R_{2S}$, wherein n is 2 and $R_{2S}$ is 5-membered heterocycloalkyl.

In some embodiments, $R_2$ is —$(CH_2)_n$—$R_{2S}$, wherein n is 2 and $R_{2S}$ is 5-membered heterocycloalkyl optionally substituted with one or more $C_1$-$C_6$ alkyl, $C_1$-$C_6$ haloalkyl, or oxo.

In some embodiments, $R_2$ is —$(CH_2)_n$—$R_{2S}$, wherein n is 2 and $R_{2S}$ is tetrahydrofuranyl optionally substituted with one or more $C_1$-$C_6$ alkyl, $C_1$-$C_6$ haloalkyl, or oxo.

In some embodiments, $R_2$ is —$(CH_2)_n$—$R_{2S}$, wherein n is 2 and $R_{2S}$ is pyrrolidinyl optionally substituted with one or more $C_1$-$C_6$ alkyl, $C_1$-$C_6$ haloalkyl, or oxo.

In some embodiments, $R_{2S}$ is 4-membered heterocycloalkyl.

In some embodiments, $R_{2S}$ is 4-membered heterocycloalkyl optionally substituted with one or more $C_1$-$C_6$ alkyl, $C_2$-$C_6$ alkenyl, $C_2$-$C_6$ alkynyl, $C_1$-$C_6$ haloalkyl, halo, —CN, —OH, —O($C_1$-$C_6$ alkyl), —$NH_2$, —NH($C_1$-$C_6$ alkyl), —N($C_1$-$C_6$ alkyl)$_2$, or oxo.

In some embodiments, $R_{2S}$ is 4-membered heterocycloalkyl optionally substituted with one or more $C_1$-$C_6$ alkyl, $C_1$-$C_6$ haloalkyl, or oxo.

In some embodiments, $R_{2S}$ is 4-membered heterocycloalkyl optionally substituted with one or more $C_1$-$C_6$ alkyl or oxo.

In some embodiments, $R_{2S}$ is 4-membered heterocycloalkyl optionally substituted with one or more $C_1$-$C_6$ alkyl or $C_1$-$C_6$ haloalkyl.

In some embodiments, $R_{2S}$ is 4-membered heterocycloalkyl optionally substituted with one or more $C_1$-$C_6$ alkyl.

In some embodiments, $R_{2S}$ is oxetanyl optionally substituted with one or more $C_1$-$C_6$ alkyl, $C_1$-$C_6$ haloalkyl, or oxo.

In some embodiments, $R_{2S}$ is oxetanyl optionally substituted with one or more $C_1$-$C_6$ alkyl or oxo.

In some embodiments, $R_{2S}$ is oxetanyl optionally substituted with one or more $C_1$-$C_6$ alkyl or $C_1$-$C_6$ haloalkyl.

In some embodiments, $R_{2S}$ is oxetanyl optionally substituted with one or more $C_1$-$C_6$ alkyl.

In some embodiments, $R_{2S}$ is oxetanyl optionally substituted with one or more methyl. In some embodiments, $R_{2S}$ is oxetanyl optionally substituted with one or more ethyl. In some embodiments, $R_{2S}$ is oxetanyl optionally substituted with one or more propyl. In some embodiments, $R_{2S}$ is oxetanyl optionally substituted with one or more butyl. In some embodiments, $R_{2S}$ is oxetanyl optionally substituted with one or more pentyl. In some embodiments, $R_{2S}$ is oxetanyl optionally substituted with one or more hexyl.

In some embodiments, $R_{2S}$ is oxetanyl optionally substituted with one or more oxo.

In some embodiments, $R_{2S}$ is oxetanyl optionally substituted with one or more $C_1$-$C_6$ haloalkyl (e.g. methyl, ethyl, propyl, butyl, pentyl, or hexyl optionally substituted with one or more halo).

In some embodiments, $R_{2S}$ is

In some embodiments, $R_{2S}$ is azetidinyl optionally substituted with one or more $C_1$-$C_6$ alkyl, $C_1$-$C_6$ haloalkyl, or oxo.

In some embodiments, $R_{2S}$ is azetidinyl optionally substituted with one or more $C_1$-$C_6$ alkyl or oxo.

In some embodiments, $R_{2S}$ is azetidinyl optionally substituted with one or more $C_1$-$C_6$ alkyl or $C_1$-$C_6$ haloalkyl.

In some embodiments, $R_{2S}$ is azetidinyl optionally substituted with one or more $C_1$-$C_6$ alkyl.

In some embodiments, $R_{2S}$ is azetidinyl optionally substituted with one or more methyl. In some embodiments, $R_{2S}$ is azetidinyl optionally substituted with one or more ethyl. In some embodiments, $R_{2S}$ is azetidinyl optionally substituted with one or more propyl. In some embodiments, $R_{2S}$ is azetidinyl optionally substituted with one or more butyl. In some embodiments, $R_{2S}$ is azetidinyl optionally substituted with one or more pentyl. In some embodiments, $R_{2S}$ is azetidinyl optionally substituted with one or more hexyl.

In some embodiments, $R_{2S}$ is azetidinyl optionally substituted with one or more oxo.

In some embodiments, $R_{2S}$ is azetidinyl optionally substituted with one or more $C_1$-$C_6$ haloalkyl (e.g. methyl, ethyl, propyl, butyl, pentyl, or hexyl optionally substituted with one or more halo).

In some embodiments, $R_{2S}$ is

[structures shown]

In some embodiments, $R_2$ is —(CH$_2$)$_n$—$R_{2S}$, wherein n is 0 and $R_{2S}$ is 4-membered heterocycloalkyl.

In some embodiments, $R_2$ is —(CH$_2$)$_n$—$R_{2S}$, wherein n is 0 and $R_{2S}$ is 4-membered heterocycloalkyl optionally substituted with one or more $C_1$-$C_6$ alkyl, $C_1$-$C_6$ haloalkyl, or oxo.

In some embodiments, $R_2$ is —(CH$_2$)$_n$—$R_{2S}$, wherein n is 0 and $R_{2S}$ is oxetanyl optionally substituted with one or more $C_1$-$C_6$ alkyl, $C_1$-$C_6$ haloalkyl, or oxo.

In some embodiments, $R_2$ is —(CH$_2$)$_n$—$R_{2S}$, wherein n is 0 and $R_{2S}$ is azetidinyl optionally substituted with one or more $C_1$-$C_6$ alkyl, $C_1$-$C_6$ haloalkyl, or oxo.

In some embodiments, $R_2$ is —(CH$_2$)$_n$—$R_{2S}$, wherein n is 1 and $R_{2S}$ is 4-membered heterocycloalkyl.

In some embodiments, $R_2$ is —(CH$_2$)$_n$—$R_{2S}$, wherein n is 1 and $R_{2S}$ is 4-membered heterocycloalkyl optionally substituted with one or more $C_1$-$C_6$ alkyl, $C_1$-$C_6$ haloalkyl, or oxo.

In some embodiments, $R_2$ is —(CH$_2$)$_n$—$R_{2S}$, wherein n is 1 and $R_{2S}$ is oxetanyl optionally substituted with one or more $C_1$-$C_6$ alkyl, $C_1$-$C_6$ haloalkyl, or oxo.

In some embodiments, $R_2$ is —(CH$_2$)$_n$—$R_{2S}$, wherein n is 1 and $R_{2S}$ is azetidinyl optionally substituted with one or more $C_1$-$C_6$ alkyl, $C_1$-$C_6$ haloalkyl, or oxo.

In some embodiments, $R_2$ is —(CH$_2$)$_n$—$R_{2S}$, wherein n is 2 and $R_{2S}$ is 4-membered heterocycloalkyl.

In some embodiments, $R_2$ is —(CH$_2$)$_n$—$R_{2S}$, wherein n is 2 and $R_{2S}$ is 4-membered heterocycloalkyl optionally substituted with one or more $C_1$-$C_6$ alkyl, $C_1$-$C_6$ haloalkyl, or oxo.

In some embodiments, $R_2$ is —(CH$_2$)$_n$—$R_{2S}$, wherein n is 2 and $R_{2S}$ is oxetanyl optionally substituted with one or more $C_1$-$C_6$ alkyl, $C_1$-$C_6$ haloalkyl, or oxo.

In some embodiments, $R_2$ is —(CH$_2$)$_n$—$R_{2S}$, wherein n is 2 and $R_{2S}$ is azetidinyl optionally substituted with one or more $C_1$-$C_6$ alkyl, $C_1$-$C_6$ haloalkyl, or oxo.

In some embodiments, $R_{2S}$ is 7-membered heterocycloalkyl.

In some embodiments, $R_{2S}$ is 7-membered heterocycloalkyl optionally substituted with one or more $C_1$-$C_6$ alkyl, $C_2$-$C_6$ alkenyl, $C_2$-$C_6$ alkynyl, $C_1$-$C_6$ haloalkyl, halo, —CN, —OH, —O($C_1$-$C_6$ alkyl), —NH$_2$, —NH($C_1$-$C_6$ alkyl), —N($C_1$-$C_6$ alkyl)$_2$, or oxo.

In some embodiments, $R_{2S}$ is 7-membered heterocycloalkyl optionally substituted with one or more $C_1$-$C_6$ alkyl, $C_1$-$C_6$ haloalkyl, or oxo.

In some embodiments, $R_{2S}$ is 7-membered heterocycloalkyl optionally substituted with one or more $C_1$-$C_6$ alkyl or oxo.

In some embodiments, $R_{2S}$ is 7-membered heterocycloalkyl optionally substituted with one or more $C_1$-$C_6$ alkyl or $C_1$-$C_6$ haloalkyl.

In some embodiments, $R_{2S}$ is 7-membered heterocycloalkyl optionally substituted with one or more $C_1$-$C_6$ alkyl.

In some embodiments, $R_{2S}$ is oxepanyl optionally substituted with one or more $C_1$-$C_6$ alkyl, $C_1$-$C_6$ haloalkyl, or oxo.

In some embodiments, $R_{2S}$ is oxepanyl optionally substituted with one or more $C_1$-$C_6$ alkyl or oxo.

In some embodiments, $R_{2S}$ is oxepanyl optionally substituted with one or more $C_1$-$C_6$ alkyl or $C_1$-$C_6$ haloalkyl.

In some embodiments, $R_{2S}$ is oxepanyl optionally substituted with one or more $C_1$-$C_6$ alkyl.

In some embodiments, $R_{2S}$ is oxepanyl optionally substituted with one or more methyl. In some embodiments, $R_{2S}$ is oxepanyl optionally substituted with one or more ethyl. In some embodiments, $R_{2S}$ is oxepanyl optionally substituted with one or more propyl. In some embodiments, $R_{2S}$ is oxepanyl optionally substituted with one or more butyl. In some embodiments, $R_{2S}$ is oxepanyl optionally substituted with one or more pentyl. In some embodiments, $R_{2S}$ is oxepanyl optionally substituted with one or more hexyl.

In some embodiments, $R_{2S}$ is oxepanyl optionally substituted with one or more oxo.

In some embodiments, $R_{2S}$ is oxepanyl optionally substituted with one or more $C_1$-$C_6$ haloalkyl (e.g. methyl, ethyl, propyl, butyl, pentyl, or hexyl optionally substituted with one or more halo).

In some embodiments, $R_{2S}$ is azepanyl optionally substituted with one or more $C_1$-$C_6$ alkyl, $C_1$-$C_6$ haloalkyl, or oxo.

In some embodiments, $R_{2S}$ is azepanyl optionally substituted with one or more $C_1$-$C_6$ alkyl or oxo.

In some embodiments, $R_{2S}$ is azepanyl optionally substituted with one or more $C_1$-$C_6$ alkyl or $C_1$-$C_6$ haloalkyl.

In some embodiments, $R_{2S}$ is azepanyl optionally substituted with one or more $C_1$-$C_6$ alkyl.

In some embodiments, $R_{2S}$ is azepanyl optionally substituted with one or more methyl. In some embodiments, $R_{2S}$ is azepanyl optionally substituted with one or more ethyl. In some embodiments, $R_{2S}$ is azepanyl optionally substituted with one or more propyl. In some embodiments, $R_{2S}$ is azepanyl optionally substituted with one or more butyl. In some embodiments, $R_{2S}$ is azepanyl optionally substituted with one or more pentyl. In some embodiments, $R_{2S}$ is azepanyl optionally substituted with one or more hexyl.

In some embodiments, $R_{2S}$ is azepanyl optionally substituted with one or more oxo.

In some embodiments, $R_{2S}$ is azepanyl optionally substituted with one or more $C_1$-$C_6$ haloalkyl (e.g. methyl, ethyl, propyl, butyl, pentyl, or hexyl optionally substituted with one or more halo).

In some embodiments, R$_{2S}$ is

[structure: N-methyl azepane attached via 4-position]

In some embodiments, R$_2$ is —(CH$_2$)$_n$—R$_{2S}$, wherein n is 0 and R$_{2S}$ is 7-membered heterocycloalkyl.

In some embodiments, R$_2$ is —(CH$_2$)$_n$—R$_{2S}$, wherein n is 0 and R$_{2S}$ is 7-membered heterocycloalkyl optionally substituted with one or more C$_1$-C$_6$ alkyl, C$_1$-C$_6$ haloalkyl, or oxo.

In some embodiments, R$_2$ is —(CH$_2$)$_n$—R$_{2S}$, wherein n is 0 and R$_{2S}$ is oxepanyl optionally substituted with one or more C$_1$-C$_6$ alkyl, C$_1$-C$_6$ haloalkyl, or oxo.

In some embodiments, R$_2$ is —(CH$_2$)$_n$—R$_{2S}$, wherein n is 0 and R$_{2S}$ is azepanyl optionally substituted with one or more C$_1$-C$_6$ alkyl, C$_1$-C$_6$ haloalkyl, or oxo.

In some embodiments, R$_2$ is —(CH$_2$)$_n$—R$_{2S}$, wherein n is 1 and R$_{2S}$ is 7-membered heterocycloalkyl.

In some embodiments, R$_2$ is —(CH$_2$)$_n$—R$_{2S}$, wherein n is 1 and R$_{2S}$ is 7-membered heterocycloalkyl optionally substituted with one or more C$_1$-C$_6$ alkyl, C$_1$-C$_6$ haloalkyl, or oxo.

In some embodiments, R$_2$ is —(CH$_2$)$_n$—R$_{2S}$, wherein n is 1 and R$_{2S}$ is oxepanyl optionally substituted with one or more C$_1$-C$_6$ alkyl, C$_1$-C$_6$ haloalkyl, or oxo.

In some embodiments, R$_2$ is —(CH$_2$)$_n$—R$_{2S}$, wherein n is 1 and R$_{2S}$ is azepanyl optionally substituted with one or more C$_1$-C$_6$ alkyl, C$_1$-C$_6$ haloalkyl, or oxo.

In some embodiments, R$_2$ is —(CH$_2$)$_n$—R$_{2S}$, wherein n is 2 and R$_{2S}$ is 7-membered heterocycloalkyl.

In some embodiments, R$_2$ is —(CH$_2$)$_n$—R$_{2S}$, wherein n is 2 and R$_{2S}$ is 7-membered heterocycloalkyl optionally substituted with one or more C$_1$-C$_6$ alkyl, C$_1$-C$_6$ haloalkyl, or oxo.

In some embodiments, R$_2$ is —(CH$_2$)$_n$—R$_{2S}$, wherein n is 2 and R$_{2S}$ is oxepanyl optionally substituted with one or more C$_1$-C$_6$ alkyl, C$_1$-C$_6$ haloalkyl, or oxo.

In some embodiments, R$_2$ is —(CH$_2$)$_n$—R$_{2S}$, wherein n is 2 and R$_{2S}$ is azepanyl optionally substituted with one or more C$_1$-C$_6$ alkyl, C$_1$-C$_6$ haloalkyl, or oxo.

In some embodiments, R$_{2S}$ is 8-membered heterocycloalkyl.

In some embodiments, R$_{2S}$ is 8-membered heterocycloalkyl optionally substituted with one or more C$_1$-C$_6$ alkyl, C$_2$-C$_6$ alkenyl, C$_2$-C$_6$ alkynyl, C$_1$-C$_6$ haloalkyl, halo, —CN, —OH, —O(C$_1$-C$_6$ alkyl), —NH$_2$, —NH(C$_1$-C$_6$ alkyl), —N(C$_1$-C$_6$ alkyl)$_2$, or oxo.

In some embodiments, R$_{2S}$ is 8-membered heterocycloalkyl optionally substituted with one or more C$_1$-C$_6$ alkyl, C$_1$-C$_6$ haloalkyl, or oxo.

In some embodiments, R$_{2S}$ is 8-membered heterocycloalkyl optionally substituted with one or more C$_1$-C$_6$ alkyl or oxo.

In some embodiments, R$_{2S}$ is 8-membered heterocycloalkyl optionally substituted with one or more C$_1$-C$_6$ alkyl or C$_1$-C$_6$ haloalkyl.

In some embodiments, R$_{2S}$ is 8-membered heterocycloalkyl optionally substituted with one or more C$_1$-C$_6$ alkyl.

In some embodiments, R$_{2S}$ is oxocanyl optionally substituted with one or more C$_1$-C$_6$ alkyl, C$_1$-C$_6$ haloalkyl, or oxo.

In some embodiments, R$_{2S}$ is oxocanyl optionally substituted with one or more C$_1$-C$_6$ alkyl or oxo.

In some embodiments, R$_{2S}$ is oxocanyl optionally substituted with one or more C$_1$-C$_6$ alkyl or C$_1$-C$_6$ haloalkyl.

In some embodiments, R$_{2S}$ is oxocanyl optionally substituted with one or more C$_1$-C$_6$ alkyl.

In some embodiments, R$_{2S}$ is oxocanyl optionally substituted with one or more methyl. In some embodiments, R$_{2S}$ is oxocanyl optionally substituted with one or more ethyl. In some embodiments, R$_{2S}$ is oxocanyl optionally substituted with one or more propyl. In some embodiments, R$_{2S}$ is oxocanyl optionally substituted with one or more butyl. In some embodiments, R$_{2S}$ is oxocanyl optionally substituted with one or more pentyl. In some embodiments, R$_{2S}$ is oxocanyl optionally substituted with one or more hexyl.

In some embodiments, R$_{2S}$ is oxocanyl optionally substituted with one or more oxo.

In some embodiments, R$_{2S}$ is oxocanyl optionally substituted with one or more C$_1$-C$_6$ haloalkyl (e.g. methyl, ethyl, propyl, butyl, pentyl, or hexyl optionally substituted with one or more halo).

In some embodiments, R$_{2S}$ is azocanyl optionally substituted with one or more C$_1$-C$_6$ alkyl, C$_1$-C$_6$ haloalkyl, or oxo.

In some embodiments, R$_{2S}$ is azocanyl optionally substituted with one or more C$_1$-C$_6$ alkyl or oxo.

In some embodiments, R$_{2S}$ is azocanyl optionally substituted with one or more C$_1$-C$_6$ alkyl or C$_1$-C$_6$ haloalkyl.

In some embodiments, R$_{2S}$ is azocanyl optionally substituted with one or more C$_1$-C$_6$ alkyl.

In some embodiments, R$_{2S}$ is azocanyl optionally substituted with one or more methyl. In some embodiments, R$_{2S}$ is azocanyl optionally substituted with one or more ethyl. In some embodiments, R$_{2S}$ is azocanyl optionally substituted with one or more propyl. In some embodiments, R$_{2S}$ is azocanyl optionally substituted with one or more butyl. In some embodiments, R$_{2S}$ is azocanyl optionally substituted with one or more pentyl. In some embodiments, R$_{2S}$ is azocanyl optionally substituted with one or more hexyl.

In some embodiments, R$_{2S}$ is azocanyl optionally substituted with one or more oxo.

In some embodiments, R$_{2S}$ is azocanyl optionally substituted with one or more C$_1$-C$_6$ haloalkyl (e.g. methyl, ethyl, propyl, butyl, pentyl, or hexyl optionally substituted with one or more halo).

In some embodiments, R$_2$ is —(CH$_2$)$_n$—R$_{2S}$, wherein n is 0 and R$_{2S}$ is 8-membered heterocycloalkyl.

In some embodiments, R$_2$ is —(CH$_2$)$_n$—R$_{2S}$, wherein n is 0 and R$_{2S}$ is 8-membered heterocycloalkyl optionally substituted with one or more C$_1$-C$_6$ alkyl, C$_1$-C$_6$ haloalkyl, or oxo.

In some embodiments, R$_2$ is —(CH$_2$)$_n$—R$_{2S}$, wherein n is 0 and R$_{2S}$ is oxocanyl optionally substituted with one or more C$_1$-C$_6$ alkyl, C$_1$-C$_6$ haloalkyl, or oxo.

In some embodiments, R$_2$ is —(CH$_2$)$_n$—R$_{2S}$, wherein n is 0 and R$_{2S}$ is azocanyl optionally substituted with one or more C$_1$-C$_6$ alkyl, C$_1$-C$_6$ haloalkyl, or oxo.

In some embodiments, R$_2$ is —(CH$_2$)$_n$—R$_{2S}$, wherein n is 1 and R$_{2S}$ is 8-membered heterocycloalkyl.

In some embodiments, R$_2$ is —(CH$_2$)$_n$—R$_{2S}$, wherein n is 1 and R$_{2S}$ is 8-membered heterocycloalkyl optionally substituted with one or more C$_1$-C$_6$ alkyl, C$_1$-C$_6$ haloalkyl, or oxo.

In some embodiments, R$_2$ is —(CH$_2$)$_n$—R$_{2S}$, wherein n is 1 and R$_{2S}$ is oxocanyl optionally substituted with one or more C$_1$-C$_6$ alkyl, C$_1$-C$_6$ haloalkyl, or oxo.

In some embodiments, R$_2$ is —(CH$_2$)$_n$—R$_{2S}$, wherein n is 1 and R$_{2S}$ is azocanyl optionally substituted with one or more C$_1$-C$_6$ alkyl, C$_1$-C$_6$ haloalkyl, or oxo.

In some embodiments, R$_2$ is —(CH$_2$)$_n$—R$_{2S}$, wherein n is 2 and R$_{2S}$ is 8-membered heterocycloalkyl.

In some embodiments, R$_2$ is —(CH$_2$)$_n$—R$_{2S}$, wherein n is 2 and R$_{2S}$ is 8-membered heterocycloalkyl optionally substituted with one or more C$_1$-C$_6$ alkyl, C$_1$-C$_6$ haloalkyl, or oxo.

In some embodiments, R$_2$ is —(CH$_2$)$_n$—R$_{2S}$, wherein n is 2 and R$_{2S}$ is oxocanyl optionally substituted with one or more C$_1$-C$_6$ alkyl, C$_1$-C$_6$ haloalkyl, or oxo.

In some embodiments, R$_2$ is —(CH$_2$)$_n$—R$_{2S}$, wherein n is 2 and R$_{2S}$ is azocanyl optionally substituted with one or more C$_1$-C$_6$ alkyl, C$_1$-C$_6$ haloalkyl, or oxo.

In some embodiments, R$_{2S}$ is spiro heterocycloalkyl optionally substituted with one or more C$_1$-C$_6$ alkyl, C$_2$-C$_6$ alkenyl, C$_2$-C$_6$ alkynyl, C$_1$-C$_6$ haloalkyl, halo, —CN, —OH, —O(C$_1$-C$_6$ alkyl), —NH$_2$, —NH(C$_1$-C$_6$ alkyl), —N(C$_1$-C$_6$ alkyl)$_2$, or oxo.

In some embodiments, R$_{2S}$ is spiro heterocycloalkyl optionally substituted with one or more C$_1$-C$_6$ alkyl, C$_1$-C$_6$ haloalkyl, or oxo.

In some embodiments, R$_2$ is —(CH$_2$)$_n$—R$_{2S}$, wherein n is 0 and R$_{2S}$ is spiro heterocycloalkyl optionally substituted with one or more C$_1$-C$_6$ alkyl, C$_1$-C$_6$ haloalkyl, or oxo.

In some embodiments, R$_2$ is —(CH$_2$)$_n$—R$_{2S}$, wherein n is 1 and R$_{2S}$ is spiro heterocycloalkyl optionally substituted with one or more C$_1$-C$_6$ alkyl, C$_1$-C$_6$ haloalkyl, or oxo.

In some embodiments, R$_2$ is —(CH$_2$)$_n$—R$_{2S}$, wherein n is 2 and R$_{2S}$ is spiro heterocycloalkyl optionally substituted with one or more C$_1$-C$_6$ alkyl, C$_1$-C$_6$ haloalkyl, or oxo.

In some embodiments, R$_{2S}$ is spiro 7-membered heterocycloalkyl optionally substituted with one or more C$_1$-C$_6$ alkyl, C$_1$-C$_6$ haloalkyl, or oxo.

In some embodiments, R$_{2S}$ is spiro 7-membered heterocycloalkyl optionally substituted with one or more C$_1$-C$_6$ alkyl.

In some embodiments, R$_{2S}$ is spiro 7-membered heterocycloalkyl optionally substituted with one or more C$_1$-C$_6$ haloalkyl.

In some embodiments, R$_{2S}$ is 2-azaspiro[3.3]heptane optionally substituted with one or more C$_1$-C$_6$ alkyl, C$_1$-C$_6$ haloalkyl, or oxo. In some embodiments, R$_{2S}$ is 2-oxaspiro[3.3]heptane optionally substituted with one or more C$_1$-C$_6$ alkyl, C$_1$-C$_6$ haloalkyl, or oxo.

In some embodiments, R$_{2S}$ is

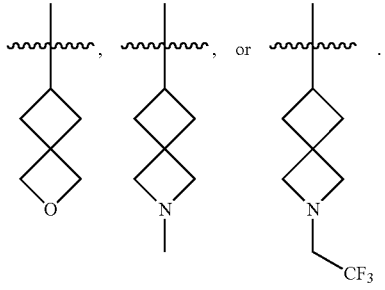

In some embodiments, R$_{2S}$ is bridged heterocycloalkyl optionally substituted with one or more C$_1$-C$_6$ alkyl, C$_2$-C$_6$ alkenyl, C$_2$-C$_6$ alkynyl, C$_1$-C$_6$ haloalkyl, halo, —CN, —OH, —O(C$_1$-C$_6$ alkyl), —NH$_2$, —NH(C$_1$-C$_6$ alkyl), —N(C$_1$-C$_6$ alkyl)$_2$, or oxo.

In some embodiments, R$_{2S}$ is bridged heterocycloalkyl optionally substituted with one or more C$_1$-C$_6$ alkyl, C$_1$-C$_6$ haloalkyl, or oxo.

In some embodiments, R$_2$ is —(CH$_2$)$_n$—R$_{2S}$, wherein n is 0 and R$_{2S}$ is bridged heterocycloalkyl optionally substituted with one or more C$_1$-C$_6$ alkyl, C$_1$-C$_6$ haloalkyl, or oxo.

In some embodiments, R$_2$ is —(CH$_2$)$_n$—R$_{2S}$, wherein n is 1 and R$_{2S}$ is bridged heterocycloalkyl optionally substituted with one or more C$_1$-C$_6$ alkyl, C$_1$-C$_6$ haloalkyl, or oxo.

In some embodiments, R$_2$ is —(CH$_2$)$_n$—R$_{2S}$, wherein n is 2 and R$_{2S}$ is bridged heterocycloalkyl optionally substituted with one or more C$_1$-C$_6$ alkyl, C$_1$-C$_6$ haloalkyl, or oxo.

In some embodiments, R$_{2S}$ is bridged 8-membered heterocycloalkyl optionally substituted with one or more C$_1$-C$_6$ alkyl, C$_1$-C$_6$ haloalkyl, or oxo.

In some embodiments, R$_{2S}$ is bridged quinuclidinyl optionally substituted with one or more C$_1$-C$_6$ alkyl, C$_1$-C$_6$ haloalkyl, or oxo.

In some embodiments, R$_{2S}$ is

In some embodiments, R$_2$ is

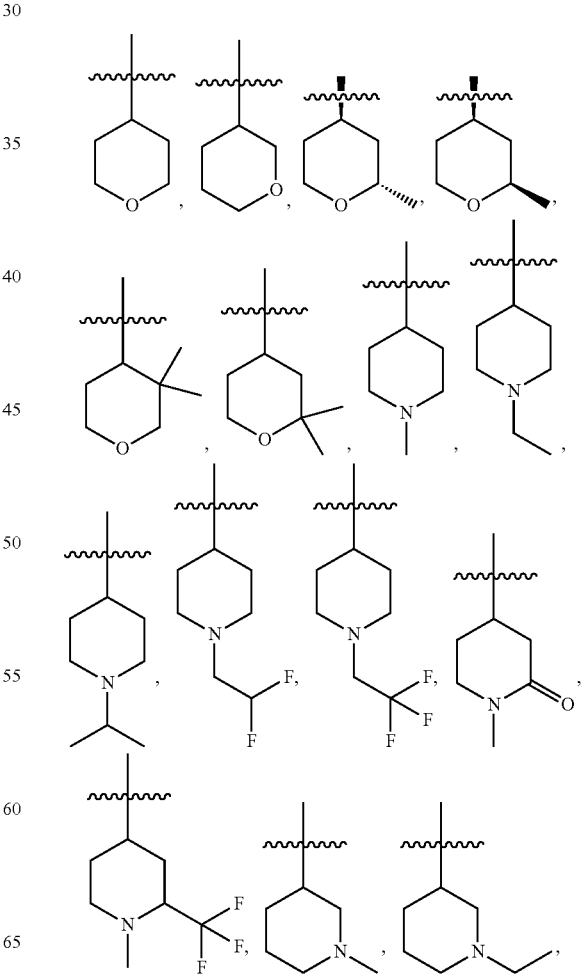

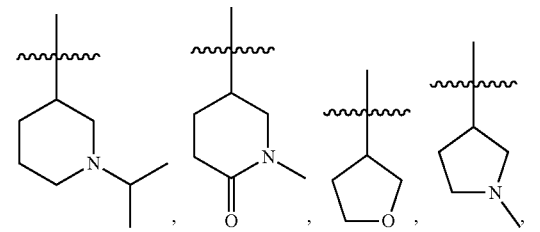
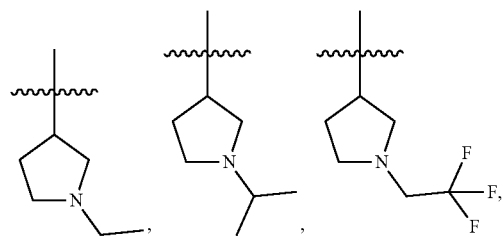
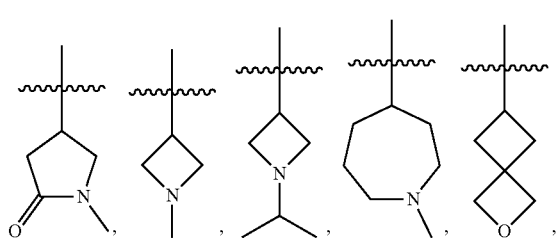
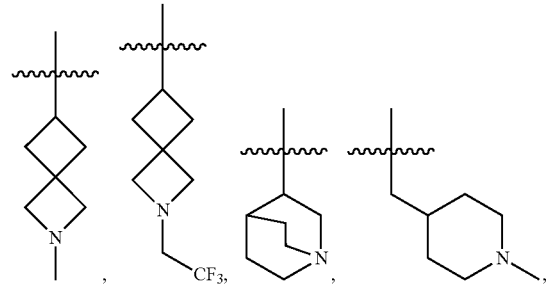
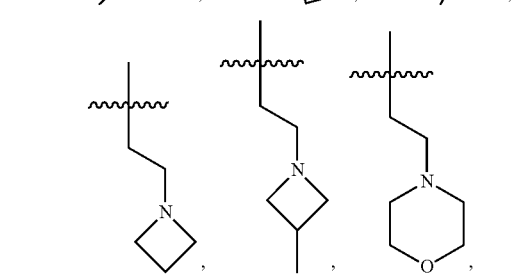

In some embodiments, R₃ is 7- to 12-membered heterocycloalkyl optionally substituted with one or more $R_{3S}$.

In some embodiments, R₃ is 7- to 12-membered heterocycloalkyl.

In some embodiments, R₃ is 8- to 11-membered heterocycloalkyl optionally substituted with one or more $R_{3S}$.

In some embodiments, R₃ is 8- to 11-membered heterocycloalkyl.

In some embodiments, R₃ is 9- or 10-membered heterocycloalkyl optionally substituted with one or more $R_{3S}$.

In some embodiments, R₃ is 9- or 10-membered heterocycloalkyl.

In some embodiments, R₃ is 9-membered heterocycloalkyl optionally substituted with one or more $R_{3S}$.

In some embodiments, R; is 9-membered heterocycloalkyl.

In some embodiments, R₃ is

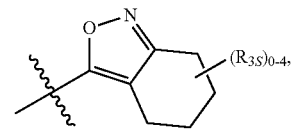

In some embodiments, $R_3$ is

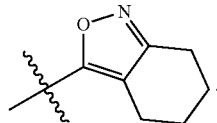

In some embodiments, $R_3$ is 5- or 6-membered heteroaryl optionally substituted with one or more $R_{3S}$, wherein each $R_{3S}$ is independently $C_1$-$C_6$ alkyl, $C_1$-$C_6$ haloalkyl, $C_3$-$C_8$ cycloalkyl, halo, or $C_3$-$C_8$ heterocycloalkyl wherein the $C_1$-$C_6$ alkyl, $C_1$-$C_6$ haloalkyl, $C_3$-$C_8$ cycloalkyl, or $C_3$-$C_8$ heterocycloalkyl is optionally substituted with —O($C_1$-$C_6$ alkyl), —N($C_1$-$C_6$ alkyl)$_2$, or —CN.

In some embodiments, $R_3$ is 5- or 6-membered heteroaryl optionally substituted with one or more $R_{3S}$, wherein each $R_{3S}$ is independently $C_1$-$C_6$ alkyl, $C_1$-$C_6$ haloalkyl, $C_3$-$C_8$ cycloalkyl, halo, or $C_3$-$C_8$ heterocycloalkyl wherein $C_1$-$C_6$ alkyl is optionally substituted with —O($C_1$-$C_6$ alkyl), —N($C_1$-$C_6$ alkyl)$_2$, halo, or —CN.

In some embodiments, $R_3$ is 5- or 6-membered heteroaryl optionally substituted with one or more $R_{3S}$, wherein each $R_{3S}$ is independently $C_1$-$C_6$ alkyl, $C_1$-$C_6$ haloalkyl, $C_3$-$C_8$ cycloalkyl, halo, or $C_3$-$C_8$ heterocycloalkyl wherein $C_1$-$C_6$ alkyl is optionally substituted with —O($C_1$-$C_6$ alkyl) or —N($C_1$-$C_6$ alkyl)$_2$.

In some embodiments, $R_3$ is 5- or 6-membered heteroaryl optionally substituted with one or more $R_{3S}$, wherein each $R_{1S}$ is independently $C_1$-$C_6$ alkyl, $C_1$-$C_6$ haloalkyl, $C_3$-$C_8$ cycloalkyl, halo, or $C_3$-$C_8$ heterocycloalkyl.

In some embodiments, $R_3$ is 5- or 6-membered heteroaryl optionally substituted with one or more $R_{3S}$, wherein each $R_{3S}$ is independently $C_1$-$C_6$ alkyl or $C_1$-$C_6$ haloalkyl.

In some embodiments, $R_3$ is 5- or 6-membered heteroaryl having one, two, or three heteroatoms.

In some embodiments, $R_3$ is 5- or 6-membered heteroaryl having one, two, or three heteroatoms selected from N and O.

In some embodiments, $R_3$ is 5- or 6-membered heteroaryl having one heteroatom selected from N and O.

In some embodiments, $R_3$ is 5- or 6-membered heteroaryl having two heteroatoms selected from N and O.

In some embodiments, $R_3$ is 5-membered heteroaryl optionally substituted with one or more $R_{3S}$, wherein each $R_{3S}$ is independently $C_1$-$C_6$ alkyl, $C_1$-$C_6$ haloalkyl, $C_3$-$C_8$ cycloalkyl, halo, or $C_3$-$C_8$ heterocycloalkyl wherein the $C_1$-$C_6$ alkyl, $C_1$-$C_6$ haloalkyl, $C_3$-$C_8$ cycloalkyl, or $C_3$-$C_8$ heterocycloalkyl is optionally substituted with —O($C_1$-$C_6$ alkyl), —N($C_1$-$C_6$ alkyl)$_2$, halo, or —CN.

In some embodiments, $R_3$ is 5-membered heteroaryl optionally substituted with one or more $R_{3S}$, wherein each $R_{3S}$ is independently $C_1$-$C_6$ alkyl, $C_1$-$C_6$ haloalkyl, $C_3$-$C_8$ cycloalkyl, halo, or $C_3$-$C_8$ heterocycloalkyl wherein $C_1$-$C_6$ alkyl is optionally substituted with —O($C_1$-$C_6$ alkyl), —N($C_1$-$C_6$ alkyl)$_2$, halo, or —CN.

In some embodiments, $R_3$ is 5-membered heteroaryl optionally substituted with one or more $R_{3S}$, wherein each $R_{3S}$ is independently $C_1$-$C_6$ alkyl, $C_1$-$C_6$ haloalkyl, $C_3$-$C_8$ cycloalkyl, halo, or $C_3$-$C_8$ heterocycloalkyl wherein $C_1$-$C_6$ alkyl is optionally substituted with —O($C_1$-$C_6$ alkyl) or —N($C_1$-$C_6$ alkyl)$_2$.

In some embodiments, R; is 5-membered heteroaryl optionally substituted with one or more $R_{3S}$, wherein each $R_{3S}$ is independently $C_1$-$C_6$ alkyl, $C_1$-$C_6$ haloalkyl, $C_3$-$C_8$ cycloalkyl, halo, or $C_3$-$C_8$ heterocycloalkyl.

In some embodiments, $R_3$ is 5-membered heteroaryl optionally substituted with one or more $R_{3S}$, wherein each $R_{3S}$ is independently $C_1$-$C_6$ alkyl, $C_1$-$C_6$ haloalkyl, or $C_3$-$C_8$ cycloalkyl.

In some embodiments, $R_3$ is 5-membered heteroaryl optionally substituted with one or more $R_{3S}$, wherein each $R_{3S}$ is independently $C_1$-$C_6$ alkyl or $C_1$-$C_6$ haloalkyl.

In some embodiments, $R_3$ is 5-membered heteroaryl optionally substituted with one or more $R_{3S}$, wherein each $R_{3S}$ is independently $C_1$-$C_6$ alkyl.

In some embodiments, $R_3$ is 6-membered heteroaryl optionally substituted with one or more $R_{3S}$, wherein each $R_{1S}$ is independently $C_1$-$C_6$ alkyl, $C_1$-$C_6$ haloalkyl, $C_3$-$C_8$ cycloalkyl, halo, or $C_3$-$C_8$ heterocycloalkyl wherein the $C_1$-$C_6$ alkyl, $C_1$-$C_6$ haloalkyl, $C_3$-$C_8$ cycloalkyl, or $C_3$-$C_8$ heterocycloalkyl is optionally substituted with —O($C_1$-$C_6$ alkyl), —N($C_1$-$C_6$ alkyl)$_2$, halo, or —CN.

In some embodiments, $R_3$ is 6-membered heteroaryl optionally substituted with one or more $R_{3S}$, wherein each $R_{3S}$ is independently $C_1$-$C_6$ alkyl, $C_1$-$C_6$ haloalkyl, $C_3$-$C_8$ cycloalkyl, halo, or $C_3$-$C_8$ heterocycloalkyl.

In some embodiments, $R_3$ is 6-membered heteroaryl optionally substituted with one or more $R_{3S}$, wherein each $R_{3S}$ is independently $C_1$-$C_6$ alkyl.

In some embodiments, $R_3$ is 5- or 6-membered heteroaryl optionally substituted with one or more $R_{3S}$.

In some embodiments, $R_3$ is 5-membered heteroaryl optionally substituted by one or more $R_{3S}$.

In some embodiments, $R_3$ is pyrrolyl optionally substituted by one or more $R_{3S}$.

In some embodiments, $R_3$ is

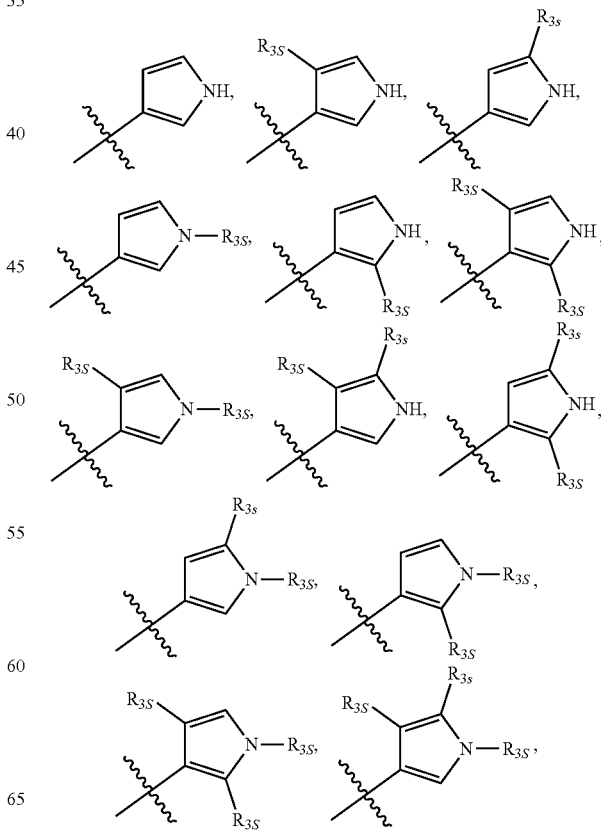

-continued
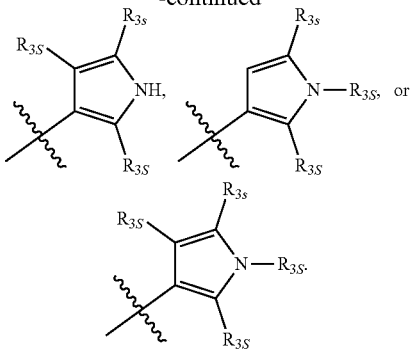
In some embodiments, R₃ is
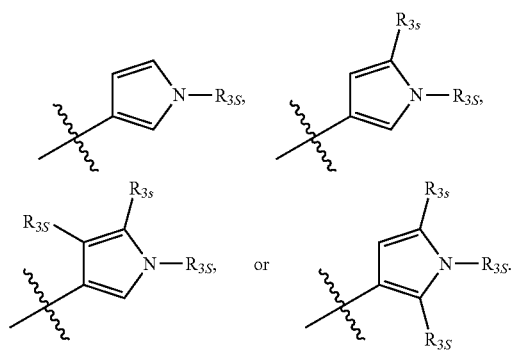
In some embodiments, R₃ is
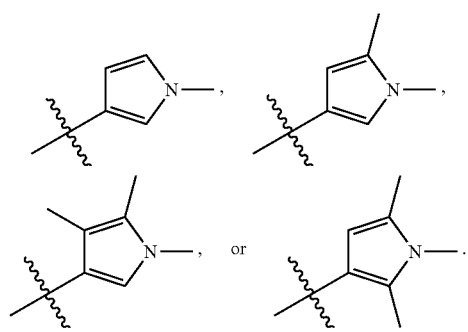
In some embodiments, R₃ is pyrazolyl optionally substituted by one or more R₃ₛ.
In some embodiments, R₃ is
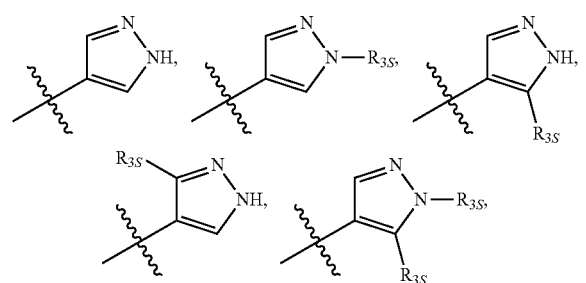
-continued
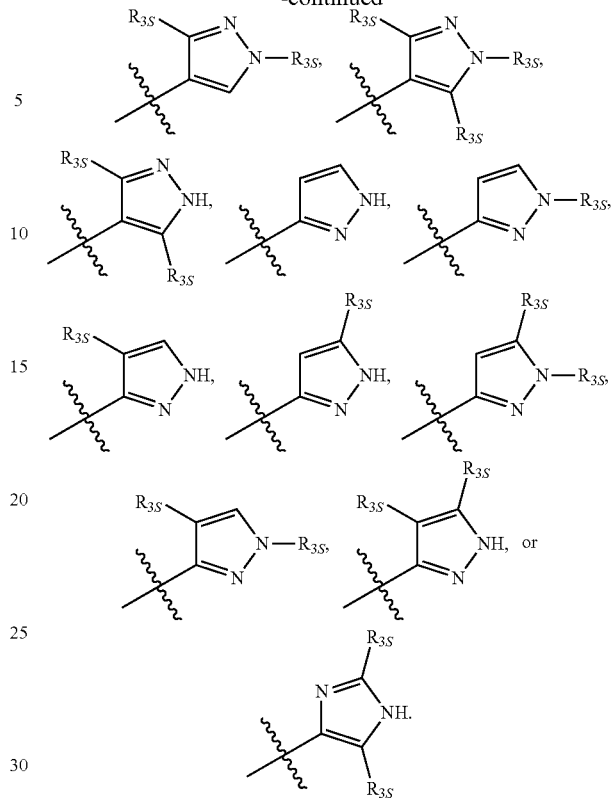
In some embodiments, R₃ is
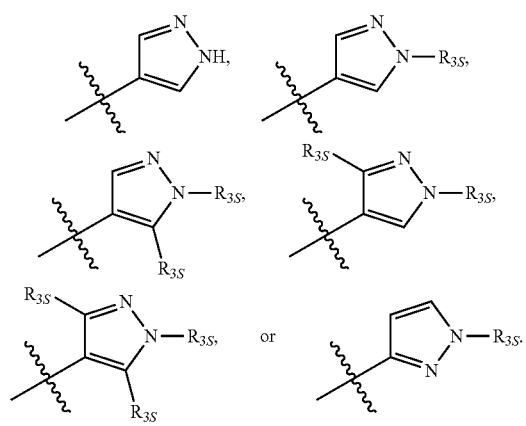
In some embodiments, R₃ is
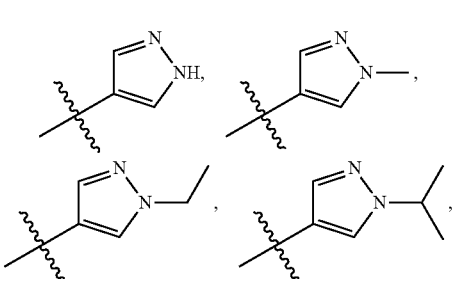

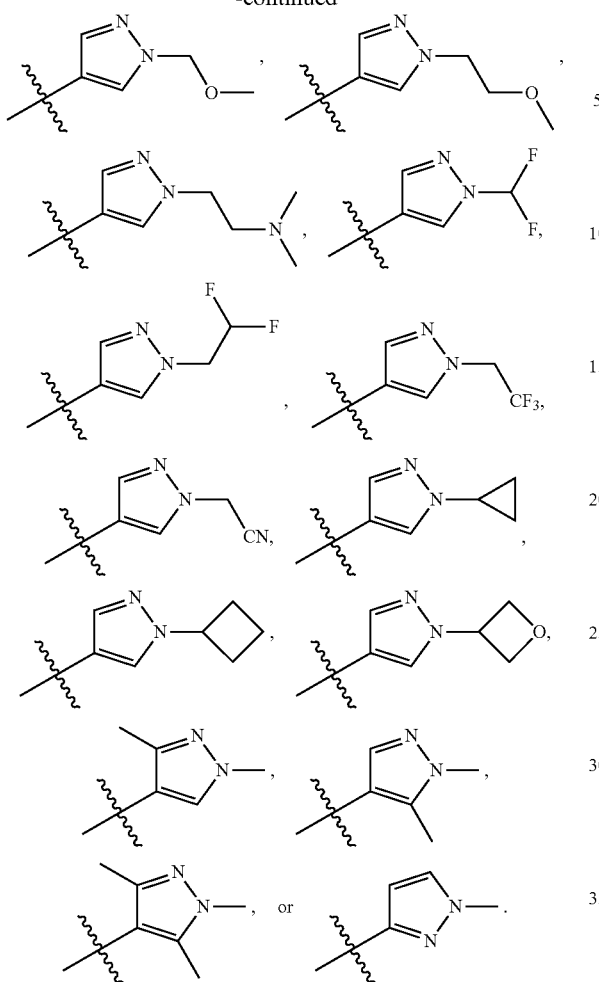
In some embodiments, R₃ is
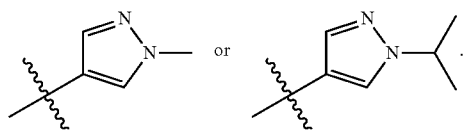
In some embodiments, R₃ is imidazolyl optionally substituted by one or more R₃ₛ.
In some embodiments, R₃ is
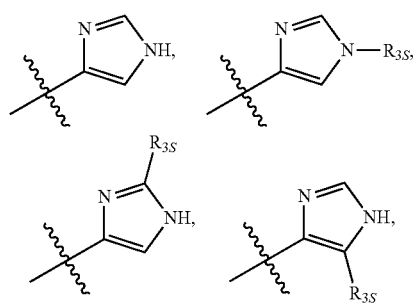
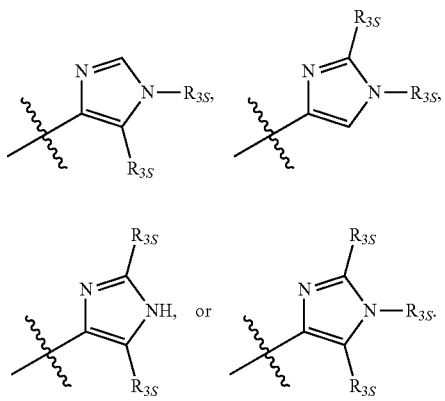
In some embodiments, R₃ is
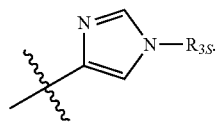
In some embodiments, R₃ is
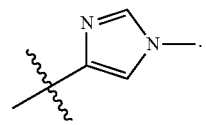 [SMILES: *c1cn(C)cn1]
In some embodiments, R₃ is triazolyl optionally substituted by one or more R₃ₛ.
In some embodiments, R₃ is
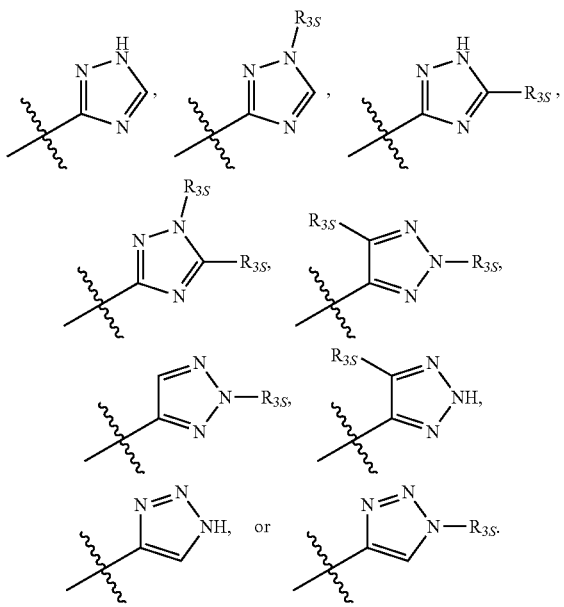

In some embodiments, R$_3$ is

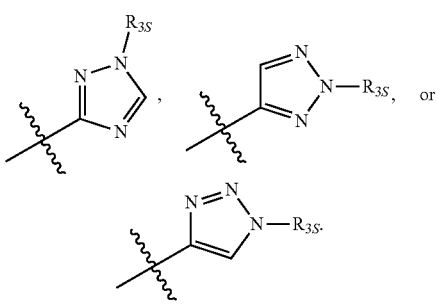

, or

In some embodiments, R$_3$ is

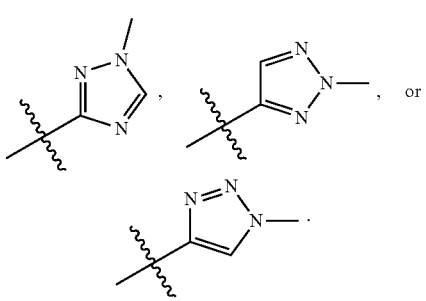

, or

In some embodiments, R$_3$ is tetrazolyl optionally substituted by one or more R$_{3S}$.

In some embodiments, R$_3$ is

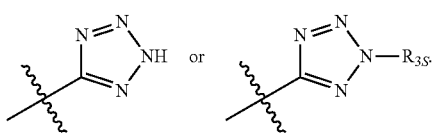

or

In some embodiments, R$_3$ is

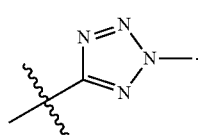 [SMILES: *c1nnn(C)n1]

In some embodiments, R$_3$ is isoxazolyl optionally substituted by one or more R$_{3S}$.

In some embodiments, R$_3$ is

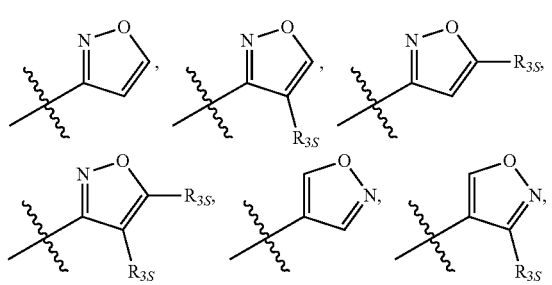

-continued

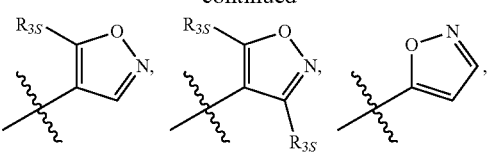

, or

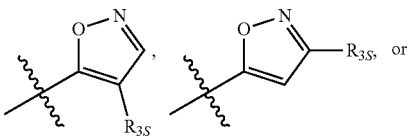

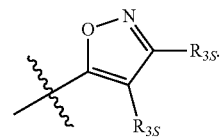

In some embodiments, R$_3$ is

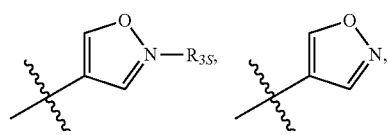

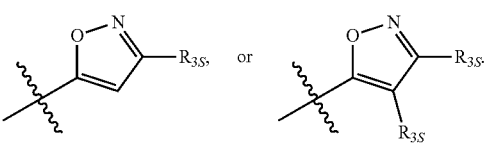

, or

In some embodiments, R$_3$ is

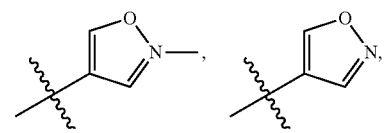

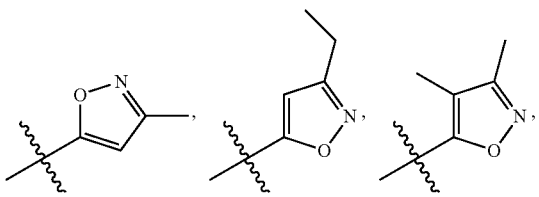

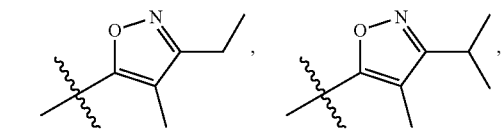

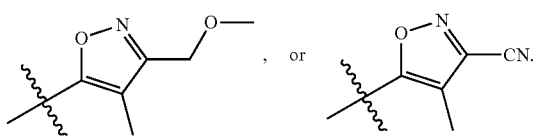

, or

In some embodiments, R$_3$ is furanyl optionally substituted by one or more R$_{3S}$.

In some embodiments, R₃ is
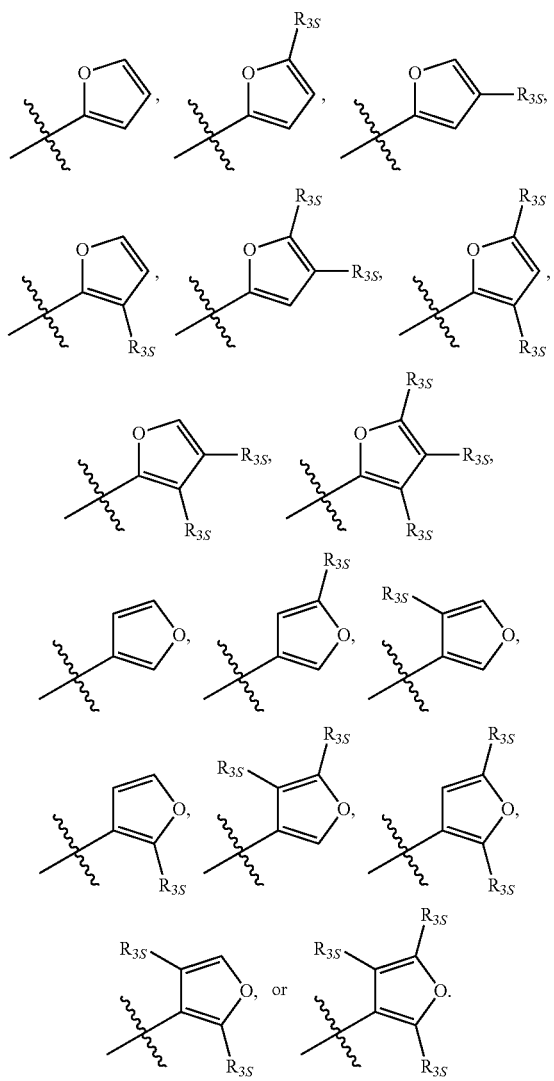
In some embodiments, R₃ is
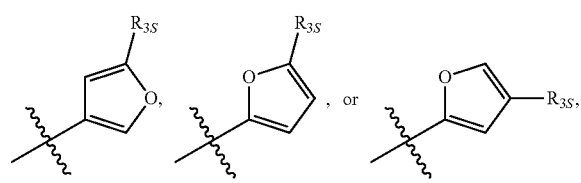
In some embodiments, R₃ is
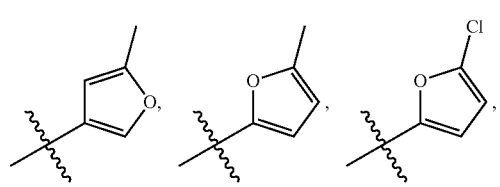
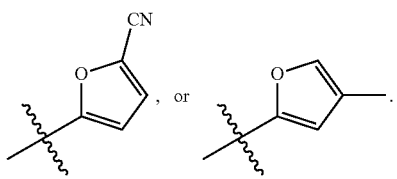
In some embodiments, R₃ is oxazolyl optionally substituted by one or more R₃ₛ.
In some embodiments, R₃ is
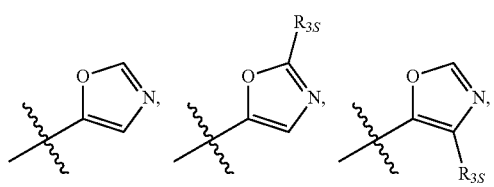
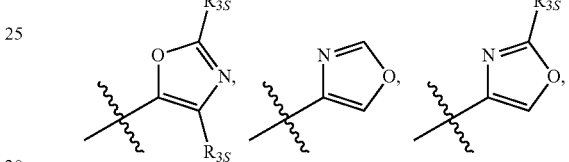
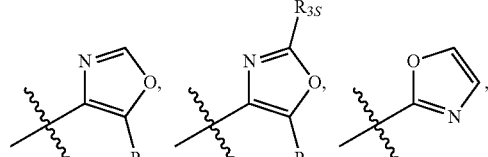
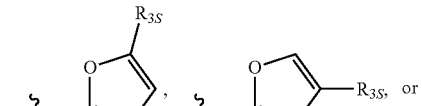
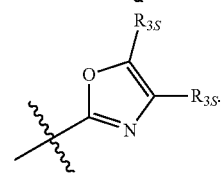
In some embodiments, R₃ is
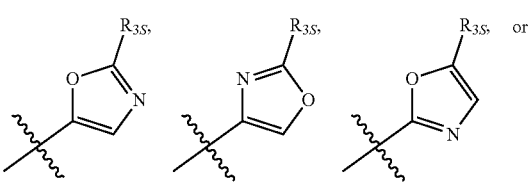

In some embodiments, $R_3$ is

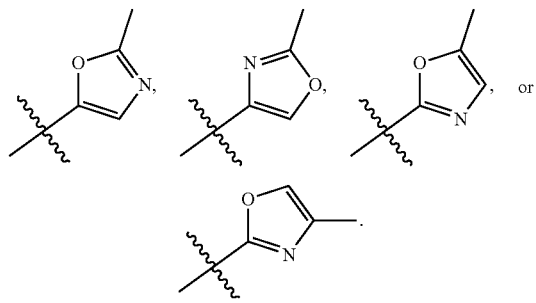, or

In some embodiments, $R_3$ is 4,5,6,7-tetrahydrobenzo[c]isoxazole optionally substituted by one or more $R_{3S}$.

In some embodiments, $R_3$ is

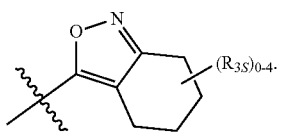

In some embodiments, $R_3$ is

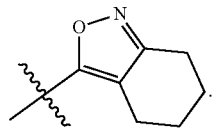 [SMILES: *c1onc2c1CCCC2]

In some embodiments, $R_3$ is isothiazolyl optionally substituted by one or more $R_{3S}$.

In some embodiments, $R_3$ is

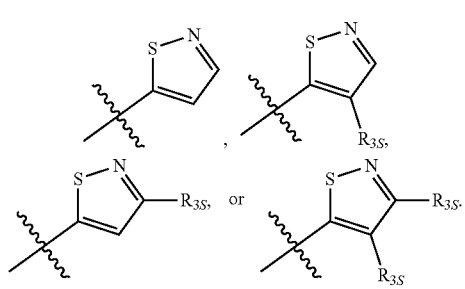

In some embodiments, $R_3$ is

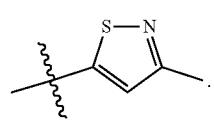 [SMILES: *c1cc(C)ns1]

In some embodiments, $R_3$ is thiazolyl optionally substituted by one or more $R_{3S}$.

In some embodiments, $R_3$ is

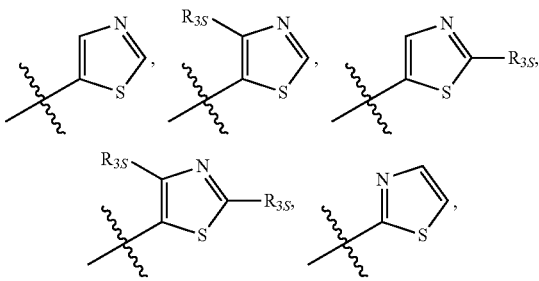

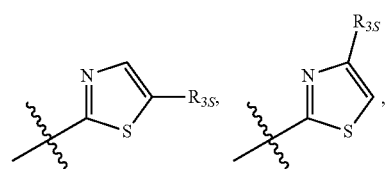

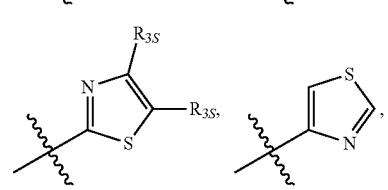

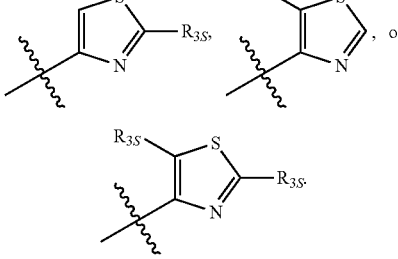

In some embodiments, $R_3$ is

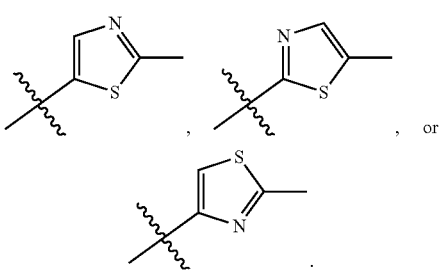

In some embodiments, $R_3$ is thiadiazolyl optionally substituted by one $R_{3S}$.

In some embodiments, $R_3$ is

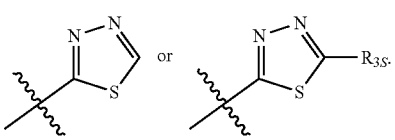

In some embodiments, R₃ is

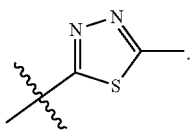

In some embodiments, R₃ is 6-membered heteroaryl optionally substituted by one or more $R_{3S}$.

In some embodiments, R₃ is pyridinyl optionally substituted by one or more $R_{3S}$. In some embodiments, R₃ is diazinyl optionally substituted by one or more $R_{3S}$. In some embodiments, R₃ is pyridazinyl optionally substituted by one or more $R_{3S}$. In some embodiments, R₃ is pyrimidinyl optionally substituted by one or more $R_{3S}$. In some embodiments, R₃ is pyrazinyl optionally substituted by one or more $R_{3S}$. In some embodiments, R₃ is triazinyl optionally substituted by one or more $R_{3S}$. In some embodiments, R₃ is tetrazinyl optionally substituted by one $R_{3S}$. In some embodiments, R₃ is pentazinyl.

In some embodiments, R₃ is

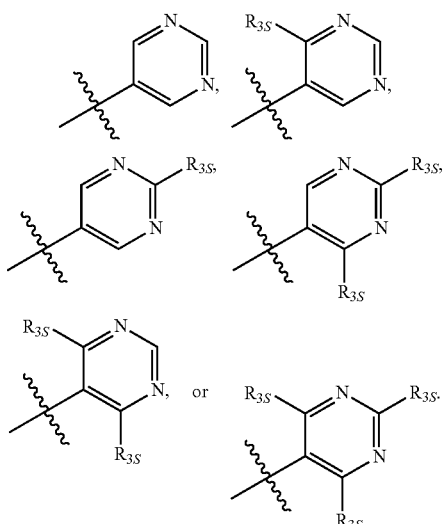

In some embodiments, R₃ is

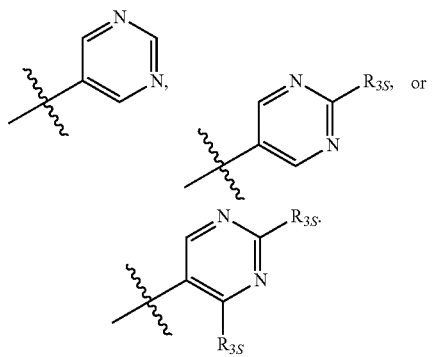

In some embodiments, R₃ is

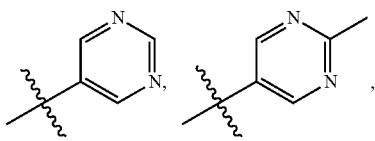

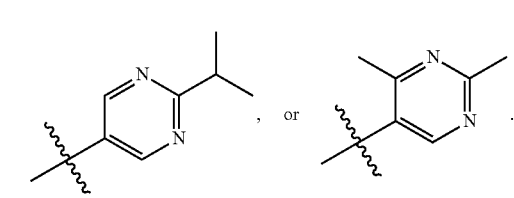

In some embodiments, R₃ is

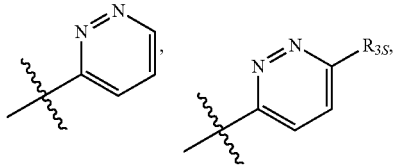

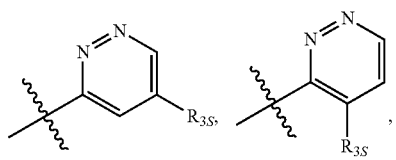

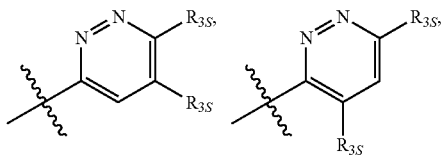

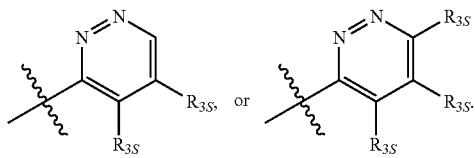

In some embodiments, R₃ is

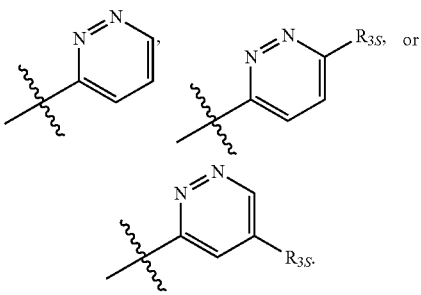

In some embodiments, R₃ is

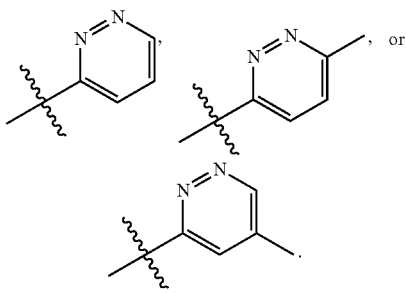

In some embodiments, at least one $R_{3S}$ is $C_1$-$C_6$ alkyl, $C_1$-$C_6$ haloalkyl, $C_3$-$C_8$ cycloalkyl, halo, or $C_3$-$C_8$ heterocycloalkyl.

In some embodiments, at least one $R_{3S}$ is $C_1$-$C_6$ alkyl, $C_1$-$C_6$ haloalkyl, or $C_3$-$C_8$ cycloalkyl.

In some embodiments, at least one $R_{3S}$ is $C_1$-$C_6$ alkyl or $C_1$-$C_6$ haloalkyl.

In some embodiments, at least one $R_{3S}$ is $C_1$-$C_6$ alkyl (e.g. linear or branched).

In some embodiments, at least one $R_{3S}$ is methyl. In some embodiments, at least one $R_{3S}$ is ethyl. In some embodiments, at least one $R_{3S}$ is propyl. In some embodiments, at least one $R_{3S}$ is butyl. In some embodiments, at least one $R_{3S}$ is pentyl. In some embodiments, at least one $R_{3S}$ is hexyl. In some embodiments, at least one $R_{3S}$ is isopropyl. In some embodiments, at least one $R_{3S}$ is isobutyl. In some embodiments, at least one $R_{3S}$ is isopentyl. In some embodiments, at least one $R_{3S}$ is isohexyl. In some embodiments, at least one $R_{3S}$ is secbutyl. In some embodiments, at least one $R_{3S}$ is secpentyl. In some embodiments, at least one $R_{3S}$ is sechexyl.

In some embodiments, at least one $R_{3S}$ is $C_1$-$C_6$ alkyl, $C_1$-$C_6$ haloalkyl, $C_3$-$C_8$ cycloalkyl, or $C_3$-$C_8$ heterocycloalkyl wherein the $C_1$-$C_6$ alkyl, $C_1$-$C_6$ haloalkyl, $C_3$-$C_8$ cycloalkyl, or $C_3$-$C_8$ heterocycloalkyl is optionally substituted with —O($C_1$-$C_6$ alkyl), —N($C_1$-$C_6$ alkyl)₂, halo, or —CN.

In some embodiments, at least one $R_{3S}$ is $C_1$-$C_6$ alkyl optionally substituted with —O($C_1$-$C_6$ alkyl), —N($C_1$-$C_6$ alkyl)₂, halo, or —CN.

In some embodiments, at least one $R_{3S}$ is $C_1$-$C_6$ alkyl optionally substituted with —O($C_1$-$C_6$ alkyl) or —N($C_1$-$C_6$ alkyl)₂.

In some embodiments, at least one $R_{3S}$ is $C_1$-$C_6$ alkyl optionally substituted with —O($C_1$-$C_6$ alkyl) (e.g. methyl, ethyl, propyl, butyl, pentyl, hexyl).

In some embodiments, at least one $R_{3S}$ is methyl optionally substituted with —O($C_1$-$C_6$ alkyl). In some embodiments, at least one $R_{3S}$ is ethyl optionally substituted with —O($C_1$-$C_6$ alkyl). In some embodiments, at least one $R_{3S}$ is propyl optionally substituted with —O($C_1$-$C_6$ alkyl). In some embodiments, at least one $R_{3S}$ is butyl optionally substituted with —O($C_1$-$C_6$ alkyl). In some embodiments, at least one $R_{3S}$ is pentyl optionally substituted with —O($C_1$-$C_6$ alkyl). In some embodiments, at least one $R_{3S}$ is hexyl optionally substituted with —O($C_1$-$C_6$ alkyl).

In some embodiments, at least one $R_{3S}$ is $C_1$-$C_6$ alkyl optionally substituted with —N($C_1$-$C_6$ alkyl)₂ (e.g. methyl, ethyl, propyl, butyl, pentyl, hexyl).

In some embodiments, at least one $R_{3S}$ is methyl optionally substituted with —N($C_1$-$C_6$ alkyl)₂. In some embodiments, at least one $R_{3S}$ is ethyl optionally substituted with —N($C_1$-$C_6$ alkyl)₂. In some embodiments, at least one $R_{3S}$ is propyl optionally substituted with —N($C_1$-$C_6$ alkyl)₂. In some embodiments, at least one $R_{3S}$ is butyl optionally substituted with —N($C_1$-$C_6$ alkyl)₂. In some embodiments, at least one $R_{3S}$ is pentyl optionally substituted with —N($C_1$-$C_6$ alkyl)₂. In some embodiments, at least one $R_{3S}$ is hexyl optionally substituted with —N($C_1$-$C_6$ alkyl)₂.

In some embodiments, at least one $R_{3S}$ is $C_1$-$C_6$ alkyl optionally substituted with —CN.

In some embodiments, at least one $R_{3S}$ is methyl optionally substituted with —CN. In some embodiments, at least one $R_{3S}$ is ethyl optionally substituted with —CN. In some embodiments, at least one $R_{3S}$ is propyl optionally substituted with —CN. In some embodiments, at least one $R_{3S}$ is butyl optionally substituted with —CN. In some embodiments, at least one $R_{3S}$ is pentyl optionally substituted with —CN. In some embodiments, at least one $R_{3S}$ is hexyl optionally substituted with —CN.

In some embodiments, at least one $R_{3S}$ is $C_1$-$C_6$ haloalkyl (e.g. methyl, ethyl, propyl, butyl, pentyl, or hexyl substituted with one or more halogen).

In some embodiments, at least one $R_{3S}$ is $C_1$-$C_6$ haloalkyl optionally substituted with —O($C_1$-$C_6$ alkyl), —N($C_1$-$C_6$ alkyl)₂, halo, or —CN.

In some embodiments, at least one $R_{3S}$ is —CH₂F, —CHF₂, —CF₃, —CH₂CH₂F, —CH₂CHF₂, or —CH₂CF₃.

In some embodiments, at least one $R_{3S}$ is —CHF₂. In some embodiments, at least one $R_{3S}$ is —CH₂CHF₂. In some embodiments, at least one $R_{3S}$ is —CH₂CF₃.

In some embodiments, at least one $R_{3S}$ is $C_3$-$C_8$ cycloalkyl.

In some embodiments, at least one $R_{3S}$ is $C_3$-$C_8$ cycloalkyl optionally substituted with —O($C_1$-$C_6$ alkyl), —N($C_1$-$C_6$ alkyl)₂, halo, or —CN.

In some embodiments, at least one $R_{3S}$ is $C_3$-$C_7$ cycloalkyl. In some embodiments, at least one $R_{3S}$ is $C_3$-$C_6$ cycloalkyl. In some embodiments, at least one $R_{3S}$ is $C_3$-$C_8$ cycloalkyl. In some embodiments, at least one $R_{3S}$ is $C_3$-$C_4$ cycloalkyl.

In some embodiments, at least one $R_{3S}$ is cyclopropyl.

In some embodiments, at least one $R_{3S}$ is cyclobutyl.

In some embodiments, at least one $R_{3S}$ is $C_3$-$C_8$ heterocycloalkyl.

In some embodiments, at least one $R_{3S}$ is $C_3$-$C_8$ heterocycloalkyl optionally substituted with —O($C_1$-$C_6$ alkyl), —N($C_1$-$C_6$ alkyl)₂, halo, or —CN.

In some embodiments, at least one $R_{3S}$ is $C_3$-$C_7$ heterocycloalkyl. In some embodiments, at least one $R_{3S}$ is $C_3$-$C_6$ heterocycloalkyl. In some embodiments, at least one $R_{1S}$ is $C_3$-$C_8$ heterocycloalkyl. In some embodiments, at least one $R_{3S}$ is $C_3$-$C_4$ heterocycloalkyl. In some embodiments, at least one $R_{3S}$ is $C_4$-$C_5$ heterocycloalkyl.

In some embodiments, at least one $R_{3S}$ is oxetanyl.

In some embodiments, at least one $R_{3S}$ is

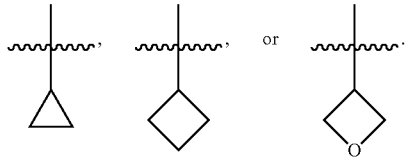

In some embodiments, at least one $R_{3S}$ is methyl, ethyl, isopropyl, —CH₂OCH₃, —CH₂CF₃, —CH₂CH₂OCH₃, —CH₂CN, CH₂CF₂, or —CH₂CH₂N(CH₃)₂.

In some embodiments, at least one $R_{3S}$ is halo.

In some embodiments, at least one $R_{3S}$ is F, Cl, Br, or I.

In some embodiments, at least one $R_{3S}$ is F or Cl.

In some embodiments, at least one $R_{3S}$ is F.

In some embodiments, at least one $R_{3S}$ is Cl.

In some embodiments, the compound is of Formula (Ia-1):

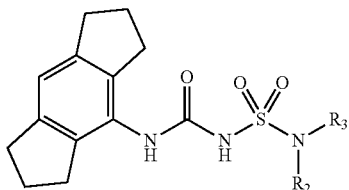

(Ia-1)

or a prodrug, solvate, or pharmaceutically acceptable salt thereof, wherein $R_2$ and $R_3$ are as described herein.

In some embodiments, the compound is of Formula (Ia-2):

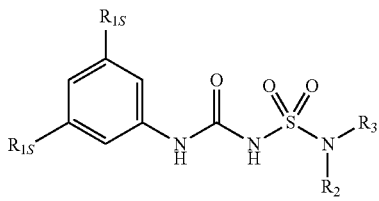

(Ia-2)

or a prodrug, solvate, or pharmaceutically acceptable salt thereof, wherein $R_{1S}$, $R_2$ and $R_3$ are as described herein.

In some embodiments, the compound is of Formula (Ib-1):

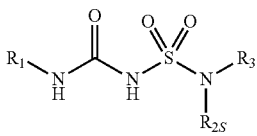

(Ib-1)

or a prodrug, solvate, or pharmaceutically acceptable salt thereof, wherein $R_1$, $R_{2S}$, and $R_3$ are as described herein.

In some embodiments, the compound is of Formula (Ib-2):

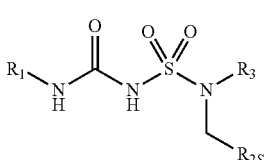

(Ib-2)

or a prodrug, solvate, or pharmaceutically acceptable salt thereof, wherein $R_1$, $R_{2S}$, and $R_3$ are as described herein.

In some embodiments, the compound is of Formula (Ib-3):

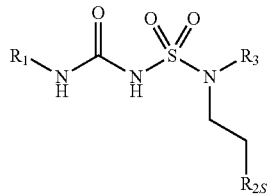

(Ib-3)

or a prodrug, solvate, or pharmaceutically acceptable salt thereof, wherein $R_1$, $R_{2S}$, and $R_3$ are as described herein.

In some embodiments, the compound is of any one of Formulae (Ib-1a), (Ib-1b), or (Ib-1c):

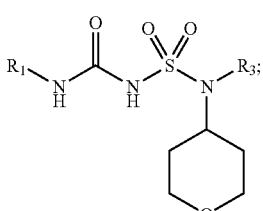

(Ib-1a)

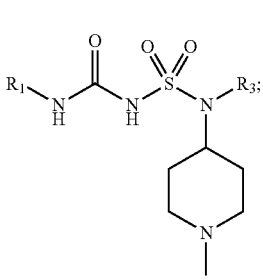

(Ib-1b)

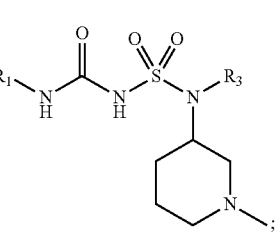

(Ib-1c)

or a prodrug, solvate, or pharmaceutically acceptable salt thereof, wherein $R_1$ and $R_3$ are as described herein.

In some embodiments, the compound is of Formula (Ib-1a) or a prodrug, solvate, or pharmaceutically acceptable salt thereof, wherein $R_1$ and $R_3$ are as described herein.

In some embodiments, the compound is of Formula (Ib-1b) or a prodrug, solvate, or pharmaceutically acceptable salt thereof, wherein $R_1$ and $R_3$ are as described herein.

In some embodiments, the compound is of Formula (Ib-1c) or a prodrug, solvate, or pharmaceutically acceptable salt thereof, wherein $R_1$ and $R_3$ are as described herein.

In some embodiments, the compound is of Formula (Ic-1), (Ic-2), (Ic-3), or (Ic-4):

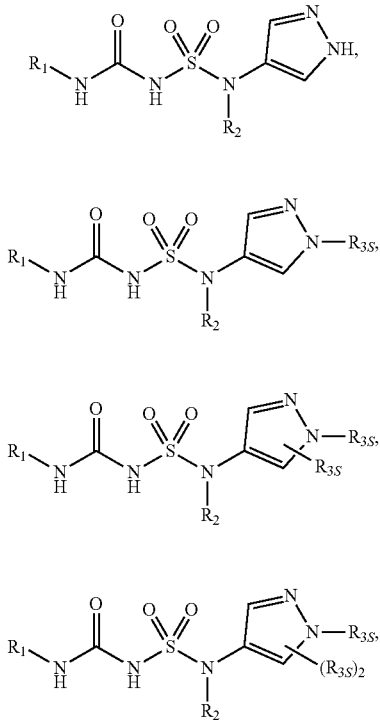

(Ic-1)

(Ic-2)

(Ic-3)

(Ic-4)

or a prodrug, solvate, or pharmaceutically acceptable salt thereof, wherein $R_1$, $R_2$ and $R_{3S}$, are as described herein.

In some embodiments, the compound is of Formula (Ic-1) or a prodrug, solvate, or pharmaceutically acceptable salt thereof, wherein $R_1$, $R_2$ and $R_{3S}$, are as described herein.

In some embodiments, the compound is of Formula (Ic-2) or a prodrug, solvate, or pharmaceutically acceptable salt thereof, wherein $R_1$, $R_2$ and $R_{3S}$, are as described herein.

In some embodiments, the compound is of Formula (Ic-3) or a prodrug, solvate, or pharmaceutically acceptable salt thereof, wherein $R_1$, $R_{12}$ and $R_{3S}$, are as described herein.

In some embodiments, the compound is of Formula (Ic-4) or a prodrug, solvate, or pharmaceutically acceptable salt thereof, wherein $R_1$, $R_2$ and $R_{3S}$, are as described herein.

In some embodiments, the compound is of Formula (Ic-5), (Ic-6), (Ic-7), or (Ic-8):

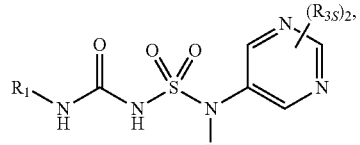

(Ic-5)

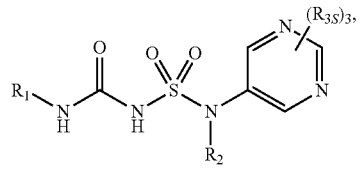

(Ic-6)

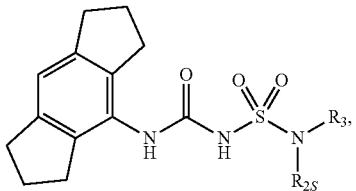

(Ic-7)

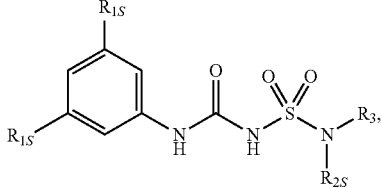

(Ic-8)

or a prodrug, solvate, or pharmaceutically acceptable salt thereof, wherein $R_1$, $R_2$ and $R_{3S}$, are as described herein.

In some embodiments, the compound is of Formula (Ic-5) or a prodrug, solvate, or pharmaceutically acceptable salt thereof, wherein $R_1$, $R_2$ and $R_{3S}$, are as described herein.

In some embodiments, the compound is of Formula (Ic-6) or a prodrug, solvate, or pharmaceutically acceptable salt thereof, wherein $R_1$, $R_2$ and $R_{3S}$, are as described herein.

In some embodiments, the compound is of Formula (Ic-7) or a prodrug, solvate, or pharmaceutically acceptable salt thereof, wherein $R_1$, $R_2$ and $R_{3S}$, are as described herein.

In some embodiments, the compound is of Formula (Ic-8) or a prodrug, solvate, or pharmaceutically acceptable salt thereof, wherein $R_1$, $R_2$ and $R_{3S}$, are as described herein.

In some embodiments, the compound is of Formula (Iab-1):

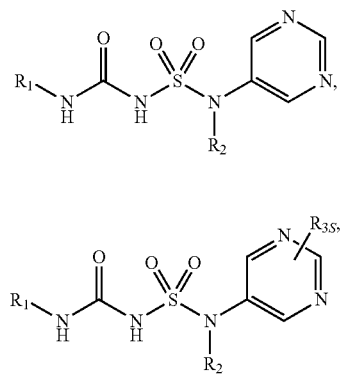

(Iab-1)

or a prodrug, solvate, or pharmaceutically acceptable salt thereof, wherein $R_{2S}$ and $R_3$ are as described herein.

In some embodiments, the compound is of Formula (Iab-2):

(Iab-2)

or a prodrug, solvate, or pharmaceutically acceptable salt thereof, wherein $R_{1S}$, $R_{2S}$, and $R_3$ are as described herein.

In some embodiments, the compound is of Formula (Iac-1):

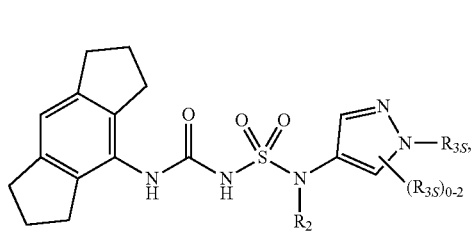
(Iac-1)

or a prodrug, solvate, or pharmaceutically acceptable salt thereof, wherein $R_2$ and $R_{3S}$ are as described herein.

In some embodiments, the compound is of Formula (Iac-2):

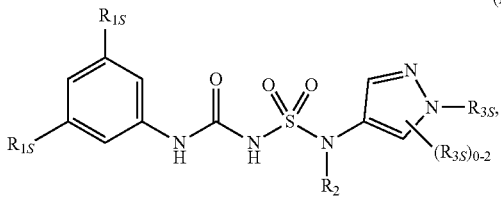
(Iac-2)

or a prodrug, solvate, or pharmaceutically acceptable salt thereof, wherein $R_{1S}$, $R_2$, and $R_{3S}$ are as described herein.

In some embodiments, the compound is of Formula (Iac-3):

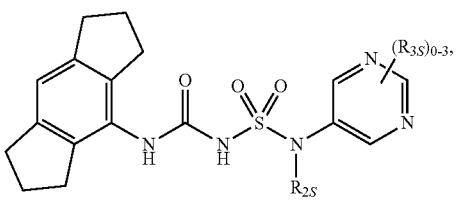
(Iac-3)

or a prodrug, solvate, or pharmaceutically acceptable salt thereof, wherein $R_2$ and $R_{3S}$ are as described herein.

In some embodiments, the compound is of Formula (Iac-4):

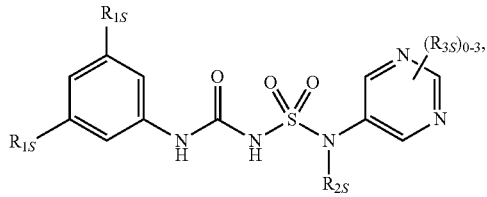
(Iac-4)

or a prodrug, solvate, or pharmaceutically acceptable salt thereof, wherein $R_{1S}$, $R_2$, and $R_{3S}$ are as described herein.

In some embodiments, the compound is of Formula (Ibc-1):

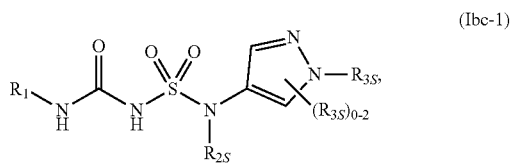
(Ibc-1)

or a prodrug, solvate, or pharmaceutically acceptable salt thereof, wherein $R_1$, $R_{2S}$, and $R_{3S}$ are as described herein.

In some embodiments, the compound is of Formula (Ibc-2):

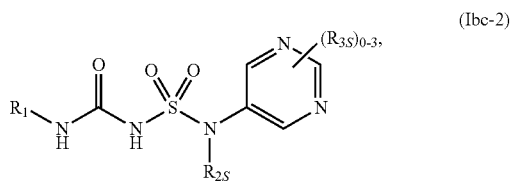
(Ibc-2)

or a prodrug, solvate, or pharmaceutically acceptable salt thereof, wherein $R_1$, $R_{2S}$, and $R_{3S}$ are as described herein.

In some embodiments, the compound is of Formula (Iabc-1):

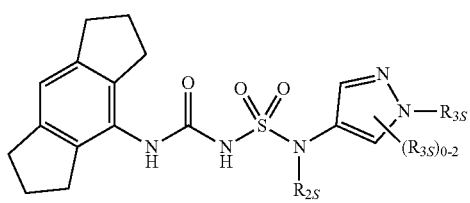

or a prodrug, solvate, or pharmaceutically acceptable salt thereof, wherein $R_{2S}$ and $R_{3S}$ are as described herein.

In some embodiments, the compound is of Formula (Iabc-1), wherein $R_{2S}$ is a 5- or 6-membered heterocycloalkyl containing 1 or 2 heteroatoms optionally chosen from N or O.

In some embodiments, the compound is of Formula (Iabc-1), wherein at least one $R_{3S}$ is independently $C_1$-$C_6$ alkyl, $C_1$-$C_6$ haloalkyl, $C_3$-$C_8$ cycloalkyl, halo, or $C_3$-$C_8$ heterocycloalkyl.

In some embodiments, the compound is of Formula (Iabc-1), wherein at least one $R_{3S}$ is independently $C_1$-$C_6$ alkyl, $C_1$-$C_6$ haloalkyl, $C_3$-$C_8$ cycloalkyl, halo, or $C_3$-$C_8$ heterocycloalkyl wherein $R_{3S}$ is optionally substituted with —O($C_1$-$C_6$ alkyl), —N($C_1$-$C_6$ alkyl)$_2$, halo, or —CN.

In some embodiments, the compound is of Formula (Iabc-1a):

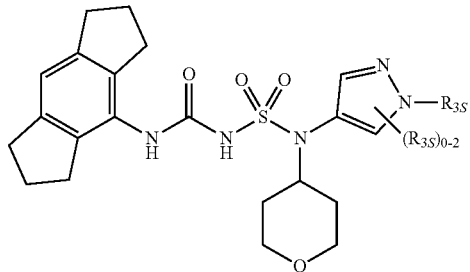
(Iabc-Ia)

or a prodrug, solvate, or pharmaceutically acceptable salt thereof, wherein $R_{3S}$ is as described herein.

In some embodiments, the compound is of Formula (Iabc-1b):

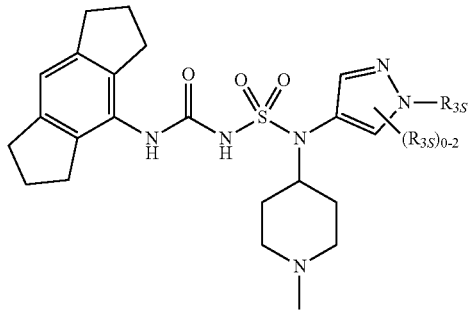
(Iabc-Ib)

or a prodrug, solvate, or pharmaceutically acceptable salt thereof, wherein $R_{3S}$ is as described herein.

It is understood that, for a compound of any one of the formulae described herein, $R_1$, $R_{1S}$, $R_2$, $R_{2S}$, $R_3$, and $R_{3S}$ can each be, where applicable, selected from the groups described herein, and any group described herein for any of $R_1$, $R_{1S}$, $R_2$, $R_{2S}$, $R_3$, and $R_{3S}$ can be combined, where applicable, with any group described herein for one or more of the remainder of $R_1$, $R_{1S}$, $R_2$, $R_{2S}$, $R_3$, and $R_{3S}$.

In some embodiments, the compound is selected from the compounds described in Tables 1 and 2 and prodrugs and pharmaceutically acceptable salts thereof.

In some embodiments, the compound is selected from the compounds described in Tables 1 and 2 and pharmaceutically acceptable salts thereof.

In some embodiments, the compound is selected from the compounds described in Table 1 and 2.

In some embodiments, the compound is selected from the compounds described in Table 1 and prodrugs and pharmaceutically acceptable salts thereof.

In some embodiments, the compound is selected from the compounds described in Table 1 and pharmaceutically acceptable salts thereof.

In some embodiments, the compound is selected from the compounds described in Table 1.

In some embodiments, the compound is selected from the compounds described in Table 2 and prodrugs and pharmaceutically acceptable salts thereof.

In some embodiments, the compound is selected from the compounds described in Table 2 and pharmaceutically acceptable salts thereof.

In some embodiments, the compound is selected from the compounds described in Table 2.

TABLE 1

| Compound No. | Structure |
|---|---|
| 1 | 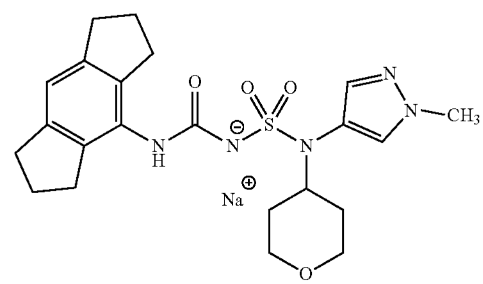 |
| 2 | 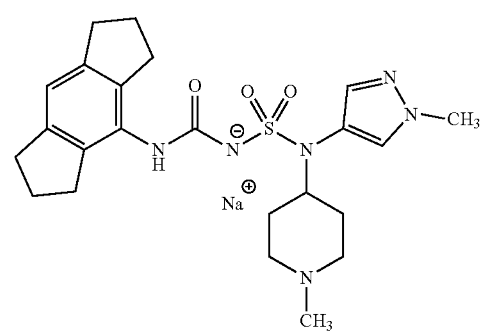 |

TABLE 1-continued
| Compound No. | Structure |
|---|---|
| 3 | 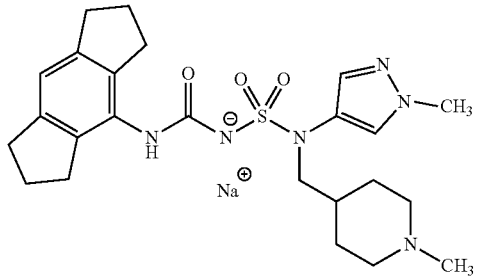 [SMILES: CN1CCC(CN(c2cnn(C)c2)S(=O)(=O)[N-]C(=O)Nc2c3c(cc4c2CCC4)CCC3)CC1 ; [Na+]] |
| 4 | 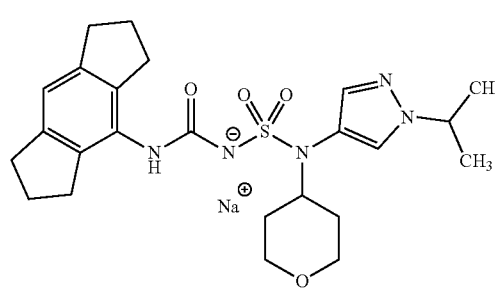 |
| 5 | 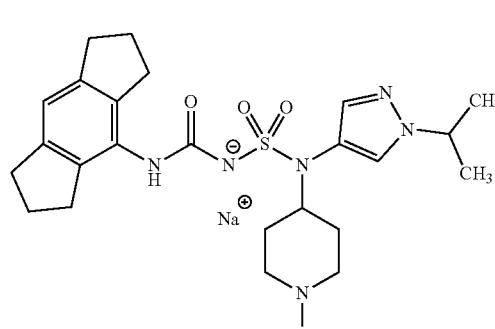 |
| 6 | 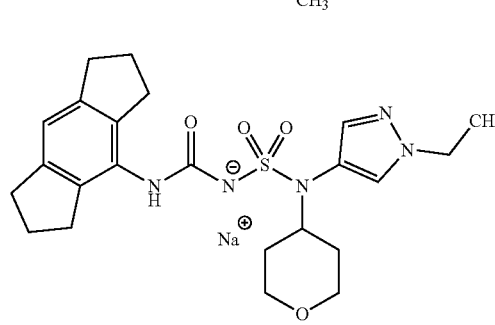 |
| 7 | 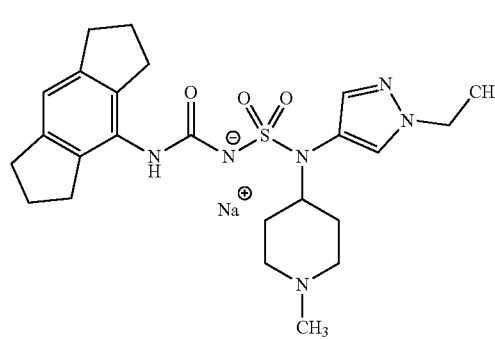 |

TABLE 1-continued

| Compound No. | Structure |
|---|---|
| 8 | 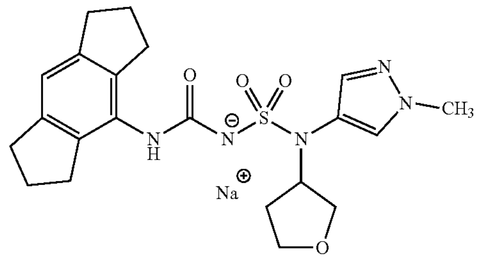 [SMILES: Cn1cc(N(C2CCOC2)S(=O)(=O)[N-]C(=O)Nc2c3c(cc4c2CCC4)CCC3)cn1 ; [Na+]] |
| 9 | 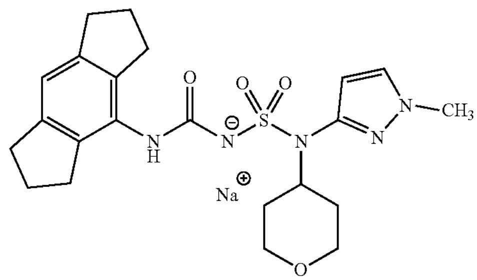 [SMILES: Cn1ccc(N(C2CCOCC2)S(=O)(=O)[N-]C(=O)Nc2c3c(cc4c2CCC4)CCC3)n1 ; [Na+]] |
| 10 | 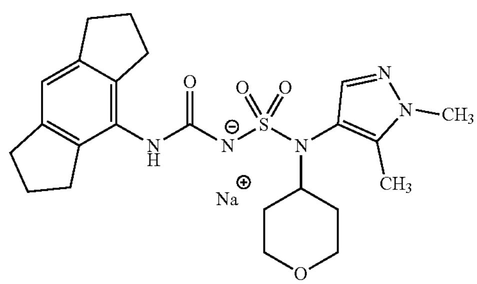 [SMILES: Cc1c(N(C2CCOCC2)S(=O)(=O)[N-]C(=O)Nc2c3c(cc4c2CCC4)CCC3)cnn1C ; [Na+]] |
| 11 | 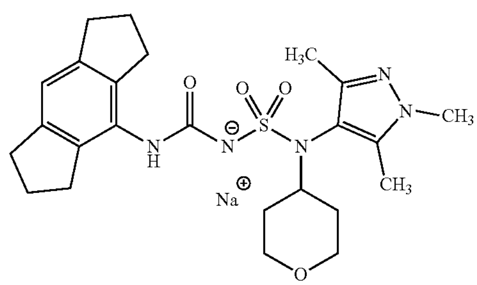 [SMILES: Cc1nn(C)c(C)c1N(C1CCOCC1)S(=O)(=O)[N-]C(=O)Nc1c2c(cc3c1CCC3)CCC2 ; [Na+]] |
| 12 | 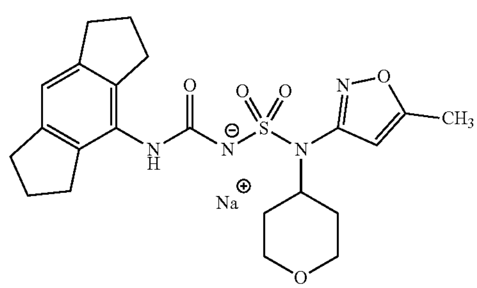 [SMILES: Cc1cc(N(C2CCOCC2)S(=O)(=O)[N-]C(=O)Nc2c3c(cc4c2CCC4)CCC3)no1 ; [Na+]] |

TABLE 1-continued
| Compound No. | Structure |
|---|---|
| 13 | 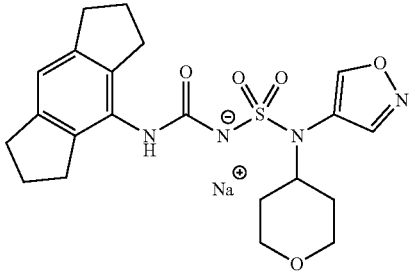 [SMILES: O=C([N-]S(=O)(=O)N(c1cnoc1)C1CCOCC1)Nc1c2c(cc3c1CCC3)CCC2 ; [Na+]] |
| 14 | 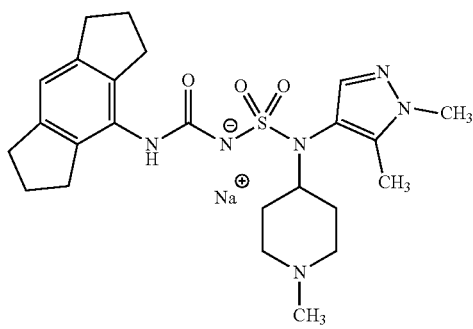 [SMILES: Cc1c(N(C2CCN(C)CC2)S(=O)(=O)[N-]C(=O)Nc2c3c(cc4c2CCC4)CCC3)cnn1C ; [Na+]] |
| 15 | 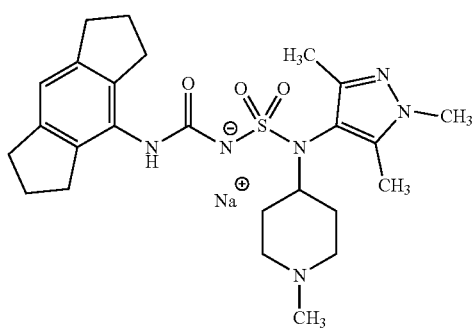 [SMILES: Cc1nn(C)c(C)c1N(C1CCN(C)CC1)S(=O)(=O)[N-]C(=O)Nc1c2c(cc3c1CCC3)CCC2 ; [Na+]] |
| 16 | 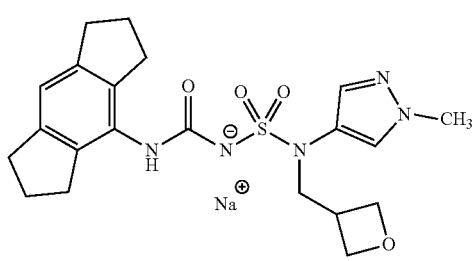 [SMILES: Cn1cc(N(CC2COC2)S(=O)(=O)[N-]C(=O)Nc2c3c(cc4c2CCC4)CCC3)cn1 ; [Na+]] |
| 17 | 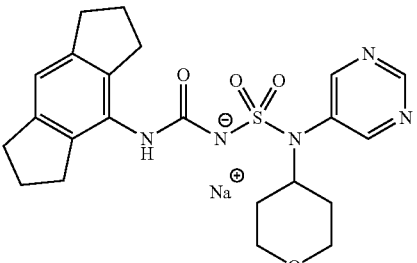 |

TABLE 1-continued
| Compound No. | Structure |
|---|---|
| 18 | 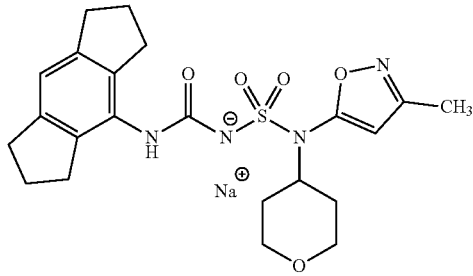 [SMILES: Cc1cc(N(C2CCOCC2)S(=O)(=O)[N-]C(=O)Nc2c3c(cc4c2CCC4)CCC3)on1 ; [Na+]] |
| 19 | 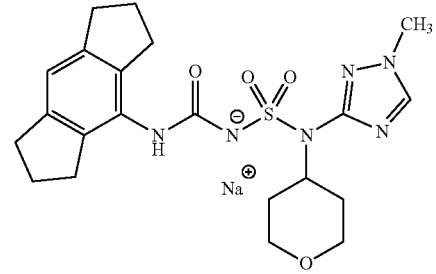 [SMILES: Cn1cnc(N(C2CCOCC2)S(=O)(=O)[N-]C(=O)Nc2c3c(cc4c2CCC4)CCC3)n1 ; [Na+]] |
| 20 | 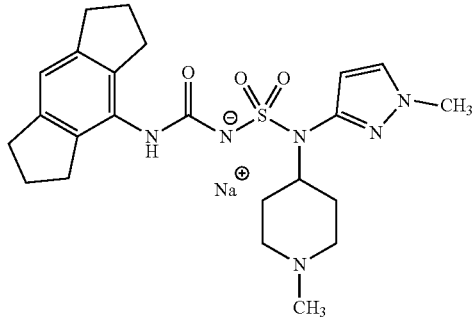 [SMILES: CN1CCC(N(c2ccn(C)n2)S(=O)(=O)[N-]C(=O)Nc2c3c(cc4c2CCC4)CCC3)CC1 ; [Na+]] |
| 21 | 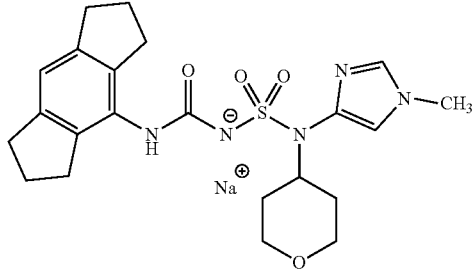 [SMILES: Cn1cnc(N(C2CCOCC2)S(=O)(=O)[N-]C(=O)Nc2c3c(cc4c2CCC4)CCC3)c1 ; [Na+]] |
| 22 | 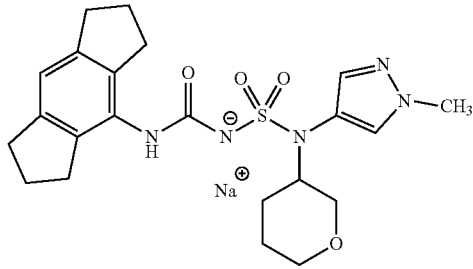 [SMILES: Cn1cc(N(C2CCCOC2)S(=O)(=O)[N-]C(=O)Nc2c3c(cc4c2CCC4)CCC3)cn1 ; [Na+]] |

TABLE 1-continued

| Compound No. | Structure |
| --- | --- |
| 23 | 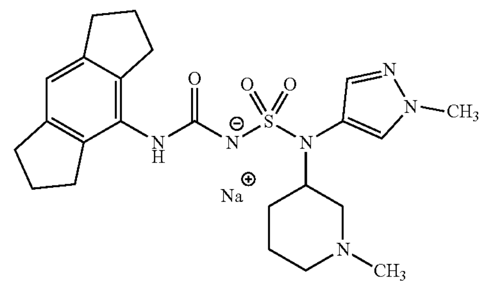 [SMILES: CN1CCCC(N(c2cnn(C)c2)S(=O)(=O)[N-]C(=O)Nc2c3c(cc4c2CCC4)CCC3)C1 ; [Na+]] |
| 24 | 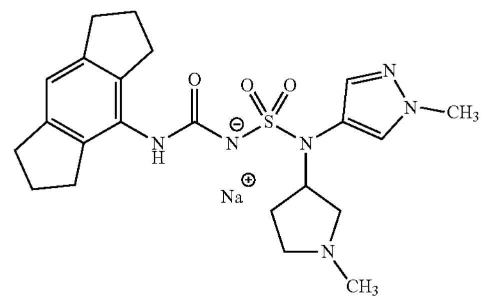 [SMILES: CN1CCC(N(c2cnn(C)c2)S(=O)(=O)[N-]C(=O)Nc2c3c(cc4c2CCC4)CCC3)C1 ; [Na+]] |
| 25 | 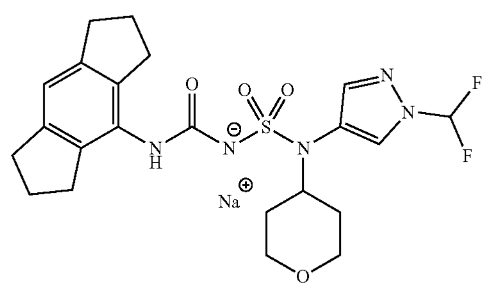 [SMILES: O=C([N-]S(=O)(=O)N(c1cnn(C(F)F)c1)C1CCOCC1)Nc1c2c(cc3c1CCC3)CCC2 ; [Na+]] |
| 26 | 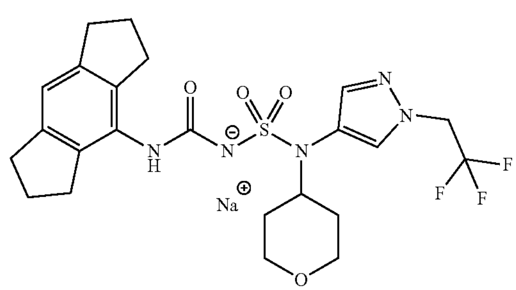 [SMILES: O=C([N-]S(=O)(=O)N(c1cnn(CC(F)(F)F)c1)C1CCOCC1)Nc1c2c(cc3c1CCC3)CCC2 ; [Na+]] |
| 27 | 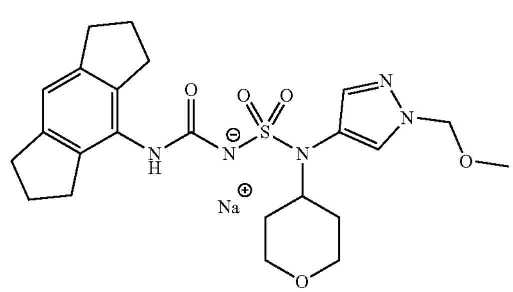 [SMILES: COCn1cc(N(C2CCOCC2)S(=O)(=O)[N-]C(=O)Nc2c3c(cc4c2CCC4)CCC3)cn1 ; [Na+]] |

TABLE 1-continued

| Compound No. | Structure |
| --- | --- |
| 28 | 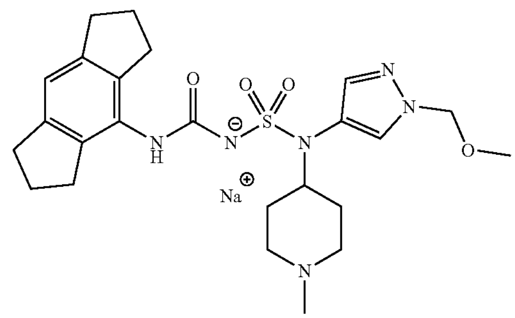 [SMILES: COCn1cc(N(C2CCN(C)CC2)S(=O)(=O)[N-]C(=O)Nc2c3c(cc4c2CCC4)CCC3)cn1 ; [Na+]] |
| 29 | 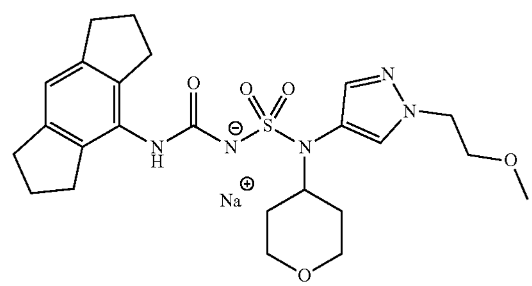 [SMILES: COCCn1cc(N(C2CCOCC2)S(=O)(=O)[N-]C(=O)Nc2c3c(cc4c2CCC4)CCC3)cn1 ; [Na+]] |
| 30 | 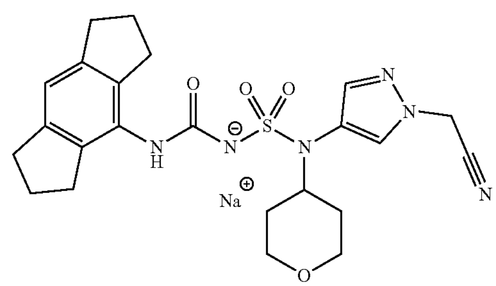 [SMILES: N#CCn1cc(N(C2CCOCC2)S(=O)(=O)[N-]C(=O)Nc2c3c(cc4c2CCC4)CCC3)cn1 ; [Na+]] |
| 31 | 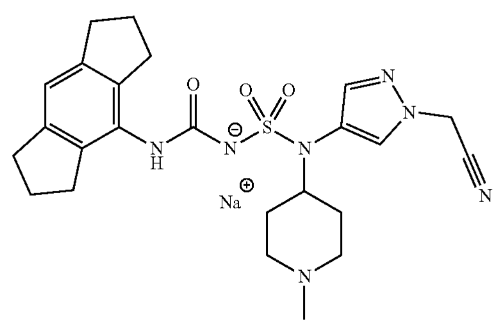 [SMILES: CN1CCC(N(c2cnn(CC#N)c2)S(=O)(=O)[N-]C(=O)Nc2c3c(cc4c2CCC4)CCC3)CC1 ; [Na+]] |
| 32 | 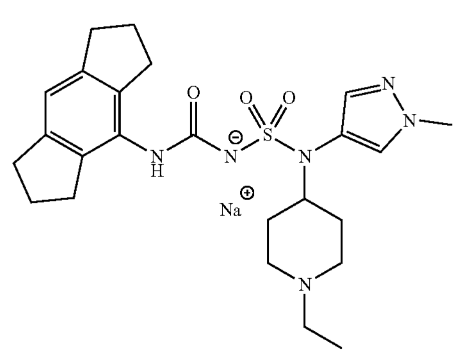 [SMILES: CCN1CCC(N(c2cnn(C)c2)S(=O)(=O)[N-]C(=O)Nc2c3c(cc4c2CCC4)CCC3)CC1 ; [Na+]] |

TABLE 1-continued
| Compound No. | Structure |
|---|---|
| 33 | 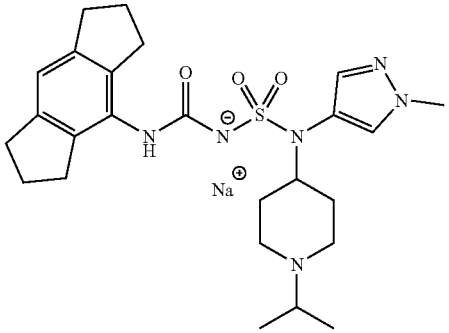 [SMILES: CC(C)N1CCC(N(c2cnn(C)c2)S(=O)(=O)[N-]C(=O)Nc2c3c(cc4c2CCC4)CCC3)CC1 ; [Na+]] |
| 34 | 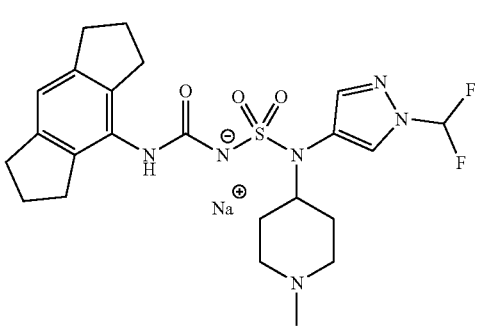 [SMILES: CN1CCC(N(c2cnn(C(F)F)c2)S(=O)(=O)[N-]C(=O)Nc2c3c(cc4c2CCC4)CCC3)CC1 ; [Na+]] |
| 35 | 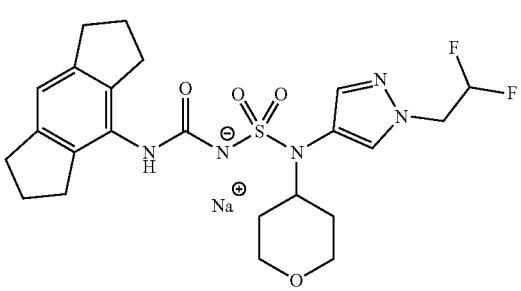 [SMILES: O=C([N-]S(=O)(=O)N(c1cnn(CC(F)F)c1)C1CCOCC1)Nc1c2c(cc3c1CCC3)CCC2 ; [Na+]] |
| 36 | 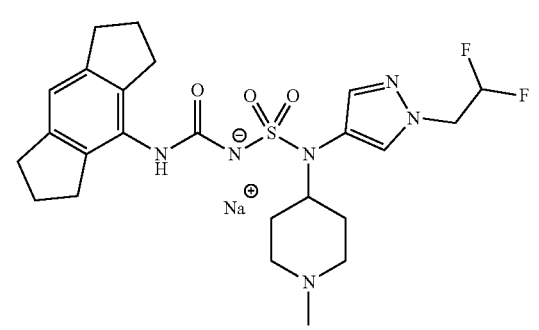 [SMILES: CN1CCC(N(c2cnn(CC(F)F)c2)S(=O)(=O)[N-]C(=O)Nc2c3c(cc4c2CCC4)CCC3)CC1 ; [Na+]] |
| 37 | 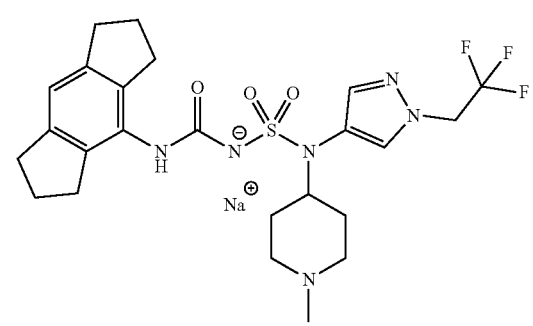 [SMILES: CN1CCC(N(c2cnn(CC(F)(F)F)c2)S(=O)(=O)[N-]C(=O)Nc2c3c(cc4c2CCC4)CCC3)CC1 ; [Na+]] |

TABLE 1-continued

| Compound No. | Structure |
|---|---|
| 38 | 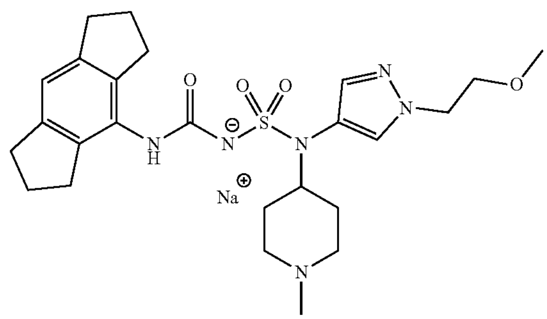 [SMILES: COCCn1cc(N(C2CCN(C)CC2)S(=O)(=O)[N-]C(=O)Nc2c3c(cc4c2CCC4)CCC3)cn1 ; [Na+]] |
| 39 | 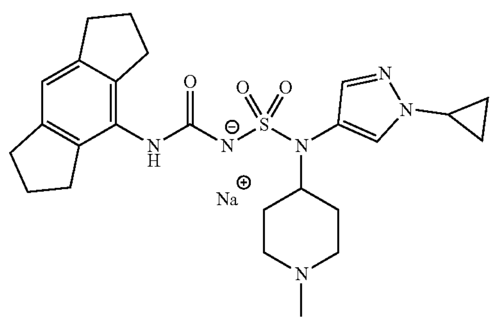 [SMILES: CN1CCC(N(c2cnn(C3CC3)c2)S(=O)(=O)[N-]C(=O)Nc2c3c(cc4c2CCC4)CCC3)CC1 ; [Na+]] |
| 40 | 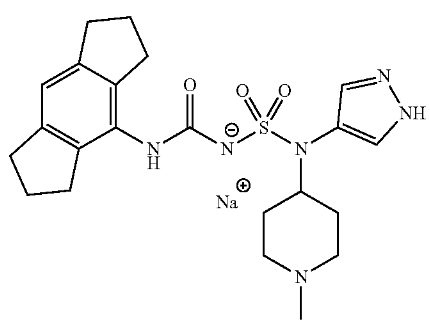 [SMILES: CN1CCC(N(c2cn[nH]c2)S(=O)(=O)[N-]C(=O)Nc2c3c(cc4c2CCC4)CCC3)CC1 ; [Na+]] |
| 41 | 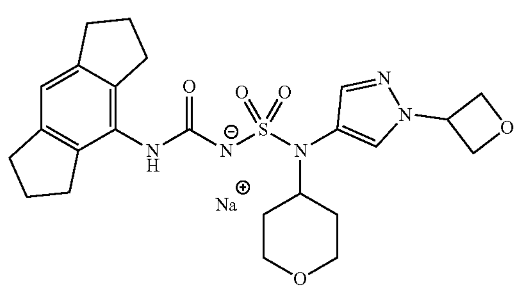 [SMILES: O=C([N-]S(=O)(=O)N(c1cnn(C2COC2)c1)C1CCOCC1)Nc1c2c(cc3c1CCC3)CCC2 ; [Na+]] |
| 42 | 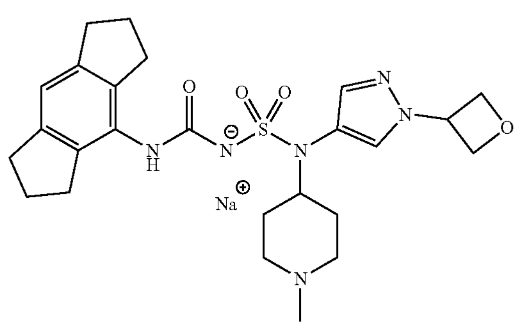 [SMILES: CN1CCC(N(c2cnn(C3COC3)c2)S(=O)(=O)[N-]C(=O)Nc2c3c(cc4c2CCC4)CCC3)CC1 ; [Na+]] |

TABLE 1-continued
| Compound No. | Structure |
|---|---|
| 43 | 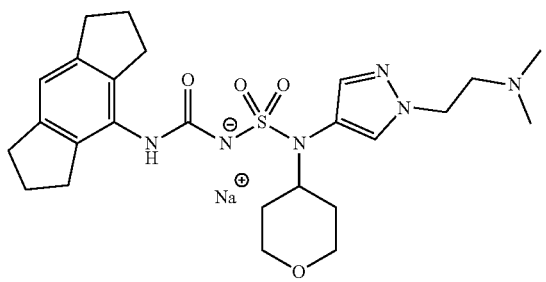 [SMILES: CN(C)CCn1cc(N(C2CCOCC2)S(=O)(=O)[N-]C(=O)Nc2c3c(cc4c2CCC4)CCC3)cn1 ; [Na+]] |
| 44 | 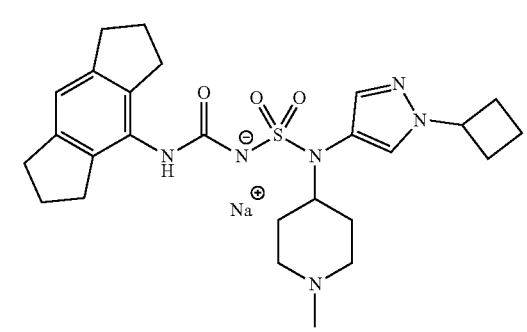 [SMILES: CN1CCC(N(c2cnn(C3CCC3)c2)S(=O)(=O)[N-]C(=O)Nc2c3c(cc4c2CCC4)CCC3)CC1 ; [Na+]] |
| 45 | 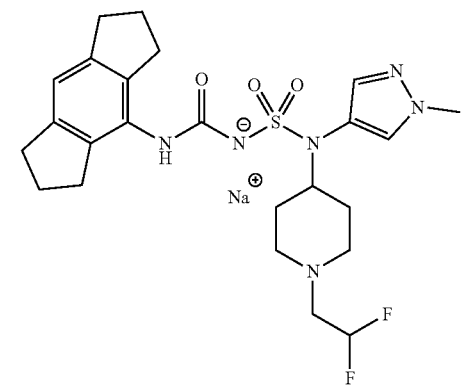 [SMILES: Cn1cc(N(C2CCN(CC(F)F)CC2)S(=O)(=O)[N-]C(=O)Nc2c3c(cc4c2CCC4)CCC3)cn1 ; [Na+]] |
| 46 | 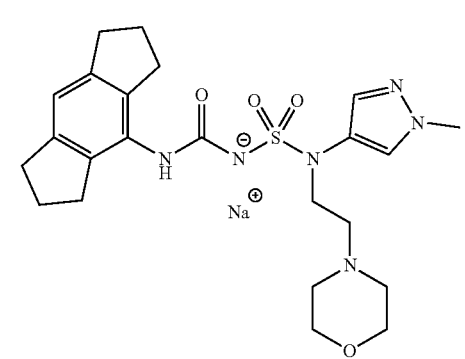 [SMILES: Cn1cc(N(CCN2CCOCC2)S(=O)(=O)[N-]C(=O)Nc2c3c(cc4c2CCC4)CCC3)cn1 ; [Na+]] |

TABLE 1-continued
| Compound No. | Structure |
|---|---|
| 47 | 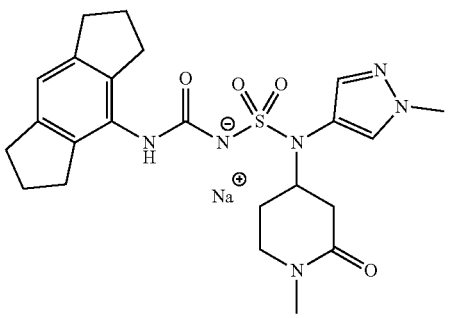 [SMILES: CN1CCC(N(c2cnn(C)c2)S(=O)(=O)[N-]C(=O)Nc2c3c(cc4c2CCC4)CCC3)CC1=O ; [Na+]] |
| 48 | 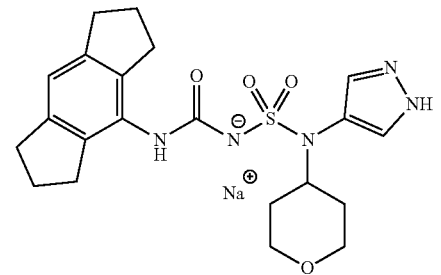 [SMILES: O=C([N-]S(=O)(=O)N(c1cn[nH]c1)C1CCOCC1)Nc1c2c(cc3c1CCC3)CCC2 ; [Na+]] |
| 49 | 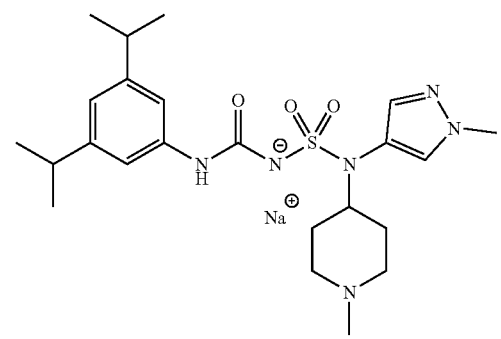 [SMILES: CC(C)c1cc(NC(=O)[N-]S(=O)(=O)N(c2cnn(C)c2)C2CCN(C)CC2)cc(C(C)C)c1 ; [Na+]] |
| 50 | 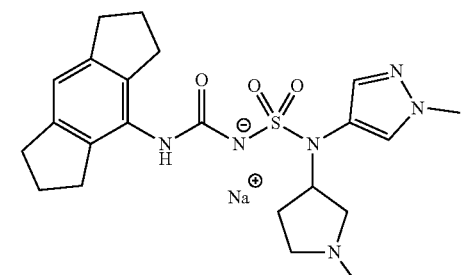 |
| 51 | 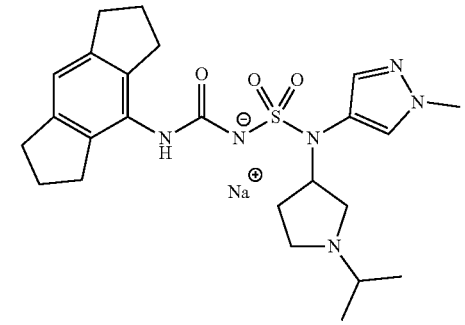 [SMILES: CC(C)N1CCC(N(c2cnn(C)c2)S(=O)(=O)[N-]C(=O)Nc2c3c(cc4c2CCC4)CCC3)C1 ; [Na+]] |

TABLE 1-continued

| Compound No. | Structure |
| --- | --- |
| 52 | 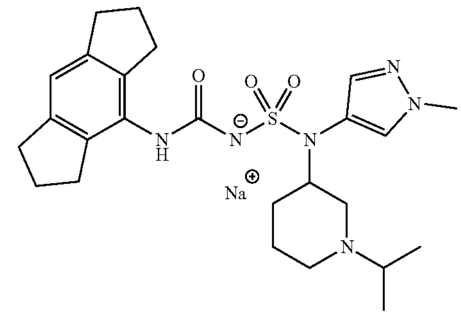 [SMILES: CC(C)N1CCCC(N(c2cnn(C)c2)S(=O)(=O)[N-]C(=O)Nc2c3c(cc4c2CCC4)CCC3)C1 ; [Na+]] |
| 53 | 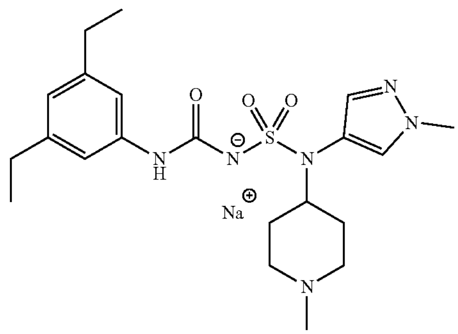 [SMILES: CCc1cc(CC)cc(NC(=O)[N-]S(=O)(=O)N(c2cnn(C)c2)C2CCN(C)CC2)c1 ; [Na+]] |
| 54 | 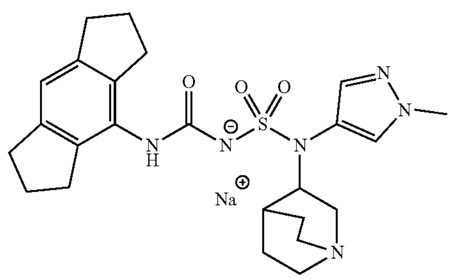 [SMILES: Cn1cc(N(C2CN3CCC2CC3)S(=O)(=O)[N-]C(=O)Nc2c3c(cc4c2CCC4)CCC3)cn1 ; [Na+]] |
| 55 | 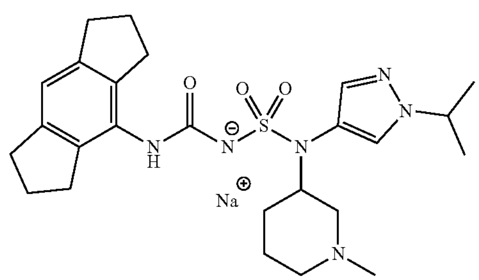 [SMILES: CC(C)n1cc(N(C2CCCN(C)C2)S(=O)(=O)[N-]C(=O)Nc2c3c(cc4c2CCC4)CCC3)cn1 ; [Na+]] |
| 56 | 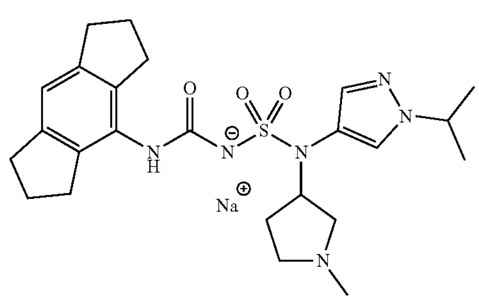 [SMILES: CC(C)n1cc(N(C2CCN(C)C2)S(=O)(=O)[N-]C(=O)Nc2c3c(cc4c2CCC4)CCC3)cn1 ; [Na+]] |

TABLE 1-continued

| Compound No. | Structure |
|---|---|
| 57 | 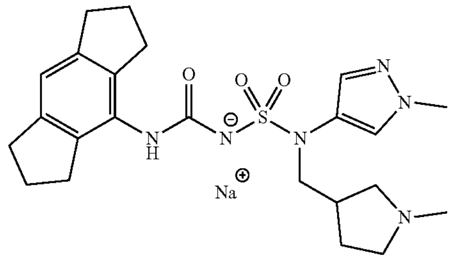 [SMILES: CN1CCC(CN(c2cnn(C)c2)S(=O)(=O)[N-]C(=O)Nc2c3c(cc4c2CCC4)CCC3)C1 ; [Na+]] |
| 58 | 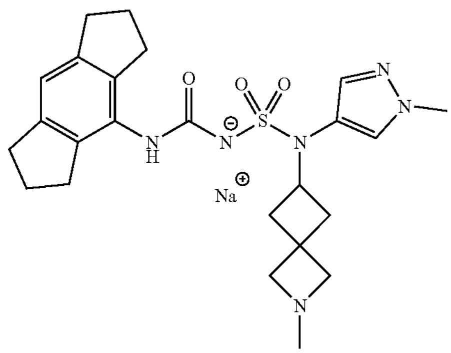 [SMILES: CN1CC2(CC(N(c3cnn(C)c3)S(=O)(=O)[N-]C(=O)Nc3c4c(cc5c3CCC5)CCC4)C2)C1 ; [Na+]] |
| 59 | 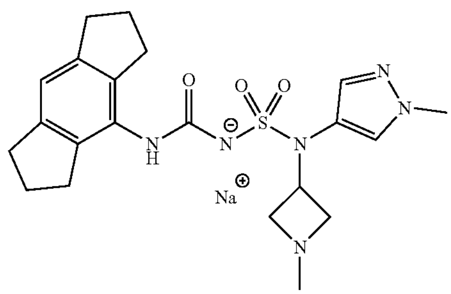 [SMILES: CN1CC(N(c2cnn(C)c2)S(=O)(=O)[N-]C(=O)Nc2c3c(cc4c2CCC4)CCC3)C1 ; [Na+]] |
| 60 | 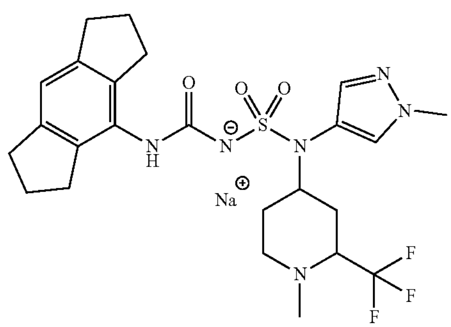 [SMILES: CN1CCC(N(c2cnn(C)c2)S(=O)(=O)[N-]C(=O)Nc2c3c(cc4c2CCC4)CCC3)CC1C(F)(F)F ; [Na+]] |
| 61 | 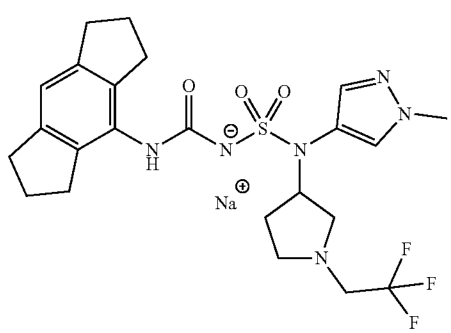 [SMILES: Cn1cc(N(C2CCN(CC(F)(F)F)C2)S(=O)(=O)[N-]C(=O)Nc2c3c(cc4c2CCC4)CCC3)cn1 ; [Na+]] |

TABLE 1-continued
| Compound No. | Structure |
|---|---|
| 62 | 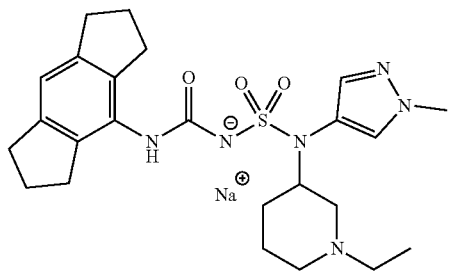 [SMILES: CCN1CCCC(N(c2cnn(C)c2)S(=O)(=O)[N-]C(=O)Nc2c3c(cc4c2CCC4)CCC3)C1 ; [Na+]] |
| 63 | 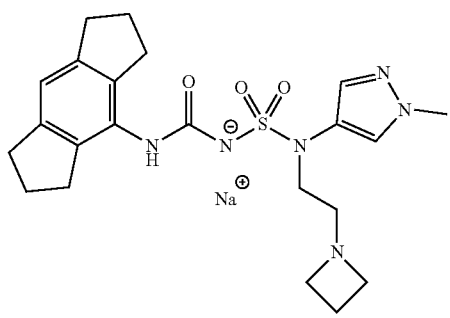 [SMILES: Cn1cc(N(CCN2CCC2)S(=O)(=O)[N-]C(=O)Nc2c3c(cc4c2CCC4)CCC3)cn1 ; [Na+]] |
| 64 | 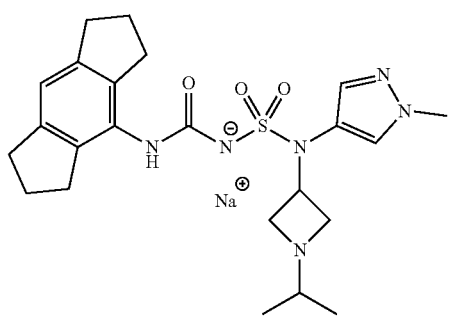 [SMILES: CC(C)N1CC(N(c2cnn(C)c2)S(=O)(=O)[N-]C(=O)Nc2c3c(cc4c2CCC4)CCC3)C1 ; [Na+]] |
| 65 | 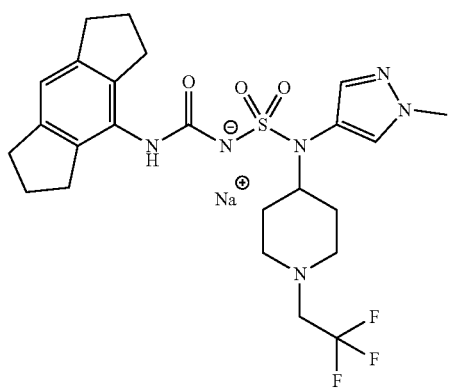 [SMILES: Cn1cc(N(C2CCN(CC(F)(F)F)CC2)S(=O)(=O)[N-]C(=O)Nc2c3c(cc4c2CCC4)CCC3)cn1 ; [Na+]] |
| 66 | 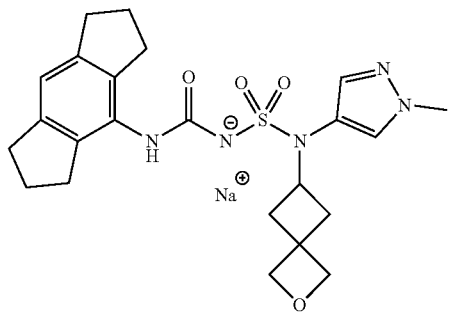 [SMILES: Cn1cc(N(C2CC3(COC3)C2)S(=O)(=O)[N-]C(=O)Nc2c3c(cc4c2CCC4)CCC3)cn1 ; [Na+]] |

TABLE 1-continued
| Compound No. | Structure |
|---|---|
| 67 | 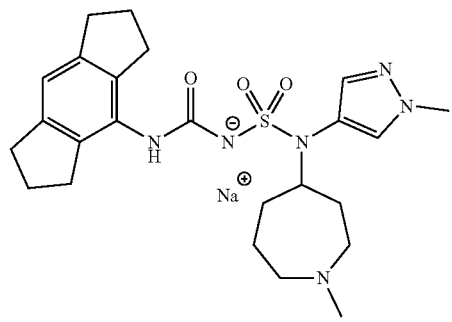 [SMILES: CN1CCCC(N(c2cnn(C)c2)S(=O)(=O)[N-]C(=O)Nc2c3c(cc4c2CCC4)CCC3)CC1 ; [Na+]] |
| 68 | 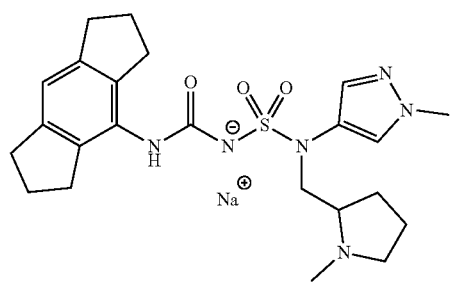 [SMILES: CN1CCCC1CN(c1cnn(C)c1)S(=O)(=O)[N-]C(=O)Nc1c2c(cc3c1CCC3)CCC2 ; [Na+]] |
| 69 | 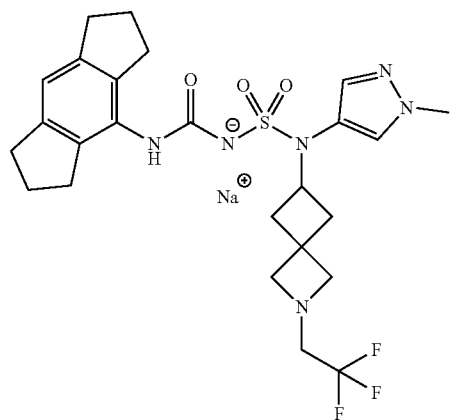 [SMILES: Cn1cc(N(C2CC3(C2)CN(CC(F)(F)F)C3)S(=O)(=O)[N-]C(=O)Nc2c3c(cc4c2CCC4)CCC3)cn1 ; [Na+]] |
| 70 | 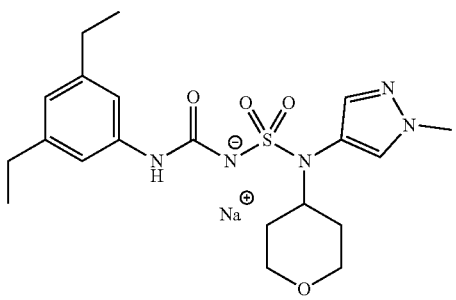 [SMILES: CCc1cc(CC)cc(NC(=O)[N-]S(=O)(=O)N(c2cnn(C)c2)C2CCOCC2)c1 ; [Na+]] |
| 71 | 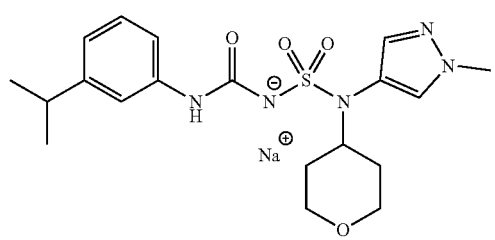 [SMILES: CC(C)c1cccc(NC(=O)[N-]S(=O)(=O)N(c2cnn(C)c2)C2CCOCC2)c1 ; [Na+]] |

TABLE 1-continued
| Compound No. | Structure |
|---|---|
| 72 | 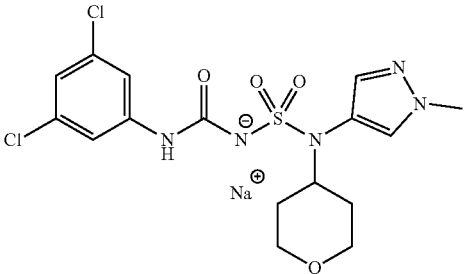 [SMILES: Cn1cc(N(C2CCOCC2)S(=O)(=O)[N-]C(=O)Nc2cc(Cl)cc(Cl)c2)cn1 ; [Na+]] |
| 73 | 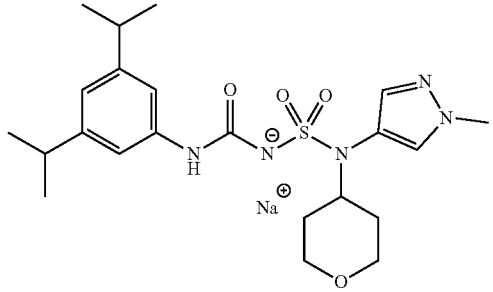 [SMILES: CC(C)c1cc(NC(=O)[N-]S(=O)(=O)N(c2cnn(C)c2)C2CCOCC2)cc(C(C)C)c1 ; [Na+]] |
| 74 | 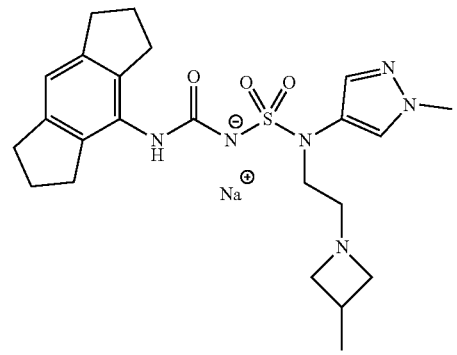 [SMILES: CC1CN(CCN(c2cnn(C)c2)S(=O)(=O)[N-]C(=O)Nc2c3c(cc4c2CCC4)CCC3)C1 ; [Na+]] |
| 75 | 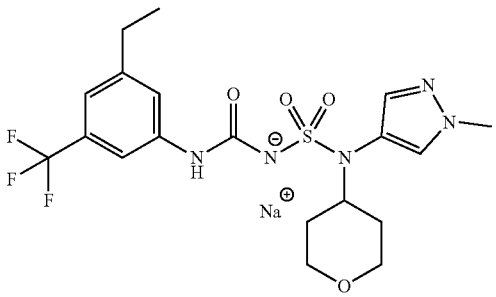 [SMILES: CCc1cc(NC(=O)[N-]S(=O)(=O)N(c2cnn(C)c2)C2CCOCC2)cc(C(F)(F)F)c1 ; [Na+]] |
| 76 | 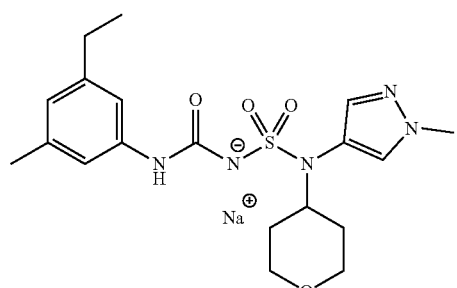 |

TABLE 1-continued
| Compound No. | Structure |
|---|---|
| 77 | 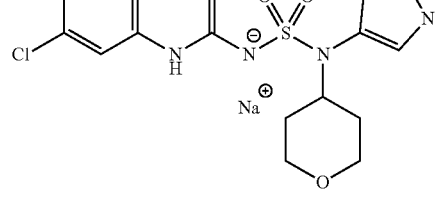 |
| 78 | 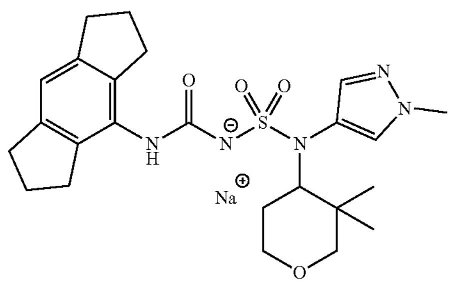 [SMILES: Cn1cc(N(C2CCOCC2(C)C)S(=O)(=O)[N-]C(=O)Nc2c3c(cc4c2CCC4)CCC3)cn1 ; [Na+]] |
| 79 | 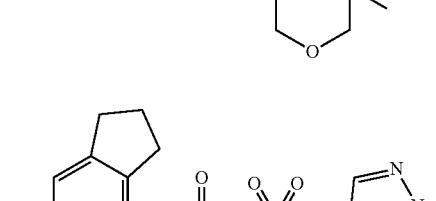 |
| 80 | 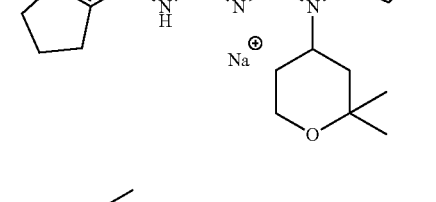 |
| 81 | 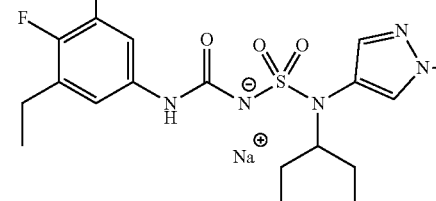 |

TABLE 1-continued
| Compound No. | Structure |
|---|---|
| 82 | 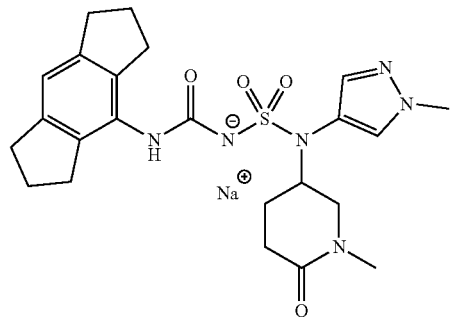 [SMILES: CN1CC(N(c2cnn(C)c2)S(=O)(=O)[N-]C(=O)Nc2c3c(cc4c2CCC4)CCC3)CCC1=O ; [Na+]] |
| 83 | 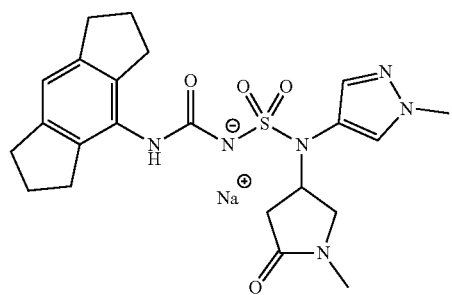 [SMILES: CN1CC(N(c2cnn(C)c2)S(=O)(=O)[N-]C(=O)Nc2c3c(cc4c2CCC4)CCC3)CC1=O ; [Na+]] |
| 84 | 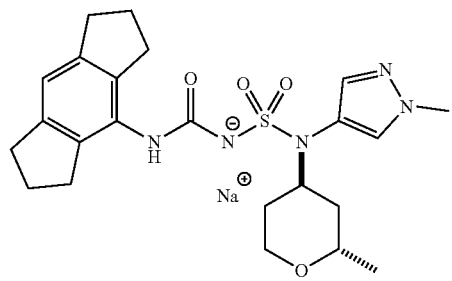 |
| 85 | 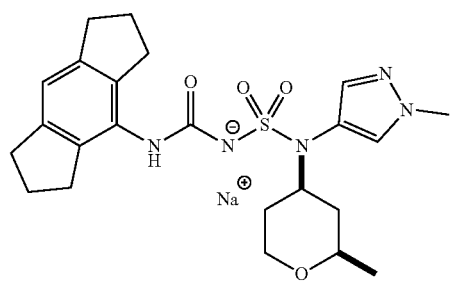 |
| 86 | 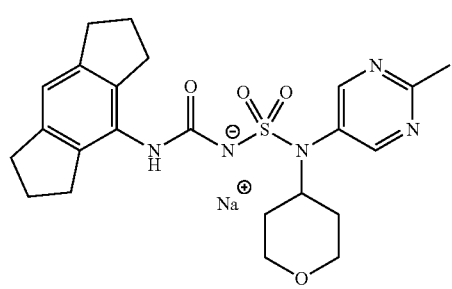 [SMILES: Cc1ncc(N(C2CCOCC2)S(=O)(=O)[N-]C(=O)Nc2c3c(cc4c2CCC4)CCC3)cn1 ; [Na+]] |

TABLE 1-continued

| Compound No. | Structure |
| --- | --- |
| 87 | 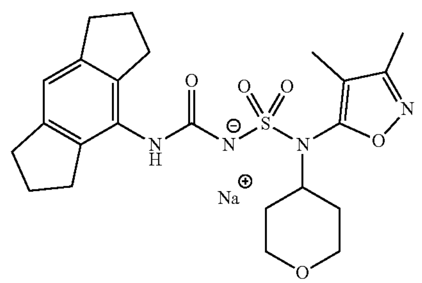 [SMILES: Cc1noc(N(C2CCOCC2)S(=O)(=O)[N-]C(=O)Nc2c3c(cc4c2CCC4)CCC3)c1C ; [Na+]] |
| 88 | 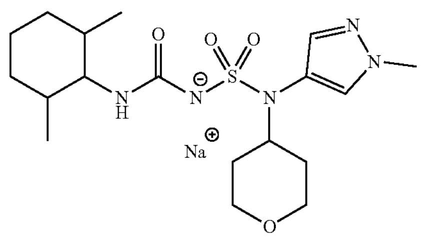 [SMILES: CC1CCCC(C)C1NC(=O)[N-]S(=O)(=O)N(c1cnn(C)c1)C1CCOCC1 ; [Na+]] |
| 89 | 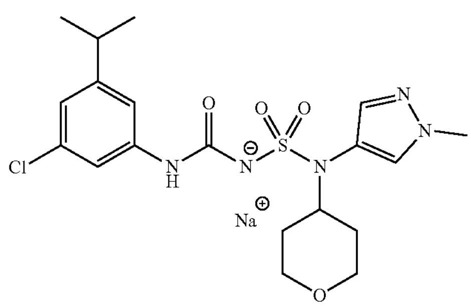 [SMILES: CC(C)c1cc(Cl)cc(NC(=O)[N-]S(=O)(=O)N(c2cnn(C)c2)C2CCOCC2)c1 ; [Na+]] |
| 90 | 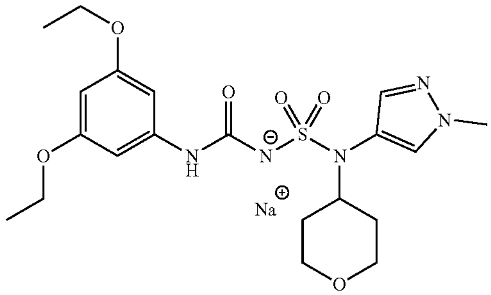 [SMILES: CCOc1cc(NC(=O)[N-]S(=O)(=O)N(c2cnn(C)c2)C2CCOCC2)cc(OCC)c1 ; [Na+]] |
| 91 | 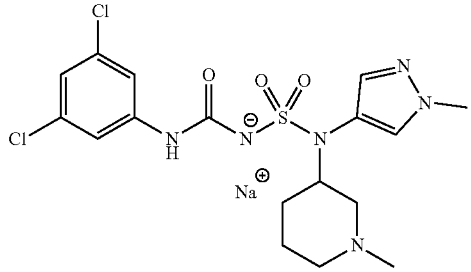 [SMILES: CN1CCCC(N(c2cnn(C)c2)S(=O)(=O)[N-]C(=O)Nc2cc(Cl)cc(Cl)c2)C1 ; [Na+]] |

TABLE 1-continued
| Compound No. | Structure |
|---|---|
| 92 | 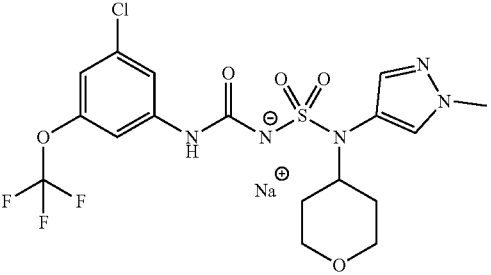 [SMILES: Cn1cc(N(C2CCOCC2)S(=O)(=O)[N-]C(=O)Nc2cc(Cl)cc(OC(F)(F)F)c2)cn1 ; [Na+]] |
| 93 | 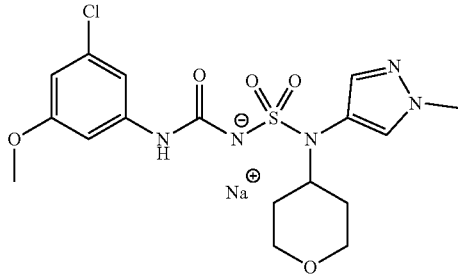 [SMILES: COc1cc(Cl)cc(NC(=O)[N-]S(=O)(=O)N(c2cnn(C)c2)C2CCOCC2)c1 ; [Na+]] |
| 94 | 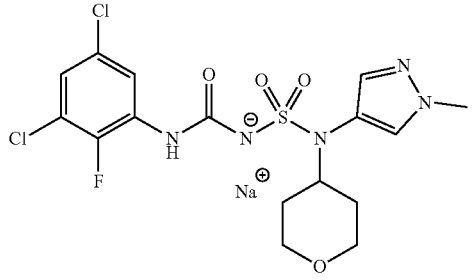 [SMILES: Cn1cc(N(C2CCOCC2)S(=O)(=O)[N-]C(=O)Nc2cc(Cl)cc(Cl)c2F)cn1 ; [Na+]] |
| 95 | 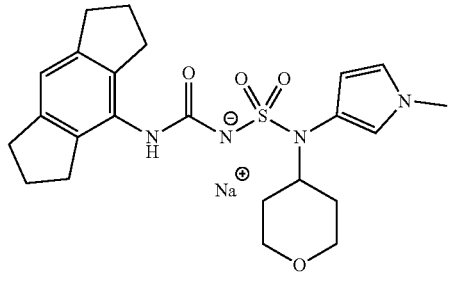 |
| 96 | 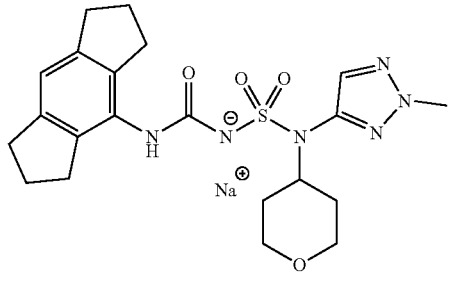 [SMILES: Cn1ncc(N(C2CCOCC2)S(=O)(=O)[N-]C(=O)Nc2c3c(cc4c2CCC4)CCC3)n1 ; [Na+]] |

TABLE 1-continued

| Compound No. | Structure |
|---|---|
| 97 | 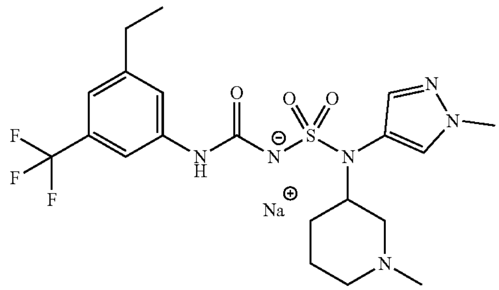 [SMILES: CCc1cc(NC(=O)[N-]S(=O)(=O)N(c2cnn(C)c2)C2CCCN(C)C2)cc(C(F)(F)F)c1 ; [Na+]] |
| 98 | 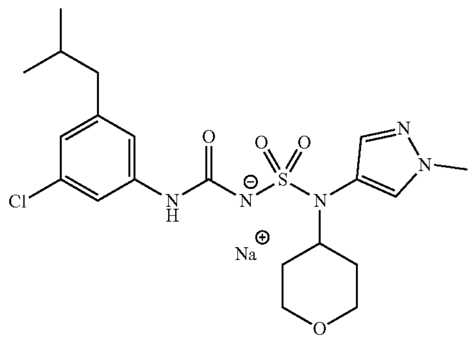 [SMILES: CC(C)Cc1cc(Cl)cc(NC(=O)[N-]S(=O)(=O)N(c2cnn(C)c2)C2CCOCC2)c1 ; [Na+]] |
| 99 | 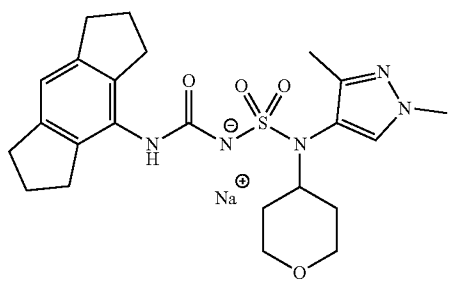 [SMILES: Cc1nn(C)cc1N(C1CCOCC1)S(=O)(=O)[N-]C(=O)Nc1c2c(cc3c1CCC3)CCC2 ; [Na+]] |
| 100 | 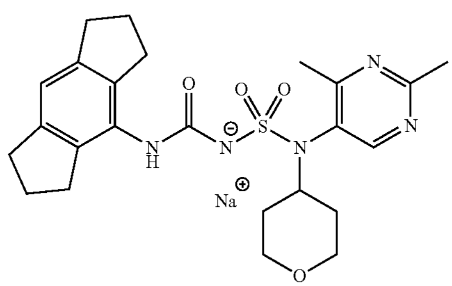 [SMILES: Cc1ncc(N(C2CCOCC2)S(=O)(=O)[N-]C(=O)Nc2c3c(cc4c2CCC4)CCC3)c(C)n1 ; [Na+]] |
| 101 | 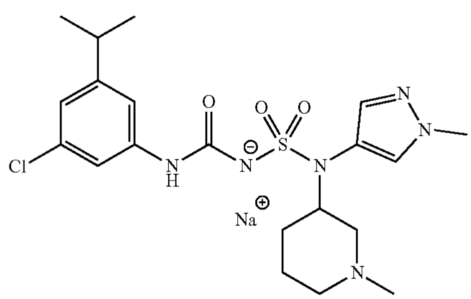 [SMILES: CC(C)c1cc(Cl)cc(NC(=O)[N-]S(=O)(=O)N(c2cnn(C)c2)C2CCCN(C)C2)c1 ; [Na+]] |

TABLE 1-continued

| Compound No. | Structure |
|---|---|
| 102 | 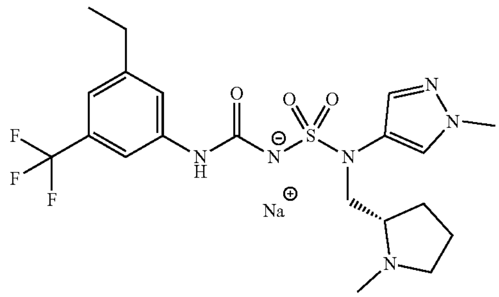 [SMILES: CCc1cc(NC(=O)[N-]S(=O)(=O)N(C[C@@H]2CCCN2C)c2cnn(C)c2)cc(C(F)(F)F)c1 ; [Na+]] |
| 103 | 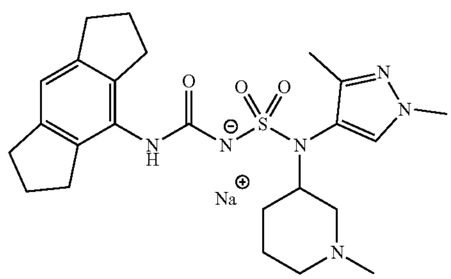 [SMILES: Cc1nn(C)cc1N(C1CCCN(C)C1)S(=O)(=O)[N-]C(=O)Nc1c2c(cc3c1CCC3)CCC2 ; [Na+]] |
| 104 | 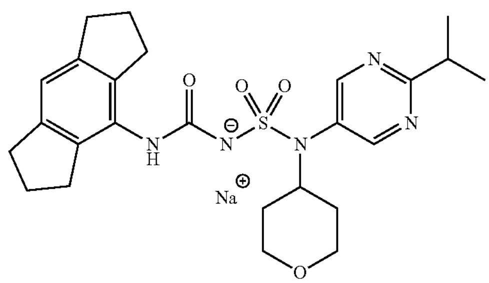 [SMILES: CC(C)c1ncc(N(C2CCOCC2)S(=O)(=O)[N-]C(=O)Nc2c3c(cc4c2CCC4)CCC3)cn1 ; [Na+]] |
| 105 | 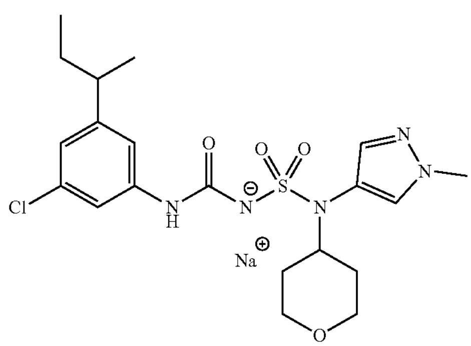 [SMILES: CCC(C)c1cc(Cl)cc(NC(=O)[N-]S(=O)(=O)N(c2cnn(C)c2)C2CCOCC2)c1 ; [Na+]] |
| 106 | 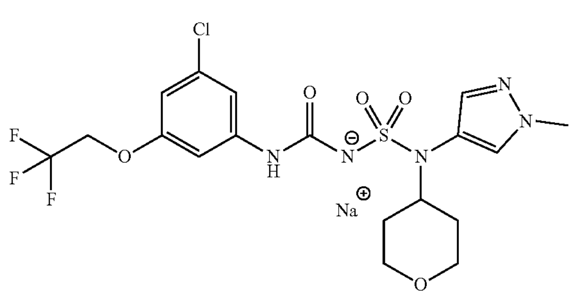 [SMILES: Cn1cc(N(C2CCOCC2)S(=O)(=O)[N-]C(=O)Nc2cc(Cl)cc(OCC(F)(F)F)c2)cn1 ; [Na+]] |

TABLE 1-continued
| Compound No. | Structure |
| --- | --- |
| 107 | 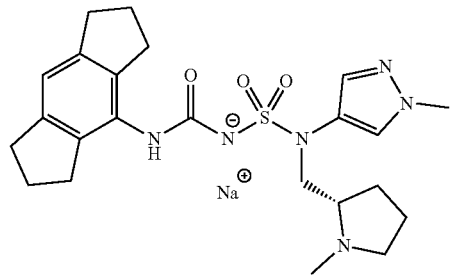 [SMILES: CN1CCC[C@H]1CN(c1cnn(C)c1)S(=O)(=O)[N-]C(=O)Nc1c2c(cc3c1CCC3)CCC2 ; [Na+]] |
| 108 | 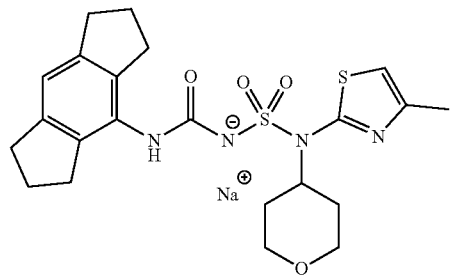 [SMILES: Cc1csc(N(C2CCOCC2)S(=O)(=O)[N-]C(=O)Nc2c3c(cc4c2CCC4)CCC3)n1 ; [Na+]] |
| 109 | 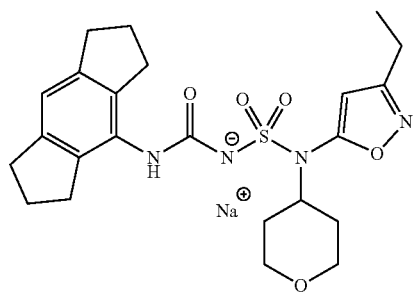 [SMILES: CCc1cc(N(C2CCOCC2)S(=O)(=O)[N-]C(=O)Nc2c3c(cc4c2CCC4)CCC3)on1 ; [Na+]] |
| 110 | 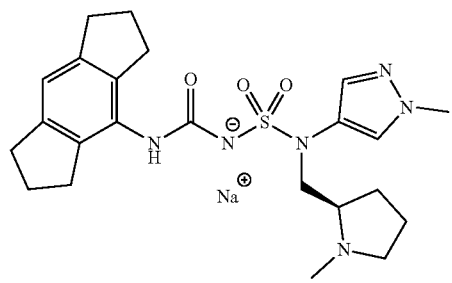 [SMILES: CN1CCC[C@@H]1CN(c1cnn(C)c1)S(=O)(=O)[N-]C(=O)Nc1c2c(cc3c1CCC3)CCC2 ; [Na+]] |
| 111 | 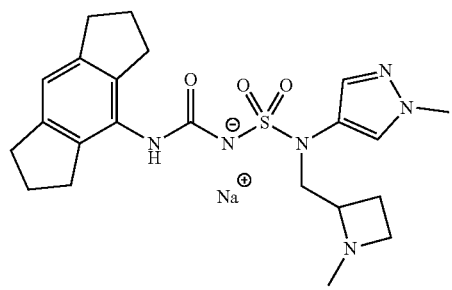 [SMILES: CN1CCC1CN(c1cnn(C)c1)S(=O)(=O)[N-]C(=O)Nc1c2c(cc3c1CCC3)CCC2 ; [Na+]] |

TABLE 1-continued
| Compound No. | Structure |
|---|---|
| 112 | 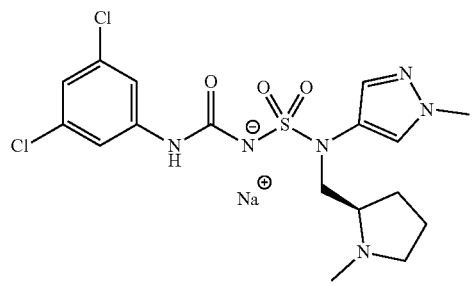 [SMILES: CN1CCC[C@@H]1CN(c1cnn(C)c1)S(=O)(=O)[N-]C(=O)Nc1cc(Cl)cc(Cl)c1 ; [Na+]] |
| 113 | 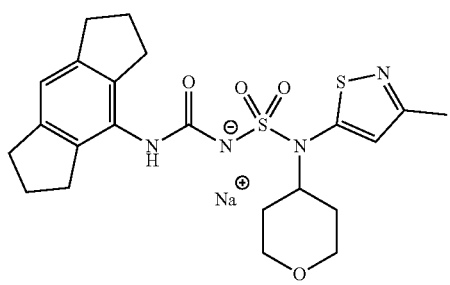 [SMILES: Cc1cc(N(C2CCOCC2)S(=O)(=O)[N-]C(=O)Nc2c3c(cc4c2CCC4)CCC3)sn1 ; [Na+]] |
| 114 | 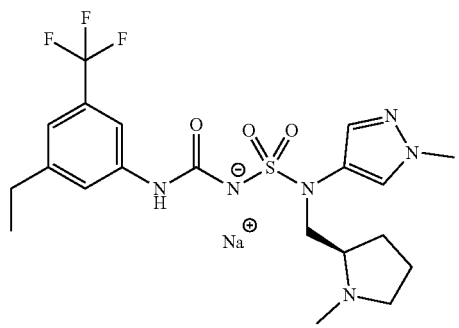 [SMILES: CCc1cc(NC(=O)[N-]S(=O)(=O)N(C[C@H]2CCCN2C)c2cnn(C)c2)cc(C(F)(F)F)c1 ; [Na+]] |
| 115 | 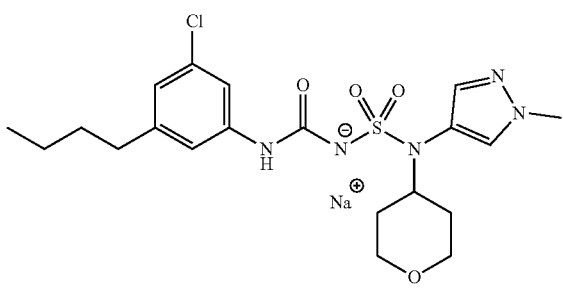 [SMILES: CCCCc1cc(Cl)cc(NC(=O)[N-]S(=O)(=O)N(c2cnn(C)c2)C2CCOCC2)c1 ; [Na+]] |
| 116 | 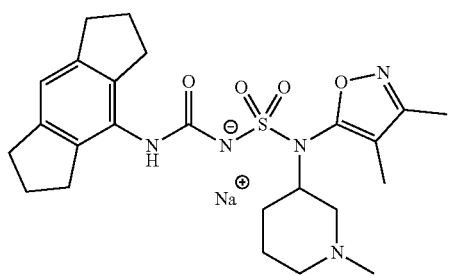 [SMILES: Cc1noc(N(C2CCCN(C)C2)S(=O)(=O)[N-]C(=O)Nc2c3c(cc4c2CCC4)CCC3)c1C ; [Na+]] |

TABLE 1-continued
| Compound No. | Structure |
|---|---|
| 117 | 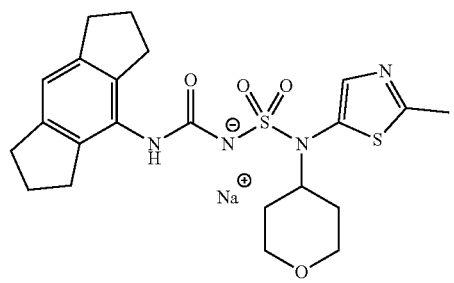 [SMILES: Cc1ncc(N(C2CCOCC2)S(=O)(=O)[N-]C(=O)Nc2c3c(cc4c2CCC4)CCC3)s1 ; [Na+]] |
| 118 | 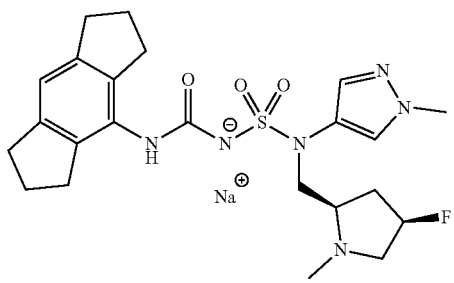 [SMILES: CN1C[C@H](F)C[C@@H]1CN(c1cnn(C)c1)S(=O)(=O)[N-]C(=O)Nc1c2c(cc3c1CCC3)CCC2 ; [Na+]] |
| 119 | 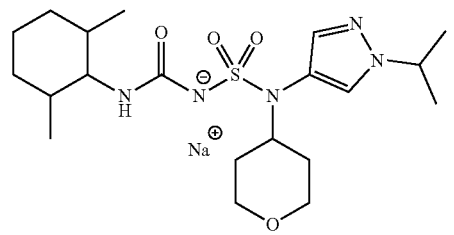 [SMILES: CC1CCCC(C)C1NC(=O)[N-]S(=O)(=O)N(c1cnn(C(C)C)c1)C1CCOCC1 ; [Na+]] |
| 120 | 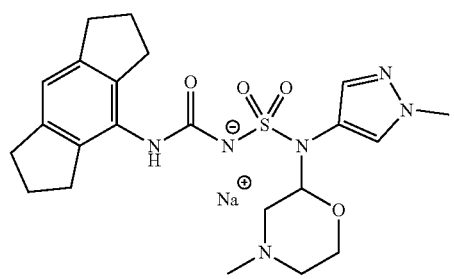 [SMILES: CN1CCOC(N(c2cnn(C)c2)S(=O)(=O)[N-]C(=O)Nc2c3c(cc4c2CCC4)CCC3)C1 ; [Na+]] |
| 121 | 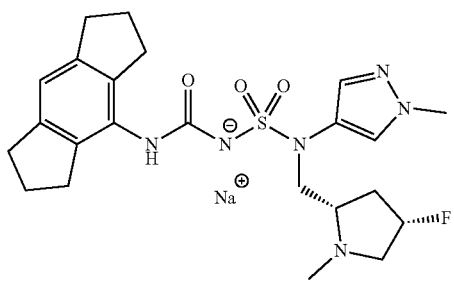 [SMILES: CN1C[C@@H](F)C[C@H]1CN(c1cnn(C)c1)S(=O)(=O)[N-]C(=O)Nc1c2c(cc3c1CCC3)CCC2 ; [Na+]] |

TABLE 1-continued
| Compound No. | Structure |
| --- | --- |
| 122 | 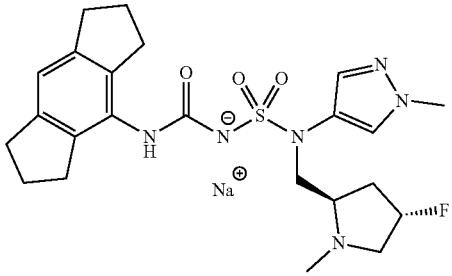 [SMILES: CN1C[C@@H](F)C[C@@H]1CN(c1cnn(C)c1)S(=O)(=O)[N-]C(=O)Nc1c2c(cc3c1CCC3)CCC2 ; [Na+]] |
| 123 | 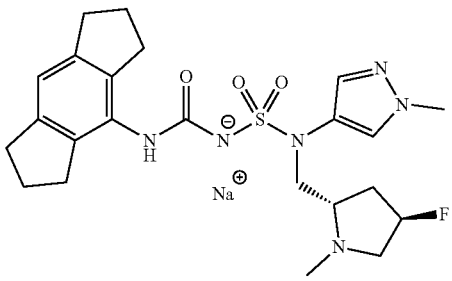 [SMILES: CN1C[C@H](F)C[C@H]1CN(c1cnn(C)c1)S(=O)(=O)[N-]C(=O)Nc1c2c(cc3c1CCC3)CCC2 ; [Na+]] |
| 124 | 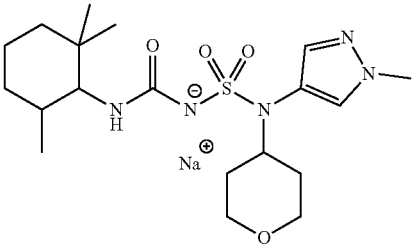 [SMILES: CC1CCCC(C)(C)C1NC(=O)[N-]S(=O)(=O)N(c1cnn(C)c1)C1CCOCC1 ; [Na+]] |
| 125 | 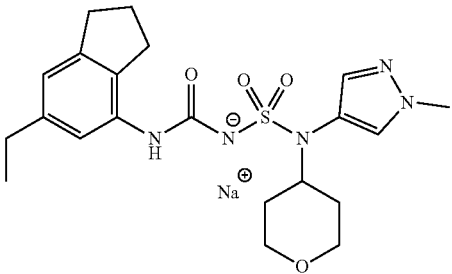 [SMILES: CCc1cc2c(c(NC(=O)[N-]S(=O)(=O)N(c3cnn(C)c3)C3CCOCC3)c1)CCC2 ; [Na+]] |
| 126 | 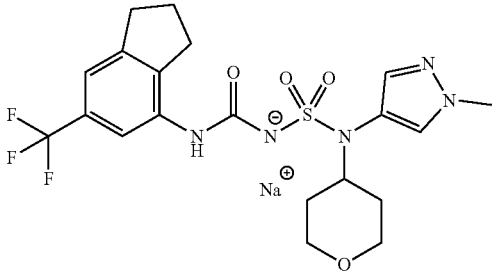 [SMILES: Cn1cc(N(C2CCOCC2)S(=O)(=O)[N-]C(=O)Nc2cc(C(F)(F)F)cc3c2CCC3)cn1 ; [Na+]] |

TABLE 1-continued

| Compound No. | Structure |
| --- | --- |
| 127 | 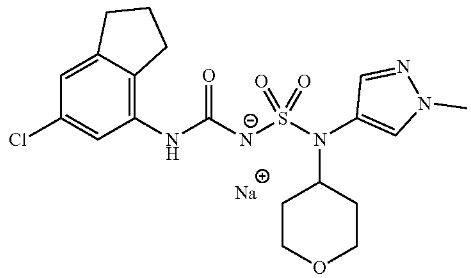 [SMILES: Cn1cc(N(C2CCOCC2)S(=O)(=O)[N-]C(=O)Nc2cc(Cl)cc3c2CCC3)cn1 ; [Na+]] |
| 128 | 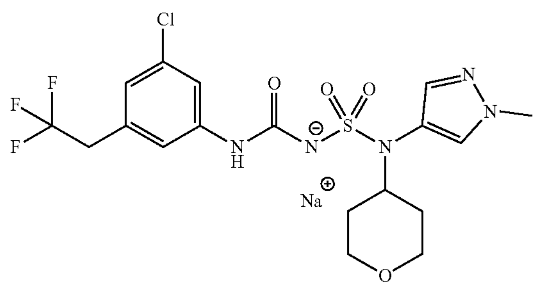 [SMILES: Cn1cc(N(C2CCOCC2)S(=O)(=O)[N-]C(=O)Nc2cc(Cl)cc(CC(F)(F)F)c2)cn1 ; [Na+]] |
| 129 | 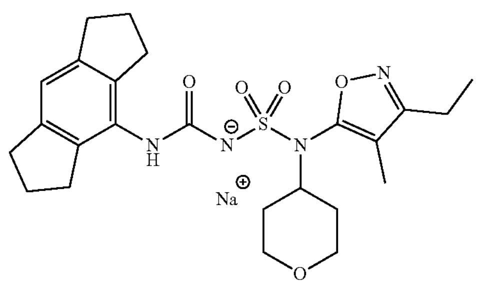 [SMILES: CCc1noc(N(C2CCOCC2)S(=O)(=O)[N-]C(=O)Nc2c3c(cc4c2CCC4)CCC3)c1C ; [Na+]] |
| 130 | 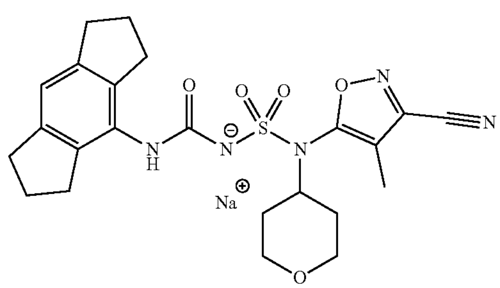 [SMILES: Cc1c(C#N)noc1N(C1CCOCC1)S(=O)(=O)[N-]C(=O)Nc1c2c(cc3c1CCC3)CCC2 ; [Na+]] |
| 131 | 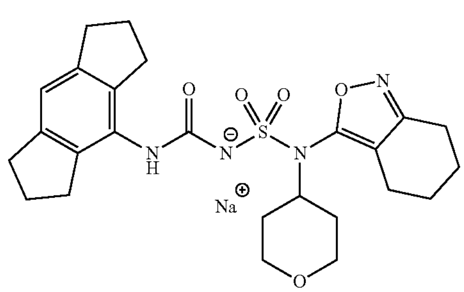 [SMILES: O=C([N-]S(=O)(=O)N(c1onc2c1CCCC2)C1CCOCC1)Nc1c2c(cc3c1CCC3)CCC2 ; [Na+]] |

TABLE 1-continued
| Compound No. | Structure |
|---|---|
| 132 | 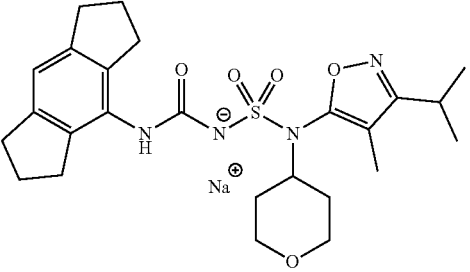 [SMILES: Cc1c(C(C)C)noc1N(C1CCOCC1)S(=O)(=O)[N-]C(=O)Nc1c2c(cc3c1CCC3)CCC2 ; [Na+]] |
| 133 | 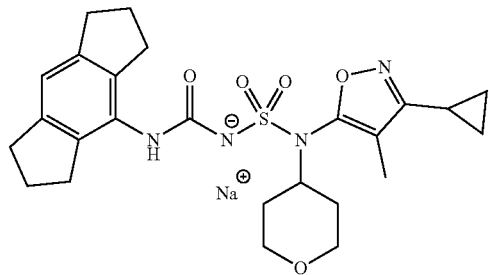 [SMILES: Cc1c(C2CC2)noc1N(C1CCOCC1)S(=O)(=O)[N-]C(=O)Nc1c2c(cc3c1CCC3)CCC2 ; [Na+]] |
| 134 | 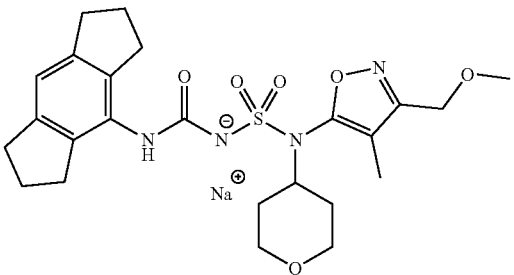 [SMILES: COCc1noc(N(C2CCOCC2)S(=O)(=O)[N-]C(=O)Nc2c3c(cc4c2CCC4)CCC3)c1C ; [Na+]] |
| 135 | 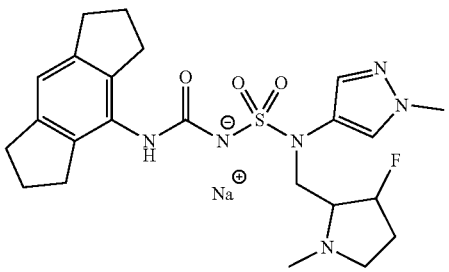 [SMILES: CN1CCC(F)C1CN(c1cnn(C)c1)S(=O)(=O)[N-]C(=O)Nc1c2c(cc3c1CCC3)CCC2 ; [Na+]] |
| 136 | 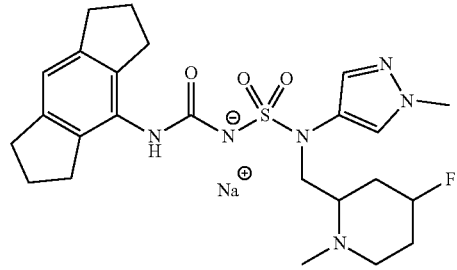 [SMILES: CN1CCC(F)CC1CN(c1cnn(C)c1)S(=O)(=O)[N-]C(=O)Nc1c2c(cc3c1CCC3)CCC2 ; [Na+]] |

TABLE 1-continued

| Compound No. | Structure |
|---|---|
| 137 | 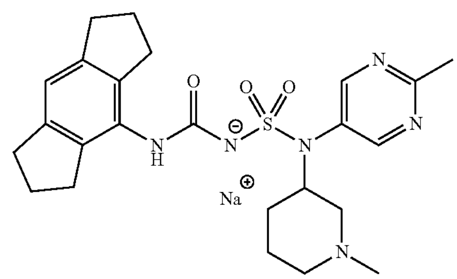 [SMILES: Cc1ncc(N(C2CCCN(C)C2)S(=O)(=O)[N-]C(=O)Nc2c3c(cc4c2CCC4)CCC3)cn1 ; [Na+]] |
| 138 | 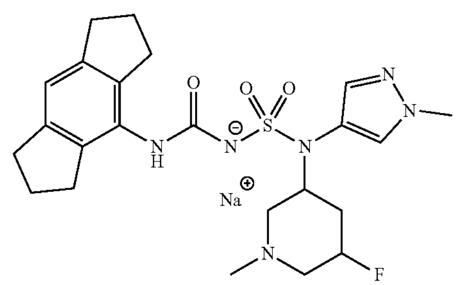 [SMILES: CN1CC(F)CC(N(c2cnn(C)c2)S(=O)(=O)[N-]C(=O)Nc2c3c(cc4c2CCC4)CCC3)C1 ; [Na+]] |
| 139 | 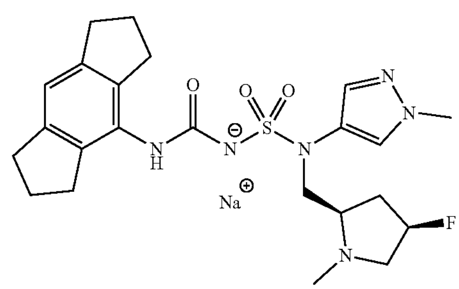 [SMILES: CN1C[C@H](F)C[C@@H]1CN(c1cnn(C)c1)S(=O)(=O)[N-]C(=O)Nc1c2c(cc3c1CCC3)CCC2 ; [Na+]] |
| 140 | 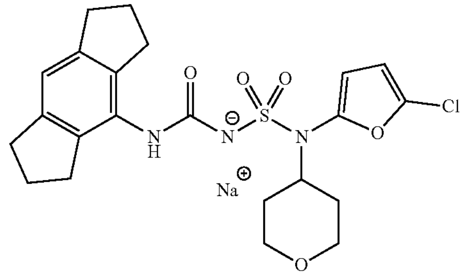 [SMILES: O=C([N-]S(=O)(=O)N(c1ccc(Cl)o1)C1CCOCC1)Nc1c2c(cc3c1CCC3)CCC2 ; [Na+]] |
| 141 | 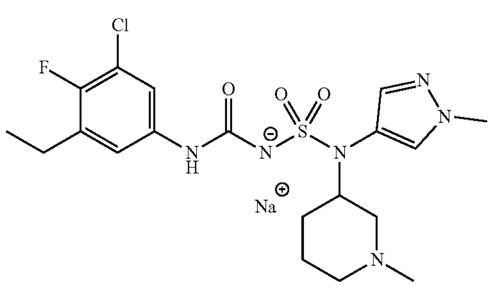 [SMILES: CCc1cc(NC(=O)[N-]S(=O)(=O)N(c2cnn(C)c2)C2CCCN(C)C2)cc(Cl)c1F ; [Na+]] |

TABLE 1-continued

| Compound No. | Structure |
| --- | --- |
| 142 | 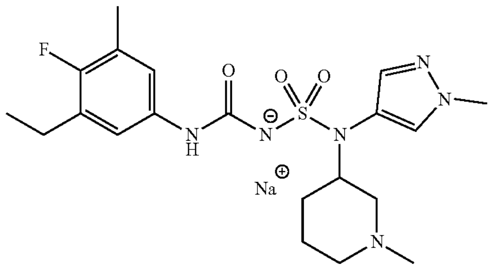 [SMILES: CCc1cc(NC(=O)[N-]S(=O)(=O)N(c2cnn(C)c2)C2CCCN(C)C2)cc(C)c1F ; [Na+]] |
| 143 | 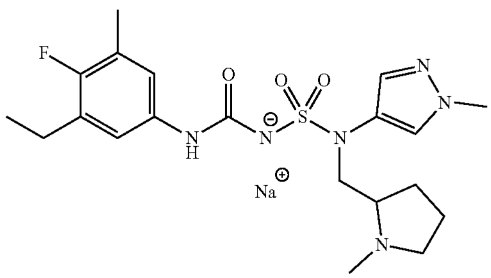 [SMILES: CCc1cc(NC(=O)[N-]S(=O)(=O)N(CC2CCCN2C)c2cnn(C)c2)cc(C)c1F ; [Na+]] |
| 144 | 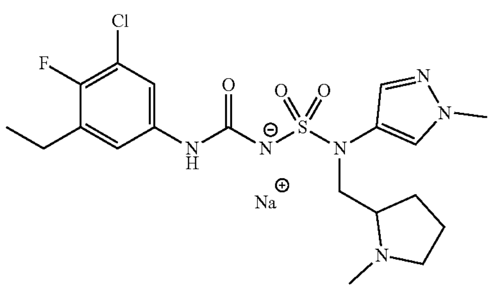 [SMILES: CCc1cc(NC(=O)[N-]S(=O)(=O)N(CC2CCCN2C)c2cnn(C)c2)cc(Cl)c1F ; [Na+]] |
| 145 | 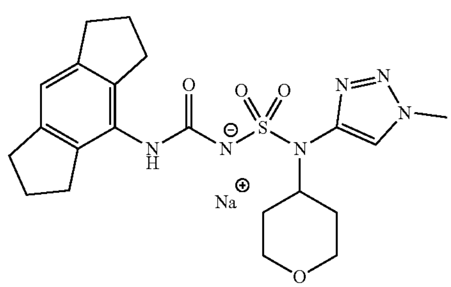 [SMILES: Cn1cc(N(C2CCOCC2)S(=O)(=O)[N-]C(=O)Nc2c3c(cc4c2CCC4)CCC3)nn1 ; [Na+]] |
| 146 | 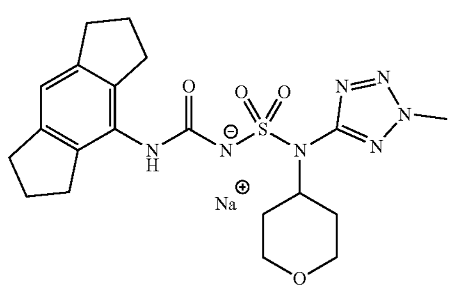 |

TABLE 1-continued
| Compound No. | Structure |
|---|---|
| 147 | 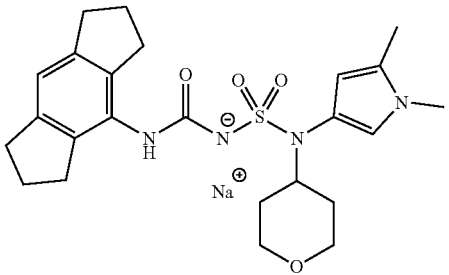 |
| 148 | 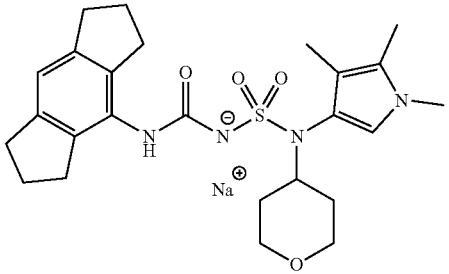 [SMILES: Cc1c(N(C2CCOCC2)S(=O)(=O)[N-]C(=O)Nc2c3c(cc4c2CCC4)CCC3)cn(C)c1C ; [Na+]] |
| 149 | 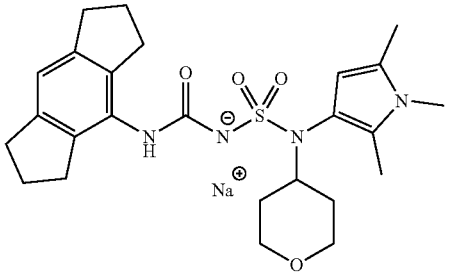 [SMILES: Cc1cc(N(C2CCOCC2)S(=O)(=O)[N-]C(=O)Nc2c3c(cc4c2CCC4)CCC3)c(C)n1C ; [Na+]] |
| 150 | 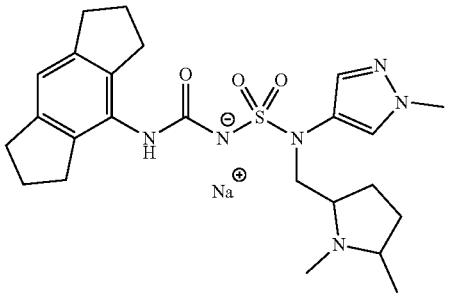 [SMILES: CC1CCC(CN(c2cnn(C)c2)S(=O)(=O)[N-]C(=O)Nc2c3c(cc4c2CCC4)CCC3)N1C ; [Na+]] |
| 151 | 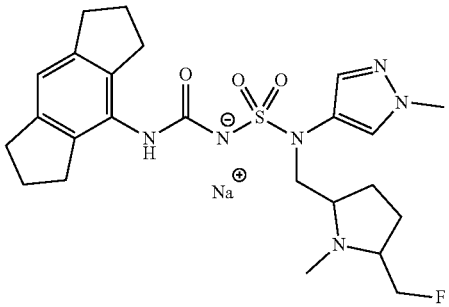 [SMILES: CN1C(CF)CCC1CN(c1cnn(C)c1)S(=O)(=O)[N-]C(=O)Nc1c2c(cc3c1CCC3)CCC2 ; [Na+]] |

TABLE 1-continued
| Compound No. | Structure |
|---|---|
| 152 | 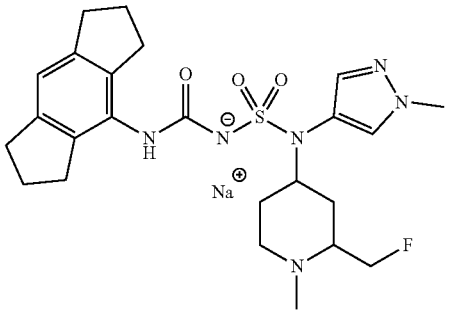 [SMILES: CN1CCC(N(c2cnn(C)c2)S(=O)(=O)[N-]C(=O)Nc2c3c(cc4c2CCC4)CCC3)CC1CF ; [Na+]] |
| 153 | 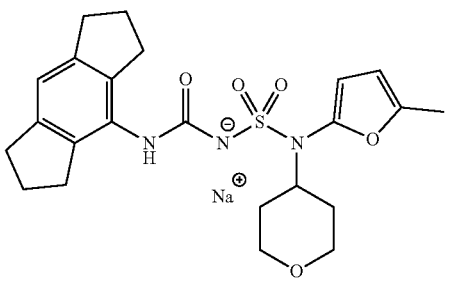 [SMILES: Cc1ccc(N(C2CCOCC2)S(=O)(=O)[N-]C(=O)Nc2c3c(cc4c2CCC4)CCC3)o1 ; [Na+]] |
| 154 | 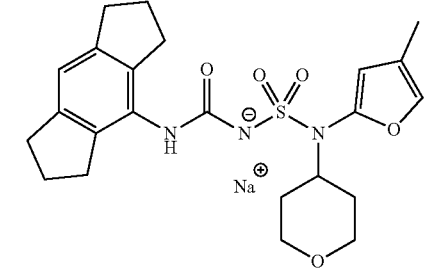 [SMILES: Cc1coc(N(C2CCOCC2)S(=O)(=O)[N-]C(=O)Nc2c3c(cc4c2CCC4)CCC3)c1 ; [Na+]] |
| 155 | 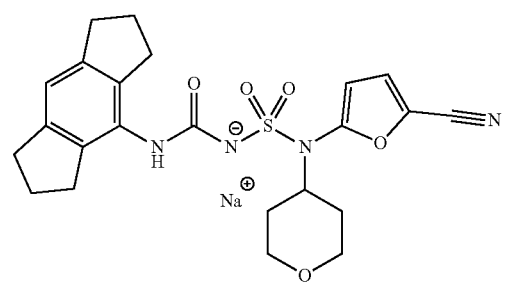 [SMILES: N#Cc1ccc(N(C2CCOCC2)S(=O)(=O)[N-]C(=O)Nc2c3c(cc4c2CCC4)CCC3)o1 ; [Na+]] |
| 156 | 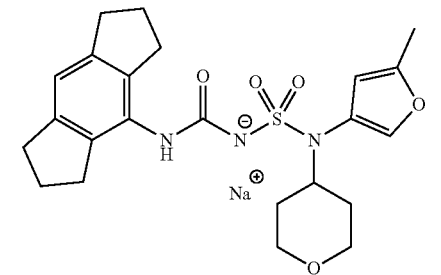 [SMILES: Cc1cc(N(C2CCOCC2)S(=O)(=O)[N-]C(=O)Nc2c3c(cc4c2CCC4)CCC3)co1 ; [Na+]] |

TABLE 1-continued
| Compound No. | Structure |
| --- | --- |
| 157 | 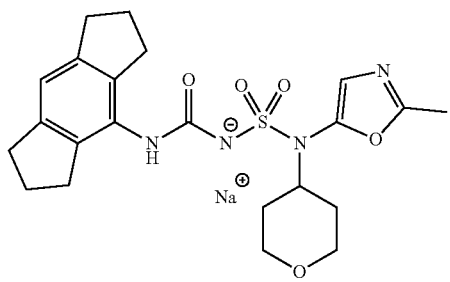 [SMILES: Cc1ncc(N(C2CCOCC2)S(=O)(=O)[N-]C(=O)Nc2c3c(cc4c2CCC4)CCC3)o1 ; [Na+]] |
| 158 | 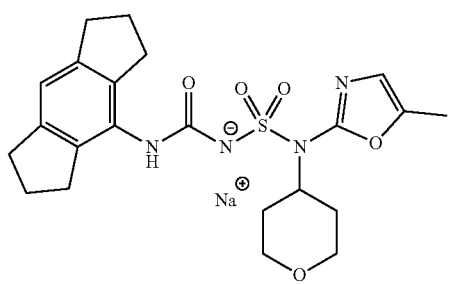 [SMILES: Cc1cnc(N(C2CCOCC2)S(=O)(=O)[N-]C(=O)Nc2c3c(cc4c2CCC4)CCC3)o1 ; [Na+]] |
| 159 | 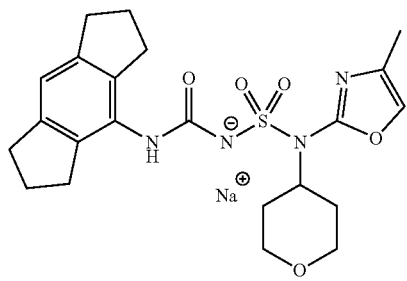 [SMILES: Cc1coc(N(C2CCOCC2)S(=O)(=O)[N-]C(=O)Nc2c3c(cc4c2CCC4)CCC3)n1 ; [Na+]] |
| 160 | 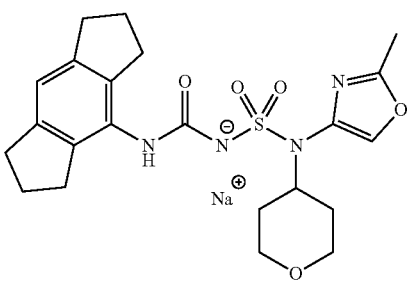 [SMILES: Cc1nc(N(C2CCOCC2)S(=O)(=O)[N-]C(=O)Nc2c3c(cc4c2CCC4)CCC3)co1 ; [Na+]] |
| 161 | 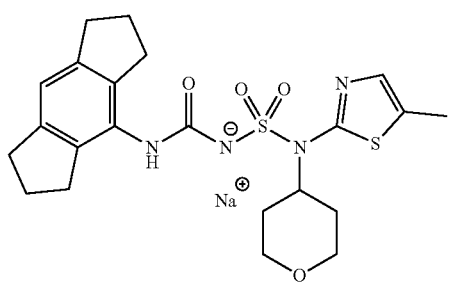 [SMILES: Cc1cnc(N(C2CCOCC2)S(=O)(=O)[N-]C(=O)Nc2c3c(cc4c2CCC4)CCC3)s1 ; [Na+]] |

TABLE 1-continued
| Compound No. | Structure |
| --- | --- |
| 162 | 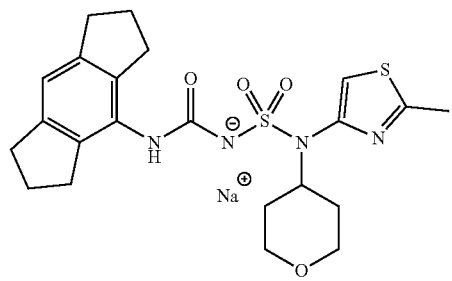 [SMILES: Cc1nc(N(C2CCOCC2)S(=O)(=O)[N-]C(=O)Nc2c3c(cc4c2CCC4)CCC3)cs1 ; [Na+]] |
| 163 | 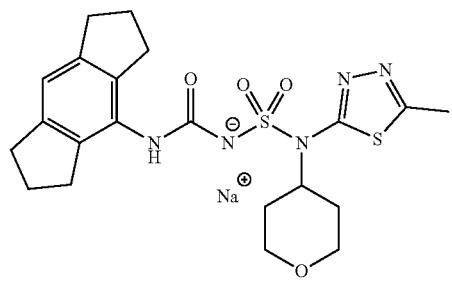 [SMILES: Cc1nnc(N(C2CCOCC2)S(=O)(=O)[N-]C(=O)Nc2c3c(cc4c2CCC4)CCC3)s1 ; [Na+]] |
| 164 | 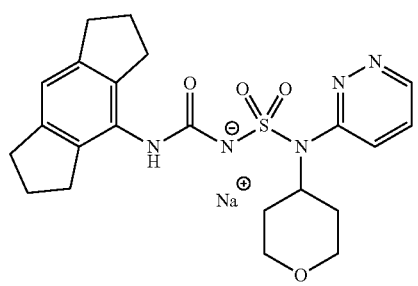 [SMILES: O=C([N-]S(=O)(=O)N(c1cccnn1)C1CCOCC1)Nc1c2c(cc3c1CCC3)CCC2 ; [Na+]] |
| 165 | 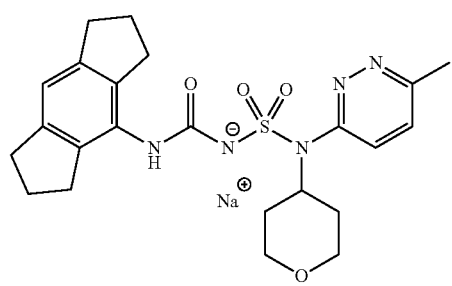 [SMILES: Cc1ccc(N(C2CCOCC2)S(=O)(=O)[N-]C(=O)Nc2c3c(cc4c2CCC4)CCC3)nn1 ; [Na+]] |
| 166 | 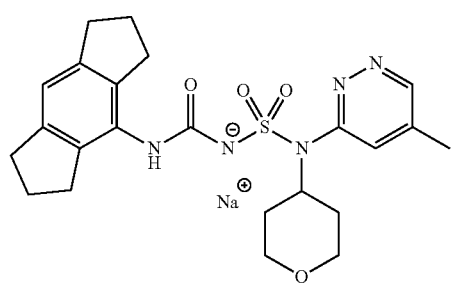 [SMILES: Cc1cnnc(N(C2CCOCC2)S(=O)(=O)[N-]C(=O)Nc2c3c(cc4c2CCC4)CCC3)c1 ; [Na+]] |

TABLE 2

| Compound No. | Structure |
|---|---|
| 1A | 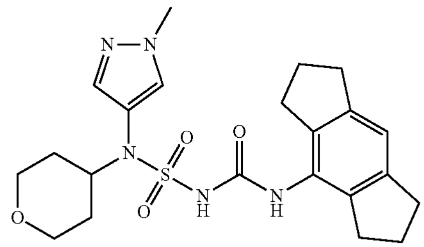 [SMILES: Cn1cc(N(C2CCOCC2)S(=O)(=O)NC(=O)Nc2c3c(cc4c2CCC4)CCC3)cn1] |
| 2A | 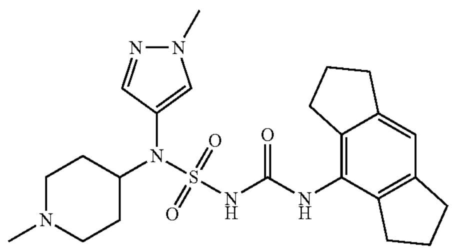 [SMILES: CN1CCC(N(c2cnn(C)c2)S(=O)(=O)NC(=O)Nc2c3c(cc4c2CCC4)CCC3)CC1] |
| 3A | 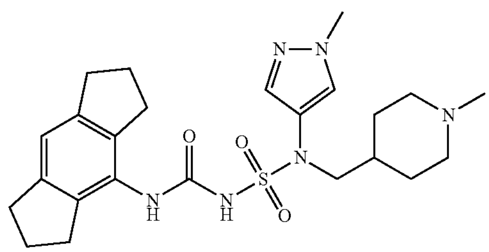 [SMILES: CN1CCC(CN(c2cnn(C)c2)S(=O)(=O)NC(=O)Nc2c3c(cc4c2CCC4)CCC3)CC1] |
| 4A | 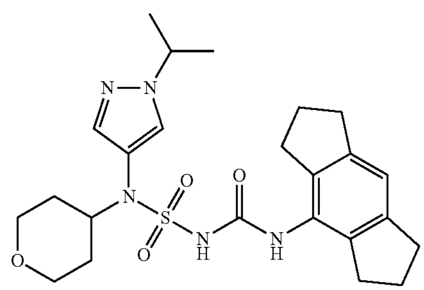 [SMILES: CC(C)n1cc(N(C2CCOCC2)S(=O)(=O)NC(=O)Nc2c3c(cc4c2CCC4)CCC3)cn1] |
| 5A | 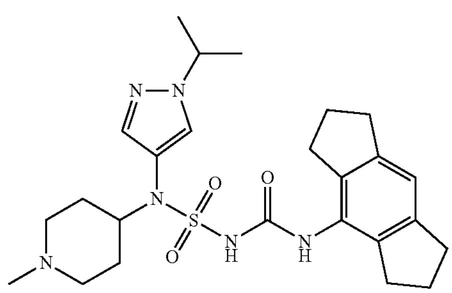 [SMILES: CC(C)n1cc(N(C2CCN(C)CC2)S(=O)(=O)NC(=O)Nc2c3c(cc4c2CCC4)CCC3)cn1] |
| 6A | 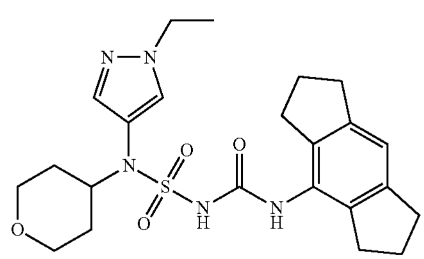 [SMILES: CCn1cc(N(C2CCOCC2)S(=O)(=O)NC(=O)Nc2c3c(cc4c2CCC4)CCC3)cn1] |

TABLE 2-continued

| Compound No. | Structure |
|---|---|
| 7A | 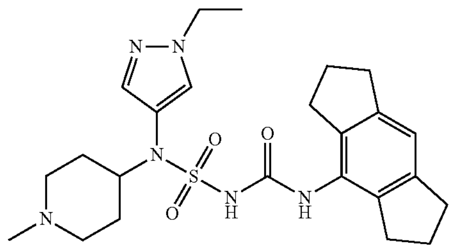 [SMILES: CCn1cc(N(C2CCN(C)CC2)S(=O)(=O)NC(=O)Nc2c3c(cc4c2CCC4)CCC3)cn1] |
| 8A | 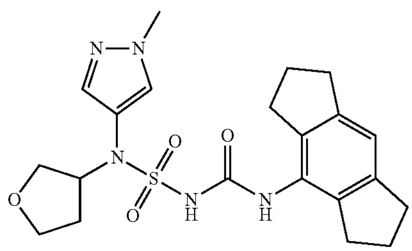 [SMILES: Cn1cc(N(C2CCOC2)S(=O)(=O)NC(=O)Nc2c3c(cc4c2CCC4)CCC3)cn1] |
| 9A | 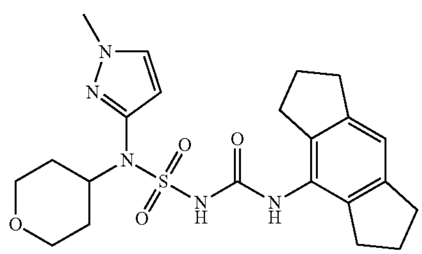 [SMILES: Cn1ccc(N(C2CCOCC2)S(=O)(=O)NC(=O)Nc2c3c(cc4c2CCC4)CCC3)n1] |
| 10A | 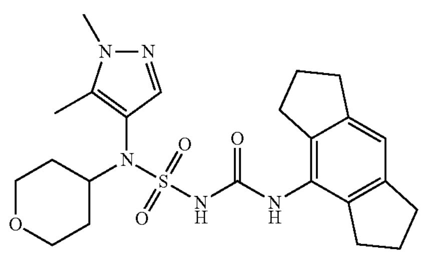 [SMILES: Cc1c(N(C2CCOCC2)S(=O)(=O)NC(=O)Nc2c3c(cc4c2CCC4)CCC3)cnn1C] |
| 11A | 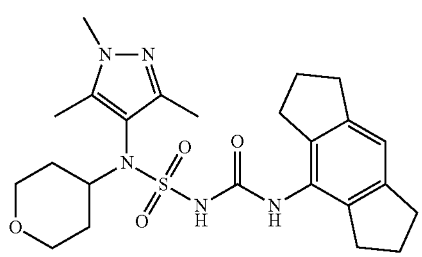 [SMILES: Cc1nn(C)c(C)c1N(C1CCOCC1)S(=O)(=O)NC(=O)Nc1c2c(cc3c1CCC3)CCC2] |
| 12A | 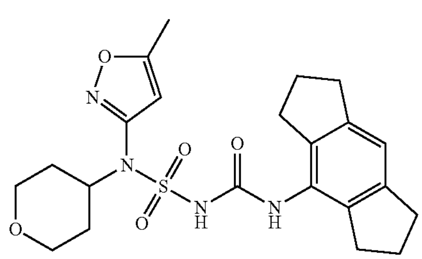 [SMILES: Cc1cc(N(C2CCOCC2)S(=O)(=O)NC(=O)Nc2c3c(cc4c2CCC4)CCC3)no1] |

TABLE 2-continued

| Compound No. | Structure |
| --- | --- |
| 13A | 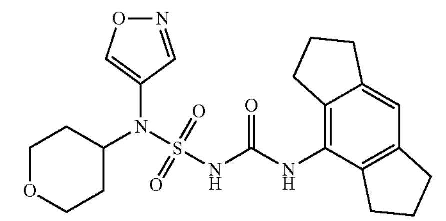 [SMILES: O=C(Nc1c2c(cc3c1CCC3)CCC2)NS(=O)(=O)N(c1cnoc1)C1CCOCC1] |
| 14A | 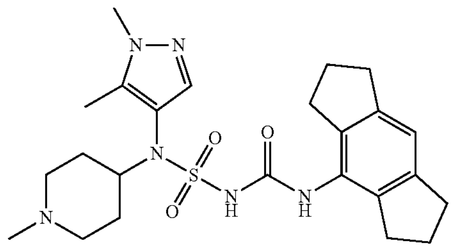 [SMILES: Cc1c(N(C2CCN(C)CC2)S(=O)(=O)NC(=O)Nc2c3c(cc4c2CCC4)CCC3)cnn1C] |
| 15A | 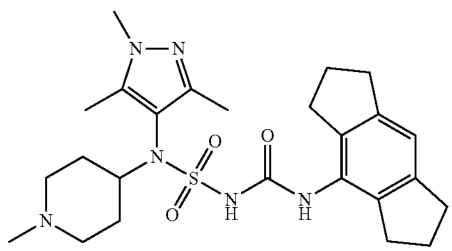 [SMILES: Cc1nn(C)c(C)c1N(C1CCN(C)CC1)S(=O)(=O)NC(=O)Nc1c2c(cc3c1CCC3)CCC2] |
| 16A | 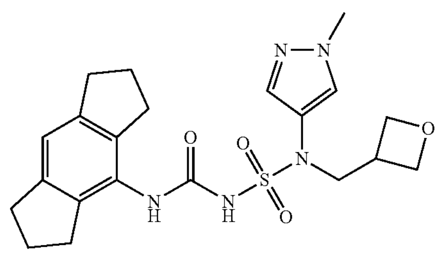 [SMILES: Cn1cc(N(CC2COC2)S(=O)(=O)NC(=O)Nc2c3c(cc4c2CCC4)CCC3)cn1] |
| 17A | 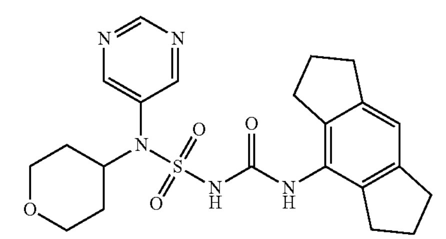 [SMILES: O=C(Nc1c2c(cc3c1CCC3)CCC2)NS(=O)(=O)N(c1cncnc1)C1CCOCC1] |
| 18A | 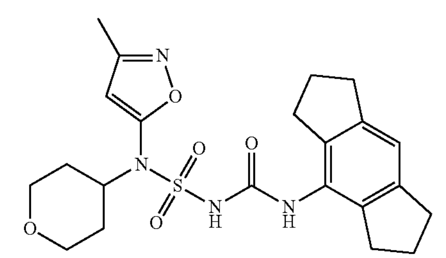 [SMILES: Cc1cc(N(C2CCOCC2)S(=O)(=O)NC(=O)Nc2c3c(cc4c2CCC4)CCC3)on1] |

TABLE 2-continued

| Compound No. | Structure |
|---|---|
| 19A | 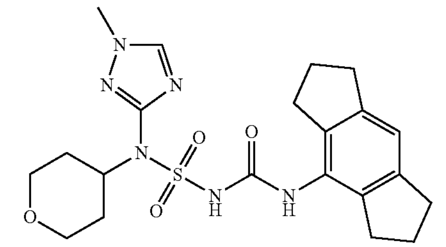 [SMILES: Cn1cnc(N(C2CCOCC2)S(=O)(=O)NC(=O)Nc2c3c(cc4c2CCC4)CCC3)n1] |
| 20A | 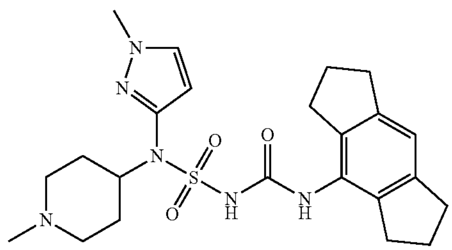 [SMILES: CN1CCC(N(c2ccn(C)n2)S(=O)(=O)NC(=O)Nc2c3c(cc4c2CCC4)CCC3)CC1] |
| 21A | 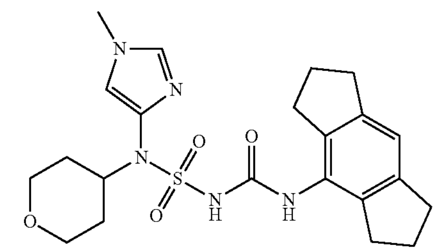 |
| 22A | 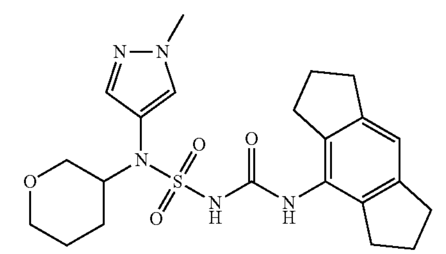 [SMILES: Cn1cc(N(C2CCCOC2)S(=O)(=O)NC(=O)Nc2c3c(cc4c2CCC4)CCC3)cn1] |
| 23A | 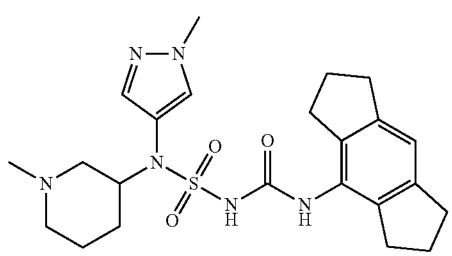 [SMILES: CN1CCCC(N(c2cnn(C)c2)S(=O)(=O)NC(=O)Nc2c3c(cc4c2CCC4)CCC3)C1] |
| 24A | 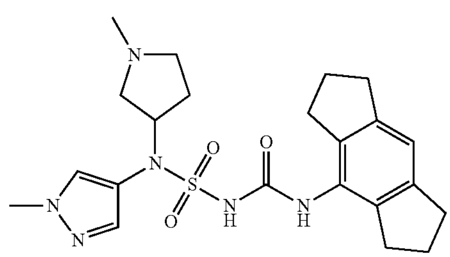 [SMILES: CN1CCC(N(c2cnn(C)c2)S(=O)(=O)NC(=O)Nc2c3c(cc4c2CCC4)CCC3)C1] |

TABLE 2-continued

| Compound No. | Structure |
|---|---|
| 25A | 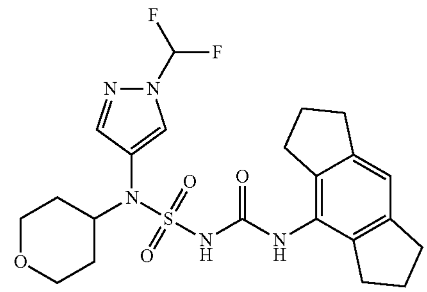 [SMILES: O=C(Nc1c2c(cc3c1CCC3)CCC2)NS(=O)(=O)N(c1cnn(C(F)F)c1)C1CCOCC1] |
| 26A | 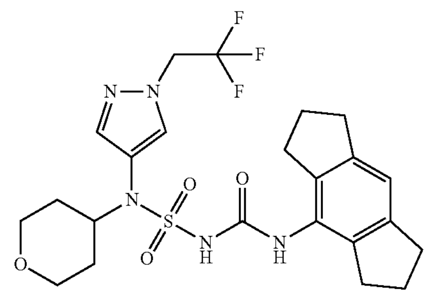 [SMILES: O=C(Nc1c2c(cc3c1CCC3)CCC2)NS(=O)(=O)N(c1cnn(CC(F)(F)F)c1)C1CCOCC1] |
| 27A | 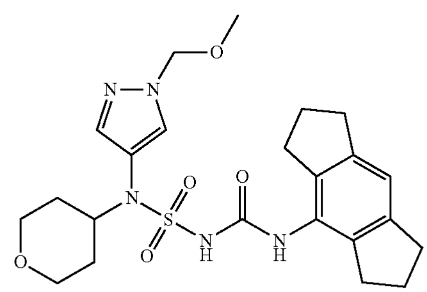 [SMILES: COCn1cc(N(C2CCOCC2)S(=O)(=O)NC(=O)Nc2c3c(cc4c2CCC4)CCC3)cn1] |
| 28A | 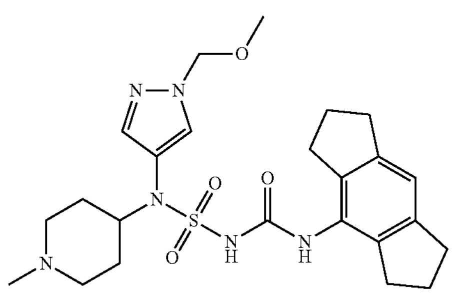 [SMILES: COCn1cc(N(C2CCN(C)CC2)S(=O)(=O)NC(=O)Nc2c3c(cc4c2CCC4)CCC3)cn1] |
| 29A | 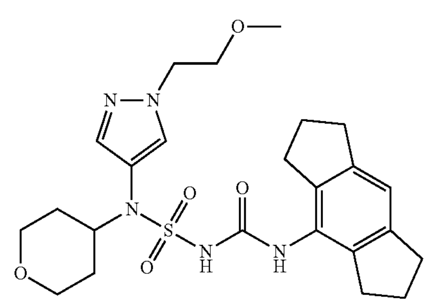 [SMILES: COCCn1cc(N(C2CCOCC2)S(=O)(=O)NC(=O)Nc2c3c(cc4c2CCC4)CCC3)cn1] |

TABLE 2-continued

| Compound No. | Structure |
| --- | --- |
| 30A | 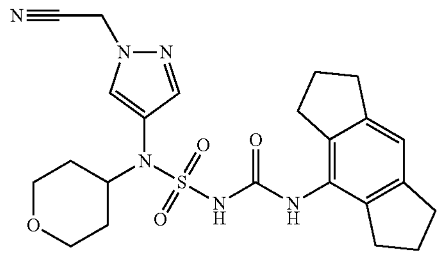 [SMILES: N#CCn1cc(N(C2CCOCC2)S(=O)(=O)NC(=O)Nc2c3c(cc4c2CCC4)CCC3)cn1] |
| 31A | 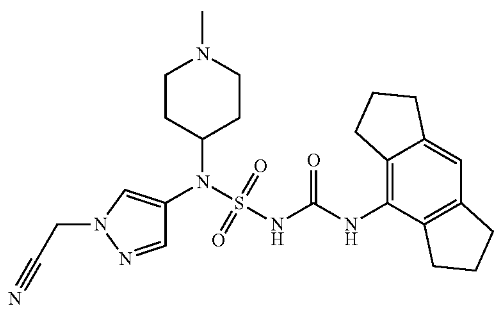 [SMILES: CN1CCC(N(c2cnn(CC#N)c2)S(=O)(=O)NC(=O)Nc2c3c(cc4c2CCC4)CCC3)CC1] |
| 32A | 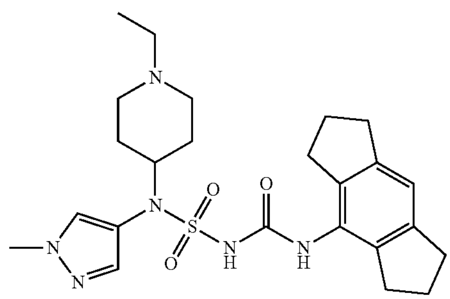 [SMILES: CCN1CCC(N(c2cnn(C)c2)S(=O)(=O)NC(=O)Nc2c3c(cc4c2CCC4)CCC3)CC1] |
| 33A | 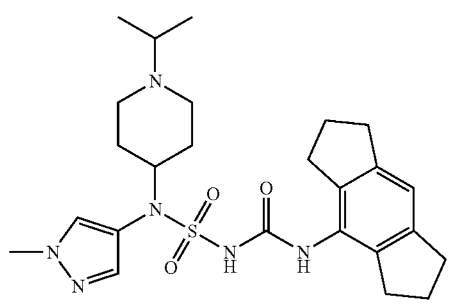 [SMILES: CC(C)N1CCC(N(c2cnn(C)c2)S(=O)(=O)NC(=O)Nc2c3c(cc4c2CCC4)CCC3)CC1] |
| 34A | 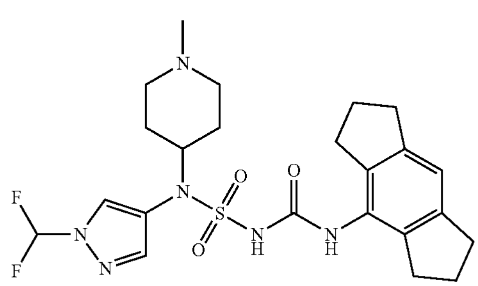 [SMILES: CN1CCC(N(c2cnn(C(F)F)c2)S(=O)(=O)NC(=O)Nc2c3c(cc4c2CCC4)CCC3)CC1] |

TABLE 2-continued
| Compound No. | Structure |
|---|---|
| 35A | 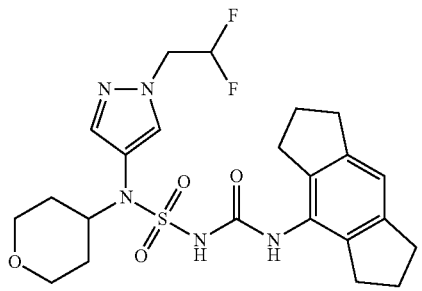 [SMILES: O=C(Nc1c2c(cc3c1CCC3)CCC2)NS(=O)(=O)N(c1cnn(CC(F)F)c1)C1CCOCC1] |
| 36A | 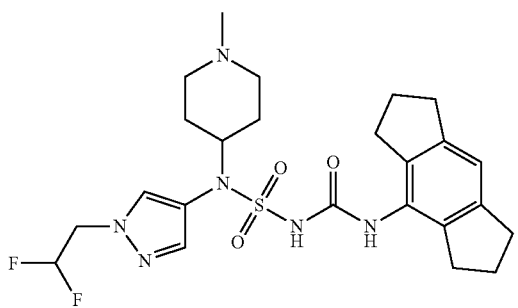 [SMILES: CN1CCC(N(c2cnn(CC(F)F)c2)S(=O)(=O)NC(=O)Nc2c3c(cc4c2CCC4)CCC3)CC1] |
| 37A | 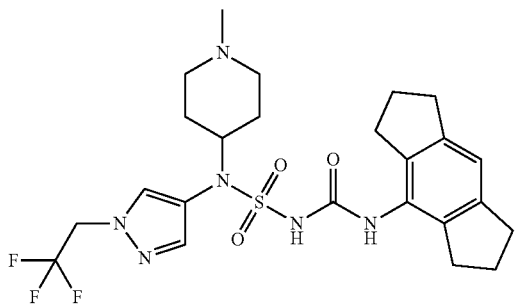 [SMILES: CN1CCC(N(c2cnn(CC(F)(F)F)c2)S(=O)(=O)NC(=O)Nc2c3c(cc4c2CCC4)CCC3)CC1] |
| 38A | 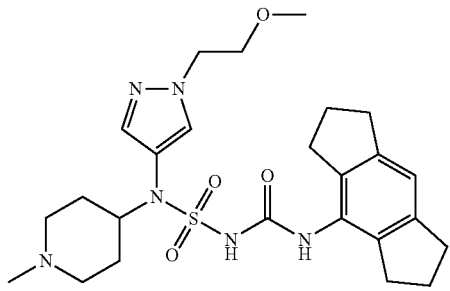 [SMILES: COCCn1cc(N(C2CCN(C)CC2)S(=O)(=O)NC(=O)Nc2c3c(cc4c2CCC4)CCC3)cn1] |
| 39A | 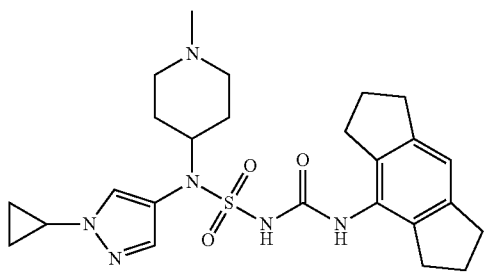 [SMILES: CN1CCC(N(c2cnn(C3CC3)c2)S(=O)(=O)NC(=O)Nc2c3c(cc4c2CCC4)CCC3)CC1] |

TABLE 2-continued
| Compound No. | Structure |
|---|---|
| 40A | 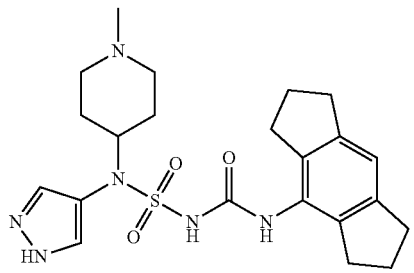 [SMILES: CN1CCC(N(c2cn[nH]c2)S(=O)(=O)NC(=O)Nc2c3c(cc4c2CCC4)CCC3)CC1] |
| 41A | 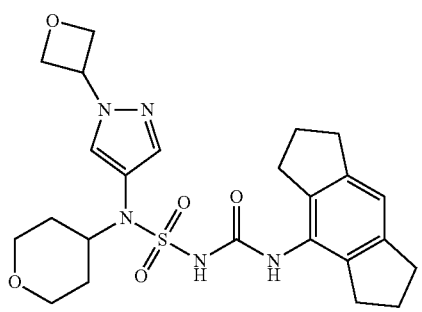 [SMILES: O=C(Nc1c2c(cc3c1CCC3)CCC2)NS(=O)(=O)N(c1cnn(C2COC2)c1)C1CCOCC1] |
| 42A | 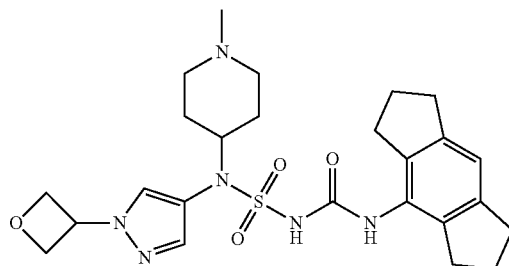 |
| 43A | 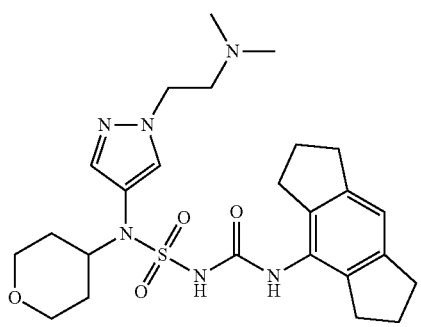 [SMILES: CN(C)CCn1cc(N(C2CCOCC2)S(=O)(=O)NC(=O)Nc2c3c(cc4c2CCC4)CCC3)cn1] |
| 44A | 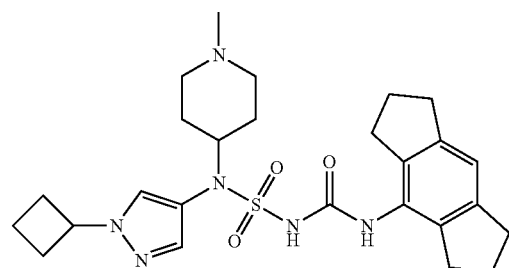 |

TABLE 2-continued
| Compound No. | Structure |
|---|---|
| 45A | 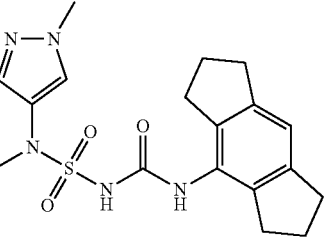 |
| 46A | 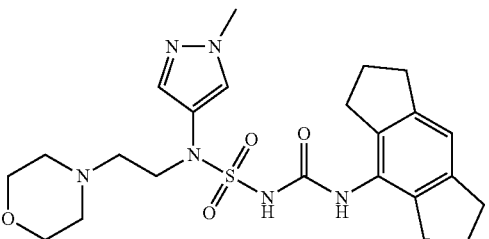 |
| 47A | 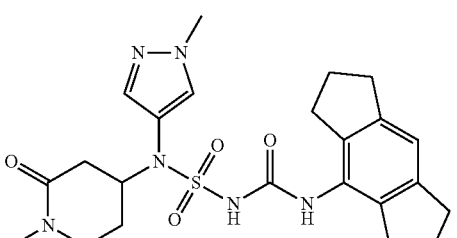 |
| 48A | 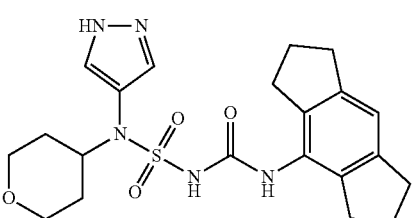 |
| 49A | 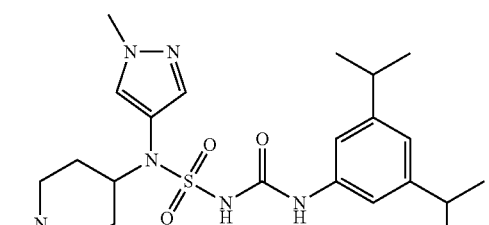 |
| 50A | 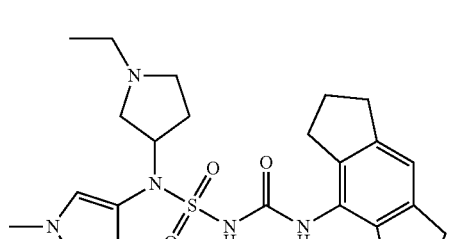 |

TABLE 2-continued
| Compound No. | Structure |
|---|---|
| 51A | 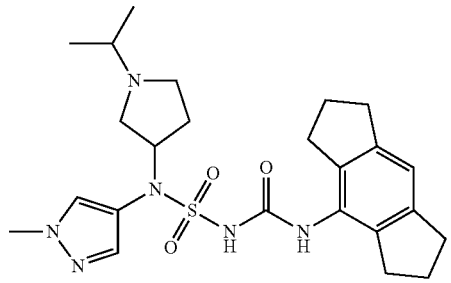 [SMILES: CC(C)N1CCC(N(c2cnn(C)c2)S(=O)(=O)NC(=O)Nc2c3c(cc4c2CCC4)CCC3)C1] |
| 52A | 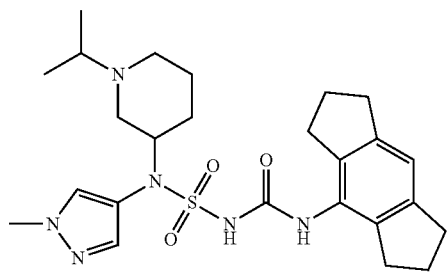 [SMILES: CC(C)N1CCCC(N(c2cnn(C)c2)S(=O)(=O)NC(=O)Nc2c3c(cc4c2CCC4)CCC3)C1] |
| 53A | 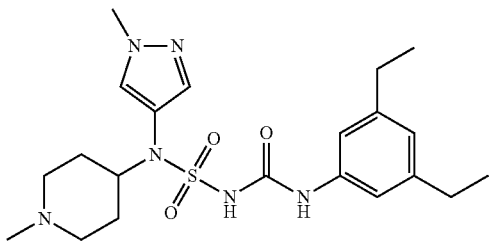 [SMILES: CCc1cc(CC)cc(NC(=O)NS(=O)(=O)N(c2cnn(C)c2)C2CCN(C)CC2)c1] |
| 54A | 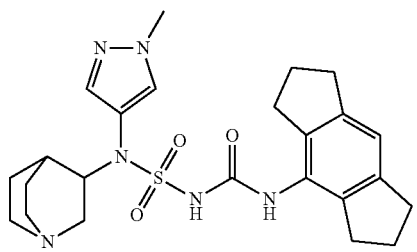 [SMILES: Cn1cc(N(C2CN3CCC2CC3)S(=O)(=O)NC(=O)Nc2c3c(cc4c2CCC4)CCC3)cn1] |
| 55A | 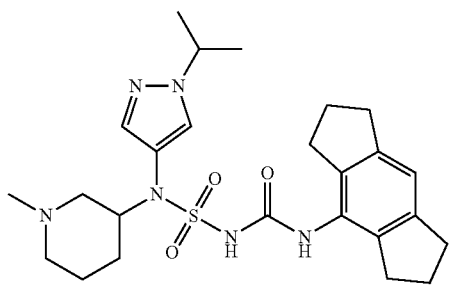 [SMILES: CC(C)n1cc(N(C2CCCN(C)C2)S(=O)(=O)NC(=O)Nc2c3c(cc4c2CCC4)CCC3)cn1] |

TABLE 2-continued
| Compound No. | Structure |
|---|---|
| 56A | 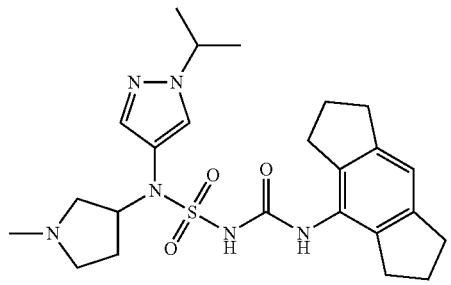 [SMILES: CC(C)n1cc(N(C2CCN(C)C2)S(=O)(=O)NC(=O)Nc2c3c(cc4c2CCC4)CCC3)cn1] |
| 57A | 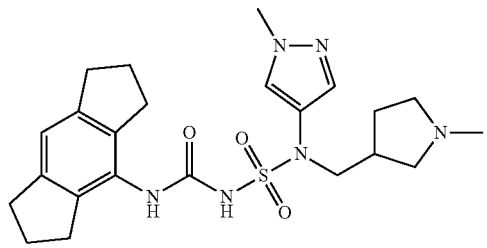 [SMILES: CN1CCC(CN(c2cnn(C)c2)S(=O)(=O)NC(=O)Nc2c3c(cc4c2CCC4)CCC3)C1] |
| 58A | 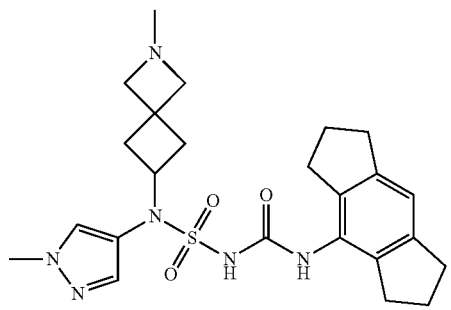 [SMILES: CN1CC2(CC(N(c3cnn(C)c3)S(=O)(=O)NC(=O)Nc3c4c(cc5c3CCC5)CCC4)C2)C1] |
| 59A | 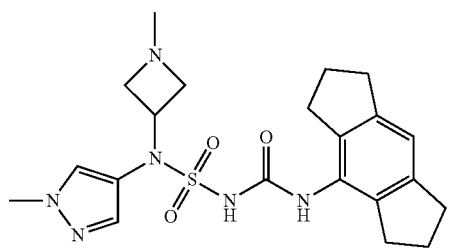 [SMILES: CN1CC(N(c2cnn(C)c2)S(=O)(=O)NC(=O)Nc2c3c(cc4c2CCC4)CCC3)C1] |
| 60A | 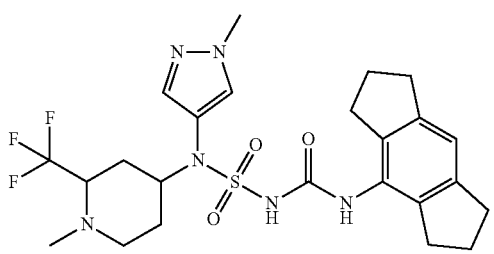 [SMILES: CN1CCC(N(c2cnn(C)c2)S(=O)(=O)NC(=O)Nc2c3c(cc4c2CCC4)CCC3)CC1C(F)(F)F] |

TABLE 2-continued

| Compound No. | Structure |
| --- | --- |
| 61A | 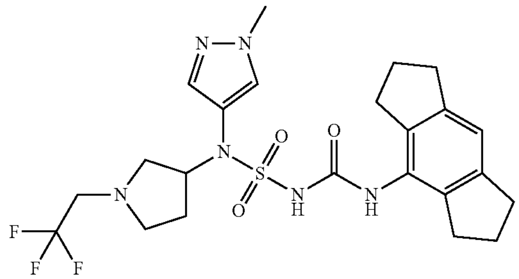 [SMILES: Cn1cc(N(C2CCN(CC(F)(F)F)C2)S(=O)(=O)NC(=O)Nc2c3c(cc4c2CCC4)CCC3)cn1] |
| 62A | 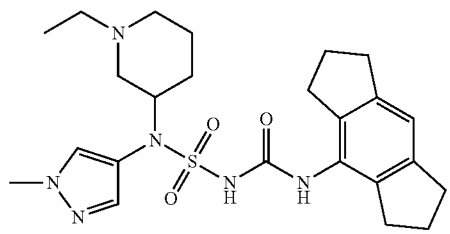 [SMILES: CCN1CCCC(N(c2cnn(C)c2)S(=O)(=O)NC(=O)Nc2c3c(cc4c2CCC4)CCC3)C1] |
| 63A | 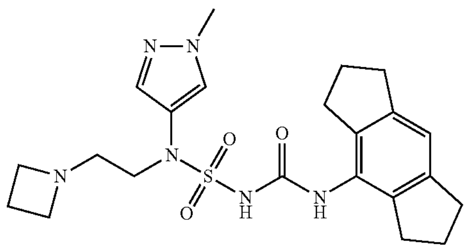 [SMILES: Cn1cc(N(CCN2CCC2)S(=O)(=O)NC(=O)Nc2c3c(cc4c2CCC4)CCC3)cn1] |
| 64A | 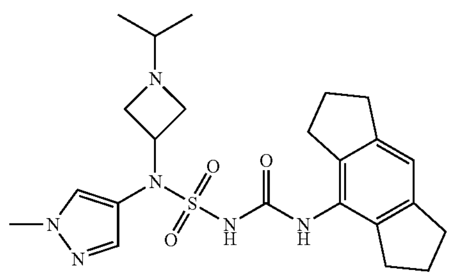 [SMILES: CC(C)N1CC(N(c2cnn(C)c2)S(=O)(=O)NC(=O)Nc2c3c(cc4c2CCC4)CCC3)C1] |
| 65A | 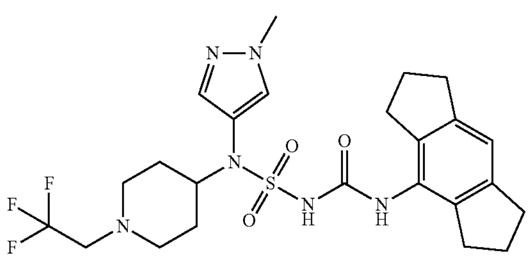 [SMILES: Cn1cc(N(C2CCN(CC(F)(F)F)CC2)S(=O)(=O)NC(=O)Nc2c3c(cc4c2CCC4)CCC3)cn1] |
| 66A | 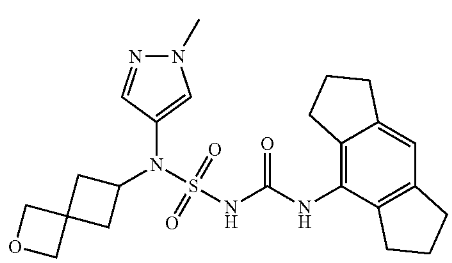 [SMILES: Cn1cc(N(C2CC3(COC3)C2)S(=O)(=O)NC(=O)Nc2c3c(cc4c2CCC4)CCC3)cn1] |

TABLE 2-continued

| Compound No. | Structure |
| --- | --- |
| 67A | 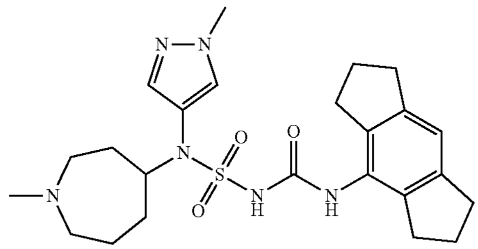 [SMILES: CN1CCCC(N(c2cnn(C)c2)S(=O)(=O)NC(=O)Nc2c3c(cc4c2CCC4)CCC3)CC1] |
| 68A | 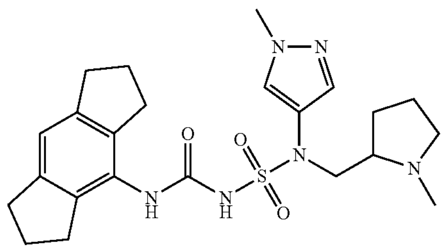 [SMILES: CN1CCCC1CN(c1cnn(C)c1)S(=O)(=O)NC(=O)Nc1c2c(cc3c1CCC3)CCC2] |
| 69A | 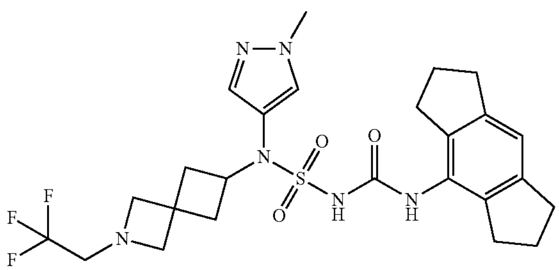 [SMILES: Cn1cc(N(C2CC3(C2)CN(CC(F)(F)F)C3)S(=O)(=O)NC(=O)Nc2c3c(cc4c2CCC4)CCC3)cn1] |
| 70A | 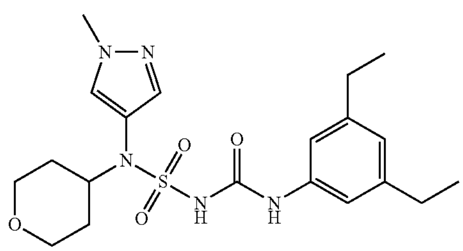 [SMILES: CCc1cc(CC)cc(NC(=O)NS(=O)(=O)N(c2cnn(C)c2)C2CCOCC2)c1] |
| 71A | 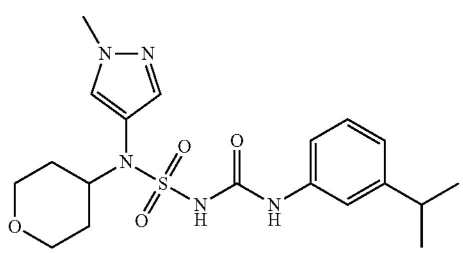 [SMILES: CC(C)c1cccc(NC(=O)NS(=O)(=O)N(c2cnn(C)c2)C2CCOCC2)c1] |
| 72A | 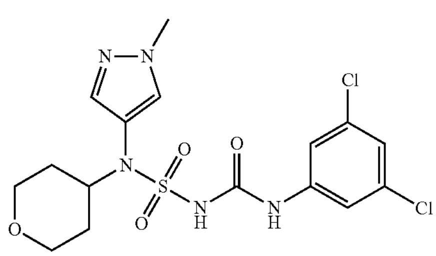 [SMILES: Cn1cc(N(C2CCOCC2)S(=O)(=O)NC(=O)Nc2cc(Cl)cc(Cl)c2)cn1] |

TABLE 2-continued

| Compound No. | Structure |
| --- | --- |
| 73A | 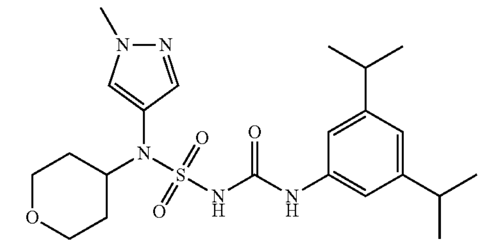 [SMILES: CC(C)c1cc(NC(=O)NS(=O)(=O)N(c2cnn(C)c2)C2CCOCC2)cc(C(C)C)c1] |
| 74A | 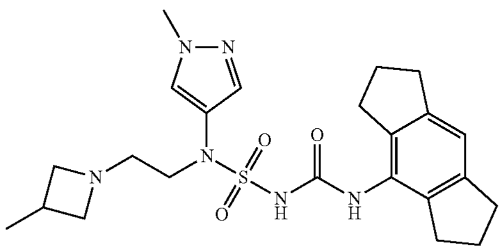 [SMILES: CC1CN(CCN(c2cnn(C)c2)S(=O)(=O)NC(=O)Nc2c3c(cc4c2CCC4)CCC3)C1] |
| 75A | 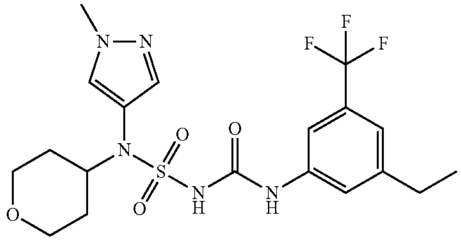 [SMILES: CCc1cc(NC(=O)NS(=O)(=O)N(c2cnn(C)c2)C2CCOCC2)cc(C(F)(F)F)c1] |
| 76A | 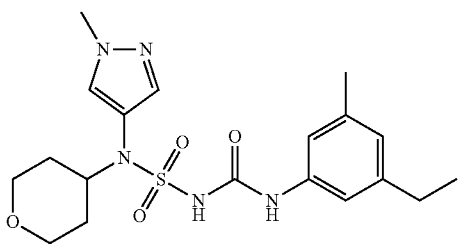 [SMILES: CCc1cc(C)cc(NC(=O)NS(=O)(=O)N(c2cnn(C)c2)C2CCOCC2)c1] |
| 77A | 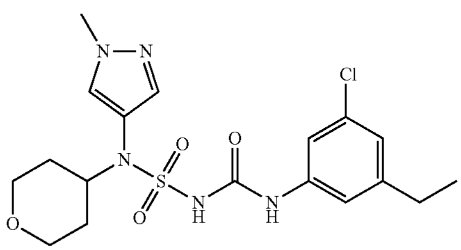 [SMILES: CCc1cc(Cl)cc(NC(=O)NS(=O)(=O)N(c2cnn(C)c2)C2CCOCC2)c1] |
| 78A | 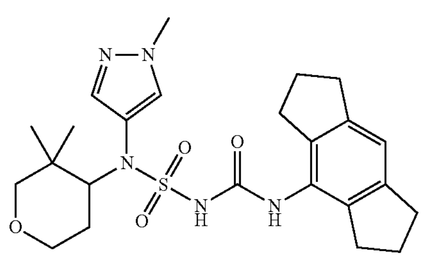 [SMILES: Cn1cc(N(C2CCOCC2(C)C)S(=O)(=O)NC(=O)Nc2c3c(cc4c2CCC4)CCC3)cn1] |

TABLE 2-continued

| Compound No. | Structure |
| --- | --- |
| 79A | 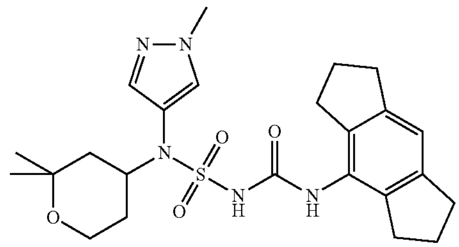 [SMILES: Cn1cc(N(C2CCOC(C)(C)C2)S(=O)(=O)NC(=O)Nc2c3c(cc4c2CCC4)CCC3)cn1] |
| 80A | 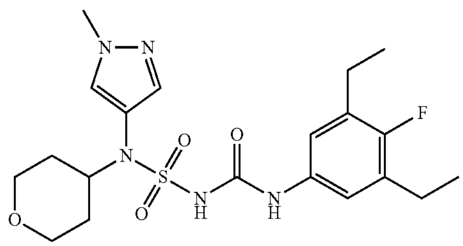 [SMILES: CCc1cc(NC(=O)NS(=O)(=O)N(c2cnn(C)c2)C2CCOCC2)cc(CC)c1F] |
| 81A | 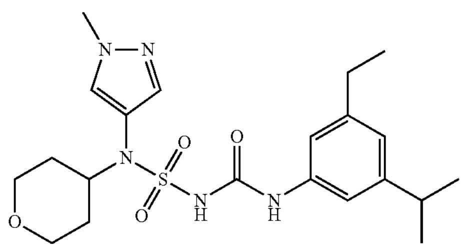 [SMILES: CCc1cc(NC(=O)NS(=O)(=O)N(c2cnn(C)c2)C2CCOCC2)cc(C(C)C)c1] |
| 82A | 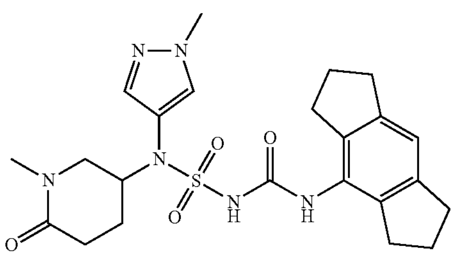 [SMILES: CN1CC(N(c2cnn(C)c2)S(=O)(=O)NC(=O)Nc2c3c(cc4c2CCC4)CCC3)CCC1=O] |
| 83A | 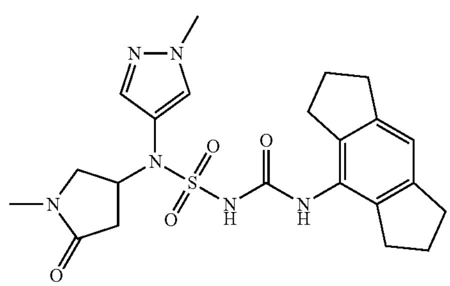 [SMILES: CN1CC(N(c2cnn(C)c2)S(=O)(=O)NC(=O)Nc2c3c(cc4c2CCC4)CCC3)CC1=O] |
| 84A | 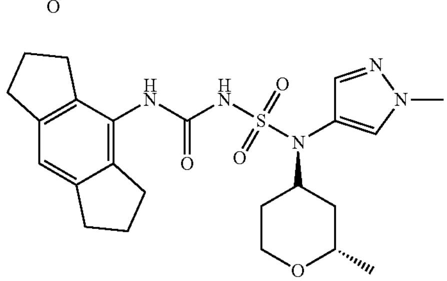 |

TABLE 2-continued

| Compound No. | Structure |
|---|---|
| 85A | 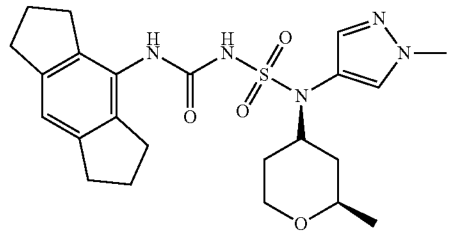 |
| 86A | 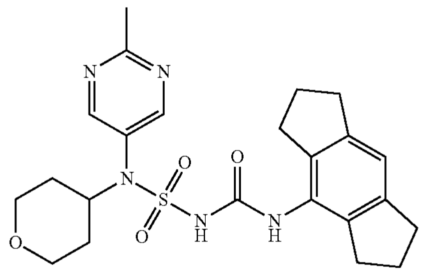 [SMILES: Cc1ncc(N(C2CCOCC2)S(=O)(=O)NC(=O)Nc2c3c(cc4c2CCC4)CCC3)cn1] |
| 87A | 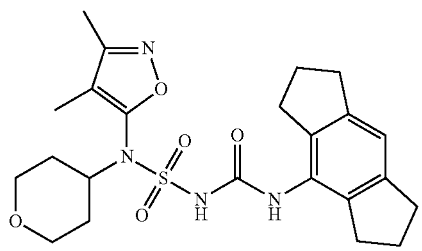 [SMILES: Cc1noc(N(C2CCOCC2)S(=O)(=O)NC(=O)Nc2c3c(cc4c2CCC4)CCC3)c1C] |
| 88A | 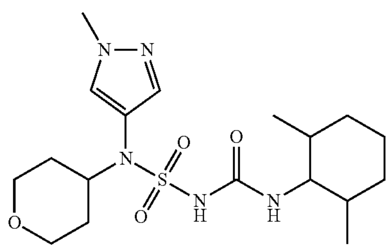 [SMILES: CC1CCCC(C)C1NC(=O)NS(=O)(=O)N(c1cnn(C)c1)C1CCOCC1] |
| 89A | 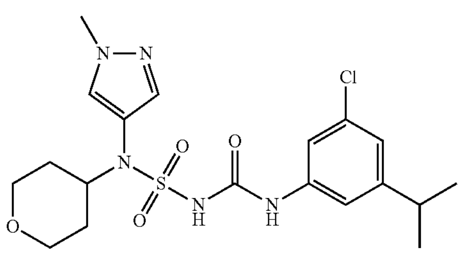 [SMILES: CC(C)c1cc(Cl)cc(NC(=O)NS(=O)(=O)N(c2cnn(C)c2)C2CCOCC2)c1] |
| 90A | 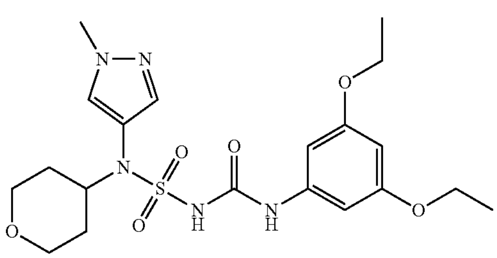 [SMILES: CCOc1cc(NC(=O)NS(=O)(=O)N(c2cnn(C)c2)C2CCOCC2)cc(OCC)c1] |

TABLE 2-continued

| Compound No. | Structure |
|---|---|
| 91A | 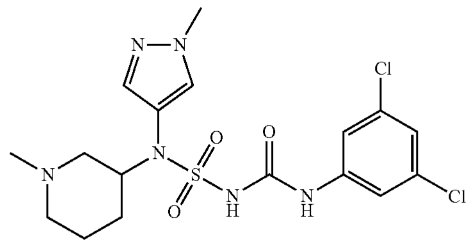 [SMILES: CN1CCCC(N(c2cnn(C)c2)S(=O)(=O)NC(=O)Nc2cc(Cl)cc(Cl)c2)C1] |
| 92A | 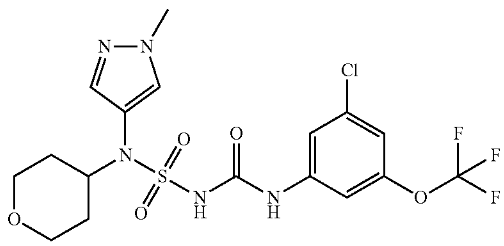 [SMILES: Cn1cc(N(C2CCOCC2)S(=O)(=O)NC(=O)Nc2cc(Cl)cc(OC(F)(F)F)c2)cn1] |
| 93A | 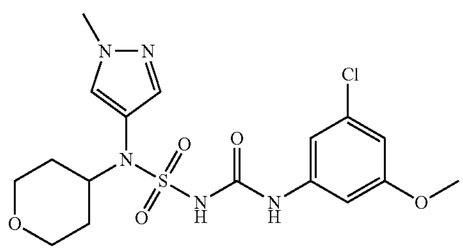 [SMILES: COc1cc(Cl)cc(NC(=O)NS(=O)(=O)N(c2cnn(C)c2)C2CCOCC2)c1] |
| 94A | 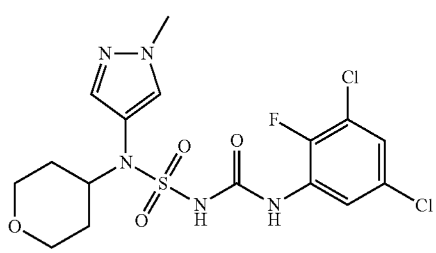 [SMILES: Cn1cc(N(C2CCOCC2)S(=O)(=O)NC(=O)Nc2cc(Cl)cc(Cl)c2F)cn1] |
| 95A | 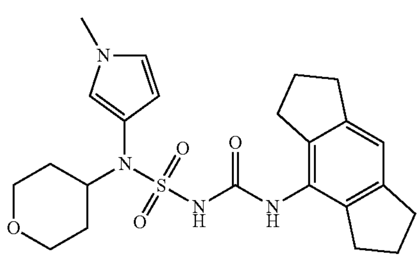 [SMILES: Cn1ccc(N(C2CCOCC2)S(=O)(=O)NC(=O)Nc2c3c(cc4c2CCC4)CCC3)c1] |
| 96A | 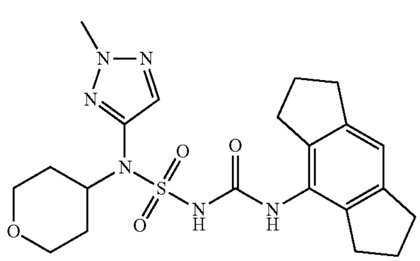 [SMILES: Cn1ncc(N(C2CCOCC2)S(=O)(=O)NC(=O)Nc2c3c(cc4c2CCC4)CCC3)n1] |

TABLE 2-continued

| Compound No. | Structure |
|---|---|
| 97A | 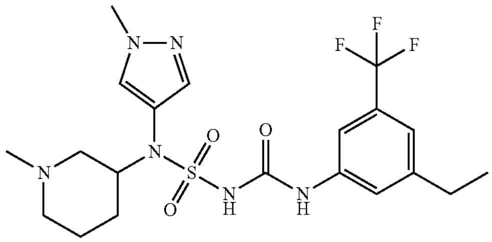 [SMILES: CCc1cc(NC(=O)NS(=O)(=O)N(c2cnn(C)c2)C2CCCN(C)C2)cc(C(F)(F)F)c1] |
| 98A | 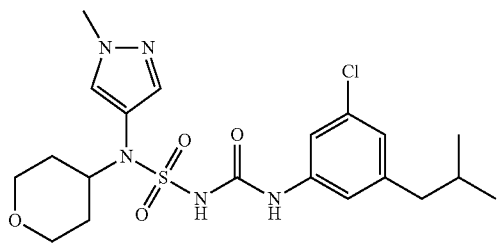 [SMILES: CC(C)Cc1cc(Cl)cc(NC(=O)NS(=O)(=O)N(c2cnn(C)c2)C2CCOCC2)c1] |
| 99A | 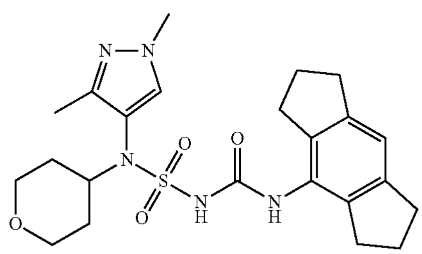 [SMILES: Cc1nn(C)cc1N(C1CCOCC1)S(=O)(=O)NC(=O)Nc1c2c(cc3c1CCC3)CCC2] |
| 100A | 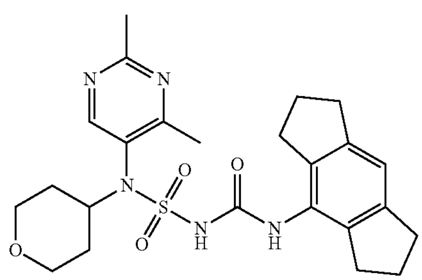 [SMILES: Cc1ncc(N(C2CCOCC2)S(=O)(=O)NC(=O)Nc2c3c(cc4c2CCC4)CCC3)c(C)n1] |
| 101A | 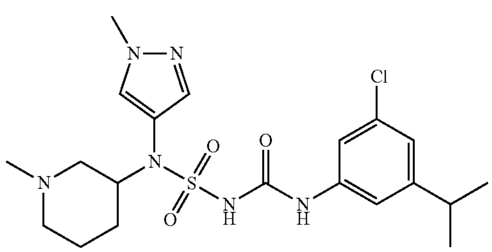 [SMILES: CC(C)c1cc(Cl)cc(NC(=O)NS(=O)(=O)N(c2cnn(C)c2)C2CCCN(C)C2)c1] |
| 102A | 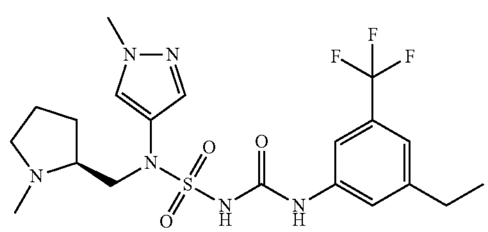 [SMILES: CCc1cc(NC(=O)NS(=O)(=O)N(C[C@@H]2CCCN2C)c2cnn(C)c2)cc(C(F)(F)F)c1] |

TABLE 2-continued
| Compound No. | Structure |
|---|---|
| 103A | 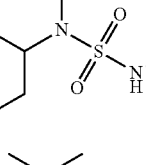 |
| 104A | 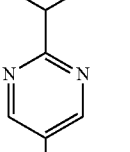 |
| 105A | 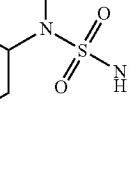 |
| 106A | 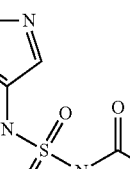 |
| 107A | 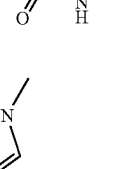 |
| 108A | 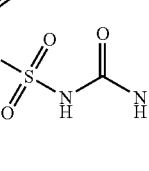 |

TABLE 2-continued

| Compound No. | Structure |
| --- | --- |
| 109A | 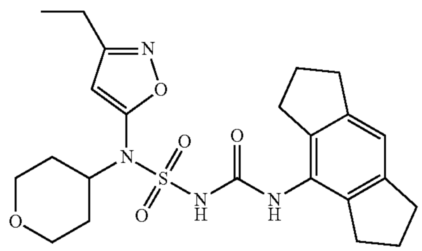 [SMILES: CCc1cc(N(C2CCOCC2)S(=O)(=O)NC(=O)Nc2c3c(cc4c2CCC4)CCC3)on1] |
| 110A | 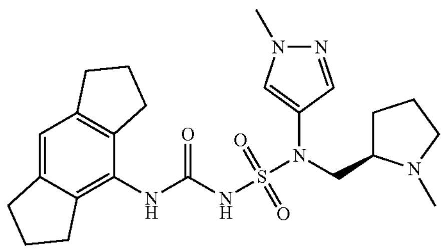 [SMILES: CN1CCC[C@@H]1CN(c1cnn(C)c1)S(=O)(=O)NC(=O)Nc1c2c(cc3c1CCC3)CCC2] |
| 111A | 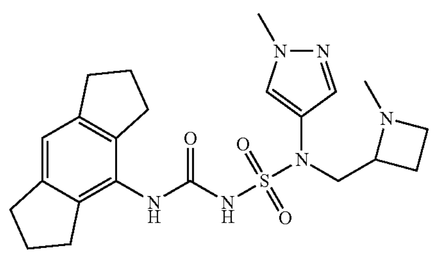 [SMILES: CN1CCC1CN(c1cnn(C)c1)S(=O)(=O)NC(=O)Nc1c2c(cc3c1CCC3)CCC2] |
| 112A | 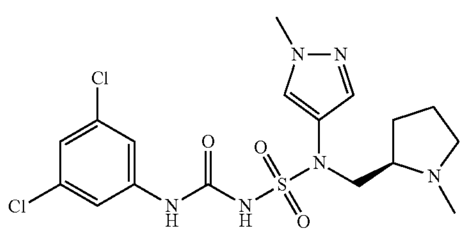 [SMILES: CN1CCC[C@@H]1CN(c1cnn(C)c1)S(=O)(=O)NC(=O)Nc1cc(Cl)cc(Cl)c1] |
| 113A | 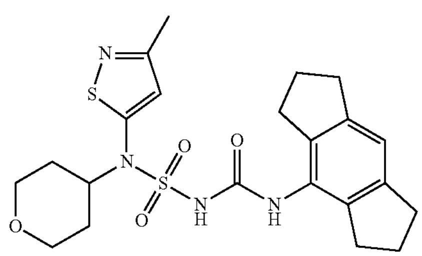 [SMILES: Cc1cc(N(C2CCOCC2)S(=O)(=O)NC(=O)Nc2c3c(cc4c2CCC4)CCC3)sn1] |
| 114A | 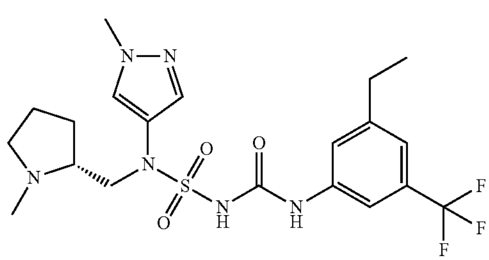 [SMILES: CCc1cc(NC(=O)NS(=O)(=O)N(C[C@H]2CCCN2C)c2cnn(C)c2)cc(C(F)(F)F)c1] |

TABLE 2-continued

| Compound No. | Structure |
| --- | --- |
| 115A | 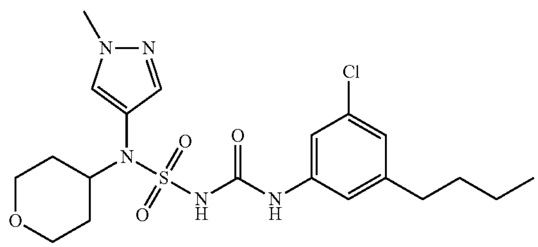 [SMILES: CCCCc1cc(Cl)cc(NC(=O)NS(=O)(=O)N(c2cnn(C)c2)C2CCOCC2)c1] |
| 116A | 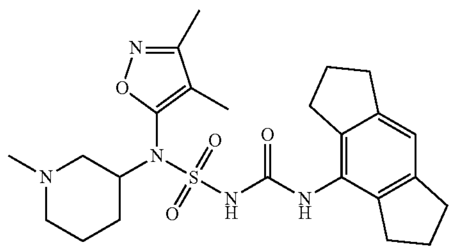 [SMILES: Cc1noc(N(C2CCCN(C)C2)S(=O)(=O)NC(=O)Nc2c3c(cc4c2CCC4)CCC3)c1C] |
| 117A | 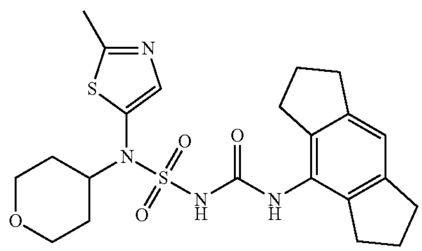 |
| 118A | 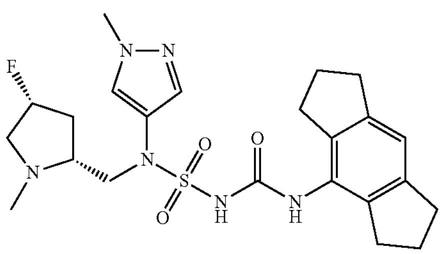 [SMILES: CN1C[C@H](F)C[C@@H]1CN(c1cnn(C)c1)S(=O)(=O)NC(=O)Nc1c2c(cc3c1CCC3)CCC2] |
| 119A | 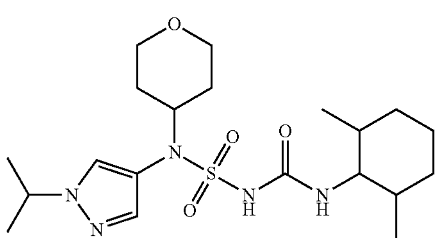 [SMILES: CC1CCCC(C)C1NC(=O)NS(=O)(=O)N(c1cnn(C(C)C)c1)C1CCOCC1] |
| 120A | 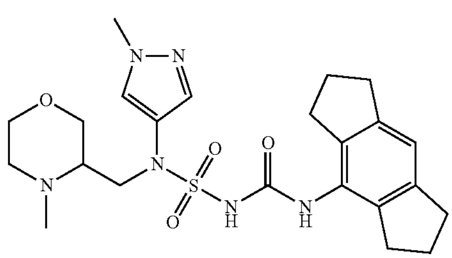 [SMILES: CN1CCOCC1CN(c1cnn(C)c1)S(=O)(=O)NC(=O)Nc1c2c(cc3c1CCC3)CCC2] |

TABLE 2-continued

| Compound No. | Structure |
|---|---|
| 121A | 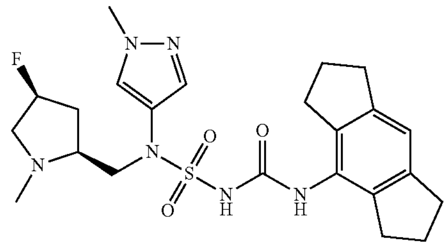 [SMILES: CN1C[C@@H](F)C[C@H]1CN(c1cnn(C)c1)S(=O)(=O)NC(=O)Nc1c2c(cc3c1CCC3)CCC2] |
| 122A | 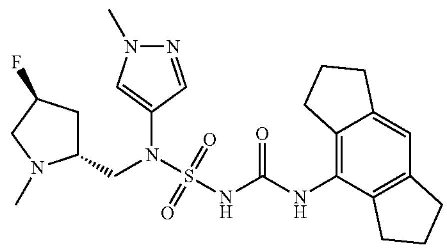 [SMILES: CN1C[C@@H](F)C[C@@H]1CN(c1cnn(C)c1)S(=O)(=O)NC(=O)Nc1c2c(cc3c1CCC3)CCC2] |
| 123A | 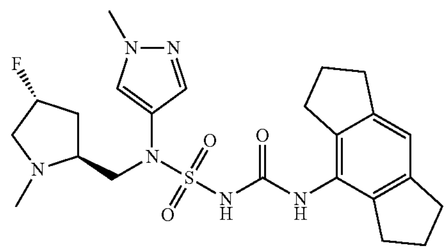 [SMILES: CN1C[C@H](F)C[C@H]1CN(c1cnn(C)c1)S(=O)(=O)NC(=O)Nc1c2c(cc3c1CCC3)CCC2] |
| 124A | 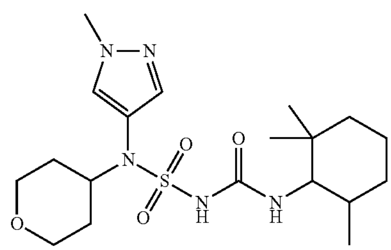 [SMILES: CC1CCCC(C)(C)C1NC(=O)NS(=O)(=O)N(c1cnn(C)c1)C1CCOCC1] |
| 125A | 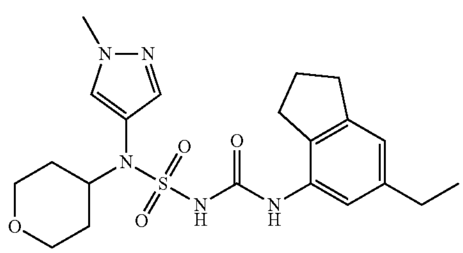 [SMILES: CCc1cc2c(c(NC(=O)NS(=O)(=O)N(c3cnn(C)c3)C3CCOCC3)c1)CCC2] |
| 126A | 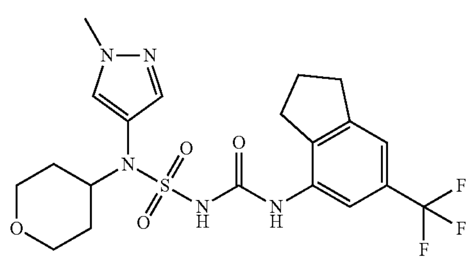 [SMILES: Cn1cc(N(C2CCOCC2)S(=O)(=O)NC(=O)Nc2cc(C(F)(F)F)cc3c2CCC3)cn1] |

TABLE 2-continued
| Compound No. | Structure |
|---|---|
| 127A | 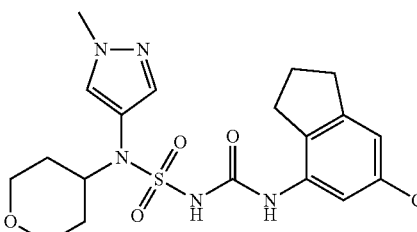 |
| 128A | 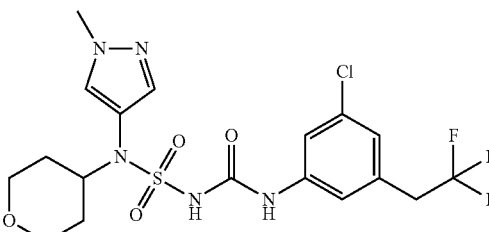 |
| 129A | 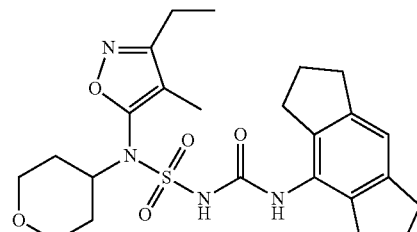 |
| 130A | 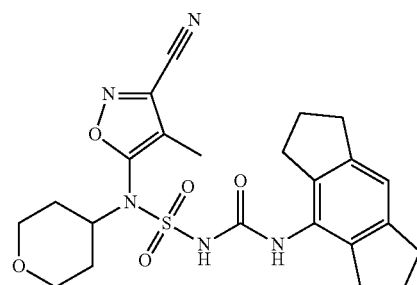 |
| 131A | 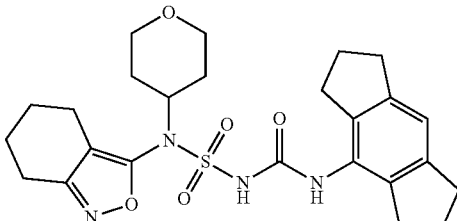 |
| 132A | 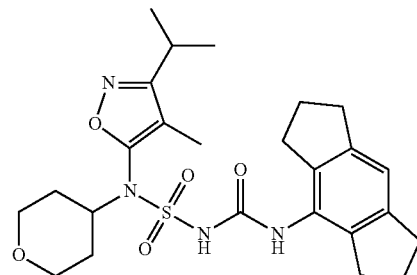 |

TABLE 2-continued

| Compound No. | Structure |
|---|---|
| 133A | 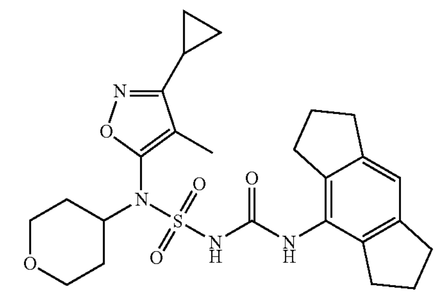 [SMILES: Cc1c(C2CC2)noc1N(C1CCOCC1)S(=O)(=O)NC(=O)Nc1c2c(cc3c1CCC3)CCC2] |
| 134A | 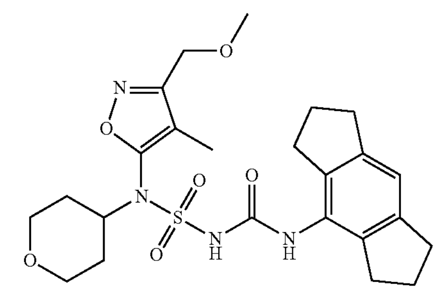 [SMILES: COCc1noc(N(C2CCOCC2)S(=O)(=O)NC(=O)Nc2c3c(cc4c2CCC4)CCC3)c1C] |
| 135A | 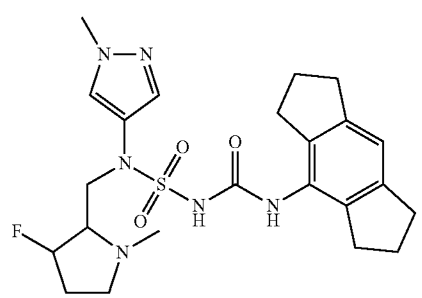 [SMILES: CN1CCC(F)C1CN(c1cnn(C)c1)S(=O)(=O)NC(=O)Nc1c2c(cc3c1CCC3)CCC2] |
| 136A | 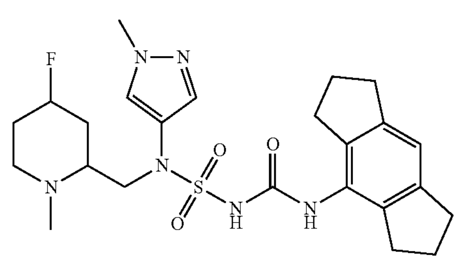 [SMILES: CN1CCC(F)CC1CN(c1cnn(C)c1)S(=O)(=O)NC(=O)Nc1c2c(cc3c1CCC3)CCC2] |
| 137A | 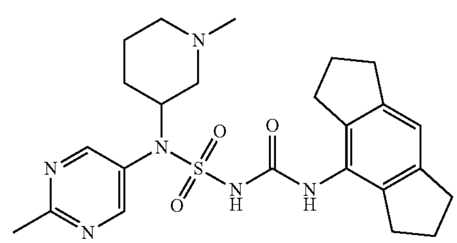 [SMILES: Cc1ncc(N(C2CCCN(C)C2)S(=O)(=O)NC(=O)Nc2c3c(cc4c2CCC4)CCC3)cn1] |

TABLE 2-continued

| Compound No. | Structure |
|---|---|
| 138A | 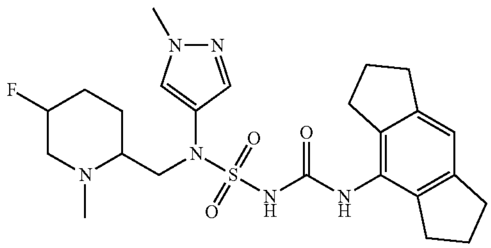 [SMILES: CN1CC(F)CCC1CN(c1cnn(C)c1)S(=O)(=O)NC(=O)Nc1c2c(cc3c1CCC3)CCC2] |
| 139A | 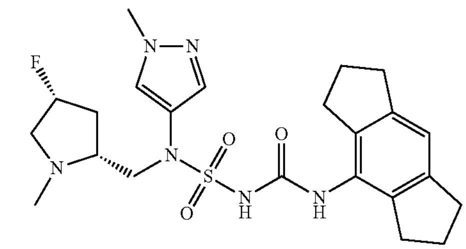 [SMILES: CN1C[C@H](F)C[C@@H]1CN(c1cnn(C)c1)S(=O)(=O)NC(=O)Nc1c2c(cc3c1CCC3)CCC2] |
| 140A | 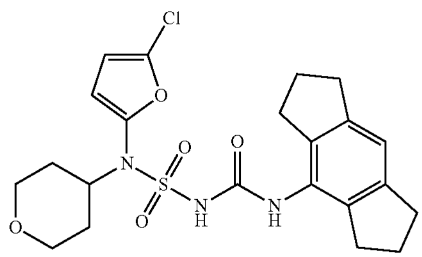 [SMILES: O=C(Nc1c2c(cc3c1CCC3)CCC2)NS(=O)(=O)N(c1ccc(Cl)o1)C1CCOCC1] |
| 141A | 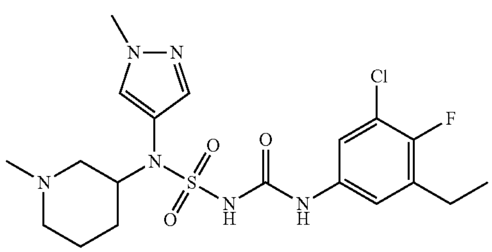 [SMILES: CCc1cc(NC(=O)NS(=O)(=O)N(c2cnn(C)c2)C2CCCN(C)C2)cc(Cl)c1F] |
| 142A | 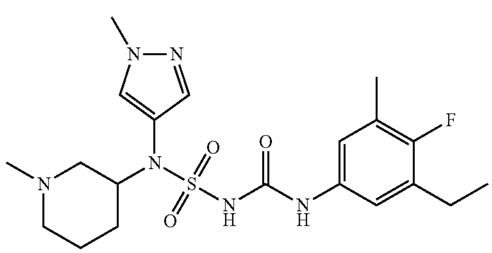 [SMILES: CCc1cc(NC(=O)NS(=O)(=O)N(c2cnn(C)c2)C2CCCN(C)C2)cc(C)c1F] |
| 143A | 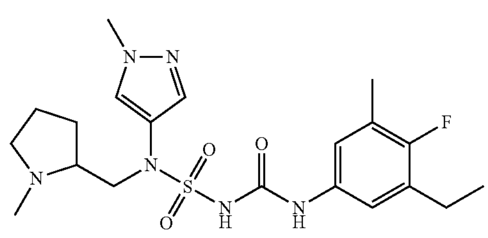 [SMILES: CCc1cc(NC(=O)NS(=O)(=O)N(CC2CCCN2C)c2cnn(C)c2)cc(C)c1F] |

TABLE 2-continued

| Compound No. | Structure |
| --- | --- |
| 144A | 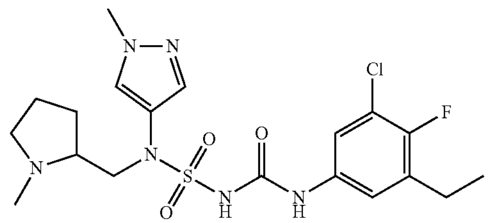 [SMILES: CCc1cc(NC(=O)NS(=O)(=O)N(CC2CCCN2C)c2cnn(C)c2)cc(Cl)c1F] |
| 145A | 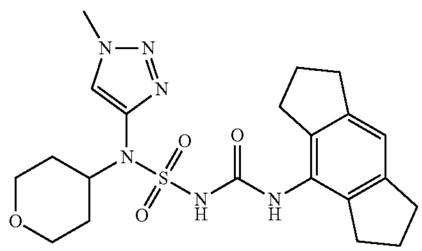 [SMILES: Cn1cc(N(C2CCOCC2)S(=O)(=O)NC(=O)Nc2c3c(cc4c2CCC4)CCC3)nn1] |
| 146A | 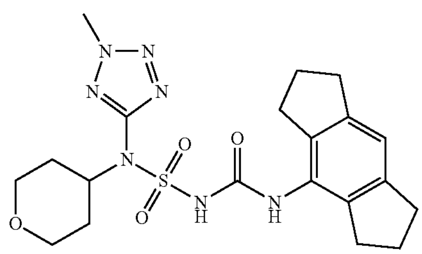 [SMILES: Cn1nnc(N(C2CCOCC2)S(=O)(=O)NC(=O)Nc2c3c(cc4c2CCC4)CCC3)n1] |
| 147A | 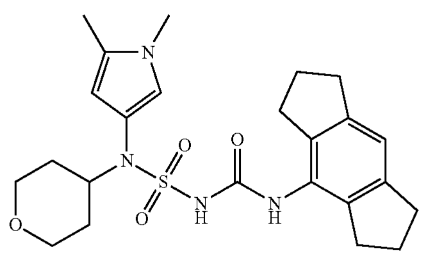 [SMILES: Cc1cc(N(C2CCOCC2)S(=O)(=O)NC(=O)Nc2c3c(cc4c2CCC4)CCC3)cn1C] |
| 148A | 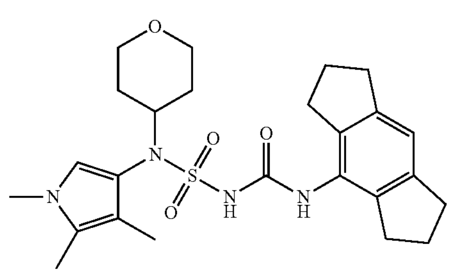 [SMILES: Cc1c(N(C2CCOCC2)S(=O)(=O)NC(=O)Nc2c3c(cc4c2CCC4)CCC3)cn(C)c1C] |
| 149A | 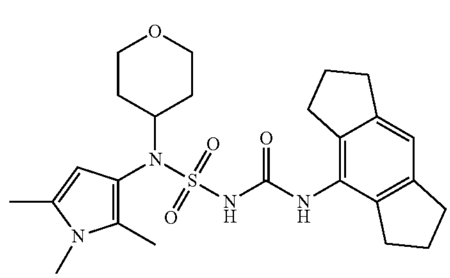 [SMILES: Cc1cc(N(C2CCOCC2)S(=O)(=O)NC(=O)Nc2c3c(cc4c2CCC4)CCC3)c(C)n1C] |

TABLE 2-continued

| Compound No. | Structure |
|---|---|
| 150A | 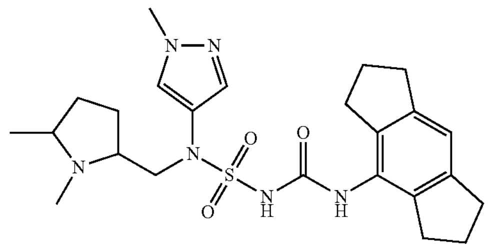 [SMILES: CC1CCC(CN(c2cnn(C)c2)S(=O)(=O)NC(=O)Nc2c3c(cc4c2CCC4)CCC3)N1C] |
| 151A | 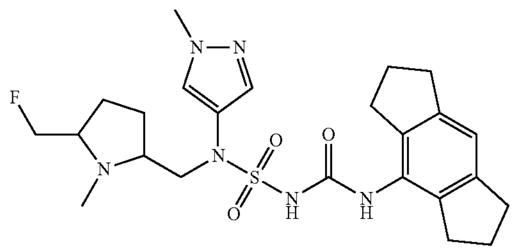 [SMILES: CN1C(CF)CCC1CN(c1cnn(C)c1)S(=O)(=O)NC(=O)Nc1c2c(cc3c1CCC3)CCC2] |
| 152A | 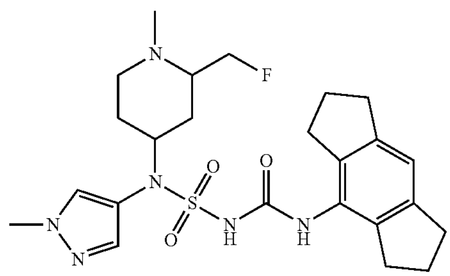 [SMILES: CN1CCC(N(c2cnn(C)c2)S(=O)(=O)NC(=O)Nc2c3c(cc4c2CCC4)CCC3)CC1CF] |
| 153A | 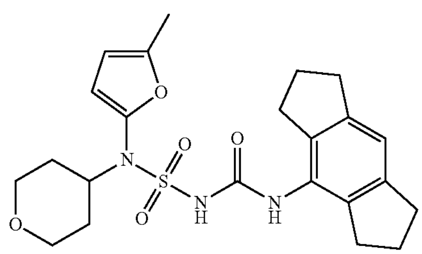 [SMILES: Cc1ccc(N(C2CCOCC2)S(=O)(=O)NC(=O)Nc2c3c(cc4c2CCC4)CCC3)o1] |
| 154A | 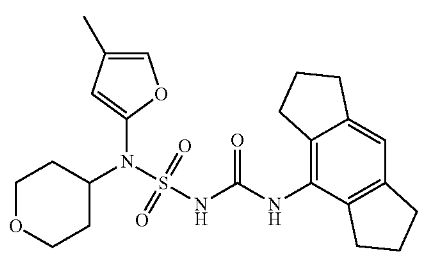 [SMILES: Cc1coc(N(C2CCOCC2)S(=O)(=O)NC(=O)Nc2c3c(cc4c2CCC4)CCC3)c1] |
| 155A | 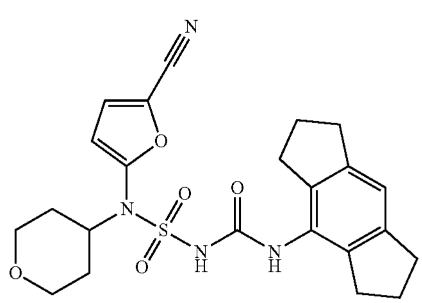 [SMILES: N#Cc1ccc(N(C2CCOCC2)S(=O)(=O)NC(=O)Nc2c3c(cc4c2CCC4)CCC3)o1] |

TABLE 2-continued

| Compound No. | Structure |
|---|---|
| 156A | 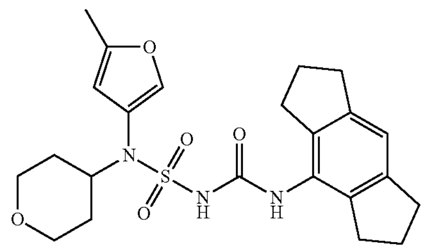 [SMILES: Cc1cc(N(C2CCOCC2)S(=O)(=O)NC(=O)Nc2c3c(cc4c2CCC4)CCC3)co1] |
| 157A | 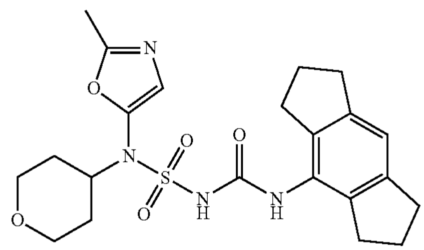 [SMILES: Cc1ncc(N(C2CCOCC2)S(=O)(=O)NC(=O)Nc2c3c(cc4c2CCC4)CCC3)o1] |
| 158A | 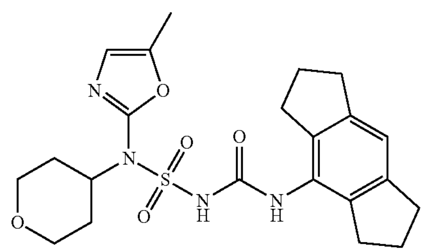 [SMILES: Cc1cnc(N(C2CCOCC2)S(=O)(=O)NC(=O)Nc2c3c(cc4c2CCC4)CCC3)o1] |
| 159A | 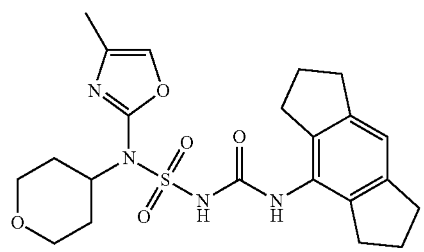 [SMILES: Cc1coc(N(C2CCOCC2)S(=O)(=O)NC(=O)Nc2c3c(cc4c2CCC4)CCC3)n1] |
| 160A | 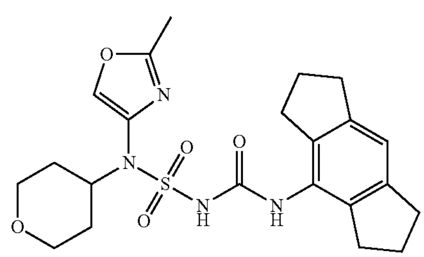 [SMILES: Cc1nc(N(C2CCOCC2)S(=O)(=O)NC(=O)Nc2c3c(cc4c2CCC4)CCC3)co1] |
| 161A | 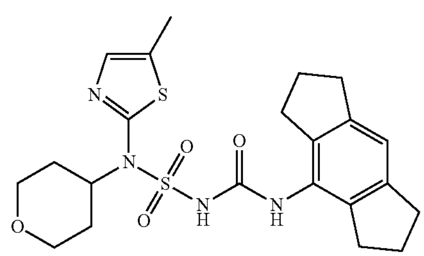 |

TABLE 2-continued

| Compound No. | Structure |
|---|---|
| 162A | 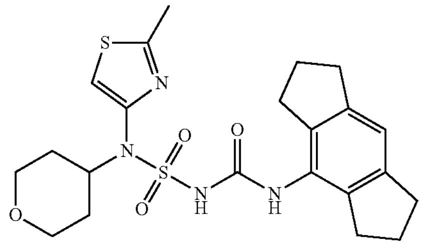 [SMILES: Cc1nc(N(C2CCOCC2)S(=O)(=O)NC(=O)Nc2c3c(cc4c2CCC4)CCC3)cs1] |
| 163A | 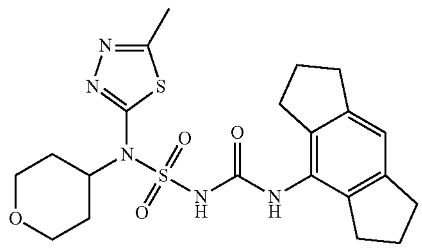 [SMILES: Cc1nnc(N(C2CCOCC2)S(=O)(=O)NC(=O)Nc2c3c(cc4c2CCC4)CCC3)s1] |
| 164A | 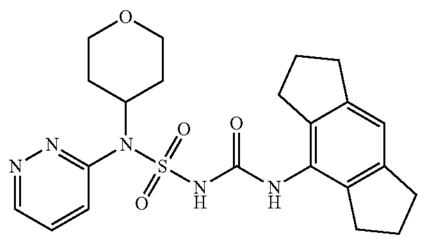 [SMILES: O=C(Nc1c2c(cc3c1CCC3)CCC2)NS(=O)(=O)N(c1cccnn1)C1CCOCC1] |
| 165A | 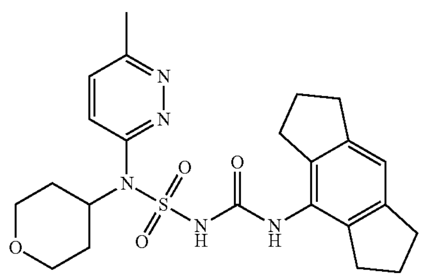 [SMILES: Cc1ccc(N(C2CCOCC2)S(=O)(=O)NC(=O)Nc2c3c(cc4c2CCC4)CCC3)nn1] |
| 166A | 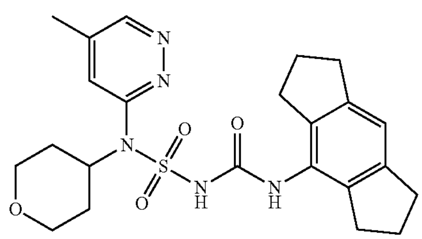 [SMILES: Cc1cnnc(N(C2CCOCC2)S(=O)(=O)NC(=O)Nc2c3c(cc4c2CCC4)CCC3)c1] |

In some aspects, the present disclosure provides a compound being an isotopic derivative (e.g., isotopically labeled compound) of any one of the compounds of the Formulae disclosed herein.

In some embodiments, the compound is an isotopic derivative of any one of the compounds described in Table 1 and prodrugs and pharmaceutically acceptable salts thereof.

In some embodiments, the compound is an isotopic derivative of any one of the compounds described in Table 1 and pharmaceutically acceptable salts thereof.

In some embodiments, the compound is an isotopic derivative of any one of the compounds described in Table 1.

In some embodiments, the compound is an isotopic derivative of any one of the compounds described in Table 2 and prodrugs and pharmaceutically acceptable salts thereof.

In some embodiments, the compound is an isotopic derivative of any one of the compounds described in Table 2 and pharmaceutically acceptable salts thereof.

In some embodiments, the compound is an isotopic derivative of any one of the compounds described in Table 2.

It is understood that the isotopic derivative can be prepared using any of a variety of art-recognised techniques. For example, the isotopic derivative can generally be prepared by carrying out the procedures disclosed in the Schemes and/or in the Examples described herein, by substituting an isotopically labeled reagent for a non-isotopically labeled reagent.

In some embodiments, the isotopic derivative is a deuterium labeled compound.

In some embodiments, the isotopic derivative is a deuterium labeled compound of any one of the compounds of the Formulae disclosed herein.

In some embodiments, the compound is a deuterium labeled compound of any one of the compounds described in Table 1 and prodrugs and pharmaceutically acceptable salts thereof.

In some embodiments, the compound is a deuterium labeled compound of any one of the compounds described in Table 1 and pharmaceutically acceptable salts thereof.

In some embodiments, the compound is a deuterium labeled compound of any one of the compounds described in Table 1.

In some embodiments, the compound is a deuterium labeled compound of any one of the compounds described in Table 2 and prodrugs and pharmaceutically acceptable salts thereof.

In some embodiments, the compound is a deuterium labeled compound of any one of the compounds described in Table 2 and pharmaceutically acceptable salts thereof.

In some embodiments, the compound is a deuterium labeled compound of any one of the compounds described in Table 2.

It is understood that the deuterium labeled compound comprises a deuterium atom having an abundance of deuterium that is substantially greater than the natural abundance of deuterium, which is 0.015%.

In some embodiments, the deuterium labeled compound has a deuterium enrichment factor for each deuterium atom of at least 3500 (52.5% deuterium incorporation at each deuterium atom), at least 4000 (60% deuterium incorporation), at least 4500 (67.5% deuterium incorporation), at least 5000 (75% deuterium), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation). As used herein, the term "deuterium enrichment factor" means the ratio between the deuterium abundance and the natural abundance of a deuterium.

It is understood that the deuterium labeled compound can be prepared using any of a variety of art-recognised techniques. For example, the deuterium labeled compound can generally be prepared by carrying out the procedures disclosed in the Schemes and/or in the Examples described herein, by substituting a deuterium labeled reagent for a non-deuterium labeled reagent.

A compound of the invention or a pharmaceutically acceptable salt or solvate thereof that contains the aforementioned deuterium atom(s) is within the scope of the invention. Further, substitution with deuterium (i.e., $^2$H) may afford certain therapeutic advantages resulting from greater metabolic stability, e.g., increased in vivo half-life or reduced dosage requirements.

For the avoidance of doubt it is to be understood that, where in this specification a group is qualified by "described herein", the said group encompasses the first occurring and broadest definition as well as each and all of the particular definitions for that group.

Particular compounds of the disclosure include, for example, compounds of any one of the Formulae disclosed herein, or pharmaceutically acceptable salt thereof, wherein, unless otherwise stated, each of $R_1$, $R_3$, $R_4$ and any associated substituent groups has any of the meanings defined hereinbefore.

The various functional groups and substituents making up the compounds of the Formula (I) are typically chosen such that the molecular weight of the compound does not exceed 1000 daltons. More usually, the molecular weight of the compound will be less than 900, for example less than 800, or less than 750, or less than 700, or less than 650 daltons. More conveniently, the molecular weight is less than 600 and, for example, is 550 daltons or less.

A suitable pharmaceutically acceptable salt of a compound of the disclosure is, for example, an acid-addition salt of a compound of the disclosure which is sufficiently basic, for example, an acid-addition salt with, for example, an inorganic or organic acid, for example hydrochloric, hydrobromic, sulphuric, phosphoric, trifluoroacetic, formic, citric methane sulphonate or maleic acid. In addition, a suitable pharmaceutically acceptable salt of a compound of the disclosure which is sufficiently acidic is an alkali metal salt, for example a sodium or potassium salt, an alkaline earth metal salt, for example a calcium or magnesium salt, an ammonium salt or a salt with an organic base which affords a pharmaceutically acceptable cation, for example a salt with methylamine, dimethylamine, diethylamine, trimethylamine, piperidine, morpholine or tris-(2-hydroxyethyl)amine.

It will be understood that the compounds of any one of the Formulae disclosed herein and any pharmaceutically acceptable salts thereof, comprise stereoisomers, mixtures of stereoisomers, polymorphs of all isomeric forms of said compounds.

As used herein, the term "isomerism" means compounds that have identical molecular formulae but differ in the sequence of bonding of their atoms or in the arrangement of their atoms in space. Isomers that differ in the arrangement of their atoms in space are termed "stereoisomers." Stereoisomers that are not mirror images of one another are termed "diastereoisomers," and stereoisomers that are non-superimposable mirror images of each other are termed "enantiomers" or sometimes optical isomers. A mixture containing equal amounts of individual enantiomeric forms of opposite chirality is termed a "racemic mixture."

As used herein, the term "chiral centre" refers to a carbon atom bonded to four nonidentical substituents.

As used herein, the term "chiral isomer" means a compound with at least one chiral centre. Compounds with more than one chiral centre may exist either as an individual diastereomer or as a mixture of diastereomers, termed "diastereomeric mixture." When one chiral centre is present, a stereoisomer may be characterised by the absolute configuration (R or S) of that chiral centre. Absolute configuration refers to the arrangement in space of the substituents attached to the chiral centre. The substituents attached to the chiral centre under consideration are ranked in accordance with the Sequence Rule of Cahn, Ingold and Prelog. (Cahn et al., *Angew. Chem. Inter. Edit.* 1966, 5, 385; errata 511; Cahn et al., *Angew. Chem.* 1966, 78, 413; Cahn and Ingold, *J. Chem. Soc.* 1951 (London), 612; Cahn et al., *Experientia* 1956, 12, 81; Cahn, *J. Chem. Educ.* 1964, 41, 116).

As used herein, the term "geometric isomer" means the diastereomers that owe their existence to hindered rotation about double bonds or a cycloalkyl linker (e.g., 1,3-cyclobutyl). These configurations are differentiated in their names by the prefixes cis and trans, or Z and E, which indicate that the groups are on the same or opposite side of the double bond in the molecule according to the Cahn-Ingold-Prelog rules.

It is to be understood that the compounds of the present disclosure may be depicted as different chiral isomers or geometric isomers. It is also to be understood that when compounds have chiral isomeric or geometric isomeric forms, all isomeric forms are intended to be included in the scope of the present disclosure, and the naming of the compounds does not exclude any isomeric forms, it being understood that not all isomers may have the same level of activity.

It is to be understood that the structures and other compounds discussed in this disclosure include all atropic isomers thereof. It is also to be understood that not all atropic isomers may have the same level of activity.

As used herein, the term "atropic isomers" are a type of stereoisomer in which the atoms of two isomers are arranged differently in space. Atropic isomers owe their existence to a restricted rotation caused by hindrance of rotation of large groups about a central bond. Such atropic isomers typically exist as a mixture, however as a result of recent advances in chromatography techniques, it has been possible to separate mixtures of two atropic isomers in select cases.

As used herein, the term "tautomer" is one of two or more structural isomers that exist in equilibrium and is readily converted from one isomeric form to another. This conversion results in the formal migration of a hydrogen atom accompanied by a switch of adjacent conjugated double bonds. Tautomers exist as a mixture of a tautomeric set in solution. In solutions where tautomerisation is possible, a chemical equilibrium of the tautomers will be reached. The exact ratio of the tautomers depends on several factors, including temperature, solvent and pH. The concept of tautomers that are interconvertible by tautomerisations is called tautomerism. Of the various types of tautomerism that are possible, two are commonly observed. In keto-enol tautomerism a simultaneous shift of electrons and a hydrogen atom occurs. Ring-chain tautomerism arises as a result of the aldehyde group (—CHO) in a sugar chain molecule reacting with one of the hydroxy groups (—OH) in the same molecule to give it a cyclic (ring-shaped) form as exhibited by glucose.

It is to be understood that the compounds of the present disclosure may be depicted as different tautomers. It should also be understood that when compounds have tautomeric forms, all tautomeric forms are intended to be included in the scope of the present disclosure, and the naming of the compounds does not exclude any tautomer form. It will be understood that certain tautomers may have a higher level of activity than others.

Compounds that have the same molecular formula but differ in the nature or sequence of bonding of their atoms or the arrangement of their atoms in space are termed "isomers". Isomers that differ in the arrangement of their atoms in space are termed "stereoisomers". Stereoisomers that are not mirror images of one another are termed "diastereomers" and those that are non-superimposable mirror images of each other are termed "enantiomers". When a compound has an asymmetric centre, for example, it is bonded to four different groups, a pair of enantiomers is possible. An enantiomer can be characterised by the absolute configuration of its asymmetric centre and is described by the R- and S-sequencing rules of Cahn and Prelog, or by the manner in which the molecule rotates the plane of polarised light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The compounds of this disclosure may possess one or more asymmetric centres; such compounds can therefore be produced as individual (R)- or (S)-stereoisomers or as mixtures thereof. Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art (see discussion in Chapter 4 of "Advanced Organic Chemistry", 4th edition J. March, John Wiley and Sons, New York, 2001), for example by synthesis from optically active starting materials or by resolution of a racemic form. Some of the compounds of the disclosure may have geometric isomeric centres (E- and Z-isomers). It is to be understood that the present disclosure encompasses all optical, diastereoisomers and geometric isomers and mixtures thereof that possess inflammasome inhibitory activity.

The present disclosure also encompasses compounds of the disclosure as defined herein which comprise one or more isotopic substitutions.

It is to be understood that the compounds of any Formula described herein include the compounds themselves, as well as their salts, and their solvates, if applicable. A salt, for example, can be formed between an anion and a positively charged group (e.g., amino) on a substituted compound disclosed herein. Suitable anions include chloride, bromide, iodide, sulphate, bisulphate, sulphamate, nitrate, phosphate, citrate, methanesulphonate, trifluoroacetate, glutamate, glucuronate, glutarate, malate, maleate, succinate, fumarate, tartrate, tosylate, salicylate, lactate, naphthalenesulphonate, and acetate (e.g., trifluoroacetate).

As used herein, the term "pharmaceutically acceptable anion" refers to an anion suitable for forming a pharmaceutically acceptable salt. Likewise, a salt can also be formed between a cation and a negatively charged group (e.g., carboxylate) on a substituted compound disclosed herein. Suitable cations include sodium ion, potassium ion, magnesium ion, calcium ion, and an ammonium cation such as tetramethylammonium ion or diethylamine ion. The substituted compounds disclosed herein also include those salts containing quaternary nitrogen atoms.

It is to be understood that the compounds of the present disclosure, for example, the salts of the compounds, can exist in either hydrated or unhydrated (the anhydrous) form or as solvates with other solvent molecules. Nonlimiting examples of hydrates include monohydrates, dihydrates, etc. Nonlimiting examples of solvates include ethanol solvates, acetone solvates, etc.

As used herein, the term "solvate" means solvent addition forms that contain either stoichiometric or non-stoichiometric amounts of solvent. Some compounds have a tendency to trap a fixed molar ratio of solvent molecules in the crystalline solid state, thus forming a solvate. If the solvent is water the solvate formed is a hydrate; and if the solvent is alcohol, the solvate formed is an alcoholate. Hydrates are formed by the combination of one or more molecules of water with one molecule of the substance in which the water retains its molecular state as $H_2O$.

As used herein, the term "analog" refers to a chemical compound that is structurally similar to another but differs slightly in composition (as in the replacement of one atom by an atom of a different element or in the presence of a particular functional group, or the replacement of one functional group by another functional group). Thus, an analog is a compound that is similar or comparable in function and appearance, but not in structure or origin to the reference compound.

As used herein, the term "derivative" refers to compounds that have a common core structure and are substituted with various groups as described herein.

As used herein, the term "bioisostere" refers to a compound resulting from the exchange of an atom or of a group of atoms with another, broadly similar, atom or group of atoms. The objective of a bioisosteric replacement is to create a new compound with similar biological properties to the parent compound. The bioisosteric replacement may be physicochemically or topologically based. Examples of carboxylic acid bioisosteres include, but are not limited to, acyl sulphonamides, tetrazoles, sulphonates and phosphonates. See, e.g., Patani and LaVoie, Chem. Rev. 96, 3147-3176, 1996.

It is also to be understood that certain compounds of any one of the Formulae disclosed herein may exist in solvated as well as unsolvated forms such as, for example, hydrated forms. A suitable pharmaceutically acceptable solvate is, for example, a hydrate such as hemi-hydrate, a mono-hydrate, a di-hydrate or a tri-hydrate. It is to be understood that the disclosure encompasses all such solvated forms that possess inflammasome inhibitory activity.

It is also to be understood that certain compounds of any one of the Formulae disclosed herein may exhibit polymorphism, and that the disclosure encompasses all such forms, or mixtures thereof, which possess inflammasome inhibitory activity. It is generally known that crystalline materials may be analysed using conventional techniques such as X-Ray Powder Diffraction analysis, Differential Scanning Calorimetry, Thermal Gravimetric Analysis, Diffuse Reflectance Infrared Fourier Transform (DRIFT) spectroscopy, Near Infrared (NIR) spectroscopy, solution and/or solid state nuclear magnetic resonance spectroscopy. The water content of such crystalline materials may be determined by Karl Fischer analysis.

Compounds of any one of the Formulae disclosed herein may exist in a number of different tautomeric forms and references to compounds of Formula (I) include all such forms. For the avoidance of doubt, where a compound can exist in one of several tautomeric forms, and only one is specifically described or shown, all others are nevertheless embraced by Formula (I). Examples of tautomeric forms include keto-, enol-, and enolate-forms, as in, for example, the following tautomeric pairs: keto/enol (illustrated below), imine/enamine, amide/imino alcohol, amidine/amidine, nitroso/oxime, thioketone/enethiol, and nitro/aci-nitro.

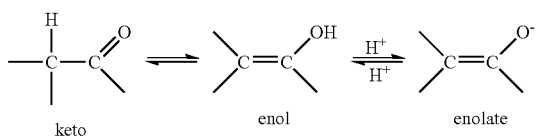

Compounds of any one of the Formulae disclosed herein containing an amine function may also form N-oxides. A reference herein to a compound of Formula (I) that contains an amine function also includes the N-oxide. Where a compound contains several amine functions, one or more than one nitrogen atom may be oxidised to form an N-oxide. Particular examples of N-oxides are the N-oxides of a tertiary amine or a nitrogen atom of a nitrogen-containing heterocycle. N-oxides can be formed by treatment of the corresponding amine with an oxidising agent such as hydrogen peroxide or a peracid (e.g. a peroxycarboxylic acid), see for example Advanced Organic Chemistry, by Jerry March, 4th Edition, Wiley Interscience, pages. More particularly, N-oxides can be made by the procedure of L. W. Deady (Syn. Comm. 1977, 7, 509-514) in which the amine compound is reacted with meta-chloroperoxybenzoic acid (mCPBA), for example, in an inert solvent such as dichloromethane.

The compounds of any one of the Formulae disclosed herein may be administered in the form of a prodrug which is broken down in the human or animal body to release a compound of the disclosure. A prodrug may be used to alter the physical properties and/or the pharmacokinetic properties of a compound of the disclosure. A prodrug can be formed when the compound of the disclosure contains a suitable group or substituent to which a property-modifying group can be attached. Examples of prodrugs include derivatives containing in vivo cleavable akyl or acyl substitutents at the sulphonylurea group in a compound of the any one of the Formulae disclosed herein.

Accordingly, the present disclosure includes those compounds of any one of the Formulae disclosed herein as defined hereinbefore when made available by organic synthesis and when made available within the human or animal body by way of cleavage of a prodrug thereof. Accordingly, the present disclosure includes those compounds of any one of the Formulae disclosed herein that are produced by organic synthetic means and also such compounds that are produced in the human or animal body by way of metabolism of a precursor compound, that is a compound of any one of the Formulae disclosed herein may be a synthetically-produced compound or a metabolically-produced compound.

A suitable pharmaceutically acceptable prodrug of a compound of any one of the Formulae disclosed herein is one that is based on reasonable medical judgment as being suitable for administration to the human or animal body without undesirable pharmacological activities and without undue toxicity. Various forms of prodrug have been described, for example in the following documents: a) Methods in Enzymology, Vol. 42, p. 309-396, edited by K. Widder, et al. (Academic Press, 1985); b) Design of Prodrugs, edited by H. Bundgaard, (Elsevier, 1985); c) A Textbook of Drug Design and Development, edited by Krogsgaard-Larsen and H. Bundgaard, Chapter 5 "Design and Application of Pro-drugs", by H. Bundgaard p. 113-191 (1991); d) H. Bundgaard, Advanced Drug Delivery Reviews, 8, 1-38 (1992); e) H. Bundgaard, et al., Journal of Pharmaceutical Sciences, 77, 285 (1988); f) N. Kakeya, et al., Chem. Pharm. Bull., 32, 692 (1984); g) T. Higuchi and V. Stella, "Pro-Drugs as Novel Delivery Systems", A.C.S. Symposium Series, Volume 14; and h) E. Roche (editor), "Bioreversible Carriers in Drug Design", Pergamon Press, 1987.

A suitable pharmaceutically acceptable prodrug of a compound of any one of the Formulae disclosed herein that possesses a hydroxy group is, for example, an in vivo cleavable ester or ether thereof. An in vivo cleavable ester or ether of a compound of any one of the Formulae disclosed herein containing a hydroxy group is, for example, a pharmaceutically acceptable ester or ether which is cleaved in the human or animal body to produce the parent hydroxy compound. Suitable pharmaceutically acceptable ester forming groups for a hydroxy group include inorganic esters such as phosphate esters (including phosphoramidic cyclic esters). Further suitable pharmaceutically acceptable ester forming groups for a hydroxy group include $C_1$-$C_{10}$ alkanoyl groups such as acetyl, benzoyl, phenylacetyl and substituted benzoyl and phenylacetyl groups, $C_1$-$C_{10}$ alkoxycarbonyl groups such as ethoxycarbonyl, N,N—$(C_1$-$C_6$ alkyl)$_2$carbamoyl, 2-dialkylaminoacetyl and 2-carboxyacetyl groups. Examples of ring substituents on the phenylacetyl and benzoyl groups include aminomethyl, N-alkylaminomethyl, N,N-dialkylaminomethyl, morpholinomethyl, piperazin-1-ylmethyl and 4-($C_1$-$C_4$ alkyl)piperazin-1-ylmethyl. Suitable pharmaceutically acceptable ether forming groups for a hydroxy group include α-acyloxyalkyl groups such as acetoxymethyl and pivaloyloxymethyl groups.

A suitable pharmaceutically acceptable prodrug of a compound of any one of the Formulae disclosed herein that possesses a carboxy group is, for example, an in vivo cleavable amide thereof, for example an amide formed with an amine such as ammonia, a $C_{1-4}$alkylamine such as methylamine, a $(C_1$-$C_4$ alkyl)$_2$amine such as dimethylamine, N-ethyl-N-methylamine or diethylamine, a $C_1$-$C_4$ alkoxy-$C_2$-$C_4$ alkylamine such as 2-methoxyethylamine, a phenyl-$C_1$-$C_4$ alkylamine such as benzylamine and amino acids such as glycine or an ester thereof.

A suitable pharmaceutically acceptable prodrug of a compound of any one of the Formulae disclosed herein that possesses an amino group is, for example, an in vivo cleavable amide derivative thereof. Suitable pharmaceutically acceptable amides from an amino group include, for example an amide formed with $C_1$-$C_{10}$ alkanoyl groups such as an acetyl, benzoyl, phenylacetyl and substituted benzoyl and phenylacetyl groups. Examples of ring substituents on the phenylacetyl and benzoyl groups include aminomethyl, N-alkylaminomethyl, N,N-dialkylaminomethyl, morpholinomethyl, piperazin-1-ylmethyl and 4-($C_1$-$C_4$ alkyl)piperazin-1-ylmethyl.

The in vivo effects of a compound of any one of the Formulae disclosed herein may be exerted in part by one or more metabolites that are formed within the human or animal body after administration of a compound of any one of the Formulae disclosed herein. As stated hereinbefore, the in vivo effects of a compound of any one of the Formulae disclosed herein may also be exerted by way of metabolism of a precursor compound (a prodrug).

Suitably, the present disclosure excludes any individual compounds not possessing the biological activity defined herein.

Methods of Synthesis

In some aspects, the present disclosure provides a method of preparing a compound of the present disclosure.

In some aspects, the present disclosure provides a method of a compound, comprising one or more steps as described herein.

In some aspects, the present disclosure provides a compound obtainable by, or obtained by, or directly obtained by a method for preparing a compound as described herein.

In some aspects, the present disclosure provides an intermediate as described herein, being suitable for use in a method for preparing a compound as described herein.

The compounds of the present disclosure can be prepared by any suitable technique known in the art. Particular processes for the preparation of these compounds are described further in the accompanying examples.

In the description of the synthetic methods described herein and in any referenced synthetic methods that are used to prepare the starting materials, it is to be understood that all proposed reaction conditions, including choice of solvent, reaction atmosphere, reaction temperature, duration of the experiment and workup procedures, can be selected by a person skilled in the art.

It is understood by one skilled in the art of organic synthesis that the functionality present on various portions of the molecule must be compatible with the reagents and reaction conditions utilised.

It will be appreciated that during the synthesis of the compounds of the disclosure in the processes defined herein, or during the synthesis of certain starting materials, it may be desirable to protect certain substituent groups to prevent their undesired reaction. The skilled chemist will appreciate when such protection is required, and how such protecting groups may be put in place, and later removed. For examples of protecting groups see one of the many general texts on the subject, for example, 'Protective Groups in Organic Synthesis' by Theodora Green (publisher: John Wiley & Sons). Protecting groups may be removed by any convenient method described in the literature or known to the skilled chemist as appropriate for the removal of the protecting group in question, such methods being chosen so as to effect removal of the protecting group with the minimum disturbance of groups elsewhere in the molecule. Thus, if reactants include, for example, groups such as amino, carboxy or hydroxy it may be desirable to protect the group in some of the reactions mentioned herein.

By way of example, a suitable protecting group for an amino or alkylamino group is, for example, an acyl group, for example an alkanoyl group such as acetyl, an alkoxycarbonyl group, for example a methoxycarbonyl, ethoxycarbonyl or t-butoxycarbonyl group, an arylmethoxycarbonyl group, for example benzyloxycarbonyl, or an aroyl group, for example benzoyl. The deprotection conditions for the above protecting groups necessarily vary with the choice of protecting group. Thus, for example, an acyl group such as an alkanoyl or alkoxycarbonyl group or an aroyl group may be removed by, for example, hydrolysis with a suitable base such as an alkali metal hydroxide, for example lithium or sodium hydroxide. Alternatively an acyl group such as a tert-butoxycarbonyl group may be removed, for example, by treatment with a suitable acid as hydrochloric, sulphuric or phosphoric acid or trifluoroacetic acid and an arylmethoxycarbonyl group such as a benzyloxycarbonyl group may be removed, for example, by hydrogenation over a catalyst such as palladium on carbon, or by treatment with a Lewis acid for example boron tris(trifluoroacetate). A suitable alternative protecting group for a primary amino group is, for example, a phthaloyl group which may be removed by treatment with an alkylamine, for example dimethylaminopropylamine, or with hydrazine.

A suitable protecting group for a hydroxy group is, for example, an acyl group, for example an alkanoyl group such as acetyl, an aroyl group, for example benzoyl, or an arylmethyl group, for example benzyl. The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium, sodium hydroxide or ammonia. Alternatively an arylmethyl group such as a benzyl group may be removed, for example, by hydrogenation over a catalyst such as palladium on carbon.

A suitable protecting group for a carboxy group is, for example, an esterifying group, for example a methyl or an ethyl group which may be removed, for example, by hydrolysis with a base such as sodium hydroxide, or for example a tert-butyl group which may be removed, for example, by treatment with an acid, for example an organic acid such as trifluoroacetic acid, or for example a benzyl group which may be removed, for example, by hydrogenation over a catalyst such as palladium on carbon.

Once a compound of Formula (I) has been synthesised by any one of the processes defined herein, the processes may then further comprise the additional steps of: (i) removing any protecting groups present; (ii) converting the compound Formula (I) into another compound of Formula (I); (iii) forming a pharmaceutically acceptable salt, hydrate or solvate thereof; and/or (iv) forming a prodrug thereof.

The resultant compounds of Formula (I) can be isolated and purified using techniques well known in the art.

Conveniently, the reaction of the compounds is carried out in the presence of a suitable solvent, which is preferably inert under the respective reaction conditions. Examples of suitable solvents comprise but are not limited to hydrocarbons, such as hexane, petroleum ether, benzene, toluene or xylene; chlorinated hydrocarbons, such as trichlorethylene, 1,2-dichloroethane, tetrachloromethane, chloroform or dichloromethane; alcohols, such as methanol, ethanol, isopropanol, n-propanol, n-butanol or tert-butanol; ethers, such as diethyl ether, diisopropyl ether, tetrahydrofuran (THF), 2-methyltetrahydrofuran, cyclopentylmethyl ether (CPME), methyl tert-butyl ether (MTBE) or dioxane; glycol ethers, such as ethylene glycol monomethyl or monoethyl ether or ethylene glycol dimethyl ether (diglyme); ketones, such as acetone, methylisobutylketone (MIBK) or butanone; amides, such as acetamide, dimethylacetamide, dimethylformamide (DMF) or N-methylpyrrolidinone (NMP); nitriles, such as acetonitrile; sulphoxides, such as dimethyl sulphoxide (DMSO); nitro compounds, such as nitromethane or nitrobenzene; esters, such as ethyl acetate or methyl acetate, or mixtures of the said solvents or mixtures with water.

The reaction temperature is suitably between about −100° C. and 300° C., depending on the reaction step and the conditions used.

Reaction times are generally in the range between a fraction of a minute and several days, depending on the reactivity of the respective compounds and the respective reaction conditions. Suitable reaction times are readily determinable by methods known in the art, for example reaction monitoring. Based on the reaction temperatures given above, suitable reaction times generally lie in the range between 10 minutes and 48 hours.

Moreover, by utilising the procedures described herein, in conjunction with ordinary skills in the art, additional compounds of the present disclosure can be readily prepared. Those skilled in the art will readily understand that known variations of the conditions and processes of the following preparative procedures can be used to prepare these compounds.

As will be understood by the person skilled in the art of organic synthesis, compounds of the present disclosure are readily accessible by various synthetic routes, some of which are exemplified in the accompanying examples. The skilled person will easily recognise which kind of reagents and reactions conditions are to be used and how they are to be applied and adapted in any particular instance—wherever necessary or useful—in order to obtain the compounds of the present disclosure. Furthermore, some of the compounds of the present disclosure can readily be synthesised by reacting other compounds of the present disclosure under suitable conditions, for instance, by converting one particular functional group being present in a compound of the present disclosure, or a suitable precursor molecule thereof, into another one by applying standard synthetic methods, like reduction, oxidation, addition or substitution reactions; those methods are well known to the skilled person. Likewise, the skilled person will apply—whenever necessary or useful—synthetic protecting (or protective) groups; suitable protecting groups as well as methods for introducing and removing them are well-known to the person skilled in the art of chemical synthesis and are described, in more detail, in, e.g., P. G. M. Wuts, T. W. Greene, "Greene's *Protective Groups in Organic Synthesis*", 4th edition (2006) (John Wiley & Sons).

General routes for the preparation of a compound of the application are described in Schemes 1-2 herein.

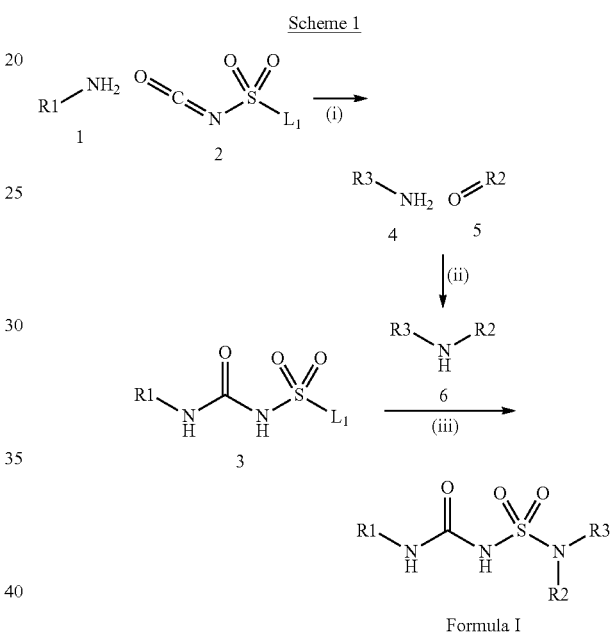

Formula I

In Scheme 1, $L_1$ is a suitable leaving group (e.g., Cl or another halide).

Reaction (i) may be performed by reacting amine 1 with isocyanate 2 in a suitable solvent (e.g., diisopropyl ether or dichloromethane) and, optionally, at a cooled temperature (e.g., 0° C. or −15° C.), yielding Intermediate 3. In some embodiments, Intermediate 3 may be used directly as a solution and not isolated.

Reaction (ii) may be performed by reacting amine 4 with carbonyl compound 5 in a suitable solvent (e.g., methanol or dichloromethane), in the presence of a reducing agent (e.g., sodium cyanoborohydride or sodium triacetoxyborohydride) and, optionally, in the presence of an acidic catalyst (e.g., acetic acid), yielding Intermediate 6. Intermediate 6 may be isolated by purification (e.g., by flash column chromatography or by preparative HPLC). In some embodiments, Intermediate 6 is isolated as a free amine or as a salt (e.g., trifluoroacetate salt).

Reaction (iii) may be performed by reacting intermediate 3 with Intermediate 6 in a suitable solvent (e.g., tetrahydrofuran), in the presence of a base (e.g., sodium hydride or sodium methoxide) and, optionally, in the presence of a catalyst (e.g., 4-(dimethylamino)-pyridine), yielding a compound of Formula (I). The compound of Formula (I) may be isolated by purification (e.g., by flash column chromatography or by preparative HPLC). In some embodiments, the compounds of Formula (I) is isolated as a neutral compound or as a salt (e.g., sodium salt).

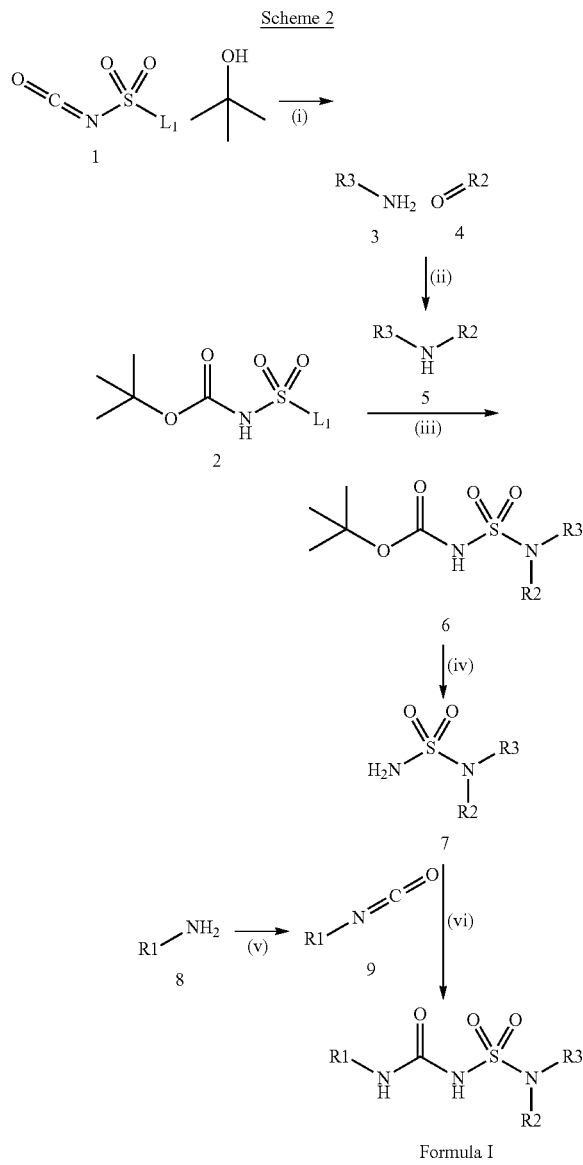

Scheme 2

In Scheme 2, $L_1$ is a suitable leaving group (e.g., Cl or another halide).

Reaction (i) may be performed by reacting isocyanate 1 with tert-butanol in a suitable solvent (e.g., tetrahydrofuran) and, optionally, at a cooled temperature (e.g., 0° C.), yielding Intermediate 2. In some embodiments, Intermediate 2 is then used directly as a solution and not directly isolated.

Reaction (ii) may be performed by reacting amine 3 with carbonyl compound 4 in a suitable solvent (e.g., methanol or dichloromethane), in the presence of a reducing agent (e.g., sodium cyanoborohydride or sodium triacetoxyborohydride) and, optionally, in the presence of an acidic catalyst (e.g., acetic acid), yielding Intermediate 5. Intermediate 5 may be isolated by purification (e.g., by flash column chromatography or by preparative HPLC). In some embodiments, Intermediate 5 is isolated as a free amine or as a salt (e.g., trifluoroacetate salt).

Reaction (iii) may be performed by reacting Intermediate 5 with intermediate 2 in a suitable solvent (e.g., tetrahydrofuran) and in the presence of a base (e.g., diisopropylethylamine), yielding Intermediate 6. Intermediate 6 may be isolated by purification (e.g., by flash column chromatography or by preparative HPLC).

Reaction (iv) may be performed by reacting intermediate 6 with a suitable acid (e.g., hydrochloric acid or trifluoroacetic acid), in a suitable solvent (e.g., 1,4-dioxane or dichloromethane) and, optionally, at a cooled temperature (e.g., 0° C.), yielding Intermediate 7.

Intermediate 7 may be isolated by purification (e.g., by flash column chromatography or by preparative HPLC). In some embodiments, Intermediate 7 is isolated as a free amine or as a salt (e.g., trifluoroacetate salt).

Reaction (v) may be performed by reacting primary amine 8 with a suitable reagent (e.g., triphosgene), in the presence of a suitable base (e.g., diisopropylethylamine or triethylamine) and in the presence of a suitable solvent (e.g., 1,4-dioxane) and, optionally, at an elevated temperature (e.g., 40° C.), yielding Intermediate 9.

Reaction (vi) may be performed by reacting Intermediate 7 with Intermediate 9 in a suitable solvent (e.g., tetrahydrofuran), in the presence of a base (e.g., sodium hydride or sodium methoxide) and, optionally, in the presence of a catalyst (e.g., 4-(dimethylamino)-pyridine), yielding a compound of Formula (I). In some embodiments, reaction (iv) may be performed at a cooled temperature (e.g., example 0° C.). The compound of Formula (I) may be isolated by purification (e.g., by flash column chromatography or by preparative HPLC). In some embodiments, the compound of Formula (I) is isolated as a neutral compound or as a salt (e.g., sodium salt).

It should be understood that in the description and formulae shown above, the various groups are as defined herein, except where otherwise indicated. Furthermore, for synthetic purposes, the compounds in the Schemes are mere representatives with elected substituents to illustrate the general synthetic methodology of a compound disclosed herein.

It is understood that a neutral compound of Formula (I) may be converted to a salt (e.g., sodium salt) using routine techniques in the art (e.g., pH adjustment and, optionally, extraction (e.g., into an organic phase)). Further, a salt (e.g., sodium salt) of a compound of Formula (I) may be converted to a neutral compound using routine techniques in the art (e.g., pH adjustment and, optionally, extraction (e.g., into an aqueous phase)).

Biological Assays

Compounds designed, selected and/or optimised by methods described above, once produced, can be characterised using a variety of assays known to those skilled in the art to determine whether the compounds have biological activity. For example, the molecules can be characterised by conventional assays, including but not limited to those assays described below, to determine whether they have a predicted activity, binding activity and/or binding specificity.

Furthermore, high-throughput screening can be used to speed up analysis using such assays. As a result, it can be possible to rapidly screen the molecules described herein for activity, using techniques known in the art. General methodologies for performing high-throughput screening are described, for example, in Devlin (1998) High Throughput Screening, Marcel Dekker; and U.S. Pat. No. 5,763,263.

High-throughput assays can use one or more different assay techniques including, but not limited to, those described below.

Various in vitro or in vivo biological assays are may be suitable for detecting the effect of the compounds of the present disclosure. These in vitro or in vivo biological assays can include, but are not limited to, enzymatic activity assays, electrophoretic mobility shift assays, reporter gene assays, in vitro cell viability assays, and the assays described herein.

Pharmaceutical Compositions

In some aspects, the present disclosure provides a pharmaceutical composition comprising a compound of the present disclosure as an active ingredient. In some embodiments, the present disclosure provides a pharmaceutical composition comprising at least one compound of each of the formulae described herein, or a pharmaceutically acceptable salt or solvate thereof, and one or more pharmaceutically acceptable carriers or excipients. In some embodiments, the present disclosure provides a pharmaceutical composition comprising at least one compound selected from Tables 1 and 2.

As used herein, the term "composition" is intended to encompass a product comprising the specified ingredients in the specified amounts, as well as any product which results, directly or indirectly, from combination of the specified ingredients in the specified amounts.

The compounds of present disclosure can be formulated for oral administration in forms such as tablets, capsules (each of which includes sustained release or timed release formulations), pills, powders, granules, elixirs, tinctures, suspensions, syrups and emulsions. The compounds of present disclosure on can also be formulated for intravenous (bolus or in-fusion), intraperitoneal, topical, subcutaneous, intramuscular or transdermal (e.g., patch) administration, all using forms well known to those of ordinary skill in the pharmaceutical arts.

The formulation of the present disclosure may be in the form of an aqueous solution comprising an aqueous vehicle. The aqueous vehicle component may comprise water and at least one pharmaceutically acceptable excipient. Suitable acceptable excipients include those selected from the group consisting of a solubility enhancing agent, chelating agent, preservative, tonicity agent, viscosity/suspending agent, buffer, and pH modifying agent, and a mixture thereof.

Any suitable solubility enhancing agent can be used. Examples of a solubility enhancing agent include cyclodextrin, such as those selected from the group consisting of hydroxypropyl-β-cyclodextrin, methyl-β-cyclodextrin, randomly methylated-β-cyclodextrin, ethylated-β-cyclodextrin, triacetyl-β-cyclodextrin, peracetylated-β-cyclodextrin, carboxymethyl-β-cyclodextrin, hydroxyethyl-β-cyclodextrin, 2-hydroxy-3-(trimethylammonio)propyl-β-cyclodextrin, glucosyl-β-cyclodextrin, sulphated β-cyclodextrin (S-β-CD), maltosyl-β-cyclodextrin, β-cyclodextrin sulphobutyl ether, branched-β-cyclodextrin, hydroxypropyl-γ-cyclodextrin, randomly methylated-γ-cyclodextrin, and trimethyl-γ-cyclodextrin, and mixtures thereof.

Any suitable chelating agent can be used. Examples of a suitable chelating agent include those selected from the group consisting of ethylenediaminetetraacetic acid and metal salts thereof, disodium edetate, trisodium edetate, and tetrasodium edetate, and mixtures thereof.

Any suitable preservative can be used. Examples of a preservative include those selected from the group consisting of quaternary ammonium salts such as benzalkonium halides (preferably benzalkonium chloride), chlorhexidine gluconate, benzethonium chloride, cetyl pyridinium chloride, benzyl bromide, phenylmercury nitrate, phenylmercury acetate, phenylmercury neodecanoate, merthiolate, methylparaben, propylparaben, sorbic acid, potassium sorbate, sodium benzoate, sodium propionate, ethyl p-hydroxybenzoate, propylaminopropyl biguanide, and butyl-β-hydroxybenzoate, and sorbic acid, and mixtures thereof.

The aqueous vehicle may also include a tonicity agent to adjust the tonicity (osmotic pressure). The tonicity agent can be selected from the group consisting of a glycol (such as propylene glycol, diethylene glycol, triethylene glycol), glycerol, dextrose, glycerin, mannitol, potassium chloride, and sodium chloride, and a mixture thereof.

The aqueous vehicle may also contain a viscosity/suspending agent. Suitable viscosity/suspending agents include those selected from the group consisting of cellulose derivatives, such as methyl cellulose, ethyl cellulose, hydroxyethylcellulose, polyethylene glycols (such as polyethylene glycol 300, polyethylene glycol 400), carboxymethyl cellulose, hydroxypropylmethyl cellulose, and cross-linked acrylic acid polymers (carbomers), such as polymers of acrylic acid cross-linked with polyalkenyl ethers or divinyl glycol (Carbopols—such as Carbopol 934, Carbopol 934P, Carbopol 971, Carbopol 974 and Carbopol 974P), and a mixture thereof.

In order to adjust the formulation to an acceptable pH (typically a pH range of about 5.0 to about 9.0, more preferably about 5.5 to about 8.5, particularly about 6.0 to about 8.5, about 7.0 to about 8.5, about 7.2 to about 7.7, about 7.1 to about 7.9, or about 7.5 to about 8.0), the formulation may contain a pH modifying agent. The pH modifying agent is typically a mineral acid or metal hydroxide base, selected from the group of potassium hydroxide, sodium hydroxide, and hydrochloric acid, and mixtures thereof, and preferably sodium hydroxide and/or hydrochloric acid. These acidic and/or basic pH modifying agents are added to adjust the formulation to the target acceptable pH range. Hence it may not be necessary to use both acid and base—depending on the formulation, the addition of one of the acid or base may be sufficient to bring the mixture to the desired pH range.

The aqueous vehicle may also contain a buffering agent to stabilise the pH. When used, the buffer is selected from the group consisting of a phosphate buffer (such as sodium dihydrogen phosphate and disodium hydrogen phosphate), a borate buffer (such as boric acid, or salts thereof including disodium tetraborate), a citrate buffer (such as citric acid, or salts thereof including sodium citrate), and ε-aminocaproic acid, and mixtures thereof.

The formulation may further comprise a wetting agent. Suitable classes of wetting agents include those selected from the group consisting of polyoxypropylene-polyoxyethylene block copolymers (poloxamers), polyethoxylated ethers of castor oils, polyoxyethylenated sorbitan esters (polysorbates), polymers of oxyethylated octyl phenol (Tyloxapol), polyoxyl 40 stearate, fatty acid glycol esters, fatty acid glyceryl esters, sucrose fatty esters, and polyoxyethylene fatty esters, and mixtures thereof.

Oral compositions generally include an inert diluent or an edible pharmaceutically acceptable carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavouring agent such as peppermint, methyl salicylate, or orange flavoring.

According to a further aspect of the disclosure there is provided a pharmaceutical composition which comprises a compound of the disclosure as defined hereinbefore, or a pharmaceutically acceptable salt, hydrate or solvate thereof, in association with a pharmaceutically acceptable diluent or carrier.

The compositions of the disclosure may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular, intraperitoneal or intramuscular dosing or as a suppository for rectal dosing).

The compositions of the disclosure may be obtained by conventional procedures using conventional pharmaceutical excipients, well known in the art. Thus, compositions intended for oral use may contain, for example, one or more colouring, sweetening, flavouring and/or preservative agents.

An effective amount of a compound of the present disclosure for use in therapy is an amount sufficient to treat or prevent an inflammasome related condition referred to herein, slow its progression and/or reduce the symptoms associated with the condition.

The size of the dose for therapeutic or prophylactic purposes of a compound of Formula (I) will naturally vary according to the nature and severity of the conditions, the age and sex of the animal or patient and the route of administration, according to well-known principles of medicine.

Methods of Use

In some aspects, the present disclosure provides a method of inhibiting inflammasome (e.g., the NLRP3 inflammasome) activity (e.g., in vitro or in vivo), comprising contacting a cell with an effective amount of a compound of the present disclosure or a pharmaceutically acceptable salt thereof.

In some aspects, the present disclosure provides a method of treating or preventing a disease or disorder disclosed herein in a subject in need thereof, comprising administering to the subject a therapeutically effective amount of a compound of the present disclosure or a pharmaceutically acceptable salt thereof, or a pharmaceutical composition of the present disclosure.

In some embodiments, the disease or disorder is associated with an implicated inflammasome activity. In some embodiments, the disease or disorder is a disease or disorder in which inflammasome activity is implicated.

In some embodiments, the disease or disorder is an inflammatory disorder, autoinflammatory disorder, an autoimmune disorder, a neurodegenerative disease, or cancer.

In some embodiments, the disease or disorder is an inflammatory disorder, autoinflammatory disorder and/or an autoimmune disorder.

In some embodiments, the disease or disorder is selected from cryopyrin-associated autoinflammatory syndrome (CAPS; e.g., familial cold autoinflammatory syndrome (FCAS), Muckle-Wells syndrome (MWS), chronic infantile neurological cutaneous and articular (CINCA) syndrome/neonatal-onset multisystem inflammatory disease (NO-MID)), familial Mediterranean fever (FMF), nonalcoholic fatty liver disease (NAFLD), non-alcoholic steatohepatitis (NASH), gout, rheumatoid arthritis, osteoarthritis, Crohn's disease, chronic obstructive pulmonary disease (COPD), chronic kidney disease (CKD), fibrosis, obesity, type 2 diabetes, multiple sclerosis, dermatological disease (e.g. acne) and neuroinflammation occurring in protein misfolding diseases (e.g., Prion diseases).

In some embodiments, the disease or disorder is a neurodegenerative disease.

In some embodiments, the disease or disorder is Parkinson's disease or Alzheimer's disease.

In some embodiments, the disease or disorder is a dermatological disease.

In some embodiments, the dermatalogical disease is acne.

In some embodiments, the disease or disorder is cancer.

In some embodiments, the cancer is metastasising cancer, gastrointestinal cancer, skin cancer, non-small-cell lung carcinoma, brain cancer (e.g. glioblastoma) or colorectal adenocarcinoma.

In some aspects, the present disclosure provides a method of treating or preventing an autoinflammatory disorder, an autoimmune disorder, a neurodegenerative disease or cancer in a subject in need thereof, comprising administering to the subject a therapeutically effective amount of a compound of the present disclosure or a pharmaceutically acceptable salt thereof, or a pharmaceutical composition of the present disclosure.

In some aspects, the present disclosure provides a method of treating or preventing an inflammatory disorder, autoinflammatory disorder and/or an autoimmune disorder selected from cryopyrin-associated autoinflammatory syndrome (CAPS; e.g., familial cold autoinflammatory syndrome (FCAS), Muckle-Wells syndrome (MWS), chronic infantile neurological cutaneous and articular (CINCA) syndrome/neonatal-onset multisystem inflammatory disease (NOMID)), familial Mediterranean fever (FMF), nonalcoholic fatty liver disease (NAFLD), non-alcoholic steatohepatitis (NASH), gout, rheumatoid arthritis, osteoarthritis, Crohn's disease, chronic obstructive pulmonary disease (COPD), chronic kidney disease (CKD), fibrosis, obesity, type 2 diabetes, multiple sclerosis, dermatological disease (e.g. acne) and neuroinflammation occurring in protein misfolding diseases (e.g., Prion diseases) in a subject in need thereof, comprising administering to the subject a therapeutically effective amount of a compound of the present disclosure or a pharmaceutically acceptable salt thereof, or a pharmaceutical composition of the present disclosure.

In some aspects, the present disclosure provides a method of treating or preventing a neurodegenerative disease (e.g., Parkinson's disease or Alzheimer's disease) in a subject in need thereof, said method comprising administering to the subject a therapeutically effective amount of a compound of the present disclosure or a pharmaceutically acceptable salt thereof, or a pharmaceutical composition of the present disclosure.

In some aspects, the present disclosure provides a method of treating or preventing cancer in a subject in need thereof, said method comprising administering to the subject a therapeutically effective amount of a compound of the present disclosure or a pharmaceutically acceptable salt thereof, or a pharmaceutical composition of the present disclosure.

In some aspects, the present disclosure provides a compound of the present disclosure or a pharmaceutically acceptable salt thereof for use in inhibiting inflammasome (e.g., the NLRP3 inflammasome) activity (e.g., in vitro or in vivo).

In some aspects, the present disclosure provides a compound of the present disclosure or a pharmaceutically acceptable salt thereof for use in treating or preventing a disease or disorder disclosed herein.

In some aspects, the present disclosure provides a compound of the present disclosure or a pharmaceutically acceptable salt thereof for use in treating or preventing an inflammatory disorder, an autoinflammatory disorder, an autoimmune disorder, a neurodegenerative disease or cancer in a subject in need thereof.

In some aspects, the present disclosure provides a compound of the present disclosure or a pharmaceutically acceptable salt thereof for use in treating or preventing an inflammatory disorder, an autoinflammatory disorder and/or an autoimmune disorder selected from cryopyrin-associated autoinflammatory syndrome (CAPS; e.g., familial cold autoinflammatory syndrome (FCAS), Muckle-Wells syndrome (MWS), chronic infantile neurological cutaneous and articular (CINCA) syndrome/neonatal-onset multisystem inflammatory disease (NOMID)), familial Mediterranean fever (FMF), nonalcoholic fatty liver disease (NAFLD), non-alcoholic steatohepatitis (NASH), gout, rheumatoid arthritis, osteoarthritis, Crohn's disease, chronic obstructive pulmonary disease (COPD), chronic kidney disease (CKD), fibrosis, obesity, type 2 diabetes, multiple sclerosis and neuroinflammation occurring in protein misfolding diseases (e.g., Prion diseases) in a subject in need thereof.

In some aspects, the present disclosure provides a compound of the present disclosure or a pharmaceutically acceptable salt thereof for use in treating or preventing a neurodegenerative disease (e.g., Parkinson's disease or Alzheimer's disease) in a subject in need thereof.

In some aspects, the present disclosure provides a compound of the present disclosure or a pharmaceutically acceptable salt thereof for use in treating or preventing cancer in a subject in need thereof.

In some aspects, the present disclosure provides use of a compound of the present disclosure or a pharmaceutically acceptable salt thereof in the manufacture of a medicament for inhibiting inflammasome (e.g., the NLRP3 inflammasome) activity (e.g., in vitro or in vivo).

In some aspects, the present disclosure provides use of a compound of the present disclosure or a pharmaceutically acceptable salt thereof in the manufacture of a medicament for treating or preventing a disease or disorder disclosed herein.

In some aspects, the present disclosure provides use of a compound of the present disclosure or a pharmaceutically acceptable salt thereof in the manufacture of a medicament for treating or preventing an inflammatory disorder, an autoinflammatory disorder, an autoimmune disorder, a neurodegenerative disease or cancer in a subject in need thereof.

In some aspects, the present disclosure provides use of a compound of the present disclosure or a pharmaceutically acceptable salt thereof in the manufacture of a medicament for treating or preventing an inflammatory disorder, an autoinflammatory disorder and/or an autoimmune disorder selected from cryopyrin-associated autoinflammatory syndrome (CAPS; e.g., familial cold autoinflammatory syndrome (FCAS), Muckle-Wells syndrome (MWS), chronic infantile neurological cutaneous and articular (CINCA) syndrome/neonatal-onset multisystem inflammatory disease (NOMID)), familial Mediterranean fever (FMF), nonalcoholic fatty liver disease (NAFLD), non-alcoholic steatohepatitis (NASH), gout, rheumatoid arthritis, osteoarthritis, Crohn's disease, chronic obstructive pulmonary disease (COPD), chronic kidney disease (CKD), fibrosis, obesity, type 2 diabetes, multiple sclerosis, dermatological disorders (e.g., acne) and neuroinflammation occurring in protein misfolding diseases (e.g., Prion diseases) in a subject in need thereof.

In some aspects, the present disclosure provides use of a compound of the present disclosure or a pharmaceutically acceptable salt thereof in the manufacture of a medicament for treating or preventing a neurodegenerative disease (e.g., Parkinson's disease or Alzheimer's disease) in a subject in need thereof.

In some aspects, the present disclosure provides use of a compound of the present disclosure or a pharmaceutically acceptable salt thereof in the manufacture of a medicament for treating or preventing cancer in a subject in need thereof.

The present disclosure provides compounds that function as inhibitors of inflammasome activity. The present disclosure therefore provides a method of inhibiting inflammasome activity in vitro or in vivo, said method comprising contacting a cell with an effective amount of a compound, or a pharmaceutically acceptable salt thereof, as defined herein.

Effectiveness of compounds of the disclosure can be determined by industry-accepted assays/disease models according to standard practices of elucidating the same as described in the art and are found in the current general knowledge.

The present disclosure also provides a method of treating a disease or disorder in which inflammasome activity is implicated in a patient in need of such treatment, said method comprising administering to said patient a therapeutically effective amount of a compound, or a pharmaceutically acceptable salt thereof, or a pharmaceutical composition as defined herein.

On a general level, the compounds of the present disclosure, which inhibit the maturation of cytokines of the IL-1 family, are effective in all therapeutic indications that are mediated or associated with elevated levels of active forms of cytokines belonging to IL-1 family of cytokines (Sims J. et al. Nature Reviews Immunology 10, 89-102 (February 2010).

Exemplary diseases and the corresponding references will be given in the following: inflammatory, autoinflammatory and autoimmune diseases like CAPS (Dinarello C A. Immunity. 2004 March; 20(3):243-4; Hoffman H M. al. Reumatologia 2005; 21 (3)), gout, rheumatoid arthritis (Gabay C et al. Arthritis Research & Therapy 2009, 11:230; Schett G. et al. Nat Rev Rheumatol. 2016 January; 12(1):14-24.), Crohn's disease (Jung Mogg Kim Korean J Gastroenterol Vol. 58 No. 6, 300-310), COPD (Mortaz E. et al. Tanaffos. 2011; 10(2): 9-14.), fibrosis (Gasse P. et al. Am J Respir Crit Care Med. 2009 May 15; 179(10):903-13), obesity, type 2 diabetes ((Dinarello C A. et al. Curr Opin Endocrinol Diabetes Obes. 2010 August; 17(4):314-21)) multiple sclerosis (see EAE-model in Coll R C. et al. Nat Med. 2015 March; 21(3):248-55) and many others (Martinon F. et al. Immunol. 2009. 27:229-65) like Parkinson's disease or Alzheimer's disease (Michael T. et al. Nature 493, 674-678 (31 Jan. 2013); Halle A. et al., Nat Immunol. 2008 August;

9(8):857-65; Saresella M. et al. Mol Neurodegener. 2016 Mar. 3; 11:23) and some oncological disorders.

Suitably, the compounds according to the present disclosure can be used for the treatment of a disease selected from the group consisting of an inflammatory disease, an autoinflammatory disease, an autoimmune disease, a neurodegenerative disease and cancer. Said inflammatory, autoinflammatory and autoimmune disease is suitably selected from the group consisting of a cryopyrin-associated autoinflammatory syndrome (CAPS, such as for example familial cold autoinflammatory syndrome (FCAS), Muckle-Wells syndrome (MWS), chronic infantile neurological cutaneous and articular (CINCA) syndrome/neonatal-onset multisystem inflammatory disease (NOMID)), familial Mediterranean fever (FMF), nonalcoholic fatty liver disease (NAFLD), non-alcoholic steatohepatitis (NASH), chronic kidney disease (CKD), gout, rheumatoid arthritis, osteoarthritis, Crohn's disease, COPD, fibrosis, obesity, type 2 diabetes, multiple sclerosis, dermatological diseases (e.g., acne) and neuroinflammation occurring in protein misfolding diseases, such as Prion diseases. Said neurodegenerative disease includes, but is not limited, to Parkinson's disease and Alzheimer's disease.

Accordingly, the compounds of the present disclosure can be used for the treatment of a disease selected from the group consisting of cryopyrin-associated autoinflammatory syndrome (CAPS, such as for example familial cold autoinflammatory syndrome (FCAS), Muckle-Wells syndrome (MWS), chronic infantile neurological cutaneous and articular (CINCA) syndrome/neonatal-onset multisystem inflammatory disease (NOMID)), familial Mediterranean fever (FMF), nonalcoholic fatty liver disease (NAFLD), non-alcoholic steatohepatitis (NASH), chronic kidney disease (CKD), gout, rheumatoid arthritis, osteoarthritis, Crohn's disease, COPD, fibrosis, obesity, type 2 diabetes, multiple sclerosis, dermatological diseases (e.g., acne) neuroinflammation occurring in protein misfolding diseases, such as Prion diseases, neurogenerative diseases (e.g., Parkinson's disease, Alzheimer's disease) and oncological disorders.

Treatment in Cancer; Links with Inflammasome

Chronic inflammation responses have long been observed to be associated with various types of cancer. During malignant transformation or cancer therapy inflammasomes may become activated in response to danger signals and this activation may be both beneficial and detrimental in cancer.

IL-1β expression is elevated in a variety of cancers (including breast, prostate, colon, lung, head and neck cancers and melanomas) and patients with IL-1β producing tumours generally have a worse prognosis (Lewis, Anne M., et al. "Interleukin-1 and cancer progression: the emerging role of interleukin-1 receptor antagonist as a novel therapeutic agent in cancer treatment." Journal of translational medicine 4.1 (2006): 48).

Cancers derived from epithelial cells (carcinoma) or epithelium in glands (adenocarcinoma) are heterogeneous; consisting of many different cell types. This may include fibroblasts, immune cells, adipocytes, endothelial cells and pericytes amongst others, all of which may be cytokine/chemokine secreting (Grivennikov, Sergei I., Florian R. Greten, and Michael Karin. "Immunity, inflammation, and cancer." Cell 140.6 (2010): 883-899). This can lead to cancer-associated inflammation through the immune cell infiltration. The presence of leukocytes in tumours is known but it has only recently become evident that an inflammatory microenvironment is an essential component of all tumours. Most tumours (>90%) are the result of somatic mutations or environmental factors rather than germline mutations and many environmental causes of cancer are associated with chronic inflammation (20% of cancers are related to chronic infection, 30% to smoking/inhaled pollutants and 35% to dietary factors (20% of all cancers are linked to obesity) (Aggarwal, Bharat B., R. V. Vijayalekshmi, and Bokyung Sung. "Targeting inflammatory pathways for prevention and therapy of cancer: short-term friend, long-term foe." Clinical Cancer Research 15.2 (2009): 425-430).

GI Cancer

Cancers of the gastrointestinal (GI) tract are frequently associated with chronic inflammation. For example, H. pylori infection is associated with gastric cancer (Amieva, Manuel, and Richard M. Peek. "Pathobiology of Helicobacter pylori-Induced Gastric Cancer." Gastroenterology 150.1 (2016): 64-78). Colorectal cancer is associated with inflammatory bowel disease (Bernstein, Charles N., et al. "Cancer risk in patients with inflammatory bowel disease." Cancer 91.4 (2001): 854-862). Chronic inflammation in stomach leads to the upregulation of IL-1 and other cytokines (Basso D, et al., (1996) Helicobacter pylori infection enhances mucosal interleukin-1 beta, interleukin-6, and the soluble receptor of interleukin-2. Int J Clin Lab Res 26:207-210) and polymorphisms in IL-1β gene can increase risk of gastric cancer (Wang P, et al., (2007) Association of interleukin-1 gene polymorphisms with gastric cancer: a meta-analysis. Int J Cancer 120:552-562).

In 19% of gastric cancer cases, caspase-1 expression is decreased which correlates with stage, lymph node metastasis and survival (Jee et al., 2005). Mycoplasma hyorhinis is associated with the development of gastric cancer its activation of the NLRP3 inflammasome may be associated with its promotion of gastric cancer metastasis (Xu et al., 2013).

Skin Cancers

Ultraviolet radiation is the greatest environmental risk for skin cancer which is promoted by causing DNA damage, immunosuppression and inflammation. The most malignant skin cancer, melanoma, is characterised by the upregulation of inflammatory cytokines, all of which can be regulated by IL-1β (Lázár-Molnár, Eszter, et al. "Autocrine and paracrine regulation by cytokines and growth factors in melanoma." Cytokine 12.6 (2000): 547-554). Systemic inflammation induces an enhancement of melanoma cell metastasis and growth by IL-1-dependent mechanisms in vivo. Using thymoquinone inhibition of metastasis in a B16F10 mouse melanoma model was shown to be dependent on inhibition of the NLRP3 inflammasome (Ahmad, Israr, et al. "Thymoquinone suppresses metastasis of melanoma cells by inhibition of NLRP3 inflammasome." Toxicology and applied pharmacology 270.1 (2013): 70-76).

Glioblastoma

NLRP3 contributes to radiotherapy resistance in glioma. Ionising radiation can induce NLRP3 expression whereas NLRP3 inhibition reduced tumour growth and prolonged mouse survival following radiation therapy. NLRP3 inflammasome inhibition can therefore provide a therapeutic strategy for radiation-resistant glioma (Li, Lianling, and Yuguang Liu. "Aging-related gene signature regulated by Nlrp3 predicts glioma progression." American journal of cancer research 5.1 (2015): 442).

Metastasis

More widely, NLRP3 is considered by the applicants to be involved in the promotion of metastasis and consequently modulation of NLRP3 should plausibly block this. IL-1 is involved in tumour genesis, tumour invasiveness, metastasis, tumour host interactions (Apte, Ron N., et al. "The involvement of IL-1 in tumorigenesis, tumour invasiveness, metastasis and tumour-host interactions." Cancer and Metastasis Reviews 25.3 (2006): 387-408) and angiogenesis (Voronov, Elena, et al. "IL-1 is required for tumor invasiveness and angiogenesis." Proceedings of the National Academy of Sciences 100.5 (2003): 2645-2650).

The IL-1 gene is frequently expressed in metastases from patients with several types of human cancers. For example, IL-1mRNA was highly expressed in more than half of all tested metastatic human tumour specimens including specifically non-small-cell lung carcinoma, colorectal adenocarcinoma, and melanoma tumour samples (Elaraj, Dina M., et al. "The role of interleukin 1 in growth and metastasis of human cancer xenografts." Clinical Cancer Research 12.4 (2006): 1088-1096) and IL-1RA inhibits xenograft growth in IL-1 producing tumours but without anti-proliferative effects in vitro.

Further, IL-1 signalling is a biomarker for predicting breast cancer patients at increased risk for developing bone metastasis. In mouse models IL-1β and its receptor are upregulated in breast cancer cells that metastasise to bone compared with cells that do not. In a mouse model the IL-1 receptor antagonist anakinra reduced proliferation and angiogenesis in addition to exerting significant effects on the tumour environment reducing bone turnover markers, IL-1β and TNF alpha (Holen, Ingunn, et al. "IL-1 drives breast cancer growth and bone metastasis in vivo." Oncotarget (2016).

IL-18 induced the production of MMP-9 in the human leukaemia cell line HL-60, thus favouring degradation of the extracellular matrix and the migration and invasiveness of cancer cells (Zhang, Bin, et al. "IL-18 increases invasiveness of HL-60 myeloid leukemia cells: up-regulation of matrix metalloproteinases-9 (MMP-9) expression." Leukemia research 28.1 (2004): 91-95). Additionally IL-18 can support the development of tumour metastasis in the liver by inducing expression of VCAM-1 on hepatic sinusoidal endothelium (Carrascal, Maria Teresa, et al. "Interleukin-18 binding protein reduces b16 melanoma hepatic metastasis by neutralizing adhesiveness and growth factors of sinusoidal endothelium." Cancer Research 63.2 (2003): 491-497).

CD36

The fatty acid scavenger receptor CD36 serves a dual role in priming gene transcription of pro-IL-1β and inducing assembly of the NLRP3 inflammasome complex. CD36 and the TLR4-TLR6 heterodimer recognise oxLDL, which initiates a signalling pathway leading to transcriptional upregulation of NLRP3 and pro-IL-1β (signal 1). CD36 also mediates the internalisation of oxLDL into the lysosomal compartment, where crystals are formed that induce lysosomal rupture and activation of the NLRP3 inflammasome (signal 2) (Kagan, J. and Horng T., "NLRP3 inflammasome activation: CD36 serves double duty." Nature immunology 14.8 (2013): 772-774).

A subpopulation of human oral carcinoma cells express high levels of the fatty acid scavenger receptor CD36 and are unique in their ability to initiate metastasis. Palmitic acid or a high fat diet boosted the metastatic potential of the CD36+ cells. Neutralising anti-CD36 antibodies blocked metastasis in orthotopic mouse models of human oral cancer. The presence of CD36+ metastasis-initiating cells correlates with a poor prognosis for numerous types of carcinomas. It is suggested that dietary lipids may promote metastasis (Pasqual, G, Avgustinova, A., Mejetta, S, Martin, M, Castellanos, A, Attolini, CS—O, Berenguer, A., Prats, N, Toll, A, Hueto, J A, Bescos, C, Di Croce, L, and Benitah, S A. 2017 "Targeting metastasis-initiating cells through the fatty acid receptor CD36" Nature 541:41-45).

In hepatocellular carcinoma exogenous palmitic acid activated an epithelial-mesenchymal transition (EMT)-like program and induced migration that was decreased by the CD36 inhibitor, sulpho-N-succinimidyl oleate (Nath, Aritro, et al. "Elevated free fatty acid uptake via CD36 promotes epithelial-mesenchymal transition in hepatocellular carcinoma." Scientific reports 5 (2015). Body mass index was not associated with the degree of EMT highlighting that it is actually CD36 and free fatty acids that are important.

Cancer stems cells (CSCs) use CD36 to promote their maintenance. Oxidised phospholipids, ligands of CD36, were present in glioblastoma and the proliferation of CSCs but not non-CSCs increased with exposure to oxidised LDL. CD36 also correlated with patient prognosis.

Chemotherapy Resistance

In addition to direct cytotoxic effects, chemotherapeutic agents harness the host immune system which contributes to anti-tumour activity. However, gemcitabine and 5-FU were shown to activate NLRP3 in myeloid-derived suppressor cells leading to production of IL-1β which curtails anti-tumour efficacy. Mechanistically these agents destabilised the lysosome to release cathepsin B to activate NLRP3. IL-1β drove the production of IL-17 from CD4+ T cells which in turn blunted the efficacy of the chemotherapy. Higher anti-tumoral effects for both gemcitabine and 5-FU were observed when tumours were established in NLRP3−/− or Caps1−/− mice, or WT mice treated with IL-1RA. Myeloid-derived suppressor cell NLRP3 activation therefore limits the anti-tumour efficacy of gemcitabine and 5-FU (Bruchard, Melanie, et al. "Chemotherapy-triggered cathepsin B release in myeloid-derived suppressor cells activates the Nlrp3 inflammasome and promotes tumour growth." Nature medicine 19.1 (2013): 57-64.). Compounds of the present disclosure may therefore be useful in chemotherapy to treat a range of cancers.

Compounds of the present disclosure, or pharmaceutically acceptable salts thereof, may be administered alone as a sole therapy or can be administered in addition with one or more other substances and/or treatments. Such conjoint treatment may be achieved by way of the simultaneous, sequential or separate administration of the individual components of the treatment.

For example, therapeutic effectiveness may be enhanced by administration of an adjuvant (i.e. by itself the adjuvant may only have minimal therapeutic benefit, but in combination with another therapeutic agent, the overall therapeutic benefit to the individual is enhanced). Alternatively, by way of example only, the benefit experienced by an individual may be increased by administering the compound of Formula (I) with another therapeutic agent (which also includes a therapeutic regimen) that also has therapeutic benefit.

In the instances where the compound of the present disclosure is administered in combination with other therapeutic agents, the compound of the disclosure need not be administered via the same route as other therapeutic agents, and may, because of different physical and chemical characteristics, be administered by a different route. For example, the compound of the disclosure may be administered orally to generate and maintain good blood levels thereof, while the other therapeutic agent may be administered intravenously. The initial administration may be made according to established protocols known in the art, and then, based upon the observed effects, the dosage, modes of administration and times of administration can be modified by the skilled clinician.

The particular choice of other therapeutic agent will depend upon the diagnosis of the attending physicians and their judgment of the condition of the individual and the appropriate treatment protocol. According to this aspect of the disclosure there is provided a combination for use in the treatment of a disease in which inflammasome activity is implicated comprising a compound of the disclosure as defined hereinbefore, or a pharmaceutically acceptable salt thereof, and another suitable agent.

According to a further aspect of the disclosure there is provided a pharmaceutical composition which comprises a compound of the disclosure, or a pharmaceutically acceptable salt thereof, in combination with a suitable, in association with a pharmaceutically acceptable diluent or carrier.

In addition to its use in therapeutic medicine, compounds of Formula (I) and pharmaceutically acceptable salts thereof are also useful as pharmacological tools in the development and standardisation of in vitro and in vivo test systems for the evaluation of the effects of inhibitors of inflammasome in laboratory animals such as dogs, rabbits, monkeys, rats and mice, as part of the search for new therapeutic agents.

In any of the above-mentioned pharmaceutical composition, process, method, use, medicament, and manufacturing features of the instant disclosure, any of the alternate embodiments of macromolecules of the present disclosure described herein also apply.

Routes of Administration

The compounds of the disclosure or pharmaceutical compositions comprising these compounds may be administered to a subject by any convenient route of administration, whether systemically/peripherally or topically (i.e., at the site of desired action).

Routes of administration include, but are not limited to, oral (e.g. by ingestion); buccal; sublingual; transdermal (including, e.g., by a patch, plaster, etc.); transmucosal (including, e.g., by a patch, plaster, etc.); intranasal (e.g., by nasal spray); ocular (e.g., by eye drops); pulmonary (e.g., by inhalation or insufflation therapy using, e.g., via an aerosol, e.g., through the mouth or nose); rectal (e.g., by suppository or enema); vaginal (e.g., by pessary); parenteral, for example, by injection, including subcutaneous, intradermal, intramuscular, intravenous, intra-arterial, intracardiac, intrathecal, intraspinal, intracapsular, subcapsular, intraorbital, intraperitoneal, intratracheal, subcuticular, intraarticular, subarachnoid, and intrasternal; by implant of a depot or reservoir, for example, subcutaneously or intramuscularly.

Additional Aspects of the Present Disclosure

According to a first aspect, the present disclosure relates to a compound of Formula (I), or a prodrug, or pharmaceutically acceptable salt thereof:

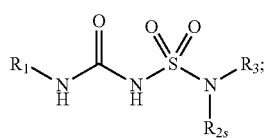

(I)

in which:

$R_1$ is a monocyclic ($C_3$-$C_8$) alkyl ring or a polycyclic alkyl ring or monocyclic ($C_5$-$C_6$) aryl ring or a 9 or 10 membered bicyclic partially unsaturated carbocyclic ring system or a 12, 13, 14, 15 or 16 membered tricyclic partially unsaturated carbocyclic ring system, $R_2$ is group:

where X is $(CH_2)_{0,1 \text{ or } 2}$ and $R_4$ is a saturated 4-7 membered heterocyclic ring comprising at least one or more of N and O; and $R_3$ is selected from a 5 or 6-membered heterocyclic aromatic ring comprising two or three different atoms independently selected from C, N, O, and S, wherein $R_3$ is linked to its adjacent N of Formula I via a C atom.

In some embodiments $R_1$ is a phenyl group or a substituted phenyl group.

In some embodiments $R_1$ has the structure:

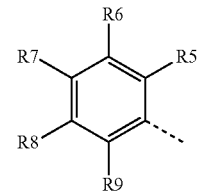

wherein each of $R_5$, $R_6$, $R_7$, $R_8$, and $R_9$ is independently selected from the group comprising H, $C_1$-$C_6$ alkyl, $C_2$-$C_6$ alkenyl, $C_2$-$C_6$ alkynyl, halo, haloalkyl, cyano, $C_1$-$C_6$ alkoxy, and amino.

In some embodiments, a first set of two adjacent groups, selected from $R_5$, $R_6$, $R_7$, $R_8$, and $R_9$, defines a 4-7 membered alkyl or aryl ring "A".

In some embodiments, a second, different set of two adjacent groups, selected from $R_5$, $R_6$, $R_7$, $R_8$, and $R_9$, defines a 4-7 membered alkyl or aryl ring "B".

In some embodiments, $R_5$ and $R_6$ form the first set.

In some embodiments, $R_8$ and $R_9$ form the second set.

Optionally, in some embodiments described above, the ring A and/or the ring B may be substituted with one or more groups independently selected from $C_1$-$C_6$ alkyl, $C_2$-$C_6$ alkenyl, $C_2$-$C_6$ alkynyl, halo, hydroxyl, haloalkyl, cyano, $C_1$-$C_6$ alkoxy, and amino.

In some embodiments $R_1$ is hexahydroindacene.

In some embodiments $R_4$ is an optionally substituted oxa-, aza-, or thia-cyclopentane, or an optionally substituted oxa-, aza-, or thia-cyclohexane.

In some embodiments $R_4$ is substituted with one or more groups independently selected from $C_1$-$C_6$ alkyl, $C_2$-$C_6$ alkenyl, $C_2$-$C_6$ alkynyl, halo, haloalkyl, cyano, alkoxy, hydroxy, keto, amino, and amido.

In further embodiments the at least one substituted group is linked to the N atom of the $R_4$ ring.

In preferred embodiments, the at least one the substituted group is a methyl group linked to the N atom of the $R_4$ ring.

In some embodiments $R_4$ is morpholine.

In some embodiments, the 5 or 6-membered heterocycle of $R_3$ comprises 1, 2 or 3 N atoms.

In some embodiments, the 5 or 6-membered heterocycle of $R_3$ comprises one N and one O atom.

In some embodiments, the 5 or 6-membered heterocycle of $R_3$ is selected from the group comprising pyrazole, isoxazole, imidazole, triazole, pyrimidine, and pyrazine, wherein the heterocycle is optionally substituted.

In some embodiments, the 5 or 6-membered heterocyclic aromatic ring of R is substituted with at least one group independently selected from straight, branched or cyclic ($C_1$-$C_6$) alkyl, alkenyl, alkynyl, halo, hydroxyl, haloalkyl, cyano, alkoxy, amino, and amido.

The substituted group is preferably a methyl, ethyl, or propyl group.

In some embodiments, the at least one substituted group is linked to the N atom of the heterocycle of $R_3$. In other embodiments, the at least one substituted group is linked to the C atom of the heterocycle of $R_3$. Where there are two or more substitutions, the groups in some embodiments may be linked to both N and C atoms of the heterocycle of $R_3$.

In preferred embodiments, the compound of the invention is selected from the group consisting of:

3-(1,2,3,5,6,7-hexahydro-s-indacen-4-yl)-1-[(1-methyl-1H-pyrazol-4-yl)(oxan-4-yl)sulfamoyl]urea sodium salt;
3-(1,2,3,5,6,7-hexahydro-s-indacen-4-yl)-1-[(1-methyl-1H-pyrazol-4-yl)(1-methylpiperidin-4-yl)sulfamoyl]urea sodium salt;
3-(1,2,3,5,6,7-hexahydro-s-indacen-4-yl)-1-[(1-methyl-1H-pyrazol-4-yl)[(1-methylpiperidin-4-yl)methyl]sulfamoyl]urea sodium salt;
3-(1,2,3,5,6,7-hexahydro-s-indacen-4-yl)-1-[(oxan-4-yl)[1-(propan-2-yl)-1H-pyrazol-4-yl]sulfamoyl]urea sodium salt;
3-(1,2,3,5,6,7-hexahydro-s-indacen-4-yl)-1-[(1-methylpiperidin-4-yl)[1-(propan-2-yl)-1H-pyrazol-4-yl]sulfamoyl]urea sodium salt;
1-[(1-ethyl-1H-pyrazol-4-yl)(oxan-4-yl)sulfamoyl]-3-(1,2,3,5,6,7-hexahydro-s-indacen-4-yl)urea sodium salt;
1-[(1-ethyl-1H-pyrazol-4-yl)(1-methylpiperidin-4-yl)sulfamoyl]-3-(1,2,3,5,6,7-hexahydro-s-indacen-4-yl)urea sodium salt;
3-(1,2,3,5,6,7-hexahydro-s-indacen-4-yl)-1-[(1-methyl-1H-pyrazol-4-yl)(oxolan-3-yl)sulfamoyl]urea sodium salt;
3-(1,2,3,5,6,7-hexahydro-s-indacen-4-yl)-1-[(1-methyl-1H-pyrazol-3-yl)(oxan-4-yl)sulfamoyl]urea sodium salt;
1-[(1,5-dimethyl-1H-pyrazol-4-yl)(oxan-4-yl)sulfamoyl]-3-(1,2,3,5,6,7-hexahydro-s-indacen-4-yl)urea sodium salt;
3-(1,2,3,5,6,7-hexahydro-s-indacen-4-yl)-1-[(oxan-4-yl)(1,3,5-trimethyl-1H-pyrazol-4-yl)sulfamoyl]urea sodium salt;
3-(1,2,3,5,6,7-hexahydro-s-indacen-4-yl)-1-[(5-methyl-1,2-oxazol-3-yl)(oxan-4-yl)sulfamoyl]urea sodium salt;
3-(1,2,3,5,6,7-hexahydro-s-indacen-4-yl)-1-[(oxan-4-yl)(1,2-oxazol-4-yl)sulfamoyl]urea sodium salt;
1-[(1,5-dimethyl-1H-pyrazol-4-yl)(1-methylpiperidin-4-yl)sulfamoyl]-3-(1,2,3,5,6,7-hexahydro-s-indacen-4-yl)urea sodium salt;
3-(1,2,3,5,6,7-hexahydro-s-indacen-4-yl)-1-[(1-methylpiperidin-4-yl)(1,3,5-trimethyl-1H-pyrazol-4-yl)sulfamoyl]urea sodium salt;
3-(1,2,3,5,6,7-hexahydro-s-indacen-4-yl)-1-[(1-methyl-1H-pyrazol-4-yl)[(oxetan-3-yl)methyl]sulfamoyl]urea sodium salt;
3-(1,2,3,5,6,7-hexahydro-s-indacen-4-yl)-1-[(oxan-4-yl)(pyrimidin-5-yl)sulfamoyl]urea sodium salt;
3-(1,2,3,5,6,7-hexahydro-s-indacen-4-yl)-1-[(3-methyl-1,2-oxazol-5-yl)(oxan-4-yl)sulfamoyl]urea sodium salt;
3-(1,2,3,5,6,7-hexahydro-s-indacen-4-yl)-1-[(1-methyl-1H-1,2,4-triazol-3-yl)(oxan-4-yl)sulfamoyl]urea sodium salt;
3-(1,2,3,5,6,7-hexahydro-s-indacen-4-yl)-1-[(1-methyl-1H-pyrazol-3-yl)(1-methylpiperidin-4-yl)sulfamoyl]urea sodium salt;
3-(1,2,3,5,6,7-hexahydro-s-indacen-4-yl)-1-[(1-methyl-1H-imidazol-4-yl)(oxan-4-yl)sulfamoyl]urea sodium salt;
3-(1,2,3,5,6,7-hexahydro-s-indacen-4-yl)-1-[(1-methyl-1H-pyrazol-4-yl)(oxan-3-yl)sulfamoyl]urea sodium salt;
3-(1,2,3,5,6,7-hexahydro-s-indacen-4-yl)-1-[(1-methyl-1H-pyrazol-4-yl)(1-methylpiperidin-3-yl)sulfamoyl]urea sodium salt; and
3-(1,2,3,5,6,7-hexahydro-s-indacen-4-yl)-1-[(1-methyl-1H-pyrazol-4-yl)(1-methylpyrrolidin-3-yl)sulfamoyl]urea sodium salt.

"(2-6C)alkenylene" means a linear divalent hydrocarbon radical of two to six carbon atoms or a branched divalent hydrocarbon radical of three to six carbon atoms, containing at least one double bond, for example, as in ethenylene, 2,4-pentadienylene, and the like.

"(2-6C)alkynylene" means a linear divalent hydrocarbon radical of two to six carbon atoms or a branched divalent hydrocarbon radical of three to six carbon atoms, containing at least one triple bond, for example, as in ethynylene, propynylene, and butynylene and the like.

"(3-8C)cycloalkyl" means a hydrocarbon ring containing from 3 to 8 carbon atoms, for example, cyclopropyl, cyclobutyl, cyclopentyl, cyclohexyl, cycloheptyl or bicyclo[2.2.1]heptyl.

Suitable values for the term "(1-6C)alkoxy" include methoxy, ethoxy, propoxy, isopropoxy and butoxy.

Suitable values for the term "(1-3C)alkylamino" include methylamino, ethylamino, propylamino, isopropylamino and butylamino.

Suitable values for the term "di-[(1-3C)alkyl]-amino" include dimethylamino, diethylamino, N-ethyl-N-methylamino and diisopropylamino.

The term "5 membered monocyclic heteroaryl ring system" when used to define the ring system wherein the ring system, optionally comprises 1, 2, 3 or 4 heteroatoms independently selected from oxygen, nitrogen and sulphur. Suitable examples include Furyl, thiophenyl, pyrrolyl, isoxazolyl, thiazolyl, isothiazolyl, pyrazolyl, imidazolyl, oxadiazolyl, thiadiazolyl, triazolyl and tetrazolyl.

The term "8, 9 or 10 membered bicyclic heteroaryl ring system" when used to define the ring system formed, optionally comprises 1, 2 or 3 heteroatoms independently selected from oxygen, nitrogen and sulphur. Suitable examples include indolyl, isoindolyl, indazolyl, benzimidazolyl, benzoxathiazolyl, benzoxadiazolyl, benzothiadiazolyl, quinolinyl, isoquinolinyl, purinyl, 1,8-naphthyridyl, pteridyl, 1H-pyrrolo[3,2-b]pyridinyl, 1H-pyrrolo[2,3-c]pyridinyl, pyrido[3,2 d]pyrimidyl and pyridoimidazolyl. The term "8, 9 or 10 membered bicyclic heteroaryl ring system" also covers partially aromatic bicyclic ring systems wherein the first ring is aromatic and the other second ring is non-aromatic, saturated or partially saturated. Suitable examples of partially aromatic bicyclic ring systems include for example, 4,5,6,7-tetrahydroindolyl, 4,5,6,7-tetrahydroisoindolyl and 2H,4H,5H,6H-cyclopenta[c]pyrrolyl.

The term "5 or 6 membered monocyclic heteroaryl ring system" refers to a 5 or 6 membered aromatic ring system comprising 1, 2 or 3 heteroatoms independently selected from oxygen, nitrogen and sulphur. Suitable examples include furyl, thiophenyl, pyrrolyl, isoxazolyl, thiazolyl, isothiazolyl, pyrazolyl, imidazolyl, oxadiazolyl, thiadiazolyl, triazolyl, tetrazolyl, pyridyl, pyrimidinyl, pyrazinyl and pyridazinyl.

The term "3, 4, 5, or 6 membered monocyclic heterocyclyl ring system" refers to a 3, 4, 5, or 6 membered non-aromatic saturated or partially saturated heterocyclic ring system, wherein the ring system optionally comprises 1 or 2 heteroatoms independently selected from oxygen, nitrogen and sulphur, wherein a ring sulphur atom is optionally oxidised to form the S-oxide(s). Suitable examples include oxiranyl, aziridinyl, azetidinyl, oxetanyl, pyrrolinyl, pyrrolidinyl, imidazolinyl, imidazolidinyl, pyrazolinyl, pyrazolidinyl, morpholinyl, thiomorpholinyl, piperidinyl, homopiperidinyl, piperazinyl, homopiperazinyl, tetrahydrofuranyl, tetrahydropyran and tetrahydro-1,4-thiazinyl.

The term "12, 13, 14, 15 or 16 membered tricyclic partially unsaturated heterocyclic ring system" when used to define the ring system refers to a 12, 13, 14, 15 or 16 partially unsaturated heterocyclic ring system, which comprises 1 or 2 heteroatoms independently selected from oxygen, nitrogen and sulphur, wherein a ring sulphur atom is optionally oxidised to form the S-oxide(s). Suitable examples include rings such as 2-azatricyclo[7.3.0.0$^3$,$^7$]dodeca-1,3 (7),8-trienyl,1,2,3,4,5,6,7,8-octahydroacridinyl, 7-azatricyclo[7.3.0.0$^2$,$^6$]dodeca-1,6,8-trienyl, 1,2,3,4,7,8,9,10-octahydrophenanthridinyl, 1H,2H,3H,6H,7H,8H,9H-cyclopenta[c]isoquinolinyl, 1H,2H,3H,6H,7H,8H,9H-cyclopenta[c]quinolonyl, 1H,2H,3H,5H,6H,7H,8H-cyclopenta[b]quinolonyl, 1H,2H,3H,5H,6H,7H-cyclopenta[b]pyrrolizinyl, 1H,2H,3H,5H,6H,7H,8H-cyclohexa[b]pyrrolizinyl, 1H,2H,3H,5H,6H,7H-cyclopenta[b]pyrrolizinyl and 1H,2H,3H,5H,6H,7H,8H-cyclopenta[b]indolizinyl.

The term "12, 13, 14, 15 or 16 membered tricyclic partially unsaturated carbocyclic ring system" comprising only carbon atoms. Suitable examples include rings such as 1,2,3,5,6,7-hexahydro-s-indacenyl, 1H,2H,3H,6H,7H,8H,9H-cyclopenta[a]naphthalenyl, 1,2,3,6,7,8-hexahydroas-indacenyl, 1,2,3,4,5,6,7,8-octahydroanthracenyl, 1,2,3,4,5,6,7,8-octahydrophenanthrenyl and 1H,2H,3H,5H,6H,7H,8H-cyclopenta[b]naphthalenyl.

The term "3, 4, 5 or 6 membered saturated or partially unsaturated carbocyclic ring system" refers to a monocyclic ring system comprising only carbon atoms. Suitable examples include cyclopropanyl, cyclopentanyl, cyclohexanyl and cyclohexenyl.

According to a further aspect of the present disclosure, there is provided a pharmaceutical composition comprising a compound as defined herein, or a pharmaceutically acceptable salt thereof, in admixture with a pharmaceutically acceptable diluent or carrier.

According to a further aspect of the present disclosure, there is provided a compound of Formula (I) or a pharmaceutically acceptable salt thereof, or a pharmaceutical composition as defined herein for use as a medicament.

According to a further aspect of the present disclosure, there is provided a compound of Formula (I) or a pharmaceutically acceptable salt thereof as defined herein, or a pharmaceutical composition as defined herein, for use in the treatment of a disorder in which inflammasome activity is implicated.

In some embodiments the composition is for use in the treatment of a cancer. In particularly preferred embodiments the cancer is selected from a metastasising cancer, brain cancer, head and neck squamous cell carcinoma, gastrointestinal cancer, skin cancer, non-small-cell lung carcinoma and colorectal adenocarcinoma.

According to a further aspect of the present disclosure, there is provided a compound of Formula (I) or a pharmaceutically acceptable salt, hydrate or solvate thereof, or a pharmaceutical composition as defined herein for use in the treatment of an inflammatory, autoinflammatory or autoimmune disorder, a neurodegenerative disease or cancer. In a particular embodiment, inflammatory, autoinflammatory or autoimmune disorder is a cryopyrin-associated autoinflammatory syndrome (CAPS, such as for example familial cold autoinflammatory syndrome (FCAS), Muckle-Wells syndrome (MWS), chronic infantile neurological cutaneous and articular (CINCA) syndrome/neonatal-onset multisystem inflammatory disease (NOMID)), familial Mediterranean fever (FMF), non-alcoholic fatty liver disease (NAFLD), non-alcoholic steatohepatitis (NASH), chronic kidney disease (CKD), gout, calcium pyrophosphate deposition disease (CPPD), calcium pyrophosphate deposition disease (CPPD), rheumatoid arthritis, osteoarthritis, Crohn's disease, COPD, fibrosis, obesity, type 2 diabetes, multiple sclerosis, dermatological disease (e.g., acne) or neuroinflammation occurring in protein misfolding diseases, such as Prion diseases. In a further embodiment, the neurodegenerative disease is Parkinson's disease or Alzheimer's disease.

According to a further aspect of the present disclosure, there is provided the use of a compound of Formula (I) or a pharmaceutically acceptable salt thereof, as defined herein in the manufacture of a medicament for the treatment of an inflammatory, autoinflammatory or autoimmune disorder, a neurodegenerative disease or cancer. Suitably, the inflammatory, autoinflammatory or autoimmune disorder is cryopyrin-associated autoinflammatory syndrome (CAPS, such as for example familial cold autoinflammatory syndrome (FCAS), Muckle-Wells syndrome (MWS), chronic infantile neurological cutaneous and articular (CINCA) syndrome/neonatal-onset multisystem inflammatory disease (NOMID)), familial Mediterranean fever (FMF), non-alcoholic fatty liver disease (NAFLD), non-alcoholic steatohepatitis (NASH), chronic kidney disease (CKD), gout, calcium pyrophosphate deposition disease (CPPD), rheumatoid arthritis, osteoarthritis, Crohn's disease, COPD, fibrosis, obesity, type 2 diabetes, multiple sclerosis, dermatological diseases (e.g., acne) or neuroinflammation occurring in protein misfolding diseases, such as Prion diseases. Suitably, the neurodegenerative disease is Parkinson's disease or Alzheimer's disease.

According to a further aspect of the present disclosure, there is provided a method of inhibiting inflammasome (such as the NLRP3 inflammasome) activity in vitro or in vivo, said method comprising contacting a cell with an effective amount of a compound of Formula (I) or a pharmaceutically acceptable salt thereof as defined herein.

According to a further aspect of the present disclosure, there is provided a method of treating a disease or disorder in which inflammasome activity is implicated in a patient in need of such treatment, said method comprising administering to said patient a therapeutically effective amount of a compound of Formula (I) a pharmaceutically acceptable salt thereof as defined herein, or a pharmaceutical composition as defined herein.

According to a further aspect of the present disclosure, there is provided a method of treating an inflammatory, autoinflammatory or autoimmune disorder, an autoimmune disorder, a neurodegenerative disease or cancer in a patient in need of such treatment, said method comprising administering to said patient a therapeutically effective amount of a compound of Formula (I) a pharmaceutically acceptable salt thereof as defined herein, or a pharmaceutical composition as defined herein.

According to a further aspect of the present disclosure, there is provided a method of treating an inflammatory, autoinflammatory or autoimmune disorder and/or an autoimmune disorder selected from cryopyrin-associated autoinflammatory syndromes (CAPS, including familial cold autoinflammatory syndrome (FCAS), Muckle-Wells syndrome (MWS), chronic infantile neurological cutaneous and articular (CINCA) syndrome/neonatal-onset multisystem inflammatory disease (NOMID)), familial Mediterranean fever and non-alcoholic fatty liver disease (NAFLD), Non-alcoholic steatohepatitis (NASH), chronic kidney disease (CKD), gout, calcium pyrophosphate deposition disease (CPPD), rheumatoid arthritis, osteoarthritis, Crohn's disease, COPD, fibrosis, obesity, type 2 diabetes, multiple sclerosis, dermatological diseases (e.g., acne) and neuroinflammation occurring in protein misfolding diseases, such as Prion diseases in a patient in need of such treatment, said method comprising administering to said patient a therapeutically effective amount of a compound of Formula (I) or a pharmaceutically acceptable salt thereof as defined herein, or a pharmaceutical composition as defined herein.

According to a further aspect of the present disclosure, there is provided a method of treating a neurodegenerative disease such as Parkinson's disease or Alzheimer's disease in a patient in need of such treatment, said method comprising administering to said patient a therapeutically effective amount of a compound of Formula (I) or a pharmaceutically acceptable salt thereof as defined herein, or a pharmaceutical composition as defined herein.

According to a further aspect of the present disclosure, there is provided a process for preparing a compound of Formula (I) or a pharmaceutically acceptable salt thereof, as defined herein.

According to a further aspect of the present disclosure, there is provided a compound of Formula (I) or a pharmaceutically acceptable salt thereof, obtainable by, or obtained by, or directly obtained by a process of preparing a compound as defined herein.

According to a further aspect of the present disclosure, there are provided novel intermediates as defined herein which are suitable for use in any one of the synthetic methods set out herein.

The disclosure having been described, the following examples are offered by way of illustration and not limitation.

Examples

For exemplary purpose, salts of the compounds of Formula (I) are synthesized and tested in the examples. It is understood that neutral compounds of Formula (I) may be similarly synthesized and tested using the exemplary procedures described in the examples. Further, it is understood that the salts (e.g., sodium salt) of the compounds of Formula (I) may be converted to the corresponding neutral compounds using routine techniques in the art (e.g., pH adjustment and, optionally, extraction (e.g., into an aqueous phase)).

Nuclear magnetic resonance (NMR) spectra were recorded at 400 MHz or 300 MHz as stated and at 300.3 K unless otherwise stated; the chemical shifts (δ) are reported in parts per million (ppm). Spectra were recorded using a Bruker or Varian instrument with 8, 16 or 32 scans.

LC-MS chromatograms and spectra were recorded using an Agilent 1200 or Shimadzu LC-20 AD&MS 2020 instrument using a C-18 column such as a Luna-C18 2.0×30 mm or Xbridge Shield RPC18 2.1×50 mm. Injection volumes were 0.7-8.0 µl and the flow rates were typically 0.8 or 1.2 ml/min. Detection methods were diode array (DAD) or evaporative light scattering (ELSD) as well as positive ion electrospray ionisation. MS range was 100-1000 Da. Solvents were gradients of water and acetonitrile both containing a modifier (typically 0.01-0.04%) such as trifluoroacetic acid or ammonium carbonate.

Abbreviations:
ACN Acetonitrile
AcOH Acetic acid
aq. Aqueous
AP atmospheric pressure
Ar Argon
BINAP 2,2'-bis(diphenylphosphino)-1,1'-binaphthyl
DCM Dichloromethane
DIAD Diisopropyl azodicarboxylate
DMF N,N-dimethylformamide
DMSO-$d_6$ Hexadeuterodimethylsulfoxide
dppf 1,1'-bis(diphenylphosphino)ferrocene
eq. Equivalents
MS ES$^+$ Positive ion electrospray ionisation mass spectroscopy
ESI Electrospray ionisation
EtOAc ethyl acetate
FCC flash column chromatography
h hour(s)
HATU N-[(dimethylamino)-1H-1,2,3-triazolo-[4,5-b]pyridin-1-ylmethylene]-N-methylmethanaminium hexafluorophosphate N-oxide
HPLC high performance liquid chromatography
LC-MS Liquid chromatography-mass spectrometry
MeOD Methanol-$d_4$
MeOH Methanol
Min Minute(s)
MTBE methyl tert-butylether
NaHMDS Sodium hexamethyldisilylazide
RM reaction mixture
Rt room temperature
sat. Saturated
SM starting material
TBAF tetra-n-butylammonium fluoride
TEA Triethylamine
TFA trifluoroacetic acid
THF Tetrahydrofuran
TLC thin layer chromatography
Y Yield
General Procedure A

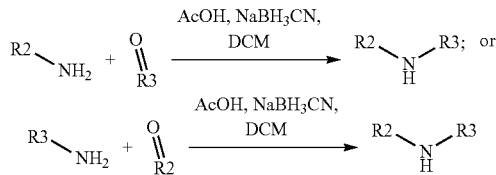

To a solution of amine (1 eq.), ketone or aldehyde (1 eq.) and acetic acid (0.5 eq.) in DCM (1.0 M) was added sodium cyanoborohydride (1.5 eq.). The reaction mixture was stirred at rt for 3 h. The mixture was concentrated in vacuo, diluted with water and extracted three times with EtOAc. The combined organic phases were washed three times with saturated brine, dried over anhydrous sodium sulphate, filtered and evaporated in vacuo. The residue was purified by column chromatography (silica eluted with ethyl acetate/petroleum ether or MeOH/dichloromethane) to give the desired product.

General procedure B

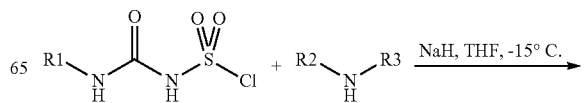

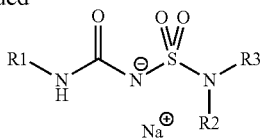

To a solution of sulphamoyl chloride (1 eq., sometimes obtained from a solution in isopropyl ether) and amine (1 eq.) in THF (0.2 M) was added NaH (60% in mineral oil, 4 eq.) at 0° C. under N$_2$. The mixture was stirred at 0° C. for 2 h. The reaction was evaporated under flow of N$_2$.
General procedure C

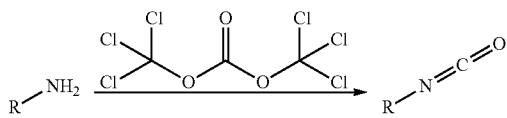

To a solution of amine (1 eq.) in dioxane (0.1 M) was added triphosgene (1.1 eq.) and a base. The RM was stirred at 40° C. for 1 h or until complete. The solvent was removed in vacuo to give the desired product.
General procedure D

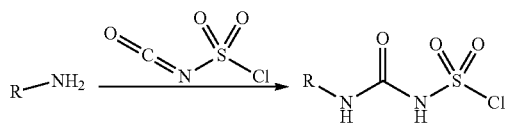

To a solution of N-(oxomethylene)sulfamoyl chloride (1 eq.) in isopropyl ether (0.4 M) cooled to −30° C. under nitrogen was added amine (1 eq.) in isopropyl ether (0.4 M). The RM was stirred at −30° C. for between 0.5 and 2 h and monitored by LC-MS (for appearance of methyl sulphonate). The product was used directly as a solution in isopropyl ether (0.2 M).
Synthesis of Intermediates {[(1,2,3,5,6,7-hexahydro-s-indacen-4-yl)carbamoyl]amino}sulfonyl chloride

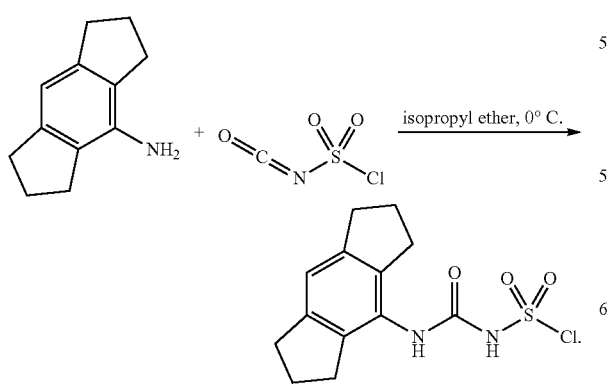

For synthesis of 1,2,3,5,6,7-hexahydro-s-indacen-4-amine patent WO 9832733 A1 may be used as a direct reference.

To a solution of N-(oxomethylene)sulfamoyl chloride (185 µL, 2.13 mmol) in isopropyl ether (20 ml) was added 1,2,3,5,6,7-hexahydro-s-indacen-4-amine (369 mg, 2.13 mmol) at −15° C. The mixture was stirred at −15° C. for 0.5 h. The reaction product was used directly in the next step. LC-MS in MeOH (ESI): m/z: [MH]$^+$=311.

4-isocyanato-1,2,3,5,6,7-hexahydro-s-indacene

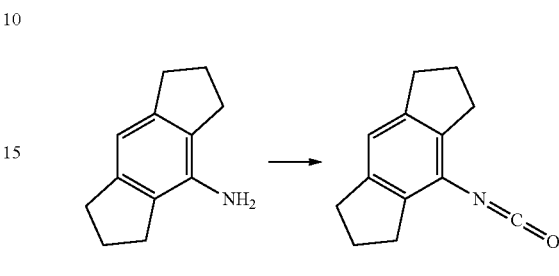

For synthesis of 1,2,3,5,6,7-hexahydro-s-indacen-4-amine see patent WO 9832733 A1.

To a mixture of triphosgene (1.71 g, 5.77 mmol) in DCM (5 ml) cooled to 0° C. under nitrogen was added portionwise 1,2,3,5,6,7-hexahydro-s-indacen-4-amine (1.00 g, 5.77 mmol) and triethylamine (1.69 ml, 12.12 mmol). The mixture was stirred at rt for 5 h. The mixture was concentrated under reduced pressure to give the title compound as a white solid. LC-MS in MeOH (ESI): m/z: [M+MeOH+H]$^+$=232

Tert-butyl N-(chlorosulfonyl)carbamate

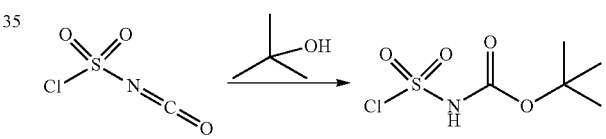

To a solution of N-(oxomethylene)sulfamoyl chloride (307 µl, 3.53 mmol) in DCM (6 ml) cooled to 0° C. was added a solution of tert-butanol (338 µl, 3.53 mmol) in DCM (6 ml). The mixture was stirred at 0° C. for 2 h. The solution was used directly in the next step.

Example 1. 3-(1,2,3,5,6,7-hexahydro-s-indacen-4-yl)-1-[(1-methyl-1H-pyrazol-4-yl)(oxan-4-yl)sulfamoyl]urea sodium salt

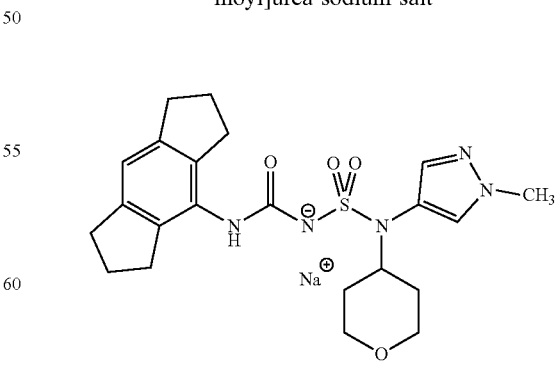

Step 1: 1-methyl-N-tetrahydropyran-4-yl-pyrazol-4-amine. General procedure A was followed using 1-methylpyrazol-4-amine and tetrahydropyran-4-one to give the title compound as a red oil. $^1$H NMR (400 MHz, CDC$_3$) δ=7.13 (s, 1H), 6.94 (s, 1H), 4.00-3.97 (m, 3H), 3.80 (s, 3H), 3.47-3.41 (m, 2H), 3.07-3.04 (m, 1H), 2.01-1.93 (m, 2H), 1.51-1.38 (m, 2H)

Step 2: 3-(1,2,3,5,6,7-hexahydro-s-indacen-4-yl)-1-[(1-methyl-1H-pyrazol-4-yl)(oxan-4-yl)sulfamoyl]urea sodium salt. General procedure B was followed using {[(1,2,3,5,6,7-hexahydro-s-indacen-4-yl) carbamoyl]amino}sulfonyl chloride and 1-methyl-N-tetrahydropyran-4-yl-pyrazol-3-amine. The crude product was purified by prep-HPLC (column: YMC-Actus Triart C18 5 μm, 100×30 mm; mobile phase: [water (10 mM NH$_4$HCO$_3$)-ACN]; B %: 20-40%, 12 min) to give the title compound as a white solid. $^1$H NMR (400 MHz, MeOD) δ=7.71 (s, 1H), 7.42 (s, 1H), 6.98 (s, 1H), 4.33 (t, J=12 Hz, 1H), 3.96-3.86 (m, 5H), 3.47 (t, J=12 Hz, 2H), 2.88 (t, J=7 Hz, 4H), 2.79 (t, J=7 Hz, 4H), 2.11-2.04 (m, 4H), 1.87 (d, J=10 Hz, 2H), 1.47-1.43 (m, 2H). LC-MS (ESI): m/z: [M−H]$^-$=458.0

Example 2. 3-(1,2,3,5,6,7-hexahydro-s-indacen-4-yl)-1-[(1-methyl-1H-pyrazol-4-yl)(1-methylpiperidin-4-yl)sulfamoyl]urea sodium salt

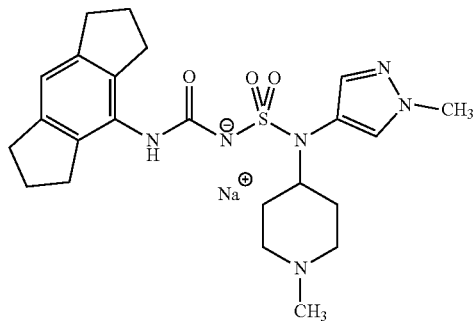 [SMILES: CN1CCC(N(c2cnn(C)c2)S(=O)(=O)[N-]C(=O)Nc2c3c(cc4c2CCC4)CCC3)CC1 ; [Na+]]

Step 1: 1-methyl-N-(1-methylpyrazol-4-yl)piperidin-4-amine. General procedure A was followed using 1-methylpyrazol-4-amine and 1-methylpiperidin-4-one to give the title compound as a red oil.

Step 2: 3-(1,2,3,5,6,7-hexahydro-s-indacen-4-yl)-1-[(1-methyl-1H-pyrazol-4-yl)(1-methylpiperidin-4-yl)sulfamoyl]urea sodium salt. General procedure B was followed using {[(1,2,3,5,6,7-hexahydro-s-indacen-4-yl)carbamoyl]amino}sulfonyl chloride and 1-methyl-N-(1-methylpyrazol-4-yl)piperidin-4-amine. The crude product was purified by prep-HPLC (column: YMC-Actus Triart C18 5 μm 100×30 mm; mobile phase: [water (10 mM NH$_4$HCO$_3$)-ACN]; B %: 20-40%, 12 min) to give the title compound as a white solid. $^1$H NMR (400 MHz, MEOD) δ=7.67 (s, 1H), 7.43 (s, 1H), 6.94 (s, 1H), 4.28-4.20 (m, 1H), 3.86 (s, 3H), 3.14 (d, J=12 Hz, 2H), 2.87 (t, J=8 Hz, 4H), 2.79 (t, J=7 Hz, 4H), 2.62 (t, J=13 Hz, 2H), 2.48 (s, 3H), 2.13-1.99 (m, 6H), 1.59-1.48 (m, 2H). LC-MS (ESI): m/z: [M−H]$^-$=471.1

Example 3. 3-(1,2,3,5,6,7-hexahydro-s-indacen-4-yl)-1-[(1-methyl-1H-pyrazol-4-yl)[(1-methylpiperidin-4-yl)methyl]sulfamoyl]urea sodium salt

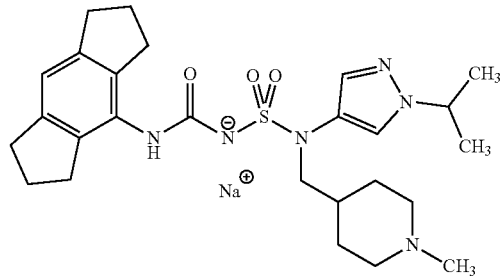 [SMILES: CC(C)n1cc(N(CC2CCN(C)CC2)S(=O)(=O)[N-]C(=O)Nc2c3c(cc4c2CCC4)CCC3)cn1 ; [Na+]]

Step 1: 1-methyl-N-(1-methylpyrazol-4-yl)piperidine-4-carboxamide. To a mixture of 1-methylpyrazol-4-amine (0.30 g, 3.09 mmol, 1 eq.) and 1-methylpiperidine-4-carboxylic acid (442 mg, 3.09 mmol, 1 eq.) in pyridine (10 ml) was added 1-ethyl-3-(3-dimethylaminopropyl)carbodiimide hydrochloride (888 mg, 4.64 mmol, 1.5 eq.) in one portion at 0° C. under N$_2$. The mixture was stirred at rt for 2 h. The mixture was concentrated in vacuo then diluted with water (10 ml). The aqueous phase was extracted with ethyl acetate (3×10 ml). The combined organic phase was washed with saturated brine (3×8 ml), dried over anhydrous Na$_2$SO$_4$, filtered and concentrated in vacuo. The residue was purified by silica gel chromatography (10-50% MeOH in ethyl acetate) to give 1-methyl-N-(1-methylpyrazol-4-yl)piperidine-4-carboxamide as a white solid. $^1$H NMR (400 MHz, DMSO-d$_6$) δ=9.83 (s, 1H), 7.90-7.78 (m, 1H), 7.82 (s, 1H), 7.44-7.29 (m, 1H), 5.89-5.70 (m, 1H), 3.75 (s, 2H), 3.02-2.93 (m, 1H), 3.02-2.93 (m, 1H), 2.78 (d, J=12 Hz, 2H), 2.10 (s, 3H), 1.90-1.78 (m, 2H), 1.49-1.45 (m, 1H).

Step 2: 1-methyl-N-((1-methylpiperidin-4-yl)methyl)-1H-pyrazol-4-amine. To a solution of 1-methyl-N-(1-methylpyrazol-4-yl)piperidine-4-carboxamide (200 mg, 900 μmol, 1 eq.) in THF (5 ml) was added lithium aluminium hydride (51 mg, 1.35 mmol, 1.5 eq). The mixture was stirred at 70° C. for 2 h. The reaction mixture was quenched by addition H$_2$O (1 ml) at 0° C., then the reaction was diluted with 10% NaOH (1 ml), filtered and concentrated in vacuo to give 1-methyl-N-((1-methylpiperidin-4-yl)methyl)-1H-pyrazol-4-amine as a red oil. LC-MS (ESI): m/z: [M+H]$^+$= 209

Step 3: 3-(1,2,3,5,6,7-hexahydro-s-indacen-4-yl)-1-[(1-methyl-1H-pyrazol-4-yl)[(1-methylpiperidin-4-yl)methyl]sulfamoyl]urea sodium salt. General procedure B was followed using {[(1,2,3,5,6,7-hexahydro-s-indacen-4-yl)carbamoyl]amino}sulfonyl chloride and 1-methyl-N-((1-methylpiperidin-4-yl)methyl)-1H-pyrazol-4-amine. The crude product was purified by prep-HPLC (column: YMC-Actus Triart C18 5 μm 100×30 mm; mobile phase: [water (10 mM NH$_4$HCO$_3$)-ACN]; B %: 20-40%, 12 min) to give the title compound as a white solid. $^1$H NMR (400 MHz, MEOD) δ ppm 7.68 (s, 1H) 7.51 (s, 1H) 6.92 (s, 1H) 3.85 (s, 3H) 3.62 (br d, J=7.28 Hz, 2H) 2.91-2.66 (m, 14H) 2.22-1.87 (m, 7H) 1.72 (br s, 1H) 1.49 (br s, 2H). LC-MS (ESI): m/z: [M−H]$^-$=485.2

Example 4. 3-(1,2,3,5,6,7-hexahydro-s-indacen-4-yl)-1-[(oxan-4-yl)[1-(propan-2-yl)-1H-pyrazol-4-yl]sulfamoyl]urea sodium salt

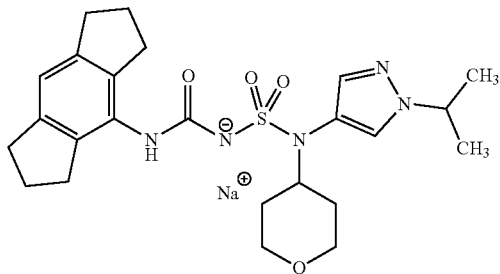 [SMILES: CC(C)n1cc(N(C2CCOCC2)S(=O)(=O)[N-]C(=O)Nc2c3c(cc4c2CCC4)CCC3)cn1 ; [Na+]]

Step 1: 1-isopropyl-N-tetrahydropyran-4-yl-pyrazol-4-amine. General procedure A was followed using 1-isopropylpyrazol-4-amine and tetrahydropyran-4-one to give the title compound as a red oil. $^1$H NMR (400 MHz, CDC$_3$) δ=7.15 (s, 1H), 7.01 (d, J=1 Hz, 1H), 4.41-4.38 (m, 1H), 4.01-3.97 (m, 2H), 3.48-3.41 (m, 2H), 3.13-3.03 (m, 1H), 2.51 (s, 1H), 2.02-1.93 (m, 2H), 1.49-1.42 (m, 8H).

Step 2: 3-(1,2,3,5,6,7-hexahydro-s-indacen-4-yl)-1-[(oxan-4-yl)[1-(propan-2-yl)-1H-pyrazol-4-yl]sulfamoyl]urea sodium salt. General procedure B was followed using {[(1,2,3,5,6,7-hexahydro-s-indacen-4-yl)carbamoyl]amino}sulfonyl chloride and 1-isopropyl-N-tetrahydropyran-4-yl-pyrazol-4-amine. The reaction was poured into MTBE, and the mixture was filtered. The filter cake was collected and washed with acetonitrile and the acetonitrile phase collected by filtration and concentrated to give crude product. This was purified by prep-HPLC (column: Phenomenex Gemini C18 10 μm 250×50 mm; mobile phase: [water (10 mM NH$_4$HCO$_3$)-ACN]; B %: 12-42%, 21 min) to give the title compound as a white solid. $^1$H NMR (400 MHz, MEOD) δ=7.73 (s, 1H), 7.45 (s, 1H), 6.95 (s, 1H), 4.50 (td, J=7, 13.2 Hz, 1H), 4.31 (t, J=12 Hz, 1H), 3.91 (dd, J=4, 12 Hz, 2H), 3.47 (t, J=12 Hz, 2H), 2.87 (t, J=7 Hz, 4H), 2.80 (t, J=7 Hz, 4H), 2.10-2.03 (m, 4H), 1.89 (d, J=13 Hz, 2H), 1.48 (d, J=7 Hz, 6H), 1.46-1.38 (m, 2H). LC-MS (ESI): m/z: [M+H]$^+$=488.3

Example 5. 3-(1,2,3,5,6,7-hexahydro-s-indacen-4-yl)-1-[(1-methylpiperidin-4-yl)[1-(propan-2-yl)-1H-pyrazol-4-yl]sulfamoyl]urea sodium salt

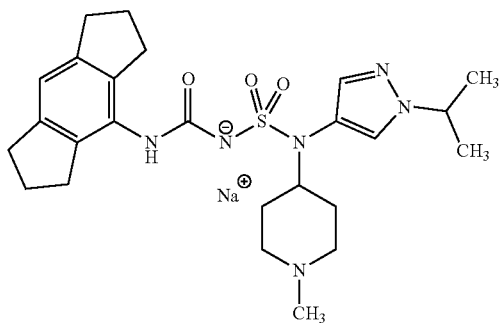 [SMILES: CC(C)n1cc(N(C2CCN(C)CC2)S(=O)(=O)[N-]C(=O)Nc2c3c(cc4c2CCC4)CCC3)cn1 ; [Na+]]

Step 1: N-(1-isopropylpyrazol-4-yl)-1-methyl-piperidin-4-amine. General procedure A was followed using 1-isopropylpyrazol-4-amine and 1-methylpiperidin-4-one. The crude product was purified by prep-HPLC (column: Phenomenex Gemini C18 10 μm 250×50 mm; mobile phase: [water (10 mM NH$_4$HCO$_3$)-ACN]; B: 0-20%, 21 min) to give the title compound as a red oil. $^1$H NMR (400 MHz, CDCl$_3$) δ=7.13 (s, 1H), 6.98 (s, 1H), 4.42-4.31 (m, 1H), 2.93-2.77 (m, 3H), 2.29 (s, 3H), 2.13-1.93 (m, 4H), 1.52-1.40 (m, 8H).

Step 2: 3-(1,2,3,5,6,7-hexahydro-s-indacen-4-yl)-1-[(1-methylpiperidin-4-yl)[1-(propan-2-yl)-1H-pyrazol-4-yl]sulfamoyl]urea sodium salt. General procedure B was followed using {[(1,2,3,5,6,7-hexahydro-s-indacen-4-yl)carbamoyl]amino}sulfonyl chloride and N-(1-isopropylpyrazol-4-yl)-1-methyl-piperidin-4-amine. The crude product was purified by prep-HPLC (column: Phenomenex Gemini C18 10 μm 250×50 mm; mobile phase: [water (10 mM NH$_4$HCO$_3$)-ACN]; B: 5-35%, 21 min) to give the title compound as a white solid. $^1$H NMR (400 MHz, MeOD) δ=7.73 (s, 1H), 7.45 (s, 1H), 6.94 (s, 1H), 4.52-4.45 (m, J=7 Hz, 1H), 4.30-4.15 (m, 1H), 3.11 (d, J=19 Hz, 2H), 3.00 (s, 1H), 2.91-2.84 (m, 5H), 2.81 (t, J=8 Hz, 4H), 2.55 (s, 2H), 2.44 (s, 2H), 2.14-1.99 (m, 6H), 1.58-1.49 (m, 2H), 1.47 (d, J=7 Hz, 6H), 1.22 (s, 2H), 1.20-1.11 (m, 1H). LC-MS (ESI): m/z: [M+H]$^+$=501.2

Example 6. 1-[(1-ethyl-1H-pyrazol-4-yl)(oxan-4-yl)sulfamoyl]-3-(1,2,3,5,6,7-hexahydro-s-indacen-4-yl)urea sodium salt

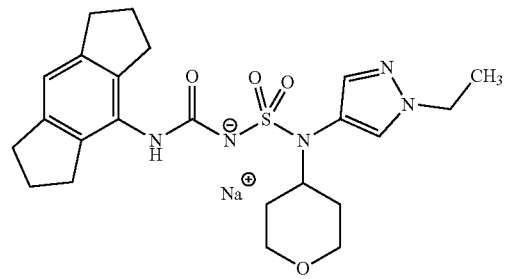 [SMILES: CCn1cc(N(C2CCOCC2)S(=O)(=O)[N-]C(=O)Nc2c3c(cc4c2CCC4)CCC3)cn1 ; [Na+]]

Step 1: 1-ethyl-N-tetrahydropyran-4-yl-pyrazol-4-amine. General procedure A was followed using 1-ethylpyrazol-4-amine and tetrahydropyran-4-one to give the title compound as a red oil. $^1$H NMR (400 MHz, CDCl$_3$) δ=7.16 (s, 1H), 7.00 (s, 1H), 4.15-4.04 (m, 2H), 4.04-3.96 (m, 2H), 3.49-3.35 (m, 2H), 3.13-3.04 (m, 1H), 2.03-1.94 (m, 2H), 1.52-1.40 (m, 5H).

Step 2: 1-[(1-ethyl-1H-pyrazol-4-yl)(oxan-4-yl)sulfamoyl]-3-(1,2,3,5,6,7-hexahydro-s-indacen-4-yl)urea sodium salt. General procedure B was followed using {[(1,2,3,5,6,7-hexahydro-s-indacen-4-yl)carbamoyl]amino}sulfonyl chloride and 1-ethyl-N-tetrahydropyran-4-yl-pyrazol-4-amine. The crude product was purified by prep-HPLC (column: Phenomenex Gemini C18 10 μm 250×50 mm; mobile phase: [water (10 mM NH$_4$HCO$_3$)-ACN]; B: 3-33%, 21 min) to give the title compound as a white solid. $^1$H NMR (400 MHz, MeOD) δ=7.75 (s, 1H), 7.44 (s, 1H), 6.98 (s, 1H), 4.40-4.28 (m, 1H), 4.21-4.15 (m, 2H), 3.90-3.93 (m, 2H), 3.47 (t, J=11 Hz, 3H), 2.92-2.84 (m, 4H), 2.80 (t, J=7 Hz, 4H), 2.11-2.04 (m, 4H), 1.88 (d, J=10 Hz, 4H), 1.48-1.42 (m, 4H). LC-MS (ESI): m/z: [M+H]$^+$=474.2

Example 7. 1-[(1-ethyl-1H-pyrazol-4-yl)(1-methylpiperidin-4-yl)sulfamoyl]-3-(1,2,3,5,6,7-hexahydro-s-indacen-4-yl)urea sodium salt

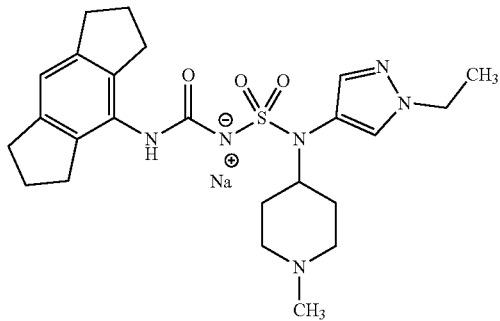 [SMILES: CCn1cc(N(C2CCN(C)CC2)S(=O)(=O)[N-]C(=O)Nc2c3c(cc4c2CCC4)CCC3)cn1 ; [Na+]]

Step 1: N-(1-ethylpyrazol-4-yl)-1-methyl-piperidin-4-amine. General procedure A was followed using 1-ethylpyrazol-4-amine and tetrahydropyran-4-one. The crude product was purified by prep-HPLC (column: Phenomenex Gemini C18 10 μm 250×50 mm; mobile phase: [water (10 mM NH₄HCO₃)-ACN]; B: 0-20%, 21 min) to give the title compound as a red oil.

Step 2: 1-[(1-ethyl-1H-pyrazol-4-yl)(1-methylpiperidin-4-yl)sulfamoyl]-3-(1,2,3,5,6,7-hexahydro-s-indacen-4-yl) urea sodium salt. General procedure B was followed using {[(1,2,3,5,6,7-hexahydro-s-indacen-4-yl)carbamoyl] amino}sulfonyl chloride and N-(1-ethylpyrazol-4-yl)-1-methyl-piperidin-4-amine. The crude product was purified by prep-HPLC (column: Phenomenex Gemini C18 10 μm 250×50 mm; mobile phase: [water (10 mM NH₄HCO₃)-ACN]; B: 6-36%, 21 min) to give the title compound as a white solid. $^1$H NMR (400 MHz, MeOH) δ=7.72 (s, 1H), 7.45 (s, 1H), 6.95 (s, 1H), 4.29-4.20 (m, 1H), 4.18-4.12 (m, 2H), 3.13 (d, J=11 Hz, 2H), 2.87 (t, J=7 Hz, 4H), 2.80 (t, J=7 Hz, 4H), 2.60 (t, J=12 Hz, 2H), 2.47 (s, 3H), 2.12-2.02 (m, 6H), 1.60-1.47 (m, 2H), 1.44 (t, J=7 Hz, 3H). LC-MS (ESI): m/z: [M+H]⁺=487.2

Example 8. 3-(1,2,3,5,6,7-hexahydro-s-indacen-4-yl)-1-[(1-methyl-1H-pyrazol-4-yl)(oxolan-3-yl)sulfamoyl]urea sodium salt

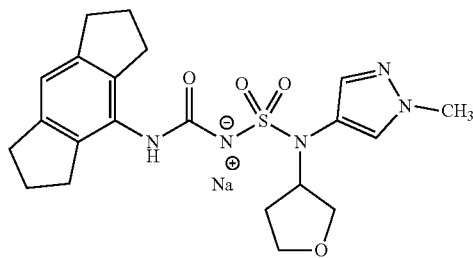 [SMILES: Cn1cc(N(C2CCOC2)S(=O)(=O)[N-]C(=O)Nc2c3c(cc4c2CCC4)CCC3)cn1 ; [Na+]]

Step 1: 1-methyl-N-tetrahydrofuran-3-yl-pyrazol-4-amine. General procedure A was followed using 1-ethylpyrazol-4-amine and tetrahydropyran-4-one. The crude product was purified by prep-HPLC (column: Agela Venusil XBP Phenyl 10 μm 250×50 mm; mobile phase: [water (10 mM NH₄HCO₃)-ACN]; B: 1-17%, 20 min) to give the title compound as a white solid.

Step 2: 3-(1,2,3,5,6,7-hexahydro-s-indacen-4-yl)-1-[(1-methyl-1H-pyrazol-4-yl)(oxolan-3-yl)sulfamoyl]urea sodium salt. General procedure B was followed using {[(1,2,3,5,6,7-hexahydro-s-indacen-4-yl)carbamoyl] amino}sulfonyl chloride and 1-methyl-N-tetrahydrofuran-3-yl-pyrazol-4-amine. The crude product was purified by prep-HPLC (column: Phenomenex Gemini C18 10 μm 250×50 mm; mobile phase: [water (10 mM NH₄HCO₃)-ACN]; B: 7-37%, 21 min) to give the title compound as a white solid. $^1$H NMR (400 MHz, MeOD) δ=7.77 (s, 1H), 7.50 (s, 1H), 6.99 (s, 1H), 5.04-4.94 (m, 1H), 3.91 (d, J=3 Hz, 1H), 3.89 (s, 3H), 3.79-3.77 (m, 1H), 3.65-3.47 (m, 2H), 2.88 (t, J=8 Hz, 4H), 2.80 (t, J=7 Hz, 4H), 2.28-2.22 (m, 1H), 2.10-2.07 (m, 4H), 1.97-1.86 (m, 1H).

LC-MS (ESI): m/z: [M+H]⁺=446.1

Example 9. 3-(1,2,3,5,6,7-hexahydro-s-indacen-4-yl)-1-[(1-methyl-1H-pyrazol-3-yl)(oxan-4-yl)sulfamoyl]urea sodium salt

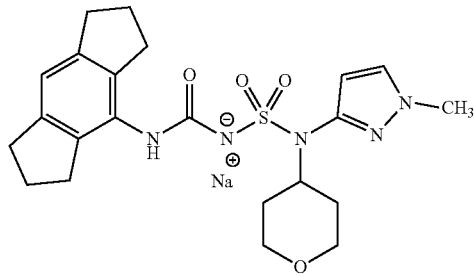 [SMILES: Cn1ccc(N(C2CCOCC2)S(=O)(=O)[N-]C(=O)Nc2c3c(cc4c2CCC4)CCC3)n1 ; [Na+]]

Step 1: 1-methyl-N-tetrahydropyran-4-yl-pyrazol-3-amine. General procedure A was followed using 1-methylpyrazol-3-amine and tetrahydropyran-4-one to give the title compound as a white solid. $^1$H NMR (400 MHz, CDCl₃) δ 7.11 (s, 1H), 5.53 (s, 1H), 3.99 (d, J=11 Hz, 2H), 3.62-3.38 (m, 3H), 2.37 (s, 1H), 2.05 (d, J=12 Hz, 2H), 1.58-1.39 (m, 2H).

Step 2: 3-(1,2,3,5,6,7-hexahydro-s-indacen-4-yl)-1-[(1-methyl-1H-pyrazol-3-yl)(oxan-4-yl)sulfamoyl]urea sodium salt. General procedure B was followed using {[(1,2,3,5,6,7-hexahydro-s-indacen-4-yl)carbamoyl]amino}sulfonyl chloride and 1-methyl-N-tetrahydropyran-4-yl-pyrazol-3-amine. The reaction mixture was poured into MTBE, filtered and the resulting solid purified by prep-HPLC (column: Phenomenex Gemini C18 10 μm 250×50 mm; mobile phase: [water (10 mM NH₄HCO₃)-ACN]; B: 10-40%, 21 min) to give the title compound as a white solid. $^1$H NMR (400 MHz, CDCl₃) δ 8.22 (s, 1H), 7.35 (d, J=2 Hz, 1H), 7.03 (s, 1H), 6.21 (d, J=2 Hz, 1H), 4.23 (s, 1H), 4.00-3.96 (m, 2H), 3.83 (s, 3H), 3.46 (t, J=12 Hz, 2H), 2.95-2.78 (m, 8H), 2.14-2.04 (m, 4H), 1.98-1.95 (m, 2H), 1.75-1.64 (m, 2H). LC-MS (ESI): m/z: [M+H]⁺=460.2

Example 10. 1-[(1,5-dimethyl-1H-pyrazol-4-yl)(oxan-4-yl)sulfamoyl]-3-(1,2,3,5,6,7-hexahydro-s-indacen-4-yl)urea sodium salt

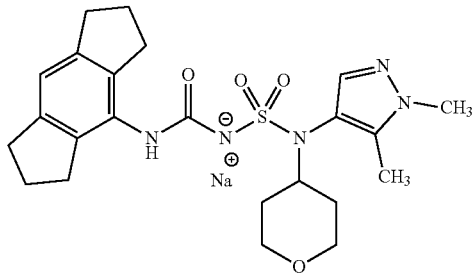 [SMILES: Cc1c(N(C2CCOCC2)S(=O)(=O)[N-]C(=O)Nc2c3c(cc4c2CCC4)CCC3)cnn1C ; [Na+]]

Step 1: 1,5-dimethyl-N-tetrahydropyran-4-yl-pyrazol-4-amine. General procedure A was followed using 1,5-dimethylpyrazol-4-amine and tetrahydropyran-4-one to give the title compound as a white solid. LC-MS (ESI): m/z: [M+H]⁺ =196.2

Step 2: 1-[(1,5-dimethyl-1H-pyrazol-4-yl)(oxan-4-yl)sulfamoyl]-3-(1,2,3,5,6,7-hexahydro-s-indacen-4-yl)urea sodium salt. General procedure B was followed using {[(1,2,3,5,6,7-hexahydro-s-indacen-4-yl)carbamoyl]amino}sulfonyl chloride and 1,5-dimethyl-N-tetrahydropyran-4-yl-pyrazol-4-amine. The crude product was purified by prep-HPLC (column: YMC-Actus Triart C18 5 μm 100×30 mm; mobile phase: [water (10 mM NH₄HCO₃)-ACN]; B: 18-38%, 55 min) to give the title compound as a white solid. $^1$H NMR (400 MHz, MeOD) δ 7.35 (s, 1H), 6.98 (s, 1H), 4.42 (t, J=12 Hz, 1H), 3.91 (d, J=11 Hz, 2H), 3.80 (s, 3H), 3.50-3.43 (m, 2H), 2.88 (t, J=7 Hz, 4H), 2.79 (t, J=7 Hz, 4H), 2.27 (s, 3H), 2.12-2.03 (m, 4H), 1.98-1.80 (m, 2H), 1.40 (s, 2H). LC-MS (ESI): m/z: [M+H]⁺=474.2

Example 11. 3-(1,2,3,5,6,7-hexahydro-s-indacen-4-yl)-1-[(oxan-4-yl)(1,3,5-trimethyl-1H-pyrazol-4-yl)sulfamoyl]urea sodium salt

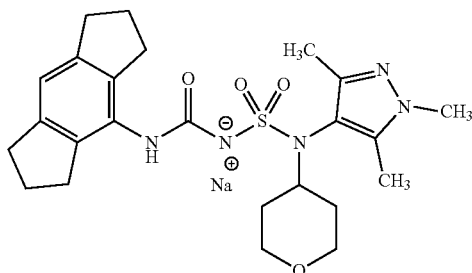

Step 1: 1,3,5-trimethyl-N-tetrahydropyran-4-yl-pyrazol-4-amine. General procedure A was followed using 1,3,5-trimethylpyrazol-4-amine and tetrahydropyran-4-one to give the title compound as a yellow oil. $^1$H NMR (400 MHz, DMSO-d₆) δ ppm 4.17-4.10 (m, 1H), 3.83-3.79 (m, 2H), 3.55 (s, 3H), 3.25-3.18 (m, 2H), 2.07 (s, 3H), 1.99 (s, 3H), 1.67-1.64 (m, 2H), 1.36-1.25 (m, 2H).

Step 2: 3-(1,2,3,5,6,7-hexahydro-s-indacen-4-yl)-1-[(oxan-4-yl)(1,3,5-trimethyl-1H-pyrazol-4-yl)sulfamoyl]urea sodium salt. General procedure B was followed using {[(1,2,3,5,6,7-hexahydro-s-indacen-4-yl)carbamoyl]amino}sulfonyl chloride and 1,3,5-trimethylpyrazol-4-amine. The crude product was purified by prep-HPLC (column: Phenomenex Gemini C18 10 μm 250×50 mm; mobile phase: [water (10 mM NH₄HCO₃)-ACN]; B: 5-35%, 21 min) to give the title compound as a white solid. $^1$H NMR (400 MHz, MeOD) δ 6.98 (s, 1H), 4.58-4.49 (m, 1H), 3.92-3.88 (m, 2H), 3.72 (s, 3H), 3.46 (t, J=11 Hz, 2H), 2.88 (t, J=7 Hz, 4H), 2.77 (t, J=7 Hz, 4H), 2.25 (s, 3H), 2.20 (s, 3H), 2.10-2.01 (m, 4H), 1.98-1.89 (m, 2H), 1.48-1.35 (m, 2H). LC-MS (ESI): m/z: [M+H]⁺=488.2

Example 12. 3-(1,2,3,5,6,7-hexahydro-s-indacen-4-yl)-1-[(5-methyl-1,2-oxazol-3-yl)(oxan-4-yl)sulfamoyl]urea sodium salt

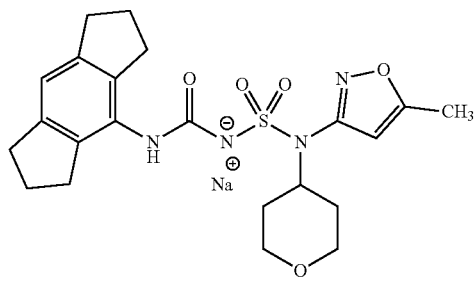 [SMILES: Cc1cc(N(C2CCOCC2)S(=O)(=O)[N-]C(=O)Nc2c3c(cc4c2CCC4)CCC3)no1 ; [Na+]]

Step 1: 5-methyl-N-tetrahydropyran-4-yl-isoxazol-3-amine. General procedure A was followed using 5-methyl-isoxazol-3-amine and tetrahydropyran-4-one to give the title compound as a yellow oil. $^1$H NMR (400 MHz, CDCl₃) δ ppm 5.47 (s, 1H), 3.69 (d, J=7 Hz, 1H), 3.42-3.31 (m, 1H), 2.83 (d, J=11 Hz, 2H), 2.30 (s, 3H), 2.18-2.07 (m, 4H), 1.59-1.47 (m, 2H).

Step 2: 3-(1,2,3,5,6,7-hexahydro-s-indacen-4-yl)-1-[(5-methyl-1,2-oxazol-3-yl)(oxan-4-yl)sulfamoyl]urea sodium salt. General procedure B was followed using {[(1,2,3,5,6,7-hexahydro-s-indacen-4-yl)carbamoyl]amino}sulfonyl chloride and 5-methyl-N-tetrahydropyran-4-yl-isoxazol-3-amine. The crude product was purified by prep-HPLC (column: YMC-Actus Triart C18 5 μm 100×30 mm; mobile phase: [water (10 mM NH₄HCO₃)-ACN]; B: 25-45%, 55 min) to give the title compound as a white solid. $^1$H NMR (400 MHz, MeOD) δ 6.95 (s, 1H), 6.35 (s, 1H), 4.47-4.36 (m, 1H), 3.96-3.92 (m, 2H), 3.49-3.43 (m, 2H), 2.86 (t, J=8 Hz, 4H), 2.78 (t, J=7 Hz, 4H), 2.40 (s, 3H), 2.10-2.01 (m, 4H), 1.96-1.84 (m, 4H). LC-MS (ESI): m/z: [M+H]⁺=461.1

Example 13. 3-(1,2,3,5,6,7-hexahydro-s-indacen-4-yl)-1-[(oxan-4-yl)(1,2-oxazol-4-yl)sulfamoyl]urea sodium salt

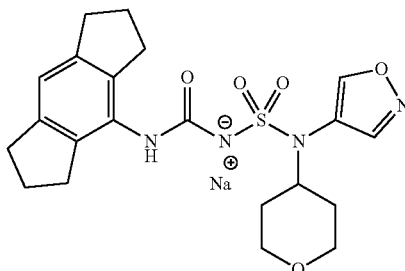

Step 1: N-tetrahydropyran-4-ylisoxazol-4-amine. General procedure A was followed using isoxazol-4-amine and tetrahydropyran-4-one to give the title compound as a yellow oil. ¹H NMR (400 MHz, CDCl₃) δ ppm 8.05 (s, 1H), 7.96 (s, 1H), 4.02-3.97 (m, 2H), 3.49-3.43 (m, 2H), 3.14-3.06 (m, 1H), 1.98 (d, J=14 Hz, 2H), 1.51-1.42 (m, 2H), 1.25 (s, 1H).

Step 2: 3-(1,2,3,5,6,7-hexahydro-s-indacen-4-yl)-1-[(oxan-4-yl)(1,2-oxazol-4-yl)sulfamoyl]urea sodium salt. General procedure B was followed using {[(1,2,3,5,6,7-hexahydro-s-indacen-4-yl)carbamoyl]amino}sulfonyl chloride and N-tetrahydropyran-4-ylisoxazol-4-amine. The crude product was purified by prep-HPLC (column: YMC-Actus Triart C18 5 μm 100×30 mm; mobile phase: [water (10 mM NH₄HCO₃)-ACN]; B: 25-45%, 12 min) to give the title compound as a white solid. ¹H NMR (400 MHz, MeOD) δ 8.88 (s, 1H), 8.48 (s, 1H), 6.51 (s, 1H), 4.28-4.26 (m, 1H), 3.98-3.91 (m, 2H), 3.48 (t, J=12 Hz, 2H), 2.80 (t, J=7 Hz, 4H), 2.70 (t, J=7 Hz, 4H), 2.10-2.01 (m, 4H), 1.87 (d, J=13 Hz, 2H), 1.47-1.42 (m, 2H). LC-MS (ESI): m/z: [M+H]⁺=447.1

Example 14. 1-[(1,5-dimethyl-1H-pyrazol-4-yl)(1-methylpiperidin-4-yl)sulfamoyl]-3-(1,2,3,5,6,7-hexahydro-s-indacen-4-yl)urea sodium salt

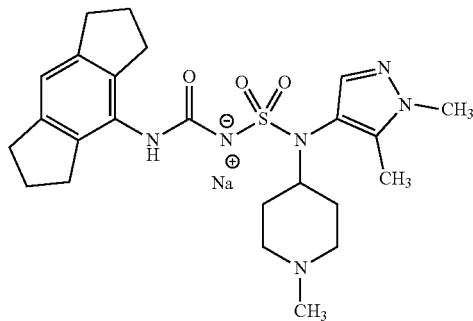 [SMILES: Cc1c(N(C2CCN(C)CC2)S(=O)(=O)[N-]C(=O)Nc2c3c(cc4c2CCC4)CCC3)cnn1C ; [Na+]]

Step 1: N-(1,5-dimethylpyrazol-4-yl)-1-methyl-piperidin-4-amine. General procedure A was followed using 1,5-dimethylpyrazol-4-amine and 1-methylpiperidin-4-one to give the title compound as a white solid. LC-MS (ESI): m/z: [M+H]⁺=209.3

Step 2: 1-[(1,5-dimethyl-1H-pyrazol-4-yl)(1-methylpiperidin-4-yl)sulfamoyl]-3-(1,2,3,5,6,7-hexahydro-s-indacen-4-yl)urea sodium salt. General procedure B was followed using {[(1,2,3,5,6,7-hexahydro-s-indacen-4-yl)carbamoyl]amino}sulfonyl chloride and N-(1,5-dimethylpyrazol-4-yl)-1-methyl-piperidin-4-amine. The crude product was purified by prep-HPLC (column: YMC-Actus Triart C18 5 μm 100×30 mm; mobile phase: [water (10 mM NH₄HCO₃)-ACN]; B: 20-40%, 55 min) to give the title compound as a white solid. ¹H NMR (400 MHz, MeOD) δ 7.36 (s, 1H), 6.95 (s, 1H), 4.37-4.27 (m, 1H), 3.76 (s, 3H), 3.10 (d, J=12 Hz, 2H), 2.87 (t, J=8 Hz, 4H), 2.80 (t, J=7 Hz, 4H), 2.65-2.50 (m, 2H), 2.45 (s, 3H), 2.26 (s, 3H), 2.10-2.03 (m, 6H), 1.47 (s, 2H). LC-MS (ESI): m/z: [M+H]⁺=487.2

Example 15. 3-(1,2,3,5,6,7-hexahydro-s-indacen-4-yl)-1-[(1-methylpiperidin-4-yl)(1,3,5-trimethyl-1H-pyrazol-4-yl)sulfamoyl]urea sodium salt

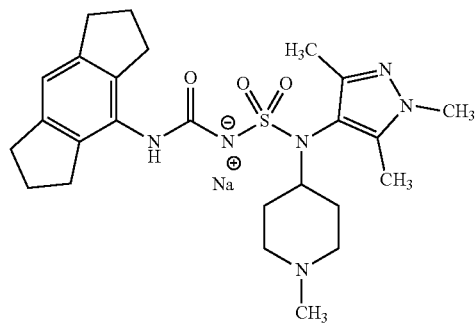 [SMILES: Cc1nn(C)c(C)c1N(C1CCN(C)CC1)S(=O)(=O)[N-]C(=O)Nc1c2c(cc3c1CCC3)CCC2 ; [Na+]]

Step 1: 1-methyl-N-(1,3,5-trimethylpyrazol-4-yl)piperidin-4-amine. General procedure A was followed using 1,3,5-trimethylpyrazol-4-amine and 1-methylpiperidin-4-one to give the title compound as a yellow solid. ¹H NMR (400 MHz, DMSO-d₆) δ ppm 3.55 (s, 3H), 3.17 (s, 3H), 3.10 (d, J=12 Hz, 2H), 2.70-2.61 (m, 1H), 2.59-2.52 (m, 2H), 2.07 (s, 3H), 1.99 (s, 2H), 2.01-1.99 (m, 1H), 1.80-1.74 (m, 2H), 1.51-1.38 (m, 2H).

Step 2: 3-(1,2,3,5,6,7-hexahydro-s-indacen-4-yl)-1-[(1-methylpiperidin-4-yl) (1,3,5-trimethyl-1H-pyrazol-4-yl)sulfamoyl]urea sodium salt. General procedure B was followed using {[(1,2,3,5,6,7-hexahydro-s-indacen-4-yl)carbamoyl]amino}sulfonyl chloride and 1-methyl-N-(1,3,5-trimethylpyrazol-4-yl)piperidin-4-amine. The crude product was purified by prep-HPLC (column: Phenomenex Gemini C18 10 μm 250×50 mm; mobile phase: [water (10 mM NH₄HCO₃)-ACN]; B: 6-36%, 21 min) to give the title compound as a white solid. ¹H NMR (400 MHz, MeOD) δ 6.95 (s, 1H), 4.43 (t, J=12 Hz, 1H), 3.66 (s, 3H), 3.03 (d, J=13 Hz, 2H), 2.87 (t, J=7 Hz, 4H), 2.79 (t, J=7 Hz, 4H), 2.44 (t, J=13 Hz, 2H), 2.38 (s, 3H), 2.24 (s, 3H), 2.20 (s, 3H), 2.14-2.02 (m, 6H), 1.60-1.35 (m, 2H). LC-MS (ESI): m/z: [M+H]⁺=501.2

Example 16. 3-(1,2,3,5,6,7-hexahydro-s-indacen-4-yl)-1-[(1-methyl-1H-pyrazol-4-yl)[(oxetan-3-yl)methyl]sulfamoyl]urea sodium salt

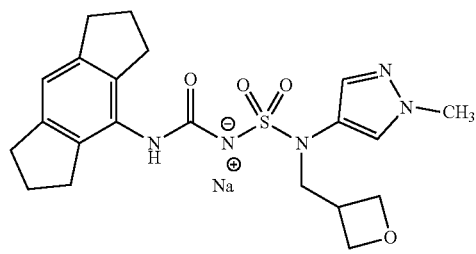 [SMILES: Cn1cc(N(CC2COC2)S(=O)(=O)[N-]C(=O)Nc2c3c(cc4c2CCC4)CCC3)cn1 ; [Na+]]

Step 1: 1-methyl-N-(oxetan-3-ylmethyl)pyrazol-4-amine. General procedure A was followed using 1-methylpyrazol-4-amine and oxetane-3-carbaldehyde to give the title compound as a red oil. ¹H NMR (400 MHz, CDCl₃) δ=7.12 (d, J=1 Hz, 1H), 6.93 (d, J=1 Hz, 1H), 4.86-4.83 (m, 2H), 4.45 (t, J=6 Hz, 2H), 3.82 (s, 3H), 3.32-3.27 (m, 2H), 3.26-3.14 (m, 1H).

Step 2: 3-(1,2,3,5,6,7-hexahydro-s-indacen-4-yl)-1-[(1-methyl-1H-pyrazol-4-yl)][(oxetan-3-yl)methyl]sulfamoyl] urea sodium salt. General procedure B was followed using {[(1,2,3,5,6,7-hexahydro-s-indacen-4-yl)carbamoyl] amino}sulfonyl chloride and 1-methyl-N-(oxetan-3-ylmethyl)pyrazol-4-amine. The crude product was purified by prep-HPLC (column: Phenomenex Luna (2) C18 10 μm 250×50 mm; mobile phase: [water (10 mM NH₄HCO₃)-ACN]; B: 7-37%, 20 min) to give the title compound as a white solid. ¹H NMR (400 MHz, MeOD) δ=7.71 (s, 1H), 7.49 (s, 1H), 6.98 (s, 1H), 4.71-4.67 (m, 2H), 4.39 (t, J=6 Hz, 2H), 4.06 (d, J=8 Hz, 2H), 3.86 (s, 3H), 3.22-3.10 (m, 1H), 2.87 (t, J=7 Hz, 4H), 2.76 (t, J=7 Hz, 4H), 2.11-2.04 (m, 4H). LC-MS (ESI): m/z: [M+H]⁺=446.1

Example 17. 3-(1,2,3,5,6,7-hexahydro-s-indacen-4-yl)-1-[(oxan-4-yl)(pyrimidin-5-yl)sulfamoyl]urea sodium salt

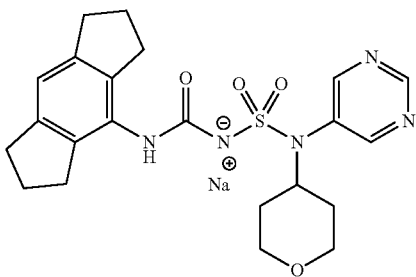 [SMILES: O=C([N-]S(=O)(=O)N(c1cncnc1)C1CCOCC1)Nc1c2c(cc3c1CCC3)CCC2 ; [Na+]]

Step 1: N-tetrahydropyran-4-ylpyrimidin-5-amine. General procedure A was followed using 1-methylpyrazol-4-amine and oxetane-3-carbaldehyde. The crude product was purified by prep-HPLC (column: Phenomenex Gemini C18 10 μm 250×50 mm; mobile phase: [water (10 mM NH₄HCO₃)-ACN]; B: 5-35%, 21 min) to give the title compound as a white solid. ¹H NMR (400 MHz, CDCl₃) δ=8.58 (s, 1H), 8.12 (s, 2H), 4.07-3.98 (m, 3H), 3.86-3.64 (m, 2H), 3.58-3.46 (m, 4H), 2.04 (d, J=13 Hz, 2H), 1.81 (s, 3H), 1.59-1.46 (m, 3H).

Step 2: 3-(1,2,3,5,6,7-hexahydro-s-indacen-4-yl)-1-[(oxan-4-yl)(pyrimidin-5-yl)sulfamoyl]urea sodium salt. General procedure B was followed using {[(1,2,3,5,6,7-hexahydro-s-indacen-4-yl)carbamoyl]amino}sulfonyl chloride and N-tetrahydropyran-4-ylpyrimidin-5-amine. The reaction was poured into MTBE and filtered. The filter cake was collected and washed with acetonitrile, and then acetonitrile phase concentrated to give the crude product. This was purified by prep-HPLC (column: Phenomenex Gemini C18 10 μm 250×50 mm; mobile phase: [water (10 mM NH₄HCO₃)-ACN]; B: 15-40%, 21 min) to give the title compound as a white solid. ¹H NMR (400 MHz, MeOD) δ=9.15 (s, 1H), 8.77 (s, 2H), 6.97 (s, 1H), 4.44 (t, J=12 Hz, 1H), 3.95-3.91 (m, 2H), 3.48 (t, J=12 Hz, 2H), 2.94-2.75 (m, 8H), 2.13-1.94 (m, 6H), 1.45-1.28 (m, 2H). LC-MS (ESI): m/z: [M+H]⁺458.2

Example 18. 3-(1,2,3,5,6,7-hexahydro-s-indacen-4-yl)-1-[(3-methyl-1,2-oxazol-5-yl)(oxan-4-yl)sulfamoyl]urea sodium salt

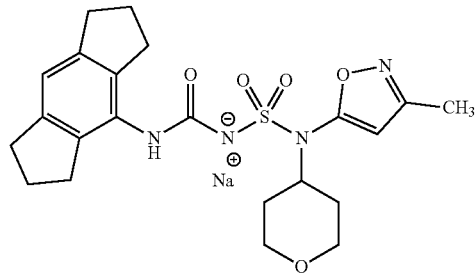 [SMILES: Cc1cc(N(C2CCOCC2)S(=O)(=O)[N-]C(=O)Nc2c3c(cc4c2CCC4)CCC3)on1 ; [Na+]]

Step 1: 3-methyl-N-tetrahydropyran-4-yl-isoxazol-5-amine. General procedure A was followed using 1-methylpyrazol-4-amine and oxetane-3-carbaldehyde. The crude product was purified by prep-HPLC (column: Phenomenex Luna C18 10 μm 250×50 mm; mobile phase: [water (0.1% TFA)-ACN]; B: 0-30%, 20 min) to give the title compound as a yellow oil. LC-MS (ESI): m/z: [M+H]⁺=183.2

Step 2: 3-(1,2,3,5,6,7-hexahydro-s-indacen-4-yl)-1-[(3-methyl-1,2-oxazol-5-yl)(oxan-4-yl)sulfamoyl]urea sodium salt. General procedure B was followed using {[(1,2,3,5,6,7-hexahydro-s-indacen-4-yl)carbamoyl]amino}sulfonyl chloride and 3-methyl-N-tetrahydropyran-4-yl-isoxazol-5-amine. The crude product was purified by prep-HPLC (column: Phenomenex Gemini C18 10 μm 250×50 mm; mobile phase: [water (10 mM NH₄HCO₃)-ACN]; B: 10-40%, 20 min) to give the title compound as a white solid. ¹H NMR (400 MHz, MeOD) δ ppm 6.90 (s, 1H), 6.15 (s, 1H), 4.42-4.32 (m, 1H), 3.96-3.92 (m, 2H), 3.51-3.46 (m, 2H), 2.85 (t, J=7 Hz, 4H), 2.79 (t, J=7 Hz, 4H), 2.24 (s, 3H), 2.07-1.93 (m, 6H), 1.79-1.67 (m, 2H). LC-MS (ESI): m/z: [M+H]⁺=461.1

Example 19. 3-(1,2,3,5,6,7-hexahydro-s-indacen-4-yl)-1-[(1-methyl-1H-1,2,4-triazol-3-yl)(oxan-4-yl)sulfamoyl]urea sodium salt

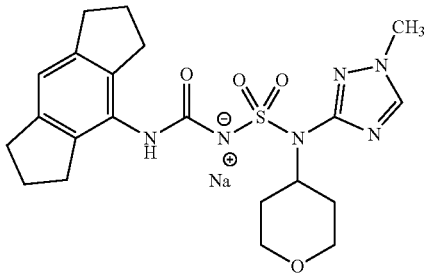 [SMILES: Cn1cnc(N(C2CCOCC2)S(=O)(=O)[N-]C(=O)Nc2c3c(cc4c2CCC4)CCC3)n1 ; [Na+]]

Step 1: 1-methyl-N-tetrahydropyran-4-yl-1,2,4-triazol-3-amine. General procedure A was followed using 1-methyl-1,2,4-triazol-3-amine and tetrahydropyran-4-one. The crude product was purified by prep-HPLC (column: Phenomenex Luna C18 10 μm 250×50 mm; mobile phase: [water (0.1% TFA)-ACN]; B: 0-15%, 20 min) to give the title compound as a white solid. ¹H NMR (400 MHz, MeOD) δ=8.62 (s, 1H), 3.97-3.94 (m, 2H), 3.81 (s, 3H), 3.63-3.60 (m, 1H), 3.52-3.47 (m, 2H), 2.02-1.97 (m, 2H), 1.60-1.55 (m, 2H). LC-MS (ESI): m/z: [M+H]$^+$=183.3

Step 2: 3-(1,2,3,5,6,7-hexahydro-s-indacen-4-yl)-1-[(1-methyl-1H-1,2,4-triazol-3-yl)(oxan-4-yl)sulfamoyl]urea sodium salt. General procedure B was followed using {[(1,2,3,5,6,7-hexahydro-s-indacen-4-yl)carbamoyl]amino}sulfonyl chloride and 1-methyl-N-tetrahydropyran-4-yl-1,2,4-triazol-3-amine. The crude product was diluted with ACN (20 ml), then the solvent was filtered under reduced pressure and the filtrate was collected. The mixture was diluted with ACN (20 ml), then the solvent was filtered under reduced pressure and the filtrate evaporated to give the title compound as a white solid. $^1$H NMR (400 MHz, MeOD) δ=7.89 (s, 1H), 7.03-6.81 (m, 1H), 4.31 (s, 1H), 3.95 (d, J=10 Hz, 2H), 3.74 (s, 2H), 3.48 (s, 3H), 2.85-2.67 (m, 10H), 2.05-1.80 (m, 4H), 1.90 (s, 2H). LC-MS (ESI): m/z: [M+H]$^+$=461.2

Example 20. 3-(1,2,3,5,6,7-hexahydro-s-indacen-4-yl)-1-[(1-methyl-1H-pyrazol-3-yl)(l-methylpiperidin-4-yl)sulfamoyl]urea sodium salt

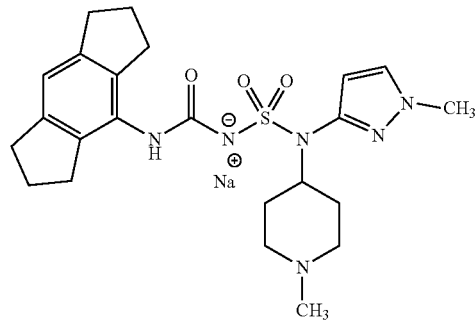 [SMILES: CN1CCC(N(c2ccn(C)n2)S(=O)(=O)[N-]C(=O)Nc2c3c(cc4c2CCC4)CCC3)CC1 ; [Na+]]

Step 1: 1-methyl-N-(1-methylpyrazol-3-yl) piperidin-4-amine. General procedure A was followed using 1-methylpyrazol-3-amine and 1-methylpiperidin-4-one to give the title compound as a yellow oil. $^1$H NMR (400 MHz, CDCl$_3$) δ=7.10 (d, J=2 Hz, 1H), 5.52 (d, J=2 Hz, 1H), 3.71-3.58 (m, 3H), 3.36 (s, 1H), 2.98 (d, J=12 Hz, 2H), 2.44 (s, 3H), 2.17-2.12 (m, 6H), 1.69-1.60 (m, 2H). LC-MS (ESI): m/z: [M+H]$^+$=195.4

Step 2: 3-(1,2,3,5,6,7-hexahydro-s-indacen-4-yl)-1-[(1-methyl-1H-pyrazol-3-yl)(l-methylpiperidin-4-yl)sulfamoyl]urea sodium salt. General procedure B was followed using {[(1,2,3,5,6,7-hexahydro-s-indacen-4-yl)carbamoyl]amino}sulfonyl chloride and 1-methyl-N-(1-methylpyrazol-3-yl) piperidin-4-amine. The mixture was diluted with acetonitrile, filtered under reduced pressure and the filtrate concentrated to give the crude product. This was purified by prep-HPLC (column: Phenomenex Gemini C18 10 μm 250×50 mm; mobile phase: [water (10 mM NH$_4$HCO$_3$)-ACN]; B: 5-35%, 20 min) to give the title compound as a white solid. $^1$H NMR (400 MHz, MeOD) δ=7.51 (d, J=2 Hz, 1H), 6.90 (s, 1H), 6.25 (d, J=2 Hz, 1H), 4.20-4.10 (m, 1H), 3.81 (s, 3H), 3.68 (s, 1H), 3.02-2.88 (m, 2H), 2.86-2.80 (m, 8H), 2.39-2.35 (m, 5H), 2.09-2.03 (m, 6H), 1.68-1.66 (m, 2H). LC-MS (ESI): m/z: [M+H]$^+$=473.3

Example 21. 3-(1,2,3,5,6,7-hexahydro-s-indacen-4-yl)-1-[(1-methyl-1H-imidazol-4-yl)(oxan-4-yl)sulfamoyl]urea sodium salt

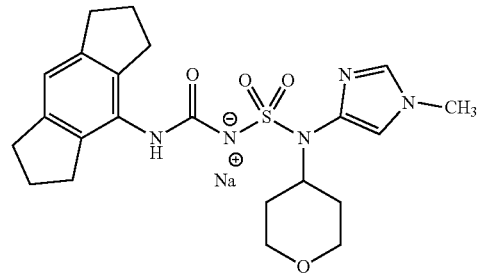 [SMILES: Cn1cnc(N(C2CCOCC2)S(=O)(=O)[N-]C(=O)Nc2c3c(cc4c2CCC4)CCC3)c1 ; [Na+]]

Step 1: 1-methyl-4-nitro-imidazole. To a solution of 4-nitro-1H-imidazole (5.0 g, 44 mmol, 1 eq.) in ACN (50 ml) was added K$_2$CO$_3$ (9.17 g, 66 mmol). Methyl iodide (7.53 g, 53 mmol, 3.30 ml) was added slowly to the mixture at rt, then the mixture was warmed to 60° C. for 14 h. The solvent was removed under reduced pressure, then the residue was diluted with water (30 ml), extracted with DCM (5×30 ml) and the combined organic layers dried over Na$_2$SO$_4$. The organic phase was concentrated in vacuo to give the title compound as a yellow solid. $^1$H NMR (400 MHz, DMSO-d$_6$) δ=8.35 (s, 1H), 7.80 (s, 1H), 3.75 (s, 3H).

Step 2: 1-methylimidazol-4-amine. To a solution of 1-methyl-4-nitro-imidazole (2 g, 15.7 mmol, 1 eq.) in MeOH (100 ml) was added 10% Pd/C (1 g, 15.7 mmol) under H$_2$. The mixture was stirred under H$_2$ (15 psi) at 25° C. for 1 h. The mixture was diluted with MeOH (50 ml) and filtered under reduced pressure. The filtrate was evaporated to give the title compound as a yellow oil. $^1$H NMR (400 MHz, CDCl$_3$) δ=7.03 (s, 1H), 6.17 (s, 1H), 3.60-3.10 (m, 5H).

Step 3: 1-methyl-N-tetrahydropyran-4-yl-imidazol-4-amine. General procedure A was followed using 1-methylimidazol-4-amine and tetrahydropyran-4-one. The crude product was purified by prep-HPLC (column: Phenomenex Luna C18 10 μm 250×50 mm; mobile phase: [water (0.1% TFA)-ACN]; B: 0-10%, 20 min) to give the title compound as a yellow oil. $^1$H NMR (400 MHz, CDCl$_3$) δ=7.82-7.76 (m, 1H), 6.03 (s, 1H), 4.01-3.96 (m, 2H), 3.76 (s, 3H), 3.50-3.47 (m, 2H), 3.45-3.13 (m, 1H), 1.96 (d, J=13 Hz, 2H), 1.69-1.61 (m, 2H). LC-MS (ESI): m/z: [M+H]$^+$=182.4

Step 4: 3-(1,2,3,5,6,7-hexahydro-s-indacen-4-yl)-1-[(1-methyl-1H-imidazol-4-yl)(oxan-4-yl)sulfamoyl]urea sodium salt. General procedure B was followed using {[(1,2,3,5,6,7-hexahydro-s-indacen-4-yl)carbamoyl]amino}sulfonyl chloride and 1-methyl-N-tetrahydropyran-4-yl-imidazol-4-amine. The crude product was purified by prep-HPLC (column: Phenomenex Gemini C18 10 μm 250×50 mm; mobile phase: [water (10 mM NH$_4$HCO$_3$)-ACN]; B: 15-40%, 21 min) to give the title compound as a white solid. LC-MS (ESI): m/z: [M+H]$^+$=460.2

Example 22. 3-(1,2,3,5,6,7-hexahydro-s-indacen-4-yl)-1-[(1-methyl-1H-pyrazol-4-yl)(oxan-3-yl)sulfamoyl]urea sodium salt

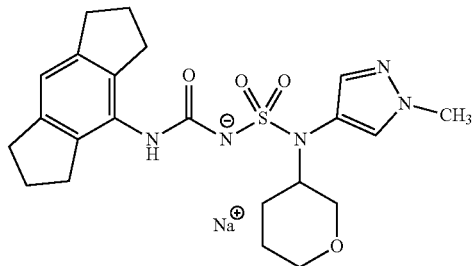 [SMILES: Cn1cc(N(C2CCCOC2)S(=O)(=O)[N-]C(=O)Nc2c3c(cc4c2CCC4)CCC3)cn1 ; [Na+]]

Step 1: 1-methyl-N-tetrahydropyran-3-yl-pyrazol-4-amine. General procedure A was followed using 1-methylpyrazol-4-amine and tetrahydropyran-3-one. The crude product was purified by prep-HPLC (column: Phenomenex Gemini C18 10 μm 250×50 mm; mobile phase: [water (10 mM NH$_4$HCO$_3$)-ACN]; B: 0-30%, 21 min) to give the title compound as a red oil. $^1$H NMR (400 MHz, chloroform-d) δ=7.12 (s, 1H), 6.93 (s, 1H), 3.92 (d, J=11 Hz, 1H), 3.81 (s, 3H), 3.77-3.68 (m, 1H), 3.59-3.48 (m, 1H), 3.38-3.30 (m, 1H), 3.12-3.01 (br. s, 1H), 2.04-1.92 (m, 1H), 1.80-1.68 (m, 1H), 1.67-1.48 (m, 2H).

Step 2: 3-(1,2,3,5,6,7-hexahydro-s-indacen-4-yl)-1-[(1-methyl-1H-pyrazol-4-yl)(oxan-3-yl)sulfamoyl]urea sodium salt. General procedure B was followed using {[(1,2,3,5,6,7-hexahydro-s-indacen-4-yl)carbamoyl]amino}sulfonyl chloride and 1-methyl-N-tetrahydropyran-3-yl-pyrazol-4-amine. The crude product was purified by prep-HPLC (column: Phenomenex Gemini C18 10 μm 250×50 mm; mobile phase: [water (10 mM NH$_4$HCO$_3$)-ACN]; B: 7-37%, 21 min) to give the title compound as a white solid. $^1$H NMR (400 MHz, MeOD) δ=7.68 (s, 1H), 7.40 (s, 1H), 6.98 (s, 1H), 4.26-4.13 (m, 1H), 4.12-4.06 m, 1H), 3.88 (s, 3H), 3.79-3.71 (m, 1H), 3.13-3.04 (m, 2H), 2.88 (t, J=8 Hz, 4H), 2.80 (t, J=7 Hz, 4H), 2.12-2.04 (m, 5H), 1.79-1.60 (m, 2H), 1.39-1.26 (m, 1H).
LC-MS (ESI): m/z: [M+H]$^+$=460.1

Example 23. 3-(1,2,3,5,6,7-hexahydro-s-indacen-4-yl)-1-[(1-methyl-1H-pyrazol-4-yl)(l-methylpiperidin-3-yl)sulfamoyl]urea sodium salt

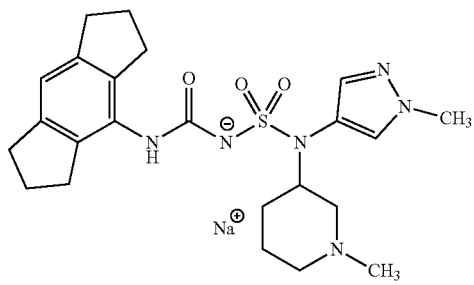 [SMILES: CN1CCCC(N(c2cnn(C)c2)S(=O)(=O)[N-]C(=O)Nc2c3c(cc4c2CCC4)CCC3)C1 ; [Na+]]

Step 1: 1-methyl-N-(1-methylpyrazol-4-yl)piperidin-3-amine. General procedure A was followed using 1-methylpyrazol-4-amine and 1-methylpiperidin-3-one. The crude product was purified by prep-HPLC (column: Phenomenex Gemini C18 10 μm 250×50 mm; mobile phase: [water (10 mM NH$_4$HCO$_3$)-ACN]; B: 0-25%, 20 min) to give the title compound as a red oil. $^1$H NMR (400 MHz, CDCl$_3$) δ=7.10 (s, 1H), 6.91 (s, 1H), 3.79 (s, 3H), 3.19-3.09 (m, 1H), 2.81-2.70 (br. s, 1H), 2.56-2.40 (br. s, 1H), 2.26 (s, 3H), 1.87-1.66 (m, 2H), 1.64-1.48 (m, 1H), 1.41-1.22 (m, 1H).

Step 2: 3-(1,2,3,5,6,7-hexahydro-s-indacen-4-yl)-1-[(1-methyl-1H-pyrazol-4-yl)(l-methylpiperidin-3-yl)sulfamoyl]urea sodium salt. General procedure B was followed using {[(1,2,3,5,6,7-hexahydro-s-indacen-4-yl)carbamoyl]amino}sulfonyl chloride and 1-methyl-N-(1-methylpyrazol-4-yl)piperidin-3-amine. The crude product was purified by prep-HPLC (column: Phenomenex Gemini C18 10 μm 250×50 mm; mobile phase: [water (10 mM NH$_4$HCO$_3$)-ACN]; B: 15-40%, 21 min) to give the title compound as a white solid. $^1$H NMR (400 MHz, MeOD) δ=7.66 (s, 1H), 7.43 (s, 1H), 6.94 (s, 1H), 4.36-4.28 (m, 1H), 3.87 (s, 3H), 3.52-3.41 (m, 1H), 3.05-3.00 (m, 1H), 2.87 (t, J=7.3 Hz, 4H), 2.81 (t, J=7 Hz, 4H), 2.55 (s, 3H), 2.40-2.16 (m, 2H), 2.11-1.99 (m, 5H), 1.92-1.81 (m, 1H), 1.80-1.66 (m, 1H), 1.28-1.12 (m, 1H).
LC-MS (ESI): m/z: [M+H]$^+$=473.2

Example 24. 3-(1,2,3,5,6,7-hexahydro-s-indacen-4-yl)-1-[(1-methyl-1H-pyrazol-4-yl)(l-methylpyrrolidin-3-yl)sulfamoyl]urea sodium salt

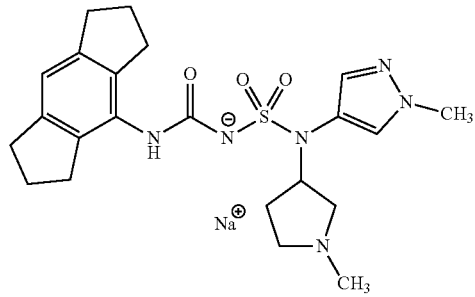 [SMILES: CN1CCC(N(c2cnn(C)c2)S(=O)(=O)[N-]C(=O)Nc2c3c(cc4c2CCC4)CCC3)C1 ; [Na+]]

Step 1: tert-butyl 3-[(1-methylpyrazol-4-yl)amino]pyrrolidine-1-carboxylate. To a solution of 1-methylpyrazol-4-amine (1.0 g, 10.3 mmol, 1 eq.) and tert-butyl 3-oxopyrrolidine-1-carboxylate (1.91 g, 10.3 mmol, 1 eq.) in DCM (10 ml) and CH$_3$COOH (1 ml) was added NaBH$_3$CN (0.97 g, 15.5 mmol, 1.5 eq.). The mixture was stirred at rt for 3 h then concentrated in vacuo. Water (10 ml) was added and the aqueous phase extracted with ethyl acetate (3×30 ml). The combined organic phases were washed with brine (3×10 ml), dried over anhydrous Na$_2$SO$_4$, filtered and concentrated in vacuo. The residue was purified by column chromatography (SiO$_2$, 0-100% EtOAc in petrol) to give the title compound as a red oil. $^1$H NMR (400 MHz, CDCl$_3$) δ=7.12 (s, 1H), 6.93 (s, 1H), 3.81 (s, 3H), 3.73-3.68 (br. s, 1H), 3.65-3.14 (m, 5H), 2.14-2.06 (m, 1H), 1.87-1.80 (br. s, 1H), 1.45 (s, 9H).

Step 2: 1-methyl-N-(1-methylpyrrolidin-3-yl)pyrazol-4-amine. To a solution of tert-butyl 3-[(1-methylpyrazol-4-yl)amino]pyrrolidine-1-carboxylate (810 mg, 3.04 mmol, 1 eq.) in THF (20 ml) was added lithium aluminium hydride (0.58 g, 15.2 mmol, 5 eq.). The mixture was stirred at 70° C. for 2 h then quenched by addition H$_2$O (3 ml) at 0° C. The reaction was diluted with 10% NaOH (3 ml), filtered and the filtrate concentrated under reduced pressure to give the title compound as a red oil, used directly.

Step 3: 3-(1,2,3,5,6,7-hexahydro-s-indacen-4-yl)-1-[(1-methyl-1H-pyrazol-4-yl)(1-methylpyrrolidin-3-yl)sulfamoyl]urea sodium salt. General procedure B was followed using {[(1,2,3,5,6,7-hexahydro-s-indacen-4-yl)carbamoyl]amino}sulfonyl chloride and 1-methyl-N-(1-methylpyrrolidin-3-yl)pyrazol-4-amine. The crude product was purified by prep-HPLC (column: Agela Durashell C18 5 μm 150×25 mm; mobile phase: [water (10 mM NH$_4$HCO$_3$) -ACN]; B: 14-44%, 10 min) to give the title compound as a white solid. $^1$H NMR (400 MHz, MeOD) δ=7.71 (s, 1H), 7.49 (s, 1H), 6.92 (s, 1H), 4.98-4.90 (m, 1H), 3.87 (s, 3H), 3.42-3.34 (m, 2H), 3.05-2.98 (m, 2H), 2.86 (t, J=7 Hz, 4H), 2.79 (t, J=7 Hz, 4H), 2.67 (s, 3H), 2.40-2.25 (m, 1H), 2.11-1.96 (m, 5H). LC-MS (ESI): m/z: [M+H]$^+$=459.1

Example 25. 1-{[1-(difluoromethyl)-1H-pyrazol-4-yl](oxan-4-yl)sulfamoyl}-3-(1,2,3,5,6,7-hexahydro-s-indacen-4-yl urea sodium salt

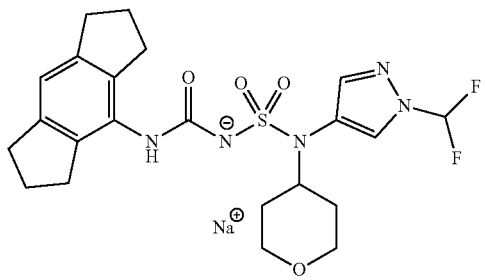 [SMILES: O=C([N-]S(=O)(=O)N(c1cnn(C(F)F)c1)C1CCOCC1)Nc1c2c(cc3c1CCC3)CCC2 ; [Na+]]

Step 1: 1-(difluoromethyl)-4-nitro-pyrazole. To a solution of 4-nitro-1H-pyrazole (2.0 g, 17.7 mmol) in DMF (20 ml) was added Cs$_2$CO$_3$ (5.76 g, 17.7 mmol), then the mixture was stirred at 120° C. for 5 min. (2-Chloro-2,2-difluoroacetyl)oxysodium (5.39 g, 35.4 mmol) was added to the mixture portionwise over 20 min. The mixture was stirred at 120° C. for 10 min. The solvent was removed under reduced pressure. The residue was diluted with water (30 ml) and extracted with EtOAc (3×20 ml). The combined organic layers were combined and washed with brine (10 ml), dried over Na$_2$SO$_4$ and concentrated to give a residue. The residue was purified by FCC (5-20% petroleum ether in ethyl acetate) to give the title compound as a light yellow oil (Y=17%). $^1$H NMR (400 MHz, chloroform-d) δ ppm 8.58 (s, 1H), 8.22 (s, 1H), 7.22 (t, J=60 Hz, 1H)

Step 2: 1-(difluoromethyl)pyrazol-4-amine. To a solution of 1-(difluoromethyl)-4-nitro-pyrazole (0.5 g, 3.07 mmol) in MeOH (10 ml) was added 10% Pd/C (100 mg) under N$_2$. The suspension was degassed and purged with H$_2$ several times. The mixture was stirred under H$_2$ (15 psi) at 25° C. for 2 hours. The reaction mixture was filtered and the filtrate concentrated under reduced pressure to give the title compound as a light brown oil, which was used directly without further purification (Y=98%). $^1$H NMR (400 MHz, chloroform-d) δ ppm 7.31 (s, 2H), 7.05 (t, J=60 Hz, 1H), 3.30-2.94 (br s., 2H).

Step 3: 1-(difluoromethyl)-N-tetrahydropyran-4-yl-pyrazol-4-amine trifluoroacetate. To a solution of 1-(difluoromethyl)pyrazol-4-amine (400 mg, 3.01 mmol) in DCM (6 ml) was added tetrahydropyran-4-one (276 μl, 3.01 mmol) and AcOH (0.70 ml, 12.24 mmol). The mixture was stirred at rt for 1 h. NaBH$_3$CN (378 mg, 6.02 mmol) was added and the mixture stirred at rt for 12 h. The solvent was removed under reduced pressure. The residue was purified by prep-HPLC (column: Acchrom C18ME 7 μm 250×50 mm; mobile phase: [water (0.1% TFA)-ACN]; B: 1-15%, 23 min) to give the title compound as a white solid (Y=40%). $^1$H NMR (400 MHz, CD3OD) δ ppm 8.37 (s, 1H), 7.89 (s, 1H), 7.54 (t, J=59 Hz, 1H), 4.03 (dd, J=4, 12 Hz, 2H), 3.65-3.59 (m, 1H), 3.48-3.38 (m, 2H), 2.02-1.92 (m, 2H), 1.72-1.66 (m, 2H).

Step 4: 1-{[1-(difluoromethyl)-1H-pyrazol-4-yl](oxan-4-yl)sulfamoyl}-3-(1,2,3,5,6,7-hexahydro-s-indacen-4-yl) urea sodium salt. General procedure B was followed using {[(1,2,3,5,6,7-hexahydro-s-indacen-4-yl)carbamoyl]amino}sulfonyl chloride and 1-(difluoromethyl)-N-tetrahydropyran-4-yl-pyrazol-4-amine trifluoroacetate. The crude product was purified by prep-HPLC (column: Agela Durashell C18 10 μm 250×50 mm; mobile phase: [water (10 mM NH$_4$HCO$_3$)-ACN]; B: 2-35%, 20 min) to give the title compound as a white solid (Y=4%). $^1$H NMR (400 MHz, methanol-d$_4$) δ ppm 8.08 (s, 1H), 7.68 (s, 1H), 7.58-7.29 (m, 1H), 6.91 (s, 1H), 4.28-4.25 (m, 1H), 3.95-3.87 (m, 2H), 3.51-3.45 (m, 2H), 2.90-2.72 (m, 8H), 2.10-1.98 (m, 4H), 1.96-1.89 (m, 2H), 1.44-1.36 (m, 2H). LC-MS (ESI): m/z: [M+H]$^+$=496.2

Example 26. 3-(1,2,3,5,6,7-hexahydro-s-indacen-4-yl)-1-[(oxan-4-yl)[1-(2,2,2-trifluoroethyl)-1H-pyrazol-4-yl]sulfamoyl]urea sodium salt

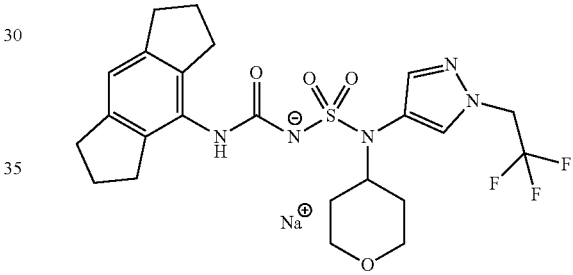

Step 1: 4-nitro-1-(2,2,2-trifluoroethyl)pyrazole. To a solution of 4-nitro-1H-pyrazole (5.0 g, 44.2 mmol) in DMF (50 ml) was added 1,1,1-trifluoro-2-iodo-ethane (6.51 ml, 66.3 mmol) and Cs$_2$CO$_3$ (17.3 g, 53.1 mmol), then the mixture was stirred at 60° C. for 18 h. The solvent was removed under reduced pressure. The residue was diluted with water (30 ml) and extracted with EtOAc (3×30 ml). The organic layers were combined and washed with brine (10 ml), dried over Na$_2$SO$_4$ and evaporated. The residue was purified by FCC (9-20% EtOAc in petroleum ether) to give the title compound as a light yellow solid (Y=30%). $^1$H NMR (400 MHz, chloroform-d) δ=8.30 (s, 1H), 8.16 (s, 1H), 4.77 (q, J=8 Hz, 2H).

Step 2: 1-(2,2,2-trifluoroethyl)pyrazol-4-amine. To a solution of 4-nitro-1-(2,2,2-trifluoroethyl)pyrazole (2.0 g, 10.25 mmol) in MeOH (30 ml) was added 10% Pd/C (200 mg) under N$_2$. The suspension was degassed under vacuum and purged with H$_2$ several times. The mixture was stirred under H$_2$ at rt for 3 h. The reaction mixture was filtered and the filtrate was concentrated under reduced pressure to give the title compound as a red-brown oil (Y=100%). $^1$H NMR (400 MHz, chloroform-d) δ=7.21 (s, 1H), 7.07 (s, 1H), 4.54 (q, J=9 Hz, 2H), 3.41 (s, 2H).

Step 3: N-tetrahydropyran-4-yl-1-(2,2,2-trifluoroethyl)pyrazol-4-amine trifluoroacetate. General procedure A was followed using 1-(2,2,2-trifluoroethyl)pyrazol-4-amine and tetrahydropyran-4-one. The crude was purified by prep- HPLC (column: C18, mobile phase: [water (0.1% TFA)-ACN]) to give the title compound as a white solid (Y=27%). ¹H NMR (400 MHz, methanol-d₄) δ=8.15 (s, 1H), 7.78 (s, 1H), 5.02 (q, J=9 Hz, 2H), 4.03 (dd, J=4, 12 Hz, 2H), 3.66-3.58 (m, 1H), 3.45-3.39 (m, 2H), 1.97-1.93 (m, 2H), 1.73-1.63 (m, 2H).

Step 4: 3-(1,2,3,5,6,7-hexahydro-s-indacen-4-yl)-1-[(oxan-4-yl)[1-(2,2,2-trifluoroethyl)-1H-pyrazol-4-yl]sulfamoyl]urea sodium salt. General procedure B was followed using {[(1,2,3,5,6,7-hexahydro-s-indacen-4-yl)carbamoyl]amino}sulfonyl chloride and N-tetrahydropyran-4-yl-1-(2,2,2-trifluoroethyl)pyrazol-4-amine trifluoroacetate. The crude product was purified by prep-HPLC (column: Agela Durashell 10 μm 250×50 mm; mobile phase: [water (10 mM ammonium carbonate)-ACN]; B: 5-35%, 20 min) to give the title compound as a white solid (Y=5%). ¹H NMR (400 MHz, methanol-d₄) δ=7.88 (s, 1H), 7.55 (s, 1H), 6.96 (s, 1H), 4.95 (q, J=9 Hz, 2H), 4.38-4.26 (m, 1H), 3.94-3.89 (m, 2H), 3.51-3.45 (m, 2H), 2.87 (t, J=7 Hz, 4H), 2.80 (t, J=7 Hz, 4H), 2.11-2.03 (m, 4H), 1.95-1.85 (m, 2H), 1.49-1.39 (m, 2H). LC-MS (ESI): m/z: [M+H]⁺=528.1

Example 27. 3-(1,2,3,5,6,7-hexahydro-s-indacen-4-yl)-1-{[1-(methoxymethyl)-1H-pyrazol-4-yl](oxan-4-yl)sulfamoyl}urea sodium salt

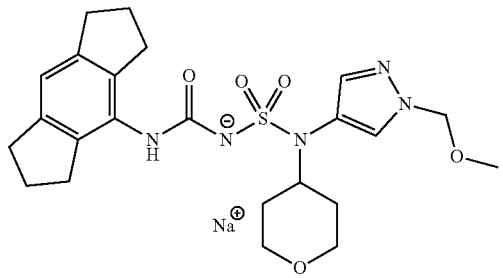 [SMILES: COCn1cc(N(C2CCOCC2)S(=O)(=O)[N-]C(=O)Nc2c3c(cc4c2CCC4)CCC3)cn1 ; [Na+]]

Step 1: 1-(methoxymethyl)-4-nitro-pyrazole. To a solution of 4-nitro-1H-pyrazole (5.0 g, 44.2 mmol) in THF (50 ml) was added sodium methoxide (2.87 g, 53.1 mmol) portionwise. The RM was stirred at rt for 30 min, then chloro(methoxy)methane (4.03 ml, 53.1 mmol) was added dropwise. The RM was stirred at rt for 15 h. The mixture was diluted with EtOAc (100 ml) and water (50 mL). The aqueous layer was separated and extracted with EtOAc (2×30 ml) and the combined organic layers washed with brine (20 ml) and dried over Na₂SO₄. The residue was purified by FCC (9-20% EtOAc in petroleum ether) to give the title compound as a white solid (Y=76%). ¹H NMR (400 MHz, chloroform-d) δ=8.32 (s, 1H), 8.13 (s, 1H), 5.43 (s, 2H), 3.42 (s, 3H).

Step 2: 1-(methoxymethyl) pyrazol-4-amine. To a solution of 1-(methoxymethyl)-4-nitro-pyrazole (3.0 g, 19.1 mmol) in MeOH (50 ml) was added 10% Pd/C (300 mg) under N₂. The suspension was degassed under vacuum and purged with H₂ several times. The mixture was stirred under H₂ (15 psi) atmosphere at rt for 3 h. The reaction mixture was filtered. The filtrate was concentrated under reduced pressure to give the title compound as a red-brown oil (Y=99%). ¹H NMR (400 MHz, chloroform-d) δ=7.20 (s, 1H), 7.13 (s, 1H), 5.23 (s, 2H), 3.27 (s, 3H), 2.98 (s, 2H).

Step 3: 1-(methoxymethyl)-N-tetrahydropyran-4-yl-pyrazol-4-amine acetate. General procedure A was followed using 1-(methoxymethyl) pyrazol-4-amine and tetrahydropyran-4-one. The crude was purified by prep-HPLC (column: Acchrom C18ME 7 μm 250×50 mm, mobile phase: [water (0.1% TFA)-ACN]; B: 1-30%, 23 min) to give the title compound as a white solid (Y=47%). ¹H NMR (400 MHz, methanol-d₄) δ=8.18 (s, 1H), 7.77 (s, 1H), 5.44 (s, 2H), 4.03 (dd, J=5, 12 Hz, 2H), 3.68-3.60 (m, 1H), 3.45-3.33 (m, 2H), 3.33 (s, 3H), 1.96 (dd, J=2, 12 Hz, 2H), 1.75-1.64 (m, 2H).

Step 4: 3-(1,2,3,5,6,7-hexahydro-s-indacen-4-yl)-1-{[1-(methoxymethyl)-1H-pyrazol-4-yl](oxan-4-yl)sulfamoyl}urea sodium salt. General procedure B was followed using {[(1,2,3,5,6,7-hexahydro-s-indacen-4-yl)carbamoyl]amino}sulfonyl chloride and 1-(methoxymethyl)-N-tetrahydropyran-4-yl-pyrazol-4-amine acetate. The crude product was purified by prep-HPLC (column: Agela Durashell 10 μm 250×50 mm; mobile phase: [water (10 mM ammonium carbonate)-ACN]; B: 2-35%, 20 min) to give the title compound as a white solid (Y=7%). ¹H NMR (400 MHz, methanol-d₄) δ=7.91 (s, 1H), 7.54 (s, 1H), 6.97 (s, 1H), 5.38 (s, 2H), 4.38-4.28 (m, 1H), 3.92 (dd, J=4, 11 Hz, 2H), 3.48 (t, J=11 Hz, 2H), 3.36-3.31 (m, 3H), 2.88 (t, J=7 Hz, 4H), 2.80 (t, J=7 Hz, 4H), 2.09-2.04 (m, 4H), 1.95-1.85 (m, 2H), 1.50-1.40 (m, 2H). LC-MS (ESI): m/z: [M+H]⁺=490.1

Example 28. 3-(1,2,3,5,6,7-hexahydro-s-indacen-4-yl)-1-{[1-(methoxymethyl)-1H-pyrazol-4-yl](1-methylpiperidin-4-yl)sulfamoyl}urea sodium salt

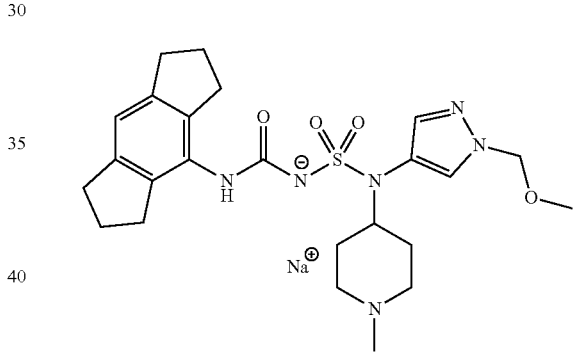

Step 1: N-[1-(methoxymethyl)pyrazol-4-yl]-1-methyl-piperidin-4-amine trifluoroacetate. General procedure A was followed using 1-(methoxymethyl) pyrazol-4-amine (for synthesis refer to Example 27) and 1-methylpiperidin-4-one. The crude was purified by prep-HPLC (column: Acchrom C18ME 7 μm 250×50 mm, mobile phase: [water (0.1% TFA)-ACN]; B: 1-20%, 23 min) to give the title compound as a white solid (Y=38%). ¹H NMR (400 MHz, methanol-d₄) δ=7.68 (s, 1H), 7.45 (s, 1H), 5.33 (s, 2H), 3.64-3.56 (m, 2H), 3.35-3.26 (m, 3H), 3.09 (t, J=13 Hz, 2H), 2.88 (s, 3H), 2.34-2.24 (m, 2H), 2.12-2.00 (br. s, 1H), 1.80-1.71 (m, 2H).

Step 2: 3-(1,2,3,5,6,7-hexahydro-s-indacen-4-yl)-1-{[1-(methoxymethyl)-1H-pyrazol-4-yl](1-methylpiperidin-4-yl)sulfamoyl}urea sodium salt. General procedure B was followed using {[(1,2,3,5,6,7-hexahydro-s-indacen-4-yl)carbamoyl]amino}sulfonyl chloride and N-[1-(methoxymethyl)pyrazol-4-yl]-1-methyl-piperidin-4-amine trifluoroacetate. The crude product was purified by prep-HPLC (column: Agela Durashell 10 μm 250×50 mm; mobile phase: [water (10 mM ammonium carbonate)-ACN]; B: 2-35%, 20 min) to give the title compound as a white solid (Y=13%). ¹H NMR (400 MHz, methanol-d₄) δ=7.89 (s, 1H), 7.54 (s, 1H), 6.95 (s, 1H), 5.36 (s, 2H), 4.32-4.25 (m, 1H), 3.33 (s, 3H), 3.18 (d, J=12 Hz, 2H), 2.87 (t, J=7 Hz, 4H), 2.80 (t, J=7 Hz, 4H), 2.72-2.64 (m, 2H), 2.51 (s, 3H), 2.14-2.03 (m, 6H), 1.61-1.51 (m, 2H). LC-MS (ESI): m/z: [M+H]⁺=503.2

Example 29. 3-(1,2,3,5,6,7-hexahydro-s-indacen-4-yl)-1-{[1-(2-methoxyethyl)-1H-pyrazol-4-yl](oxan-4-yl)sulfamoyl}urea sodium salt

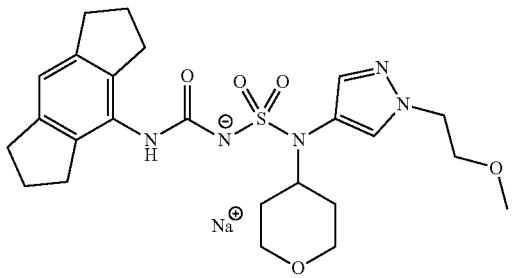 [SMILES: COCCn1cc(N(C2CCOCC2)S(=O)(=O)[N-]C(=O)Nc2c3c(cc4c2CCC4)CCC3)cn1 ; [Na+]]

Step 1: 1-(2-methoxyethyl)-4-nitro-pyrazole. To a solution of 4-nitro-1H-pyrazole (5.0 g, 44.2 mmol) in CH₃CN (100 ml) was added 1-bromo-2-methoxyethane (4.15 ml, 44.2 mmol, 4.15 mL) and K₂CO₃ (12.22 g, 88.4 mmol). The mixture was stirred at 80° C. for 12 h. The solvent was removed under reduced pressure. The residue was diluted with water (30 ml) and extracted with EtOAc (3×50 ml), the organic layers were combined and washed with brine (20 ml), dried over Na₂SO₄, and concentrated. The resulting residue was purified by FCC (10-25% petroleum ether in ethyl acetate) to give the title compound as a colourless oil (Y=79%). ¹H NMR (400 MHz, chloroform-d) δ ppm 8.24 (s, 1H), 8.08 (s, 1H), 4.32 (t, J=5 Hz, 2H), 3.75 (t, J=5 Hz, 2H), 3.36 (s, 3H).

Step 2: 1-(2-methoxyethyl) pyrazol-4-amine. To a solution of 1-(2-methoxyethyl)-4-nitro-pyrazole (3.0 g, 17.53 mmol) in MeOH (50 ml) was added 10% Pd/C (300 mg) under N₂. The suspension was degassed and purged with H₂ several times. The mixture was stirred under a H₂ atmosphere at 25° C. for 3 h. The reaction mixture was filtered. The filtrate was concentrated under reduced pressure to give the title compound as a red oil (Y=97%). ¹H NMR (400 MHz, chloroform-d) δ ppm 7.16 (s, 1H), 7.09 (s, 1H), 4.16 (t, J=5 Hz, 2H), 3.69 (t, J=5 Hz, 2H), 3.32 (s, 3H), 2.93-2.83 (br. s, 2H).

Step 3: 1-(2-methoxyethyl)-N-tetrahydropyran-4-yl-pyrazol-4-amine. General procedure A was followed using 1-(2-methoxyethyl) pyrazol-4-amine and tetrahydropyran-4-one to give the title compound as a pale brown oil (Y=50%). ¹H NMR (400 MHz, methanol-d₄) δ ppm 8.00 (s, 1H), 7.68 (s, 1H), 4.34 (t, J=5 Hz, 2H), 4.03 (dd, J=4, 12 Hz, 2H), 3.74 (t, J=5 Hz, 2H), 3.68-3.55 (m, 1H), 3.42 (t, J=12 Hz, 2H), 3.31 (s, 3H), 2.00-1.90 (m, 2H), 1.75-1.61 (m, 2H).

Step 4: 3-(1,2,3,5,6,7-hexahydro-s-indacen-4-yl)-1-{[1-(2-methoxyethyl)-1H-pyrazol-4-yl](oxan-4-yl)sulfamoyl}urea sodium salt. General procedure B was followed using {[(1,2,3,5,6,7-hexahydro-s-indacen-4-yl)carbamoyl]amino}sulfonyl chloride and 1-(2-methoxyethyl)-N-tetrahydropyran-4-yl-pyrazol-4-amine. The crude product was purified by prep-HPLC (column: Agela Durashell C18 10 μm 250×50 mm; mobile phase: [water (10 mM NH₄HCO₃)-ACN]; B: 3-33%, 20 min) to give the title compound as a white solid (Y=10%). ¹H NMR (400 MHz, methanol-d₄) δ ppm 7.67 (s, 1H), 7.45 (s, 1H), 6.90 (s, 1H), 4.33-4.19 (m, 3H), 3.90 (dd, J=4, 11 Hz, 2H), 3.71 (t, J=5 Hz, 2H), 3.47 (t, J=11 Hz, 2H), 3.29 (s, 3H), 2.92-2.75 (m, 8H), 2.11-2.00 (m, 4H), 1.91 (d, J=11 Hz, 2H), 1.44-1.41 (m, 2H). LC-MS (ESI): m/z: [M+H]⁺=504.2

Example 30. 1-{[1-(cyanomethyl)-1H-pyrazol-4-yl](oxan-4-yl)sulfamoyl}-3-(1,2,3,5,6,7-hexahydro-s-indacen-4-yl)urea sodium salt

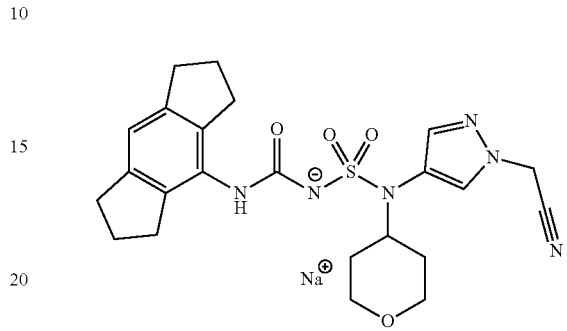

Step 1: 2-(4-nitropyrazol-1-yl)acetonitrile. To a solution of 4-nitro-1H-pyrazole (5.0 g, 44.2 mmol) in DMF (50 ml) was added 2-bromoacetonitrile (5.89 ml, 88.4 mmol) and K₂CO₃ (18.3 g, 133 mmol), then the mixture was stirred at 80° C. for 5 h. The solvent was removed under reduced pressure. The residue was diluted with water (30 ml) and extracted with EtOAc (3×50 ml). The combined organic layers were washed with brine (20 ml), dried over Na₂SO₄ and concentrated in vacuo. The residue was purified by FCC (9-25% EtOAc in petroleum ether) to give the title compound as a light brown solid (Y=89%). ¹H NMR (400 MHz, chloroform-d) δ ppm 8.36 (s, 1H), 8.17 (s, 1H), 5.15 (s, 2H).

Step 2: 2-(4-aminopyrazol-1-yl)acetonitrile. A mixture of 2-(4-nitropyrazol-1-yl)acetonitrile (6.0 g, 39.4 mmol), Fe (8.8 g, 158 mmol) and NH₄Cl (8.4 g, 158 mmol) in MeOH (120 ml) and H₂O (20 ml) was stirred at 80° C. for 4 h. The reaction mixture was filtered and the filtrate concentrated under reduced pressure. The residue was purified by FCC (5-17% MeOH in DCM) to give the title compound as a brown solid (Y=87%). ¹H NMR (400 MHz, chloroform-d) δ ppm 7.24 (s, 1H), 7.10 (s, 1H), 4.95 (s, 2H), 3.02 (s, 2H).

Step 3: 2-[4-(tetrahydropyran-4-ylamino)pyrazol-1-yl]acetonitrile. General procedure A was followed using 2-(4-aminopyrazol-1-yl)acetonitrile and tetrahydropyran-4-one to give the title compound as a colourless oil (Y=59%). ¹H NMR (400 MHz, methanol-d₄) δ ppm 7.31 (s, 1H), 7.27 (s, 1H), 5.16 (s, 2H), 3.99-3.92 (m, 2H), 3.52-3.42 (m, 2H), 3.15-3.06 (m, 1H), 1.98-1.91 (m, 2H), 1.50-1.37 (m, 2H).

Step 4: 1-{[1-(cyanomethyl)-1H-pyrazol-4-yl](oxan-4-yl)sulfamoyl}-3-(1,2,3,5,6,7-hexahydro-s-indacen-4-yl)urea sodium salt. General procedure B was followed using {[(1,2,3,5,6,7-hexahydro-s-indacen-4-yl)carbamoyl]amino}sulfonyl chloride and 2-[4-(tetrahydropyran-4-ylamino)pyrazol-1-yl]acetonitrile. The crude product was purified by prep-HPLC (column: Agela Durashell C18 10 μm 250×50 mm; mobile phase: [water (10 mM NH₄HCO₃)-ACN]; B: 3-33%, 20 min) to give the title compound as a white solid (Y=13%). ¹H NMR (400 MHz, methanol-d₄) δ ppm 7.90 (s, 1H), 7.56 (s, 1H), 6.99 (s, 1H), 5.34 (s, 2H), 4.42-4.27 (m, 1H), 3.96-3.88 (m, 2H), 3.48 (t, J=12 Hz, 2H), 2.88 (t, J=7 Hz, 4H), 2.80 (t, J=7 Hz, 4H), 2.13-2.04 (m, 4H), 1.92-1.85 (m, 2H), 1.53-1.38 (m, 2H). LC-MS (ESI): m/z: [M+H]⁺=485.2

Example 31. 1-{[1-(cyanomethyl)-1H-pyrazol-4-yl](1-methylpiperidin-4-yl)sulfamoyl}-3-(1,2,3,5,6,7-hexahydro-s-indacen-4-yl)urea sodium salt

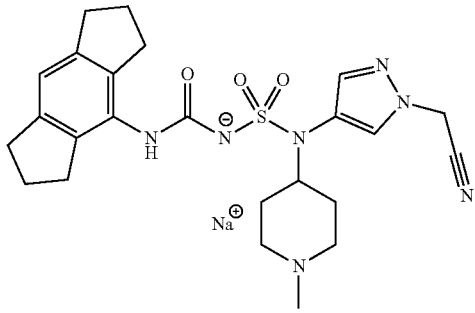 [SMILES: CN1CCC(N(c2cnn(CC#N)c2)S(=O)(=O)[N-]C(=O)Nc2c3c(cc4c2CCC4)CCC3)CC1 ; [Na+]]

Step 1: 2-[4-[(1-methyl-4-piperidyl)amino]pyrazol-1-yl]acetonitrile trifluoroacetate. General procedure A was followed using 2-(4-aminopyrazol-1-yl)acetonitrile (for synthesis refer to Example 30) and 1-methylpiperidin-4-one to give the title compound as a white solid (Y=48%). ¹H NMR (400 MHz, methanol-d₄) δ ppm 7.77 (s, 1H), 7.56 (s, 1H), 5.29 (s, 2H), 3.65-3.57 (m, 2H), 3.53-3.42 (m, 1H), 3.14-3.04 (m, 2H), 2.87 (s, 3H), 2.34-2.24 (m, 2H), 1.92-1.75 (m, 2H).

Step 2: 1-{[1-(cyanomethyl)-1H-pyrazol-4-yl](1-methylpiperidin-4-yl)sulfamoyl}-3-(1,2,3,5,6,7-hexahydro-s-indacen-4-yl)urea sodium salt. General procedure B was followed using {[(1,2,3,5,6,7-hexahydro-s-indacen-4-yl)carbamoyl]amino}sulfonyl chloride and 2-[4-[(1-methyl-4-piperidyl)amino]pyrazol-1-yl]acetonitrile trifluoroacetate. The crude product was purified by prep-HPLC (column: Agela Durashell C18 10 μm 250×50 mm; mobile phase: [water (10 mM NH₄HCO₃)-ACN]; B: 5-35%, 20 min) to give the title compound as a white solid (Y=8%). ¹H NMR (400 MHz, methanol-d₄) δ ppm 7.87 (s, 1H), 7.56 (s, 1H), 6.96 (s, 1H), 5.31 (s, 2H), 4.39-4.26 (m, 1H), 3.29-3.20 (m, 2H), 2.95-2.75 (m, 10H), 2.59 (s, 3H), 2.20-1.95 (m, 6H), 1.65-1.50 (m, 2H). LC-MS (ESI): m/z: [M+H]⁺=498.2

Example 32. 1-[(1-ethylpiperidin-4-yl)(1-methyl-1H-pyrazol-4-yl)sulfamoyl]-3-(1,2,3,5,6,7-hexahydro-s-indacen-4-yl)urea sodium salt

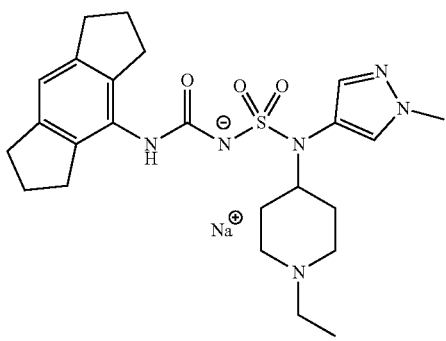 [SMILES: CCN1CCC(N(c2cnn(C)c2)S(=O)(=O)[N-]C(=O)Nc2c3c(cc4c2CCC4)CCC3)CC1 ; [Na+]]

Step 1: 1-ethyl-N-(1-methylpyrazol-4-yl) piperidin-4-amine trifluoroacetate. To a solution of 1-methylpyrazol-4-amine (1 g, 10.3 mmol) in DCM (10 ml) was added 1-ethylpiperidin-4-one (1.63 ml, 12.4 mmol) and AcOH (2.0 ml, 35 mmol). The mixture was stirred at rt for 1 h, after which NaBH₃CN (1.29 g, 20.6 mmol) was added. The mixture was stirred at rt for a further 12 h. The solvent was removed under reduced pressure. The residue was purified by prep HPLC (column: Acchrom C18ME 7 μm, 250×50 mm; mobile phase: [water (0.1% TFA)-ACN]; B: 1-30%, 23 min) to give the title compound as a yellow oil (Y=69%). ¹H NMR (400 MHz, methanol-d₄) δ ppm 7.87 (s, 1H), 7.59 (s, 1H), 3.91 (s, 3H), 3.72-3.59 (m, 3H), 3.22-3.16 (m, 2H), 3.08-2.98 (m, 2H), 2.35-2.27 (m, 2H), 2.01-1.90 (m, 2H), 1.34 (t, J=7 Hz, 3H).

Step 2: 1-[(1-ethylpiperidin-4-yl)(1-methyl-1H-pyrazol-4-yl)sulfamoyl]-3-(1,2,3,5,6,7-hexahydro-s-indacen-4-yl)urea sodium salt. General procedure B was followed using {[(1,2,3,5,6,7-hexahydro-s-indacen-4-yl)carbamoyl]amino}sulfonyl chloride and 1-ethyl-N-(1-methylpyrazol-4-yl) piperidin-4-amine trifluoroacetate. The crude product was purified by prep-HPLC (column: Waters Xbridge Prep OBD C18 150×40 10 μm; mobile phase: [water (10 mM NH₄HCO₃)-ACN]; B: 5-35%, 11 min) to give the title compound as a white solid (Y=3%). ¹H NMR (400 MHz, methanol-d₄) δ ppm 7.67 (s, 1H), 7.43 (s, 1H), 6.93 (s, 1H), 4.32-4.26 (m, 1H), 3.85 (s, 3H), 2.88-2.83 (m, 6H), 2.82-2.78 (m, 6H), 2.77-2.66 (m, 2H), 2.22-2.03 (m, 6H), 1.62-1.51 (m, 2H), 1.17 (t, J=7 Hz, 3H). LC-MS (ESI): m/z: [M+H]⁺=487.2

Example 33. 3-(1,2,3,5,6,7-hexahydro-s-indacen-4-yl)-1-[(1-methyl-1H-pyrazol-4-yl)[1-(propan-2-yl)piperidin-4-yl]sulfamoyl]urea sodium salt

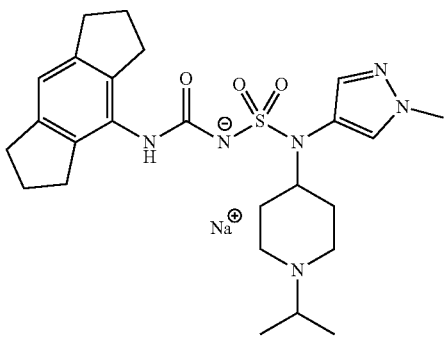 [SMILES: CC(C)N1CCC(N(c2cnn(C)c2)S(=O)(=O)[N-]C(=O)Nc2c3c(cc4c2CCC4)CCC3)CC1 ; [Na+]]

Step 1: 1-isopropyl-N-(1-methylpyrazol-4-yl) piperidin-4-amine trifluoroacetate. General procedure A was followed using 1-methylpyrazol-4-amine and 1-isopropylpiperidin-4-one. The crude was purified by prep-HPLC (column: Acchrom C18ME 7 μm 250×50 mm, mobile phase: [water (0.1% TFA)-ACN]; B: 1-20%, 23 min) to give the title compound as a pale brown oil (Y=36%). ¹H NMR (400 MHz, methanol-d₄) δ=7.93 (s, 1H), 7.63 (s, 1H), 3.92 (s, 3H), 3.70-3.53 (m, 4H), 3.17-3.09 (m, 2H), 2.37-2.29 (m, 2H), 2.06-1.96 (m, 2H), 1.35 (d, J=7 Hz, 6H).

Step 2: 3-(1,2,3,5,6,7-hexahydro-s-indacen-4-yl)-1-[(1-methyl-1H-pyrazol-4-yl)[1-(propan-2-yl)piperidin-4-yl]sulfamoyl]urea sodium salt. General procedure B was followed using {[(1,2,3,5,6,7-hexahydro-s-indacen-4-yl)carbamoyl]amino}sulfonyl chloride and 1-isopropyl-N-(1-methylpyrazol-4-yl) piperidin-4-amine trifluoroacetate. The crude product was purified by prep-HPLC (column: Agela Durashell 10 μm 250×50 mm; mobile phase: [water (10 mM ammonium carbonate)-ACN]; B: 2-35%, 20 min) to give the title compound as a white solid (Y=8%). ¹H NMR (400 MHz, methanol-d$_4$) δ=7.66 (s, 1H), 7.43 (s, 1H), 6.92 (s, 1H), 4.34-4.27 (m, 1H), 3.83 (s, 3H), 3.26-3.23 (m, 3H), 2.98-2.92 (m, 2H), 2.86 (t, J=7 Hz, 4H), 2.79 (t, J=7 Hz, 4H), 2.24-2.14 (m, 2H), 2.10-2.02 (m, 4H), 1.65-1.54 (m, 2H), 1.22 (d, J=7 Hz, 6H). LC-MS (ESI): m/z: [M+H]$^+$=501.2

Example 34. 1-{[1-(difluoromethyl)-1H-pyrazol-4-yl](1-methylpiperidin-4-yl)sulfamoyl}-3-(1,2,3,5,6,7-hexahydro-s-indacen-4-yl)urea sodium salt

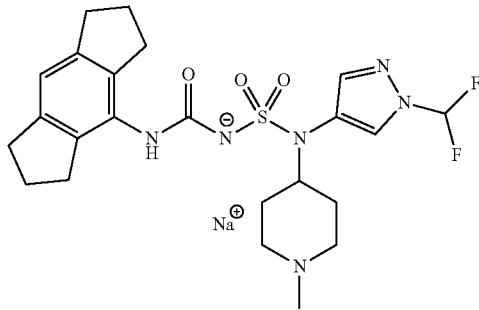 [SMILES: CN1CCC(N(c2cnn(C(F)F)c2)S(=O)(=O)[N-]C(=O)Nc2c3c(cc4c2CCC4)CCC3)CC1 ; [Na+]]

Step 1: 1-(difluoromethyl)-4-nitro-pyrazole. To a solution of 4-nitro-1H-pyrazole (9.0 g, 79.6 mmol) in DMF (90 ml) was added Cs$_2$CO$_3$ (25.9 g, 79.6 mmol). The mixture was stirred at 120° C. for 5 min then (2-chloro-2,2-difluoroacetyl)oxysodium (24.3 g, 159.2 mmol) was added to the mixture portionwise over 20 min. The mixture was stirred at 120° C. for 10 min. The solvent was removed under reduced pressure. The residue was diluted with water (50 ml) and extracted with EtOAc (3×60 ml). The combined organic layers were washed with brine (30 ml) and dried over Na$_2$SO$_4$. The residue was purified by FCC (5-20% petroleum ether in ethyl acetate) to give the title compound as a light yellow oil (Y=77%). $^1$H NMR (400 MHz, chloroform-d) δ ppm 8.59 (s, 1H), 8.21 (s, 1H), 7.27 (t, J=60 Hz, 1H).

Step 2: 1-(difluoromethyl)pyrazol-4-amine. To a solution of 1-(difluoromethyl)-4-nitro-pyrazole (3.0 g, 18.4 mmol) in MeOH (30 ml) was added 10% Pd/C (300 mg) under nitrogen. The suspension was degassed under vacuum and purged with H$_2$ several times. The mixture was stirred under a H$_2$ (15 psi) atmosphere at rt for 3 h. The mixture was filtered under reduced pressure, and the filtrate was distilled to give the title compound as a yellow oil (Y=88%). $^1$H NMR (400 MHz, chloroform-d) δ ppm 7.33 (s, 2H), 7.05 (t, J=60 Hz, 1H), 3.32-2.80 (br. s, 2H).

Step 3: N-[1-(difluoromethyl)pyrazol-4-yl]-1-methyl-piperidin-4-amine trifluoroacetate. General procedure A was followed using 1-(difluoromethyl)pyrazol-4-amine and 1-methylpiperidin-4-one. The residue was purified by prep-HPLC (column: Acchrom C18ME 7 µm 250×50 mm; mobile phase: [water (0.1% TFA)-ACN]; B: 1-20%, 23 min) to give the title compound as a white solid (Y=66%). $^1$H NMR (400 MHz, methanol-d$_4$) δ ppm 7.56-7.13 (m, 3H), 3.60-3.52 (m, 2H), 3.27-3.22 (m, 1H), 3.14-3.04 (m, 2H), 2.88 (s, 3H), 2.32-2.24 (m, 2H), 1.69-1.59 (m, 2H).

Step 4: 1-{[1-(difluoromethyl)-1H-pyrazol-4-yl](1-methylpiperidin-4-yl)sulfamoyl}-3-(1,2,3,5,6,7-hexahydro-s-indacen-4-yl)urea sodium salt. General procedure B was followed using {[(1,2,3,5,6,7-hexahydro-s-indacen-4-yl)carbamoyl]amino}sulfonyl chloride and N-[1-(difluoromethyl)pyrazol-4-yl]-1-methyl-piperidin-4-amine trifluoroacetate. The crude product was purified by prep-HPLC (column: Agela Durashell 10 µm 250×50 mm; mobile phase: [water (0.05% ammonium hydroxide v/v)-ACN]; B: 2-35%, 20 min) to give the title compound as a white solid (Y=4%). $^1$H NMR (400 MHz, D$_2$O) δ ppm 8.12 (s, 1H), 7.71 (s, 1H), 7.40 (t, J=60 Hz, 1H), 7.05 (s, 1H), 4.27-4.18 (m, 1H), 3.51-3.44 (m, 2H), 3.17-3.07 (m, 2H), 2.87-2.80 (m, 4H), 2.77 (s, 3H), 2.70-2.62 (m, 4H), 2.20-2.12 (m, 2H), 2.05-1.91 (m, 4H), 1.61-1.52 (m, 2H). LC-MS (ESI): m/z: [M+H]$^+$=509.2

Example 35. 1-{[1-(2,2-difluoroethyl)-1H-pyrazol-4-yl](oxan-4-yl)sulfamoyl}-3-(1,2,3,5,6,7-hexahydro-s-indacen-4-yl)urea sodium salt

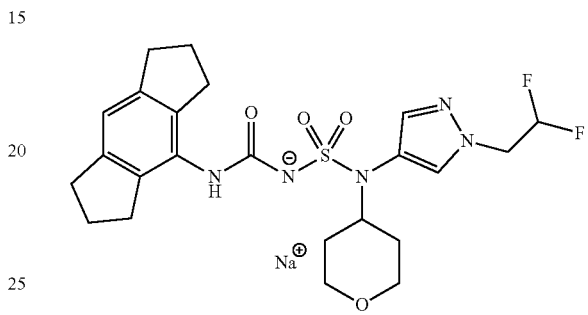

Step 1: 1-(2,2-difluoroethyl)-4-nitropyrazole. To a solution of 4-nitro-1H-pyrazole (5.0 g, 44.2 mmol) in THF (100 ml) was added 2,2-difluoroethanol (4.35 g, 53.1 mmol) and triphenylphosphine (17.40 g, 66.3 mmol) at rt under N$_2$ atmosphere. The RM was cooled to 0° C. and diisopropyl azodicarboxylate (10.3 ml, 53.1 mmol) was added. The RM was allowed to warm to rt and then stirred for 12 h. The solvent was removed under reduced pressure. The residue was purified by FCC (5-20% EtOAc in petroleum ether) to give the title compound as a white solid (Y=83%). $^1$H NMR (400 MHz, chloroform-d) δ ppm 8.25 (s, 1H), 8.14 (s, 1H), 6.31-5.99 (m, 1H), 4.57-4.49 (m, 2H).

Step 2: 1-(2,2-difluoroethyl)pyrazol-4-amine. To a solution of 1-(2,2-difluoroethyl)-4-nitropyrazole (2.0 g, 11.3 mmol) in MeOH (50 ml) was added 10% Pd/C (200 mg) under N$_2$. The suspension was degassed under vacuum and purged with H$_2$ several times. The mixture was then stirred under a H$_2$ (15 psi) atmosphere at rt for 3 h. The mixture was stirred under H$_2$ atmosphere (15 psi) at rt for 3 h. The reaction mixture was filtered and the filtrate concentrated under reduced pressure to give the title compound as a brown oil (Y=96%). $^1$H NMR (400 MHz, methanol-d$_4$) δ ppm 7.25 (s, 1H), 7.21 (s, 1H), 6.25-5.90 (m, 1H), 4.44-4.35 (m, 2H).

Step 3: 1-(2,2-difluoroethyl)-N-tetrahydropyran-4-yl-pyrazol-4-amine trifluoroacetate. To a solution of 1-(2,2-difluoroethyl)pyrazol-4-amine (900 mg, 6.12 mmol) in AcOH (2 ml) and DCM (10 ml) was added tetrahydropyran-4-one (562 µl, 6.12 mmol). The RM was stirred at rt for 30 min. NaBH$_3$CN (769 mg, 12.2 mmol) was added and the RM stirred at rt for a further 1.5 h. The mixture was evaporated under reduced pressure to give a residue. The residue was purified by prep-HPLC (column: Phenomenex Luna C18 250×50 mm 10 µm; mobile phase: [water (0.1% TFA)-ACN]; B: 0-20%, 20 min) to give the title compound as a yellow oil (Y=24%). $^1$H NMR (400 MHz, methanol-d$_4$) δ ppm 8.10 (s, 1H), 7.77 (d, J=1 Hz, 1H), 6.36-6.07 (m, 1H), 4.68-4.60 (m, 2H), 4.07-3.99 (m, 2H), 3.68-3.58 (m, 1H), 3.49-3.40 (m, 2H), 1.98-1.93 (m, 2H), 1.74-1.64 (m, 2H).

Step 4: 1-{[1-(2,2-difluoroethyl)-1H-pyrazol-4-yl](oxan-4-yl)sulfamoyl}-3-(1,2,3,5,6,7-hexahydro-s-indacen-4-yl)urea sodium salt. General procedure B was followed using {[(1,2,3,5,6,7-hexahydro-s-indacen-4-yl)carbamoyl]amino}sulfonyl chloride and 1-(2,2-difluoroethyl)-N-tetrahydropyran-4-yl-pyrazol-4-amine trifluoroacetate. The crude product was purified by prep-HPLC (column: Agela Durashell C18 250×50 mm 10 μm; mobile phase: [water (0.05% ammonia hydroxide v/v)-ACN]; B: 5-35%, 20 min) to give the title compound as a white solid (Y=5%). ¹H NMR (400 MHz, methanol-d₄) δ ppm 7.83 (s, 1H), 7.52 (s, 1H), 6.99 (s, 1H), 6.33-6.06 (m, 1H), 4.61-4.54 (m, 2H), 4.39-4.32 (m, 1H), 3.94-3.90 (m, 2H), 3.47 (t, J=12 Hz, 2H), 2.88 (t, J=7 Hz, 4H), 2.80 (t, J=7 Hz, 4H), 2.10-2.05 (m, 4H), 1.90-1.86 (m, 2H), 1.49-1.40 (m, 2H). LC-MS (ESI): m/z: [M+H]⁺=510.2

Example 36. 1-{[1-(2,2-difluoroethyl)-1H-pyrazol-4-yl](1-methylpiperidin-4-yl)sulfamoyl}-3-(1,2,3,5,6,7-hexahydro-s-indacen-4-yl)urea sodium salt

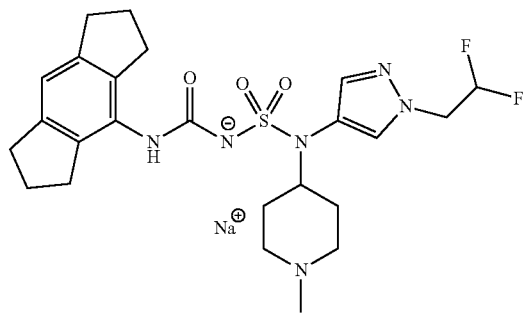 [SMILES: CN1CCC(N(c2cnn(CC(F)F)c2)S(=O)(=O)[N-]C(=O)Nc2c3c(cc4c2CCC4)CCC3)CC1 ; [Na+]]

Step 1: N-[1-(2,2-difluoroethyl) pyrazol-4-yl]-1-methyl-piperidin-4-amine trifluoroacetate. General procedure A was followed using 1-(2,2-difluoroethyl)pyrazol-4-amine (for synthesis refer to Example 35) and 1-methylpiperidin-4-one. The crude product was purified by prep-HPLC (column: Phenomenex Luna C18 250×50 mm 10 μm; mobile phase: [water (0.1% TFA)-ACN]; B: 0-20%, 20 min) to give the title compound as a yellow oil (Y=68%). ¹H NMR (400 MHz, methanol-d₄) δ ppm 7.94 (s, 1H), 7.66 (s, 1H), 6.18 (t, J=55 Hz, 1H), 4.62-4.58 (m, 2H), 3.65-3.57 (m, 3H), 3.15-3.05 (m, 2H), 2.88 (s, 3H), 2.36-2.25 (m, 2H), 1.99-1.90 (m, 2H).

Step 2: 1-{[1-(2,2-difluoroethyl)-1H-pyrazol-4-yl](1-methylpiperidin-4-yl)sulfamoyl}-3-(1,2,3,5,6,7-hexahydro-s-indacen-4-yl)urea sodium salt. General procedure B was followed using {[(1,2,3,5,6,7-hexahydro-s-indacen-4-yl)carbamoyl]amino}sulfonyl chloride and N-[1-(2,2-difluoroethyl)pyrazol-4-yl]-1-methyl-piperidin-4-amine trifluoroacetate. The crude product was purified by prep-HPLC (column: Nano-Micro Unisil 8-120 C18 Ultra Plus 250×50 mm; mobile phase: [water (10 mM NH₄HCO₃)-ACN]; B: 2-35%, 20 min) to give the title compound as a white solid (Y=12%). ¹H NMR (400 MHz, methanol-d₄) δ ppm 7.80 (s, 1H), 7.52 (s, 1H), 6.95 (s, 1H), 6.32-6.02 (m, 1H), 4.58-4.50 (m, 2H), 4.30-4.24 (m, 1H), 3.20-3.14 (m, 2H), 2.90-2.76 (m, 8H), 2.71-2.63 (m, 2H), 2.50 (s, 3H), 2.12-2.03 (m, 6H), 1.59-1.50 (m, 2H). LC-MS (ESI): m/z: [M+H]⁺=523.2

Example 37. 3-(1,2,3,5,6,7-hexahydro-s-indacen-4-yl)-1-[(1-methylpiperidin-4-yl)[1-(2,2,2-trifluoroethyl)-1H-pyrazol-4-yl]sulfamoyl]urea sodium salt

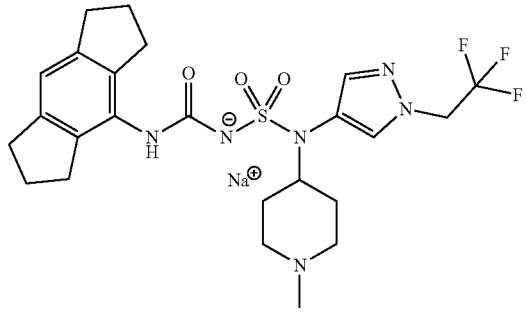 [SMILES: CN1CCC(N(c2cnn(CC(F)(F)F)c2)S(=O)(=O)[N-]C(=O)Nc2c3c(cc4c2CCC4)CCC3)CC1 ; [Na+]]

Step 1: 4-nitro-1-(2,2,2-trifluoroethyl)pyrazole. To a solution of 4-nitro-1H-pyrazole (5.0 g, 44.2 mmol) in DMF (50 ml) was added 1,1,1-trifluoro-2-iodoethane (6.51 ml, 66.3 mmol) and Cs₂CO₃ (17.29 g, 53.1 mmol). The RM was stirred at 60° C. for 18 h. The solvent was removed under reduced pressure. The residue was diluted with water (30 ml) and extracted with EtOAc (3×30 ml). The combined organics were washed with brine (10 ml), dried over Na₂SO₄ and filtered. The residue was purified by FCC (10-25% EtOAc in petroleum ether) to give the title compound as a light yellow solid (Y=30%). ¹H NMR (400 MHz, chloroform-d) δ ppm 8.30 (s, 1H), 8.16 (s, 1H), 4.81-4.73 (m, 2H).

Step 2: 1-(2,2,2-trifluoroethyl)pyrazol-4-amine. To a solution of 4-nitro-1-(2,2,2-trifluoroethyl)pyrazole (2.0 g, 10.25 mmol) in MeOH (30 ml) was added 10% Pd/C (200 mg) under N₂. The suspension was degassed under vacuum and purged with H₂ several times. The mixture was stirred under H₂ atmosphere at rt for 3 h. The reaction mixture was filtered. The filtrate was concentrated under reduced pressure to give the title compound as red brown oil (Y=100%). ¹H NMR (400 MHz, chloroform-d) δ ppm 7.21 (s, 1H), 7.07 (s, 1H), 4.59-4.50 (m, 2H), 3.41 (s, 2H).

Step 3: 1-methyl-N-[1-(2,2,2-trifluoroethyl)pyrazol-4-yl]piperidin-4-amine trifluoroacetate. General procedure A was followed using 1-(2,2,2-trifluoroethyl)pyrazol-4-amine and 1-methylpiperidin-4-one. The crude product was purified by prep-HPLC (column: Phenomenex Luna C18 250×50 mm 10 μm; mobile phase: [water (0.1% TFA)-ACN]; B: 0-20%, 20 min) to give the title compound as a white solid (Y=44%). ¹H NMR (400 MHz, methanol-d₄) δ ppm 7.43 (s, 1H), 7.33 (s, 1H), 4.82-4.78 (m, 2H), 3.57 (d, J=13 Hz, 2H), 3.27-3.21 (m, 1H), 3.08 (t, J=13 Hz, 2H), 2.87 (s, 3H), 2.26 (d, J=14 Hz, 2H), 1.71-1.61 (m, 2H).

Step 4: 3-(1,2,3,5,6,7-hexahydro-s-indacen-4-yl)-1-[(1-methylpiperidin-4-yl)[1-(2,2,2-trifluoroethyl)-1H-pyrazol-4-yl]sulfamoyl]urea sodium salt. General procedure B was followed using {[(1,2,3,5,6,7-hexahydro-s-indacen-4-yl)carbamoyl]amino}sulfonyl chloride and 1-methyl-N-[1-(2,2,2-trifluoroethyl)pyrazol-4-yl]piperidin-4-amine trifluoroacetate. The crude product was purified by prep-HPLC (column: Agela Durashell 10 μm 250×50 mm; mobile phase: [water (0.05% ammonium hydroxide v/v)-ACN]; B: 2-38%, 20 min) to give the title compound as a white solid (Y=6%). ¹H NMR (400 MHz, methanol-d₄) δ ppm 7.86 (s, 1H), 7.56 (s, 1H), 6.94 (s, 1H), 5.00-4.90 (m, 2H), 4.27-4.24 (m, 1H), 3.18-3.13 (m, 2H), 2.87 (t, J=7 Hz, 4H), 2.80 (t, J=7 Hz, 4H), 2.70-2.64 (m, 2H), 2.49 (s, 3H), 2.13-2.05 (m, 6H), 1.57-1.48 (m, 2H). LC-MS (ESI): m/z: [M+H]$^+$=541.2

Example 38. 3-(1,2,3,5,6,7-hexahydro-s-indacen-4-yl)-1-{[1-(2-methoxyethyl)-1H-pyrazol-4-yl](1-methylpiperidin-4-yl)sulfamoyl}urea sodium salt

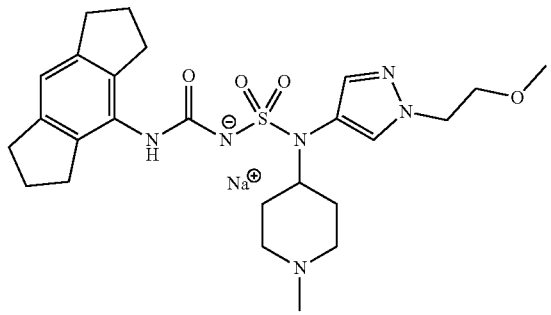 [SMILES: COCCn1cc(N(C2CCN(C)CC2)S(=O)(=O)[N-]C(=O)Nc2c3c(cc4c2CCC4)CCC3)cn1 ; [Na+]]

Step 1: N-[1-(2-methoxyethyl) pyrazol-4-yl]-1-methyl-piperidin-4-amine trifluoroacetate. General procedure A was followed using 1-(2-methoxyethyl)pyrazol-4-amine (for synthesis refer to Example 29) and 1-methylpiperidin-4-one. The crude product was purified by prep-HPLC (column: Phenomenex Luna C18 10 μm 250×50 mm; mobile phase: [water (0.1% TFA)-ACN]; B: 0-10%, 20 min) to give the title compound as a pale brown oil (Y=48%). $^1$H NMR (400 MHz, methanol-d$_4$) δ ppm 7.84 (s, 1H), 7.57 (s, 1H), 4.32-4.24 (m, 2H), 3.75-3.69 (m, 2H), 3.65-3.52 (m, 3H), 3.31 (s, 3H), 3.13-3.06 (m, 2H), 2.88 (s, 3H), 2.32-2.21 (d, 2H), 2.00-1.89 (m, 2H).

Step 2: 3-(1,2,3,5,6,7-hexahydro-s-indacen-4-yl)-1-{[1-(2-methoxyethyl)-1H-pyrazol-4-yl](1-methylpiperidin-4-yl)sulfamoyl}urea sodium salt. General procedure B was followed using {[(1,2,3,5,6,7-hexahydro-s-indacen-4-yl)carbamoyl]amino}sulfonyl chloride and N-[1-(2-methoxyethyl) pyrazol-4-yl]-1-methyl-piperidin-4-amine trifluoroacetate. The crude product was purified by prep-HPLC (column: Agela Durashell 10 μm 250×50 mm; mobile phase: [water (0.05% ammonium hydroxide v/v)-ACN]; B: 5-35%, 20 min) to give the title compound as a white solid (Y=3%). $^1$H NMR (400 MHz, methanol-d$_4$) δ ppm 7.72 (s, 1H), 7.46 (s, 1H), 6.95 (s, 1H), 4.27-4.23 (m, 3H), 3.71 (t, J=5 Hz, 2H), 3.30 (s, 3H), 3.18-3.10 (m, 2H), 2.87 (t, J=7 Hz, 4H), 2.81 (t, J=7 Hz, 4H), 2.67-2.60 (m, 2H), 2.47 (s, 3H), 2.10-2.03 (m, 6H), 1.59-1.50 (m, 2H). LC-MS (ESI): m/z: [M+H]$^+$=517.2

Example 39. 1-[(1-cyclopropyl-1H-pyrazol-4-yl)(1-methylpiperidin-4-yl)sulfamoyl]-3-(1,2,3,5,6,7-hexahydro-s-indacen-4-yl)urea sodium salt

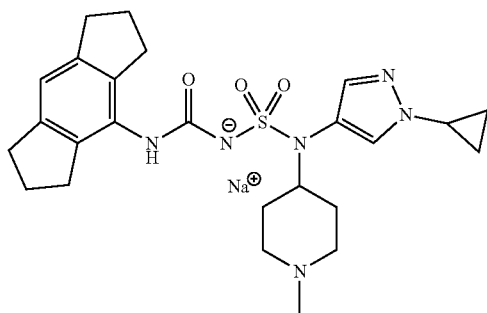 [SMILES: CN1CCC(N(c2cnn(C3CC3)c2)S(=O)(=O)[N-]C(=O)Nc2c3c(cc4c2CCC4)CCC3)CC1 ; [Na+]]

Step 1: 1-cyclopropyl-4-nitro-pyrazole. To a solution of 4-nitro-1H-pyrazole (2.0 g, 17.7 mmol) in DCE (50 ml) was added cyclopropylboronic acid (3.04 g, 35.4 mmol), 4-tert-butyl-2-(4-tert-butyl-2-pyridyl)pyridine (4.75 g, 17.7 mmol), Na$_2$CO$_3$ (3.75 g, 35.4 mmol) and CuSO$_4$ (2.71 ml, 17.7 mmol). The RM was heated at 70° C. for 16 h. The solvent was removed under reduced pressure. The residue was partitioned between EtOAc (50 ml) and H$_2$O (50 ml). The aqueous phase was extracted with EtOAc (3×50 ml) and the combined organics washed with brine (50 ml), dried over Na$_2$SO$_4$ and concentrated. The residue was purified by FCC (5-33% EtOAc in petroleum ether) to give the title compound as a white solid (Y=41%). $^1$H NMR (400 MHz, chloroform-d) δ=8.20 (d, J=4 Hz, 1H), 8.04 (d, J=4 Hz, 1H), 3.71-3.66 (m, 1H), 1.21-1.13 (m, 4H).

Step 2: 1-cyclopropylpyrazol-4-amine. To a solution of 1-cyclopropyl-4-nitro-pyrazole (700 mg, 4.57 mmol) in MeOH (20 ml) was added 10% Pd/C (100 mg) under nitrogen atmosphere. The suspension was degassed under vacuum and purged with H$_2$ several times. The mixture was then stirred at rt under H$_2$ (15 psi) for 3 h. The reaction mixture was filtered and the filtrate concentrated under reduced pressure to give the title compound as a purple oil (Y=99%). $^1$H NMR (400 MHz, chloroform-d) δ=7.13 (s, 1H), 7.07 (s, 1H), 3.51-3.45 (m, 1H), 2.86-2.75 (m, 2H), 1.08-1.04 (m, 2H), 0.97-0.92 (m, 2H).

Step 3: N-(1-cyclopropylpyrazol-4-yl)-1-methyl-piperidin-4-amine trifluoroacetate. General procedure A was followed using 1-cyclopropylpyrazol-4-amine and 1-methylpiperidin-4-one. The crude was purified by prep-HPLC (column: Agela Innoval ods-2 250×80 mm; mobile phase: [water (0.1% TFA)-ACN]; B: 0-9%, 20 min) to give the title compound as a white solid (Y=46%). $^1$H NMR (400 MHz, methanol-d$_4$) δ ppm 7.80 (s, 1H), 7.48 (s, 1H), 3.67-3.52 (m, 3H), 3.50-3.45 (m, 1H), 3.14-3.05 (m, 2H), 2.88 (s, 3H), 2.32-2.24 (m, 2H), 1.90-1.80 (m, 2H), 1.10-1.03 (m, 4H).

Step 4: 1-[(1-cyclopropyl-1H-pyrazol-4-yl)(1-methylpiperidin-4-yl)sulfamoyl]-3-(1,2,3,5,6,7-hexahydro-s-indacen-4-yl)urea sodium salt. General procedure B was followed using {[(1,2,3,5,6,7-hexahydro-s-indacen-4-yl)carbamoyl]amino}sulfonyl chloride and N-(1-cyclopropylpyrazol-4-yl)-1-methyl-piperidin-4-amine trifluoroacetate. The crude product was purified by prep-HPLC (column: Nano-Micro Unisil 8-120 C18 Ultra Plus 250×50 mm; mobile phase: [water (10 mM NH$_4$HCO$_3$)-ACN]; B: 5-35%, 20 min) to give the title compound as a white solid (Y=4%). $^1$H NMR (400 MHz, methanol-d$_4$) δ ppm 7.74 (s, 1H), 7.43 (s, 1H), 6.95 (s, 1H), 4.27-4.21 (m, 1H), 3.66-3.61 (m, 1H), 3.20-3.12 (m, 2H), 2.87 (t, J=7 Hz, 4H), 2.80 (t, J=7 Hz, 4H), 2.68-2.60 (m, 2H), 2.50 (s, 3H), 2.11-2.02 (m, 6H), 1.57-1.48 (m, 2H), 1.07-1.02 (m, 4H). LC-MS (ESI): m/z: [M+H]$^+$=499.2

Example 40. 3-(1,2,3,5,6,7-hexahydro-s-indacen-4-yl)-1-[(1-methylpiperidin-4-yl)(1H-pyrazol-4-yl)sulfamoyl]urea sodium salt

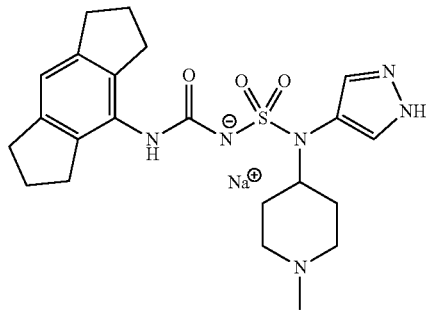 [SMILES: CN1CCC(N(c2cn[nH]c2)S(=O)(=O)[N-]C(=O)Nc2c3c(cc4c2CCC4)CCC3)CC1 ; [Na+]]

Step 1: 1-methyl-N-(1H-pyrazol-4-yl)piperidin-4-amine trifluoroacetate. General procedure A was followed using 1H-pyrazol-4-amine and 1-methylpiperidin-4-one. The crude product was purified by prep-HPLC (column: Acchrom C18ME 250×50 mm 7 μm; mobile phase: [water (0.1% TFA)-ACN]; 23 min) to give the title compound as a yellow solid (Y=34%). $^1$H NMR (400 MHz, methanol-$d_4$) δ ppm 7.82 (s, 2H), 3.51-3.45 (m, 1H), 3.18-3.01 (m, 2H), 2.88-2.75 (m, 5H), 2.42-2.15 (m, 2H), 2.10-1.85 (m, 2H).

Step 2: 3-(1,2,3,5,6,7-hexahydro-s-indacen-4-yl)-1-[(1-methylpiperidin-4-yl)(1H-pyrazol-4-yl)sulfamoyl]urea sodium salt. General procedure B was followed using {[(1,2,3,5,6,7-hexahydro-s-indacen-4-yl)carbamoyl]amino}sulfonyl chloride and 1-methyl-N-(1H-pyrazol-4-yl)piperidin-4-amine trifluoroacetate. The crude product was purified by prep-HPLC (column: Nano-Micro UniSil 5-100 C18 Ultra 100×250 mm 5 μm; mobile phase: [water (10 mM NH$_4$HCO$_3$)-ACN]; B: 5-35%, 20 min) to give the title compound as a white solid (Y=3%). $^1$H NMR (400 MHz, methanol-$d_4$) δ ppm 7.82-7.45 (br. s, 2H), 6.95 (s, 1H), 4.38-4.22 (m, 1H), 3.21-3.12 (m, 2H), 2.87 (t, J=7 Hz, 4H), 2.80 (t, J=7 Hz, 4H), 2.72-2.61 (m, 2H), 2.50 (s, 3H), 2.15-2.01 (m, 6H), 1.63-1.48 (m, 2H). LC-MS (ESI): m/z: [M+H]$^+$=459.2

Example 41. 3-(1,2,3,5,6,7-hexahydro-s-indacen-4-yl)-1-[(oxan-4-yl)[1-(oxetan-3-yl)-1H-pyrazol-4-yl]sulfamoyl]urea sodium salt

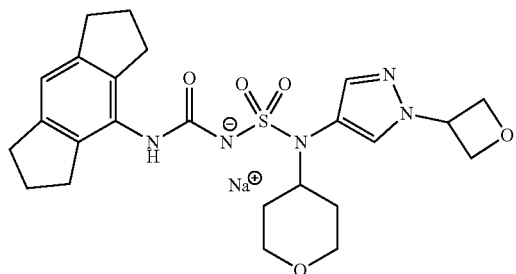 [SMILES: O=C([N-]S(=O)(=O)N(c1cnn(C2COC2)c1)C1CCOCC1)Nc1c2c(cc3c1CCC3)CCC2 ; [Na+]]

Step 1: 4-nitro-1-(oxetan-3-yl)pyrazole. To a solution of 4-nitro-1H-pyrazole (5.0 g, 44.2 mmol) in DMF (50 ml) was added 3-iodooxetane (8.14 g, 44.2 mmol) and Cs$_2$CO$_3$ (21.6 g, 66.3 mmol), then the mixture was stirred at 100° C. for 2 h. The solvent was removed under reduced pressure. The residue was diluted with water (30 ml) and extracted with EtOAc (3×50 ml). The combined organics were washed with brine (20 ml), dried over Na$_2$SO$_4$ and concentrated in vacuo. The resulting residue was purified by FCC (9-33% EtOAc in petroleum ether) to give the title compound as a yellow solid (Y=84%). $^1$H NMR (400 MHz, chloroform-d) δ ppm 8.32 (s, 1H), 8.18 (s, 1H), 5.55-5.41 (m, 1H), 5.14-5.01 (m, 4H).

Step 2: 1-(oxetan-3-yl)pyrazol-4-amine. To a solution of 4-nitro-1-(oxetan-3-yl)pyrazole (1.2 g, 7.09 mmol) in MeOH (20 ml) was added 10% Pd/C (300 mg) under N$_2$. The suspension was degassed under vacuum and purged with H$_2$ several times. The mixture was stirred under H$_2$ (15 psi) at rt for 3 h. The RM was filtered and the filtrate concentrated under reduced pressure to give the title compound as a purple solid (Y=99%). $^1$H NMR (400 MHz, methanol-$d_4$) δ ppm 7.36 (s, 1H), 7.25 (s, 1H), 5.44-5.34 (m, 1H), 5.03-4.92 (m, 4H), 3.31 (s, 2H).

Step 3: 1-(oxetan-3-yl)-N-tetrahydropyran-4-yl-pyrazol-4-amine. General procedure A was followed using 1-(oxetan-3-yl)pyrazol-4-amine and tetrahydropyran-4-one to give the title compound as a pale red oil (Y=76%). $^1$H NMR (400 MHz, methanol-$d_4$) δ ppm 7.40 (s, 1H), 7.28 (s, 1H), 5.47-5.35 (m, 1H), 5.07-4.89 (m, 4H), 3.98-3.94 (m, 2H), 3.49-3.42 (m, 2H), 3.15-3.04 (m, 1H), 1.98-1.90 (m, 2H), 1.50-1.36 (m, 2H).

Step 4: 3-(1,2,3,5,6,7-hexahydro-s-indacen-4-yl)-1-[(oxan-4-yl)[1-(oxetan-3-yl)-1H-pyrazol-4-yl]sulfamoyl]urea sodium salt. General procedure B was followed using {[(1,2,3,5,6,7-hexahydro-s-indacen-4-yl)carbamoyl]amino}sulfonyl chloride and 1-(oxetan-3-yl)-N-tetrahydropyran-4-yl-pyrazol-4-amine. The crude product was purified by prep-HPLC (column: Nano-Micro UniSil 5-100 C18 ULTRA 5 μm 100×250 mm; mobile phase: [water (10 mM NH$_4$HCO$_3$)-ACN]; B: 5-35%, 20 min) to give the title compound as a white solid (Y=7%). $^1$H NMR (400 MHz, methanol-$d_4$) δ ppm 7.88 (s, 1H), 7.58 (s, 1H), 6.99 (s, 1H), 5.62-5.50 (m, 1H), 5.03 (d, J=7 Hz, 4H), 4.40-4.28 (m, 1H), 3.96-3.86 (m, 2H), 3.52-3.42 (m, 2H), 2.88 (t, J=7 Hz, 4H), 2.80 (t, J=7 Hz, 4H), 2.14-2.02 (m, 4H), 1.93-1.84 (m, 2H), 1.48-1.45 (m, 2H). LC-MS (ESI): m/z: [M+H]$^+$=502.2

Example 42. 3-(1,2,3,5,6,7-hexahydro-s-indacen-4-yl)-1-[(1-methylpiperidin-4-yl)[1-(oxetan-3-yl)-1H-pyrazol-4-yl]sulfamoyl]urea sodium salt

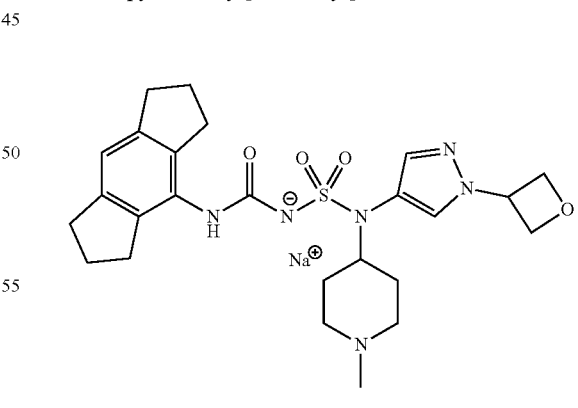

Step 1: 1-methyl-N-[1-(oxetan-3-yl)pyrazol-4-yl]piperidin-4-amine trifluoroacetate. General procedure A was followed using 1-(oxetan-3-yl)pyrazol-4-amine (for synthesis refer to Example 41) and 1-methylpiperidin-4-one. The crude product was purified by prep-HPLC (column: Phenomenex Luna 10 μm C18 250×50 mm; mobile phase: [water (0.1% TFA)-ACN]; B: 0-10%, 20 min) to give the title compound as a pale yellow solid (Y=52%). ¹H NMR (400 MHz, methanol-d₄) δ ppm 7.93 (s, 1H), 7.66 (s, 1H), 5.63-5.46 (m, 1H), 5.07-4.96 (m, 4H), 3.69-3.52 (m, 3H), 3.17-3.03 (m, 2H), 2.88 (s, 3H), 2.36-2.24 (m, 2H), 1.99-1.80 (m, 2H).

Step 2: 3-(1,2,3,5,6,7-hexahydro-s-indacen-4-yl)-1-[(1-methylpiperidin-4-yl)[1-(oxetan-3-yl)-1H-pyrazol-4-yl]sulfamoyl]urea sodium salt. General procedure B was followed using {[(1,2,3,5,6,7-hexahydro-s-indacen-4-yl)carbamoyl]amino}sulfonyl chloride and 1-methyl-N-[1-(oxetan-3-yl)pyrazol-4-yl]piperidin-4-amine trifluoroacetate. The crude product was purified by prep-HPLC (column: Nano-Micro UniSil 5-100 C18 ULTRA 5 μm 100×250 mm; mobile phase: [water (10 mM NH₄HCO₃)-ACN]; B: 3-32%, 20 min) to give the title compound as a white solid (Y=3%). ¹H NMR (400 MHz, methanol-d₄) δ ppm 7.86 (s, 1H), 7.57 (s, 1H), 6.95 (s, 1H), 5.59-5.47 (m, 1H), 5.07-4.95 (m, 4H), 4.34-4.19 (m, 1H), 3.20-3.12 (m, 2H), 2.87 (t, J=7 Hz, 4H), 2.80 (t, J=7 Hz, 4H), 2.73-2.55 (m, 2H), 2.50 (s, 3H), 2.14-2.01 (m, 6H), 1.65-1.45 (m, 2H). LC-MS (ESI): m/z: [M+H]⁺=515.2

Example 43. 1-({1-[2-(dimethylamino)ethyl]-1H-pyrazol-4-yl}(oxan-4-yl)sulfamoyl}-3-(1,2,3,5,6,7-hexahydro-s-indacen-4-yl)urea sodium salt

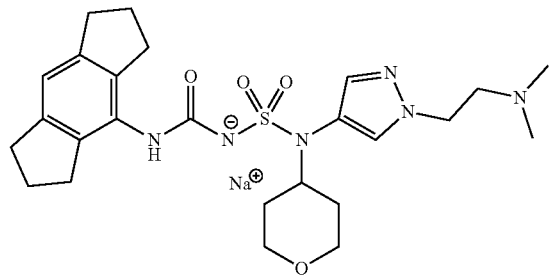 [SMILES: CN(C)CCn1cc(N(C2CCOCC2)S(=O)(=O)[N-]C(=O)Nc2c3c(cc4c2CCC4)CCC3)cn1 ; [Na+]]

Step 1: N,N-dimethyl-2-(4-nitropyrazol-1-yl)ethanamine. To a solution of 4-nitro-1H-pyrazole (3.0 g, 26.53 mmol) in DMF (40 ml) was added 2-chloro-N,N-dimethylethanamine hydrochloride (5.73 g, 39.80 mmol) and Cs₂CO₃ (12.97 g, 39.80 mmol). The RM was stirred at 90° C. for 3 h, then the solvent was concentrated under reduced pressure. The residue was partitioned between EtOAc (50 ml) and H₂O (50 ml). The aqueous phase was further extracted with EtOAc (3×50 ml) and the combined organics washed with brine (50 ml), dried oved Na₂SO₄ and concentrated under reduced pressure. The residue was purified by FCC (25-85% EtOAc in petroleum ether) to give the title compound as a white solid (Y=39%). ¹H NMR (400 MHz, chloroform-d) δ ppm 8.29 (s, 1H), 8.06 (s, 1H), 4.23 (t, J=6 Hz, 2H), 2.75 (t, J=6 Hz, 2H), 2.28 (s, 6H).

Step 2: 1-[2-(dimethylamino)ethyl]pyrazol-4-amine. To a solution of N,N-dimethyl-2-(4-nitropyrazol-1-yl)ethanamine (1.2 g, 6.51 mmol) in MeOH (20 ml) was added 10% Pd/C (100 mg) under N₂. The suspension was degassed under vacuum and purged with H₂ several times, then the mixture was stirred under a H₂ atmosphere at rt for 3 h. The reaction mixture was filtered and the solvent removed under reduced pressure to give the title compound as a purple oil (Y=100%). ¹H NMR (400 MHz, methanol-d₄) δ ppm 7.24 (s, 1H), 7.14 (s, 1H), 4.13 (t, J=7 Hz, 2H), 2.73 (t, J=7 Hz, 2H), 2.25 (s, 6H).

Step 3: 1-[2-(dimethylamino)ethyl]-N-tetrahydropyran-4-yl-pyrazol-4-amine. General procedure A was followed using 1-[2-(dimethylamino)ethyl]pyrazol-4-amine and tetrahydropyran-4-one to give the title compound as a colourless oil (Y=78%). ¹H NMR (400 MHz, methanol-d₄) δ ppm 7.35 (s, 1H), 7.26 (s, 1H), 4.43 (t, J=6 Hz, 2H), 3.99-3.92 (m, 2H), 3.57-3.52 (m, 2H), 3.51-3.43 (m, 2H), 3.15-3.05 (m, 1H), 2.87 (s, 6H), 1.97-1.91 (m, 2H), 1.53-1.35 (m, 2H).

Step 4: 1-({1-[2-(dimethylamino)ethyl]-1H-pyrazol-4-yl}(oxan-4-yl)sulfamoyl}-3-(1,2,3,5,6,7-hexahydro-s-indacen-4-yl)urea sodium salt. General procedure B was followed using {[(1,2,3,5,6,7-hexahydro-s-indacen-4-yl)carbamoyl]amino}sulfonyl chloride and 1-[2-(dimethylamino)ethyl]-N-tetrahydropyran-4-yl-pyrazol-4-amine. The crude product was purified by prep-HPLC (column: Agela Durashell 10 μm 250×50 mm; mobile phase: [water (10 mM NH₄HCO₃)-ACN]; B: 5-35%, 20 min) to give the title compound as a white solid (Y=3%). ¹H NMR (400 MHz, methanol-d₄) δ ppm 7.80 (s, 1H), 7.48 (s, 1H), 6.97 (s, 1H), 4.40-4.25 (m, 3H), 3.92 (dd, J=4, 11 Hz, 2H), 3.48 (t, J=11 Hz, 2H), 3.03 (t, J=6 Hz, 2H), 2.88 (t, J=7 Hz, 4H), 2.80 (t, J=7 Hz, 4H), 2.49 (s, 6H), 2.13-2.03 (m, 4H), 1.91-1.85 (m, 2H), 1.56-1.41 (m, 2H). LC-MS (ESI): m/z: [M+H]⁺=517.2

Example 44. 1-[(1-cyclobutyl-1H-pyrazol-4-yl)(1-methylpiperidin-4-yl)sulfamoyl]-3-(1,2,3,5,6,7-hexahydro-s-indacen-4-yl)urea sodium salt

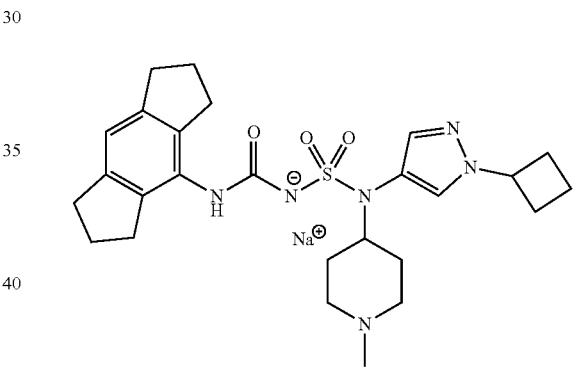

Step 1: 1-cyclobutyl-4-nitro-pyrazole. To a solution of 4-nitro-1H-pyrazole (5 g, 44.22 mmol) in DMF (50 ml) cooled to 0° C. was added NaH (60% in mineral oil (3.54 g, 88.44 mmol) and then bromocyclobutane (4.17 ml, 44.22 mmol). The RM was heated at 60° C. for 12 h. The solvent was removed under reduced pressure. The residue was diluted with water (30 ml) and extracted with EtOAc (3×50 ml). The combined organics were washed with brine (20 ml), dried over Na₂SO₄ and evaporated to dryness. The residue was purified by FCC (10-25% EtOAc in petroleum ether) to give the title compound as a colourless oil (Y=15%). ¹H NMR (400 MHz, chloroform-d) δ ppm 8.17 (s, 1H), 8.09 (s, 1H), 4.86-4.70 (m, 1H), 2.62-2.46 (m, 4H), 2.04-1.84 (m, 2H).

Step 2: 1-cyclobutylpyrazol-4-amine. To a solution of 1-cyclobutyl-4-nitro-pyrazole (1.0 g, 5.98 mmol) in MeOH (20 ml) was added 10% Pd/C (100 mg) under N₂. The suspension was degassed under vacuum and purged with H₂ several times. The mixture was stirred under H₂ (15 psi) at rt for 3 h. The reaction mixture was filtered through Celite and the filtrate was concentrated under reduced pressure to give the title compound as a brown oil (Y=97%). ¹H NMR (400 MHz, chloroform-d) δ ppm 7.17 (s, 1H), 7.08 (s, 1H), 4.71-4.55 (m, 1H), 2.88 (br, 2H), 2.53-2.39 (m, 4H), 1.90-1.74 (m, 2H).

Step 3: N-(1-cyclobutylpyrazol-4-yl)-1-methyl-piperidin-4-amine trifluoroacetate. General procedure A was followed using 1-cyclobutylpyrazol-4-amine and 1-methylpiperidin-4-one. The residue was purified by prep-HPLC (column: Phenomenex Luna C18 10 μm 250×50 mm; mobile phase: [water (0.1% TFA)-ACN]; B: 0-5%, 20 min) to give the title compound as a white solid (Y=79%). $^1$H NMR (400 MHz, methanol-$d_4$) δ ppm 7.75-7.57 (m, 1H), 7.50-7.38 (m, 1H), 4.79-4.73 (m, 1H), 3.64-3.56 (m, 2H), 3.47-3.38 (m, 1H), 3.13-3.02 (m, 2H), 2.88 (s, 3H), 2.55-2.41 (m, 4H), 2.31-2.25 (m, 2H), 1.92-1.69 (m, 4H).

Step 4: 1-[(1-cyclobutyl-1H-pyrazol-4-yl)(1-methylpiperidin-4-yl)sulfamoyl]-3-(1,2,3,5,6,7-hexahydro-s-indacen-4-yl)urea sodium salt. General procedure B was followed using {[(1,2,3,5,6,7-hexahydro-s-indacen-4-yl)carbamoyl]amino}sulfonyl chloride and N-(1-cyclobutylpyrazol-4-yl)-1-methyl-piperidin-4-amine trifluoroacetate. The crude product was purified by prep-HPLC (column: Nano-Micro Unisil 8-120 C18 Ultra Plus 250×50 mm; mobile phase: [water (10 mM $NH_4HCO_3$)-ACN]; B: 3-35%, 20 min) to give the title compound as a white solid (Y=5%). $^1$H NMR (400 MHz, methanol-$d_4$) δ ppm 7.78 (s, 1H), 7.48 (s, 1H), 6.95 (s, 1H), 4.84-4.73 (m, 1H), 4.31-4.18 (m, 1H), 3.19-3.11 (m, 2H), 2.87 (t, J=7 Hz, 4H), 2.80 (t, J=7 Hz, 4H), 2.63 (t, J=12 Hz, 2H), 2.55-2.41 (m, 7H), 2.13-2.02 (m, 6H), 1.93-1.83 (m, 2H), 1.61-1.50 (m, 2H). LC-MS (ESI): m/z: $[M+H]^+$=513.2

Example 45. 1-{[1-(2,2-difluoroethyl)piperidin-4-yl](1-methyl-1H-pyrazol-4-yl)sulfamoyl}-3-(1,2,3,5,6,7-hexahydro-s-indacen-4-yl)urea sodium salt

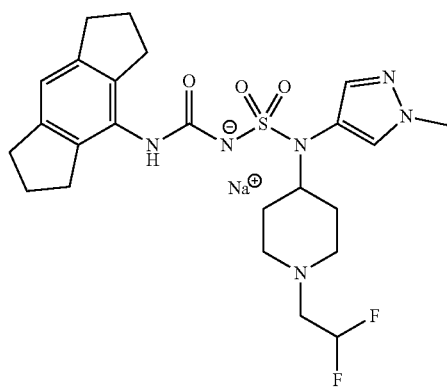 [SMILES: Cn1cc(N(C2CCN(CC(F)F)CC2)S(=O)(=O)[N-]C(=O)Nc2c3c(cc4c2CCC4)CCC3)cn1 ; [Na+]]

Step 1: tert-butyl 4-[(1-methylpyrazol-4-yl)amino]piperidine-1-carboxylate. General procedure A was followed using 1-methylpyrazol-4-amine and tert-butyl 4-oxopiperidine-1-carboxylate to give the title compound as a brown oil (Y=28%). $^1$H NMR (400 MHz, methanol-$d_4$) δ ppm 7.21 (s, 1H), 7.14 (s, 1H), 4.09-3.95 (m, 2H), 3.78 (s, 3H), 3.06-2.97 (m, 1H), 2.96-2.80 (m, 2H), 2.00-1.88 (m, 2H), 1.45 (s, 9H), 1.34-1.20 (m, 2H).

Step 2: N-(1-methylpyrazol-4-yl)piperidin-4-amine hydrochloride. A mixture of tert-butyl 4-[(1-methylpyrazol-4-yl)amino]piperidine-1-carboxylate (3.0 g, 10.70 mmol) and 4 M HCl in EtOAc (60 ml) was stirred at rt for 12 h. The resulting solid was collected by filtration to give the title compound as a pale red solid (Y=99%). $^1$H NMR (400 MHz, methanol-$d_4$) δ ppm 8.07 (s, 1H), 7.73 (s, 1H), 3.95 (s, 3H), 3.84-3.74 (m, 1H), 3.60-3.52 (m, 2H), 3.17-3.06 (m, 2H), 2.35-2.25 (m, 2H), 2.05-1.97 (m, 2H).

Step 3: 1-(2,2-difluoroethyl)-N-(1-methylpyrazol-4-yl)piperidin-4-amine trifluoroacetate. To a solution of N-(1-methylpyrazol-4-yl)piperidin-4-amine hydrochloride (1.20 g, 5.55 mmol) in DMF (10 ml) cooled to 0° C. was added 1,1-difluoro-2-iodo-ethane (440 μl, 4.99 mmol) and $K_2CO_3$ (1.15 g, 8.32 mmol). The mixture was stirred at rt for 2 h then concentrated under reduced pressure. The crude was purified by prep HPLC (column: Phenomenex Luna C18 10 μm, 250×50 mm; mobile phase: [water (0.1% TFA)-ACN]; B: 0-10%, 20 min) to give the title compound as a white solid (Y=35%). $^1$H NMR (400 MHz, methanol-$d_4$) δ ppm 7.75 (s, 1H), 7.43 (s, 1H), 6.39 (t, J=54 Hz, 1H), 3.82 (s, 3H), 3.51-3.18 (m, 5H), 2.98-2.62 (m, 2H), 2.12-1.92 (m, 2H), 1.65-1.55 (m, 2H).

Step 4: 1-{[1-(2,2-difluoroethyl)piperidin-4-yl](1-methyl-1H-pyrazol-4-yl)sulfamoyl}-3-(1,2,3,5,6,7-hexahydro-s-indacen-4-yl)urea sodium salt. General procedure B was followed using {[(1,2,3,5,6,7-hexahydro-s-indacen-4-yl)carbamoyl]amino}sulfonyl chloride and 1-(2,2-difluoroethyl)-N-(1-methylpyrazol-4-yl)piperidin-4-amine trifluoroacetate. The crude product was purified by prep-HPLC (column: Nano-Micro Unisil 8-120 C18 Ultra Plus 250×50 mm; mobile phase: [water (10 mM $NH_4HCO_3$)-ACN]; B: 3-33%, 20 min) to give the title compound as a white solid (Y=8%). $^1$H NMR (400 MHz, methanol-$d_4$) δ ppm 7.71 (s, 1H), 7.42 (s, 1H), 6.98 (s, 1H), 6.03-5.73 (m, 1H), 4.19-4.01 (m, 1H), 3.89 (s, 3H), 3.00-2.92 (m, 2H), 2.88 (t, J=7 Hz, 4H), 2.79 (t, J=7 Hz, 4H), 2.72-2.62 (m, 2H), 2.32 (t, J=12 Hz, 2H), 2.13-2.02 (m, 4H), 1.95-1.85 (m, 2H), 1.56-1.40 (m, 2H). LC-MS (ESI): m/z: $[M+H]^+$=523.2

Example 46. 3-(1,2,3,5,6,7-hexahydro-s-indacen-4-yl)-1-[(1-methyl-1H-pyrazol-4-yl)[2-(morpholin-4-yl)ethyl]sulfamoyl]urea sodium salt

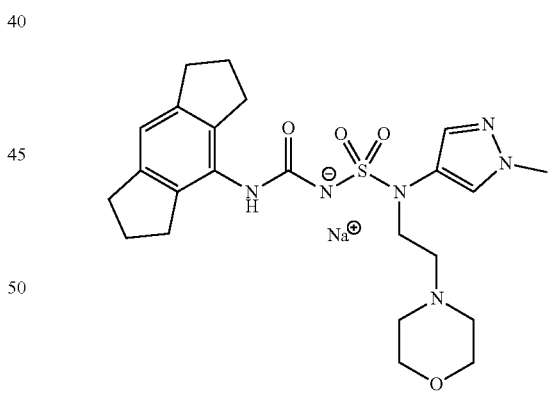

Step 1: 1-methyl-N-(2-morpholinoethyl)pyrazol-4-amine trifluoroacetate. To a solution of 1-methylpyrazol-4-amine (400 mg, 4.12 mmol) in DMF (10 ml) was added 4-(2-chloroethyl)morpholine (616 mg, 4.12 mmol), $Cs_2CO_3$ (2.01 g, 6.18 mmol) and KI (684 mg, 4.12 mmol). The RM was stirred at 100° C. for 12 h then the solvent was removed under reduced pressure. The residue was purified by prep-HPLC (column: Phenomenex Luna C18 10 μm 250×50 mm; mobile phase: [water (0.1% TFA)-ACN]; B: 0-4%, 20 min) to give the title compound as a brown oil (Y=13%). $^1$H NMR (400 MHz, methanol-$d_4$) δ ppm 7.30 (s, 1H), 7.21 (s, 1H), 3.95-3.90 (m, 4H), 3.80 (s, 3H), 3.40-3.33 (m, 8H).

Step 2: 3-(1,2,3,5,6,7-hexahydro-s-indacen-4-yl)-1-[(1-methyl-1H-pyrazol-4-yl)[2-(morpholin-4-yl)ethyl]sulfamoyl]urea sodium salt. General procedure B was followed using {[(1,2,3,5,6,7-hexahydro-s-indacen-4-yl)carbamoyl]amino}sulfonyl chloride and 1-methyl-N-(2-morpholinoethyl)pyrazol-4-amine trifluoroacetate. The crude product was purified by prep-HPLC (column: Agela Durashell 10 μm 250×50 mm; mobile phase: [water (10 mM NH$_4$HCO$_3$)-ACN]; B: 2-32%, 20 min) to give the title compound as a white solid (Y=7%). $^1$H NMR (400 MHz, methanol-d$_4$) δ ppm 7.74 (s, 1H), 7.55 (s, 1H), 6.95 (s, 1H), 3.99-3.92 (m, 2H), 3.92-3.83 (m, 7H), 3.27-3.20 (br. s, 4H), 3.12-3.06 (m, 2H), 2.88 (t, J=7 Hz, 4H), 2.82 (t, J=7 Hz, 4H), 2.14-2.02 (m, 4H). LC-MS (ESI): m/z: [M+H]$^+$=489.2

Example 47. 3-(1,2,3,5,6,7-hexahydro-s-indacen-4-yl)-1-[(1-methyl-1H-pyrazol-4-yl)(1-methyl-2-oxopiperidin-4-yl)sulfamoyl]urea sodium salt

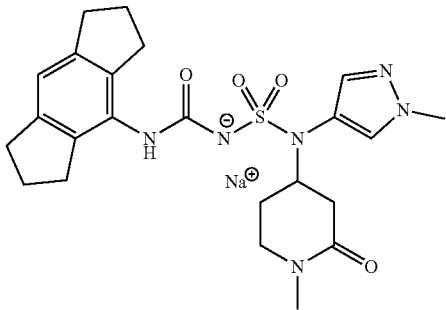 [SMILES: CN1CCC(N(c2cnn(C)c2)S(=O)(=O)[N-]C(=O)Nc2c3c(cc4c2CCC4)CCC3)CC1=O ; [Na+]]

Step 1: 1-methyl-4-[(1-methylpyrazol-4-yl)amino]piperidin-2-one trifluoroacetate. General procedure A was followed using 1-methylpyrazol-4-amine and 1-methylpiperidine-2,4-dione. The crude was purified by prep-HPLC (column: Phenomenex Luna C18 10 μm 250×50 mm; mobile phase: [water (0.1% TFA)-ACN]; B: 0-10%, 20 min) to give the title compound as a pale yellow oil (Y=47%). $^1$H NMR (400 MHz, methanol-d$_4$) δ ppm 7.94 (s, 1H), 7.63 (s, 1H), 3.94 (s, 3H), 3.91-3.81 (m, 1H), 3.51-3.38 (m, 2H), 2.94 (s, 3H), 2.82-2.73 (m, 1H), 2.49-2.40 (m, 1H), 2.33-2.23 (m, 1H), 2.01-1.88 (m, 1H).

Step 2: 3-(1,2,3,5,6,7-hexahydro-s-indacen-4-yl)-1-[(1-methyl-1H-pyrazol-4-yl)(1-methyl-2-oxopiperidin-4-yl)sulfamoyl]urea sodium salt. General procedure B was followed using {[(1,2,3,5,6,7-hexahydro-s-indacen-4-yl)carbamoyl]amino}sulfonyl chloride and 1-methyl-4-[(1-methylpyrazol-4-yl)amino]piperidin-2-one trifluoroacetate. The crude product was purified by prep-HPLC (column: Nano-Micro Unisil 8-120 C18 Ultra Plus 250×50 mm; mobile phase: [water (10 mM NH$_4$HCO$_3$)-ACN]; B: 5-35%, 20 min) to give the title compound as a white solid (Y=13%). $^1$H NMR (400 MHz, methanol-d$_4$) δ ppm 7.77 (s, 1H), 7.47 (s, 1H), 6.99 (s, 1H), 4.69-4.55 (m, 1H), 3.90 (s, 3H), 3.45-3.40 (m, 1H), 2.92-2.79 (m, 11H), 2.74-2.66 (m, 1H), 2.28-2.16 (m, 2H), 2.14-2.01 (m, 5H), 1.70-1.55 (m, 1H). LC-MS (ESI): m/z: [M+H]$^+$=487.1

Example 48. 3-(1,2,3,5,6,7-hexahydro-s-indacen-4-yl)-1-[(oxan-4-yl)(1H-pyrazol-4-yl)sulfamoyl]urea sodium salt

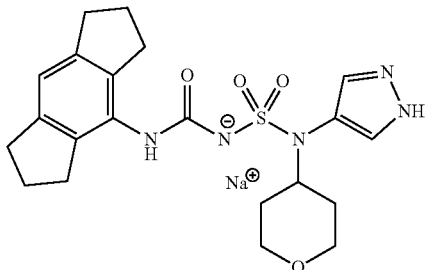

Step 1: N-tetrahydropyran-4-yl-1H-pyrazol-4-amine trifluoroacetate. General procedure A was followed using 1H-pyrazol-4-amine and tetrahydropyran-4-one. The crude was purified by prep-HPLC (column: Phenomenex Luna C18 10 μm 250×50 mm; mobile phase: [water (0.1% TFA)-ACN]; B: 0-10%, 20 min) to give the title compound as a white solid (Y=53%). $^1$H NMR (400 MHz, methanol-d$_4$) δ ppm 7.89 (s, 2H), 4.03 (dd, J=4, 12 Hz, 2H), 3.68-3.58 (m, 1H), 3.46-3.38 (m, 2H), 2.00-1.91 (m, 2H), 1.76-1.62 (m, 2H).

Step 2: 3-(1,2,3,5,6,7-hexahydro-s-indacen-4-yl)-1-[(oxan-4-yl)(1H-pyrazol-4-yl)sulfamoyl]urea sodium salt. General procedure B was followed using {[(1,2,3,5,6,7-hexahydro-s-indacen-4-yl)carbamoyl]amino}sulfonyl chloride and N-tetrahydropyran-4-yl-1H-pyrazol-4-amine trifluoroacetate. The crude product was purified by prep-HPLC (column: Agela Durashell 10 μm 250×50 mm; mobile phase: [water (10 mM NH$_4$HCO$_3$)-ACN]; B: 2-32%, 20 min) to give the title compound as a white solid (Y=13%). $^1$H NMR (400 MHz, methanol-d$_4$) δ ppm 7.75 (s, 1H), 7.52 (s, 1H), 6.98 (s, 1H), 4.44-4.32 (m, 1H), 3.91 (dd, J=4, 12 Hz, 2H), 3.48 (t, J=11 Hz, 2H), 2.88 (t, J=7 Hz, 4H), 2.80 (t, J=7 Hz, 4H), 2.15-2.02 (m, 4H), 1.94-1.85 (m, 2H), 1.51-1.38 (m, 2H). LC-MS (ESI): m/z: [M+H]$^+$=446.2

Example 49. 3-[3,5-bis(propan-2-yl)phenyl]-1-[(1-methyl-1H-pyrazol-4-yl)(1-methylpiperidin-4-yl)sulfamoyl]urea sodium salt

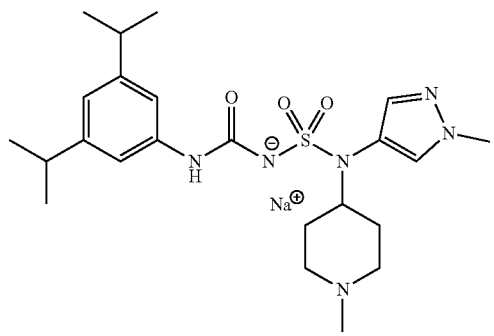 [SMILES: CC(C)c1cc(NC(=O)[N-]S(=O)(=O)N(c2cnn(C)c2)C2CCN(C)CC2)cc(C(C)C)c1 ; [Na+]]

Step 1: 3,5-diisopropenylaniline. To a solution of 3,5-dibromoaniline (5.0 g, 19.9 mmol) in dioxane (50 ml) and H$_2$O (5 ml) was added 2-isopropenyl-4,4,5,5-tetramethyl-1,3,2-dioxaborolane (10.19 ml, 53.8 mmol) and Pd(dppf)Cl$_2$ (729 mg, 1.00 mmol) and Cs$_2$CO$_3$ (19.48 g, 59.8 mmol) at rt under N$_2$. The reaction was stirred at 100° C. for 12 h under N$_2$. The solution was concentrated in vacuo and the resulting residue was poured into water (50 ml) and stirred for 0.5 h. The aqueous phase was extracted with ethyl acetate (3×100 ml). The combined organic phase was concentrated in vacuo. The crude product was purified by FCC (17% EtOAc in petroleum ether) to give the title compound as a yellow oil (Y=78%). $^1$H NMR (400 MHz, DMSO-d$_6$) δ ppm 6.76 (s, 1H), 6.64 (s, 2H), 5.23 (s, 2H), 5.10 (s, 2H), 5.01 (s, 2H), 2.06 (s, 6H).

Step 2: 3,5-diisopropylaniline. To a solution of 3,5-diisopropenylaniline (1.0 g, 5.77 mmol) in MeOH (10 ml) was added 10% Pd/C (200 mg) at rt under N$_2$. The suspension was degassed under vacuum and purged with H$_2$ several times. The mixture was then stirred under H$_2$ (15 psi) at rt for 3 h. The RM was filtered and the solid was washed with MeOH (100 ml). The filtrate was concentrated in vacuo. The crude was purified by FCC (17% EtOAc in petroleum ether) to give the title compound as an oil (Y=44%). $^1$H NMR (400 MHz, DMSO-d$_6$) δ ppm 6.25 (s, 3H), 4.86 (s, 2H), 2.70-2.62 (m, 2H), 1.13 (d, J=7 Hz, 12H).

Step 3: N-[(3,5-diisopropylphenyl)carbamoyl]sulfamoyl chloride. To a solution of N-(oxomethylene)sulfamoyl chloride (50 μl, 0.58 mmol) in isopropyl ether (1 ml) cooled to −15° C. was added a solution of 3,5-diisopropylaniline (103 mg, 0.58 mmol) in isopropyl ether (1 ml). The mixture was stirred at −15° C. for 0.5 h to give the title compound as a solution in isopropyl ether (2 ml). The mixture was used for the next step directly (Y=100%). LC-MS in MeOH (ESI): m/z: [M+MeOH+H]$^+$=315.3

Step 4: 3-[3,5-bis(propan-2-yl)phenyl]-1-[(1-methyl-1H-pyrazol-4-yl)(1-methylpiperidin-4-yl)sulfamoyl]urea sodium salt. General procedure B was followed using N-[(3,5-diisopropylphenyl)carbamoyl]sulfamoyl chloride and 1-methyl-N-(1-methylpyrazol-4-yl)piperidin-4-amine (for synthesis refer to Example 2). The crude product was purified by prep-HPLC (column: Agela Durashell 10 μm 250×50 mm; mobile phase: [water (10 mM NH$_4$HCO$_3$)-ACN]; B: 2-32%, 20 min) to give the title compound as a white solid (Y=10%). $^1$H NMR (400 MHz, methanol-d$_4$) δ ppm 7.68 (s, 1H), 7.44 (s, 1H), 7.11 (s, 2H), 6.78 (s, 1H), 4.45-4.27 (m, 1H), 3.82 (s, 3H), 3.30-3.26 (m, 2H), 2.95-2.76 (m, 4H), 2.63 (s, 3H), 2.20-2.12 (m, 2H), 1.66-1.51 (m, 2H), 1.23 (d, J=7 Hz, 12H). LC-MS (ESI): m/z: [M+H]$^+$=477.3

Example 50. 1-[(1-ethylpyrrolidin-3-yl)(1-methyl-1H-pyrazol-4-yl)sulfamoyl]-3-(1,2,3,5,6,7-hexahydro-s-indacen-4-yl)urea sodium salt

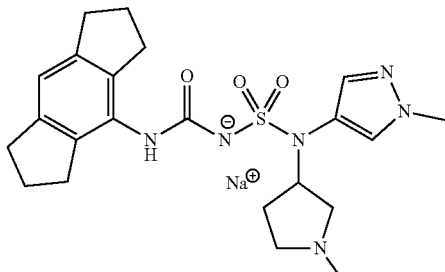

Step 1: tert-butyl 3-[(1-methylpyrazol-4-yl)amino]pyrrolidine-1-carboxylate. General procedure A was followed using 1-methylpyrazol-4-amine and tert-butyl 3-oxopyrrolidine-1-carboxylate to give the title compound as a yellow oil (Y=73%). $^1$H NMR (400 MHz, DMSO-d$_6$) δ ppm 7.70 (s, 1H), 7.42 (s, 1H), 5.29-5.21 (m, 1H), 3.88 (s, 3H), 3.80-3.69 (m, 1H), 3.48-3.40 (m, 1H), 3.35-3.22 (m, 2H), 3.07-3.01 (m, 1H), 1.81-1.75 (m, 2H), 1.39 (s, 9H).

Step 2: 1-methyl-N-pyrrolidin-3-yl-pyrazol-4-amine hydrochloride. To a solution of tert-butyl 3-[(1-methylpyrazol-4-yl)amino]pyrrolidine-1-carboxylate (5.0 g, 18.77 mmol) was added 4 M HCl in EtOAc (51.6 ml). The RM was stirred at rt for 1 h. The solution was filtered and the resulting solid dried to give the title compound as a white solid (Y=100%). $^1$H NMR (400 MHz, methanol-d$_4$) δ=8.05 (s, 1H), 7.82 (s, 1H), 4.05 (s, 3H), 3.69-3.67 (m, 1H), 3.59-3.54 (m, 2H), 3.44-3.40 (m, 2H), 2.45-2.34 (m, 2H).

Step 3: N-(1-ethylpyrrolidin-3-yl)-1-methyl-pyrazol-4-amine trifluoroacetate. General procedure A was followed using 1-methyl-N-pyrrolidin-3-yl-pyrazol-4-amine hydrochloride and acetaldehyde. The crude was purified by prep-HPLC (column: Phenomenex Luna C18 10 μm 250×50 mm; mobile phase: [water (0.1% TFA)-ACN]; B: 1-25%, 20 min) to give the title compound as a white solid (Y=24%). $^1$H NMR (400 MHz, DMSO-d$_6$) δ=9.91 (s, 1H), 7.77 (s, 1H), 7.52 (s, 1H), 3.88 (s, 3H), 3.87-3.84 (m, 1H), 3.69-3.60 (m, 1H), 3.20-3.09 (m, 4H), 2.89-2.84 (m, 1H), 2.43-2.40 (m, 1H), 2.22-2.10 (m, 1H), 1.83-1.80 (m, 1H), 1.20 (t, J=7 Hz, 3H).

Step 4: 1-[(1-ethylpyrrolidin-3-yl)(1-methyl-1H-pyrazol-4-yl)sulfamoyl]-3-(1,2,3,5,6,7-hexahydro-s-indacen-4-yl)urea sodium salt. General procedure B was followed using {[(1,2,3,5,6,7-hexahydro-s-indacen-4-yl)carbamoyl]amino}sulfonyl chloride and N-(1-ethylpyrrolidin-3-yl)-1-methyl-pyrazol-4-amine trifluoroacetate. The crude product was purified by prep-HPLC (column: Nano-Micro Unisil 8-120 C18 Ultra Plus 250×50 mm; mobile phase: [water (10 mM NH$_4$HCO$_3$)-ACN]; B: 3-33%, 20 min) to give the title compound as a white solid (Y=3%). $^1$H NMR (400 MHz, methanol-d$_4$) δ ppm 7.73 (s, 1H), 7.50 (s, 1H), 6.94 (s, 1H), 5.02-4.97 (m, 1H), 3.87 (s, 3H), 3.65-3.51 (m, 1H), 3.21-2.99 (m, 5H), 2.89-2.78 (m, 8H), 2.40-2.25 (m, 1H), 2.10-1.94 (m, 5H), 1.24 (t, J=7 Hz, 3H). LC-MS (ESI): m/z: [M+H]$^+$=473.2

Example 51. 3-(1,2,3,5,6,7-hexahydro-s-indacen-4-yl)-1-[(1-methyl-1H-pyrazol-4-yl)[1-(propan-2-yl)pyrrolidin-3-yl]sulfamoyl]urea sodium salt

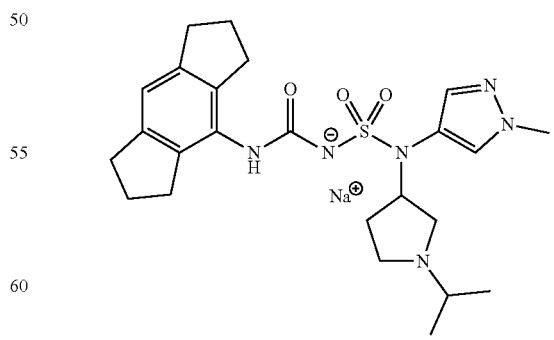

Step 1: N-(1-isopropylpyrrolidin-3-yl)-1-methyl-pyrazol-4-amine trifluoroacetate. General procedure A was followed using 1-methyl-N-pyrrolidin-3-yl-pyrazol-4-amine hydrochloride (for synthesis refer to Example 50) and acetone.

The crude was purified by prep-HPLC (column: Phenomenex Luna C18 10 μm 250×50 mm; mobile phase: [water (0.1% TFA)-ACN]; B: 1-25%, 20 min) to give the title compound as a white solid (Y=52%). $^1$H NMR (400 MHz, DMSO-$d_6$) δ=10.05-9.96 (m, 1H), 7.77 (s, 1H), 7.52 (s, 1H), 3.90 (s, 3H), 3.89-3.83 (m, 1H), 3.65-3.50 (m, 1H), 3.49-3.41 (m, 1H), 3.33-3.14 (m, 2H), 2.44-2.38 (m, 2H), 1.84-1.80 (m, 1H), 1.24 (d, J=3 Hz, 6H).

Step 2: 3-(1,2,3,5,6,7-hexahydro-s-indacen-4-yl)-1-[(1-methyl-1H-pyrazol-4-yl)[1-(propan-2-yl)pyrrolidin-3-yl]sulfamoyl]urea sodium salt. General procedure B was followed using {[(1,2,3,5,6,7-hexahydro-s-indacen-4-yl)carbamoyl]amino}sulfonyl chloride and N-(1-isopropylpyrrolidin-3-yl)-1-methyl-pyrazol-4-amine trifluoroacetate. The crude product was purified by prep-HPLC (column: Nano-Micro Unisil 8-120 C18 Ultra Plus 250×50 mm; mobile phase: [water (10 mM NH$_4$HCO$_3$)-ACN]; B: 3-33%, 20 min) to give the title compound as a white solid (Y=5%). $^1$H NMR (400 MHz, methanol-$d_4$) δ ppm 7.72 (s, 1H), 7.50 (s, 1H), 6.92 (s, 1H), 4.97-4.92 (m, 1H), 3.87 (s, 3H), 3.64-3.54 (m, 1H), 3.20-3.12 (m, 4H), 2.89-2.79 (m, 8H), 2.34-2.24 (m, 1H), 2.11-2.07 (m, 4H), 1.99-1.88 (m, 1H), 1.32-1.23 (m, 6H). LC-MS (ESI): m/z: [M+H]$^+$=487.2

Example 52. 3-(1,2,3,5,6,7-hexahydro-s-indacen-4-yl)-1-[(1-methyl-1H-pyrazol-4-yl)[1-(propan-2-yl)piperidin-3-yl]sulfamoyl]urea sodium salt

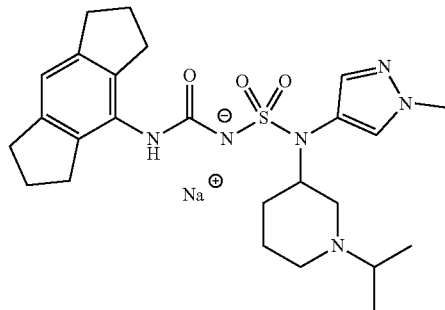 [SMILES: CC(C)N1CCCC(N(c2cnn(C)c2)S(=O)(=O)[N-]C(=O)Nc2c3c(cc4c2CCC4)CCC3)C1 ; [Na+]]

Step 1: N-(1-methylpyrazol-4-yl)piperidin-3-amine hydrochloride. A solution of tert-butyl 3-[(1-methylpyrazol-4-yl)amino]piperidine-1-carboxylate (2.0 g, 7.13 mmol) (for synthesis refer to Example 62) in 4M HCl in EtOAc (21.4 ml) was stirred at rt for 1 h. The solution was filtered to give the title compound as a yellow solid (Y=78%).

Step 2: 1-isopropyl-N-(1-methylpyrazol-4-yl)piperidin-3-amine trifluoroacetate. General procedure A was followed using N-(1-methylpyrazol-4-yl)piperidin-3-amine hydrochloride and acetone. The crude product was purified by prep-HPLC (column: Phenomenex Luna 10 μm C18 250×50 mm; mobile phase: [water (0.1% TFA)-ACN]; B: 1-5%, 20 min) to give the title compound as a yellow oil (Y=64%). $^1$H NMR (400 MHz, DMSO-$d_6$) δ ppm 9.49 (s, 1H), 7.40 (s, 1H), 7.19 (s, 1H), 3.75 (s, 3H), 3.56-3.53 (m, 1H), 3.44-3.33 (m, 3H), 2.89-2.79 (m, 1H), 2.70-2.63 (m, 1H), 2.03-1.92 (m, 2H), 1.73-1.70 (m, 1H), 1.40-1.37 (m, 1H), 1.25-1.22 (m, 6H). One NH not seen.

Step 3: 3-(1,2,3,5,6,7-hexahydro-s-indacen-4-yl)-1-[(1-methyl-1H-pyrazol-4-yl)[1-(propan-2-yl)piperidin-3-yl]sulfamoyl]urea sodium salt. General procedure B was followed using {[(1,2,3,5,6,7-hexahydro-s-indacen-4-yl)carbamoyl]amino}sulfonyl chloride and 1-isopropyl-N-(1-methylpyrazol-4-yl)piperidin-3-amine trifluoroacetate. The crude product was purified by prep-HPLC (column: Nano-Micro Unisil 8-120 C18 Ultra Plus 250×50 mm; mobile phase: [water (10 mM NH$_4$HCO$_3$)-ACN]; B: 3-33%, 20 min) to give the title compound as a white solid (Y=10%). $^1$H NMR (400 MHz, methanol-$d_4$) δ ppm 7.66 (s, 1H), 7.44 (s, 1H), 6.92 (s, 1H), 4.45-4.35 (m, 1H), 3.86 (s, 3H), 3.66-3.58 (m, 1H), 3.20-3.10 (m, 1H), 2.88-2.75 (m, 8H), 2.65-2.50 (m, 2H), 2.10-1.92 (m, 6H), 1.85-1.70 (m, 1H), 1.32-1.20 (m, 8H). NH not seen. LC-MS (ESI): m/z: [M+H]$^+$=501.2

Example 53. 3-(3,5-diethylphenyl)-1-[(1-methyl-1H-pyrazol-4-yl)(1-methylpiperidin-4-yl)sulfamoyl]urea sodium salt

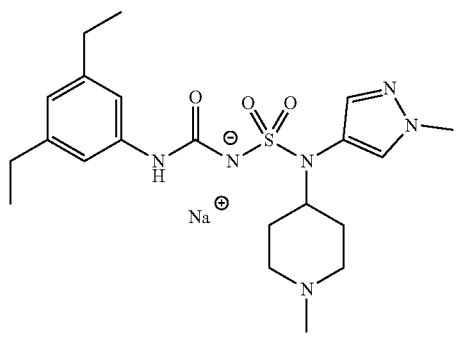 [SMILES: CCc1cc(CC)cc(NC(=O)[N-]S(=O)(=O)N(c2cnn(C)c2)C2CCN(C)CC2)c1 ; [Na+]]

Step 1: 3,5-diethenylaniline. To a solution of 3,5-dibromoaniline (5.0 g, 19.9 mmol) in 1,4-dioxane (50 ml) and H$_2$O (5 ml) was added 4,4,5,5-tetramethyl-2-vinyl-1,3,2-dioxaborolane (9.13 ml, 53.8 mmol), Cs$_2$CO$_3$ (19.5 g, 59.8 mmol) and Pd(dppf)Cl$_2$ (729 mg, 1.0 mmol). The mixture was stirred at 100° C. under N$_2$ for 5 h. The solution was concentrated in vacuo and the residue was poured into water (60 ml) and the resulting mixture stirred for 0.5 h. The aqueous phase was extracted with ethyl acetate (3×100 ml). The combined organics were concentrated in vacuo. The crude was purified by FCC (17% EtOAc in petroleum ether) to give the title compound as an oil (Y=17%). $^1$H NMR (400 MHz, DMSO-$d_6$) δ ppm 6.71 (s, 1H), 6.60-6.52 (m, 4H), 5.70-5.64 (m, 2H), 5.17 (d, J=12 Hz, 2H), 5.10-5.06 (m, 2H).

Step 2: 3,5-diethylaniline. To a solution of 3,5-diethenylaniline (600 mg, 4.13 mmol) in MeOH (8 ml) was added 10% Pd/C (200 mg) and the mixture was stirred under H$_2$ (15 psi) for 2 h. The solution was filtered and the filtrate was concentrated in vacuo. The residue was purified by FCC (25% EtOAc in petroleum ether) to give the title compound as a green oil (Y=18%). $^1$H NMR (400 MHz, DMSO-$d_6$) δ=6.22-6.18 (m, 3H), 4.82 (s, 2H), 2.44-2.37 (m, 4H), 1.14-1.09 (m, 6H).

Step 3: {[(3,5-diethylphenyl)carbamoyl]amino}sulfonyl chloride. General procedure D was followed using 3,5-diethylaniline to give the title compound as a solution in isopropyl ether. LC-MS in MeOH (ESI): m/z: =287.3

Step 4: 3-(3,5-diethylphenyl)-1-[(1-methyl-1H-pyrazol-4-yl)(1-methylpiperidin-4-yl)sulfamoyl]urea sodium salt. General procedure B was followed using {[(3,5-diethylphenyl)carbamoyl]amino}sulfonyl chloride and 1-methyl-N-(1-methylpyrazol-4-yl) piperidin-4-amine trifluoroacetate (for synthesis refer to Example 2). The crude product was purified by prep-HPLC (column: Nano-Micro Unisil 8-120 C18 Ultra Plus 250×50 mm; mobile phase: [water (10 mM NH$_4$HCO$_3$)-ACN]; B: 3-33%, 20 min) to give the title compound as a white solid (Y=7%). ¹H NMR (400 MHz, methanol-d₄) δ ppm 7.65 (s, 1H), 7.42 (s, 1H), 7.07 (s, 2H), 6.71 (s, 1H), 4.31-4.25 (m, 1H), 3.81 (s, 3H), 3.23 (d, J=12 Hz, 2H), 2.76 (t, J=12 Hz, 2H), 2.63-2.53 (m, 7H), 2.13 (d, J=13 Hz, 2H), 1.64-1.51 (m, 2H), 1.21 (t, J=8 Hz, 6H). LC-MS (ESI): m/z: [M+H]⁺=449.2

Example 54. 1-({1-azabicyclo[2.2.2]octan-3-yl)(1-methyl-1H-pyrazol-4-yl)sulfamoyl}-3-(1,2,3,5,6,7-hexahydro-s-indacen-4-yl)urea sodium salt

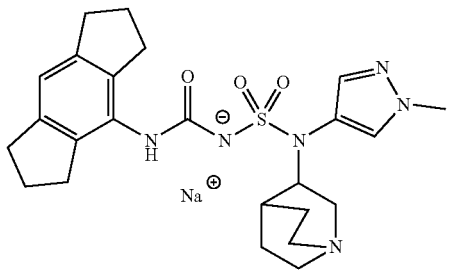 [SMILES: Cn1cc(N(C2CN3CCC2CC3)S(=O)(=O)[N-]C(=O)Nc2c3c(cc4c2CCC4)CCC3)cn1 ; [Na+]]

Step 1: tert-butyl N-(1-methylpyrazol-4-yl)quinuclidin-3-amine trifluoroacetate. General procedure A was followed using 1-methylpyrazol-4-amine and quinuclidin-3-one. The crude product was purified by prep-HPLC (column: Phenomenex Luna C18 10 μm 250×50 mm; mobile phase: [water (0.1% TFA)-ACN]; B: 1-35%, 20 min) to give the title compound as a yellow oil (Y=39%). ¹H NMR (400 MHz, methanol-d₄) δ ppm 7.24 (s, 1H), 7.17 (s, 1H), 3.80 (s, 3H), 3.68-3.62 (m, 2H), 3.36-3.27 (m, 4H), 3.02-3.00 (m, 1H), 2.29-2.16 (m, 2H), 2.12-2.06 (m, 1H), 2.02-1.91 (m, 1H), 1.89-1.79 (m, 1H).

Step 2: 1-({1-azabicyclo[2.2.2]octan-3-yl)(1-methyl-1H-pyrazol-4-yl)sulfamoyl}-3-(1,2,3,5,6,7-hexahydro-s-indacen-4-yl)urea sodium salt. General procedure B was followed using {[(1,2,3,5,6,7-hexahydro-s-indacen-4-yl)carbamoyl]amino}sulfonyl chloride and tert-butyl N-(1-methylpyrazol-4-yl)quinuclidin-3-amine trifluoroacetate. The crude product was purified by prep-HPLC (column: Nano-Micro Unisil 8-120 C18 Ultra Plus 250×50 mm; mobile phase: [water (10 mM NH₄HCO₃)-ACN]; B: 3-33%, 20 min) to give the title compound as a white solid (Y=30%). ¹H NMR (400 MHz, methanol-d₄) δ ppm 7.69 (s, 1H), 7.50 (s, 1H), 6.91 (s, 1H), 4.54-4.52 (m, 1H), 3.86 (s, 3H), 3.68-3.60 (m, 1H), 3.52-3.44 (m, 1H), 3.42-3.34 (m, 1H), 3.16-3.05 (m, 3H), 2.90-2.78 (m, 8H), 2.24 (s, 1H), 2.09-2.03 (m, 4H), 1.99-1.89 (m, 3H), 1.56-1.53 (m, 1H). LC-MS (ESI): m/z: [M+H]⁺=485.3

Example 55. 3-(1,2,3,5,6,7-hexahydro-s-indacen-4-yl)-1-[(1-methylpiperidin-3-yl)[1-(propan-2-yl)-1H-pyrazol-4-yl]sulfamoyl]urea sodium salt

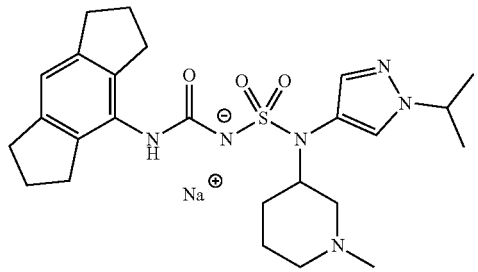 [SMILES: CC(C)n1cc(N(C2CCCN(C)C2)S(=O)(=O)[N-]C(=O)Nc2c3c(cc4c2CCC4)CCC3)cn1 ; [Na+]]

Step 1: tert-butyl 3-[(1-isopropylpyrazol-4-yl)amino]piperidine-1-carboxylate. General procedure A was followed using 1-isopropylpyrazol-4-amine (for synthesis refer to Example 56) and tert-butyl 3-oxopiperidine-1-carboxylate. The crude product was purified by prep-HPLC (column: Agela Innoval ods-2 250×80 mm; mobile phase: [water (0.1% TFA)-ACN]; B: 20-60%, 20 min) to give the title compound as a yellow liquid (Y=17%). ¹H NMR (400 MHz, methanol-d₄) δ ppm 7.26 (s, 1H), 7.15 (s, 1H), 4.92-4.89 (m, 1H), 4.44-4.34 (m, 1H), 3.87-3.67 (m, 1H), 3.15-2.90 (m, 3H), 2.07-2.01 (m, 1H), 1.76-1.73 (m, 1H), 1.52-1.42 (m, 16H), 1.27-1.25 (m, 1H).

Step 2: N-(1-isopropylpyrazol-4-yl)-1-methyl-piperidin-3-amine trifluoroacetate. To a solution of tert-butyl 3-[(1-isopropylpyrazol-4-yl)amino]piperidine-1-carboxylate (550 mg, 1.78 mmol) in THF (7 ml) cooled to 0° C. was added lithium aluminium hydride (677 mg, 17.8 mmol). The RM was stirred at 75° C. for 2 h. The RM was allowed to cool to rt and quenched with H₂O (0.66 ml) and 10% sodium hydroxide solution (0.66 ml). The mixture was filtered and concentrated under reduced pressure to give a residue. The residue was purified by prep-HPLC (column: Phenomenex Luna C18 10 μm 250×50 mm; mobile phase: [water (0.1% TFA)-ACN]; B: 0-25%, 20 min) to give the title compound as a yellow liquid (Y=32%). LC-MS (ESI): m/z: [M+H]⁺=223.4

Step 3: 3-(1,2,3,5,6,7-hexahydro-s-indacen-4-yl)-1-[(1-methylpiperidin-3-yl)[1-(propan-2-yl)-1H-pyrazol-4-yl]sulfamoyl]urea sodium salt. General procedure B was followed using {[(1,2,3,5,6,7-hexahydro-s-indacen-4-yl)carbamoyl]amino}sulfonyl chloride and N-(1-isopropylpyrazol-4-yl)-1-methyl-piperidin-3-amine trifluoroacetate. The crude product was purified by prep-HPLC (column: YMC-Actus Triart C18 5 μm 250×50 mm; mobile phase: [water (10 mM NH₄HCO₃)-ACN]; B: 25-35%, 12 min) to give the title compound as a white solid (Y=6%). ¹H NMR (400 MHz, methanol-d₄) δ ppm 7.71 (s, 1H), 7.45 (s, 1H), 6.95 (s, 1H), 4.51-4.45 (m, 1H), 4.37-4.31 (m, 1H), 3.53-3.45 (m, 1H), 3.06-3.00 (m, 1H), 2.87 (t, J=7 Hz, 4H), 2.82 (t, J=7 Hz, 4H), 2.57 (s, 3H), 2.40-2.21 (m, 2H), 2.10-1.98 (m, 5H), 1.88-1.84 (m, 1H), 1.79-1.69 (m, 1H), 1.48 (d, J=7 Hz, 6H), 1.22-1.12 (m, 1H). LC-MS (ESI): m/z: [M+H]⁺=501.3

Example 56. 3-(1,2,3,5,6,7-hexahydro-s-indacen-4-yl)-1-[(1-methylpyrrolidin-3-yl)[1-(propan-2-yl)-1H-pyrazol-4-yl]sulfamoyl]urea sodium salt

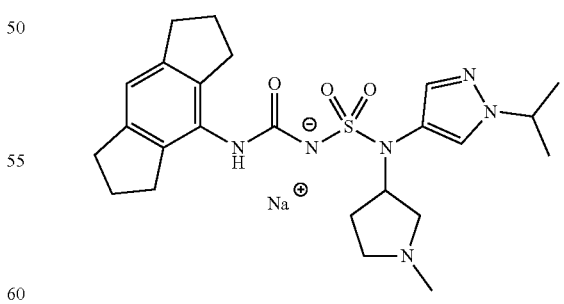

Step 1: 1-isopropyl-4-nitro-pyrazole. To a solution of 4-nitro-1H-pyrazole (10.0 g, 88.44 mmol) in THF (200 ml) was added propan-2-ol (8.12 ml, 106.1 mmol) and PPh₃ (32.5 g, 123.8 mmol) at rt under N₂. The RM was cooled to 0° C. then DIAD (20.6 ml, 106.1 mmol) was added. The RM was stirred at rt for 12 h then the solvent was removed under reduced pressure. The residue was purified by FCC (9-20% EtOAc in petroleum ether) to give the title compound as a white solid (Y=58%).

Step 2: 1-isopropylpyrazol-4-amine. To a solution of 1-isopropyl-4-nitro-pyrazole (3.0 g, 19.34 mmol) in MeOH (40 ml) under a nitrogen atmosphere was added 10% Pd/C (600 mg). The RM was purged then stirred under $H_2$ atmosphere at 15 psi for 2 h. The mixture was evaporated under reduced pressure to give the title compound as a brown liquid (Y=99%). $^1$H NMR (400 MHz, methanol-$d_4$) δ ppm 7.23 (s, 1H), 7.13 (s, 1H), 4.40-4.33 (m, 1H), 1.42 (d, J=6 Hz, 6H).

Step 3: tert-butyl 3-[(1-isopropylpyrazol-4-yl)amino]pyrrolidine-1-carboxylate. General procedure A was followed using 1-isopropylpyrazol-4-amine and tert-butyl 3-oxopyrrolidine-1-carboxylate. The crude product was purified by prep-HPLC (column: Agela Innoval ods-2 250×80 mm; mobile phase: [water (0.1% TFA)-ACN]; B: 27-57%, 20 min) to give the title compound as a yellow liquid (Y=32%). $^1$H NMR (400 MHz, methanol-$d_4$) δ ppm 7.68 (s, 1H), 7.37 (s, 1H), 5.12-5.02 (m, 1H), 3.85-3.77 (m, 1H), 3.61-3.55 (m, 1H), 3.48-3.41 (m, 2H), 3.21 (dd, J=4, 11 Hz, 1H), 2.21-2.13 (m, 1H), 1.92-1.78 (m, 1H), 1.50 (d, J=7 Hz, 6H), 1.46 (s, 9H).

Step 4: 1-isopropyl-N-(1-methylpyrrolidin-3-yl)pyrazol-4-amine. To a solution of tert-butyl 3-[(1-isopropylpyrazol-4-yl)amino]pyrrolidine-1-carboxylate (600 mg, 0.204 mmol) in THF (10 ml) cooled to 0° C. was added lithium aluminium hydride (774 mg, 0.204 mmol) portionwise. The RM was heated at 80° C. for 2 h. The mixture was diluted with $H_2O$ (1 ml and 10% NaOH (aq.) (1 ml). The mixture was filtered. The filtrate was concentrated under reduced pressure to give a residue, which was used for the next step directly.

Step 5: 3-(1,2,3,5,6,7-hexahydro-s-indacen-4-yl)-1-[(1-methylpyrrolidin-3-yl)[1-(propan-2-yl)-1H-pyrazol-4-yl]sulfamoyl]urea sodium salt. General procedure B was followed using {[(1,2,3,5,6,7-hexahydro-s-indacen-4-yl)carbamoyl]amino}sulfonyl chloride and 1-isopropyl-N-(1-methylpyrrolidin-3-yl)pyrazol-4-amine. The crude product was purified by prep-HPLC (column: Agela Durashell 10 μm 250×50 mm; mobile phase: [water (10 mM $NH_4HCO_3$)-ACN]; B: 8-38%, 20 min) to give the title compound as a white solid (Y=5%). $^1$H NMR (400 MHz, methanol-$d_4$) δ ppm 7.78 (s, 1H), 7.53 (s, 1H), 6.93 (s, 1H), 5.00-4.94 (m, 1H), 4.52-4.45 (m, 1H), 3.49-3.44 (m, 1H), 3.13-3.03 (m, 2H), 2.87 (t, J=7 Hz, 4H), 2.81 (t, J=7 Hz, 4H), 2.70 (s, 3H), 2.39-2.30 (m, 1H), 2.10-1.99 (m, 6H), 1.48 (d, J=7 Hz, 6H). LC-MS (ESI): m/z: [M+H]$^+$=487.2

Example 57. 3-(1,2,3,5,6,7-hexahydro-s-indacen-4-yl)-1-[(1-methyl-1H-pyrazol-4-yl)[(1-methylpyrrolidin-3-yl)methyl]sulfamoyl]urea sodium salt

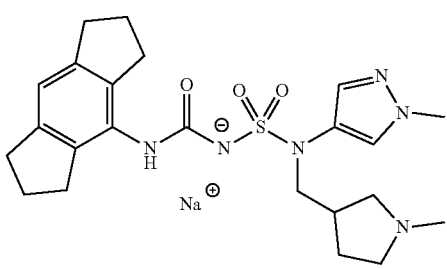 [SMILES: CN1CCC(CN(c2cnn(C)c2)S(=O)(=O)[N-]C(=O)Nc2c3c(cc4c2CCC4)CCC3)C1 ; [Na+]]

Step 1: tert-butyl 2-[[(1-methylpyrazol-4-yl)amino]methyl]pyrrolidine-1-carboxylate. General procedure A was followed using 1-methylpyrazol-4-amine and tert-butyl 3-formylpyrrolidine-1-carboxylate. The crude product was purified by prep-HPLC (column: Agela Innoval ods-2 250×80 mm; mobile phase: [water (0.1% TFA)-ACN]) to give the title compound as a red solid (Y=49%). $^1$H NMR (400 MHz, methanol-$d_4$) δ ppm 7.94 (s, 1H), 7.65 (s, 1H), 3.92 (s, 3H), 3.64-3.57 (m, 1H), 3.54-3.47 (m, 1H), 3.41 (d, J=7 Hz, 2H), 3.36-3.33 (m, 1H), 3.13-3.01 (m, 1H), 2.62-2.49 (m, 1H), 2.18-2.07 (m, 1H), 1.80-1.66 (m, 1H), 1.46 (s, 9H).

Step 2: 1-methyl-N-[(1-methylpyrrolidin-3-yl)methyl]pyrazol-4-amine trifluoroacetate. A mixture of tert-butyl 3-[[(1-methylpyrazol-4-yl)amino]methyl]pyrrolidine-1-carboxylate (1.0 g, 3.57 mmol) in THF (5 ml) was degassed and purged with $N_2$ three times. The RM was cooled to 0° C. and treated portionwise with lithium aluminium hydride (134 mg, 3.57 mmol). The mixture was heated at 85° C. for 5 h under $N_2$ atmosphere. The RM was allowed to cool to rt and treated with water (0.13 ml) and 10% aqueous NaOH (0.13 ml). The resulting mixture was filtered and the filtrate was concentrated under reduced pressure to give a residue. The residue was purified by prep-HPLC (column: C18; mobile phase: [water (10 mM $NH_4HCO_3$)-ACN]) to give the title compound as a red oil (Y=54%). $^1$H NMR (400 MHz, methanol-$d_4$) δ=7.80 (s, 1H), 7.56 (s, 1H), 3.89 (s, 3H), 3.84-3.53 (m, 3H), 3.49-3.38 (m, 2H), 3.21-3.13 (m, 1H), 2.95 (s, 3H), 2.88-2.73 (m, 1H), 2.42-2.27 (m, 1H), 2.04-1.90 (m, 1H).

Step 3: 3-(1,2,3,5,6,7-hexahydro-s-indacen-4-yl)-1-[(1-methyl-1H-pyrazol-4-yl)[(1-methylpyrrolidin-3-yl)methyl]sulfamoyl]urea sodium salt. General procedure B was followed using {[(1,2,3,5,6,7-hexahydro-s-indacen-4-yl)carbamoyl]amino}sulfonyl chloride and 1-methyl-N-[(1-methylpyrrolidin-3-yl)methyl]pyrazol-4-amine trifluoroacetate. The crude product was purified by prep-HPLC (column: C18; mobile phase: [water (10 mM $NH_4HCO_3$)-ACN]) to give the title compound as a white solid (Y=11%). $^1$H NMR (400 MHz, methanol-$d_4$) δ ppm 7.68 (s, 1H), 7.51 (s, 1H), 6.91 (s, 1H), 3.92-3.75 (m, 4H), 3.68-3.42 (m, 3H), 3.27-3.16 (m, 1H), 3.15-3.06 (m, 1H), 2.90-2.73 (m, 11H), 2.69-2.55 (m, 1H), 2.20-2.11 (m, 1H), 2.09-1.95 (m, 4H), 1.91-1.83 (m, 1H). LC-MS (ESI): m/z: [M+H]$^+$=473.2

Example 58. 3-(1,2,3,5,6,7-hexahydro-s-indacen-4-yl)-1-[(1-methyl-1H-pyrazol-4-yl)({2-methyl-2-azaspiro[3.3]heptan-6-yl})sulfamoyl]urea sodium salt

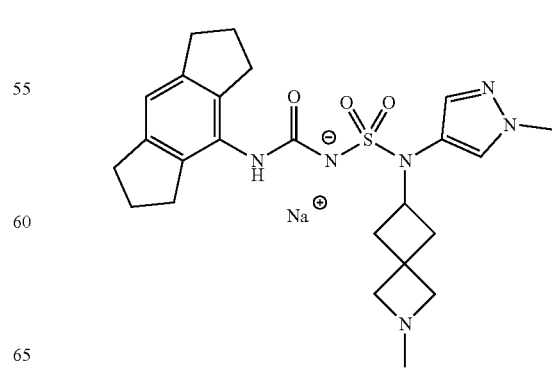

Step 1: tert-butyl 6-[(1-methylpyrazol-4-yl)amino]-2-azaspiro[3.3]heptane-2-carboxylate. General procedure A was followed using 1-methylpyrazol-4-amine and tert-butyl 6-oxo-2-azaspiro[3.3]heptane-2-carboxylate. The crude was purified by prep-HPLC (column: C18; mobile phase: [water (0.1% TFA)-ACN]) to give the title compound as a red solid (Y=63%). $^1$H NMR (400 MHz, methanol-d$_4$) δ ppm 7.90 (s, 1H), 7.59 (s, 1H), 3.99-3.87 (m, 8H), 2.65-2.56 (m, 2H), 2.44-2.34 (m, 2H), 1.42 (s, 9H).

Step 2: 2-methyl-N-(1-methylpyrazol-4-yl)-2-azaspiro[3.3]heptan-6-amine trifluoroacetate. To a solution of tert-butyl 6-[(1-methylpyrazol-4-yl)amino]-2-azaspiro[3.3]heptane-2-carboxylate (945 mg, 3.23 mmol) in THF (10 ml) cooled 0° C. was added lithium aluminium hydride (1.23 g, 32.3 mmol) portionwise. The RM was heated at 85° C. for 12 h under a N$_2$ atmosphere. The reaction mixture was quenched with water (1.3 ml) and 10% aqueous NaOH (1.3 ml). The mixture was filtered and the filtrate concentrated under reduced pressure to give a residue. The residue was purified by prep-HPLC (column: C18; mobile phase: [water (0.1% TFA)-ACN]) to give the title compound as a red solid (Y=85%). $^1$H NMR (400 MHz, methanol-d$_4$) δ ppm 7.74 (s, 1H), 7.48 (s, 1H), 4.40-4.27 (m, 2H), 4.10-4.03 (m, 2H), 3.94-3.90 (m, 1H), 3.88 (s, 3H), 2.88 (s, 3H), 2.78-2.65 (m, 2H), 2.55-2.39 (m, 2H).

Step 3: 3-(1,2,3,5,6,7-hexahydro-s-indacen-4-yl)-1-[(1-methyl-1H-pyrazol-4-yl)({2-methyl-2-azaspiro[3.3]heptan-6-yl})sulfamoyl]urea sodium salt. General procedure B was followed using {[(1,2,3,5,6,7-hexahydro-s-indacen-4-yl)carbamoyl]amino}sulfonyl chloride and 2-methyl-N-(1-methylpyrazol-4-yl)-2-azaspiro[3.3]heptan-6-amine trifluoroacetate. The crude product was purified by prep-HPLC (column: C18; mobile phase: [water (10 mM NH$_4$HCO$_3$)-ACN]) to give the title compound as a white solid (Y=12%). $^1$H NMR (400 MHz, methanol-d$_4$) δ ppm 7.63 (s, 1H), 7.43 (s, 1H), 6.92 (s, 1H), 4.58-4.46 (m, 1H), 4.02 (s, 2H), 3.84 (s, 3H), 3.76 (s, 2H), 2.86 (t, J=7 Hz, 4H), 2.77 (t, J=7 Hz, 4H), 2.70 (s, 3H), 2.57-2.46 (m, 2H), 2.16-1.96 (m, 6H). LC-MS (ESI): m/z: [M+H]$^+$=485.2

Example 59. 3-(1,2,3,5,6,7-hexahydro-s-indacen-4-yl)-1-[(1-methyl-1H-pyrazol-4-yl)(1-methylazetidin-3-yl)sulfamoyl]urea sodium salt

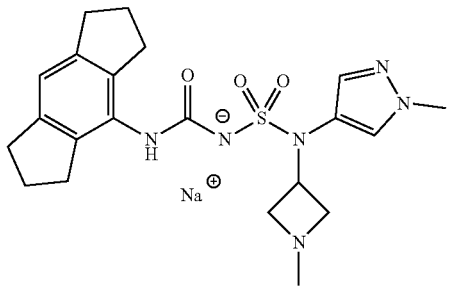 [SMILES: CN1CC(N(c2cnn(C)c2)S(=O)(=O)[N-]C(=O)Nc2c3c(cc4c2CCC4)CCC3)C1 ; [Na+]]

Step 1: tert-butyl 3-[(1-methylpyrazol-4-yl)amino]azetidine-1-carboxylate. General procedure A was followed using 1-methylpyrazol-4-amine and tert-butyl 3-oxoazetidine-1-carboxylate. The crude product was purified by prep-HPLC (column: Agela Innoval ods-2 350×100 mm; mobile phase: [water (0.1% TFA)-ACN]; B: 3-35%, 23 min) to give the title compound as a red solid (Y=37%). $^1$H NMR (400 MHz, methanol-d$_4$) δ ppm 7.12 (s, 1H), 7.08 (s, 1H), 4.50-4.47 (m, 1H), 4.19-4.09 (m, 4H), 3.77 (s, 3H), 1.44 (s, 9H).

Step 2: 1-methyl-N-(1-methylazetidin-3-yl)pyrazol-4-amine trifluoroacetate. To a solution of tert-butyl 3-[(1-methylpyrazol-4-yl)amino]azetidine-1-carboxylate (1.0 g, 2.73 mmol) in THF (10 ml) cooled to 0° C. was added lithium aluminium hydride (1.04 g, 27.3 mmol). The mixture was stirred at 0° C. for 0.5 h, then the mixture was heated at 85° C. for 2.5 h. The RM was diluted with water (1 ml) and 8% NaOH solution (1 ml), then the mixture was filtered. The filtrate was concentrated under reduced pressure to give a residue. The residue was purified by prep-HPLC (column: Xtimate C18 10 μm 250×50 mm; mobile phase: [water (10 mM NH$_4$HCO$_3$)-ACN]; B: 0-8%, 20 min) to give the title compound as a red oil (Y=39%). $^1$H NMR (400 MHz, methanol-d$_4$) δ=7.18 (s, 1H), 7.11 (s, 1H), 4.61-4.57 (m, 1H), 4.24-4.08 (m, 3H), 3.84-3.81 (m, 1H), 3.78 (s, 3H), 2.96 (s, 3H).

Step 3: 3-(1,2,3,5,6,7-hexahydro-s-indacen-4-yl)-1-[(1-methyl-1H-pyrazol-4-yl)(1-methylazetidin-3-yl)sulfamoyl]urea sodium salt. General procedure B was followed using {[(1,2,3,5,6,7-hexahydro-s-indacen-4-yl)carbamoyl]amino}sulfonyl chloride and 1-methyl-N-(1-methylazetidin-3-yl)pyrazol-4-amine trifluoroacetate. The crude product was purified by prep-HPLC (column: YMC-Triart prep C18-s 250×50 mm; mobile phase: [water (10 mM NH$_4$HCO$_3$)-ACN]; B: 5-35%, 20 min) to give the title compound as a white solid (Y=3%). $^1$H NMR (400 MHz, methanol-d$_4$) δ ppm 7.68 (s, 1H), 7.51 (s, 1H), 6.91 (s, 1H), 5.00-4.96 (m, 1H), 4.02-3.96 (m, 2H), 3.88 (s, 3H), 3.64-3.58 (m, 2H), 2.88-2.84 (m, 4H), 2.82-2.78 (m, 4H), 2.57 (s, 3H), 2.10-2.05 (m, 4H). LC-MS (ESI): m/z: [M+H]$^+$=445.1

Example 60. 3-(1,2,3,5,6,7-hexahydro-s-indacen-4-yl)-1-[(1-methyl-1H-pyrazol-4-yl)[1-methyl-2-(trifluoromethyl)piperidin-4-yl]sulfamoyl]urea sodium salt

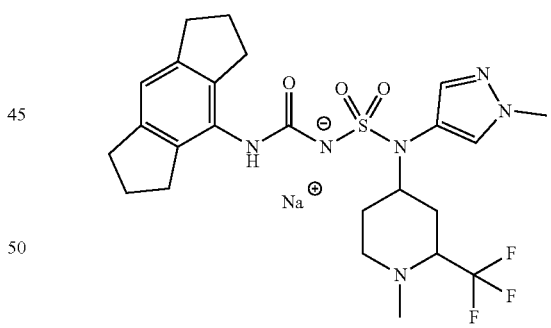

Step 1: tert-butyl 4-[(1-methylpyrazol-4-yl) amino]-2-(trifluoromethyl) piperidine-1-carboxylate. General procedure A was followed using 1-methylpyrazol-4-amine and tert-butyl 4-oxo-2-(trifluoromethyl)piperidine-1-carboxylate. The crude product was purified by prep-HPLC (column: Nano-Micro Unisil 8-120 C18 Ultra Plus 250×50 mm; mobile phase: [water (10 mM NH$_4$HCO$_3$)-ACN]; B: 35-45%, 20 min) to give the title compound as a yellow oil (Y=23%). $^1$H NMR (400 MHz, DMSO-d$_6$) δ=7.17 (s, 1H), 6.96 (s, 1H), 4.80-4.69 (m, 1H), 4.34-4.26 (m, 1H), 3.87-3.80 (m, 1H), 3.68 (s, 3H), 3.10-3.03 (m, 1H), 2.19-2.13 (m, 1H), 2.09-2.01 (m, 1H), 1.60-1.52 (m, 1H), 1.42 (s, 9H), 1.38-1.35 (m, 1H).

Step 2: 1-methyl-N-(1-methylpyrazol-4-yl)-2-(trifluoromethyl)piperidin-4-amine trifluoroacetate. To a solution of tert-butyl 4-[(1-methylpyrazol-4-yl)amino]-2-(trifluoromethyl)piperidine-1-carboxylate (250 mg, 0.72 mmol) in THF (3 ml) cooled to 0° C. was added lithium aluminium hydride (272 mg, 7.2 mmol). The RM was heated at 90° C. for 3.5 h. The RM was cooled to 0° C. and H$_2$O (0.3 ml) was added to quench the reaction. The RM was then diluted with 10% aqueous NaOH and stirred for 10 min. The mixture was filtered and the solid washed with 10:1 DCM/MeOH (20 ml) and filtered again. The filtrate was concentrated under reduced pressure and the residue was purified by prep-HPLC (column: Phenomenex Luna C18 10 μm 250×50 mm; mobile phase: [water (0.1% TFA)-ACN]; B: 1-20%, 20 min) to give the title compound as a yellow oil (Y=37%). $^1$H NMR (400 MHz, DMSO-d$_6$) δ ppm 7.84 (s, 1H), 7.49 (s, 1H), 3.83 (s, 3H), 3.45-3.25 (m, 3H), 3.09-3.01 (m, 1H), 2.41 (s, 3H), 2.14-2.03 (m, 1H), 1.94-1.84 (m, 1H), 1.64-1.48 (m, 2H).

Step 3: 3-(1,2,3,5,6,7-hexahydro-s-indacen-4-yl)-1-[(1-methyl-1H-pyrazol-4-yl)[1-methyl-2-(trifluoromethyl)piperidin-4-yl]sulfamoyl]urea sodium salt. General procedure B was followed using {[(1,2,3,5,6,7-hexahydro-s-indacen-4-yl)carbamoyl]amino}sulfonyl chloride and 1-methyl-N-(1-methylpyrazol-4-yl)-2-(trifluoromethyl)piperidin-4-amine trifluoroacetate. The crude product was purified by prep-HPLC (column: Agela Durashell C18 250×50 mm 10 μm; mobile phase: [water (10 mM NH$_4$HCO$_3$)-ACN]; B: 10-40%, 20 min) to give the title compound as a white solid (Y=8%). $^1$H NMR (400 MHz, DMSO-d$_6$) δ ppm 7.85 (s, 1H), 7.80 (s, 1H), 7.31 (s, 1H), 6.96 (s, 1H), 4.17-4.11 (m, 1H), 3.84 (s, 3H), 2.93-2.90 (m, 1H), 2.86-2.76 (m, 5H), 2.72-2.69 (m, 4H), 2.37-2.34 (m, 1H), 2.20 (s, 3H), 2.03-1.95 (m, 5H), 1.76-1.70 (m, 1H), 1.34-1.12 (m, 2H). LC-MS (ESI): m/z: [M+H]$^+$=541.2

Example 61. 3-(1,2,3,5,6,7-hexahydro-s-indacen-4-yl)-1-[(1-methyl-1H-pyrazol-4-yl)[1-(2,2,2-trifluoroethyl)pyrrolidin-3-yl]sulfamoyl]urea sodium salt

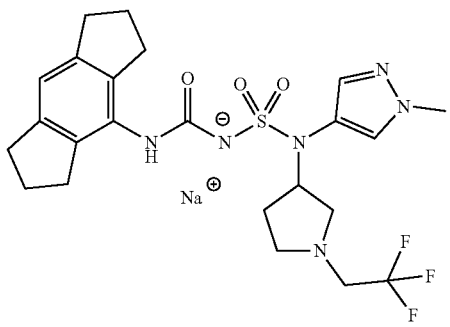 [SMILES: Cn1cc(N(C2CCN(CC(F)(F)F)C2)S(=O)(=O)[N-]C(=O)Nc2c3c(cc4c2CCC4)CCC3)cn1 ; [Na+]]

Step 1: tert-butyl 3-[(1-methylpyrazol-4-yl) amino]pyrrolidine-1-carboxylate. General procedure A was followed using 1-methylpyrazol-4-amine and tert-butyl 3-oxopyrrolidine-1-carboxylate to give the title compound as a yellow oil (Y=42%). $^1$H NMR (400 MHz, DMSO-d$_6$) δ=7.08 (s, 1H), 6.93 (s, 1H), 4.56-4.50 (m, 1H), 3.68 (s, 3H), 3.63-3.53 (m, 1H), 3.45-3.38 (m, 1H), 3.28-3.23 (m, 1H), 3.08-3.03 (m, 1H), 2.05-1.97 (m, 1H), 1.81-1.65 (m, 1H), 1.49-1.45 (m, 1H), 1.38 (s, 9H).

Step 2: 1-methyl-N-pyrrolidin-3-yl-pyrazol-4-amine hydrochloride. A solution of tert-butyl 3-[(1-methylpyrazol-4-yl)amino]pyrrolidine-1-carboxylate (3.0 g, 11.26 mmol) in 4M HCl in EtOAc (2.82 ml, 11.26 mmol) was stirred at rt for 12 h. The solution was concentrated in vacuo to give the title compound as a yellow solid (Y=96%). $^1$H NMR (400 MHz, DMSO-d$_6$) δ ppm 9.61 (s, 1H), 9.50 (s, 1H), 7.87 (s, 1H), 7.57 (s, 1H), 3.90 (s, 3H), 3.54-3.42 (m, 1H), 3.35-3.17 (m, 3H), 3.06-2.98 (m, 1H), 2.18-2.09 (m, 1H), 1.90-1.81 (m, 1H).

Step 3: 2,2,2-trifluoro-1-[3-[(1-methylpyrazol-4-yl)amino]pyrrolidin-1-yl]ethanone. To a solution of 1-methyl-N-pyrrolidin-3-yl-pyrazol-4-amine hydrochloride (608 mg, 3.01 mmol) in MeOH (5 ml) was added ethyl 2,2,2-trifluoroacetate (5.00 ml, 36.3 mmol). The RM was stirred at rt for 1 h. DIPEA (2.10 ml, 12.0 mmol) was then added into the solution. The mixture was stirred at rt for a further 10 h. The RM was concentrated and the residue purified by prep-HPLC (column: Phenomenex Luna C18 10 μm 250×50 mm; mobile phase: [water (0.1% TFA)-ACN]; B: 0-22%, 20 min) to give the title compound as a yellow oil (Y=19%). LC-MS (ESI): m/z: [M+H]$^+$=263.1

Step 4: 1-methyl-N-[1-(2,2,2-trifluoroethyl)pyrrolidin-3-yl]pyrazol-4-amine trifluoroacetate. 2,2,2-trifluoro-1-[3-[(1-methylpyrazol-4-yl)amino]pyrrolidin-1-yl]ethanone trifluoroacetate (270 mg, 0.72 mmol) was added into 10 M BH$_3$-Me$_2$S (3 ml). The mixture was stirred at rt for 23 h. The solution was cooled to 0° C. and treated dropwise with MeOH (20 ml). The resulting solution was concentrated in vacuo. The crude product was purified by prep-HPLC (column: Phenomenex Luna C18 10 μm 250×50 mm; mobile phase: [water (0.1% TFA)-ACN]; B: 0-25%, 23 min) to give the title compound as a yellow oil (Y=58%). $^1$H NMR (400 MHz, DMSO-d$_6$) δ ppm 7.87 (s, 1H), 7.53 (s, 1H), 4.01-3.95 (m, 1H), 3.83 (s, 3H), 3.38 (q, J=10 Hz, 2H), 3.00-2.86 (m, 3H), 2.72-2.66 (m, 1H), 2.19-2.11 (m, 1H), 1.85-1.76 (m, 1H). NH protons not seen.

Step 5: 3-(1,2,3,5,6,7-hexahydro-s-indacen-4-yl)-1-[(1-methyl-1H-pyrazol-4-yl)[1-(2,2,2-trifluoroethyl)pyrrolidin-3-yl]sulfamoyl]urea sodium salt. General procedure B was followed using {[(1,2,3,5,6,7-hexahydro-s-indacen-4-yl)carbamoyl]amino}sulfonyl chloride and 1-methyl-N-[1-(2,2,2-trifluoroethyl)pyrrolidin-3-yl]pyrazol-4-amine trifluoroacetate. The crude product was purified by prep-HPLC (column: Xtimate C18 10 μm 250×50 mm; mobile phase: [water (10 mM NH$_4$HCO$_3$)-ACN]; B: 1-35%, 30 min) to give the title compound as an off-white solid (Y=5%). $^1$H NMR (400 MHz, methanol-d$_4$) δ ppm 7.74 (s, 1H), 7.50 (s, 1H), 6.97 (s, 1H), 3.87 (s, 3H), 3.13-2.96 (m, 4H), 2.88-2.77 (m, 8H), 2.71-2.67 (m, 1H), 2.65-2.53 (m, 2H), 2.22-2.12 (m, 1H), 2.10-2.02 (m, 4H), 1.83-1.78 (m, 1H). LC-MS (ESI): m/z: [M+H]$^+$=527.2

Example 62. 1-[(1-ethylpiperidin-3-yl)(1-methyl-1H-pyrazol-4-yl)sulfamoyl]-3-(1,2,3,5,6,7-hexahydro-s-indacen-4-yl)urea sodium salt

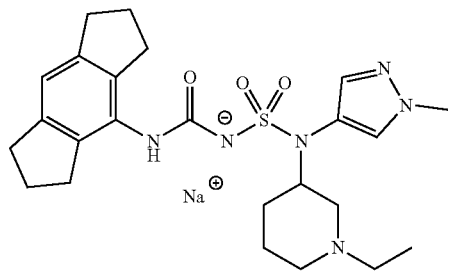 [SMILES: CCN1CCCC(N(c2cnn(C)c2)S(=O)(=O)[N-]C(=O)Nc2c3c(cc4c2CCC4)CCC3)C1 ; [Na+]]

Step 1: tert-butyl 3-[(1-methylpyrazol-4-yl)amino]piperidine-1-carboxylate. General procedure A was followed using 1-methylpyrazol-4-amine and tert-butyl 3-oxopiperidine-1-carboxylate to give the title compound as a yellow oil (Y=55%). $^1$H NMR (400 MHz, DMSO-$d_6$) δ=7.04 (s, 1H), 6.94 (s, 1H), 4.38-4.23 (m, 1H), 3.89-3.79 (m, 1H), 3.68 (s, 3H), 2.92-2.61 (m, 2H), 1.96-1.84 (m, 1H), 1.66-1.63 (m, 1H), 1.37 (s, 9H), 1.34-1.27 (m, 2H).

Step 2: tert-butyl 3-[(1-methylpyrazol-4-yl)-(2,2,2-trifluoroacetyl)amino]piperidine-1-carboxylate. To a solution of tert-butyl 3-[(1-methylpyrazol-4-yl)amino]piperidine-1-carboxylate (3.0 g, 10.7 mmol) in DCM (20 ml) cooled to 0° C. was added triethylamine (2.23 ml, 16.1 mmol) and trifluoroacetic anhydride (1.49 ml, 10.7 mmol). The mixture was stirred at 0° C. for 2 h. The solution was concentrated in vacuo. The crude reaction product was purified by FCC (0-100% EtOAc in petroleum ether) to give the title compound as a yellow oil (Y=52%). $^1$H NMR (400 MHz, DMSO-$d_6$) δ ppm 7.96 (s, 1H), 7.50 (s, 1H), 4.21-4.14 (m, 1H), 3.84 (s, 3H), 2.87-2.81 (m, 1H), 1.83-1.77 (m, 1H), 1.65-1.59 (m, 1H), 1.39 (s, 9H), 1.18-1.07 (m, 4H).

Step 3: 2,2,2-trifluoro-N-(1-methylpyrazol-4-yl)-N-(3-piperidyl)acetamide hydrochloride. A solution of tert-butyl 3-[(1-methylpyrazol-4-yl)-(2,2,2-trifluoroacetyl)amino]piperidine-1-carboxylate (2.0 g, 5.31 mmol) and 4M HCl in EtOAc (1.33 ml, 5.31 mmol) was stirred at rt for 3 h. The solution was concentrated in vacuo to give the title compound as a yellow solid (Y=90%). $^1$H NMR (400 MHz, DMSO-$d_6$) δ ppm 7.99 (s, 1H), 7.92-7.62 (br. s, 2H), 7.52 (s, 1H), 4.73-4.66 (m, 1H), 3.85 (s, 3H), 3.38-3.30 (m, 1H), 3.14-3.06 (m, 1H), 2.69-2.62 (m, 1H), 2.49-2.43 (m, 1H), 1.87-1.75 (m, 3H), 1.36-1.26 (m, 1H).

Step 4: N-(1-ethyl-3-piperidyl)-2,2,2-trifluoro-N-(1-methylpyrazol-4-yl)acetamide trifluoroacetate. To a solution of 2,2,2-trifluoro-N-(1-methylpyrazol-4-yl)-N-(3-piperidyl)acetamide hydrochloride (1.13 g, 3.62 mmol) in DMF (10 ml) was added iodoethane (579 μl, 7.24 mmol) and $K_2CO_3$ (1.00 g, 7.24 mmol). The mixture was stirred at rt for 3 h then concentrated in vacuo. The residue was purified by prep-HPLC (column: Phenomenex Luna C18 10 μm 250×50 mm; mobile phase: [water (0.1% TFA)-ACN]; B: 1-20%, 20 min) to give the title compound as a yellow oil (Y=40%). $^1$H NMR (400 MHz, DMSO-$d_6$) δ ppm 9.69 (s, 1H), 7.98 (s, 1H), 7.54 (s, 1H), 4.72-4.65 (m, 1H), 3.85 (s, 3H), 3.61 (d, J=11 Hz, 1H), 3.37 (d, J=12 Hz, 1H), 3.16-3.08 (m, 2H), 2.74-2.59 (m, 2H), 1.93-1.84 (m, 2H), 1.78-1.68 (m, 1H), 1.27-1.20 (m, 4H).

Step 5: 1-ethyl-N-(1-methylpyrazol-4-yl)piperidin-3-amine trifluoroacetate. To a solution of N-(1-ethyl-3-piperidyl)-2,2,2-trifluoro-N-(1-methylpyrazol-4-yl)acetamide trifluoroacetate (756 mg, 1.81 mmol) in MeOH (5 ml) and $H_2O$ (5 ml) was added NaOH (145 mg, 3.61 mmol). The RM was stirred at rt for 5 h. The solution was concentrated in vacuo. The crude product was purified by prep-HPLC (column: Phenomenex Luna C18 10 μm 250×50 mm; mobile phase: [water (0.1% TFA)-ACN]; B: 0-15%, 23 min) to give the title compound as a yellow oil (Y=65%). $^1$H NMR (400 MHz, DMSO-$d_6$) δ ppm 9.41 (s, 1H), 7.20 (s, 1H), 7.04 (s, 1H), 3.71 (s, 3H), 3.52-3.34 (m, 2H), 3.24-3.00 (m, 4H), 2.81-2.69 (m, 1H), 2.02-1.89 (m, 2H), 1.77-1.65 (m, 2H), 1.32-1.18 (m, 4H).

Step 6: 1-[(1-ethylpiperidin-3-yl)(1-methyl-1H-pyrazol-4-yl)sulfamoyl]-3-(1,2,3,5,6,7-hexahydro-s-indacen-4-yl)urea sodium salt. General procedure B was followed using {[(1,2,3,5,6,7-hexahydro-s-indacen-4-yl)carbamoyl]amino}sulfonyl chloride and 1-ethyl-N-(1-methylpyrazol-4-yl)piperidin-3-amine trifluoroacetate. The crude product was purified by prep-HPLC (column: Xtimate C18 10 μm 250× 50 mm; mobile phase: [water (10 mM $NH_4HCO_3$)-ACN]; B: 1-33%, 25 min) to give the title compound as an off-white solid (Y=10%). $^1$H NMR (400 MHz, methanol-$d_4$) δ ppm 7.67 (s, 1H), 7.44 (s, 1H), 6.94 (s, 1H), 4.41-4.33 (m, 1H), 3.87 (s, 3H), 3.67-3.59 (m, 1H), 3.23-3.15 (m, 1H), 2.93-2.78 (m, 10H), 2.52-2.25 (m, 2H), 2.12-1.98 (m, 5H), 1.94-1.85 (m, 1H), 1.83-1.69 (m, 1H), 1.31-1.18 (m, 4H). LC-MS (ESI): m/z: [M+H]$^+$=487.2

Example 63. 1-{[2-(azetidin-1-yl)ethyl](1-methyl-1H-pyrazol-4-yl)sulfamoyl}-3-(1,2,3,5,6,7-hexahydro-s-indacen-4-yl)urea sodium salt

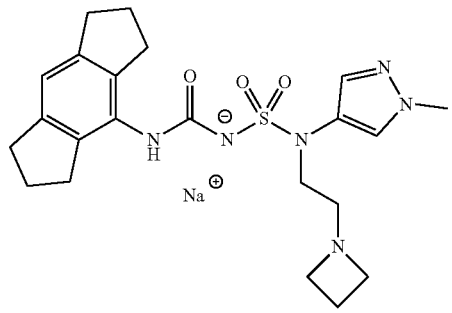 [SMILES: Cn1cc(N(CCN2CCC2)S(=O)(=O)[N-]C(=O)Nc2c3c(cc4c2CCC4)CCC3)cn1 ; [Na+]]

Step 1: N-[2-(azetidin-1-yl)ethyl]-1-methyl-pyrazol-4-amine trifluoroacetate. To a solution of 1-methylpyrazol-4-amine (406 mg, 4.18 mmol) in DMF (2 ml) was added 1-(2-chloroethyl)azetidine (500 mg, 4.18 mmol), $Cs_2CO_3$ (2.04 g, 6.27 mmol) and KI (763 mg, 4.60 mmol). The RM was stirred at 100° C. for 12 h. The solvent was removed under reduced pressure. The residue was purified by prep-HPLC (column: Phenomenex Luna C18 10 μm 250×50 mm; mobile phase: [water (0.1% TFA)-ACN]; B: 0-5%, 20 min) to give the title compound as a colourless oil. $^1$H NMR (400 MHz, methanol-$d_4$) δ ppm 7.20 (s, 1H), 7.13 (s, 1H), 4.29-4.02 (m, 4H), 3.78 (s, 3H), 3.37-3.33 (m, 2H), 3.21-3.13 (m, 2H), 2.69-2.34 (m, 2H).

Step 2: 1-{[2-(azetidin-1-yl)ethyl](1-methyl-1H-pyrazol-4-yl)sulfamoyl}-3-(1,2,3,5,6,7-hexahydro-s-indacen-4-yl)urea sodium salt. General procedure B was followed using {[(1,2,3,5,6,7-hexahydro-s-indacen-4-yl)carbamoyl]amino}sulfonyl chloride and N-[2-(azetidin-1-yl)ethyl]-1-methyl-pyrazol-4-amine trifluoroacetate. The crude product was purified by prep-HPLC (column: YMC-Triart prep C18-s 250×50 mm; mobile phase: [water (10 mM $NH_4HCO_3$)-ACN]; B: 1-31%, 20 min) to give the title compound as a white solid (Y=5%). $^1$H NMR (400 MHz, methanol-$d_4$) δ ppm 7.67 (s, 1H), 7.50 (s, 1H), 6.92 (s, 1H), 4.27-4.06 (m, 4H), 3.85 (s, 3H), 3.81-3.75 (m, 2H), 3.28-3.22 (m, 2H), 2.86 (t, J=7 Hz, 4H), 2.80 (t, J=7 Hz, 4H), 2.53-2.40 (m, 2H), 2.12-2.01 (m, 4H). LC-MS (ESI): m/z: [M+H]$^+$=459.2

Example 64. 3-(1,2,3,5,6,7-hexahydro-s-indacen-4-yl)-1-[(1-methyl-1H-pyrazol-4-yl)[1-(propan-2-yl)azetidin-3-yl]sulfamoyl]urea sodium salt

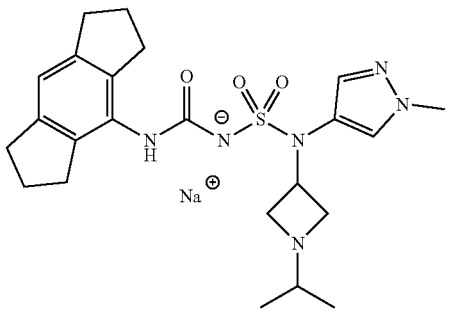 [SMILES: CC(C)N1CC(N(c2cnn(C)c2)S(=O)(=O)[N-]C(=O)Nc2c3c(cc4c2CCC4)CCC3)C1 ; [Na+]]

Step 1: tert-butyl 3-[(1-methylpyrazol-4-yl)amino]azetidine-1-carboxylate. General procedure A was followed using 1-methylpyrazol-4-amine and tert-butyl 3-oxoazetidine-1-carboxylate. The crude product was purified by prep-HPLC (column: Agela Innoval ods-2 350×100 mm; mobile phase: [water (0.1% TFA)-ACN]; B: 3-35%, 23 min) to give the title compound as a red solid (Y=58%). $^1$H NMR (400 MHz, methanol-$d_4$) δ ppm 7.24 (s, 1H), 7.16 (s, 1H), 4.22-4.14 (m, 2H), 4.03-3.99 (m, 1H), 3.80 (s, 3H), 3.76-3.70 (m, 2H), 1.44 (s, 9H).

Step 2: tert-butyl 3-[(1-methylpyrazol-4-yl)-(2,2,2-trifluoroacetyl)amino]azetidine-1-carboxylate. To a solution of tert-butyl 3-[(1-methylpyrazol-4-yl)amino]azetidine-1-carboxylate (1.5 g, 5.95 mmol) and triethylamine (1.65 ml, 11.9 mmol) in DCM (15 ml) cooled to 0° C. was added dropwise (2,2,2-trifluoroacetyl)2,2,2-trifluoroacetate (0.99 ml, 7.13 mmol). The RM was stirred at 0° C. for 2 h. The solvent was removed under reduced pressure to give a residue. The residue was purified by FCC (0-40% ethyl acetate in petroleum ether) to give the title compound as a yellow oil (Y=63%). $^1$H NMR (400 MHz, methanol-$d_4$) δ=7.94 (s, 1H), 7.62 (s, 1H), 5.23-5.16 (m, 1H), 4.17-4.11 (m, 2H), 3.95 (s, 3H), 3.83-3.77 (m, 2H), 1.38 (s, 9H).

Step 3: N-(azetidin-3-yl)-2,2,2-trifluoro-N-(1-methylpyrazol-4-yl)acetamide hydrochloride. A mixture of tert-butyl 3-[(1-methylpyrazol-4-yl)-(2,2,2-trifluoroacetyl)amino]azetidine-1-carboxylate (1.0 g, 2.16 mmol) in 4M HCl in EtOAc (10 ml) was stirred at rt for 23 h. The solvent was removed under reduced pressure to give a residue. The residue was purified by prep-HPLC (column: Phenomenex Luna C18 10 μm 250×50 mm; mobile phase: [water (0.1% TFA)-ACN]; B: 1-20%, 20 min) to give the title compound as a white solid (Y=49%). $^1$H NMR (400 MHz, methanol-$d_4$) δ=7.94 (s, 1H), 7.64 (s, 1H), 5.32 (q, J=8 Hz, 1H), 4.28-4.22 (m, 2H), 4.16-4.11 (m, 2H), 3.96 (s, 3H).

Step 4: 2,2,2-trifluoro-N-(1-isopropylazetidin-3-yl)-N-(1-methylpyrazol-4-yl)acetamide hydrochloride. General Procedure A was followed using N-(azetidin-3-yl)-2,2,2-trifluoro-N-(1-methylpyrazol-4-yl)acetamide hydrochloride and acetone to give the title compound as a white solid (Y=89%). $^1$H NMR (400 MHz, methanol-$d_4$) δ=7.91 (s, 1H), 7.59 (s, 1H), 5.03-4.99 (m, 1H), 4.04-3.96 (m, 2H), 3.94 (s, 3H), 3.92-3.86 (m, 1H), 3.60-3.47 (m, 2H), 1.06 (d, J=6 Hz, 6H).

Step 5: N-(1-isopropylazetidin-3-yl)-1-methyl-pyrazol-4-amine trifluoroacetate. To a solution of 2,2,2-trifluoro-N-(1-isopropylazetidin-3-yl)-N-(1-methylpyrazol-4-yl)acetamide hydrochloride (254 mg, 0.78 mmol) in MeOH (1.5 ml) and H$_2$O (1.5 ml) was added NaOH (62 mg, 1.55 mmol). The mixture was stirred at rt for 2 h. The solvent was removed under reduced pressure to give a residue. The residue was purified by prep-HPLC (column: Phenomenex Luna C18 10 μm 250×50 mm; mobile phase: [water (0.1% TFA)-ACN]; B: 0-5%, 20 min) to give the title compound as a colourless liquid (Y=67%). $^1$H NMR (400 MHz, methanol-$d_4$) δ=7.22-7.14 (m, 1H), 7.12 (s, 1H), 4.50-4.42 (m, 1H), 4.34-4.26 (m, 1H), 4.14-4.10 (m, 1H), 4.01-3.94 (m, 1H), 3.93-3.84 (m, 1H), 3.78 (s, 3H), 3.45-3.38 (m, 1H), 1.25 (d, J=6 Hz, 6H).

Step 6: 3-(1,2,3,5,6,7-hexahydro-s-indacen-4-yl)-1-[(1-methyl-1H-pyrazol-4-yl)[1-(propan-2-yl)azetidin-3-yl]sulfamoyl]urea sodium salt. General procedure B was followed using {[(1,2,3,5,6,7-hexahydro-s-indacen-4-yl)carbamoyl]amino}sulfonyl chloride and N-(1-isopropylazetidin-3-yl)-1-methyl-pyrazol-4-amine trifluoroacetate. The crude product was purified by prep-HPLC (column: Xtimate C18 10 μm 250×50 mm; mobile phase: [water (10 mM NH$_4$HCO$_3$)-ACN]; B: 1-30%, 25 min) to give the title compound as a white solid (Y=11%). $^1$H NMR (400 MHz, methanol-$d_4$) δ ppm 7.70 (s, 1H), 7.52 (s, 1H), 6.92 (s, 1H), 5.09-5.05 (m, 1H), 4.21-4.11 (m, 2H), 3.88-3.82 (m, 5H), 3.16-3.08 (m, 1H), 2.86 (t, J=7 Hz, 4H), 2.79 (t, J=7 Hz, 4H), 2.11-2.01 (m, 4H), 1.11 (d, J=6 Hz, 6H). LC-MS (ESI): m/z: [M+H]$^+$=473.2

Example 65. 3-(1,2,3,5,6,7-hexahydro-s-indacen-4-yl)-1-[(1-methyl-1H-pyrazol-4-yl)[1-(2,2,2-trifluoroethyl)piperidin-4-yl]sulfamoyl]urea sodium salt

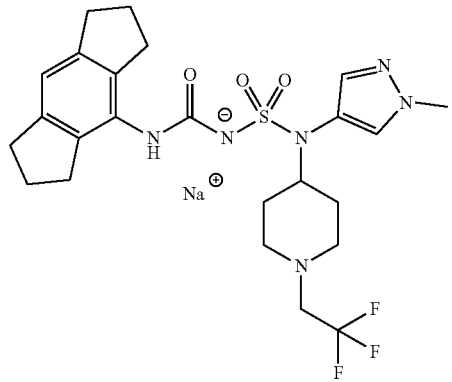 [SMILES: Cn1cc(N(C2CCN(CC(F)(F)F)CC2)S(=O)(=O)[N-]C(=O)Nc2c3c(cc4c2CCC4)CCC3)cn1 ; [Na+]]

Step 1: 2,2,2-trifluoro-1-[4-[(1-methylpyrazol-4-yl)amino]-1-piperidyl]ethanone. To a solution of N-(1-methylpyrazol-4-yl) piperidin-4-amine hydrochloride (800 mg, 3.69 mmol) (for synthesis refer to Example 45) in MeOH (8 ml) was added ethyl 2,2,2-trifluoroacetate (6.66 ml, 48.3 mmol) and DIPEA (1.29 ml, 7.38 mmol). The RM was stirred at rt for 10 h. The solution was concentrated in vacuo. The residue was purified by prep-HPLC (column: Phenomenex Luna C18 10 μm 250×50 mm; mobile phase: [water (0.1% TFA)-ACN]; B: 0-30%, 20 min) to give the title compound as a yellow oil (Y=85%). $^1$H NMR (400 MHz, DMSO-$d_6$) δ=7.90 (s, 1H), 7.53 (s, 1H), 4.35-4.27 (m, 1H), 3.94-3.86 (m, 1H), 3.83 (s, 3H), 3.60-3.50 (m, 1H), 3.27 (t, J=12 Hz, 1H), 2.92 (t, J=12 Hz, 1H), 2.08-1.98 (m, 2H), 1.53-1.37 (m, 2H). NH not seen.

Step 2: N-(1-methylpyrazol-4-yl)-1-(2,2,2-trifluoroethyl) piperidin-4-amine trifluoroacetate. To a solution of 2,2,2-trifluoro-1-[4-[(1-methylpyrazol-4-yl)amino]-1-piperidyl]ethanone (870 mg, 3.15 mmol) was added 10 M BH$_3$-Me$_2$S (10 ml). The mixture was stirred at rt for 24 h. The reaction mixture was quenched by addition of MeOH (10 ml) at 0° C., then concentrated in vacuo. The residue was purified by prep-HPLC column: Phenomenex Luna C18 10 µm 250×50 mm; mobile phase: [water (0.1% TFA)-ACN]; B: 1-25%, 20 min) to give the title compound (Y=10%). $^1$H NMR (400 MHz, DMSO-d$_6$) δ=7.98 (s, 1H), 7.60 (s, 1H), 3.86 (s, 3H), 3.34-3.20 (m, 3H), 3.01-2.93 (m, 2H), 2.39 (t, J=12 Hz, 2H), 1.89-1.81 (m, 2H), 1.59-1.49 (m, 2H). NH protons not seen.

Step 3: 3-(1,2,3,5,6,7-hexahydro-s-indacen-4-yl)-1-[(1-methyl-1H-pyrazol-4-yl)[1-(2,2,2-trifluoroethyl)piperidin-4-yl]sulfamoyl]urea sodium salt. General procedure B was followed using {[(1,2,3,5,6,7-hexahydro-s-indacen-4-yl)carbamoyl]amino}sulfonyl chloride and N-(1-methylpyrazol-4-yl)-1-(2,2,2-trifluoroethyl) piperidin-4-amine trifluoroacetate. The crude product was purified by prep-HPLC (column: Xtimate C18 10 µm 250×50 mm; mobile phase: [water (10 mM NH$_4$HCO$_3$)-ACN]; B: 5-40%, 30 min) to give the title compound as a yellow solid (Y=10%). $^1$H NMR (400 MHz, methanol-d$_4$) δ ppm 7.71 (s, 1H), 7.43 (s, 1H), 6.99 (s, 1H), 4.17-4.02 (m, 1H), 3.90 (s, 3H), 3.04-2.93 (m, 4H), 2.91-2.77 (m, 8H), 2.48 (t, J=12 Hz, 2H), 2.13-2.03 (m, 5H), 1.94-1.84 (m, 2H), 1.54-1.41 (m, 2H). LC-MS (ESI): m/z: [M+H]$^+$=541.2

Example 66. 3-(1,2,3,5,6,7-hexahydro-s-indacen-4-yl)-1-[(1-methyl-1H-pyrazol-4-yl)({2-oxaspiro[3.3]heptan-6-yl})sulfamoyl]urea sodium salt

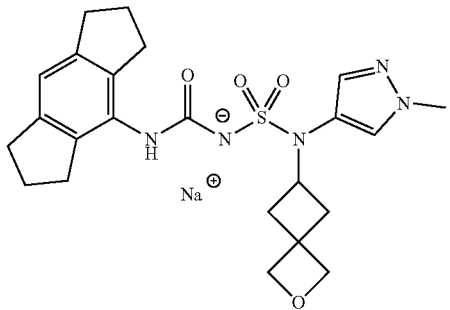 [SMILES: Cn1cc(N(C2CC3(COC3)C2)S(=O)(=O)[N-]C(=O)Nc2c3c(cc4c2CCC4)CCC3)cn1 ; [Na+]]

Step 1: 1-methyl-N-(2-oxaspiro[3.3]heptan-6-yl)pyrazol-4-amine trifluoroacetate. General procedure A was followed using 1-methylpyrazol-4-amine and 2-oxaspiro[3.3]heptan-6-one. The crude product was purified by prep-HPLC (column: C18; mobile phase: [water (0.1% TFA)-ACN]) to give the title compound as a red oil (Y=36%). $^1$H NMR (400 MHz, methanol-d$_4$) δ ppm 8.10 (s, 1H), 7.77 (s, 1H), 4.47 (s, 1H), 3.93 (s, 3H), 3.82 (s, 2H), 3.76 (s, 2H), 2.20 (d, J=6 Hz, 2H), 1.87-1.81 (m, 2H).

Step 2: 3-(1,2,3,5,6,7-hexahydro-s-indacen-4-yl)-1-[(1-methyl-1H-pyrazol-4-yl)({2-oxaspiro[3.3]heptan-6-yl})sulfamoyl]urea sodium salt. General procedure B was followed using {[(1,2,3,5,6,7-hexahydro-s-indacen-4-yl)carbamoyl]amino}sulfonyl chloride and 1-methyl-N-(2-oxaspiro[3.3]heptan-6-yl)pyrazol-4-amine trifluoroacetate. The crude product was purified by prep-HPLC (column: YMC-Actus Triart C18 5 µm 250×50 mm; mobile phase: [water (10 mM NH$_4$HCO$_3$)-ACN]; B: 1-35%, 20 min) to give the title compound as a white solid (Y=1%). $^1$H NMR (400 MHz, methanol-d$_4$) δ ppm 7.25 (s, 1H), 7.19 (s, 1H), 6.99 (s, 1H), 4.52 (s, 2H), 3.97 (s, 1H), 3.78 (s, 3H), 3.15 (s, 2H), 2.87 (t, J=7 Hz, 4H), 2.79 (t, J=7 Hz, 4H), 2.09-2.01 (m, 4H), 1.93-1.86 (m, 2H), 1.65-1.58 (m, 2H). LC-MS (ESI): m/z: [M+H]$^+$=472.2

Example 67. 3-(1,2,3,5,6,7-hexahydro-s-indacen-4-yl)-1-[(1-methyl-1H-pyrazol-4-yl)(l-methylazepan-4-yl)sulfamoyl]urea sodium salt

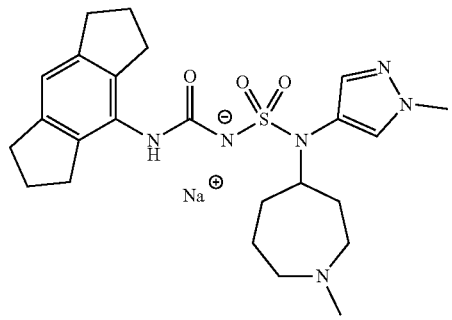 [SMILES: CN1CCCC(N(c2cnn(C)c2)S(=O)(=O)[N-]C(=O)Nc2c3c(cc4c2CCC4)CCC3)CC1 ; [Na+]]

Step 1: tert-butyl 4-[(1-methylpyrazol-4-yl)amino]azepane-1-carboxylate. General procedure A was followed using 1-methylpyrazol-4-amine and tert-butyl 4-oxoazepane-1-carboxylate. The crude product was purified by prep-HPLC (column: Agela Innoval ods-2 250×80 mm; mobile phase: [water (0.1% TFA)-ACN]; B: 5-38%, 20 min) to give the title compound as a red solid (Y=33%). $^1$H NMR (400 MHz, methanol-d$_4$) δ ppm 7.16 (s, 1H), 7.11 (s, 1H), 3.78 (s, 3H), 3.52-3.45 (m, 1H), 3.43-3.40 (m, 1H), 3.39-3.36 (m, 1H), 3.27-3.25 (m, 1H), 3.01-2.96 (m, 1H), 2.06-1.96 (m, 1H), 1.95-1.87 (m, 1H), 1.86-1.78 (m, 1H), 1.62-1.53 (m, 3H), 1.47 (s, 9H).

Step 2: 1-methyl-N-(1-methylpyrazol-4-yl)azepan-4-amine trifluoroacetate. To a solution of tert-butyl 4-[(1-methylpyrazol-4-yl)amino]azepane-1-carboxylate (1.0 g, 3.40 mmol) in THF (10 ml) cooled to 0° C. was added lithium aluminium hydride (0.93 g, 24.5 mmol). The RM was stirred at 0° C. for 0.5 h, then heated at 85° C. for 2.5 h. The reaction mixture was quenched with water (1 ml) and 8% NaOH aqueous solution (1 ml). The mixture was filtered and the filtrate evaporated under reduced pressure to give a residue. The residue was purified by prep-HPLC (column: Phenomenex Luna C18 10 µm 250×50 mm; mobile phase: [water (0.1% TFA)-ACN]; B: 0-5%, 20 min) to give the title compound as a yellow solid (Y=37%). $^1$H NMR (400 MHz, methanol-d$_4$) δ ppm 7.69 (s, 1H), 7.47 (s, 1H), 3.88 (s, 3H), 3.59-3.48 (m, 3H), 3.21-3.04 (m, 2H), 2.91 (s, 3H), 2.56-1.81 (m, 6H).

Step 3: 3-(1,2,3,5,6,7-hexahydro-s-indacen-4-yl)-1-[(1-methyl-1H-pyrazol-4-yl)(1-methylazepan-4-yl)sulfamoyl]urea sodium salt. General procedure B was followed using {[(1,2,3,5,6,7-hexahydro-s-indacen-4-yl)carbamoyl]amino}sulfonyl chloride and 1-methyl-N-(1-methylpyrazol-4-yl)azepan-4-amine trifluoroacetate. The crude product was purified by prep-HPLC (column: YMC-Actus Triart C18 5 µm 250×50 mm; mobile phase: [water (10 mM NH$_4$HCO$_3$)-ACN]; B: 5-35%, 20 min) to give the title compound as a white solid (Y=15%). $^1$H NMR (400 MHz, methanol-d$_4$) δ ppm 7.69 (s, 1H), 7.45 (s, 1H), 6.94 (s, 1H), 4.43-4.38 (m, 1H), 3.86 (s, 3H), 3.16-3.09 (m, 4H), 2.95-2.76 (m, 8H), 2.71 (s, 3H), 2.42-2.28 (m, 1H), 2.25-2.12 (m, 1H), 2.05-1.95 (m, 4H), 1.86-1.78 (m, 3H), 1.62-1.58 (m, 1H). LC-MS (ESI): m/z: [M+H]$^+$=487.2

Example 68. 3-(1,2,3,5,6,7-hexahydro-s-indacen-4-yl)-1-[(1-methyl-1H-pyrazol-4-yl)[(1-methylpyrrolidin-2-yl)methyl]sulfamoyl]urea sodium salt

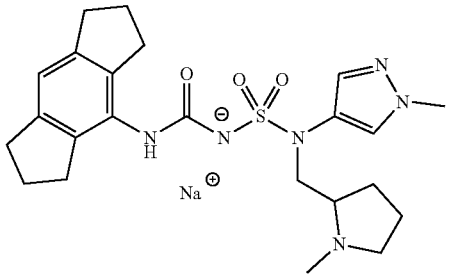 [SMILES: CN1CCCC1CN(c1cnn(C)c1)S(=O)(=O)[N-]C(=O)Nc1c2c(cc3c1CCC3)CCC2 ; [Na+]]

Step 1: tert-butyl 2-[[(1-methylpyrazol-4-yl)amino]methyl]pyrrolidine-1-carboxylate. General procedure A was followed using 1-methylpyrazol-4-amine and tert-butyl 2-formylpyrrolidine-1-carboxylate. The crude product was purified by prep-HPLC (column: Phenomenex Luna C18 10 μm 250×50 mm; mobile phase: [water (0.1% TFA)-ACN]; B: 5-35%, 20 min) to give the title compound as a yellow oil (Y=28%). $^1$H NMR (400 MHz, methanol-$d_4$) δ ppm 7.20 (s, 1H), 7.11 (s, 1H), 4.01-3.91 (m, 1H), 3.76 (s, 3H), 3.38-3.30 (m, 2H), 3.18-3.10 (m, 1H), 2.90-2.85 (m, 1H), 1.95-1.75 (m, 4H), 1.47 (s, 9H).

Step 2: 1-methyl-N-[(1-methylpyrrolidin-2-yl)methyl]pyrazol-4-amine trifluoroacetate. To a solution of tert-butyl 2-[[(1-methylpyrazol-4-yl)amino]methyl]pyrrolidine-1-carboxylate (50 mg, 0.18 mmol) in THF (1 ml) was added lithium aluminium hydride (68 mg, 1.78 mmol). The RM was stirred at 80° C. for 1 h. The mixture was diluted with $H_2O$ (0.8 ml) and then 10% aqueous sodium hydroxide solution (0.8 ml). The RM was filtered under reduced pressure and the filtrate concentrated under reduced pressure to give a residue. The residue was purified by prep-HPLC (TFA condition; column: Phenomenex Luna C18 10 μm 250×50 mm; mobile phase: [water (0.1% TFA)-ACN]; B: 0-5%, 20 min) to give the title compound as red liquid.

Step 3: 3-(1,2,3,5,6,7-hexahydro-s-indacen-4-yl)-1-[(1-methyl-1H-pyrazol-4-yl)[(1-methylpyrrolidin-2-yl)methyl]sulfamoyl]urea sodium salt. General procedure B was followed using {[(1,2,3,5,6,7-hexahydro-s-indacen-4-yl)carbamoyl]amino}sulfonyl chloride and 1-methyl-N-[(1-methylpyrrolidin-2-yl)methyl]pyrazol-4-amine trifluoroacetate. The crude product was purified by prep-HPLC (column: Waters Xbridge Prep OBD C18 10 μm 150×40 mm; mobile phase: [water (10 mM $NH_4HCO_3$)-ACN]; B: 15-35%, 11 min) to give the title compound as a white solid (Y=3%). $^1$H NMR (400 MHz, methanol-$d_4$) δ ppm 7.70 (s, 1H), 7.55 (s, 1H), 6.92 (s, 1H), 4.21-4.13 (m, 1H), 3.86 (s, 3H), 3.82-3.75 (m, 3H), 3.53-3.41 (m, 1H), 3.14-3.09 (m, 2H), 2.93 (s, 3H), 2.88-2.83 (m, 8H), 2.14-1.97 (m, 6H). LC-MS (ESI): m/z: [M+H]$^+$=473.2

Example 69. 3-(1,2,3,5,6,7-hexahydro-s-indacen-4-yl)-1-[(1-methyl-1H-pyrazol-4-yl)[2-(2,2,2-trifluoroethyl)-2-azaspiro[3.3]heptan-6-yl]sulfamoyl]urea sodium salt

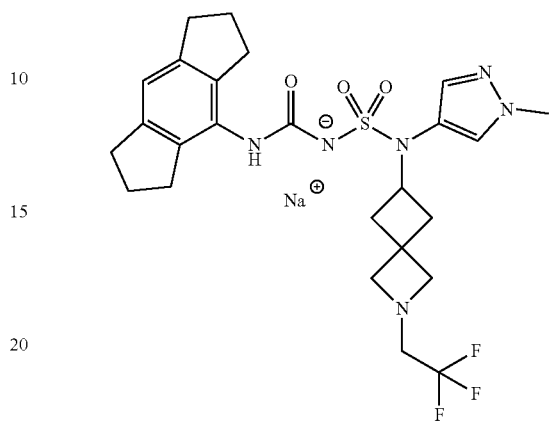

Step 1: N-(1-methylpyrazol-4-yl)-2-azaspiro[3.3]heptan-6-amine hydrochloride. A mixture of tert-butyl 6-[(1-methylpyrazol-4-yl)amino]-2-azaspiro[3.3]heptane-2-carboxylate (600 mg, 2.05 mmol) (for synthesis refer to Example 58) in 4M HCl in EtOAc (0.51 ml, 2.05 mmol) was stirred at rt for 16 h. The solution was concentrated in vacuo to give the title compound as a yellow solid (Y=85%). $^1$H NMR (400 MHz, DMSO-$d_6$) δ ppm 12.00-11.60 (br. s, 1H), 9.02 (s, 1H), 8.20 (s, 1H), 8.05-8.01 (m, 1H), 7.59 (d, J=7 Hz, 1H), 4.09-3.90 (m, 5H), 3.85 (s, 3H), 3.11-3.04 (m, 1H), 2.56-2.51 (m, 2H), 2.41-2.30 (m, 1H).

Step 2: 2,2,2-trifluoro-1-[6-[(1-methylpyrazol-4-yl)amino]-2-azaspiro[3.3]heptan-2-yl]ethanone. To a solution of N-(1-methylpyrazol-4-yl)-2-azaspiro[3.3]heptan-6-amine hydrochloride (400 mg, 1.75 mmol) in MeOH (1 ml) was added ethyl 2,2,2-trifluoroacetate (3.36 ml, 24.4 mmol). The solution was stirred at rt for 1 h. DIPEA (0.91 ml, 5.25 mmol) was added and the RM was stirred at rt for 14 h. The solution was concentrated in vacuo. The crude reaction product was purified by prep-TLC (10:1 ethyl acetate/methanol. Rf=0.56) to give the title compound as a yellow oil (Y=40%). LC-MS (ESI): m/z: [M+H]$^+$=289.2

Step 3: N-(1-methylpyrazol-4-yl)-2-(2,2,2-trifluoroethyl)-2-azaspiro[3.3]heptan-6-amine trifluoroacetate. A mixture of 2,2,2-trifluoro-1-[6-[(1-methylpyrazol-4-yl)amino]-2-azaspiro[3.3]heptan-2-yl]ethanone (200 mg, 0.69 mmol) in 10 M $BH_3$-$Me_2S$ (3 ml) was stirred at rt for 7 h. The solution was cooled to 0° C. and MeOH (20 ml) was added dropwise. The RM was concentrated in vacuo. The crude reaction product was purified by prep-HPLC (column: Phenomenex Luna C18 10 μm 250×50 mm; mobile phase: [water (0.1% TFA)-ACN]; B: 1-20%, 20 min) to give the title compound as a yellow oil (Y=22%). $^1$H NMR (400 MHz, DMSO-$d_6$) δ ppm 8.35 (s, 1H), 7.69 (s, 1H), 4.31 (s, 1H), 3.80 (s, 3H), 3.69-3.58 (m, 6H), 3.17-3.11 (m, 2H), 2.25-2.19 (m, 1H), 2.01 (s, 1H).

Step 4: 3-(1,2,3,5,6,7-hexahydro-s-indacen-4-yl)-1-[(1-methyl-1H-pyrazol-4-yl)[2-(2,2,2-trifluoroethyl)-2-azaspiro[3.3]heptan-6-yl]sulfamoyl]urea sodium salt. General procedure B was followed using {[(1,2,3,5,6,7-hexahydro-s-indacen-4-yl)carbamoyl]amino}sulfonyl chloride and N-(1-methylpyrazol-4-yl)-2-(2,2,2-trifluoroethyl)-2-azaspiro[3.3]heptan-6-amine trifluoroacetate. The crude product was purified by prep-HPLC (column: Xtimate C18 5 μm 150×25 mm; mobile phase: [water (10 mM NH₄HCO₃)-ACN]; B: 30-40%, 12 min) to give the title compound as an off-white solid (Y=7%). ¹H NMR (400 MHz, methanol-d₄) δ ppm 7.72 (s, 1H), 7.44 (s, 1H), 6.99 (s, 1H), 4.63-4.58 (m, 1H), 3.90 (s, 3H), 3.44 (s, 2H), 3.19 (s, 2H), 3.08-3.00 (m, 2H), 2.90-2.76 (m, 8H), 2.46-2.41 (m, 2H), 2.12-2.00 (m, 6H). LC-MS (ESI): m/z: [M+H]⁺=553.2

Example 70. 3-(3,5-diethylphenyl)-1-[(1-methyl-1H-pyrazol-4-yl)(oxan-4-yl)sulfamoyl]urea sodium salt

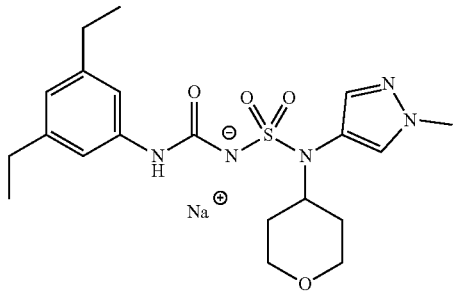 [SMILES: CCc1cc(CC)cc(NC(=O)[N-]S(=O)(=O)N(c2cnn(C)c2)C2CCOCC2)c1 ; [Na+]]

Step 1: N-[(3,5-diethylphenyl)carbamoyl]sulfamoyl chloride. To a solution of N-(oxomethylene)sulfamoyl chloride (58 μl, 0.67 mmol) in isopropyl ether (1 ml) cooled to −30° C. was added a solution of 3,5-diethylaniline (156 μl, 0.67 mmol) in isopropyl ether (1 ml). The RM was stirred at −30° C. for 2 h to give the title compound as a solution in isopropyl ether (2 ml). This was used immediately.

Step 2: 3-(3,5-diethylphenyl)-1-[(1-methyl-1H-pyrazol-4-yl)(oxan-4-yl)sulfamoyl]urea sodium salt. General procedure B was followed using N-[(3,5-diethylphenyl)carbamoyl]sulfamoyl chloride and 1-methyl-N-tetrahydropyran-3-yl-pyrazol-4-amine (for synthesis refer to Example 1). The crude product was purified by prep-HPLC (column: Nano-Micro Unisil 8-120 C18 Ultra Plus 250×50 mm; mobile phase: [water (10 mM NH₄HCO₃)-ACN]; B: 0-30%, 26 min) to give the title compound as a white solid (Y=2%). ¹H NMR (400 MHz, methanol-d₄) δ ppm 7.68 (s, 1H), 7.42 (s, 1H), 7.07 (s, 2H), 6.70 (s, 1H), 4.38-4.19 (m, 1H), 3.96-3.88 (m, 2H), 3.83 (s, 3H), 3.52-3.44 (m, 2H), 2.58 (q, J=7 Hz, 4H), 1.94-1.86 (m, 2H), 1.51-1.38 (m, 2H), 1.21 (t, J=7 Hz, 6H). LC-MS (ESI): m/z: [M+H]⁺=436.2

Example 71. 1-[(1-methyl-1H-pyrazol-4-yl)(oxan-4-yl)sulfamoyl]-3-[3-(propan-2-yl)phenyl]urea sodium salt

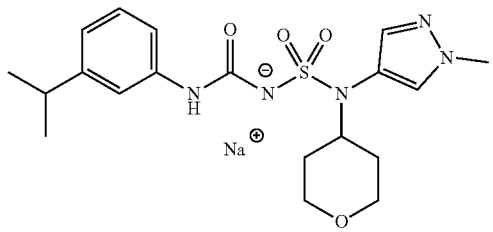 [SMILES: CC(C)c1cccc(NC(=O)[N-]S(=O)(=O)N(c2cnn(C)c2)C2CCOCC2)c1 ; [Na+]]

Step 1: N-[(3-isopropylphenyl)carbamoyl]sulfamoyl chloride. To a solution of N-(oxomethylene)sulfamoyl chloride (96 μl, 1.11 mmol) in isopropyl ether (2 ml) cooled to −30° C. was added a solution of 3-isopropylaniline (156 μl, 1.11 mmol) in isopropyl ether (2 ml). The mixture was stirred at −30° C. for 2 h to give the title compound as a solution in isopropyl ether (4 ml) (Y=98%). LC-MS in MeOH (ESI): m/z: [M+MeOH+H]⁺=273.1

Step 2: 1-[(1-methyl-1H-pyrazol-4-yl)(oxan-4-yl)sulfamoyl]-3-[3-(propan-2-yl)phenyl]urea sodium salt. General procedure B was followed using N-[(3-isopropylphenyl)carbamoyl]sulfamoyl chloride and 1-methyl-N-tetrahydropyran-3-yl-pyrazol-4-amine (for synthesis refer to Example 1). The crude product was purified by prep-HPLC (column: Nano-Micro Unisil 8-120 C18 Ultra Plus 250×50 mm; mobile phase: [water (10 mM NH₄HCO₃)-ACN]; B: 0-30%, 25 min) to give the title compound as a white solid (Y=24%). ¹H NMR (400 MHz, methanol-d₄) δ ppm 7.72 (s, 1H), 7.44 (s, 1H), 7.27-7.19 (m, 3H), 6.99 (d, J=6 Hz, 1H), 4.41-4.31 (m, 1H), 3.99-3.88 (m, 2H), 3.86 (s, 3H), 3.54-3.44 (m, 2H), 2.99-2.82 (m, 1H), 1.92-1.84 (m, 2H), 1.52-1.42 (m, 2H), 1.24 (d, J=7 Hz, 6H). LC-MS (ESI): m/z: [M+H]⁺=422.1

Example 72. 3-(3,5-dichlorophenyl)-1-[(1-methyl-1H-pyrazol-4-yl)(oxan-4-yl)sulfamoyl]urea sodium salt

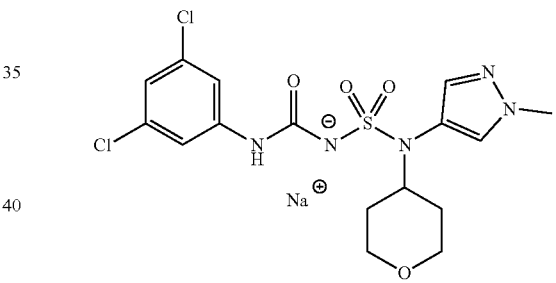

Step 1: N-[(3,5-dichlorophenyl)carbamoyl]sulfamoyl chloride. To a solution of N-(oxomethylene)sulfamoyl chloride (169 μl 1.94 mmol) in isopropyl ether (3 ml) cooled to −78° C. was added 3,5-dichloroaniline (196 μl, 1.85 mmol) in isopropyl ether (3 ml). The RM was stirred at −78° C. for 2 h to give the title compound as a solution in isopropyl ether (6 ml). LC-MS in MeOH (ESI): m/z: [M+MeOH+H]⁺=299.0

Step 2: 3-(3,5-dichlorophenyl)-1-[(1-methyl-1H-pyrazol-4-yl)(oxan-4-yl)sulfamoyl]urea sodium salt. General procedure B was followed using N-[(3,5-dichlorophenyl)carbamoyl]sulfamoyl chloride and 1-methyl-N-tetrahydropyran-3-yl-pyrazol-4-amine (for synthesis refer to Example 1). The crude product was purified by prep-HPLC (column: Nano-Micro Unisil 8-120 C18 Ultra Plus 250×50 mm; mobile phase: [water (10 mM NH₄HCO₃)-ACN]; B: 0-30%, 25 min) to give the title compound as a white solid (Y=17%). ¹H NMR (400 MHz, methanol-d₄) δ ppm 7.63 (s, 1H), 7.48 (d, J=2 Hz, 2H), 7.40 (s, 1H), 6.97-6.94 (d, J=2 Hz, 2H), 4.33-4.24 (m, 1H), 3.94-3.88 (m, 2H), 3.84 (s, 3H), 3.54-3.44 (m, 2H), 1.91 (d, J=10 Hz, 2H), 1.45-1.39 (m, 2H). LC-MS (ESI): m/z: [M+H]⁺=448.0

Example 73. 3-[3,5-bis(propan-2-yl)phenyl]-1-[(1-methyl-1H-pyrazol-4-yl)(oxan-4-yl)sulfamoyl]urea sodium salt

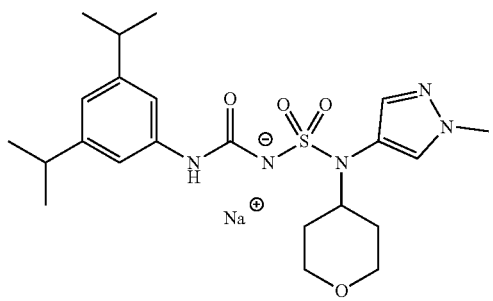 [SMILES: CC(C)c1cc(NC(=O)[N-]S(=O)(=O)N(c2cnn(C)c2)C2CCOCC2)cc(C(C)C)c1 ; [Na+]]

Step 1: N-[(3,5-diisopropylphenyl) carbamoyl]sulfamoyl chloride. To a solution of N-(oxomethylene)sulfamoyl chloride (73 μl, 0.85 mmol) in diisopropyl ether (3 ml) cooled to −30° C. was added 3,5-diisopropylaniline (156 μl, 0.85 mmol) in diisopropyl ether (3 ml). The RM was stirred at −30° C. for 1 h to give the title compound as a solution in diisopropyl ether (6 ml). LC-MS in MeOH (ESI): m/z: =315.3

Step 2: 3-[3,5-bis(propan-2-yl)phenyl]-1-[(1-methyl-1H-pyrazol-4-yl)(oxan-4-yl)sulfamoyl]urea sodium salt. General procedure B was followed using N-[(3,5-diisopropylphenyl)carbamoyl]sulfamoyl chloride and 1-methyl-N-tetrahydropyran-4-yl-pyrazol-4-amine (for synthesis refer to Example 1). The crude product was purified by prep-HPLC (column: Nano-Micro Unisil 8-120 C18 Ultra Plus 250×50 mm; mobile phase: [water (10 mM $NH_4HCO_3$)-ACN]; B: 5-35%, 28 min) to give the title compound as a white solid (Y=10%). $^1$H NMR (400 MHz, methanol-$d_4$) δ ppm 7.70 (s, 1H), 7.42 (s, 1H), 7.10 (s, 2H), 6.84 (s, 1H), 4.43-4.33 (m, 1H), 3.93 (dd, J=11, 4 Hz, 2H), 3.84 (s, 3H), 3.49 (t, J=12 Hz, 2H), 2.92-2.77 (m, 2H), 1.89 (dd, J=12, 2 Hz, 2H), 1.50-1.36 (m, 2H), 1.24 (d, J=7 Hz, 12H). LC-MS (ESI): m/z: [M+H]$^+$=464.2

Example 74. 3-(1,2,3,5,6,7-hexahydro-s-indacen-4-yl)-1-[(1-methyl-1H-pyrazol-4-yl)[2-(3-methylazetidin-1-yl)ethyl]sulfamoyl]urea sodium salt

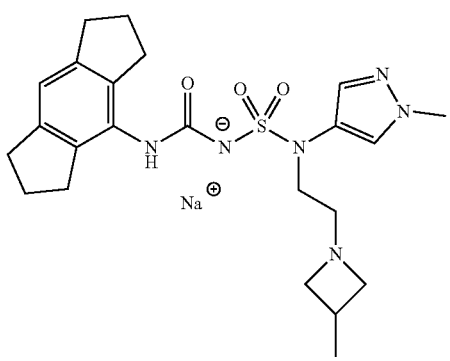 [SMILES: CC1CN(CCN(c2cnn(C)c2)S(=O)(=O)[N-]C(=O)Nc2c3c(cc4c2CCC4)CCC3)C1 ; [Na+]]

Step 1: tert-butyl N-(1-methylpyrazol-4-yl)carbamate. To a mixture of 1-methylpyrazol-4-amine (5.0 g, 51.5 mmol) in DCM (50 ml) was added triethylamine (14.33 ml, 103 mmol) and di-tert-butyl dicarbonate (14.2 ml, 61.8 mmol). The RM was stirred at rt for 3 h. The solution was concentrated in vacuo. The crude product was purified by FCC (50% EtOAc in petroleum ether) to give the title compound as an oil (Y=98%). $^1$H NMR (400 MHz, DMSO-$d_6$) δ 9.09 (s, 1H), 7.60 (s, 1H), 7.24 (s, 1H), 3.72 (s, 3H), 1.41 (s, 9H).

Step 2: tert-butyl N-[2-[tert-butyl(dimethyl)silyl]oxyethyl]-N-(1-methylpyrazol-4-yl)carbamate. To a solution of tert-butyl N-(1-methylpyrazol-4-yl)carbamate (10 g, 50.7 mmol) in DMF (20 ml) cooled to 0° C. was added NaH (60% in mineral oil, 4.06 g, 101 mmol). The RM was stirred at 0° C. for 0.5 h. 2-Bromoethoxy-tert-butyl-dimethylsilane (24.3 g, 101 mmol) was added, keeping the reaction at 0° C. The RM was allowed to warm to rt and stirred for 2 h. $H_2O$ (100 ml) was added and the organics extracted with EtOAc (3×100 ml). The combined organic phases were dried with anhydrous $Na_2SO_4$, filtered and concentrated in vacuo. The crude product was purified by FCC (9% EtOAc in petroleum ether) to give the title compound as a yellow oil (Y=51%). $^1$H NMR (400 MHz, DMSO-$d_6$) δ 7.80-7.50 (m, 1H), 7.45-7.25 (m, 1H), 3.75 (s, 3H), 3.69-3.51 (m, 4H), 1.42 (s, 9H), 0.82 (s, 9H), −0.03 (s, 6H).

Step 3: tert-butyl N-(2-hydroxyethyl)-N-(1-methylpyrazol-4-yl)carbamate. Tert-butyl N-[2-[tert-butyl(dimethyl)silyl]oxyethyl]-N-(1-methylpyrazol-4-yl)carbamate (2.0 g, 5.63 mmol) was treated with 1M TBAF in THF (8.44 ml) under $N_2$ atmosphere. The RM was stirred at rt for 2 h. The solution was concentrated in vacuo. The crude product was purified by FCC (0-100% EtOAc in petroleum ether) to give the title compound as a yellow oil (Y=77%). $^1$H NMR (400 MHz, DMSO-$d_6$) δ 7.80-7.45 (m, 1H), 7.36 (s, 1H), 4.68 (s, 1H), 3.74 (s, 3H), 3.52-3.47 (m, 4H), 1.40 (s, 9H).

Step 4: tert-butyl N-(1-methylpyrazol-4-yl)-N-(2-oxoethyl)carbamate. A solution of oxalyl chloride (330 μl, 3.77 mmol) in DCM (3 ml) was cooled to −78° C. and treated with a solution of DMSO (567 μl, 7.25 mmol) in DCM (3 ml). The RM was stirred at −78° C. for 10 min. The RM was treated dropwise with a solution of tert-butyl N-(2-hydroxyethyl)-N-(1-methylpyrazol-4-yl)carbamate (700 mg, 2.90 mmol) in DCM (3 ml). The RM was stirred at −78° C. for 15 min, treated with triethylamine (2.10 ml, 15.1 mmol) and stirred for as further 5 min. $H_2O$ (10 ml) was added and the resulting mixture extracted with DCM (10 ml). The organic phase was washed with $NH_4Cl$ (3×10 ml), dried with $Na_2SO_4$, filtered and concentrated in vacuo to give the title compound as a yellow oil (Y=73%). $^1$H NMR (400 MHz, DMSO-$d_6$) δ 9.60-9.52 (m, 1H), 7.78-7.56 (m, 1H), 7.45-7.24 (m, 1H), 4.41 (d, J=15 Hz, 2H), 3.76 (s, 3H), 1.41 (s, 9H).

Step 5: tert-butyl N-[2-(3-methylazetidin-1-yl)ethyl]-N-(1-methylpyrazol-4-yl)carbamate trifluoroacetate. General procedure A was followed using 3-methylazetidine and tert-butyl N-(1-methylpyrazol-4-yl)-N-(2-oxoethyl)carbamate. The crude product was purified by prep-HPLC (column: Phenomenex Luna C18 10 μm 250×50 mm; mobile phase: [water (0.1% TFA)-ACN]; B: 1-30%, 20 min) to give the title compound as a white solid (Y=41%). $^1$H NMR (400 MHz, methanol-$d_4$) δ ppm 10.08-9.96 (m, 1H), 7.74 (s, 1H), 7.45 (s, 1H), 4.12-4.04 (m, 2H), 3.79 (s, 3H), 3.73-3.68 (m, 4H), 3.32-3.26 (m, 2H), 2.86-2.82 (m, 1H), 1.44 (s, 9H), 1.18-1.11 (m, 3H).

Step 6: 1-methyl-N-[2-(3-methylazetidin-1-yl)ethyl]pyrazol-4-amine. To a solution of tert-butyl N-[2-(3-methylazetidin-1-yl)ethyl]-N-(1-methylpyrazol-4-yl) carbamate trifluoroacetate (486 mg, 1.19 mmol) in DCM (5 ml) was added TFA (1 ml). The RM was stirred at rt for 2 h. The solution was concentrated in vacuo to give the title compound as a yellow oil (Y=100%). $^1$H NMR (400 MHz, DMSO-$d_6$) δ

7.29 (s, 1H), 7.11 (s, 1H), 6.24-5.50 (br. s, 2H), 4.11 (t, J=10 Hz, 2H), 3.73-3.67 (m, 5H), 3.32-3.24 (m, 2H), 3.11-3.03 (m, 2H), 3.09-3.05 (m, 1H), 1.20-1.15 (m, 3H).

Step 7: 3-(1,2,3,5,6,7-hexahydro-s-indacen-4-yl)-1-[(1-methyl-1H-pyrazol-4-yl)[2-(3-methylazetidin-1-yl)ethyl]sulfamoyl]urea sodium salt. General procedure B was followed using N-(1,2,3,5,6,7-hexahydro-s-indacen-4-ylcarbamoyl)sulfamoyl chloride and 1-methyl-N-[2-(3-methylazetidin-1-yl)ethyl]pyrazol-4-amine trifluoroacetate. The crude product was purified by prep-HPLC (column: Nano-Micro Unisil 8-120 C18 Ultra Plus 250×50 mm; mobile phase: [water (10 mM NH$_4$HCO$_3$)-ACN]; B: 5-40%, 28 min) to give the title compound as a white solid (Y=4%). $^1$H NMR (400 MHz, methanol-d$_4$) δ ppm 7.67 (s, 1H), 7.50 (s, 1H), 6.92 (s, 1H), 4.28-4.16 (m, 2H), 3.85 (s, 3H), 3.80-3.65 (m, 4H), 3.26-3.18 (m, 2H), 2.95-2.79 (m, 9H), 2.07-2.03 (m, 4H), 1.26 (d, J=6 Hz, 3H). LC-MS (ESI): m/z: [M+H]$^+$=473.2

Example 75. 3-[3-ethyl-5-(trifluoromethyl)phenyl]-1-[(1-methyl-1H-pyrazol-4-yl)(oxan-4-yl)sulfamoyl]urea sodium salt

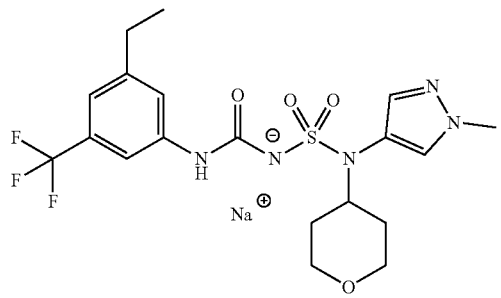 [SMILES: CCc1cc(NC(=O)[N-]S(=O)(=O)N(c2cnn(C)c2)C2CCOCC2)cc(C(F)(F)F)c1 ; [Na+]]

Step 1: 3-ethyl-5-(trifluoromethyl)aniline. To a solution of 3-ethenyl-5-(trifluoromethyl)aniline (500 mg, 2.67 mmol) in MeOH (5 ml) under a nitrogen atmosphere was added 10% Pd/C (100 mg). The suspension was degassed under vacuum and purged with H$_2$ several times. The mixture was stirred under H$_2$ (15 psi) at rt for 12 h. The reaction mixture was filtered through Celite and the filtrate was concentrated in vacuo to give the title compound as a green oil (Y=87%). $^1$H NMR (400 MHz, DMSO-d$_6$) δ ppm 6.66 (s, 1H), 6.64 (s, 1H), 6.60 (s, 1H), 5.46 (s, 2H), 2.52-2.36 (m, 2H), 1.14 (t, J=7 Hz, 3H).

Step 2: ({[3-ethyl-5-(trifluoromethyl)phenyl]carbamoyl}amino)sulfonyl chloride. General procedure D was followed using 3-ethyl-5-(trifluoromethyl)aniline to give the title compound as a solution in isopropyl ether. LC-MS in MeOH (ESI): m/z: =327.2

Step 3: 3-[3-ethyl-5-(trifluoromethyl)phenyl]-1-[(1-methyl-1H-pyrazol-4-yl)(oxan-4-yl)sulfamoyl]urea sodium salt. General procedure B was followed using ({[3-ethyl-5-(trifluoromethyl)phenyl]carbamoyl}amino)sulfonyl chloride and 1-methyl-N-tetrahydropyran-4-yl-pyrazol-4-amine (for synthesis refer to Example 1). The crude product was purified by prep-HPLC (column: Nano-Micro Unisil 8-120 C18 Ultra Plus 250×50 mm; mobile phase: [water (10 mM NH$_4$HCO$_3$)-ACN]; B: 5-35%, 25 min) to give the title compound as a white solid (Y=14%). $^1$H NMR (400 MHz, methanol-d$_4$) δ ppm 7.71 (s, 1H), 7.69 (s, 1H), 7.44 (s, 1H), 7.42 (s, 1H), 7.18 (s, 1H), 4.39-4.30 (m, 1H), 3.95-3.90 (m, 2H), 3.85 (s, 3H), 3.53-3.46 (m, 2H), 2.70 (q, J=8 Hz, 2H), 1.92-1.88 (m, 2H), 1.51-1.44 (m, 2H), 1.26 (t, J=8 Hz, 3H). LC-MS (ESI): m/z: [M+H]$^+$=476.1

Example 76. 3-(3-ethyl-5-methylphenyl)-1-[(1-methyl-1H-pyrazol-4-yl)(oxan-4-yl)sulfamoyl]urea sodium salt

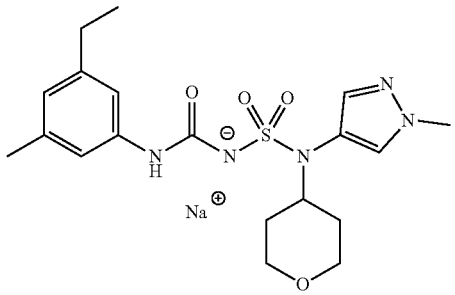

Step 1: 3-ethenyl-5-methylaniline. To a solution of 3-bromo-5-methyl-aniline (2.0 g, 10.75 mmol) in dioxane (20 ml) and H$_2$O (2 ml) was added 4,4,5,5-tetramethyl-2-vinyl-1,3,2-dioxaborolane (4.92 ml, 29.0 mmol), Pd(dppf)Cl$_2$ (1.18 g, 1.61 mmol) and Cs$_2$CO$_3$ (10.5 g, 32.3 mmol). The mixture was stirred at 100° C. for 12 h under N$_2$. The solution was filtered and the filtrate was concentrated in vacuo. The residue was purified by FCC (25% EtOAc in petroleum ether) to the title compound as a yellow oil. $^1$H NMR (400 MHz, DMSO-d$_6$) δ ppm 6.57-6.49 (m, 1H), 6.45 (s, 1H), 6.43 (s, 1H), 6.32 (s, 1H), 5.62 (d, J=16 Hz, 1H), 5.12 (d, J=11 Hz, 1H), 4.97 (s, 2H), 2.15 (s, 3H).

Step 2: 3-ethyl-5-methyl-aniline. To a solution of 3-ethenyl-5-methylaniline (0.98 g, 7.36 mmol) in MeOH (10 ml) under a nitrogen atmosphere was added 10% Pd/C (200 mg). The suspension was degassed under vacuum and purged with H$_2$ several times. The mixture was stirred under H$_2$ (15 psi) at rt for 12 h. The solution was filtered and the filtrate was concentrated in vacuo to give the title compound as a black oil (Y=80%). $^1$H NMR (400 MHz, DMSO-d$_6$) δ ppm 6.25-6.19 (m, 3H), 4.82 (s, 2H), 2.41 (q, J=8 Hz, 2H), 2.11 (s, 3H), 1.11 (t, J=8 Hz, 3H).

Step 3: {[(3-ethyl-5-methylphenyl)carbamoyl]amino}sulfonyl chloride. General procedure D was followed using 3-ethyl-5-methyl-aniline to give the title compound as a solution in isopropyl ether. LC-MS in MeOH (ESI): m/z: =273.1

Step 4: 3-(3-ethyl-5-methylphenyl)-1-[(1-methyl-1H-pyrazol-4-yl)(oxan-4-yl)sulfamoyl]urea sodium salt. General procedure B was followed using {[(3-ethyl-5-methylphenyl)carbamoyl]amino}sulfonyl chloride and 1-methyl-N-tetrahydropyran-4-yl-pyrazol-4-amine (for synthesis refer to Example 1). The crude product was purified by prep-HPLC (column: Nano-Micro Unisil 5-100 C18 Ultra 5 μm 250×100 mm; mobile phase: [water (10 mM NH$_4$HCO$_3$)-ACN]; B: 5-35%, 22 min) to give the title compound as a white solid (Y=13%). $^1$H NMR (400 MHz, methanol-d$_4$) δ ppm 7.70 (s, 1H), 7.41 (s, 1H), 7.04 (d, J=4 Hz, 2H), 6.77 (s, 1H), 4.40-4.35 (m, 1H), 3.94-3.87 (m, 2H), 3.85 (s, 3H), 3.49 (t, J=11 Hz, 2H), 2.58 (q, J=8 Hz, 2H), 2.29 (s, 3H), 1.91-1.86 (m, 2H), 1.51-1.43 (m, 2H), 1.21 (t, J=8 Hz, 3H). LC-MS (ESI): m/z: [M+H]$^+$=422.1

Example 77. 3-(3-chloro-5-ethylphenyl)-1-[(1-methyl-1H-pyrazol-4-yl)(oxan-4-yl)sulfamoyl]urea sodium salt

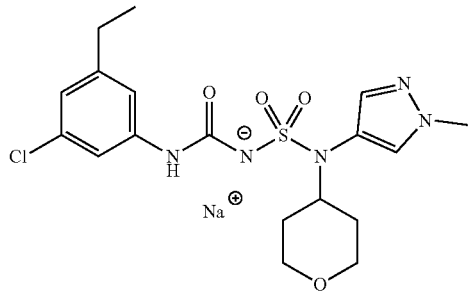 [SMILES: CCc1cc(Cl)cc(NC(=O)[N-]S(=O)(=O)N(c2cnn(C)c2)C2CCOCC2)c1 ; [Na+]]

Step 1: 3-chloro-5-ethenylaniline. A mixture of 3-bromo-5-chloro-aniline (5.0 g, 24.2 mmol), 4,4,5,5-tetramethyl-2-vinyl-1,3,2-dioxaborolane (11.1 ml, 65.4 mmol), Cs$_2$CO$_3$ (7.89 g, 24.2 mmol) and Pd(dppf)Cl$_2$ (2.66 g, 3.6 mmol) in dioxane (50 ml) and H$_2$O (5 ml) was heated at 100° C. under N$_2$ for 22 h. The solution was filtered and the filtrate concentrated in vacuo. The residue was purified by FCC (0-100% EtOAc in petroleum ether) to give the title compound as a yellow oil (Y=24%). $^1$H NMR (400 MHz, DMSO-d$_6$) δ=6.63 (s, 1H), 6.58-6.53 (m, 2H), 6.52-6.50 (m, 1H), 5.71 (d, J=18 Hz, 1H), 5.41 (s, 2H), 5.22 (d, J=11 Hz, 1H).

Step 2: 3-chloro-5-ethyl-aniline. To a solution of 3-chloro-5-ethenylaniline (500 mg, 3.26 mmol) in MeOH (5 ml) was added 10% Pd/C (100 mg) under N$_2$. The suspension was degassed under vacuum and purged with H$_2$ several times. The mixture was stirred under H$_2$ (30 psi) at rt for 12 h. The RM was filtered and the filtrate concentrated and diluted with water (20 ml). The aqueous phase was extracted with ethyl acetate (3×20 ml). The combined organic phases were washed with brine (20 ml), dried with anhydrous Na$_2$SO$_4$, filtered and concentrated in vacuo to give the title compound as an oil. $^1$H NMR (400 MHz, DMSO-d$_6$) δ=6.44 (t, J=2 Hz, 1H), 6.39 (s, 1H), 6.37 (s, 1H), 2.43 (q, J=8 Hz, 2H), 1.11 (t, J=8 Hz, 3H). NH protons not seen.

Step 3: {[(3-chloro-5-ethylphenyl)carbamoyl]amino}sulfonyl chloride. General procedure D was followed using 3-chloro-5-ethyl-aniline to give the title compound as a solution in isopropyl ether. LC-MS in MeOH (ESI): m/z: =293.2

Step 4: 3-(3-chloro-5-ethylphenyl)-1-[(1-methyl-1H-pyrazol-4-yl)(oxan-4-yl)sulfamoyl]urea sodium salt. General procedure B was followed using {[(3-chloro-5-ethylphenyl)carbamoyl]amino}sulfonyl chloride and 1-methyl-N-tetrahydropyran-4-yl-pyrazol-4-amine (for synthesis refer to Example 1). The crude product was purified by prep-HPLC (column: Xtimate C18 10 μm 250×50 mm; mobile phase: [water (10 mM NH$_4$HCO$_3$)-ACN]; B: 2-30%, 27 min) to give the title compound as a yellow solid (Y=10%). $^1$H NMR (400 MHz, methanol-d$_4$) δ ppm 7.60 (s, 1H), 7.48 (t, J=2 Hz, 1H), 7.40 (s, 1H), 7.05 (s, 1H), 6.75 (s, 1H), 4.28-4.20 (m, 1H), 3.90 (dd, J=4, 12 Hz, 2H), 3.83 (s, 3H), 3.53-3.46 (m, 2H), 2.56 (q, J=8 Hz, 2H), 1.95-1.89 (m, 2H), 1.47-1.36 (m, 2H), 1.20 (t, J=8 Hz, 3H). LC-MS (ESI): m/z: [M+H]$^+$=442.1

Example 78. 1-[(3,3-dimethyloxan-4-yl)(1-methyl-1H-pyrazol-4-yl)sulfamoyl]-3-(1,2,3,5,6,7-hexahydro-s-indacen-4-yl)urea sodium salt

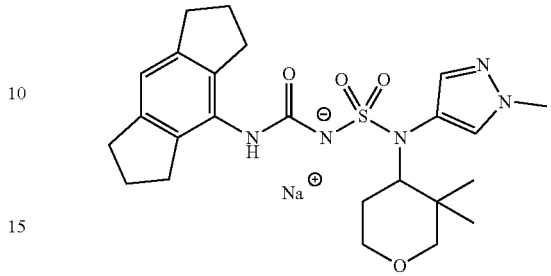

Step 1: N-(3,3-dimethyltetrahydropyran-4-yl)-1-methyl-pyrazol-4-amine trifluoroacetate. General procedure A was followed using 1-methylpyrazol-4-amine and 3,3-dimethyltetrahydropyran-4-one. The crude was purified by prep-HPLC (column: C18, mobile phase: [water (0.1% TFA)-ACN]) to give the title compound as a red solid (Y=43%). $^1$H NMR (400 MHz, methanol-d$_4$) δ=7.98 (s, 1H), 7.68 (s, 1H), 4.01 (dd, J=5, 5 Hz, 1H), 3.94 (s, 3H), 3.51 (d, J=12 Hz, 1H), 3.39-3.31 (m, 2H), 3.18 (d, J=11 Hz, 1H), 1.87-1.71 (m, 2H), 1.18 (s, 3H), 1.12 (s, 3H). LC-MS (ESI): m/z: [M+H]$^+$=210.3

Step 2: 1-[(3,3-dimethyloxan-4-yl)(1-methyl-1H-pyrazol-4-yl)sulfamoyl]-3-(1,2,3,5,6,7-hexahydro-s-indacen-4-yl)urea sodium salt. General procedure B was followed using N-(1,2,3,5,6,7-hexahydro-s-indacen-4-ylcarbamoyl)sulfamoyl chloride and N-(3,3-dimethyltetrahydropyran-4-yl)-1-methyl-pyrazol-4-amine trifluoroacetate. The crude product was purified by prep-HPLC (column: C18; mobile phase: [water (10 mM NH$_4$HCO$_3$)-ACN]) to give the title compound as a pink solid (Y=2%). $^1$H NMR (400 MHz, methanol-d$_4$) δ ppm 7.73 (s, 1H), 7.43 (s, 1H), 6.98 (s, 1H), 4.27-4.20 (m, 1H), 4.02-3.92 (m, 1H), 3.89 (s, 3H), 3.51 (t, J=11 Hz, 1H), 3.40-3.35 (m, 1H), 3.22-3.14 (m, 1H), 2.92-2.84 (m, 4H), 2.82-2.74 (m, 4H), 2.12-2.04 (m, 4H), 1.96-1.88 (m, 1H), 1.83-1.75 (m, 1H), 1.05 (s, 3H), 0.82 (s, 3H). LC-MS (ESI): m/z: [M+H]$^+$=488.2

Example 79. 1-[(2,2-dimethyloxan-4-yl)(1-methyl-1H-pyrazol-4-yl)sulfamoyl]-3-(1,2,3,5,6,7-hexahydro-s-indacen-4-yl)urea sodium salt

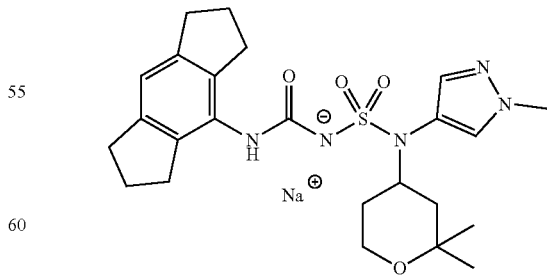

Step 1: N-(2,2-dimethyltetrahydropyran-4-yl)-1-methyl-pyrazol-4-amine trifluoroacetate. General procedure A was followed using 1-methylpyrazol-4-amine and 2,2-dimethyltetrahydropyran-4-one. The crude product was purified by prep-HPLC (column: C18, mobile phase: [water (0.1% TFA)-ACN]) to give the title compound as a red solid (Y=25%). ¹H NMR (400 MHz, methanol-d₄) δ=7.97 (s, 1H), 7.66 (s, 1H), 3.95 (s, 3H), 3.86-3.67 (m, 3H), 1.97-1.93 (m, 2H), 1.60-1.41 (m, 2H), 1.27 (s, 3H), 1.23 (s, 3H). LC-MS (ESI): m/z: [M+H]⁺=210.2

Step 2: 1-[(2,2-dimethyloxan-4-yl)(1-methyl-1H-pyrazol-4-yl)sulfamoyl]-3-(1,2,3,5,6,7-hexahydro-s-indacen-4-yl) urea sodium salt. General procedure B was followed using N-(1,2,3,5,6,7-hexahydro-s-indacen-4-ylcarbamoyl)sulfamoyl chloride and N-(2,2-dimethyltetrahydropyran-4-yl)-1-methyl-pyrazol-4-amine trifluoroacetate. The crude product was purified by prep-HPLC (column: C18; mobile phase: [water (10 mM NH₄HCO₃)-ACN]) to give the title compound as a solid (Y=12%). ¹H NMR (400 MHz, methanol-d₄) δ ppm 7.71 (s, 1H), 7.41 (s, 1H), 6.99 (s, 1H), 4.59-4.50 (m, 1H), 3.90 (s, 3H), 3.77-3.67 (m, 2H), 2.89 (t, J=8 Hz, 4H), 2.80 (t, J=7 Hz, 4H), 2.12-2.05 (m, 4H), 1.86 (dd, J=4, 4 Hz, 2H), 1.35-1.24 (m, 5H), 1.15 (s, 3H). LC-MS (ESI): m/z: [M+H]⁺=488.2

Example 80. 3-(3,5-diethyl-4-fluorophenyl)-1-[(1-methyl-1H-pyrazol-4-yl)(oxan-4-yl)sulfamoyl]urea sodium salt

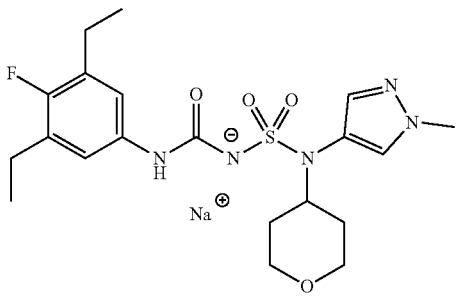 [SMILES: CCc1cc(NC(=O)[N-]S(=O)(=O)N(c2cnn(C)c2)C2CCOCC2)cc(CC)c1F ; [Na+]]

Step 1: 4-fluoro-3,5-ethenyl-aniline. To a solution of 3,5-dibromo-4-fluoro-aniline (1.0 g, 3.72 mmol) in dioxane (10 ml) and H₂O (1 ml) was added 4,4,5,5-tetramethyl-2-vinyl-1,3,2-dioxaborolane (1.70 ml, 10.0 mmol), Pd(dppf)Cl₂ (408 mg, 0.56 mmol) and Cs₂CO₃ (3.63 g, 11.2 mmol) at rt under N₂. The mixture was stirred at 100° C. for 12 h under N₂. The solution was filtered and the filtrate was concentrated in vacuo. The residue was purified by FCC (25% ethyl acetate in petrol) to give the title compound as a yellow solid (Y=25%). ¹H NMR (400 MHz, DMSO-d₆) δ ppm 6.80-6.68 (m, 4H), 5.72 (d, J=18 Hz, 2H), 5.34 (d, J=11 Hz, 2H), 4.96 (s, 2H).

Step 2: 3,5-diethyl-4-fluoroaniline. To a solution of 4-fluoro-3,5-ethenyl-aniline (150 mg, 0.92 mmol) in MeOH (3 ml) was added 10% Pd/C (50 mg) under N₂. The suspension was degassed under vacuum and purged with H₂ several times. The mixture was stirred under H₂ (15 psi) at rt for 12 h. The solution was filtered and the filtrate was concentrated in vacuo to give the title compound as a yellow oil (Y=98%). ¹H NMR (400 MHz, methanol-d₄) δ ppm 6.34 (d, J=6 Hz, 2H), 2.49-2.41 (m, 4H), 1.12-1.05 (m, 6H).

Step 3: {[(3,5-diethyl-4-fluorophenyl)carbamoyl]amino}sulfonyl chloride. General procedure D was followed using 3,5-diethyl-4-fluoroaniline to give the title compound as a solution in isopropyl ether. LC-MS in MeOH (ESI): m/z: =305.3

Step 4: 3-(3,5-diethyl-4-fluorophenyl)-1-[(1-methyl-1H-pyrazol-4-yl)(oxan-4-yl)sulfamoyl]urea sodium salt. General procedure B was followed using {[(3,5-diethyl-4-fluorophenyl)carbamoyl]amino}sulfonyl chloride and 1-methyl-N-tetrahydropyran-4-yl-pyrazol-4-amine (for synthesis refer to Example 1). The crude product was purified by prep-HPLC (column: Agela Durashell 10 μm 250×50 mm; mobile phase: [water (10 mM NH₄HCO₃) -ACN]; B: 5-30%, 20 min) to give the title compound as a white solid (Y=2%). ¹H NMR (400 MHz, methanol-d₄) δ ppm 7.61 (s, 1H), 7.41 (s, 1H), 7.10 (d, J=6 Hz, 2H), 4.26-4.21 (m, 1H), 3.90 (dd, J=4, 12 Hz, 2H), 3.83 (s, 3H), 3.48 (t, J=11 Hz, 2H), 2.59 (q, J=8 Hz 4H), 1.95-1.86 (m, 2H), 1.44-1.38 (m, 2H), 1.20 (t, J=8 Hz, 6H). LC-MS (ESI): m/z: [M+H]⁺=454.2

Example 81. 3-[3-ethyl-5-(propan-2-yl)phenyl]-1-[(1-methyl-1H-pyrazol-4-yl)(oxan-4-yl)sulfamoyl]urea sodium salt

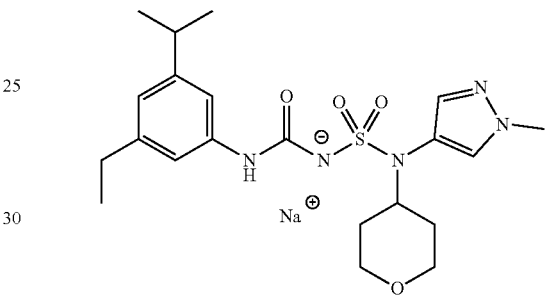

Step 1: 3-ethenyl-5-(prop-1-en-2-yl)aniline. To a solution of 3-bromo-5-ethenylaniline (900 mg, 4.54 mmol) in dioxane (10 ml) and H₂O (1 ml) was added 2-isopropenyl-4,4,5,5-tetramethyl-1,3,2-dioxaborolane (2.06 g, 12.3 mmol), Pd(dppf)Cl₂ (0.50 g, 0.68 mmol) and Cs₂CO₃ (4.44 g, 13.6 mmol). The RM was stirred at 100° C. under N₂ for 12 h. The solution was filtered and the filtrate was concentrated in vacuo. The residue was purified by prep-HPLC (column: Phenomenex Luna C18 10 μm 250×50 mm; mobile phase: [water (0.1% TFA)-ACN]; B: 5-35%, 20 min) to give the title compound as a white solid (Y=47%). LC-MS (ESI): m/z: [M+H]⁺=160.1

Step 2: 3-ethyl-5-isopropylaniline. To a solution of 3-ethenyl-5-(prop-1-en-2-yl)aniline (400 mg, 2.51 mmol) in MeOH (5 ml) was added 10% Pd/C (100 mg) under H₂. The suspension was degassed under vacuum and purged with H₂ several times. The mixture was stirred under H₂ (15 psi) at rt for 2 h. The solution was filtered and the filtrate was concentrated in vacuo to give the title compound as a yellow oil (Y=98%). ¹H NMR (400 MHz, DMSO-d₆) δ ppm 6.95 (s, 1H), 6.86 (s, 1H), 6.83 (s, 1H), 4.00-3.28 (br. s, 2H), 2.87-2.80 (m, 1H), 2.58 (q, J=8 Hz, 2H), 1.19-1.15 (m, 9H).

Step 3: ({[3-ethyl-5-(propan-2-yl)phenyl]carbamoyl}amino)sulfonyl chloride. General procedure D was followed using 3-ethyl-5-isopropylaniline to give the title compound as a solution in isopropyl ether. LC-MS in MeOH (ESI): m/z: =301.1

Step 4: 3-[3-ethyl-5-(propan-2-yl)phenyl]-1-[(1-methyl-1H-pyrazol-4-yl)(oxan-4-yl)sulfamoyl]urea sodium salt. General procedure B was followed using ({[3-ethyl-5-(propan-2-yl)phenyl]carbamoyl}amino)sulfonyl chloride and 1-methyl-N-tetrahydropyran-4-yl-pyrazol-4-amine (for synthesis refer to Example 1). The crude product was purified by prep-HPLC (column: Agela Durashell 10 μm 250×50 mm; mobile phase: [water (10 mM NH₄HCO₃) -ACN]; B: 5-35%, 20 min) to give the title compound as a white solid (Y=2%). ¹H NMR (400 MHz, methanol-d₄) δ ppm 7.71 (s, 1H), 7.42 (s, 1H), 7.08 (s, 2H), 6.83 (s, 1H), 4.42-4.32 (m, 1H), 3.93 (dd, J=4, 12 Hz, 2H), 3.85 (s, 3H), 3.49 (t, J=10 Hz, 2H), 2.91-2.80 (m, 1H), 2.61 (q, J=8 Hz, 2H), 1.89 (dd, J=2, 12 Hz, 1H), 1.53-1.45 (m, 1H), 1.25-1.20 (m, 9H). LC-MS (ESI): m/z: [M+H]⁺=450.2

Example 82. 3-(1,2,3,5,6,7-hexahydro-s-indacen-4-yl)-1-[(1-methyl-1H-pyrazol-4-yl)(1-methyl-6-oxopiperidin-3-yl)sulfamoyl]urea sodium salt

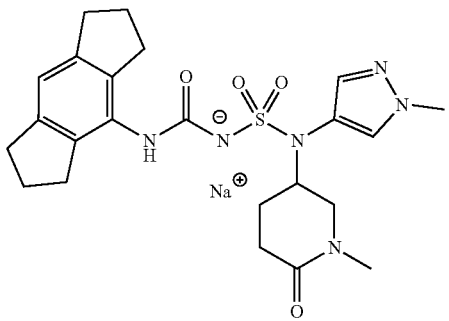 [SMILES: CN1CC(N(c2cnn(C)c2)S(=O)(=O)[N-]C(=O)Nc2c3c(cc4c2CCC4)CCC3)CCC1=O ; [Na+]]

Step 1: 1-methyl-5-[(1-methylpyrazol-3-yl)amino]piperidin-2-one. A mixture of 5-amino-1-methyl-piperidin-2-one (100 mg, 0.78 mmol), 3-iodo-1-methyl-pyrazole (160 mg, 0.77 mmol), sodium tert-butoxide (142 mg, 1.48 mmol) and [2-(2-aminoethyl)phenyl]-chloro-palladium; di-tert-butyl-[2-(2,4,6-triisopropylphenyl) phenyl]phosphane (also known as tBuXPhos Pd GI) (51 mg, 74 μmol) in toluene (1 ml) was stirred at 110° C. under N₂ for 1 h.

The solvent was removed under reduced pressure and the residue was purified by prep-HPLC (column: Nano-micro Kromasil C18 5 μm 100×30 mm; mobile phase: [water (0.1% TFA)-ACN]; B: 1-20%, 10 min) to give the title compound as a colourless gum (Y=26%). ¹H NMR (400 MHz, methanol-d₄) δ ppm 7.66 (s, 1H), 7.45 (s, 1H), 3.88 (s, 3H), 3.77-3.67 (m, 1H), 3.64-3.58 (m, 1H), 3.38-3.33 (m, 1H), 2.94 (s, 3H), 2.56-2.38 (m, 2H), 2.23-2.11 (m, 1H), 1.98-1.85 (m, 1H).

Step 2: 3-(1,2,3,5,6,7-hexahydro-s-indacen-4-yl)-1-[(1-methyl-1H-pyrazol-4-yl)(1-methyl-6-oxopiperidin-3-yl)sulfamoyl]urea sodium salt. General procedure B was followed using {[(1,2,3,5,6,7-hexahydro-s-indacen-4-yl)carbamoyl]amino}sulfonyl chloride and 1-methyl-5-[(1-methylpyrazol-3-yl)amino]piperidin-2-one. The crude product was purified by prep-HPLC (column: Luna C18 5 μm 100×30 mm; mobile phase: [water (10 mM NH₄HCO₃) -ACN]; B: 20-37%, 10 min) to give the title compound as a white solid (Y=8%). ¹H NMR (400 MHz, methanol-d₄) δ ppm 7.76 (s, 1H), 7.47 (s, 1H), 7.00 (s, 1H), 4.69-4.60 (m, 1H), 3.89 (s, 3H), 3.65-3.56 (m, 1H), 3.29-3.22 (m, 1H), 2.94-2.76 (m, 11H), 2.54-2.35 (m, 2H), 2.14-2.04 (m, 5H), 1.68-1.54 (m, 1H). LC-MS (ESI): m/z: [M+H]⁺=487.2

Example 83. 3-(1,2,3,5,6,7-hexahydro-s-indacen-4-yl)-1-[(1-methyl-1H-pyrazol-4-yl)(1-methyl-5-oxopyrrolidin-3-yl)sulfamoyl]urea sodium salt

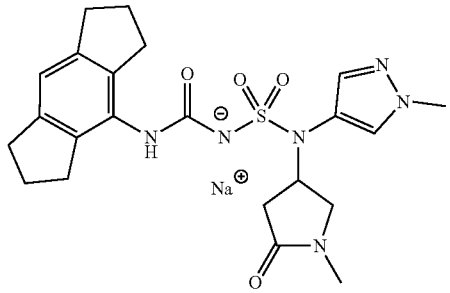 [SMILES: CN1CC(N(c2cnn(C)c2)S(=O)(=O)[N-]C(=O)Nc2c3c(cc4c2CCC4)CCC3)CC1=O ; [Na+]]

Step 1: 1-methyl-4-[(1-methylpyrazol-4-yl)amino]pyrrolidin-2-one trifluoroacetate. To a solution of 4-amino-1-methyl-pyrrolidin-2-one (100 mg, 0.88 mmol) in toluene (2 ml) was added 4-iodo-1-methyl-pyrazole (200 mg, 0.96 mmol), sodium tert-butoxide (168 mg, 1.75 mmol) and [2-(2-aminoethyl)phenyl]-chloro-palladium; ditert-butyl-[2-(2,4,6-triisopropylphenyl)phenyl]phosphane (also known as tBuKPhos Pd G1) (60 mg, 88 μmol), then the mixture was stirred at 100° C. for 3 h. The mixture was concentrated under reduced pressure. The residue was purified by prep-HPLC (column: Waters Xbridge Prep OBD C18 5 μm 150×30; mobile phase: [water (0.1% TFA)-ACN]; B: 1-30%, 10 min) to give the title compound as colourless gum (Y=20%). ¹H NMR (400 MHz, methanol-d₄) δ ppm 7.63 (s, 1H), 7.43 (s, 1H), 4.17-4.05 (m, 1H), 3.87 (s, 3H), 3.84-3.76 (m, 1H), 3.43 (dd, J=3, 11 Hz, 1H), 2.90-2.79 (m, 4H), 2.41 (dd, J=3, 18 Hz, 1H).

Step 2: 3-(1,2,3,5,6,7-hexahydro-s-indacen-4-yl)-1-[(1-methyl-1H-pyrazol-4-yl)(1-methyl-5-oxopyrrolidin-3-yl)sulfamoyl]urea sodium salt. General procedure B was followed using {[(1,2,3,5,6,7-hexahydro-s-indacen-4-yl)carbamoyl]amino}sulfonyl chloride and 1-methyl-4-[(1-methylpyrazol-4-yl)amino]pyrrolidin-2-one trifluoroacetate. The crude product was purified by prep-HPLC (column: Agela Durashell C18 10 μm 250×50 mm; mobile phase: [water (10 mM NH₄HCO₃)-ACN]; B: 5-30%, 20 min) to give the title compound as a white solid (Y=6%). ¹H NMR (400 MHz, methanol-d₄) δ ppm 7.73 (s, 1H), 7.49 (s, 1H), 6.94 (s, 1H), 5.10-4.96 (m, 1H), 3.85 (s, 3H), 3.83-3.78 (m, 1H), 3.53-3.48 (m, 1H), 2.87 (t, J=7 Hz, 4H), 2.81 (t, J=7 Hz, 4H), 2.77-2.67 (m, 1H), 2.63 (s, 3H), 2.45-2.35 (m, 1H), 2.13-2.02 (m, 4H). LC-MS (ESI): m/z: [M+H]⁺=473.2

Example 84. 3-(1,2,3,5,6,7-hexahydro-s-indacen-4-yl)-1-[(1-methyl-1H-pyrazol-4-yl)[rac-trans-(2-methyloxan-4-yl)]sulfamoyl]urea sodium salt

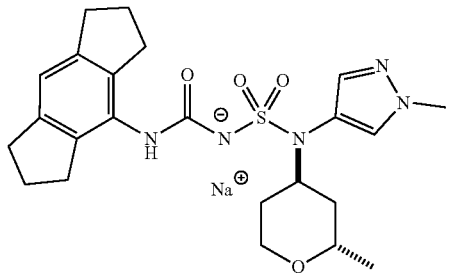

Step 1: 1-methyl-N-(2-methyltetrahydropyran-4-yl)pyrazol-4-amine trifluoroacetate. General procedure A was followed using 1-methylpyrazol-4-amine and 2-methyltetrahydropyran-4-one. The crude was purified by prep-HPLC (column: Phenomenex Luna C18 10 μm 250×50 mm; mobile phase: [water (0.1% TFA)-ACN]; B: 0-25%, 20 min) to give the title compound as a solid (Y=38%). $^1$H NMR (400 MHz, methanol-d$_4$) δ=7.96 (s, 1H), 7.66 (s, 1H), 4.06-3.99 (m, 1H), 3.95 (s, 3H), 3.83-3.77 (m, 2H), 3.50-3.43 (m, 1H), 2.02-1.78 (m, 4H), 1.24-1.22 (m, 3H).

Step 2: tert-butyl (1-methyl-1H-pyrazol-4-yl)((rac-trans)-2-methyltetrahydro-2H-pyran-4-yl)carbamate and tert-butyl (1-methyl-1H-pyrazol-4-yl)((rac-cis)-2-methyltetrahydro-2H-pyran-4-yl)carbamate. To a solution of 1-methyl-N-(2-methyltetrahydropyran-4-yl)pyrazol-4-amine trifluoroacetate (400 mg, 2.05 mmol) in DCM (10 ml) was added di-tert-butyldicarbonate (565 μl, 2.46 mmol) and Et$_3$N (0.57 ml, 4.10 mmol). The RM was stirred at rt for 12 h. The solvent was removed under reduced pressure to give a residue. The residue was purified by prep-HPLC (column: Phenomenex Luna C18 10 μm 250×50 mm; mobile phase: [water (0.1% TFA)-ACN]; B: 16-46%, 20 min) to give the title compounds. Tert-butyl (1-methyl-1H-pyrazol-4-yl)((rac-cis)-2-methyltetrahydro-2H-pyran-4-yl)carbamate (350 mg) was obtained as a yellow oil. Tert-butyl (1-methyl-1H-pyrazol-4-yl)((rac-trans)-2-methyltetrahydro-2H-pyran-4-yl)carbamate (320 mg) was obtained as a yellow oil.

Tert-butyl (1-methyl-1H-pyrazol-4-yl)((rac-cis)-2-methyltetrahydro-2H-pyran-4-yl)carbamate. $^1$H NMR (400 MHz, methanol-d$_4$) δ=7.55 (s, 1H), 7.29 (s, 1H), 4.53-4.48 (m, 1H), 4.12-4.06 (m, 1H), 3.88 (s, 3H), 3.82-3.78 (m, 1H), 3.63-3.60 (m, 1H), 1.70-1.63 (m, 3H), 1.47-1.42 (m, 1H), 1.40 (s, 9H), 1.30 (d, J=7 Hz, 3H).

Tert-butyl (1-methyl-1H-pyrazol-4-yl)((rac-trans)-2-methyltetrahydro-2H-pyran-4-yl)carbamate. $^1$H NMR (400 MHz, methanol-d$_4$) δ=7.54 (s, 1H), 7.29 (s, 1H), 4.27-4.21 (m, 1H), 3.95-3.90 (m, 1H), 3.88 (s, 3H), 3.53-3.47 (m, 2H), 1.77-1.66 (m, 3H), 1.48-1.37 (m, 10H), 1.13 (d, J=6 Hz, 3H).

Step 3: 1-methyl-N-((rac-trans)-2-methyltetrahydro-2H-pyran-4-yl)-1H-pyrazol-4-amine trifluoroacetate. To a solution of tert-butyl (1-methyl-1H-pyrazol-4-yl)((rac-trans)-2-methyltetrahydro-2H-pyran-4-yl)carbamate (320 mg, 0.78 mmol) in DCM (2 ml) was added TFA (0.40 ml, 5.40 mmol). The RM was stirred at rt for 3 h. The solvent was removed under reduced pressure to give the title compound as a yellow oil (Y=42%). $^1$H NMR (400 MHz, methanol-d$_4$) δ=7.98 (s, 1H), 7.66 (s, 1H), 4.04-4.00 (m, 1H), 3.94 (s, 3H), 3.84-3.78 (m, 3H), 2.10-1.99 (m, 1H), 1.98-1.86 (m, 1H), 1.81-1.74 (m, 2H), 1.22 (d, J=6 Hz, 3H).

Step 4: 3-(1,2,3,5,6,7-hexahydro-s-indacen-4-yl)-1-[(1-methyl-1H-pyrazol-4-yl)[rac-trans-(2-methyloxan-4-yl)]sulfamoyl]urea sodium salt. General procedure B was followed using {[(1,2,3,5,6,7-hexahydro-s-indacen-4-yl)carbamoyl]amino}sulfonyl chloride and 1-methyl-N-((rac-trans)-2-methyltetrahydro-2H-pyran-4-yl)-1H-pyrazol-4-amine trifluoroacetate. The crude product was purified by prep-HPLC (column: Agela Durashell C18 10 μm 250×50 mm; mobile phase: [water (10 mM NH$_4$HCO$_3$)-ACN]; B: 10-35%, 20 min) to give the title compound as a white solid (Y=2%). $^1$H NMR (400 MHz, methanol-d$_4$) δ ppm 7.72 (s, 1H), 7.42 (s, 1H), 6.99 (s, 1H), 4.63-4.57 (m, 1H), 4.12-3.97 (m, 1H), 3.90 (s, 3H), 3.86-3.74 (m, 1H), 3.65-3.54 (m, 1H), 2.88 (t, J=7 Hz, 4H), 2.79 (t, J=7 Hz, 4H), 2.15-2.01 (m, 4H), 1.90-1.82 (m, 1H), 1.78-1.68 (m, 1H), 1.67-1.62 (m, 1H), 1.56-1.42 (m, 1H), 1.27 (d, J=7 Hz, 3H). LC-MS (ESI): m/z: [M+H]$^+$=474.1

Example 85. 3-(1,2,3,5,6,7-hexahydro-s-indacen-4-yl)-1-[(1-methyl-1H-pyrazol-4-yl)[rac-cis-(2-methyloxan-4-yl)]sulfamoyl]urea sodium salt

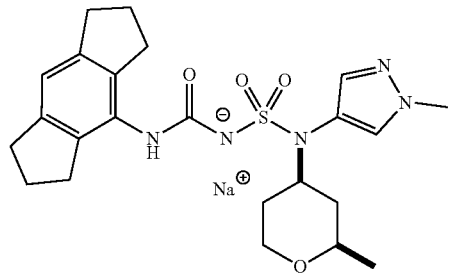

Step 1: 1-methyl-N-((rac-cis)-2-methyltetrahydro-2H-pyran-4-yl)-1H-pyrazol-4-amine trifluoroacetate. To a solution of tert-butyl (1-methyl-1H-pyrazol-4-yl)((rac-cis)-2-methyltetrahydro-2H-pyran-4-yl)carbamate (310 mg, 0.76 mmol)(for synthesis refer to Example 84) in DCM (2 ml) was added TFA (0.40 ml, 5.40 mmol). The RM was stirred at rt for 3 h. The solvent was removed under reduced pressure to give the title compound as a yellow oil (Y=43%). $^1$H NMR (400 MHz, methanol-d$_4$) δ=7.97 (s, 1H), 7.65 (s, 1H), 4.04-4.02 (m, 1H), 3.94 (s, 3H), 3.67-3.56 (m, 1H), 3.53-3.42 (m, 2H), 2.03-1.93 (m, 2H), 1.63-1.58 (m, 1H), 1.30-1.22 (m, 1H), 1.21 (d, J=6 Hz, 3H).

Step 2: 3-(1,2,3,5,6,7-hexahydro-s-indacen-4-yl)-1-[(1-methyl-1H-pyrazol-4-yl)[rac-cis-(2-methyloxan-4-yl)]sulfamoyl]urea sodium salt. General procedure B was followed using {[(1,2,3,5,6,7-hexahydro-s-indacen-4-yl)carbamoyl]amino}sulfonyl chloride and 1-methyl-N-((rac-cis)-2-methyltetrahydro-2H-pyran-4-yl)-1H-pyrazol-4-amine trifluoroacetate. The crude product was purified by prep-HPLC (column: Agela Durashell C18 10 μm 250×50 mm; mobile phase: [water (10 mM NH$_4$HCO$_3$)-ACN]; B: 10-35%, 20 min) to give the title compound as a white solid (Y=4%). $^1$H NMR (400 MHz, methanol-d$_4$) δ ppm 7.72 (s, 1H), 7.42 (s, 1H), 6.99 (s, 1H), 4.42-4.27 (m, 1H), 3.94-3.92 (m, 1H), 3.90 (s, 3H), 3.54-3.48 (m, 2H), 2.88 (t, J=7 Hz, 4H), 2.79 (t, J=7 Hz, 4H), 2.15-2.02 (m, 4H), 1.98-1.89 (m, 1H), 1.87-1.76 (m, 1H), 1.48-1.31 (m, 1H), 1.11 (d, J=6 Hz, 3H), 1.09-1.01 (m, 1H). LC-MS (ESI): m/z: [M+H]$^+$=474.1

Example 86. 3-(1,2,3,5,6,7-hexahydro-s-indacen-4-yl)-1-[(2-methylpyrimidin-5-yl)(oxan-4-yl)sulfamoyl]urea sodium salt

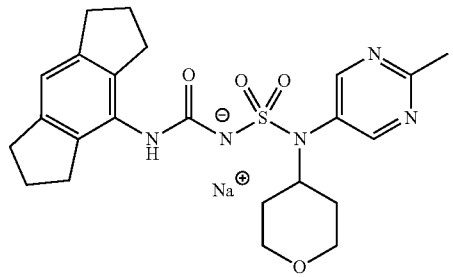 [SMILES: Cc1ncc(N(C2CCOCC2)S(=O)(=O)[N-]C(=O)Nc2c3c(cc4c2CCC4)CCC3)cn1 ; [Na+]]

Step 1: 2-methyl-N-tetrahydropyran-4-yl-pyrimidin-5-amine. To a solution of 5-bromo-2-methyl-pyrimidine (700 mg, 4.05 mmol) and tetrahydropyran-4-amine (818 mg, 8.09 mmol) in toluene (12 ml) was added BINAP (504 mg, 0.81 mmol), Pd(OAc)₂ (91 mg, 0.40 mmol) and Cs₂CO₃ (2.64 g, 8.09 mmol). The mixture was stirred under N₂ at 100° C. for 3 h. The mixture was poured into ethyl acetate (100 ml) and washed with 10:1 H₂O/methanol (4×100 ml). The EtOAc phase was concentrated in vacuo. The residue was purified by FCC (33-100% EtOAc in petroleum ether) to give the title compound as a white solid (Y=45%). ¹H NMR (400 MHz, chloroform-d) δ ppm 8.07 (s, 2H), 4.05-3.95 (m, 2H), 3.57-3.48 (m, 3H), 2.61 (s, 3H), 2.06-2.00 (m, 2H), 1.55-1.44 (m, 2H).

Step 2: 3-(1,2,3,5,6,7-hexahydro-s-indacen-4-yl)-1-[(2-methylpyrimidin-5-yl)(oxan-4-yl)sulfamoyl]urea sodium salt. General procedure B was followed using {[(1,2,3,5,6,7-hexahydro-s-indacen-4-yl)carbamoyl]amino}sulfonyl chloride and 2-methyl-N-tetrahydropyran-4-yl-pyrimidin-5-amine. The crude product was purified by prep-HPLC (column: Agela Durashell C18 10 μm 250×50 mm; mobile phase: [water (10 mM NH₄HCO₃)-ACN]; B: 5-30%, 20 min) to give the title compound as a white solid (Y=7%). ¹H NMR (400 MHz, methanol-d₄) δ ppm 8.63 (s, 2H), 7.00 (s, 1H), 5.17 (s, 1H), 4.54-4.40 (m, 1H), 3.93 (dd, J=4, 11 Hz, 2H), 3.53-3.43 (m, 2H), 2.89 (t, J=7 Hz, 4H), 2.81 (t, J=7 Hz, 4H), 2.75 (s, 3H), 2.13-2.03 (m, 4H), 2.01-1.94 (m, 2H), 1.47-1.30 (m, 2H). LC-MS (ESI): m/z: [M+H]⁺=472.1

Example 87. 1-[(3,4-dimethyl-1,2-oxazol-5-yl)(oxan-4-yl)sulfamoyl]-3-(1,2,3,5,6,7-hexahydro-s-indacen-4-yl)urea sodium salt

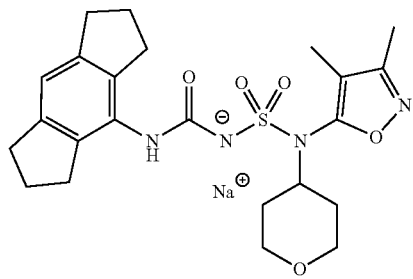 [SMILES: Cc1noc(N(C2CCOCC2)S(=O)(=O)[N-]C(=O)Nc2c3c(cc4c2CCC4)CCC3)c1C ; [Na+]]

Step 1: tert-butyl N-chlorosulfonylcarbamate. To a solution of N-(oxomethylene)sulfamoyl chloride (491 μl, 5.65 mmol) in DCM (5 ml) cooled to 0° C. under N₂ was added a solution of tert-butanol (541 μl, 5.65 mmol) in DCM (5 ml). The RM was stirred at 0° C. for 2 h to give a solution of the title compound in DCM (10 ml). The mixture was used into the next step without work-up.

Step 2: 3,4-dimethyl-N-tetrahydropyran-4-yl-isoxazol-5-amine trifluoroacetate. General procedure A was followed using 3,4-dimethylisoxazol-5-amine and tetrahydropyran-4-one. The crude product was purified by prep-HPLC (column: Phenomenex Luna C18 10 μm 250×50 mm; mobile phase: [water (0.1% TFA)-ACN]; B: 5-35%, 20 min) to give the title compound as a yellow oil (Y=58%). ¹H NMR (400 MHz, chloroform-d) δ ppm 8.75-8.25 (br. s, 1H), 4.06-4.01 (m, 2H), 3.75-3.65 (m, 1H), 3.55-3.49 (m, 2H), 2.18 (s, 3H), 2.05-1.99 (m, 2H), 1.77 (s, 3H), 1.61-1.52 (m, 2H).

Step 3: tert-butyl N-[(3,4-dimethylisoxazol-5-yl)-tetrahydropyran-4-yl sulfamoyl]carbamate. To a solution of 3,4-dimethyl-N-tetrahydropyran-4-yl-isoxazol-5-amine trifluoroacetate (600 mg, 1.93 mmol) in DCM (6 ml) was added a solution of tert-butyl N-chlorosulfonylcarbamate (417 mg, 1.93 mmol) in DCM (3.42 ml). DIPEA (1.01 ml, 5.80 mmol) was added and the RM stirred at rt for 2 h. The solvent was removed under reduced pressure to give a residue. The residue was purified by prep-HPLC (column: Phenomenex Luna C18 10 μm 250×50 mm; mobile phase: [water (0.1% TFA)-ACN]; B: 20-50%, 20 min) to give the title compound as a white solid (Y=16%). ¹H NMR (400 MHz, methanol-d₄) δ ppm 4.52-4.35 (m, 1H), 3.95 (dd, J=4, 11 Hz, 2H), 3.47 (t, J=11 Hz, 2H), 2.25 (s, 3H), 2.02-1.98 (m, 2H), 1.95 (s, 3H), 1.51 (s, 9H), 1.49-1.42 (m, 2H).

Step 4: 3,4-dimethyl-5-[sulfamoyl(tetrahydropyran-4-yl)amino]isoxazole trifluoroacetate. To a solution of tert-butyl N-[(3,4-dimethylisoxazol-5-yl)-tetrahydropyran-4-yl-sulfamoyl]carbamate (100 mg, 0.20 mmol) in DCM (2 ml) was added TFA (400 μl, 5.40 mmol), then the RM was stirred at rt for 3 h. The solvent was removed under reduced pressure to give the title compound as white solid (Y=88%).

Step 5: 1-[(3,4-dimethyl-1,2-oxazol-5-yl)(oxan-4-yl)sulfamoyl]-3-(1,2,3,5,6,7-hexahydro-s-indacen-4-yl)urea sodium salt. To a solution of 3,4-dimethyl-5-[sulfamoyl(tetrahydropyran-4-yl)amino]isoxazole trifluoroacetate (100 mg, 0.26 mmol) in THF (2 ml) cooled to 0° C. was added NaH (60% in mineral oil, 41 mg, 1.03 mmol). The RM was stirred at 0° C. for 0.5 h, then 4-isocyanato-1,2,3,5,6,7-hexahydro-s-indacene (51 mg, 0.26 mmol) was added. The RM was allowed to warm to rt and stirred for 1.5 h. The solvent was removed under reduced pressure to give a residue. The residue was purified by prep-HPLC (column: Agela Durashell 10 μm 250×50 mm; mobile phase: [water (10 mM NH₄HCO₃)-ACN]; B: 10-36%, 20 min) to give the title compound as a white solid (Y=19%). ¹H NMR (400 MHz, methanol-d₄) δ ppm 6.98 (s, 1H), 4.52-4.48 (m, 1H), 3.96-3.88 (m, 2H), 3.46 (t, J=11 Hz, 2H), 2.93-2.78 (m, 8H), 2.24 (s, 3H), 2.11-2.04 (m, 6H), 1.99 (s, 3H), 1.47-1.39 (m, 2H). LC-MS (ESI): m/z: [M+H]⁺=475.1

Example 88. 1-(2,6-dimethylcyclohexyl)-3-[(1-methyl-1H-pyrazol-4-yl)(oxan-4-yl)sulfamoyl]urea sodium salt

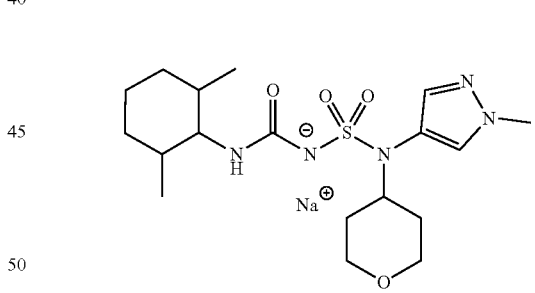

Step 1: N-(2,6-dimethylcyclohexylidene)hydroxylamine. To a solution of 2,6-dimethylcyclohexanone (1.5 g, 11.9 mmol) in EtOH (15 ml) and H₂O (3 ml) was added hydroxylamine hydrochloride (1.24 g, 17.8 mmol) and sodium acetate (1.56 g, 19.0 mmol). The RM was heated at 80° C. for 2 h. The RM was concentrated to remove the EtOH, then diluted with water (10 ml). The aqueous phase was extracted with EtOAc (3×30 ml), dried with anhydrous Na₂SO₄, filtered and concentrated in vacuo to give the title compound as a yellow oil (Y=91%). ¹H NMR (400 MHz, DMSO-d₆) δ ppm 10.13 (s, 1H), 1.45-1.18 (m, 8H), 1.10-0.96 (m, 6H).

Step 2: 2,6-dimethylcyclohexanamine. To a solution of N-(2,6-dimethylcyclohexylidene)hydroxylamine (1.52 g, 10.8 mmol) in MeOH (8 ml) was added Raney-Ni (400 mg). The RM was stirred under H₂ (50 psi) for 12 h. The RM was filtered and the filtrate concentrated in vacuo to give the title compound as a yellow oil (Y=64%). ¹H NMR (400 MHz, DMSO-d₆) δ=2.50-2.44 (m, 1H), 2.06-2.02 (m, 2H), 1.74-1.71 (m, 2H), 1.47-1.35 (m, 6H), 0.89 (d, J=7 Hz, 6H).

Step 3: 2-isocyanato-1,3-dimethyl-cyclohexane. General procedure C was followed using 2,6-dimethylcyclohexanamine to give the title compound as a yellow solid. LC-MS in benzylamine (ESI): m/z: =261.2

Step 4: tert-butyl N-[(1-methylpyrazol-4-yl)-tetrahydropyran-4-yl-sulfamoyl]carbamate. To a solution of 1-methyl-N-tetrahydropyran-4-yl-pyrazol-4-amine (1.26 g, 6.94 mmol) (for synthesis refer to Example 1) in DCM (20 ml) was added DIPEA (3.63 ml, 20.8 mmol) and the RM stirred at rt for 0.5 h. The RM was treated dropwise with a solution of tert-butyl N-chlorosulfonylcarbamate (1.5 g, 6.96 mmol) (for synthesis refer to Example 87) in DCM (12 ml) and the mixture stirred at rt for 4.5 h. The solution was concentrated in vacuo. The crude product was purified by FCC (0-100% EtOAc in petroleum ether) to give the title compound as a pink solid (Y=76%). ¹H NMR (400 MHz, DMSO-d₆) δ ppm 11.04 (s, 1H), 7.73 (s, 1H), 7.25 (s, 1H), 4.21-4.13 (m, 1H), 3.84-3.81 (m, 5H), 3.37-3.34 (m, 2H), 1.72-1.69 (m, 2H), 1.45 (s, 9H), 1.35-1.24 (m, 2H).

Step 5: 1-methyl-4-[sulfamoyl(tetrahydropyran-4-yl)amino]pyrazole. A mixture of tert-butyl N-[(1-methylpyrazol-4-yl)-tetrahydropyran-4-yl-sulfamoyl]carbamate (1.0 g, 2.77 mmol)) in 4 M HCl in EtOAc (15 ml) was stirred at rt for 12 h. The solution was concentrated in vacuo to give the title compound as a white solid. ¹H NMR (400 MHz, DMSO-d₆) δ ppm 7.72 (s, 1H), 7.35 (s, 1H), 5.50-4.98 (br. s, 2H), 4.05-3.95 (m, 1H), 3.85-3.80 (m, 5H), 3.33 (t, J=12 Hz, 2H), 1.90-1.83 (m, 2H), 1.17-1.08 (m, 2H).

Step 6: 1-(2,6-dimethylcyclohexyl)-3-[(1-methyl-1H-pyrazol-4-yl)(oxan-4-yl)sulfamoyl]urea sodium salt. To a solution of 1-methyl-4-[sulfamoyl(tetrahydropyran-4-yl)amino]pyrazole (147 mg, 0.49 mmol) in THF (1.5 ml) was added NaH (60% in mineral oil, 39 mg, 0.98 mmol). To the RM was added 2-isocyanato-1,3-dimethyl-cyclohexane (60 mg, 0.39 mmol) and the RM stirred for 2 h. The solution was concentrated in vacuo. The residue was purified by prep-HPLC (column: Huapu C8 Extreme BDS 5 μm 15030 mm; mobile phase: [water (10 mM NH₄HCO₃)-ACN]; B: 15-45%, 10 min) to give the title compound as a white solid (Y=7%). ¹H NMR (400 MHz, methanol-d₄) δ ppm 7.64 (s, 1H), 7.37 (s, 1H), 4.29-4.25 (m, 1H), 3.93-3.87 (m, 4H), 3.50-3.41 (m, 3H), 2.20-1.95 (m, 1H), 1.88-1.41 (m, 10H), 1.18-1.09 (m, 1H), 1.02-0.82 (m, 7H). LC-MS (ESI): m/z: [M+H]⁺=414.2

Example 89. 1-[3-chloro-5-(propan-2-yl)phenyl]-3-[(1-methyl-1H-pyrazol-4-yl)(oxan-4-yl)sulfamoyl]urea sodium salt

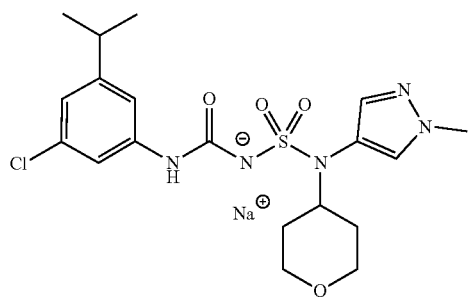 [SMILES: CC(C)c1cc(Cl)cc(NC(=O)[N-]S(=O)(=O)N(c2cnn(C)c2)C2CCOCC2)c1 ; [Na+]]

Step 1: 3-chloro-5-isopropenylaniline. To a solution of 3-bromo-5-chloro-aniline (3.0 g, 14.5 mmol) in dioxane (30 ml) and H₂O (3 ml) was added 2-isopropenyl-4,4,5,5-tetramethyl-1,3,2-dioxaborolane (2.93 g, 17.44 mmol), Pd(dppf)Cl₂ (1.06 g, 1.45 mmol) and Cs₂CO₃ (14.20 g, 43.6 mmol). The mixture was stirred at 130° C. for 3 h. The solution was filtered and the filtrate was concentrated in vacuo. The residue was purified by FCC (25% ethyl acetate in petroleum ether) to give the title compound as a yellow oil (Y=82%). LC-MS (ESI): m/z: [M+H]⁺=168.3

Step 2: 3-chloro-5-isopropylaniline. To a solution of 3-chloro-5-isopropenylaniline (2.0 g, 11.93 mmol) in MeOH (20 ml) was added 10% Pd/C (200 mg) under N₂. The suspension was degassed under vacuum and purged with H₂ several times. The mixture was stirred under H₂ (15 psi) at rt for 2 h. The solution was filtered and the filtrate was concentrated in vacuo to give the title compound as a green oil (Y=47%). ¹H NMR (400 MHz, DMSO-d₆) δ ppm 6.46-6.41 (m, 3H), 2.74-2.61 (m, 1H), 1.13 (d, J=7 Hz, 6H). NH₂ not seen.

Step 3: 1-chloro-3-isocyanato-5-(propan-2-yl)benzene. General procedure C was followed using 3-chloro-5-isopropylaniline to give the title compound as a yellow solid.

Step 4: 1-[3-chloro-5-(propan-2-yl)phenyl]-3-[(1-methyl-1H-pyrazol-4-yl)(oxan-4-yl)sulfamoyl]urea sodium salt. To a solution of 1-methyl-4-[sulfamoyl(tetrahydropyran-4-yl)amino]pyrazole (182 mg, 0.61 mmol) (for synthesis refer to Example 88) in THF (2 ml) cooled to 0° C. under nitrogen was added NaH (60% in mineral oil, 61 mg, 1.53 mmol) and then 1-chloro-3-isocyanato-5-(propan-2-yl)benzene (120 mg, 0.61 mmol). The RM was stirred at rt for 2 h. The solution was concentrated in vacuo. The residue was purified by prep-HPLC (column: Agela Durashell 10 μm 250×50 mm; mobile phase: [water (10 mM NH₄HCO₃) -ACN]; B: 8-38%, 20 min) to give the title compound as a white solid (Y=47%). ¹H NMR (400 MHz, methanol-d₄) δ ppm 7.70 (s, 1H), 7.44 (s, 1H), 7.41 (s, 1H), 7.09 (s, 1H), 6.94 (s, 1H), 4.43-4.26 (m, 1H), 3.96-3.88 (m, 2H), 3.85 (s, 3H), 3.52-3.46 (m, 2H), 2.88-2.84 (m, 1H), 1.93-1.85 (m, 2H), 1.50-1.42 (m, 2H), 1.23 (d, J=7 Hz, 6H).

Example 90. 3-(3,5-diethoxyphenyl)-1-[(1-methyl-1H-pyrazol-4-yl)(oxan-4-yl)sulfamoyl]urea sodium salt

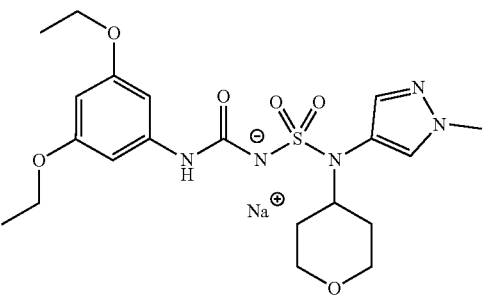 [SMILES: CCOc1cc(NC(=O)[N-]S(=O)(=O)N(c2cnn(C)c2)C2CCOCC2)cc(OCC)c1 ; [Na+]]

Step 1: 1,3-diethoxy-5-isocyanato-benzene. General procedure C was followed using 3,5-diethoxyaniline to give the title compound as a yellow solid (Y=100%). LC-MS in MeOH (ESI): m/z: =239.9

Step 2: 3-(3,5-diethoxyphenyl)-1-[(1-methyl-1H-pyrazol-4-yl)(oxan-4-yl)sulfamoyl]urea sodium salt. To a solution of 1-methyl-4-[sulfamoyl(tetrahydropyran-4-yl)amino]pyrazole (150 mg, 0.40 mmol)(for synthesis refer to &le 88) in THF (2 ml) cooled to 0° C. was added NaH (60% in mineral oil, 64 mg, 1.60 mmol). The RM was stirred at 0° C. for 0.5 h, then 1,3-diethoxy-5-isocyanato-benzene (83 mg, 0.40 mmol) was added to the reaction mixture. The RM was stirred at 0° C. for a further 1.5 h. The RM was diluted with MTBE (20 ml) and the solvent was removed under reduced pressure to give a residue. The residue was purified by prep-HPLC (column: Agela Durashell 10 μm 250×50 mm; mobile phase: [water (10 mM $NH_4HCO_3$)-ACN]; B: 5-30%, 20 min) to give the title compound as a white solid (Y=16%). $^1$H NMR (400 MHz, methanol-$d_4$) δ ppm 7.68 (s, 1H), 7.41 (s, 1H), 6.61 (s, 1H), 6.60 (s, 1H), 6.18 (s, 1H), 4.37-4.30 (m, 1H), 3.99 (q, J=7 Hz, 4H), 3.94-3.90 (m, 2H), 3.84 (s, 3H), 3.49 (t, J=11 Hz, 2H), 1.93-1.85 (m, 2H), 1.51-1.43 (m, 2H), 1.36 (t, J=7 Hz, 6H). LC-MS (ESI): m/z: [M+H]$^+$=468.1

Example 91. 3-(3,5-dichlorophenyl)-1-[(1-methyl-1H-pyrazol-4-yl)(1-methylpiperidin-3-yl)sulfamoyl]urea sodium salt

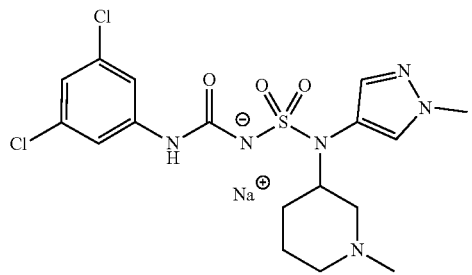 [SMILES: CN1CCCC(N(c2cnn(C)c2)S(=O)(=O)[N-]C(=O)Nc2cc(Cl)cc(Cl)c2)C1 ; [Na+]]

Step 1: 1,3-dichloro-5-isocyanato-benzene. General procedure C was followed using 3,5-dichloroaniline to give the title compound as a brown liquid (Y=99%).

Step 2: tert-butyl N-[(1-methyl-3-piperidyl)-(1-methylpyrazol-4-yl)sulfamoyl]carbamate trifluoroacetate. To a solution of 1-methyl-N-(1-methylpyrazol-4-yl)piperidin-3-amine (600 mg, 2.78 mmol) (for synthesis refer to Example 23) in DCM (10 ml) was added DIPEA (1.45 ml, 8.34 mmol) and the solution stirred at rt for 0.5 h. The RM was treated dropwise with a solution of tert-butyl N-chlorosulfonylcarbamate (599 mg, 2.78 mmol) (for synthesis refer to Example 87) in DCM (5 ml) and the mixture stirred at rt for 0.5 h. The solution was concentrated in vacuo. The crude product was purified by prep-HPLC (column: Phenomenex Luna C18 10 μm 250×50 mm; mobile phase: [water (0.1% TFA)-ACN]; B: 5-35%, 20 min) to give the title compound as a yellow solid (Y=52%). $^1$H NMR (400 MHz, DMSO-$d_6$) δ ppm 11.30 (s, 1H), 10.00 (s, 1H), 7.80 (s, 1H), 7.29 (s, 1H), 4.41-4.35 (m, 1H), 3.85 (s, 3H), 3.48 (d, J=9 Hz, 1H), 3.28 (d, J=12 Hz, 1H), 2.78 (s, 3H), 2.77-2.61 (m, 2H), 1.94-1.84 (m, 2H), 1.74-1.63 (m, 1H), 1.47 (s, 9H), 1.20-1.11 (m, 1H).

Step 3: 1-methyl-3-[(1-methylpyrazol-4-yl)-sulfamoyl-amino]piperidine trifluoroacetate. To a solution of tert-butyl N-[(1-methyl-3-piperidyl)-(1-methylpyrazol-4-yl)sulfamoyl]carbamate trifluoroacetate (700 mg, 1.87 mmol) in DCM (10 ml) was added TFA (2 ml) and the reaction stirred at rt for 5 h. The solution was concentrated in vacuo to give the title compound as a yellow oil (Y=96%). $^1$H NMR (400 MHz, DMSO-$d_6$) δ ppm 9.77 (s, 1H), 7.77 (s, 1H), 7.38 (s, 1H), 7.05 (s, 2H), 4.19-4.12 (m, 1H), 3.82 (s, 3H), 3.54-3.50 (m, 1H), 3.29-3.25 (m, 1H), 2.76 (d, J=4 Hz, 3H), 2.73-2.60 (m, 2H), 1.96-1.84 (m, 2H), 1.72-1.62 (m, 1H), 1.23-1.11 (m, 1H).

Step 4: 3-(3,5-dichlorophenyl)-1-[(1-methyl-1H-pyrazol-4-yl)(1-methylpiperidin-3-yl)sulfamoyl]urea sodium salt. To a solution of 1-methyl-3-[(1-methylpyrazol-4-yl)-sulfamoyl-amino]piperidine trifluoroacetate (100 mg, 0.26 mmol) in THF (3 ml) cooled to 0° C. was added NaH (60% in mineral oil, 41 mg, 1.0 mmol), then the mixture was stirred at 0° C. for 0.5 h. To this mixture was added 1,3-dichloro-5-isocyanato-benzene (35 μl, 0.26 mmol) and the RM stirred was at 0° C. for 1.5 h. The mixture was diluted with MTBE (20 ml). The solvent was evaporated under reduced pressure to give a residue. The residue was purified by prep-HPLC (column: Agela Durashell 10 μm 250×50 mm; mobile phase: [water (10 mM $NH_4HCO_3$)-ACN]; B: 8-35%, 20 min) to give the title compound as a white solid (Y=19%). $^1$H NMR (400 MHz, methanol-$d_4$) δ ppm 7.63 (s, 1H), 7.48 (s, 2H), 7.42 (s, 1H), 6.93 (t, J=2 Hz, 1H), 4.43-4.37 (m, 1H), 3.83 (s, 3H), 3.68-3.62 (m, 1H), 3.23-3.17 (m, 1H), 2.72 (s, 3H), 2.56-2.49 (m, 2H), 2.11-2.05 (m, 1H), 1.96-1.92 (m, 1H), 1.87-1.77 (m, 1H), 1.30-1.20 (m, 1H). LC-MS (ESI): m/z: [M+H]$^+$=461.0

Example 92. 1-[3-chloro-5-(trifluoromethoxy)phenyl]-3-[(1-methyl-1H-pyrazol-4-yl)(oxan-4-yl)sulfamoyl]urea sodium salt

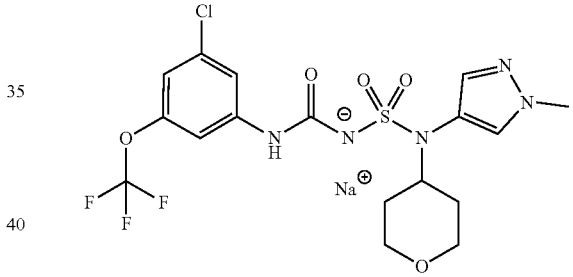

Step 1: 1-chloro-3-isocyanato-5-(trifluoromethoxy)benzene. General procedure C was followed using 3-chloro-5-(trifluoromethoxy)aniline to give the title compound as a yellow solid (Y=100%). LC-MS in MeOH (ESI): m/z: = 270.2

Step 2: 1-[3-chloro-5-(trifluoromethoxy)phenyl]-3-[(1-methyl-1H-pyrazol-4-yl)(oxan-4-yl)sulfamoyl]urea sodium salt. To a solution of 1-methyl-4-[sulfamoyl(tetrahydropyran-4-yl)amino]pyrazole (150 mg, 0.51 mmol) (for synthesis refer to Example 106) in THF (3 ml) cooled to 0° C. was added NaH (60% in mineral oil, 81 mg, 2.0 mmol). The RM was stirred at 0° C. for 0.5 h then treated with 1-chloro-3-isocyanato-5-(trifluoromethoxy)benzene (120 mg, 0.50 mmol). The RM was stirred at 0° C. for 1.5 h. The RM was diluted with MTBE (20 ml) and the solvent was removed under reduced pressure to give a residue. The residue was purified by prep-HPLC (column: Xtimate C18 10 μm 250×50 mm; mobile phase: [water (10 mM $NH_4HCO_3$)-ACN]; B: 2-35%, 20 min) to give the title compound as a white solid (Y=22%). $^1$H NMR (400 MHz, methanol-$d_4$) δ ppm 7.67 (s, 1H), 7.52 (t, J=2 Hz, 1H), 7.43 (s, 1H), 7.41 (s, 1H), 6.92 (s, 1H), 4.35-4.29 (m, 1H), 3.92 (dd, J=4, 12 Hz, 2H), 3.85 (s, 3H), 3.53-3.47 (m, 2H), 1.90 (dd, J=2, 12 Hz, 2H), 1.50-1.40 (m, 2H). LC-MS (ESI): m/z: [M+H]$^+$=498.0

Example 93. 3-(3-chloro-5-methoxyphenyl)-1-[(1-methyl-1H-pyrazol-4-yl)(oxan-4-yl)sulfamoyl]urea sodium salt

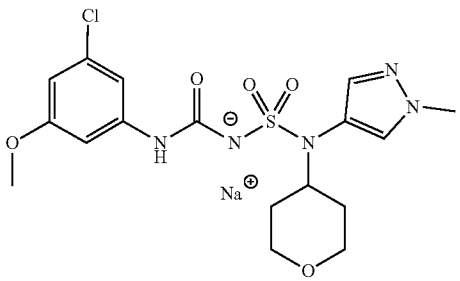 [SMILES: COc1cc(Cl)cc(NC(=O)[N-]S(=O)(=O)N(c2cnn(C)c2)C2CCOCC2)c1 ; [Na+]]

Step 1: 3-chloro-5-methoxy-aniline. To a solution of 1-chloro-3-methoxy-5-nitro-benzene (500 mg, 2.67 mmol) in MeOH (3 ml) was added NH$_4$Cl (1.28 g, 24.0 mmol), H$_2$O (1 ml) and Fe (1.04 g, 18.7 mmol) under a N$_2$ atmosphere. The mixture was stirred at 80° C. for 1 h. The reaction mixture was allowed to cool to rt, filtered, and the filtrate concentrated to give the title compound as a brown oil (Y=71%). $^1$H NMR (400 MHz, DMSO-d$_6$) δ ppm 6.19 (t, J=4 Hz, 1H), 6.10 (t, J=4 Hz, 1H), 6.06 (t, J=4 Hz, 1H), 5.62-5.15 (br. s, 2H), 3.65 (s, 3H).

Step 2: 1-chloro-3-isocyanato-5-methoxy-benzene. General procedure C was followed using 3-chloro-5-methoxy-aniline to give the title compound as a yellow solid (Y=86%). LC-MS in MeOH (ESI): m/z: =216.0

Step 3: 3-(3-chloro-5-methoxyphenyl)-1-[(1-methyl-1H-pyrazol-4-yl)(oxan-4-yl)sulfamoyl]urea sodium salt. To a solution of 1-methyl-4-[sulfamoyl(tetrahydropyran-4-yl)amino]pyrazole (170 mg, 0.66 mmol) (for synthesis refer to Example 88) in THF (5 ml) cooled to 0° C. was added NaH (60% in mineral oil, 105 mg, 2.61 mmol). The RM was stirred at 0° C. for 0.5 h. The RM was treated with 1-chloro-3-isocyanato-5-methoxy-benzene (0.12 g, 0.66 mmol) and stirred at 0° C. for a further 0.5 h. The RM was diluted with MTBE (10 ml) and then concentrated. The resulting residue was purified by prep-HPLC (column: Agela Durashell 10 μm 250×50 mm; mobile phase: [water (10 mM NH$_4$HCO$_3$)-ACN]; B: 5-30%, 20 min) to give the title compound as a white solid (Y=40%). $^1$H NMR (400 MHz, methanol-d$_4$) δ ppm 7.69 (s, 1H), 7.41 (s, 1H), 7.10 (t, J=2 Hz, 1H), 6.96 (t, J=2 Hz, 1H), 6.63 (t, J=2 Hz, 1H), 4.43-4.28 (m, 1H), 3.94-3.91 (m, 2H), 3.84 (s, 3H), 3.77 (s, 3H), 3.52-3.46 (m, 2H), 1.90-1.87 (m, 2H), 1.50-1.40 (m, 2H). LC-MS (ESI): m/z: [M+H]$^+$=444.1

Example 94. 3-(3,5-dichloro-2-fluorophenyl)-1-[(1-methyl-1H-pyrazol-4-yl)(oxan-4-yl)sulfamoyl]urea sodium salt

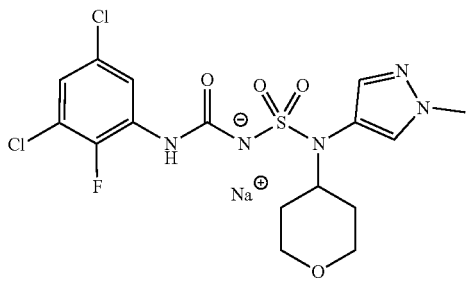 [SMILES: Cn1cc(N(C2CCOCC2)S(=O)(=O)[N-]C(=O)Nc2cc(Cl)cc(Cl)c2F)cn1 ; [Na+]]

Step 1: 1,5-dichloro-2-fluoro-3-isocyanato-benzene. General procedure C was followed using 3,5-dichloro-2-fluoro-aniline to give the title compound as a yellow solid (Y=87%). LC-MS in MeOH (ESI): m/z: =238.0

Step 2: 3-(3,5-dichloro-2-fluorophenyl)-1-[(1-methyl-1H-pyrazol-4-yl)(oxan-4-yl)sulfamoyl]urea sodium salt. To a solution of 1-methyl-4-[sulfamoyl(tetrahydropyran-4-yl)amino]pyrazole (253 mg, 0.97 mmol) (for synthesis refer to Example 88) in THF (3 ml) cooled to 0° C. was added NaH (60% in mineral oil, 155 mg, 3.88 mmol). The RM was stirred at 0° C. for 0.5 h. The RM was treated with 1,5-dichloro-2-fluoro-3-isocyanato-benzene (0.20 g, 0.97 mmol) and stirred at 0° C. for a further 0.5 h. The RM was diluted with MTBE (10 ml) and then concentrated. The resulting residue was purified by prep-HPLC (column: Agela Durashell 10 μm 250×50 mm; mobile phase: [water (10 mM NH$_4$HCO$_3$)-ACN]; B: 10-35%, 20 min) to give the title compound as a white solid (Y=10%). $^1$H NMR (400 MHz, methanol-d$_4$) δ ppm 8.21-8.18 (m, 1H), 7.71 (s, 1H), 7.41 (s, 1H), 7.20-7.18 (m, 1H), 4.37-4.31 (m, 1H), 3.95-3.91 (m, 2H), 3.86 (s, 3H), 3.52-3.47 (m, 2H), 1.93-1.85 (m, 2H), 1.51-1.42 (m, 2H). LC-MS (ESI): m/z: [M+H]$^+$=466.0

Example 95. 3-(1,2,3,5,6,7-hexahydro-s-indacen-4-yl)-1-[(1-methyl-1H-pyrrol-3-yl)(oxan-4-yl)sulfamoyl]urea sodium salt

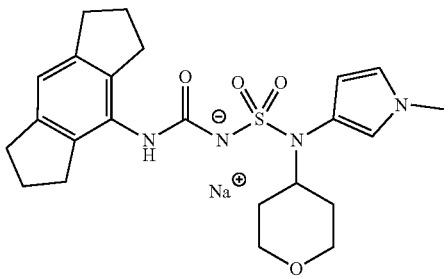 [SMILES: Cn1ccc(N(C2CCOCC2)S(=O)(=O)[N-]C(=O)Nc2c3c(cc4c2CCC4)CCC3)c1 ; [Na+]]

Step 1: 1-methyl-3-nitro-pyrrole. To a solution of 3-nitro-1H-pyrrole (2.2 g, 19.63 mmol) in DMF (40 ml) was added K$_2$CO$_3$ (5.43 g, 39.26 mmol) and MeI (2.44 ml, 39.26 mmol) and the mixture stirred at rt for 12 h. The solution was diluted with water (50 ml) and extracted with ethyl acetate (3×50 ml). The combined organic phases were washed with brine (20 ml), dried with anhydrous Na$_2$SO$_4$, filtered and concentrated in vacuo to give the title compound as a yellow solid (Y=97%). $^1$H NMR (400 MHz, DMSO-d$_6$) δ=7.91 (t, J=2 Hz, 1H), 6.87 (t, J=3 Hz, 1H), 6.73-6.59 (m, 1H), 3.70 (s, 3H).

Step 2: 1-methylpyrrol-3-amine. To a solution of 1-methyl-3-nitro-pyrrole (0.5 g, 3.96 mmol) in MeOH (20 ml) was added 10% Pd/C (200 mg) under N$_2$. The suspension was degassed under vacuum and purged with H$_2$ several times. The mixture was stirred at rt under H$_2$ (15 psi pressure) for 20 h. The mixture was filtered and the filtrate was concentrated in vacuo to give the title compound as a brown oil (Y=92%). $^1$H NMR (400 MHz, DMSO-d$_6$) δ=6.28 (t, J=2 Hz, 1H), 5.98 (t, J=2 Hz, 1H), 5.43 (t, J=2 Hz, 1H), 3.40 (s, 3H). NH$_2$ not seen.

Step 3: 1-methyl-N-tetrahydropyran-4-yl-pyrrol-3-amine trifluoroacetate. General procedure A was followed using 1-methylpyrrol-3-amine and tetrahydropyran-4-one. The crude product was purified by prep-HPLC (column: Phenomenex Luna C18 10 μm 250×50 mm; mobile phase:

[water (0.1% TFA)-ACN]; B: 0-20%, 20 min) to give the title compound as a yellow oil (Y=33%). ¹H NMR (400 MHz, methanol-d₄) δ ppm 7.94 (s, 1H), 7.66 (s, 1H), 6.18 (t, J=55 Hz, 1H), 4.62-4.58 (m, 2H), 3.65-3.57 (m, 3H), 3.15-3.05 (m, 2H), 2.88 (s, 3H), 2.36-2.25 (m, 2H), 1.99-1.90 (m, 2H).

Step 4: tert-butyl N-[(1-methylpyrrol-3-yl)-tetrahydropyran-4-yl-sulfamoyl]carbamate. To a solution of 1-methyl-N-tetrahydropyran-4-yl-pyrrol-3-amine trifluoroacetate (250 mg, 0.85 mmol) in DCM (2 ml) was added DIPEA (444 μl, 2.55 mmol) and the solution stirred at rt for 0.5 h. A solution of tert-butyl N-chlorosulfonylcarbamate (183 mg, 0.85 mmol) in DCM (6 ml) was added into the solution and the RM was stirred at rt for 2 h. The solution was concentrated in vacuo. The crude product was purified by FCC (0-100% EtOAc in petroleum ether) to give the title compound as a yellow oil (Y=49%). ¹H NMR (400 MHz, DMSO-d₆) δ ppm 10.80 (s, 1H), 6.66-6.63 (m, 2H), 5.78 (t, J=2 Hz, 1H), 4.20-4.13 (m, 1H), 3.85-3.73 (m, 2H), 3.60 (s, 3H), 3.36-3.31 (m, 1H), 3.15-3.09 (m, 1H), 1.70-1.62 (m, 2H), 1.42 (s, 9H), 1.37-1.31 (m, 2H).

Step 5: 1-methyl-3-[sulfamoyl(tetrahydropyran-4-yl)amino]pyrrole. A mixture of tert-butyl N-[(1-methylpyrrol-3-yl)-tetrahydropyran-4-yl-sulfamoyl]carbamate (100 mg, 0.28 mmol) in TFA (0.4 ml) and DCM (2 ml) was stirred at rt for 7 min. The solution was concentrated in vacuo to give the title compound as a yellow oil (Y=96%). ¹H NMR (400 MHz, DMSO-d₆) δ ppm 6.67 (t, J=2 Hz, 1H), 6.61 (t, J=3 Hz, 1H), 5.92 (t, J=2 Hz, 1H), 3.97-3.87 (m, 3H), 3.59 (s, 3H), 3.33 (t, J=11 Hz, 2H), 1.73-1.69 (m, 2H), 1.40-1.32 (m, 2H).

Step 6: 3-(1,2,3,5,6,7-hexahydro-s-indacen-4-yl)-1-[(1-methyl-1H-pyrrol-3-yl)(oxan-4-yl)sulfamoyl]urea sodium salt. To a solution of 1-methyl-3-[sulfamoyl(tetrahydropyran-4-yl)amino]pyrrole (100 mg, 0.27 mmol) in THF (2 ml) cooled to 0° C. was added NaH (60% in mineral oil, 43 mg, 1.07 mmol). The RM was stirred at 0° C. for 15 min. A solution of 4-isocyanato-1,2,3,5,6,7-hexahydro-s-indacene (53 mg, 0.27 mmol) in THF (1 ml) was added and RM stirred at 0° C. for 15 min. The solution was concentrated in vacuo. The crude product was purified by prep-HPLC (column: Agela Durashell 10 μm 250×50 mm; mobile phase: [water (10 mM NH₄HCO₃)-ACN]; B: 15-45%, 20 min) to give the title compound as a yellow solid (Y=23%). ¹H NMR (400 MHz, methanol-d₄) δ ppm 6.98 (s, 1H), 6.71 (t, J=2 Hz, 1H), 6.64 (t, J=3 Hz, 1H), 6.02-6.00 (m, 1H), 4.38-4.28 (m, 1H), 3.92-3.87 (m, 2H), 3.66 (s, 3H), 3.49-3.42 (m, 2H), 2.90-2.76 (m, 8H), 2.15-1.99 (m, 4H), 1.86-1.81 (m, 2H), 1.59-1.48 (m, 2H).
LC-MS (ESI): m/z: [M+H]⁺=459.1

Example 96. 3-(1,2,3,5,6,7-hexahydro-s-indacen-4-yl)-1-[(2-methyl-2H-1,2,3-triazol-4-yl)(oxan-4-yl)sulfamoyl]urea sodium salt

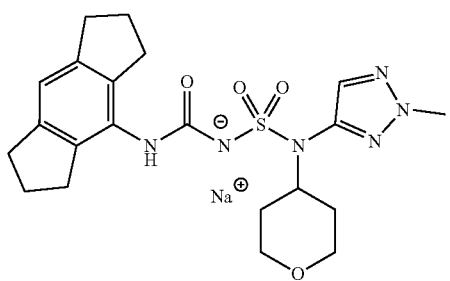 [SMILES: Cn1ncc(N(C2CCOCC2)S(=O)(=O)[N-]C(=O)Nc2c3c(cc4c2CCC4)CCC3)n1 ; [Na+]]

Step 1: 2-methyl-N-tetrahydro pyran-4-yl-triazol-4-amine trifluoroacetate. General procedure A was followed using 2-methyltriazol-4-amine and tetrahydropyran-4-one. The crude product was purified by prep-HPLC (column: Phenomenex Luna C18 10 μm 250×50 mm; mobile phase: [water (0.1% TFA)-ACN]; B: 0-16%, 20 min) to give the title compound as a white solid (Y=28%). ¹H NMR (400 MHz, methanol-d₄) δ ppm 6.92 (s, 1H), 4.85-4.58 (br. s, 2H), 3.88 (s, 3H), 3.86-3.80 (m, 2H), 3.39-3.28 (m, 3H), 1.88-1.83 (m, 2H), 1.43-1.31 (m, 2H).

Step 2: tert-butyl N-[(2-methyltriazol-4-yl)-tetrahydropyran-4-yl-sulfamoyl]carbamate. To a solution of 2-methyl-N-tetrahydropyran-4-yl-triazol-4-amine trifluoroacetate (220 mg, 0.74 mmol) in DCM (5 ml) was added DIPEA (388 μl, 2.23 mmol). The solution was cooled to 0° C. and treated dropwise with a solution of tert-butyl N-chlorosulfonylcarbamate (160 mg, 0.74 mmol) (for synthesis refer to Example 87) in DCM (1 ml). The RM was stirred at rt for 1.5 h. The solution was concentrated in vacuo and the resulting residue purified by prep-HPLC (column: Agela Durashell 10 μm 250×50 mm; mobile phase: [water (10 mM NH₄HCO₃)-ACN]; B: 1-20%, 20 min) to give the title compound as a white solid (Y=71%). ¹H NMR (400 MHz, DMSO-d₆) δ ppm 11.45-1.19 (br. s, 1H), 7.64 (s, 1H), 4.25-4.16 (m, 1H), 4.13 (s, 3H), 3.87-3.81 (m, 2H), 3.37-3.34 (m, 2H), 1.78-1.68 (m, 2H), 1.43 (s, 9H), 1.28-1.20 (m, 2H).

Step 3: 2-methyl-4-[sulfamoyl(tetrahydropyran-4-yl)amino]triazole trifluoroacetate. A solution of tert-butyl N-[(2-methyltriazol-4-yl)-tetrahydropyran-4-yl-sulfamoyl]carbamate (40 mg, 0.11 mmol) in 5:1 DCM/TFA (5 ml) was stirred at rt for 1.5 h. The solution was concentrated under reduced pressure to give the title compound as a yellow oil and used to next step directly without further purification. LC-MS (ESI): m/z: [M+H]⁺=262.0

Step 4: 3-(1,2,3,5,6,7-hexahydro-s-indacen-4-yl)-1-[(2-methyl-2H-1,2,3-triazol-4-yl)(oxan-4-yl)sulfamoyl]urea sodium salt. To a solution of 2-methyl-4-[sulfamoyl(tetrahydropyran-4-yl)amino]triazole trifluoroacetate (30 mg, 0.10 mmol) in THF (0.5 ml) cooled to 0° C. was added NaH (60% in mineral oil, 12 mg, 0.30 mmol). The RM was treated dropwise with 4-isocyanato-1,2,3,5,6,7-hexahydro-s-indacene (22 mg, 0.11 mmol) and then stirred at rt for 1 h. The RM was filtered and the filtrate concentrated under reduced pressure. The resulting residue was purified by prep-HPLC (column: Waters Xbridge Prep OBD C18 10 μm 150×40 mm; mobile phase: [water (10 mM NH₄HCO₃)-ACN]; B: 10-30%, 11 min) to give the title compound as a white solid (Y=45%). ¹H NMR (400 MHz, methanol-d₄) δ ppm 7.64 (s, 1H), 6.98 (s, 1H), 4.44-4.33 (m, 1H), 4.14 (s, 3H), 3.91 (dd, J=4, 12 Hz, 2H), 3.46 (t, J=12 Hz, 2H), 2.88 (t, J=7 Hz, 4H), 2.81 (t, J=7 Hz, 4H), 2.11-2.03 (m, 4H), 1.96-1.88 (m, 2H), 1.61-1.47 (m, 2H). LC-MS (ESI): m/z: [M+H]⁺=461.2

Example 97. 3-[3-ethyl-5-(trifluoromethyl)phenyl]-1-[(1-methyl-1H-pyrazol-4-yl)(1-methylpiperidin-3-yl)sulfamoyl]urea sodium salt

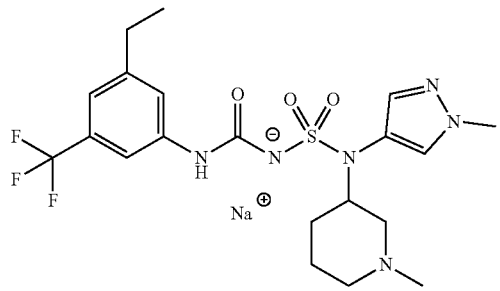 [SMILES: CCc1cc(NC(=O)[N-]S(=O)(=O)N(c2cnn(C)c2)C2CCCN(C)C2)cc(C(F)(F)F)c1 ; [Na+]]

Step 1: 1-ethyl-3-isocyanato-5-(trifluoromethyl)benzene. General procedure C was followed using 3-ethyl-5-(trifluoromethyl)aniline (for synthesis refer to Example 75) to give the title compound as a yellow oil (Y=75%). LC-MS in MeOH (ESI): m/z: [M+MeOH+H]$^+$=248.2

Step 2: 1-methyl-3-[(1-methylpyrazol-4-yl)-sulfamoylamino]piperidine trifluoroacetate. A solution of tert-butyl N-[(1-methyl-3-piperidyl)-(1-methylpyrazol-4-yl) sulfamoyl]carbamate trifluoroacetate (200 mg, 0.41 mmol) (for synthesis refer to Example 91) in DCM (3 ml) and TFA (0.6 ml) was stirred at rt for 0.5 h. The RM was concentrated in vacuo to give the title compound as a yellow oil. $^1$H NMR (400 MHz, DMSO-d$_6$) δ=9.70 (s, 1H), 7.77 (s, 1H), 7.38 (s, 1H), 7.05 (s, 2H), 4.20-4.13 (m, 1H), 3.82 (s, 3H), 3.56-3.48 (m, 1H), 3.31-3.23 (m, 1H), 2.77 (d, J=4 Hz, 3H), 2.71-2.59 (m, 2H), 1.99-1.83 (m, 2H), 1.72-1.62 (m, 1H), 1.26-1.08 (m, 1H).

Step 3: 3-[3-ethyl-5-(trifluoromethyl)phenyl]-1-[(1-methyl-1H-pyrazol-4-yl)(1-methylpiperidin-3-yl)sulfamoyl]urea sodium salt. To a solution of 1-methyl-3-[(1-methylpyrazol-4-yl)-sulfamoyl-amino]piperidine trifluoroacetate (210 mg, 0.54 mmol) in THF (2 ml) cooled to 0° C. was added NaH (60% in mineral oil, 87 mg, 2.17 mmol) and the solution stirred at 0° C. for 15 min. 1-Ethyl-3-isocyanato-5-(trifluoromethyl)benzene (117 mg, 0.54 mmol) was added and the mixture stirred at 0° C. for 1 h. The solution was concentrated in vacuo. The crude product was purified by prep-HPLC (column: Agela Durashell 10 μm 250×50 mm; mobile phase: [water (10 mM NH$_4$HCO$_3$)-ACN]; B: 10-40%, 20 min) to give the title compound as a white solid (Y=18%). $^1$H NMR (400 MHz, methanol-d$_4$) δ ppm 7.77 (s, 1H), 7.64 (s, 1H), 7.42 (s, 1H), 7.39 (s, 1H), 7.06 (s, 1H), 4.46-4.37 (m, 1H), 3.82 (s, 3H), 3.71-3.63 (m, 1H), 3.26-3.22 (m, 2H), 2.76 (s, 3H), 2.66 (q, J=7 Hz, 3H), 2.12-2.04 (m, 1H), 2.00-1.91 (m, 1H), 1.87-1.71 (m, 1H), 1.25 (t, J=7 Hz, 4H). LC-MS (ESI): m/z: [M+H]$^+$=489.2

Example 98. 3-[3-chloro-5-(2-methylpropyl)phenyl]-1-[(1-methyl-1H-pyrazol-4-yl)(oxan-4-yl)sulfamoyl]urea sodium salt

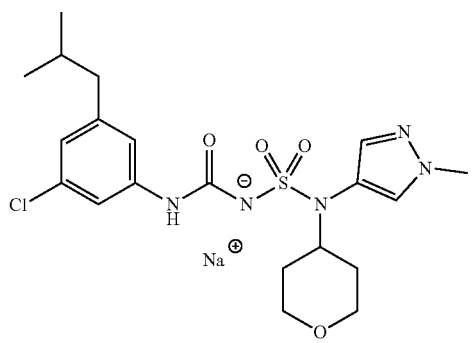 [SMILES: CC(C)Cc1cc(Cl)cc(NC(=O)[N-]S(=O)(=O)N(c2cnn(C)c2)C2CCOCC2)c1 ; [Na+]]

Step 1: 3-chloro-5-(2-methylprop-1-enyl)aniline. To a solution of 3-bromo-5-chloro-aniline (500 mg, 2.42 mmol) in 1,4-dioxane (10 ml) and H$_2$O (1 ml) was added 4,4,5,5-tetramethyl-2-(2-methylprop-1-enyl)-1,3,2-dioxaborolane (529 mg, 2.90 mmol), Pd(dppf)Cl$_2$ (177 mg, 0.24 mmol) and Cs$_2$CO$_3$ (2.37 g, 7.26 mmol). The RM was heated to 120° C. for 12 h under N$_2$. The solution was concentrated in vacuo. The residue was purified by FCC (25% EtOAc in petroleum ether) to give the title compound as a green oil (Y=41%). $^1$H NMR (400 MHz, DMSO-d$_6$) δ ppm 6.42 (t, J=2 Hz, 1H), 6.37 (s, 1H), 6.34 (s, 1H), 6.08 (s, 1H), 5.35 (s, 2H), 1.83 (s, 3H), 1.80 (s, 3H).

Step 2: 3-chloro-5-isobutyl-aniline. To a solution of 3-chloro-5-(2-methylprop-1-enyl)aniline (75 mg, 0.41 mmol) in MeOH (5 ml) was added 10% Pd/C (50 mg) under N$_2$. The suspension was degassed under vacuum and purged with H$_2$ several times. The mixture was then stirred under H$_2$ (15 psi) at rt for 15 min. The mixture was filtered through Celite and the filtrate concentrated in vacuo to give the title compound as a green oil. $^1$H NMR (400 MHz, DMSO-d$_6$) δ ppm 7.34 (t, J=8 Hz, 1H), 7.12-7.07 (m, 1H), 7.04 (s, 1H), 3.70-3.30 (br. s, 2H), 2.47-2.42 (m, 2H), 1.83-1.77 (m, 1H), 0.86 (d, J=7 Hz, 6H).

Step 3: 1-chloro-3-isobutyl-5-isocyanato-benzene. General procedure C was followed using 3-chloro-5-isobutyl-aniline to give the title compound as a yellow oil. LC-MS in MeOH (ESI): m/z: [M+MeOH+H]$^+$=242.1

Step 4: 3-[3-chloro-5-(2-methylpropyl)phenyl]-1-[(1-methyl-1H-pyrazol-4-yl)(oxan-4-yl)sulfamoyl]urea sodium salt. To a solution of 1-methyl-4-[sulfamoyl(tetrahydropyran-4-yl)amino]pyrazole (100 mg, 0.34 mmol) (for synthesis refer to Example 88) in THF (2 ml) cooled to 0° C. was added NaH (60% in mineral oil, 27 mg, 0.67 mmol). 1-Chloro-3-isobutyl-5-isocyanato-benzene (71 mg, 0.34 mmol) was then added and the RM was stirred at rt for 2 h. The residue was concentrated in vacuo and purified by prep-HPLC (column: HUAPU C8 Extreme BDS 5 μm 150×30 mm; mobile phase: [water (10 mM NH$_4$HCO$_3$)-ACN]; B: 30-50%, 10 min) to give the title compound as a white solid (Y=16%). $^1$H NMR (400 MHz, methanol-d$_4$) δ ppm 7.71 (s, 1H), 7.46 (t, J=2 Hz, 1H), 7.41 (s, 1H), 7.03 (s, 1H), 6.87 (s, 1H), 4.43-4.26 (m, 1H), 3.92 (dd, J=5, 11 Hz, 2H), 3.85 (s, 3H), 3.49 (t, J=11 Hz, 2H), 2.44 (d, J=7 Hz, 2H), 1.94-1.80 (m, 3H), 1.50-1.43 (m, 2H), 0.91 (d, J=7 Hz, 6H). LC-MS (ESI): m/z: [M+H]$^+$=470.2

Example 9. 1-[(1,3-dimethyl-1H-pyrazol-4-yl)(oxan-4-yl)sulfamoyl]-3-(1,2,3,5,6,7-hexahydro-s-indacen-4-yl)urea sodium salt

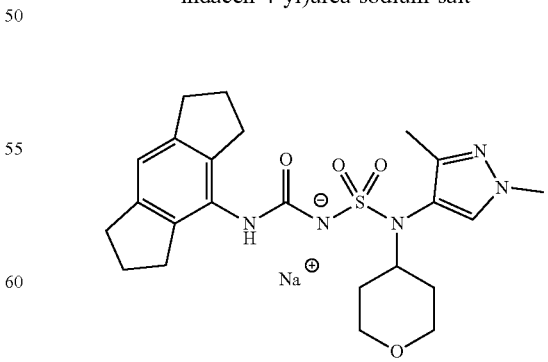

Step 1: 1,3-dimethyl-N-tetrahydropyran-4-yl-pyrazol-4-amine. General procedure A was followed using 1,3-dimethylpyrazol-4-amine and tetrahydropyran-4-one to give the title compound as a white solid (Y=89%). ¹H NMR (400 MHz, methanol-d₄) δ ppm 7.16 (s, 1H), 4.00-3.90 (m, 2H), 3.72 (s, 3H), 3.46-3.40 (m, 2H), 3.08-2.92 (m, 1H), 2.13 (s, 3H), 1.97-1.86 (m, 2H), 1.53-1.38 (m, 2H).

Step 2: 1-[(1,3-dimethyl-1H-pyrazol-4-yl)(oxan-4-yl)sulfamoyl]-3-(1,2,3,5,6,7-hexahydro-s-indacen-4-yl)urea sodium salt. General procedure B was followed using {[(1,2,3,5,6,7-hexahydro-s-indacen-4-yl)carbamoyl]amino}sulfonyl chloride and 1,3-dimethyl-N-tetrahydropyran-4-yl-pyrazol-4-amine. The crude product was purified by prep-HPLC (column: Agela Durashell C18 10 μm 250×50 mm; mobile phase: [water (10 mM NH₄HCO₃) -ACN]; B: 10-35%, 20 min) to give the title compound as a white solid (Y=10%). ¹H NMR (400 MHz, methanol-d₄) δ ppm 7.58 (s, 1H), 6.98 (s, 1H), 4.42-4.28 (m, 1H), 3.93-3.89 (m, 2H), 3.82 (s, 3H), 3.53-3.42 (m, 2H), 2.88 (t, J=7 Hz, 4H), 2.77 (t, J=7 Hz, 4H), 2.19 (s, 3H), 2.14-2.01 (m, 4H), 1.96-1.82 (m, 2H), 1.50-1.38 (m, 2H). LC-MS (ESI): m/z: [M+H]⁺=474.2

Example 100. 1-[(2,4-dimethylpyrimidin-5-yl)(oxan-4-yl)sulfamoyl]-3-(1,2,3,5,6,7-hexahydro-s-indacen-4-yl)urea sodium salt

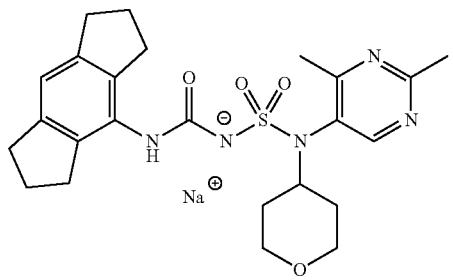 [SMILES: Cc1ncc(N(C2CCOCC2)S(=O)(=O)[N-]C(=O)Nc2c3c(cc4c2CCC4)CCC3)c(C)n1 ; [Na+]]

Step 1: 2,4-dimethyl-N-tetrahydropyran-4-yl-pyrimidin-5-amine. To a solution of tetrahydropyran-4-amine (1.35 g, 13.4 mmol) in toluene (5 ml) was added 5-bromo-2,4-dimethyl-pyrimidine (500 mg, 2.67 mmol), BINAP (333 mg, 0.53 mmol), Cs₂CO₃ (1.74 g, 5.35 mmol) and Pd(OAc)₂ (60 mg, 0.27 mmol) at rt under N₂. The mixture was heated at 120° C. for 3 h under a N₂ atmosphere. H₂O (10 ml) was added and the mixture was extracted with EtOAc (3×10 ml). The combined organic layers were washed with brine (5 ml), dried over Na₂SO₄, filtered and concentrated under reduced pressure to give a residue. The residue was purified by FCC (0-50% MeOH in EtOAc) to give the title compound as a brown solid (Y=90%). ¹H NMR (400 MHz, methanol-d₄) δ ppm 7.98 (s, 1H), 4.02-3.99 (m, 2H), 3.62-3.54 (m, 3H), 2.51 (s, 3H), 2.39 (s, 3H), 2.05-1.92 (m, 2H), 1.66-1.56 (m, 2H).

Step 2: 1-[(2,4-dimethylpyrimidin-5-yl)(oxan-4-yl)sulfamoyl]-3-(1,2,3,5,6,7-hexahydro-s-indacen-4-yl)urea sodium salt. General procedure B was followed using {[(1,2,3,5,6,7-hexahydro-s-indacen-4-yl)carbamoyl]amino}sulfonyl chloride and 2,4-dimethyl-N-tetrahydropyran-4-yl-pyrimidin-5-amine. The crude product was purified by prep-HPLC (column: Agela Durashell C18 10 μm 250×50 mm; mobile phase: [water (10 mM NH₄HCO₃) -ACN]; B: 10-35%, 20 min) to give the title compound as a white solid (Y=12%). ¹H NMR (400 MHz, methanol-d₄) δ ppm 8.58 (s, 1H), 6.92 (s, 1H), 4.46-4.39 (m, 1H), 3.97-3.87 (m, 2H), 3.50-3.42 (m, 2H), 2.86 (t, J=7 Hz, 4H), 2.80 (t, J=7 Hz, 4H), 2.65 (s, 3H), 2.59 (s, 3H), 2.10-2.03 (m, 6H), 1.32-1.26 (m, 2H). LC-MS (ESI): m/z: [M+H]⁺=486.2

Example 101. 3-[3-chloro-5-(propan-2-yl)phenyl]-1-[(1-methyl-1H-pyrazol-4-yl)(1-methylpiperidin-3-yl)sulfamoyl]urea sodium salt

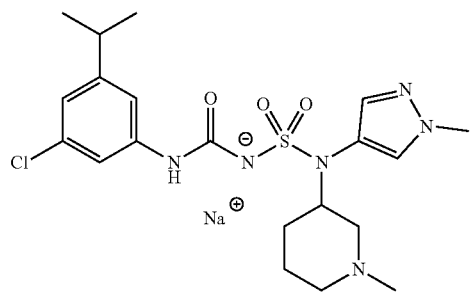 [SMILES: CC(C)c1cc(Cl)cc(NC(=O)[N-]S(=O)(=O)N(c2cnn(C)c2)C2CCCN(C)C2)c1 ; [Na+]]

Step 1: 1-chloro-3-isocyanato-5-isopropylbenzene. General procedure C was followed using 3-chloro-5-isopropylaniline to give the title compound as a pale yellow gum. LC-MS in MeOH (ESI): m/z: [M+MeOH+H]⁺=228.2

Step 2: 3-[3-chloro-5-(propan-2-yl)phenyl]-1-[(1-methyl-1H-pyrazol-4-yl)(1-methylpiperidin-3-yl)sulfamoyl]urea sodium salt. To a solution of 1-methyl-3-[(1-methylpyrazol-4-yl)-sulfamoyl-amino]piperidine (104 mg, 0.27 mmol) (for synthesis refer to Example 97) in THF (1 ml) cooled to 0° C. was added NaH (60% in mineral oil, 43 mg, 1.07 mmol). The RM was stirred at 0° C. for 15 min then treated with 1-chloro-3-isocyanato-5-isopropylbenzene (53 mg, 0.27 mmol). The RM was stirred at rt for a further 2 h. The solvent was removed under reduced pressure. The residue was purified by prep-HPLC (column: Xtimate C18 5 μm 150×25 mm; mobile phase: [water (10 mM NH₄HCO₃)-ACN]; B: 20-50%, 10 min) to give the title compound as a white solid (Y=8%). ¹H NMR (400 MHz, methanol-d₄) δ ppm 7.66 (s, 1H), 7.52 (s, 1H), 7.43 (s, 1H), 7.08 (s, 1H), 6.85 (s, 1H), 4.53-4.36 (m, 1H), 3.84 (s, 3H), 3.73-3.63 (m, 1H), 3.27-3.23 (m, 1H), 2.88-2.80 (m, 1H), 2.79 (s, 3H), 2.72-2.46 (m, 2H), 2.17-2.03 (m, 1H), 2.01-1.91 (m, 1H), 1.89-1.76 (m, 1H), 1.36-1.25 (m, 1H), 1.23 (d, J=7 Hz, 6H). LC-MS (ESI): m/z: [M+H]⁺=469.2

Example 102. 1-[3-ethyl-5-(trifluoromethyl)phenyl]-3-[(1-methyl-1H-pyrazol-4-yl)({[(2S)-1-methylpyrrolidin-2-yl]methyl})sulfamoyl]urea sodium salt

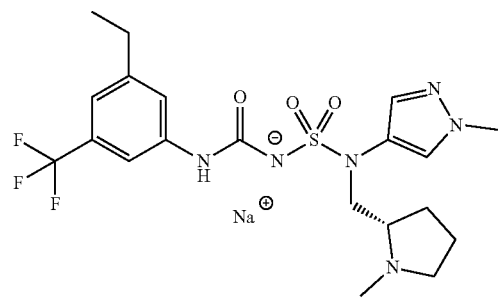 [SMILES: CCc1cc(NC(=O)[N-]S(=O)(=O)N(C[C@@H]2CCCN2C)c2cnn(C)c2)cc(C(F)(F)F)c1 ; [Na+]]

Step 1: 1-ethyl-3-isocyanato-5-(trifluoromethyl)benzene. General procedure C was followed using 3-ethyl-5-(trifluoromethyl)aniline to give the title compound as a yellow oil (Y=75%). LC-MS in MeOH (ESI): m/z: [M+MeOH+H]⁺=248.1

Step 2: tert-butyl N-[(1-methylpyrazol-4-yl)-[[(2S)-1-methylpyrrolidin-2-yl]methyl]sulfamoyl]carbamate trifluoroacetate. To a solution of 1-methyl-N-[[(2S)-1-methylpyrrolidin-2-yl]methyl]pyrazol-4-amine (1.32 g, 6.78 mmol) (for synthesis refer to Example 107) in DCM (10 ml) was added DIPEA (3.54 ml, 20.3 mmol). The RM was cooled to 0° C. and treated with a solution of tert-butyl N-chlorosulfonylcarbamate (1.9 g, 8.81 mmol) in THF (10 ml). The RM was stirred at 0° C. for 2 h. The mixture was concentrated in vacuo. The residue was purified by prep-HPLC (column: Phenomenex Luna C18 10 μm 250×50 mm; mobile phase: [water (0.1% TFA)-ACN]; B: 0-35%, 20 min) to give the title compound as a white gum (Y=60%). LC-MS (ESI): m/z: [M+H]⁺=374.1

Step 3: 1-methyl-4-[[(2S)-1-methylpyrrolidin-2-yl]methylsulfamoylamino]pyrazole trifluoroacetate. A solution of tert-butyl N-[(1-methylpyrazol-4-yl)-[[(2S)-1-methylpyrrolidin-2-yl]methyl]sulfamoyl]carbamate trifluoroacetate (123 mg, 0.33 mmol) in DCM (3 ml) and TFA (0.6 ml) was stirred at rt for 1 h. The RM was concentrated in vacuo to give the title compound as a yellow oil (Y=100%). LC-MS (ESI): m/z: [M+H]⁺=274.1

Step 4: 1-[3-ethyl-5-(trifluoromethyl)phenyl]-3-[(1-methyl-1H-pyrazol-4-yl)({[(2S)-1-methylpyrrolidin-2-yl]methyl})sulfamoyl]urea sodium salt. To a solution of 1-methyl-4-[[(2S)-1-methylpyrrolidin-2-yl]methyl-sulfamoyl-amino]pyrazole trifluoroacetate (127 mg, 0.33 mmol) in THF (3 ml) cooled to 0° C. was added NaH (60% in mineral oil, 52 mg, 1.31 mmol) and the solution stirred at 0° C. for 15 min. The RM was treated with 1-ethyl-3-isocyanato-5-(trifluoromethyl)benzene (71 mg, 0.33 mmol) and the RM stirred at 0° C. for 1 h. The solution was concentrated in vacuo. The crude product was purified by prep-HPLC (column: Agela Durashell 10 μm 250×50 mm; mobile phase: [water (10 mM NH₄HCO₃)-ACN]; B: 10-40%, 20 min) to give the title compound as a yellow solid (Y=31%). ¹H NMR (400 MHz, methanol-d₄) δ ppm 7.85 (s, 1H), 7.66 (s, 1H), 7.48 (s, 1H), 7.42 (s, 1H), 7.06 (s, 1H), 4.23-4.17 (m, 1H), 3.93-3.78 (m, 5H), 3.58-3.47 (m, 1H), 3.29-3.18 (m, 1H), 3.02 (s, 3H), 2.67 (q, J=8 Hz, 2H), 2.18-2.07 (m, 3H), 2.05-1.94 (m, 1H), 1.25 (t, J=8 Hz, 3H). LC-MS (ESI): m/z: [M+H]⁺=489.2

Example 103. 1-[(1,3-dimethyl-1H-pyrazol-4-yl)(1-methylpiperidin-3-yl)sulfamoyl]-3-(1,2,3,5,6,7-hexahydro-s-indacen-4-yl)urea sodium salt

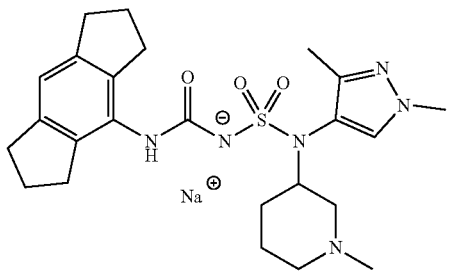 [SMILES: Cc1nn(C)cc1N(C1CCCN(C)C1)S(=O)(=O)[N-]C(=O)Nc1c2c(cc3c1CCC3)CCC2 ; [Na+]]

Step 1: tert-butyl 3-[(1,3-dimethylpyrazol-4-yl)amino]piperidine-1-carboxylate. General procedure A was followed using 1,3-dimethylpyrazol-4-amine and tert-butyl 3-oxopiperidine-1-carboxylate to give the title compound as a yellow gum (Y=68%). ¹H NMR (400 MHz, methanol-d₄) δ ppm 7.14 (s, 1H), 4.09-3.76 (m, 2H), 3.72 (s, 3H), 3.00-2.81 (m, 2H), 2.12 (s, 3H), 2.08-2.00 (m, 1H), 1.84-1.66 (m, 1H), 1.52-1.36 (m, 12H)

Step 2: N-(1,3-dimethylpyrazol-4-yl)-1-methylpiperidin-3-amine. To a solution of tert-butyl 3-[(1,3-dimethylpyrazol-4-yl)amino]piperidine-1-carboxylate (1.0 g, 3.40 mmol) in THF (10 ml) cooled to 0° C. was added LiAlH₄ (1.29 g, 34 mmol). The RM was heated at 80° C. for 5 h. The reaction was cooled to rt and quenched with H₂O (1 ml) and 10% aqueous NaOH (1 ml). The RM was filtered through Celite and the filtrate was concentrated in vacuo to give the title compound as a white solid (Y=64%). ¹H NMR (400 MHz, methanol-d₄) δ ppm 7.12 (s, 1H), 3.72 (s, 3H), 3.00-2.89 (m, 2H), 2.79-2.70 (m, 1H), 2.27 (s, 3H), 2.12 (s, 3H), 1.97-1.86 (m, 2H), 1.78-1.72 (m, 1H), 1.66-1.53 (m, 1H), 1.28-1.18 (m, 1H).

Step 3: 1-[(1,3-dimethyl-1H-pyrazol-4-yl)(1-methylpiperidin-3-yl)sulfamoyl]-3-(1,2,3,5,6,7-hexahydro-s-indacen-4-yl)urea sodium salt. General procedure B was followed using {[(1,2,3,5,6,7-hexahydro-s-indacen-4-yl)carbamoyl]amino}sulfonyl chloride and N-(1,3-dimethylpyrazol-4-yl)-1-methylpiperidin-3-amine. The crude product was purified by prep-HPLC (column: Agela Durashell C18 10 μm 250×50 mm; mobile phase: [water (10 mM NH₄HCO₃)-ACN]; B: 10-35%, 20 min) to give the title compound as a white solid (Y=14%). ¹H NMR (400 MHz, methanol-d₄) δ ppm 7.54 (s, 1H), 6.94 (s, 1H), 4.45-4.32 (m, 1H), 3.79 (s, 3H), 3.53-3.44 (m, 1H), 3.3-2.97 (m, 1H), 2.87 (t, J=7 Hz, 4H), 2.79 (t, J=7 Hz, 4H), 2.54 (s, 3H), 2.34-2.17 (m, 5H), 2.13-1.98 (m, 5H), 1.89-1.68 (m, 2H), 1.25-1.06 (m, 1H). LC-MS (ESI): m/z: [M+H]⁺=487.3

Example 104. 3-(1,2,3,5,6,7-hexahydro-s-indacen-4-yl)-1-[(oxan-4-yl)[2-(propan-2-yl)pyrimidin-5-yl]sulfamoyl]urea sodium salt

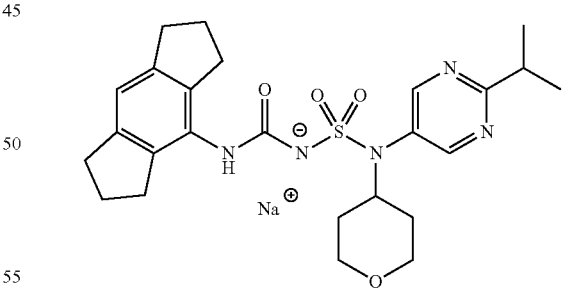

Step 1: 2-isopropyl-N-tetrahydropyran-4-yl-pyrimidin-5-amine. To a solution of 5-bromo-2-isopropylpyrimidine (500 mg, 2.49 mmol) and tetrahydropyran-4-amine (1.26 g, 12.43 mmol) in toluene (8 ml) was added BINAP (310 mg, 0.50 mmol), Cs₂CO₃ (1.62 g, 4.97 mmol) and Pd(OAc)₂ (56 mg, 0.25 mmol). The RM was heated under nitrogen at 120° C. for 12 h. The mixture was concentrated under reduced pressure. The residue was purified by FCC (9-18% EtOAc in petroleum ether) to give the title compound as a dark brown solid (Y=55%). ¹H NMR (400 MHz, methanol-d₄) δ ppm 8.10 (s, 2H), 3.99-3.95 (m, 2H), 3.58-3.52 (m, 3H), 3.13-2.99 (m, 1H), 2.01-1.95 (m, 2H), 1.55-1.44 (m, 2H), 1.26 (d, J=7 Hz, 6H).

Step 2: 3-(1,2,3,5,6,7-hexahydro-s-indacen-4-yl)-1-[(oxan-4-yl)[2-(propan-2-yl)pyrimidin-5-yl]sulfamoyl]urea sodium salt. General procedure B was followed using {[(1,2,3,5,6,7-hexahydro-s-indacen-4-yl)carbamoyl]amino}sulfonyl chloride and 2-isopropyl-N-tetrahydropyran-4-yl-pyrimidin-5-amine. The crude product was purified by prep-HPLC (column: Agela Durashell C18 10 µm 250× 50 mm; mobile phase: [water (10 mM NH$_4$HCO$_3$) -ACN]; B: 12-38%, 20 min) to give the title compound as a white solid (Y=17%). $^1$H NMR (400 MHz, chloroform-d) δ ppm 8.61 (s, 2H), 7.04 (s, 1H), 4.52-4.40 (br. s, 1H), 4.00-3.90 (m, 2H), 3.49-3.42 (m, 2H), 3.31-3.22 (m, 1H), 2.88 (t, J=7 Hz, 4H), 2.80-2.70 (m, 4H), 2.13-2.03 (m, 4H), 2.02-1.96 (m, 2H), 1.47-1.38 (m, 2H), 1.37 (d, J=7 Hz, 6H). LC-MS (ESI): m/z: [M+H]$^+$=500.2

Example 105. 3-[3-(Butan-2-yl)-5-chlorophenyl]-1-[(1-methyl-1H-pyrazol-4-yl)(oxan-4-yl)sulfamoyl] urea sodium salt

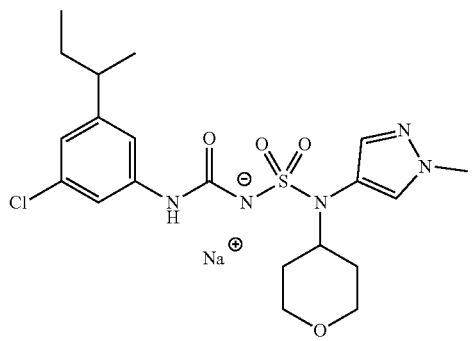 [SMILES: CCC(C)c1cc(Cl)cc(NC(=O)[N-]S(=O)(=O)N(c2cnn(C)c2)C2CCOCC2)c1 ; [Na+]]

Step 1: 3-(But-2-en-2-yl)-5-chloroaniline. To a solution of 3-bromo-5-chloro-aniline (280 mg, 1.36 mmol) in 1,4-dioxane (5 ml) and H$_2$O (0.5 ml) was added 4,4,5,5-tetramethyl-2-[1-methylprop-1-enyl]-1,3,2-dioxaborolane (296 mg, 1.63 mmol), Pd(dppf)Cl$_2$ (99 mg, 0.14 mmol) and Cs$_2$CO$_3$ (1.33 g, 4.07 mmol) under N$_2$. The mixture was heated at 130° C. for 12 h under N$_2$. The solution was filtered and concentrated in vacuo. The residue was purified by FCC (25% EtOAc in petroleum ether) to give the title compound as a green oil (Y=81%). LC-MS (ESI): m/z: [M+H]$^+$=182.1

Step 2: 3-Chloro-5-sec-butyl-aniline. To a solution of 3-(but-2-en-2-yl)-5-chloroaniline (160 mg, 0.88 mmol) in MeOH (5 ml) was added 10% Pd/C (20 mg) under N$_2$. The suspension was degassed under vacuum and purged with H$_2$ several times. The mixture was stirred at rt under H$_2$ (15 psi) atmosphere for 10 min. The RM was filtered through Celite and the filtrate was concentrated in vacuo to give the title compound as a green oil. LC-MS (ESI): m/z: [M+H]$^+$=184.1

Step 3: 1-Chloro-3-isocyanato-5-sec-butyl-benzene. General procedure C was followed using 3-chloro-5-sec-butyl-aniline to give the title compound as a yellow oil. LC-MS in MeOH (ESI): m/z: [M+MeOH+H]$^+$=242.1

Step 4: 3-[3-(Butan-2-yl)-5-chlorophenyl]-1-[(1-methyl-1H-pyrazol-4-yl)(oxan-4-yl)sulfamoyl]urea sodium salt. To a solution of 1-methyl-4-[sulfamoyl(tetrahydropyran-4-yl)amino]pyrazole (273 mg, 1.05 mmol) (for synthesis refer to Example 106) in THF (4 ml) cooled to 0° C. was added NaH (60% in mineral oil, 105 mg, 2.63 mmol). 1-Chloro-3-isocyanato-5-sec-butyl-benzene (220 mg, crude, 1.05 mmol) was then added and the mixture stirred at 0° C. for 2 h. The residue was concentrated in vacuo. The residue was purified by prep-HPLC (column: Waters Xbridge Prep OBD C18 10 µm 150×40 mm; mobile phase: [water (10 mM NH$_4$HCO$_3$)-ACN]; B: 15-35%, 11 min) to give the title compound as a white solid (Y=14%). $^1$H NMR (400 MHz, methanol-d$_4$) δ ppm 7.70 (s, 1H), 7.47 (t, J=2 Hz, 1H), 7.42 (s, 1H), 7.05 (s, 1H), 6.88 (s, 1H), 4.39-4.29 (m, 1H), 3.92 (dd, J=4, 11 Hz, 2H), 3.85 (s, 3H), 3.49 (t, J=11 Hz, 2H), 2.59-2.53 (m, 1H), 1.93-1.86 (m, 2H), 1.65-1.54 (m, 2H), 1.51-1.40 (m, 2H), 1.22 (d, J=7 Hz, 3H), 0.83 (t, J=7 Hz, 3H). LC-MS (ESI): m/z: [M+H]$^+$=470.2

Example 106. 3-[3-Chloro-5-(2,2,2-trifluoroethoxy) phenyl]-1-[(1-methyl-1H-pyrazol-4-yl)(oxan-4-yl) sulfamoyl]urea sodium salt

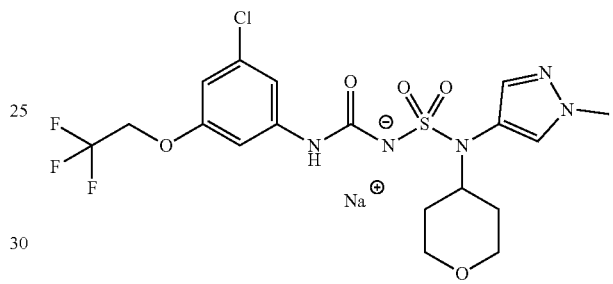

Step 1: 3-chloro-5-(2,2,2-Trifluoroethoxy)aniline. To a solution of 3-amino-5-chlorophenol (350 mg, 2.44 mmol) and 1,1,1-trifluoro-2-iodoethane (263 µl, 2.68 mmol) in DMF (4 ml) was added K$_2$CO$_3$ (505 mg, 3.66 mmol). The RM was heated at 100° C. for 8 h. The RM was diluted by H$_2$O (8 ml) and the mixture was extracted with EtOAc (3×12 ml). The combined organic phases were dried and concentrated under reduced pressure to give a residue. The residue was purified by FCC (0-100% EtOAc in petroleum ether) to give the title compound as a yellow oil (Y=27%). $^1$H NMR (400 MHz, chloroform-d) δ ppm 6.38 (t, J=2 Hz, 1H), 6.33 (t, J=2 Hz, 1H), 6.16 (t, J=2 Hz, 1H), 4.29 (q, J=8 Hz, 2H), 3.84-3.74 (br. s, 2H).

Step 2: 1-Chloro-3-isocyanato-5-(2,2,2-trifluoroethoxy) benzene. General procedure C was followed using 3-chloro-5-(2,2,2-trifluoroethoxy)aniline to give the title compound as a yellow oil. LC-MS in MeOH (ESI): m/z: [M+MeOH+H]$^+$=284.0

Step 3: tert-Butyl N-[(1-methylpyrazol-4-yl)-tetrahydro-pyran-4-yl-sulfamoyl]carbamate. To a solution of 1-methyl-N-tetrahydropyran-4-yl-pyrazol-4-amine (7.0 g, 38.6 mmol) (or synthesis refer to Example 1) in DCM (70 ml) cooled to 0° C. was added DIPEA (20.2 ml, 116 mmol). To this solution was added portionwise tert-butyl N-chlorosulfonyl-carbamate (8.33 g, 38.6 mmol) and the RM was stirred at 0° C. for 2 h. The solution was concentrated in vacuo. The residue was purified by prep-HPLC (column: Phenomenex Luna C18 10 µm 250×100 mm; mobile phase: [water (0.1% TFA)-ACN]; B: 5-35%, 20 min) to give the title compound as a yellow oil (Y=26%). LC-MS (ESI): m/z: [M+H]$^+$: 361.0

Step 4: 1-Methyl-4-[sulfamoyl(tetrahydropyran-4-yl) amino]pyrazole. A solution of tert-butyl N-[(1-methylpyrazol-4-yl)-tetrahydropyran-4-yl-sulfamoyl]carbamate (560 mg, 1.55 mmol) in 4 M HCl in EtOAc (10 ml) was stirred at rt for 12 h. The solution was concentrated in vacuo to give the title compound as a white solid. LC-MS (ESI): m/z: [M+H]⁺: 261.0

Step 5: 3-[3-Chloro-5-(2,2,2-trifluoroethoxy)phenyl]-1-[(1-methyl-1H-pyrazol-4-yl)(oxan-4-yl)sulfamoyl]urea sodium salt. To a solution of 1-methyl-4-[sulfamoyl(tetrahydropyran-4-yl)amino]pyrazole (0.12 g, 0.40 mmol) in THF (2 ml) cooled to 0° C. was added NaH (60% in mineral oil, 40 mg, 1.0 mmol). The resulting mixture was treated dropwise with 1-chloro-3-isocyanato-5-(2,2,2-trifluoroethoxy)benzene (112 mg, 0.44 mmol) and the RM was stirred at rt for 2 h. The solution was concentrated in vacuo. The resulting residue was purified by prep-HPLC (column: Huapu C18 Extreme BDS 5 μm 150×30 mm; mobile phase: [water (10 mM $NH_4HCO_3$)-ACN]; B: 20-40%, 10 min) to give the title compound as a white solid (Y=35%). ¹H NMR (400 MHz, methanol-$d_4$) δ ppm 7.67 (s, 1H), 7.41 (s, 1H), 7.19 (t, J=2 Hz, 1H), 7.10 (t, J=2 Hz, 1H), 6.70 (t, J=2 Hz, 1H), 4.53 (q, J=8 Hz, 2H), 4.38-4.25 (m, 1H), 3.95-3.90 (m, 2H), 3.84 (s, 3H), 3.49 (t, J=11 Hz, 2H), 1.93-1.86 (m, 2H), 1.50-1.38 (m, 2H). LC-MS (ESI): m/z: [M+H]⁺: 512.1

Example 107. 3-(1,2,3,5,6,7-Hexahydro-s-indacen-4-yl)-1-[(1-methyl-1H-pyrazol-4-yl)({[(2S)-1-methylpyrrolidin-2-yl]methyl})sulfamoyl]urea sodium salt

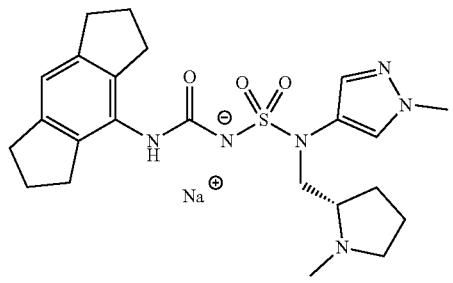 [SMILES: CN1CCC[C@H]1CN(c1cnn(C)c1)S(=O)(=O)[N-]C(=O)Nc1c2c(cc3c1CCC3)CCC2 ; [Na+]]

Step 1: tert-Butyl (2S)-2-[(1-methylpyrazol-4-yl)carbamoyl]pyrrolidine-1-carboxylate. To a solution of (2S)-1-tert-butoxycarbonylpyrrolidine-2-carboxylic acid (5.0 g, 23.2 mmol) in DMF (60 ml) cooled to 0° C. was added HATU (13.25 g, 35 mmol and the mixture stirred for 0.5 h. DIPEA (12.1 ml, 70 mmol) and 1-methylpyrazol-4-amine (2.48 g, 25.6 mmol) were added and the RM stirred at 0° C. for 2 h. The reaction mixture was diluted with $H_2O$ (10 ml) and extracted with EtOAc (3×10 ml). The combined organic layers were washed with $H_2O$ (10 ml), dried over $Na_2SO_4$, filtered and concentrated in vacuo to give a residue. The residue was purified by FCC (0-100% EtOAc in petroleum ether) to give the title compound as a yellow solid. ¹H NMR (400 MHz, DMSO-$d_6$) δ ppm 8.17 (s, 1H), 7.84 (s, 1H), 7.40 (s, 1H), 4.11-4.06 (m, 1H), 3.77 (s, 3H), 3.67-3.56 (m, 1H), 3.16-3.11 (m, 1H), 2.21-2.07 (m, 1H), 1.91-1.72 (m, 3H), 1.26 (s, 9H).

Step 2: 1-Methyl-N-[[(2S)-1-methylpyrrolidin-2-yl]methyl]pyrazol-4-amine. To a solution of tert-butyl (2S)-2-[(1-methylpyrazol-4-yl)carbamoyl]pyrrolidine-1-carboxylate (8.0 g, 27.2 mmol) in THF (100 ml) cooled to 0° C. was added lithium aluminium hydride (10.3 g, 272 mmol). The RM was heated at 70° C. for 12 h. The RM was allowed to cool and poured into ice-water (10 ml), then stirred for 20 min. The resulting mixture was poured into 1M NaOH (10 ml), filtered through Celite and the filtrate concentrated in vacuo to give the title compound as a colourless oil (Y=78%). ¹H NMR (400 MHz, DMSO-$d_6$) δ ppm 7.02 (s, 1H), 6.93 (s, 1H), 4.05-4.01 (m, 1H), 3.67 (s, 3H), 3.40-3.36 (m, 1H), 2.97-2.88 (m, 2H), 2.74-2.67 (m, 1H), 2.25 (s, 3H), 1.89-1.81 (m, 1H), 1.61-1.57 (m, 1H), 1.42-1.34 (m, 1H), 1.33-1.27 (m, 1H). NH not seen.

Step 3: 3-(1,2,3,5,6,7-Hexahydro-s-indacen-4-yl)-1-[(1-methyl-1H-pyrazol-4-yl)({[(2S)-1-methylpyrrolidin-2-yl]methyl})sulfamoyl]urea sodium salt. General procedure B was followed using {[(1,2,3,5,6,7-hexahydro-s-indacen-4-yl)carbamoyl]amino}sulfonyl chloride and 1-methyl-N-[[(2S)-1-methylpyrrolidin-2-yl]methyl]pyrazol-4-amine.

The crude product was purified by prep-HPLC (column: Huapu C8 Extreme BDS 5 μm 150×30 mm; mobile phase: [water (10 mM $NH_4HCO_3$)-ACN]; B: 25-45%, 10 min) to give the title compound as a white solid (Y=9%). ¹H NMR (400 MHz, methanol-$d_4$) δ ppm 7.70 (s, 1H), 7.55 (s, 1H), 6.92 (s, 1H), 4.17 (dd, J=3, 16 Hz, 1H), 3.86 (s, 3H), 3.84-3.72 (m, 2H), 3.52-3.44 (m, 1H), 3.14-3.07 (m, 1H), 2.93 (s, 3H), 2.89-2.78 (m, 8H), 2.11-2.00 (m, 7H), 1.99-1.90 (m, 1H). LC-MS (ESI): m/z: [M+H]⁺=473.2

Example 108. 3-(1,2,3,5,6,7-Hexahydro-s-indacen-4-yl)-1-[(4-methyl-1,3-thiazol-2-yl)(oxan-4-yl)sulfamoyl]urea sodium salt

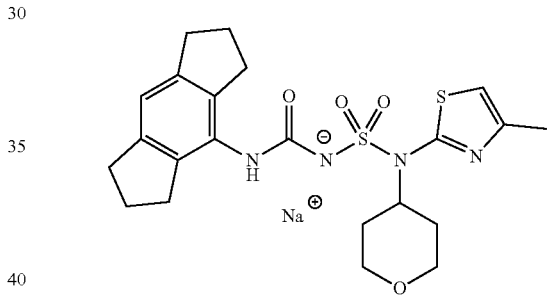

Step 1: 4-Methyl-N-tetrahydropyran-4-yl-thiazol-2-amine trifluoroacetate. General procedure A was followed using 4-methylthiazol-2-amine and tetrahydropyran-4-one. The crude product was purified by prep-HPLC (column: Phenomenex Luna C18 10 μm 250×50 mm; mobile phase: [water (0.1% TFA)-ACN]; B: 1-20%, 22 min) to give the title compound as a yellow solid (Y=10%). ¹H NMR (400 MHz, DMSO-$d_6$) δ ppm 9.43 (s, 1H), 6.47 (s, 1H), 5.82-5.66 (m, 1H), 3.89-3.85 (m, 3H), 3.41-3.35 (m 2H), 2.17 (s, 3H), 1.94-1.88 (m, 2H), 1.55-1.38 (m, 2H).

Step 2: 3-(1,2,3,5,6,7-Hexahydro-s-indacen-4-yl)-1-[(4-methyl-1,3-thiazol-2-yl)(oxan-4-yl)sulfamoyl]urea sodium salt. General procedure B was followed using {[(1,2,3,5,6,7-hexahydro-s-indacen-4-yl)carbamoyl]amino}sulfonyl chloride and 4-methyl-N-tetrahydropyran-4-yl-thiazol-2-amine trifluoroacetate. The crude product was purified by prep-HPLC (column: Huapu C8 Extreme BDS 5 μm 150×30 mm; mobile phase: [water (10 mM $NH_4HCO_3$)-ACN]; B: 20-40%, 10 min) to give the title compound as a white solid (Y=1%). ¹H NMR (400 MHz, methanol-$d_4$) δ ppm 7.16 (s, 1H), 6.99 (s, 1H), 4.52-4.40 (m, 1H), 3.94 (dd, J=5, 11 Hz, 2H), 3.47 (t, J=11 Hz, 2H), 2.92-2.78 (m, 8H), 2.38 (s, 3H), 2.09-2.01 (m, 4H), 2.00-1.91 (m, 2H), 1.80-1.69 (m, 2H). LC-MS (ESI): m/z: [M+H]⁺=477.1

Example 109. 1-[(3-Ethyl-1,2-oxazol-5-yl)(oxan-4-yl)sulfamoyl]-3-(1,2,3,5,6,7-hexahydro-s-indacen-4-yl)urea sodium salt

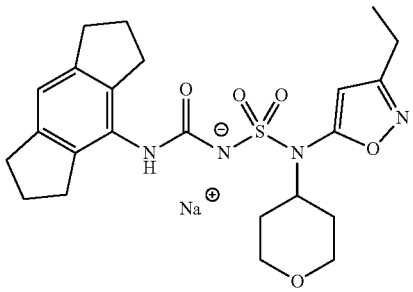 [SMILES: CCc1cc(N(C2CCOCC2)S(=O)(=O)[N-]C(=O)Nc2c3c(cc4c2CCC4)CCC3)on1 ; [Na+]]

Step 1: 3-Ethyl-N-tetrahydropyran-4-yl-isoxazol-5-amine. General procedure A was followed using 3-ethyl-isoxazol-5-amine and tetrahydropyran-4-one. The crude product was purified by prep-HPLC (column: Phenomenex Luna C18 10 μm 250×50 mm; mobile phase: [water (0.1% TFA)-ACN]; B: 5-40%, 23 min) to give the title compound as a white solid (Y=38%). $^1$H NMR (400 MHz, chloroform-d) δ ppm 4.87 (s, 1H), 4.43-4.35 (m, 1H), 4.04-3.98 (m, 2H), 3.52-3.45 (m, 3H), 2.55 (q, J=8 Hz, 2H), 2.04-1.96 (m, 2H), 1.59-1.51 (m, 2H), 1.23 (t, J=8 Hz, 3H).

Step 2: tert-butyl N-[(3-ethylisoxazol-5-yl)-tetrahydropyran-4-yl-sulfamoyl]carbamate. To a solution of 3-ethyl-N-tetrahydropyran-4-yl-isoxazol-5-amine (200 mg, 1.02 mmol) in DCM (10 ml) cooled to 0° C. were added tert-butyl N-chlorosulfonylcarbamate (220 mg, 1.02 mmol) and DIPEA (533 μl, 3.06 mmol). The RM was stirred at 0° C. for 6 h. The solvent was removed under reduced pressure to give a residue. The residue was purified by prep-HPLC (column: Welch Ultimate AQ-C18 5 μm 150×30 mm; mobile phase: [water (0.1% TFA)-ACN]; B: 35-65%, 12 min) to give the title compound as a white solid (Y=52%). $^1$H NMR (400 MHz, chloroform-d) δ ppm 7.33 (s, 1H), 6.15 (s, 1H), 4.50-4.46 (m, 1H), 4.00 (dd, J=4, 11 Hz, 2H), 3.51-3.46 (m, 2H), 2.71 (q, J=8 Hz, 2H), 1.98-1.95 (m, 2H), 1.67-1.58 (m, 2H), 1.52 (s, 9H), 1.30 (t, J=8 Hz, 3H).

Step 3: 4-Ethyl-5-[sulfamoyl(tetrahydropyran-4-yl)amino]isoxazole. To a solution of tert-butyl N-[(4-ethyl-isoxazol-5-yl)-tetrahydropyran-4-yl-sulfamoyl]carbamate (100 mg, 0.27 mmol) in DCM (1 ml) was added TFA (1.30 ml, 17.6 mmol). The RM was stirred at rt for 4 h. The solvent was removed under reduced pressure to give the title compound as a yellow oil.

Step 4: 1-[(3-Ethyl-1,2-oxazol-5-yl)(oxan-4-yl)sulfamoyl]-3-(1,2,3,5,6,7-hexahydro-s-indacen-4-yl)urea sodium salt. To a solution of 3-ethyl-5-[sulfamoyl(tetrahydropyran-4-yl)amino]isoxazole (70 mg, 0.25 mmol) in THF (2 ml) cooled to 0° C. was added NaH (60% in mineral oil, 10 mg, 0.25 mmol). The RM was stirred at 0° C. for 0.5 h. The RM was treated with 4-isocyanato-1,2,3,5,6,7-hexahydro-s-indacene (51 mg, 0.25 mmol) and stirred at rt for a further 1.5 h. The solvent was removed under reduced pressure to give a residue. The residue was purified by prep-HPLC (column: Agela Durashell 10 μm 250×50 mm; mobile phase: [water (10 mM NH$_4$HCO$_3$)-ACN]; B: 10-36%, 20 min) to give the title compound as a white solid (Y=20%). $^1$H NMR (400 MHz, chloroform-d) δ ppm 7.04 (s, 1H), 6.16 (s, 1H), 4.34-4.27 (m, 1H), 3.98 (dd, J=4, 12 Hz, 2H), 3.43 (t, J=12 Hz, 2H), 2.89 (t, J=7 Hz, 4H), 2.80 (t, J=7 Hz, 4H), 2.67 (q, J=8 Hz, 2H), 2.10-2.06 (m, 4H), 2.03-1.87 (m, 2H), 1.66-1.55 (m, 2H), 1.27 (t, J=8 Hz, 3H). NH not seen. LC-MS (ESI): m/z: [M+H]$^+$=475.2

Example 110. 3-(1,2,3,5,6,7-Hexahydro-s-indacen-4-yl)-1-[(1-methyl-1H-pyrazol-4-yl)({[(2R)-1-methylpyrrolidin-2-yl]methyl})sulfamoyl]urea sodium salt

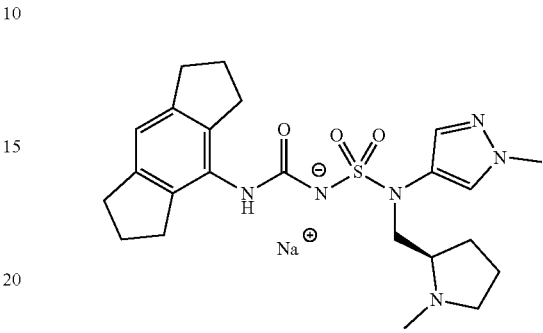

Step 1: tert-Butyl (2R)-2-[(1-methylpyrazol-4-yl)carbamoyl]pyrrolidine-1-carboxylate. To a solution of 1-methylpyrazol-4-amine (2.48 g, 25.6 mmol) in DMF (60 ml) at 0° C. was added HATU (13.25 g, 34.8 mmol) and the mixture was stirred for 0.5 h. The RM was treated with DIPEA (12.14 ml, 69.7 mmol) and (2R)-1-tert-butoxycarbonylpyrrolidine-2-carboxylic acid (5.00 g, 23.2 mmol) and stirred at 0° C. for 2 h. The reaction mixture was diluted with H$_2$O (10 ml) and extracted with EtOAc (3×10 ml). The combined organic layers were washed with H$_2$O (80 ml), dried over Na$_2$SO$_4$, filtered, and concentrated in vacuo to give a residue. The residue was purified by FCC (0-100% EtOAc in petroleum ether) to give the title compound as a yellow solid. $^1$H NMR (400 MHz, DMSO-d$_6$) δ ppm 9.93 (s, 1H), 7.84 (s, 1H), 7.40 (s, 1H), 4.12-4.08 (m, 1H), 3.77 (s, 3H), 3.45-3.37 (m, 2H), 2.25-2.08 (m, 2H), 1.84-1.78 (m, 2H), 1.40-1.25 (m, 9H).

Step 2: 1-Methyl-N-[[(2R)-1-methylpyrrolidin-2-yl]methyl]pyrazol-4-amine. To a solution of tert-butyl (2R)-2-[(1-methylpyrazol-4-yl)carbamoyl]pyrrolidine-1-carboxylate (2.0 g, 6.79 mmol) in THF (20 ml) cooled to 0° C. was added lithium aluminium hydride (3.09 g, 81.5 mmol). The RM was heated at 70° C. for 12 h. The reaction mixture was cooled to rt, poured into ice-water, and stirred for 20 min. The resulting mixture was poured into 1M NaOH (30 ml) and stirred. The reaction mixture was filtered through Celite and the filtrate concentrated in vacuo to give the title compound as a yellow oil (Y=61%). LC-MS (ESI): m/z: [M+H]$^+$=195.2

Step 3: 3-(1,2,3,5,6,7-Hexahydro-s-indacen-4-yl)-1-[(1-methyl-1H-pyrazol-4-yl)({[(2R)-1-methylpyrrolidin-2-yl]methyl})sulfamoyl]urea sodium salt. General procedure B was followed using {[(1,2,3,5,6,7-hexahydro-s-indacen-4-yl)carbamoyl]amino}sulfonyl chloride and 1-methyl-N-[[(2R)-1-methylpyrrolidin-2-yl]methyl]pyrazol-4-amine. The crude product was purified by prep-HPLC (column: Huapu C8 Extreme BDS 5 μm 150×30 mm; mobile phase: [water (10 mM NH$_4$HCO$_3$)-ACN]; B: 25-45%, 10 min) to give the title compound as a white solid (Y=7%). $^1$H NMR (400 MHz, methanol-d$_4$) δ ppm 7.70 (s, 1H), 7.55 (s, 1H), 6.92 (s, 1H), 4.16 (dd, J=3, 16 Hz, 1H), 3.86 (s, 3H), 3.83-3.72 (m, 2H), 3.50-3.45 (m, 1H), 3.14-3.06 (m, 1H), 2.92 (s, 3H), 2.89-2.80 (m, 8H), 2.10-2.00 (m, 7H), 1.99-1.89 (m, 1H). LC-MS (ESI): m/z: [M+H]$^+$=473.2

Example 111. 3-(1,2,3,5,6,7-Hexahydro-s-indacen-4-yl)-1-[(1-methyl-1H-pyrazol-4-yl)[(1-methylazetidin-2-yl)methyl]sulfamoyl]urea sodium salt

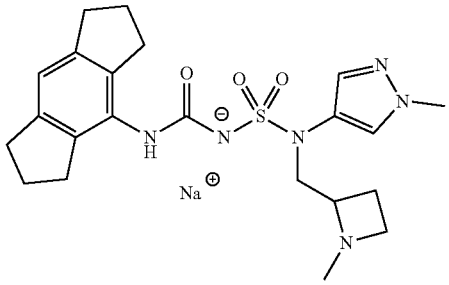 [SMILES: CN1CCC1CN(c1cnn(C)c1)S(=O)(=O)[N-]C(=O)Nc1c2c(cc3c1CCC3)CCC2 ; [Na+]]

Step 1: tert-Butyl-2-[(1-methylpyrazol-4-yl)carbamoyl]azetidine-1-carboxylate. To a mixture of 1-tert-butoxycarbonylazetidine-2-carboxylic acid (900 mg, 4.47 mmol) in DMF (9 ml) cooled to 0° C. was added HATU (2.04 g, 5.37 mmol). The mixture was stirred at 0° C. for 1 h then treated with 1-methylpyrazol-4-amine (478 mg, 4.92 mmol) and DIPEA (1.56 ml, 8.95 mmol). The mixture was stirred at 0° C. for 2 h. H$_2$O (10 ml) was added and the RM was extracted with ethyl acetate (3×10 ml). The combined organic layers were washed with saturated brine (5 ml), dried over Na$_2$SO$_4$, filtered, and concentrated under reduced pressure to give a residue. The residue was purified by FCC (20-100% EtOAc in petroleum ether) to give the title compound as a brown oil (Y=71%). $^1$H NMR (400 MHz, methanol-d$_4$) δ ppm 7.92 (s, 1H), 7.53 (s, 1H), 4.68-4.64 (m, 1H), 4.00-3.92 (m, 2H), 3.86 (s, 3H), 2.56-2.47 (m, 1H), 2.27-2.18 (m, 1H), 1.40-1.34 (m, 9H).

Step 2: 1-Methyl-N-[(1-methylazetidin-2-yl)methyl]pyrazol-4-amine. To a solution of tert-butyl 2-[(1-methylpyrazol-4-yl)carbamoyl]azetidine-1-carboxylate (500 mg, 1.78 mmol) in THF (5 ml) cooled to 0° C. under nitrogen was added portionwise LiAlH$_4$ (677 mg, 17.8 mmol). The mixture was stirred at 0° C. for 20 min, then heated at 70° C. for 1 h. The reaction mixture was cooled 0° C. and quenched by addition of H$_2$O (0.6 ml) and 10% aqueous NaOH (0.6 ml) solution. The RM was filtered and concentrated under reduced pressure to give the title compound as a brown oil (Y=52%). $^1$H NMR (400 MHz, methanol-d$_4$) δ ppm 7.14 (s, 1H), 7.10 (s, 1H), 3.77 (s, 3H), 3.40-3.36 (m, 1H), 3.28-3.26 (m, 1H), 3.10-2.98 (m, 2H), 2.91-2.85 (m, 1H), 2.37 (s, 3H), 2.11-2.06 (m, 1H), 1.98-1.89 (m, 1H).

Step 3: 3-(1,2,3,5,6,7-Hexahydro-s-indacen-4-yl)-1-[(1-methyl-1H-pyrazol-4-yl)[(1-methylazetidin-2-yl)methyl]sulfamoyl]urea sodium salt. General procedure B was followed using {[(1,2,3,5,6,7-hexahydro-s-indacen-4-yl)carbamoyl]amino}sulfonyl chloride and 1-methyl-N-[(1-methylazetidin-2-yl)methyl]pyrazol-4-amine. The crude product was purified by prep-HPLC (column: Agela Durashell C18 10 μm 250×50 mm; mobile phase: [water (10 mM NH$_4$HCO$_3$)-ACN]; B: 15-40%, 20 min) to give the title compound as a white solid (Y=18%). $^1$H NMR (400 MHz, methanol-d$_4$) δ ppm 7.73 (s, 1H), 7.57 (s, 1H), 6.94 (s, 1H), 4.44-4.39 (m, 2H), 4.02-3.92 (m, 1H), 3.87 (s, 3H), 3.78-3.71 (m, 1H), 3.50-3.44 (m, 1H), 2.91-2.83 (m, 11H), 2.58-2.53 (m, 1H), 2.20-2.17 (m, 1H), 2.08-2.04 (m, 4H). LC-MS (ESI): m/z: [M+H]$^+$=459.2

Example 112. 1-(3,5-Dichlorophenyl)-3-[(1-methyl-1H-pyrazol-4-yl)({[(2R)-1-methylpyrrolidin-2-yl]methyl})sulfamoyl]urea sodium salt

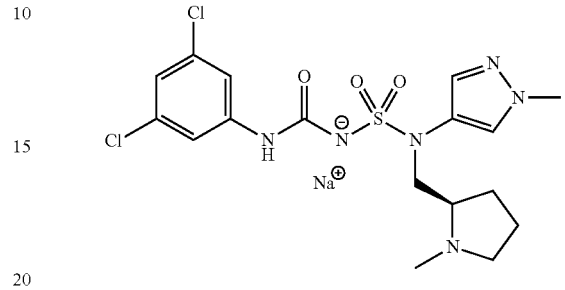

Step 1: 1,3-Dichloro-5-isocyanato-benzene. General procedure C was followed using 3,5-dichloroaniline to give the title compound as a white solid (Y=100%). LC-MS in MeOH (ESI): m/z: =220.0

Step 2: tert-Butyl N-(chlorosulfonyl)carbamate. To a solution of N-(oxomethylene)sulfamoyl chloride (368 μl, 4.24 mmol) in THF (3 ml) cooled to 0° C. was added dropwise 2-methylpropan-2-ol (405 μl, 4.24 mmol). The RM was stirred at 0° C. for 2 h to give the title compound as a solution in THF (3 ml).

Step 3: tert-Butyl N-[(1-methylpyrazol-4-yl)-[[(2R)-1-methylpyrrolidin-2-yl]methyl]sulfamoyl]carbamate trifluoroacetate. To a solution of 1-methyl-N-[[(2R)-1-methylpyrrolidin-2-yl]methyl]pyrazol-4-amine (300 mg, 1.54 mmol) (for synthesis refer to Example 110) in THF (4 ml) cooled to 0° C. was added DIPEA (807 μl, 4.63 mmol) and tert-butyl N-chlorosulfonylcarbamate (500 mg, 2.32 mmol). The RM was stirred at 0° C. for 2 h. The solvent was removed under reduced pressure. The residue was purified by prep-HPLC (column: Agela Durashell 10 μm 250×50 mm; mobile phase: [water (0.1% TFA)-ACN]; B: 2-30%, 20 min) to give the title compound as a white solid (Y=53%). $^1$H NMR (400 MHz, methanol-d$_4$) δ=7.82 (s, 1H), 7.54 (s, 1H), 4.28-4.13 (m, 2H), 3.89 (s, 3H), 3.81-3.71 (m, 1H), 3.61-3.52 (m, 1H), 3.25-3.18 (m, 1H), 3.04 (s, 3H), 2.36-2.24 (m, 1H), 2.17-2.02 (m, 2H), 1.94-1.83 (m, 1H), 1.51 (s, 9H).

Step 4: 1-Methyl-4-[[(2R)-1-methylpyrrolidin-2-yl]methyl-sulfamoyl-amino]pyrazole trifluoroacetate. To a solution of tert-butyl N-[(1-methylpyrazol-4-yl)-[[(2R)-1-methylpyrrolidin-2-yl]methyl]sulfamoyl]carbamate trifluoroacetate (100 mg, 0.21 mmol) in DCM (2 ml) was added TFA (0.4 ml, 5.4 mmol). The RM was stirred at rt for 1 h. The solvent was removed under reduced pressure to give the title compound as a colourless gum (Y=100%). LC-MS (ESI): m/z: [M+H]$^+$=274.2

Step 5: 1-(3,5-Dichlorophenyl)-3-[(1-methyl-1H-pyrazol-4-yl)({[(2R)-1-methylpyrrolidin-2-yl]methyl})sulfamoyl]urea sodium salt. To a solution of 1-methyl-4-[[(2R)-1-methylpyrrolidin-2-yl]methyl-sulfamoyl-amino]pyrazole trifluoroacetate (79 mg, 0.21 mmol) in THF (2 ml) cooled to 0° C. was added NaH (60% in mineral oil, 33 mg, 0.82 mmol). The RM was stirred at 0° C. for 15 min then treated with 1,3-dichloro-5-isocyanato-benzene (39 mg, 0.21 mmol). The RM was stirred at rt for 1 h. The solvent was removed under reduced pressure. The residue was purified by prep-HPLC (column: Agela Durashell 10 μm 250×50 mm; mobile phase: [water (10 mM NH$_4$HCO$_3$)-ACN]; B: 18-45%, 20 min) to give the title compound as a white solid (Y=45%). $^1$H NMR (400 MHz, methanol-d$_4$) δ ppm 7.67 (s, 1H), 7.52 (d, 2H), 7.49 (s, 1H), 6.97 (t, J=2 Hz, 1H), 4.18 (dd, J=3, 16 Hz, 1H), 3.93-3.85 (m, 2H), 3.83 (s, 3H), 3.59-3.47 (m, 1H), 3.29-3.21 (m, 1H), 3.03 (s, 3H), 2.19-2.08 (m, 3H), 2.01-1.92 (m, 1H). LC-MS (ESI): m/z: [M+H]$^+$=461.1

Example 113. Biological Activity of the Compounds of the Present Disclosure

The biological activity of the compounds of the present disclosure was determined utilising the assay described herein.

PBMC IC$_{50}$ Determination Assay

The compounds of the present disclosure were tested for their inhibitory activity against IL-1β release upon NLRP3 activation in peripheral blood mononuclear cells (PBMC).

Protocol A

PBMC were isolated from buffy coats by density gradient centrifugation on Histopaque-1077 (Sigma, cat no. 10771). Isolated cells were seeded into the wells of a 96-well plate and incubated for 3 h with lipopolysaccharide (LPS). Following medium exchange, the compounds of the present disclosure were added (a single compound per well) and the cells were incubated for 30 min. Next, the cells were stimulated either with ATP (5 mM) or nigericin (10 μM) for 1 h and the cell culture media from the wells were collected for further analysis.

The release of IL1-β into the media was determined by a quantitative detection of IL-1β in the media using an IL-1β enzyme-linked immunosorbent assay (ELISA) Ready-SET-Go!, eBioscience cat. No. 88-7261-88. Briefly, in a first step, high affinity binding plates (Corning, Costar 9018 or NUNC Maxisorp Cat No. 44-2404) were coated overnight at 4° C. with specific capture antibody included in the kit (anti-human IL-1β ref. 14-7018-68). Subsequently, plates were blocked with blocking buffer for 1 h at room temperature (rt) and after washing with a buffer (PBS with 0.05% Tween-20) incubated with protein standard and culture media. After 2 h of incubation at rt, plates were washed and incubated with biotinylated detection antibody included in the kit (anti-human IL-1β Biotin ref. 33-7110-68) for 1 h at rt. Plates were washed and incubated with HRP-streptavidin for 30 min at rt and washed again. The signal was developed after addition of 3,3',5,5'-tetramethylbenzidine-peroxidase (TMB) until colour appeared and the reaction was stopped by 2 M H$_2$SO$_4$. A microplate spectrophotometer (BioTek) was used to detect signals with 450 nm. The detection range of IL-1β ELISA was 2-150 ng/ml.

Protocol B

PBMC were isolated from buffy coats by density gradient centrifugation on Histopaque-1077 (Sigma, cat no. 10771). Isolated cells were seeded into the wells (280,000 cells/well) of a 96-well plate and incubated for 3 h with lipopolysaccharide (LPS, 1 μg/ml diluted 1000× from a 1 mg/ml stock solution). The compounds of the present disclosure were added (a single compound per well) and the cells were incubated for 30 min. Next, the cells were stimulated with ATP (5 mM final concentration diluted 20× from a 100 mM stock solution) for 1 h and the cell culture media from the wells were collected for further analysis.

The release of IL-1β into the media was determined by quantitative detection of IL-1β in the media using HTRF®, CisBio cat. No. 62HIL1BPEH. Briefly, cell culture supernatant were dispensed directly into the assay plate containing antibodies labelled with the HTRF® donor and acceptor. A microplate spectrophotometer (BMG) was used to detect signals at 655 nm and 620 nm. The detection range of IL-1β HTRF® was 39-6500 pg/ml.

The determination of the IC$_{50}$ values was preformed using the Graph Pad Prism software and the measured IC$_{50}$ values of compounds of the present disclosure are shown in Table A below ("++++" means ≤1 μM; "+++" means ≥1 and ≤3 μM; "++" means ≥3 and <10 μM; "+" means ≥10 and <50 μM). These results show that the compounds of the present disclosure are capable of inhibiting IL-1β release upon inflammasome activation.

TABLE A

| Compound No. | Average PBMC IC$_{50}$ (μM) |
|---|---|
| 1 | ++++ |
| 2 | ++++ |
| 3 | +++ |
| 4 | ++++ |
| 5 | ++++ |
| 6 | ++++ |
| 7 | ++++ |
| 8 | ++++ |
| 9 | ++++ |
| 10 | ++++ |
| 11 | ++++ |
| 12 | ++ |
| 13 | ++++ |
| 14 | ++++ |
| 15 | +++ |
| 16 | ++++ |
| 17 | ++++ |
| 18 | ++++ |
| 19 | ++ |
| 20 | ++++ |
| 21 | ++ |
| 22 | ++++ |
| 23 | ++++ |
| 24 | ++++ |
| 25 | ++++ |
| 26 | ++++ |
| 27 | ++++ |
| 28 | ++++ |
| 29 | ++++ |
| 30 | ++++ |
| 31 | ++++ |
| 32 | ++++ |
| 33 | +++ |
| 34 | ++++ |
| 35 | ++++ |
| 36 | ++++ |
| 37 | ++++ |
| 38 | ++++ |
| 39 | ++++ |
| 40 | +++ |
| 41 | ++++ |
| 42 | ++++ |
| 43 | ++++ |
| 44 | ++++ |
| 45 | +++ |
| 46 | ++++ |
| 47 | +++ |
| 48 | ++++ |
| 49 | ++++ |
| 50 | ++++ |
| 51 | ++++ |
| 52 | ++++ |
| 53 | ++++ |
| 54 | ++++ |
| 55 | ++++ |
| 56 | ++++ |
| 57 | ++++ |
| 58 | + |
| 59 | ++++ |

TABLE A-continued

| Compound No. | Average PBMC IC$_{50}$ (μM) |
|---|---|
| 60 | ++++ |
| 61 | ++++ |
| 62 | ++++ |
| 63 | ++++ |
| 64 | ++++ |
| 65 | +++ |
| 66 | +++ |
| 67 | ++++ |
| 68 | ++++ |
| 69 | ++ |
| 70 | ++ |
| 71 | + |
| 72 | +++ |
| 73 | +++ |
| 74 | ++ |
| 75 | ++++ |
| 76 | +++ |
| 77 | +++ |
| 78 | ++++ |
| 79 | ++++ |
| 80 | +++ |
| 81 | +++ |
| 82 | ++++ |
| 83 | +++ |
| 84 | ++++ |
| 85 | ++++ |
| 86 | ++++ |
| 87 | ++++ |
| 88 | ++++ |
| 89 | +++ |
| 90 | + |
| 91 | ++++ |
| 92 | +++ |
| 93 | ++++ |
| 94 | +++ |
| 95 | ++++ |
| 96 | ++++ |
| 97 | ++++ |
| 98 | +++ |
| 99 | ++++ |
| 100 | +++ |
| 101 | ++++ |
| 102 | ++++ |
| 103 | ++++ |
| 104 | ++++ |
| 105 | ++++ |
| 106 | ++++ |
| 107 | ++++ |
| 108 | ++++ |
| 109 | ++++ |
| 110 | ++++ |
| 111 | ++++ |
| 112 | ++++ |
| 113 | ++++ |
| 114 | ++++ |
| 115 | ++++ |
| 116 | ++++ |

EQUIVALENTS

The details of one or more embodiments of the disclosure are set forth in the accompanying description above. Although any methods and materials similar or equivalent to those described herein can be used in the practice or testing of the present disclosure, the preferred methods and materials are now described. Other features, objects, and advantages of the disclosure will be apparent from the description and from the claims. In the specification and the appended claims, the singular forms include plural referents unless the context clearly dictates otherwise. Unless defined otherwise, all technical and scientific terms used herein have the same meaning as commonly understood by one of ordinary skill in the art to which this disclosure belongs. All patents and publications cited in this specification are incorporated by reference.

The foregoing description has been presented only for the purposes of illustration and is not intended to limit the disclosure to the precise form disclosed, but by the claims appended hereto.

The invention claimed is:

1. A compound of Formula (Iac-1):

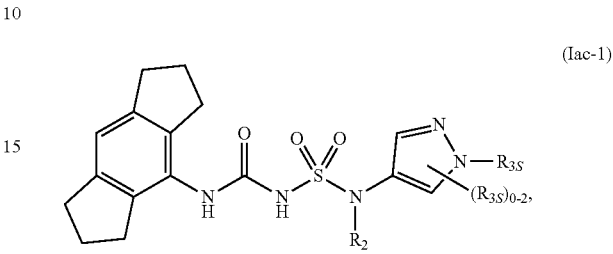

(Iac-1)

or a prodrug, solvate, or pharmaceutically acceptable salt thereof, wherein:

$R_2$ is $-(CX_2X_2)_n-R_{2S}$, wherein n is 0, 1, or 2, and each $X_2$ is independently H, $C_1$-$C_6$ alkyl, $C_2$-$C_6$ alkenyl, or $C_2$-$C_6$ alkynyl, wherein the $C_1$-$C_6$ alkyl, $C_2$-$C_6$ alkenyl, or $C_2$-$C_6$ alkynyl is optionally substituted with one or more halo, —CN, —OH, —O($C_1$-$C_6$ alkyl), —NH$_2$, —NH($C_1$-$C_6$ alkyl), —N($C_1$-$C_6$ alkyl)$_2$, or oxo;

$R_{2S}$ is 4- to 8-membered heterocycloalkyl optionally substituted with one or more $C_1$-$C_6$ alkyl, $C_2$-$C_6$ alkenyl, $C_2$-$C_6$ alkynyl, $C_1$-$C_6$ haloalkyl, halo, —CN, —OH, —O($C_1$-$C_6$ alkyl), —NH$_2$, —NH($C_1$-$C_6$ alkyl), —N($C_1$-$C_6$ alkyl)$_2$, or oxo; and each $R_{3S}$ is independently $C_1$-$C_6$ alkyl, $C_1$-$C_6$ haloalkyl, $C_3$-$C_8$ cycloalkyl, halo, or $C_3$-$C_8$ heterocycloalkyl, wherein the $C_1$-$C_6$ alkyl, $C_1$-$C_6$ haloalkyl, $C_3$-$C_8$ cycloalkyl, or $C_3$-$C_8$ heterocycloalkyl is optionally substituted with —O($C_1$-$C_6$ alkyl), —N($C_1$-$C_6$ alkyl)$_2$, halo, or —CN.

2. The compound of claim 1, or prodrug, solvate, or pharmaceutically acceptable salt thereof, wherein $R_2$ is —$R_{2S}$.

3. The compound of claim 1, or prodrug, solvate, or pharmaceutically acceptable salt thereof, wherein $R_2$ is —(CH$_2$)—$R_{2S}$.

4. The compound of claim 2, or prodrug, solvate, or pharmaceutically acceptable salt thereof, wherein $R_{2S}$ is 4- to 6-membered heterocycloalkyl optionally substituted with one or more $C_1$-$C_6$ alkyl, $C_2$-$C_6$ alkenyl, $C_2$-$C_6$ alkynyl, $C_1$-$C_6$ haloalkyl, halo, —CN, —OH, —O($C_1$-$C_6$ alkyl), —NH$_2$, —NH($C_1$-$C_6$ alkyl), —N($C_1$-$C_6$ alkyl)$_2$, or oxo.

5. The compound of claim 4, or prodrug, solvate, or pharmaceutically acceptable salt thereof, wherein $R_{2S}$ is

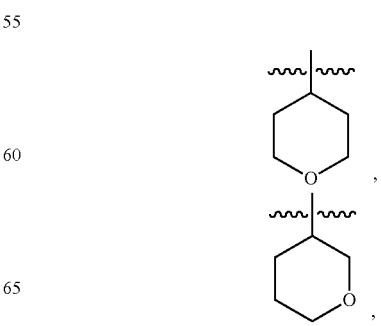

-continued

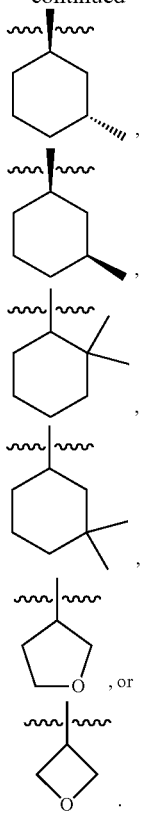

6. The compound of claim 1, or prodrug, solvate, or pharmaceutically acceptable salt thereof, wherein each $R_{3S}$ is independently $C_1$-$C_6$ alkyl optionally substituted with —O($C_1$-$C_6$ alkyl), —N($C_1$-$C_6$ alkyl)$_2$, halo, or —CN.

7. The compound of claim 6, or prodrug, solvate, or pharmaceutically acceptable salt thereof, wherein at least one $R_{3S}$ is methyl, ethyl, or isopropyl.

8. A compound of Formula (Iabc-1):

(Iabc-1)

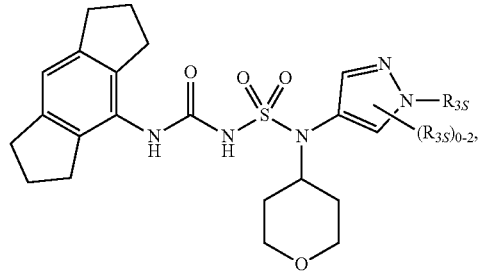

or a prodrug, solvate, or pharmaceutically acceptable salt thereof, wherein:
  $R_{2S}$ is 4- to 8-membered heterocycloalkyl optionally substituted with one or more $C_1$-$C_6$ alkyl, $C_1$-$C_6$ haloalkyl, or oxo; and
  each $R_{3S}$ is independently $C_1$-$C_6$ alkyl, $C_1$-$C_6$ haloalkyl, $C_3$-$C_8$ cycloalkyl, halo, or $C_3$-$C_8$ heterocycloalkyl, wherein the $C_1$-$C_6$ alkyl, $C_1$-$C_6$ haloalkyl, $C_3$-$C_8$ cycloalkyl, or $C_3$-$C_8$ heterocycloalkyl is optionally substituted with —O($C_1$-$C_6$ alkyl), —N($C_1$-$C_6$ alkyl)$_2$, halo, or —CN.

9. The compound of claim 1, wherein the compound is of Formula (Iabc-1a):

(Iabc-1a)

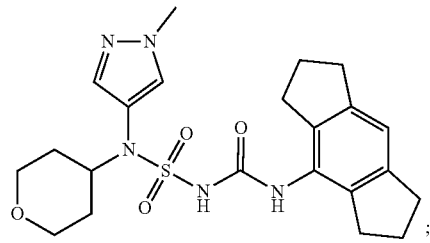

or the prodrug, solvate, or pharmaceutically acceptable salt thereof.

10. A compound selected from:

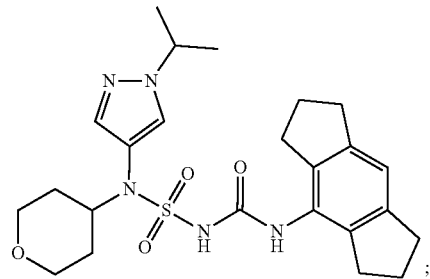

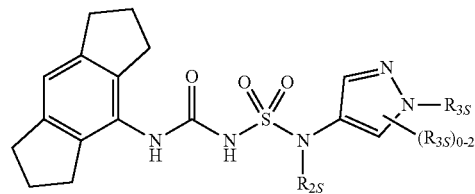

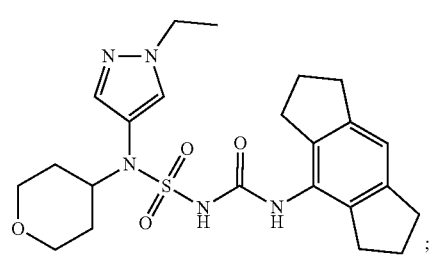

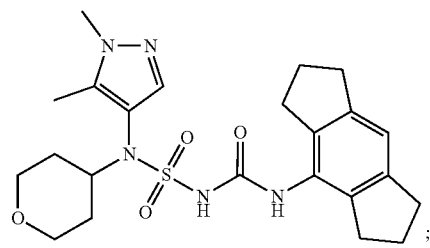

335
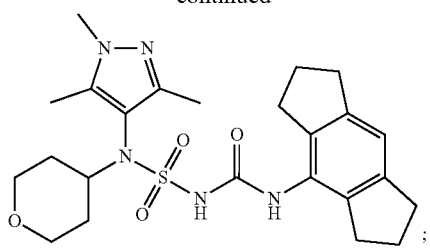
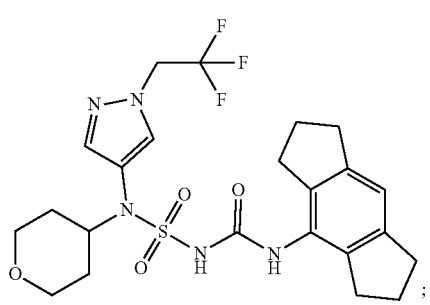
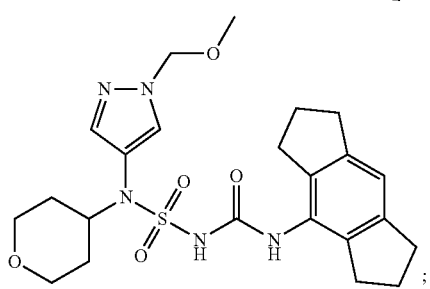
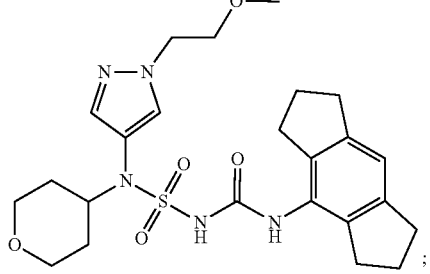
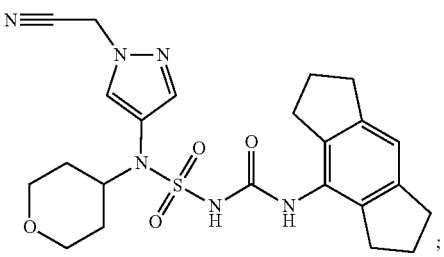
336
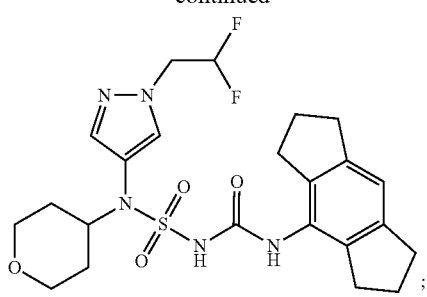
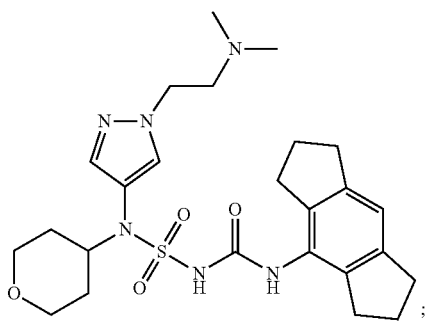
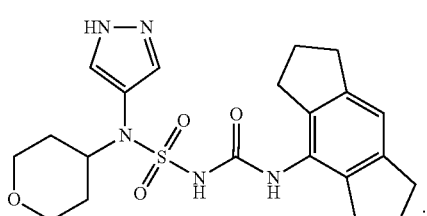
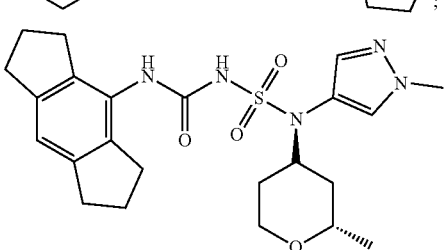
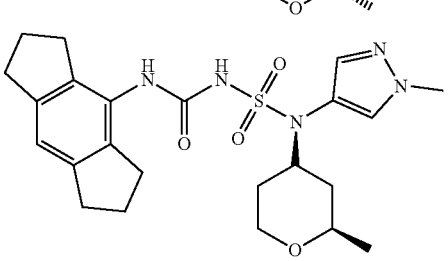

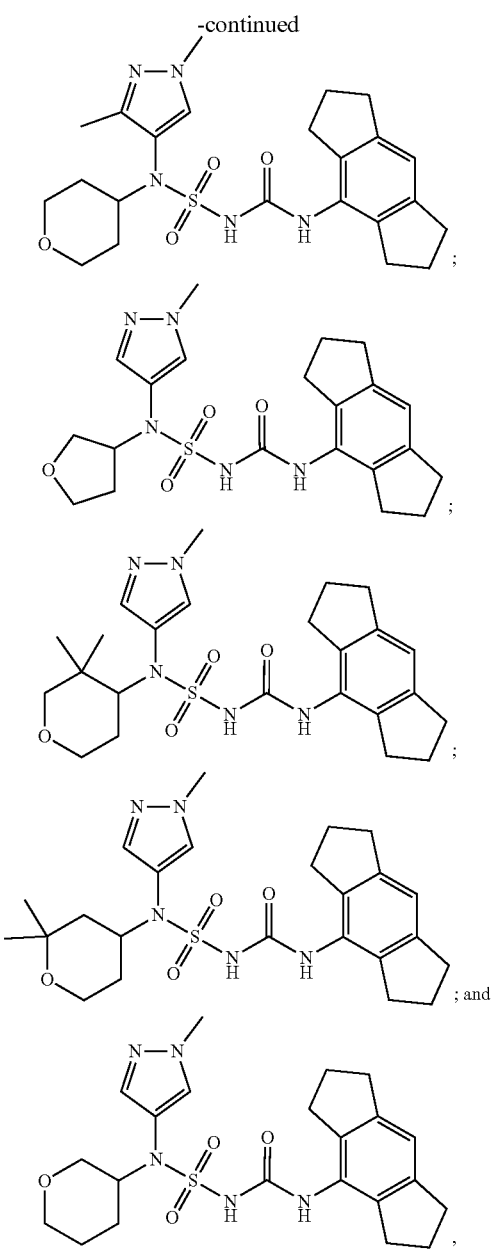

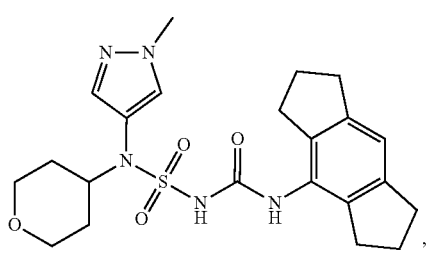 [SMILES: Cn1cc(N(C2CCOCC2)S(=O)(=O)NC(=O)Nc2c3c(cc4c2CCC4)CCC3)cn1]

or a prodrug, solvate, or pharmaceutically acceptable salt thereof.

11. The compound of claim 1, wherein the compound is:

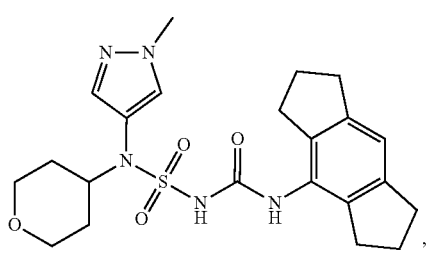 [SMILES: Cn1cc(N(C2CCOCC2)S(=O)(=O)NC(=O)Nc2c3c(cc4c2CCC4)CCC3)cn1]

or the prodrug, solvate, or pharmaceutically acceptable salt thereof.

12. The compound of claim 1, wherein the compound is:

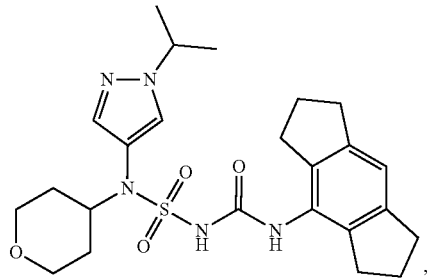 [SMILES: CC(C)n1cc(N(C2CCOCC2)S(=O)(=O)NC(=O)Nc2c3c(cc4c2CCC4)CCC3)cn1]

or the prodrug, solvate, or pharmaceutically acceptable salt thereof.

13. The compound of claim 1, wherein the compound is:

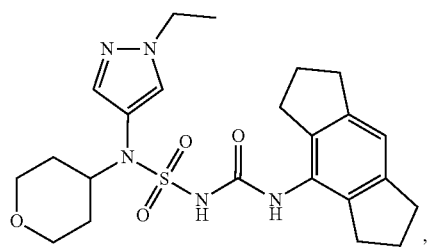 [SMILES: CCn1cc(N(C2CCOCC2)S(=O)(=O)NC(=O)Nc2c3c(cc4c2CCC4)CCC3)cn1]

or the prodrug, solvate, or pharmaceutically acceptable salt thereof.

14. The compound of claim 1, wherein the compound is:

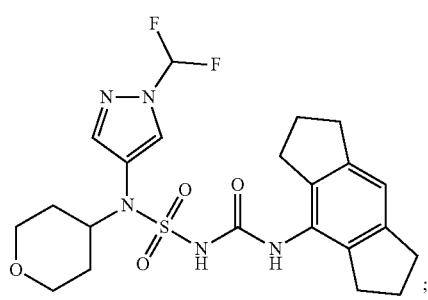 [SMILES: O=C(Nc1c2c(cc3c1CCC3)CCC2)NS(=O)(=O)N(c1cnn(C(F)F)c1)C1CCOCC1]

or the prodrug, solvate, or pharmaceutically acceptable salt thereof.

15. The compound of claim 1, wherein the compound is:

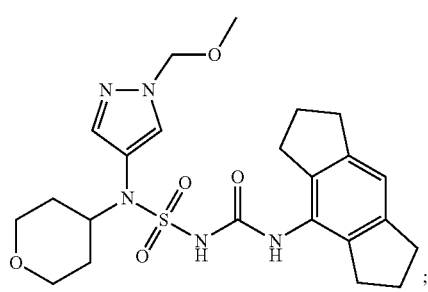 [SMILES: COCn1cc(N(C2CCOCC2)S(=O)(=O)NC(=O)Nc2c3c(cc4c2CCC4)CCC3)cn1]

or the prodrug, solvate, or pharmaceutically acceptable salt thereof.

16. A pharmaceutical composition comprising the compound of claim 11, or the prodrug, solvate, or pharmaceutically acceptable salt thereof, and a pharmaceutically acceptable diluent or carrier.

17. A pharmaceutical composition comprising the compound of claim 12, or the prodrug, solvate, or pharmaceutically acceptable salt thereof, and a pharmaceutically acceptable diluent or carrier.

18. A pharmaceutical composition comprising the compound of claim 13, or the prodrug, solvate, or pharmaceutically acceptable salt thereof, and a pharmaceutically acceptable diluent or carrier.

19. A pharmaceutical composition comprising the compound of claim 14, or the prodrug, solvate, or pharmaceutically acceptable salt thereof, and a pharmaceutically acceptable diluent or carrier.

20. A pharmaceutical composition comprising the compound of claim 15, or the prodrug, solvate, or pharmaceutically acceptable salt thereof, and a pharmaceutically acceptable diluent or carrier.

* * * * *